United States Patent
Chen et al.

(10) Patent No.: US 11,498,928 B2
(45) Date of Patent: Nov. 15, 2022

(54) MACROCYCLIC SPIROETHERS AS MCL-1 INHIBITORS

(71) Applicants: ASCENTAGE PHARMA (SUZHOU) CO., LTD., Suzhou (CN); THE REGENTS OF THE UNIVERSITY OF MICHIGAN, Ann Arbor, MI (US); ASCENTAGE PHARMA GROUP CORP LIMITED, Hong Kong (CN)

(72) Inventors: Jianyong Chen, Suzhou (CN); Yunlong Zhou, Suzhou (CN); Guozhi Tang, Suzhou (CN); Chengzhe Wu, Suzhou (CN); Leilei Zhao, Suzhou (CN); Lingling Jiao, Suzhou (CN); Binghua Sheng, Suzhou (CN); Shaomeng Wang, Superior Township, MI (US); Chao-Yie Yang, Ann Arbor, MI (US); Hao Chen, Suzhou (CN); Wenliang Hu, Suzhou (CN); Yu Jing, Suzhou (CN)

(73) Assignees: ASCENTAGE PHARMA (SUZHOU) CO., LTD., Suzhou (CN); THE REGENTS OF THE UNIVERSITY OF MICHIGAN, Ann Arbor, MI (US); ASCENTAGE PHARMA GROUP CORP LIMITED, Hong Kong (CN)

( * ) Notice: Subject to any disclaimer, the term of this patent is extended or adjusted under 35 U.S.C. 154(b) by 0 days.

(21) Appl. No.: 17/049,100

(22) PCT Filed: Jan. 17, 2020

(86) PCT No.: PCT/CN2020/072565
§ 371 (c)(1),
(2) Date: Oct. 20, 2020

(87) PCT Pub. No.: WO2020/147802
PCT Pub. Date: Jul. 23, 2020

(65) Prior Publication Data
US 2021/0340158 A1 Nov. 4, 2021

(30) Foreign Application Priority Data

Jan. 18, 2019 (WO) ............... PCT/CN2019/072347
Aug. 7, 2019 (WO) ............... PCT/CN2019/099673

(51) Int. Cl.
*C07D 513/20* (2006.01)
*C07D 515/20* (2006.01)
*C07D 498/08* (2006.01)
(Continued)

(52) U.S. Cl.
CPC ............ *C07D 513/20* (2013.01); *A61P 35/00* (2018.01); *C07D 513/10* (2013.01); *C07D 519/00* (2013.01)

(58) Field of Classification Search
CPC ................ C07D 513/20; C07D 515/20; C07D 498/08; A61K 31/553
See application file for complete search history.

(56) References Cited

U.S. PATENT DOCUMENTS

| | | |
|---|---|---|
| 5,093,330 A | 3/1992 | Caravatti et al. |
| 10,023,575 B2 | 7/2018 | Hoenke et al. |
| 10,533,010 B2 | 1/2020 | Lee et al. |

FOREIGN PATENT DOCUMENTS

| | | |
|---|---|---|
| CN | 106456602 A | 2/2017 |
| CN | 108137602 A | 6/2018 |
| WO | WO-2016/033486 A1 | 3/2016 |

(Continued)

OTHER PUBLICATIONS

Caenepeel et al., AMG 176, a Selective MCL1 Inhibitor, Is Effective in Hematologic Cancer Models Alone and in Combination with Established Therapies, Cancer Discov., 8(12):1582-97 (Dec. 2018).
European Patent Application No. 20742097.7, European Search Report, dated Apr. 14, 2021.
Adams et al., The Bcl-2 apoptotic switch in cancer development and therapy, Oncogene, 26(9):1324-37 (2007).
Amundson et al., An informatics approach identifying markers of chemosensitivity in human cancer cell lines, Cancer Res., 60(21):6101-10 (2000).
Beroukhim et al., The landscape of somatic copy-number alteration across human cancers, Nature, 463(7283):899-905 (Feb. 2010).
Bingham et al., Over one hundred solvates of sulfathiazole, Chem. Commun., 603-4 (2001).

(Continued)

*Primary Examiner* — Bruck Kifle
(74) *Attorney, Agent, or Firm* — Marshall, Gerstein & Borun LLP

(57) ABSTRACT

Provided are compounds represented by Formula (I-A) and the pharmaceutically acceptable salts and solvates thereof, wherein $R^8$, $R^{9a}$, $R^{9b}$, $R^{9c}$, $R^{9d}$, X, Y, Z, $Z^1$, W, and (aa) are as defined as set forth in the specification. Provided are also compounds of Formula (I-A) for use to treat a condition or disorder responsive to Mcl-1 inhibition such as cancer.

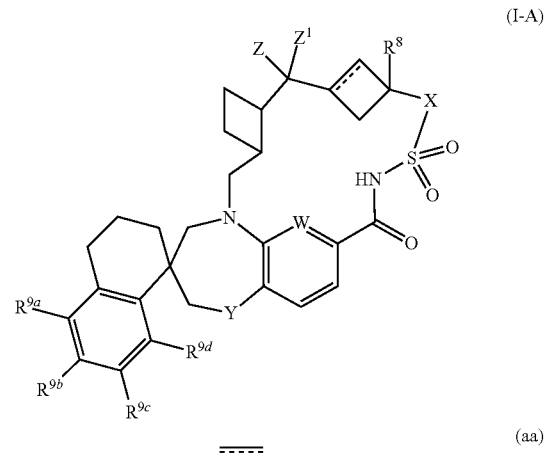

47 Claims, 15 Drawing Sheets

(51) Int. Cl.
- *A61K 31/553* (2006.01)
- *A61P 35/00* (2006.01)
- *C07D 513/10* (2006.01)
- *C07D 519/00* (2006.01)

(56) References Cited

FOREIGN PATENT DOCUMENTS

| WO | WO-2017/147410 A1 | 8/2017 |
| WO | WO-2018/183418 A1 | 10/2018 |
| WO | WO-2019/036575 A1 | 2/2019 |
| WO | WO-2019/046150 A1 | 3/2019 |

OTHER PUBLICATIONS

Caira et al., Preparation and crystal characterization of a polymorph, a monohydrate, and an ethyl acetate solvate of the antifungal fluconazole, J. Pharm. Sci., 93(3):601-11 (2004).

Danial et al., Cell death: critical control points, Cell, 116(2):205-19 (2004).

International Application No. PCT/CN2020/072565, International Search Report and Written Opinion, dated Apr. 15, 2020.

Kirkin et al., The role of Bcl-2 family members in tumorigenesis, Biochim. Biophys. Acta, 1644(2-3):229-49 (2004).

Moss, Basic terminology of stereochemistry, Pure & Appl. Chem., 68(12):2193-222 (1996).

VanTonder et al., Preparation and physicochemical characterization of 5 niclosamide solvates and 1 hemisolvate, AAPS PharmSciTech., 5(1):E12 (2004).

Wei et al., Inducing apoptosis and enhancing chemosensitivity to gemcitabine via RNA interference targeting Mcl-1 gene in pancreatic carcinoma cell, Cancer Chemother. Pharmacol., 62(6):1055-64 (Nov. 2008).

Wertz et al., Sensitivity to antitubulin chemotherapeutics is regulated by MCL1 and FBW7, Nature, 471(7336):110-4 (Mar. 2011).

Willis et al., Apoptosis initiated when BH3 ligands engage multiple Bcl-2 homologs, not Bax or Bak, Science, 315(5813):856-9 (2007).

MACROCYCLIC SPIROETHERS AS MCL-1 INHIBITORS

CROSS-REFERENCE TO RELATED APPLICATIONS

This is the U.S. national phase of International Application No. PCT/CN2020/072565, filed Jan. 17, 2020, which claims the benefit of International Application No. PCT/CN2019/072347, filed Jan. 18, 2019, and International Application No. PCT/CN2019/099673, filed Jan. 7, 2019.

BACKGROUND OF THE INVENTION

Field of the Invention

The present disclosure provides Mcl-1 inhibitors, synthetic intermediates and methods to prepare Mcl-1 inhibitors, and therapeutic methods of treating conditions and diseases, e.g., cancer, wherein inhibition of Mcl-1 provides a benefit.

Background

Abnormal regulation of apoptosis pays an important role in cancer. The apoptosis pathway can be initiated by various extracellular and intracellular stresses, including growth factor deprivation, DNA damage, oncogene induction, and cytotoxic drugs (Danial and Korsmeyer, *Cell* 116:205-219 (2004)). The death signal leads to the oligomerization of the pro-apoptotic proteins Bax and Bak. Upon activation, they permeabilize the mitochondrial outer membrane and release apoptogenic factors into the cytoplasm. This process is tightly regulated by both pro-apoptotic (Bax, Bak, Bad, Bid, Bim, Bmf, NOXA, PUMA) and anti-apoptotic (Bcl-2, Bcl-xL, Bcl-w, Bcl2-A1, Mcl-1) members of the Bcl-2 family of proteins. The anti-apoptotic Bcl-2 proteins function to protect the cell from apoptotic insults, primarily by preventing disruption of mitochondrial outer membrane integrity by binding to the pro-apoptotic proteins. Adams and Cory *Oncogene* 26:1324-1337 (2007); Willis et al., *Science* 315: 856-859 (2007). Because tumor cells are under stress, alterations in their apoptotic signaling pathways are crucial for their survival.

Down-regulated apoptosis is implicated in the onset of cancer. Research has shown, for example, that anti-apoptotic proteins are over-expressed in many cancer cell types. Beroukhim et al., *Nature* 463:899-905 (2010); Kirkin et al., *Biochimica et Biophysica Acta* 1644:229-249 (2004); and Amundson et al., *Cancer Research* 60:6101-6110 (2000). This dysregulation results in the survival of cells that would otherwise have undergone apoptosis such as cancer cells. This suggests that neutralizing the function of anti-apoptotic Bcl-2 proteins may offer an effective strategy for the elimination of cancer cells. In addition, resistance to chemotherapy can be caused by the upregulation of anti-apoptotic Bcl-2 family proteins. Resistance to chemotherapy is a major cause of treatment failure and poor prognosis in many cancers.

An important anti-apoptotic member of the Bcl-2 family is myeloid cell leukemia-1 protein (Mcl-1) protein. Mcl-1 is one of the most frequently amplified anti-apoptotic genes in human cancers including prostate, lung, pancreatic, breast, ovarian, and cervical cancers, as well as melanoma, B-cell chronic lymphocytic leukemia (B-CLL), acute myeloid leukemia (AML) and acute lymphoblastic leukemia (ALL) Beroukhim et al., *Nature* 463:899-905 (2010). Moreover, its overexpression is implicated as a resistance factor for multiple therapies including widely prescribed microtubule-targeted agents for breast cancers, such as paclitaxel, vincristine, and gemcitabine. Wei et al., *Cancer Chemother Pharmacol* 62:1055-1064 (2008) and Wertz et al., *Nature* 471:110-114 (2011). These data suggest that Mcl-1 is an important target for a wide variety of cancers.

In many cancer cell types, the cancer cell's survival is attributed to the dysregulation of the apoptotic pathway caused by the over-expression of one or more anti-apoptotic Bcl-2 protein family members. Because of the important role for Bcl-2 family of proteins in regulating apoptosis in both cancerous and non-cancerous cells, and the inter-cell variability of Bcl-2 family protein expression, it could be advantageous to have a small molecule inhibitor that selectively targets and preferably binds to one type or a subset of anti-apoptotic Bcl-2 protein(s). A selective compound also may confer certain advantages in the clinical setting, by providing flexibility to select a dosing regimen to reduce on-target toxic effects in normal cells.

Because Mcl-1 protein is an important Bcl-2 family member associated with a number of diseases, there is a need for compounds which bind to and inhibit the activity of Mcl-1 protein.

BRIEF SUMMARY OF THE INVENTION

In one aspect, the present disclosure provides compounds represented by any one of Formulae I-XVII or Formulae I-A, II-A, III-A, IV-A, V-A, VI-A, VII-A, VIII-A, IX-A, X-A, XI-A, XII-A, XIII-A, XIV-A, XV-A, XVI-A, or XVII-A, below, and the pharmaceutically acceptable salts and solvates, e.g., hydrates, thereof, collectively referred to as "Compounds of the Disclosure." Compounds of the Disclosure are Mcl-1 inhibitors and/or synthetic intermediates used to prepare Mcl-1 inhibitors. Mcl-1 inhibitors are useful in treating or preventing diseases or conditions such as cancer wherein Mcl-1 inhibition provides a benefit.

In another aspect, the present disclosure provides compounds represented by any one of Formulae XVIII-XXXIV or Formulae XVIII-A, XIX-A, XX-A, XXI-A, XXII-A, XXIII-A, XXIV-A, XXV-A, XXVI-A, XXVII-A, XXVIII-A, XXIX-A, XXX-A, XXXI-A, XXXII-A, XXXIII-A, or XXXIV-A, below, and the pharmaceutically acceptable salts and solvates, e.g., hydrates, thereof, collectively referred to as "Intermediates of the Disclosure." Intermediates of the Disclosure are synthetic intermediates that can be used to prepare Compounds of the Disclosure.

In another aspect, the present disclosure provides methods of treating or preventing a condition or disease by administering a therapeutically effective amount of a Compound of the Disclosure to a subject, e.g., a human patient, in need thereof. The disease or condition of interest treatable or preventable by inhibition of Mcl-1 is, for example, a cancer, a chronic autoimmune disorder, an inflammatory condition, a proliferative disorder, sepsis, or a viral infection. Also provided are methods of preventing the proliferation of unwanted proliferating cells, such as in cancer, in a subject comprising administering a therapeutically effective amount of a Compound of the Disclosure to a subject at risk of developing a condition characterized by unwanted proliferating cells. In some embodiments, the Compounds of the Disclosure may reduce the proliferation of unwanted cells by inducing apoptosis in those cells.

In another aspect, the present disclosure provides a method of inhibiting Mcl-1 in a subject, comprising administering to the subject a therapeutically effective amount of at least one Compound of the Disclosure.

In another aspect, the present disclosure provides a pharmaceutical composition comprising a Compound of the Disclosure and an excipient and/or pharmaceutically acceptable carrier.

In another aspect, the present disclosure provides a composition comprising a Compound of the Disclosure and an excipient and/or pharmaceutically acceptable carrier for use treating or preventing diseases or conditions wherein inhibition of Mcl-1 provides a benefit, e.g., cancer.

In another aspect, the present disclosure provides a composition comprising: (a) a Compound of the Disclosure; (b) a second therapeutically active agent; and (c) optionally an excipient and/or pharmaceutically acceptable carrier.

In another aspect, the present disclosure provides a Compound of the Disclosure for use in the treatment or prevention of a disease or condition of interest, e.g., cancer.

In another aspect, the present disclosure provides a use of a Compound of the Disclosure for the manufacture of a medicament for treating a disease or condition of interest, e.g., cancer.

In another aspect, the present disclosure provides a kit comprising a Compound of the Disclosure, and, optionally, a packaged composition comprising a second therapeutic agent useful in the treatment of a disease or condition of interest, and a package insert containing directions for use in the treatment of a disease or condition, e.g., cancer.

In another aspect, the present disclosure provides methods of preparing Compounds of the Disclosure and Intermediates of the Disclosure.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

I. Compounds of the Disclosure

Figure 1:
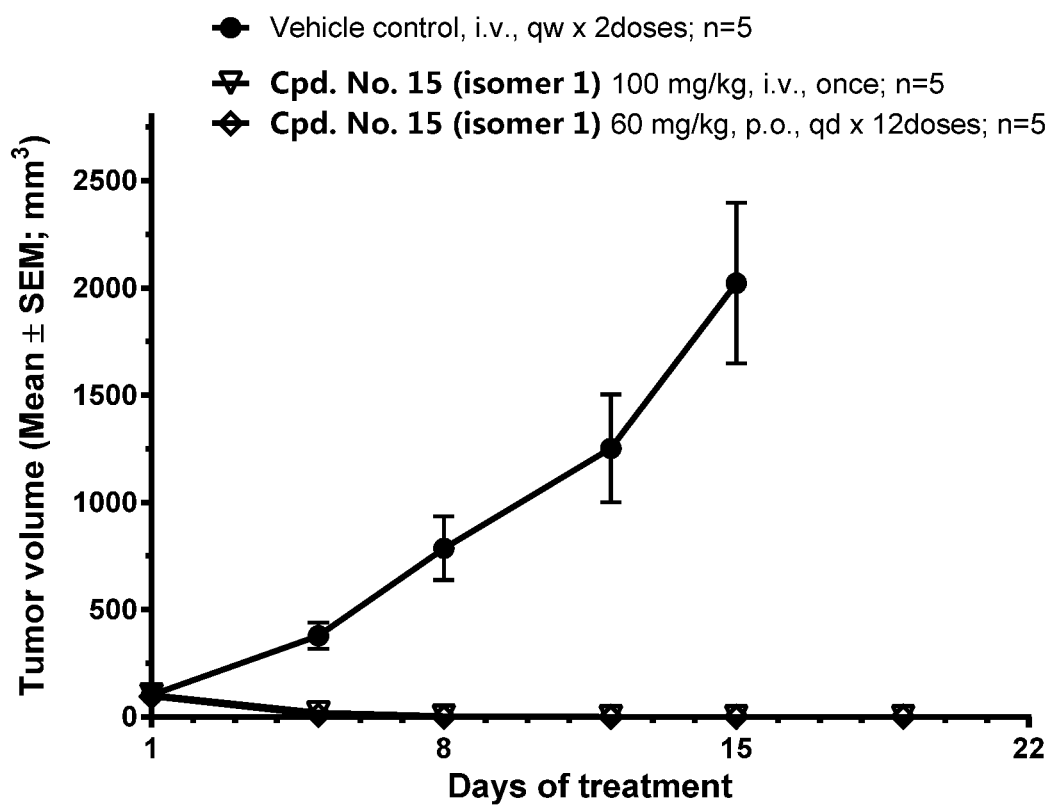
FIG. 1 is a line graph showing the anti-tumor efficacy of Cpd. No. 15 (isomer 1) in the subcutaneous tumor model of NCI-H929 at the indicated doses and routes of administration.

Compounds of the Disclosure are Mcl-1 inhibitors and/or synthetic intermediates used to prepare Mcl-1 inhibitors. In one embodiment, Compounds of the Disclosure are compounds of Formula I-A:

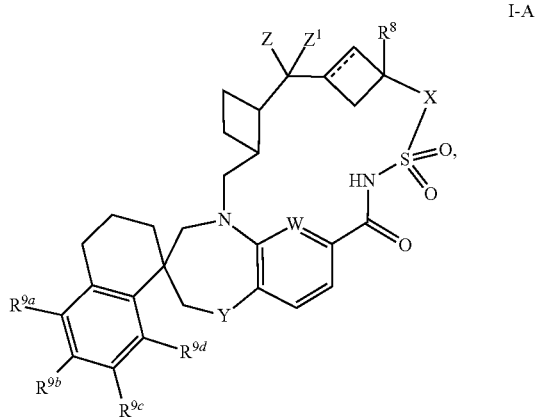

wherein:

X is selected from the group consisting of:

and wherein the bond projecting to the right is attached to the —S(=O)$_2$— group;

R$^8$ is selected from the group consisting of hydrogen and C$_1$-C$_3$ alkyl; or X and R$^8$ taken together form a spirocycle of Formula X-3:

wherein the bond projecting to the right is attached to the —S(=O)$_2$— group;

Y is selected from the group consisting of —O— and —S—;

Z is selected from the group consisting of —R, —N(R$^{1a}$)(R$^{1b}$), and —OR$^1$;

Z$^1$ is selected from the group consisting of hydrogen, (hydroxy)C$_1$-C$_4$ alkyl, (C$_1$-C$_3$ alkoxy)C$_1$-C$_3$ alkyl, (heterocyclo)C$_1$-C$_4$ alkyl, (alkylsulfonyl)C$_1$-C$_4$ alkyl, (phenyl)C$_1$-C$_4$ alkyl, (heteroaryl) C$_1$-C$_4$ alkyl, (amino)C$_1$-C$_4$ alkyl, (amido)C$_1$-C$_4$ alkyl, (carboxy)C$_1$-C$_4$ alkyl, (alkoxycarbonyl)C$_1$-C$_4$ alkyl, (aminocarbonyl)C$_1$-C$_4$ alkyl, (aminosulfonyl)C$_1$-C$_4$ alkyl, and —C(=O)R$^{15}$;

R is selected from the group consisting of C$_1$-C$_6$ alkyl, C$_3$-C$_6$ cycloalkyl, and 4- to 10-membered heterocyclo;

R$^1$ is selected from the group consisting of hydrogen, C$_1$-C$_6$ alkyl, (hydroxy)C$_1$-C$_4$ alkyl, (C$_1$-C$_3$ alkoxy)C$_1$-C$_3$ alkyl, (heterocyclo)C$_1$-C$_4$ alkyl, (alkylsulfonyl)C$_1$-C$_4$ alkyl, (phenyl)C$_1$-C$_4$ alkyl, (heteroaryl)C$_1$-C$_4$ alkyl, (amino)C$_1$-C$_4$ alkyl, (amido)C$_1$-C$_4$ alkyl, (carboxy)C$_1$-C$_4$ alkyl, (alkoxycarbonyl)C$_1$-C$_4$ alkyl, (aminocarbonyl)C$_1$-C$_4$ alkyl, and (aminosulfonyl)C$_1$-C$_4$ alkyl;

R$^{1a}$ is selected from the group consisting of hydrogen, C$_1$-C$_6$ alkyl, (hydroxy)C$_1$-C$_4$ alkyl, (C$_1$-C$_3$ alkoxy)C$_1$-C$_3$ alkyl, (heterocyclo)C$_1$-C$_4$ alkyl, (alkylsulfonyl)C$_1$-C$_4$ alkyl, (phenyl)C$_1$-C$_4$ alkyl, (heteroaryl)C$_1$-C$_4$ alkyl, (amino)C$_1$-C$_4$ alkyl, (amido)C$_1$-C$_4$ alkyl, (carboxy)C$_1$-C$_4$ alkyl, (alkoxycarbonyl)C$_1$-C$_4$ alkyl, (aminocarbonyl)C$_1$-C$_4$ alkyl, and (aminosulfonyl)C$_1$-C$_4$ alkyl;

R$^{1b}$ is selected from the group consisting of hydrogen and C$_1$-C$_3$ alkyl;

R$^{2a}$ is selected from the group consisting of hydrogen and C$_1$-C$_3$ alkyl;

R$^{3a}$ is selected from the group consisting of hydrogen and C$_1$-C$_3$ alkyl; or R$^{2a}$ and R$^{3a}$ taken together with the carbon atoms to which they are attached form a C$_3$-C$_6$ cycloalkyl or 4- to 10-membered heterocyclo;

R$^{2b}$ is selected from the group consisting of hydrogen and C$_1$-C$_3$ alkyl;

R$^{2c}$ is selected from the group consisting of hydrogen and C$_1$-C$_3$ alkyl;

R$^{2d}$ is selected from the group consisting of hydrogen and C$_1$-C$_3$ alkyl;

R$^{3b}$ is selected from the group consisting of hydrogen and C$_1$-C$_3$ alkyl;

R$^{3c}$ is selected from the group consisting of hydrogen, C$_1$-C$_6$ alkyl, (hydroxy)C$_1$-C$_4$ alkyl, (C$_1$-C$_3$ alkoxy)C$_1$-C$_3$ alkyl, (heterocyclo)C$_1$-C$_4$ alkyl, (alkylsulfonyl)C$_1$-C$_4$ alkyl, (phenyl)C$_1$-C$_4$ alkyl, (heteroaryl)C$_1$-C$_4$ alkyl, (amino)C$_1$-C$_4$ alkyl, (amido)C$_1$-C$_4$ alkyl, (carboxy)C$_1$-C$_4$ alkyl, (alkoxycarbonyl)C$_1$-C$_4$ alkyl, (aminocarbonyl)C$_1$-C$_4$ alkyl, and (aminosulfonyl)C$_1$-C$_4$ alkyl;

R$^{9a}$, R$^{9b}$, and R$^{9d}$ are independently selected from the group consisting of hydrogen and halo;

R$^{9b}$ is halo;

R$^{15}$ is 4- to 10-membered heterocyclo;

W is selected from the group consisting of —CH= and —N=;

=== represents a single or double bond;

each C$_3$-C$_7$ cycloalkyl is unsubstituted or substituted with one, two, or three substituents independently selected from the group consisting of halo, hydroxy, amino, cyano, C$_1$-C$_6$ alkyl, C$_1$-C$_4$ alkoxy, C$_3$-C$_6$ cycloalkyl, 4- to 7-membered heterocyclo, alkylsulfonyl, alkylcarbonyl, and phenyl;

each 4- to 10-membered heterocyclo is unsubstituted or substituted with one, two, three, or four substituents independently selected from the group consisting of halo, hydroxy, amino, cyano, C$_1$-C$_6$ alkyl, C$_1$-C$_4$ alkoxy, C$_3$-C$_6$ cycloalkyl, 4- to 7-membered heterocyclo, alkylsulfonyl, alkylcarbonyl, and phenyl; and each phenyl is unsubstituted or substituted with one, two, three, or four substituents independently selected from the group consisting of halo, hydroxy, amino, cyano, C$_1$-C$_6$ alkyl, C$_1$-C$_4$ alkoxy, C$_3$-C$_6$ cycloalkyl, 4- to 7-membered heterocyclo, alkylsulfonyl, alkylcarbonyl, and phenyl, or a pharmaceutically acceptable salt or solvate thereof.

In another embodiment, Compounds of the Disclosure are compounds of Formula I-A selected from the group consisting of:

III-A
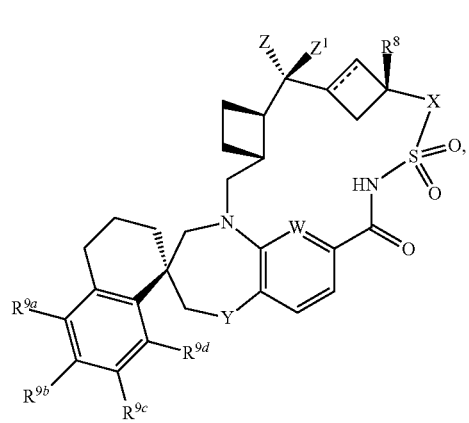
IV-A
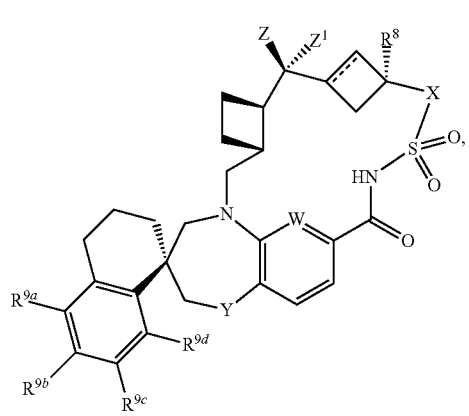
V-A
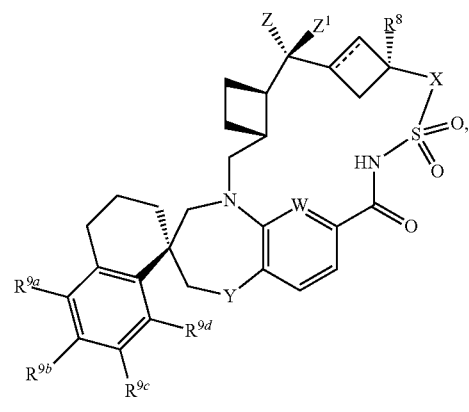
VI-A
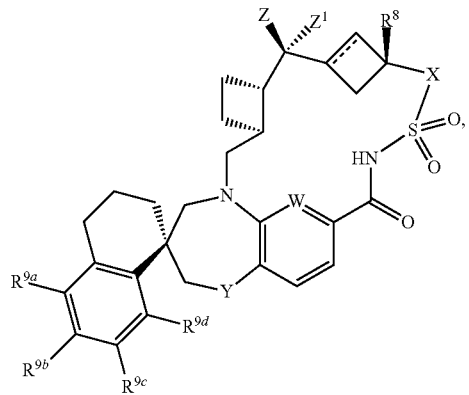
VII-A
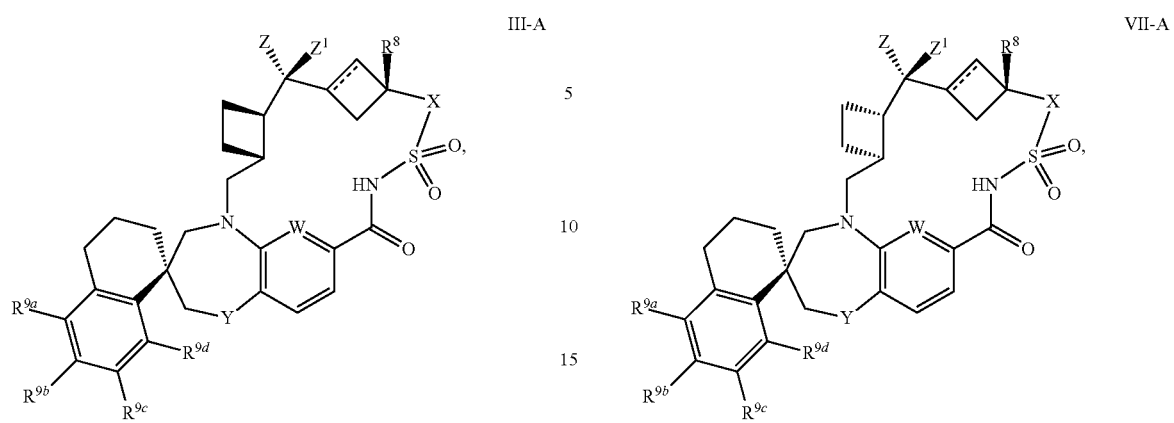
VIII-A
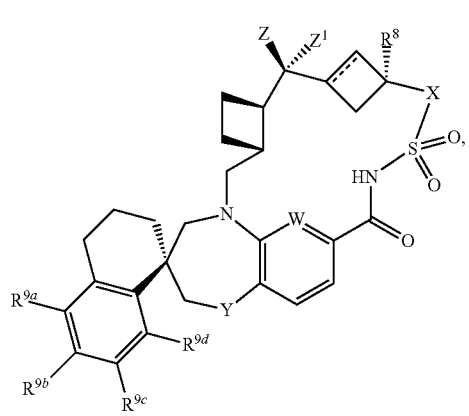
IX-A
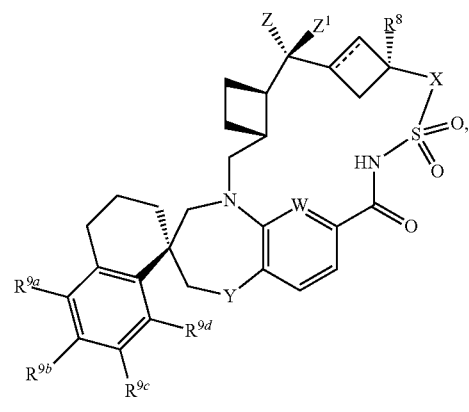
X-A
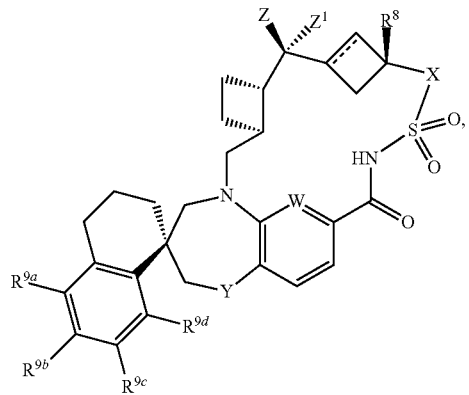

XI-A
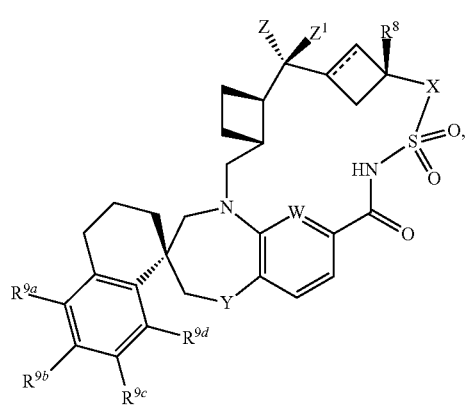
XII-A
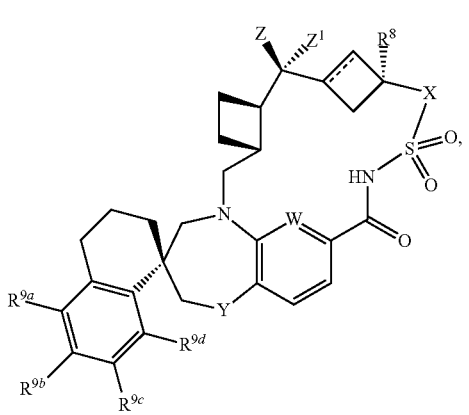
XIII-A
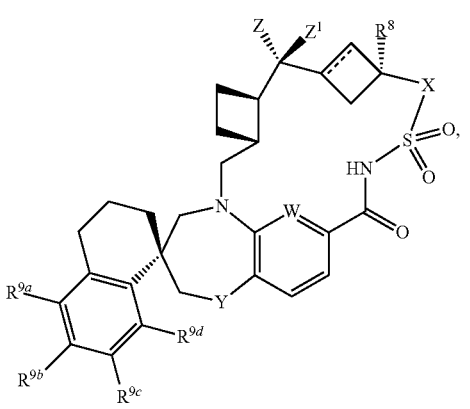
XIV-A
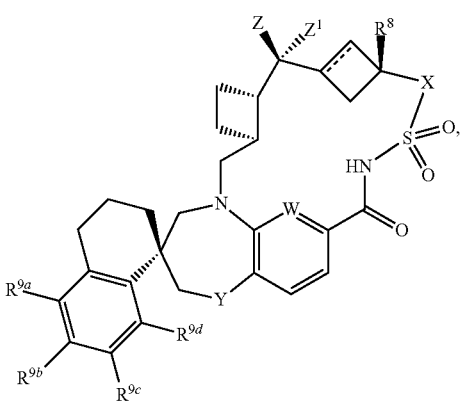
XV-A
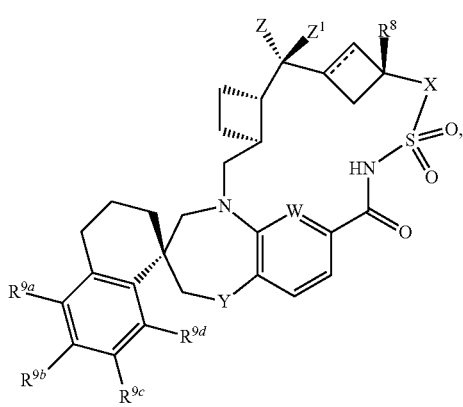
XVI-A
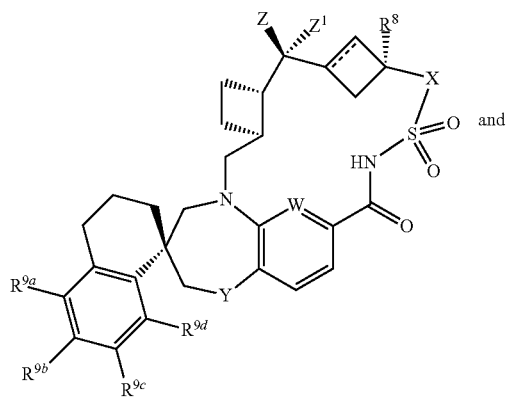
and
XVII-A
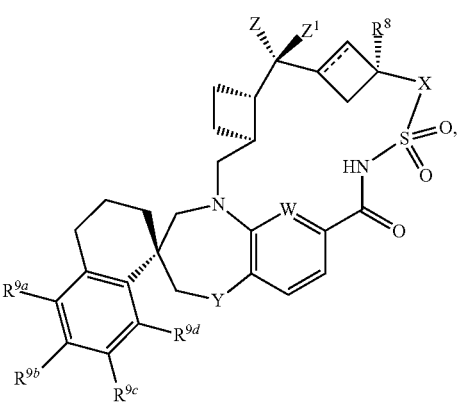
or a pharmaceutically acceptable salt or solvate thereof.
In another embodiment, Compounds of the Disclosure are compounds of any one of Formula I-A, II-A, III-A, IV-A, V-A, VI-A, VII-A, VIII-A, IX-A, X-A, XI-A, XII-A, XIII-A, XIV-A, XV-A, XVI-A, or XVII-A, wherein X is selected from the group consisting of:
X-1-A
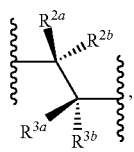

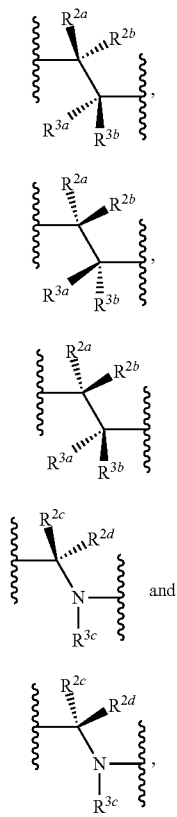

or a pharmaceutically acceptable salt or solvate thereof.

In another embodiment, Compounds of the Disclosure are compounds of having the specific combination of Formulae II-A, III-A, IV-A, V-A, VI-A, VII-A, VIII-A, IX-A, X-A, XI-A, XII-A, XIII-A, XIV-A, XV-A, XVI-A, or XVII-A, and X that are described in Table 1-A, or a pharmaceutically acceptable salt or solvate thereof. For example, a Compound of the Disclosure is selected from the group consisting of a compound of Formula II-A, wherein X is X-1-A, a compound of Formula II-A, wherein X is X-1-B, a compound of Formula II-A, wherein X is X-1-C, and so on.

TABLE 1-A

| Formula | X | Formula | X |
|---------|-----|---------|-----|
| II-A | X-1-A | III-A | X-1-A |
| II-A | X-1-B | III-A | X-1-B |
| II-A | X-1-C | III-A | X-1-C |
| II-A | X-1-D | III-A | X-1-D |
| II-A | X-2-A | III-A | X-2-A |
| II-A | X-2-B | III-A | X-2-B |
| IV-A | X-1-A | V-A | X-1-A |
| IV-A | X-1-B | V-A | X-1-B |
| IV-A | X-1-C | V-A | X-1-C |
| IV-A | X-1-D | V-A | X-1-D |
| IV-A | X-2-A | V-A | X-2-A |
| IV-A | X-2-B | V-A | X-2-B |
| VI-A | X-1-A | VII-A | X-1-A |
| VI-A | X-1-B | VII-A | X-1-B |
| VI-A | X-1-C | VII-A | X-1-C |
| VI-A | X-1-D | VII-A | X-1-D |
| VI-A | X-2-A | VII-A | X-2-A |
| VI-A | X-2-B | VII-A | X-2-B |
| VIII-A | X-1-A | IX-A | X-1-A |
| VIII-A | X-1-B | IX-A | X-1-B |
| VIII-A | X-1-C | IX-A | X-1-C |

TABLE 1-A-continued

| Formula | X | Formula | X |
|---------|-----|---------|-----|
| VIII-A | X-1-D | IX-A | X-1-D |
| VIII-A | X-2-A | IX-A | X-2-A |
| VIII-A | X-2-B | IX-A | X-2-B |
| X-A | X-1-A | XI-A | X-1-A |
| X-A | X-1-B | XI-A | X-1-B |
| X-A | X-1-C | XI-A | X-1-C |
| X-A | X-1-D | XI-A | X-1-D |
| X-A | X-2-A | XI-A | X-2-A |
| X-A | X-2-B | XI-A | X-2-B |
| XII-A | X-1-A | XIII-A | X-1-A |
| XII-A | X-1-B | XIII-A | X-1-B |
| XII-A | X-1-C | XIII-A | X-1-C |
| XII-A | X-1-D | XIII-A | X-1-D |
| XII-A | X-2-A | XIII-A | X-2-A |
| XII-A | X-2-B | XIII-A | X-2-B |
| XIV-A | X-1-A | XV-A | X-1-A |
| XIV-A | X-1-B | XV-A | X-1-B |
| XIV-A | X-1-C | XV-A | X-1-C |
| XIV-A | X-1-D | XV-A | X-1-D |
| XIV-A | X-2-A | XV-A | X-2-A |
| XIV-A | X-2-B | XV-A | X-2-B |
| XVI-A | X-1-A | XVII-A | X-1-A |
| XVI-A | X-1-B | XVII-A | X-1-B |
| XVI-A | X-1-C | XVII-A | X-1-C |
| XVI-A | X-1-D | XVII-A | X-1-D |
| XVI-A | X-2-A | XVII-A | X-2-A |
| XVI-A | X-2-B | XVII-A | X-2-B |

In another embodiment, Compounds of the Disclosure are compounds of any one of Formula I-A, II-A, III-A, IV-A, V-A, VI-A, VII-A, VIII-A, IX-A, X-A, XI-A, XII-A, XIII-A, XIV-A, XV-A, XVI-A, or XVII-A, wherein X is X-1-A, X-1-B, X-1-C, or X-1-D, or a pharmaceutically acceptable salt or solvate thereof.

In another embodiment, Compounds of the Disclosure are compounds of any one of Formula I-A, II-A, III-A, IV-A, V-A, VI-A, VII-A, VIII-A, IX-A, X-A, XI-A, XII-A, XIII-A, XIV-A, XV-A, XVI-A, or XVII-A, wherein X is X-2-A or X-2-B, or a pharmaceutically acceptable salt or solvate thereof.

In another embodiment, Compounds of the Disclosure are compounds of any one of Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein Z is —$OR^1$ and $Z^1$ is hydrogen, or a pharmaceutically acceptable salt or solvate thereof. In another embodiment, le is selected from the group consisting of (hydroxy)$C_1$-$C_4$ alkyl, ($C_1$-$C_3$ alkoxy)$C_1$-$C_3$ alkyl, (heterocyclo)$C_1$-$C_4$ alkyl, (alkylsulfonyl)$C_1$-$C_4$ alkyl, (phenyl)$C_1$-$C_4$ alkyl, (heteroaryl) $C_1$-$C_4$ alkyl, (amino)$C_1$-$C_4$ alkyl, (amido)$C_1$-$C_4$ alkyl, (carboxy)$C_1$-$C_4$ alkyl, (alkoxycarbonyl)$C_1$-$C_4$ alkyl, (aminocarbonyl)$C_1$-$C_4$ alkyl, (aminosulfonyl)$C_1$-$C_4$ alkyl, and —C(=O)$R^{15}$, or a pharmaceutically acceptable salt or solvate thereof.

In another embodiment, Compounds of the Disclosure are compounds of any one of Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein Z is —R and $Z^1$ is hydrogen, or a pharmaceutically acceptable salt or solvate thereof.

In another embodiment, Compounds of the Disclosure are compounds of any one of Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein Z is —N($R^{1a}$)($R^{1b}$) and $Z^1$ is hydrogen, or a pharmaceutically acceptable salt or solvate thereof.

In another embodiment, Compounds of the Disclosure are compounds of any one of Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein:

Z is —$OR^1$;
$R^1$ is selected from the group consisting of hydrogen and $C_1$-$C_3$ alkyl; and
$Z^1$ is selected from the group consisting of (hydroxy)$C_1$-$C_4$ alkyl, ($C_1$-$C_3$ alkoxy)$C_1$-$C_3$ alkyl, (heterocyclo)$C_1$-$C_4$ alkyl, (alkylsulfonyl)$C_1$-$C_4$ alkyl, (phenyl)$C_1$-$C_4$ alkyl, (heteroaryl) $C_1$-$C_4$ alkyl, (amino)$C_1$-$C_4$ alkyl, (amido)$C_1$-$C_4$ alkyl, (carboxy)$C_1$-$C_4$ alkyl, (alkoxycarbonyl)$C_1$-$C_4$ alkyl, (aminocarbonyl)$C_1$-$C_4$ alkyl, (aminosulfonyl)$C_1$-$C_4$ alkyl, and —C(=O)$R^{15}$, or a pharmaceutically acceptable salt or solvate thereof.

In another embodiment, Compounds of the Disclosure are compounds of any one of Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein W is —CH=, or a pharmaceutically acceptable salt or solvate thereof.

In another embodiment, Compounds of the Disclosure are compounds of any one of Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein W is —N=, or a pharmaceutically acceptable salt or solvate thereof.

In another embodiment, Compounds of the Disclosure are compounds of any one of Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein $R^{3c}$ is selected from the group consisting of hydrogen, $C_1$-$C_4$ alkyl, and (heterocyclo)$C_1$-$C_4$ alkyl, or a pharmaceutically acceptable salt or solvate thereof.

In another embodiment, Compounds of the Disclosure are compounds of Formula I:

I wherein:
X is:

X-1 wherein the bond projecting to the right is attached to the —S(=O)$_2$— group,

Y is selected from the group consisting of —O— and —S—;

Z is —$OR^1$;

$R^1$ is selected from the group consisting of $C_1$-$C_3$ alkyl and ($C_1$-$C_3$ alkoxy)$C_1$-$C_3$ alkyl;

$R^{2a}$ is selected from the group consisting of hydrogen and $C_1$-$C_3$ alkyl;

$R^{3a}$ is selected from the group consisting of hydrogen and $C_1$-$C_3$ alkyl; or $R^{2a}$ and $R^{3a}$ taken together with the carbon atoms to which they are attached form a $C_3$-$C_6$ cycloalkyl or 4- to 7-membered heterocyclo;

$R^{2b}$ is selected from the group consisting of hydrogen and $C_1$-$C_3$ alkyl;

$R^{3b}$ is selected from the group consisting of hydrogen and $C_1$-$C_3$ alkyl;

$R^8$ is selected from the group consisting of hydrogen and $C_1$-$C_3$ alkyl;

$R^{9a}$, $R^{9c}$, and $R^{9d}$ are independently selected from the group consisting of hydrogen and halo;

$R^{9b}$ is halo; and represents a single or double bond, wherein each $C_3$-$C_6$ cycloalkyl, or 4- to 7-membered heterocyclo is unsubstituted or substituted with one, two, or three substituents independently selected from the group consisting of halo, $C_1$-$C_3$ alkyl, and $C_1$-$C_3$ alkoxy, or a pharmaceutically acceptable salt or solvate thereof.

In another embodiment, Compounds of the Disclosure are compounds of selected from the group consisting of:

II

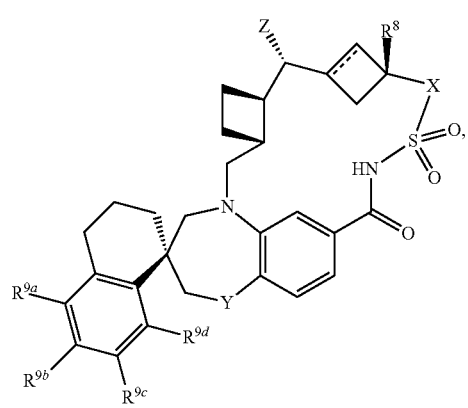 III
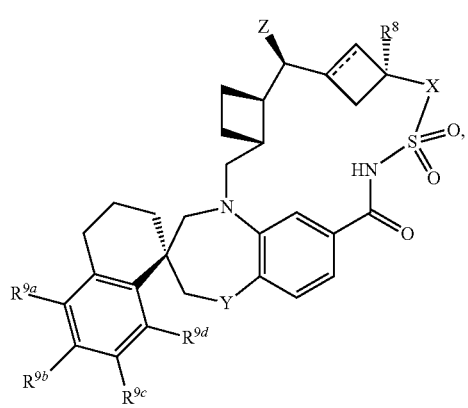 IV
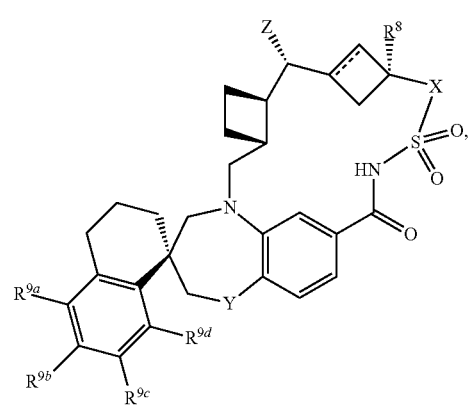 V
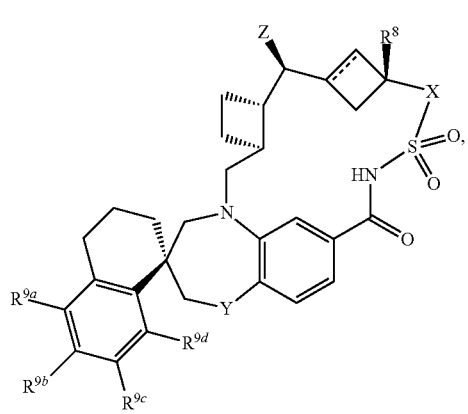 VI
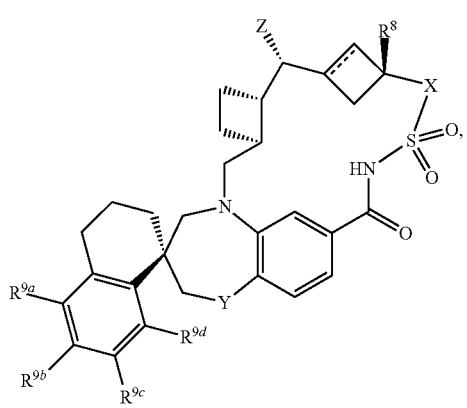 VII
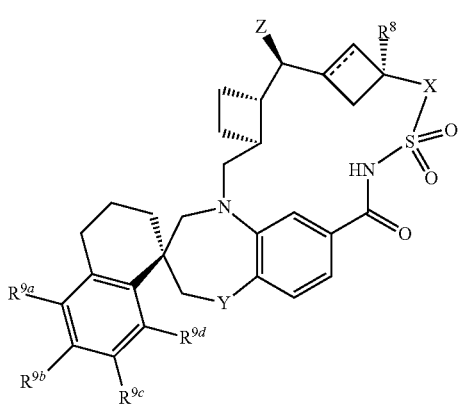 VIII
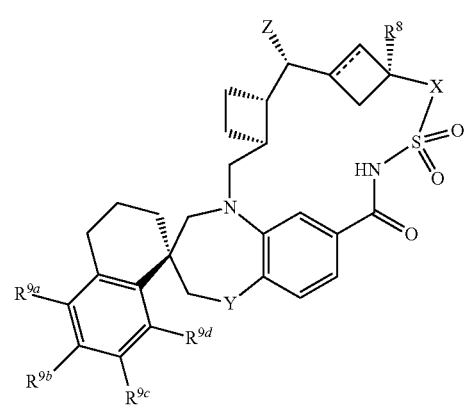 IX
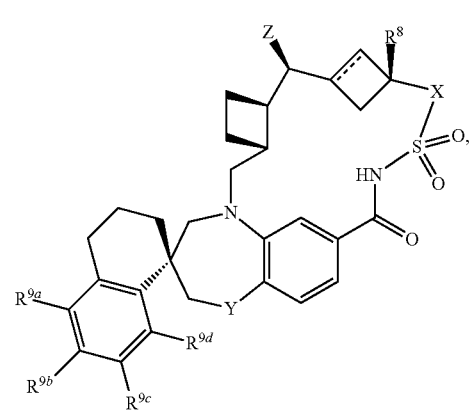 X XI
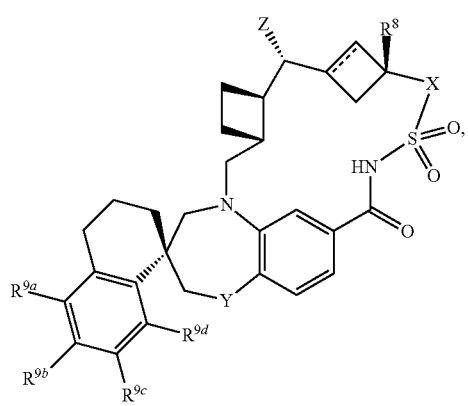
XII
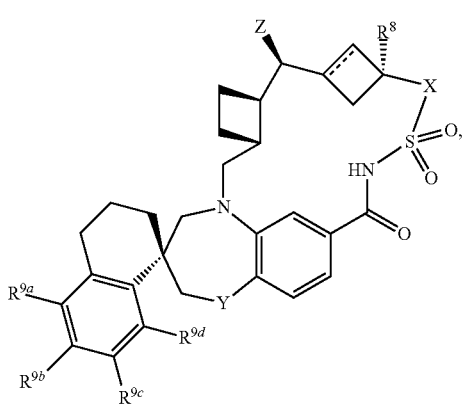
XIII
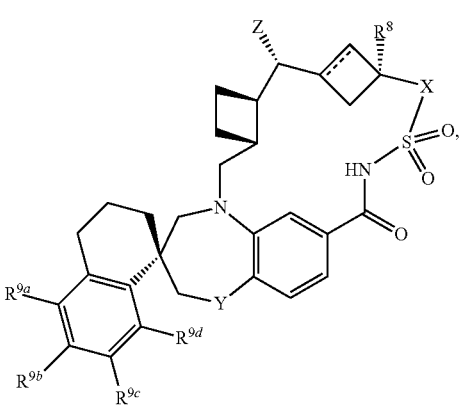
XIV
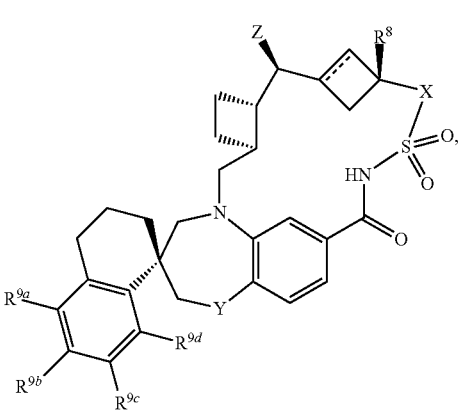
XV
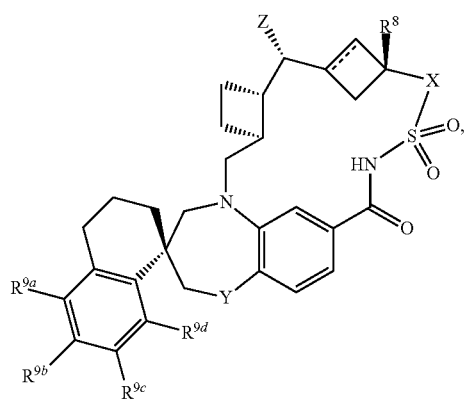
XVI
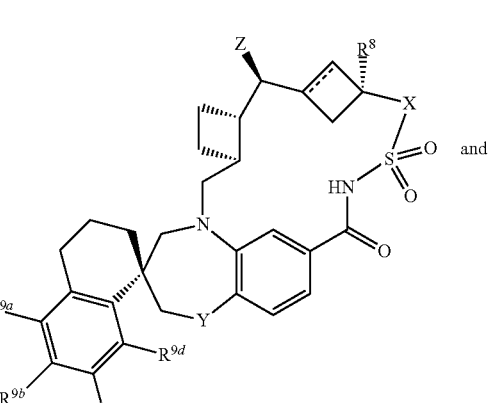
and
XVII
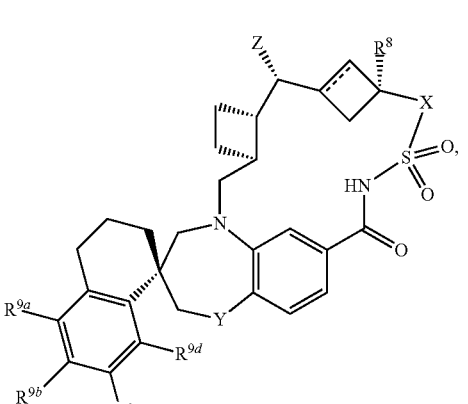
wherein $R^8$, $R^{9a}$, $R^{9b}$, $R^{9c}$, $R^{9d}$, X, Y, Z, and ═══ are as defined in connection with Formula I, or a pharmaceutically acceptable salt or solvate thereof.
In another embodiment, Compounds of the Disclosure are compounds of any one of Formula I-XVII, wherein X is X-1, and X-1 is selected from the group consisting of:
X-1-A
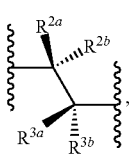

-continued

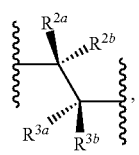
X-1-B

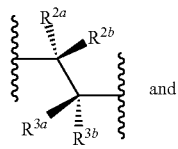
X-1-C

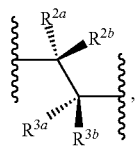
X-1-D or a pharmaceutically acceptable salt or solvate thereof.

In another embodiment, Compounds of the Disclosure are compounds of Formula I having the specific combination of Formulae II-XVII and X that are described in Table 1, or a pharmaceutically acceptable salt or solvate thereof. For example, a Compound of the Disclosure is selected from the group consisting of a compound of Formula II, wherein X is X-1-A, a compound of Formula II, wherein X is X-1-B, a compound of Formula II, wherein X is X-1-C, and so on.

TABLE 1

| Formula | X | Formula | X |
|---|---|---|---|
| II | X-1-A | III | X-1-A |
| II | X-1-B | III | X-1-B |
| II | X-1-C | III | X-1-C |
| II | X-1-D | III | X-1-D |
| IV | X-1-A | V | X-1-A |
| IV | X-1-B | V | X-1-B |
| IV | X-1-C | V | X-1-C |
| IV | X-1-D | V | X-1-D |
| VI | X-1-A | VII | X-1-A |
| VI | X-1-B | VII | X-1-B |
| VI | X-1-C | VII | X-1-C |
| VI | X-1-D | VII | X-1-D |
| VIII | X-1-A | IX | X-1-A |
| VIII | X-1-B | IX | X-1-B |
| VIII | X-1-C | IX | X-1-C |
| VIII | X-1-D | IX | X-1-D |
| X | X-1-A | XI | X-1-A |
| X | X-1-B | XI | X-1-B |
| X | X-1-C | XI | X-1-C |
| X | X-1-D | XI | X-1-D |
| XII | X-1-A | XIII | X-1-A |
| XII | X-1-B | XIII | X-1-B |
| XII | X-1-C | XIII | X-1-C |
| XII | X-1-D | XIII | X-1-D |
| XIV | X-1-A | XV | X-1-A |
| XIV | X-1-B | XV | X-1-B |
| XIV | X-1-C | XV | X-1-C |
| XIV | X-1-D | XV | X-1-D |
| XVI | X-1-A | XVII | X-1-A |
| XVI | X-1-B | XVII | X-1-B |
| XVI | X-1-C | XVII | X-1-C |
| XVI | X-1-D | XVII | X-1-D |

In another embodiment, Compounds of the Disclosure are compounds of any one of Formulae I-XVII (including the specific combinations listed in Table 1) or Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein Z is —OR$^1$, and R$^1$ is C$_1$-C$_3$ alkyl, or a pharmaceutically acceptable salt or solvate thereof.

In another embodiment, Compounds of the Disclosure are compounds of any one of Formulae I-XVII (including the specific combinations listed in Table 1) or Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein R$^1$ is methyl, or a pharmaceutically acceptable salt or solvate thereof.

In another embodiment, Compounds of the Disclosure are compounds of any one of Formulae I-XVII (including the specific combinations listed in Table 1) or Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein R$^1$ is —CH$_2$CH$_2$OCH$_3$, or a pharmaceutically acceptable salt or solvate thereof.

In another embodiment, Compounds of the Disclosure are compounds of any one of Formulae I-XVII (including the specific combinations listed in Table 1) or Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein R$^{2a}$ is hydrogen, or a pharmaceutically acceptable salt or solvate thereof.

In another embodiment, Compounds of the Disclosure are compounds of any one of Formulae I-XVII (including the specific combinations listed in Table 1) or Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein R$^{2a}$ is methyl, or a pharmaceutically acceptable salt or solvate thereof.

In another embodiment, Compounds of the Disclosure are compounds of any one of Formulae I-XVII (including the specific combinations listed in Table 1) or Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein R$^{2a}$ is ethyl, or a pharmaceutically acceptable salt or solvate thereof.

In another embodiment, Compounds of the Disclosure are compounds of any one of Formulae I-XVII (including the specific combinations listed in Table 1) or Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein R$^{2b}$ is hydrogen, or a pharmaceutically acceptable salt or solvate thereof.

In another embodiment, Compounds of the Disclosure are compounds of any one of Formulae I-XVII (including the specific combinations listed in Table 1) or Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein R$^{2b}$ is methyl, or a pharmaceutically acceptable salt or solvate thereof.

In another embodiment, Compounds of the Disclosure are compounds of any one of Formulae I-XVII (including the specific combinations listed in Table 1) or Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein $R^{3a}$ is hydrogen, or a pharmaceutically acceptable salt or solvate thereof.

In another embodiment, Compounds of the Disclosure are compounds of any one of Formulae I-XVII (including the specific combinations listed in Table 1) or Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein $R^{3a}$ is methyl, or a pharmaceutically acceptable salt or solvate thereof.

In another embodiment, Compounds of the Disclosure are compounds of any one of Formulae I-XVII (including the specific combinations listed in Table 1) or Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein $R^{3b}$ is hydrogen, or a pharmaceutically acceptable salt or solvate thereof.

In another embodiment, Compounds of the Disclosure are compounds of any one of Formulae I-XVII (including the specific combinations listed in Table 1) or Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein $R^{3b}$ is methyl, or a pharmaceutically acceptable salt or solvate thereof.

In another embodiment, Compounds of the Disclosure are compounds of any one of Formulae I-XVII (including the specific combinations listed in Table 1) or Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein $R^{2a}$ and $R^{3a}$ taken together with the carbon atoms to which they are attached form a $C_3$-$C_6$ cycloalkyl or 4- to 7-membered heterocyclo, or a pharmaceutically acceptable salt or solvate thereof.

In another embodiment, Compounds of the Disclosure are compounds of any one of Formulae I-XVII (including the specific combinations listed in Table 1) or Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein $R^8$ is hydrogen, or a pharmaceutically acceptable salt or solvate thereof.

In another embodiment, Compounds of the Disclosure are compounds of any one of Formulae I-XVII (including the specific combinations listed in Table 1) or Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein $R^8$ is methyl, or a pharmaceutically acceptable salt or solvate thereof.

In another embodiment, Compounds of the Disclosure are compounds of any one of Formulae I-XVII (including the specific combinations listed in Table 1) or Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein $R^{9b}$ is chloro, or a pharmaceutically acceptable salt or solvate thereof.

In another embodiment, Compounds of the Disclosure are compounds of any one of Formulae I-XVII (including the specific combinations listed in Table 1) or Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein $R^{9a}$ and $R^{9c}$ are independently selected from the group consisting of hydrogen and fluoro, or a pharmaceutically acceptable salt or solvate thereof.

In another embodiment, Compounds of the Disclosure are compounds of any one of Formulae I-XVII (including the specific combinations listed in Table 1) or Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein $R^{9d}$ is hydrogen, or a pharmaceutically acceptable salt or solvate thereof.

In another embodiment, Compounds of the Disclosure are compounds of any one of Formulae I-XVII (including the specific combinations listed in Table 1) or Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein ≡≡≡ represents a single bond, or a pharmaceutically acceptable salt or solvate thereof.

In another embodiment, Compounds of the Disclosure are compounds of any one of Formulae I-XVII (including the specific combinations listed in Table 1) or Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein ≡≡≡ represents a double bond, or a pharmaceutically acceptable salt or solvate thereof.

In another embodiment, Compounds of the Disclosure are compounds of any one of Formulae I-XVII (including the specific combinations listed in Table 1) or Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein Y is —O—, or a pharmaceutically acceptable salt or solvate thereof.

In another embodiment, Compounds of the Disclosure are compounds of any one of Formulae I-XVII (including the specific combinations listed in Table 1) or Formula I-A, II-A, III-A, IV-A, V-A, VI-A, VII-A, VIII-A, IX-A, X-A, XI-A, XII-A, XIII-A, XIV-A, XV-A, XVI-A, or XVII-A (including the specific combinations in Table 1-A), wherein Y is —S—, or a pharmaceutically acceptable salt or solvate thereof.

In another embodiment, Compounds of the Disclosure are compounds of Formula I selected from group consisting of the compounds of Table 2, or a pharmaceutically acceptable salt or solvate thereof.

TABLE 2

| Cpd. No. | Structure | Mcl-1 (FP, nM) | OPM-2 (5% FBS, nM) | H929 (5% FBS, nM) |
| --- | --- | --- | --- | --- |
| 1 (Isomer 1) | 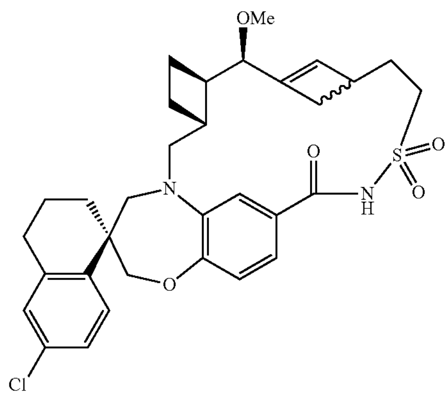 [SMILES: CO[C@H]1C2=CC(CCS(=O)(=O)NC(=O)c3ccc4c(c3)N(C[C@@H]3CC[C@H]31)C[C@@]1(CCCc3cc(Cl)ccc31)CO4)C2] | 6.8 | 547 | 360 |
| 1 (Isomer 2) | | 5.7 | 2430 | 1500 |
| 2 | 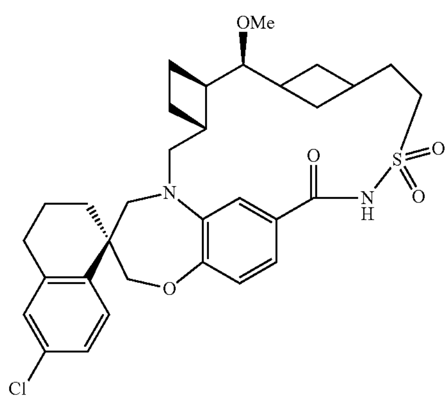 [SMILES: CO[C@H]1C2CC(CCS(=O)(=O)NC(=O)c3ccc4c(c3)N(C[C@@H]3CC[C@H]31)C[C@@]1(CCCc3cc(Cl)ccc31)CO4)C2] | 10.0 | 460 | 400 |
| 3 | 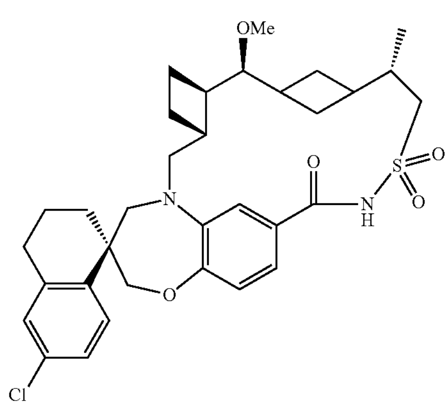 [SMILES: CO[C@H]1C2CC(C2)[C@H](C)CS(=O)(=O)NC(=O)c2ccc3c(c2)N(C[C@@H]2CC[C@H]21)C[C@@]1(CCCc2cc(Cl)ccc21)CO3] | 8.0 | 5446 | 3000 |

TABLE 2-continued

| Cpd. No. | Structure | Mcl-1 (FP, nM) | OPM-2 (5% FBS, nM) | H929 (5% FBS, nM) |
|---|---|---|---|---|
| 4 (Isomer 1) | 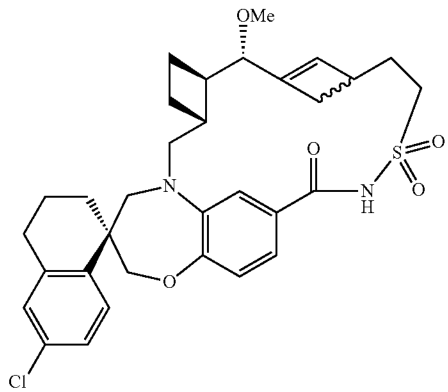 [SMILES: CO[C@@H]1C2=CC(CCS(=O)(=O)NC(=O)c3ccc4c(c3)N(C[C@@H]3CC[C@H]31)C[C@@]1(CCCc3cc(Cl)ccc31)CO4)C2] | 8.3 | 5719 | 4200 |
| 4 (Isomer 2) | | 12 | 2116 | 1600 |
| 5 (Isomer 1) | 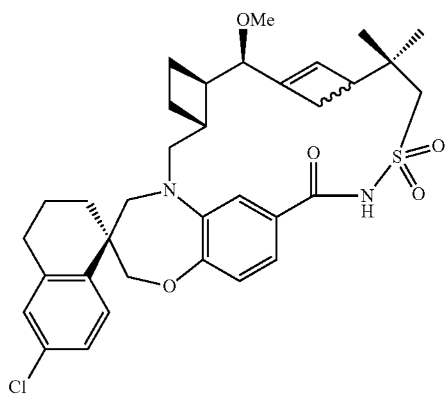 | 4.8 | 411 | 120 |
| 5 (Isomer 2) | | 8.3 | 5207 | 1600 |
| 6 (Isomer 1) | 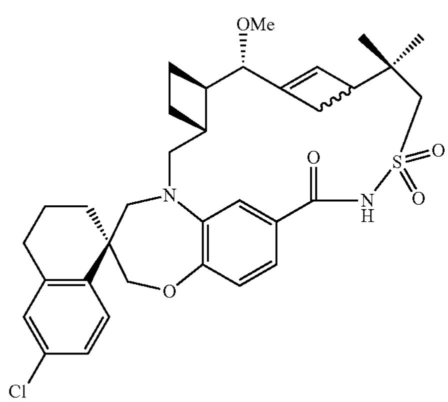 | 5.2 | 1305 | 870 |
| 6 (Isomer 2) | | 6.3 | 2873 | 3400 |

TABLE 2-continued

| Cpd. No. | Structure | Mcl-1 (FP, nM) | OPM-2 (5% FBS, nM) | H929 (5% FBS, nM) |
|---|---|---|---|---|
| 7 (Isomer 1) | 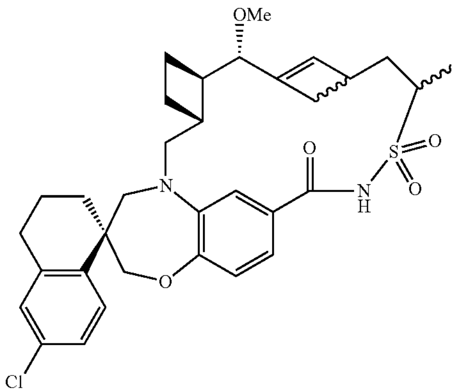 [SMILES: CO[C@@H]1C2=CC(C2)CC(C)S(=O)(=O)NC(=O)c2ccc3c(c2)N(C[C@@H]2CC[C@H]21)C[C@@]1(CCCc2cc(Cl)ccc21)CO3] | 4.2 | 1117 | 600 |
| 7 (Isomer 2) | | 4.2 | 2963 | 1900 |
| 7 (mixture) | | 5.1 | 5577 | 2300 |
| 9 (Isomer 1) | 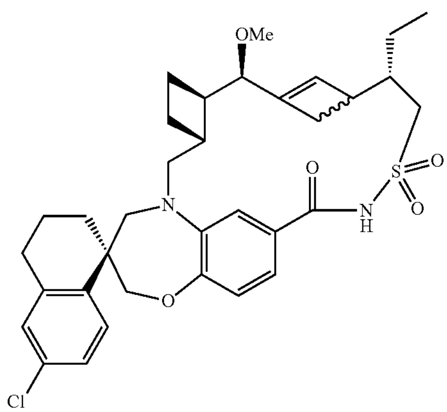 [SMILES: CC[C@@H]1CS(=O)(=O)NC(=O)c2ccc3c(c2)N(C[C@@H]2CC[C@H]2[C@@H](OC)C2=CC1C2)C[C@@]1(CCCc2cc(Cl)ccc21)CO3] | 4.4 | 1167 | 680 |
| 9 (Isomer 2) | | 3.9 | 260 | 210 |
| 10 (Isomer 1) | 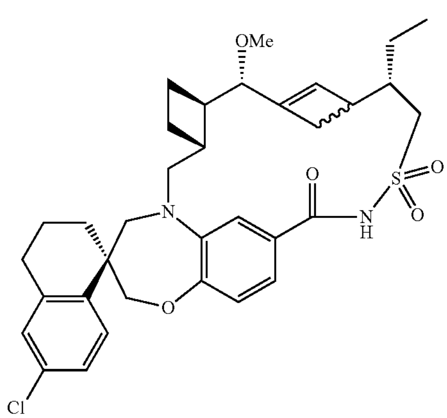 [SMILES: CC[C@@H]1CS(=O)(=O)NC(=O)c2ccc3c(c2)N(C[C@@H]2CC[C@H]2[C@H](OC)C2=CC1C2)C[C@@]1(CCCc2cc(Cl)ccc21)CO3] | 4.9 | 2497 | 1700 |
| 10 (Isomer 2) | | 4.9 | 1134 | 780 |

TABLE 2-continued

| Cpd. No. | Structure | Mcl-1 (FP, nM) | OPM-2 (5% FBS, nM) | H929 (5% FBS, nM) |
|---|---|---|---|---|
| 11 (Isomer 1) | 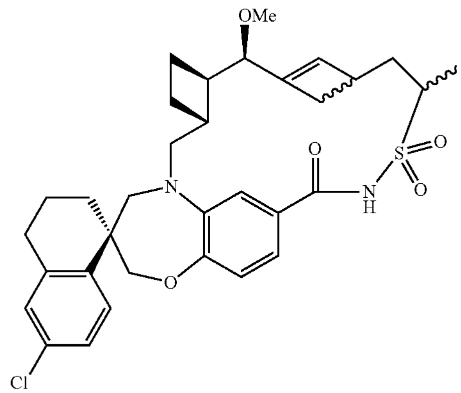 [SMILES: CO[C@H]1C2=CC(C2)CC(C)S(=O)(=O)NC(=O)c2ccc3c(c2)N(C[C@@H]2CC[C@H]21)C[C@@]1(CCCc2cc(Cl)ccc21)CO3] | 6.5 | 87 | 86 |
| 11 (Isomer 2) | | 6.0 | 3859 | 2239 |
| 11 (mixture) | | 5.5 | 967 | 270 |
| 11 (Isomer 4) | | | | |
| 12 (Isomer 1) | 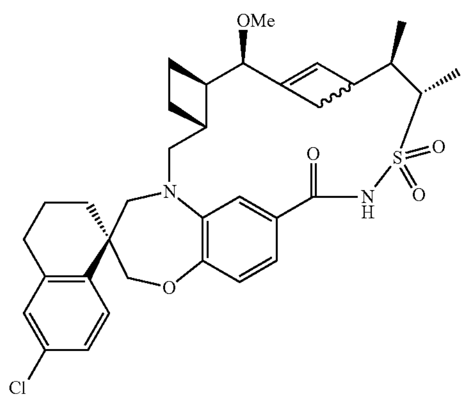 [SMILES: CO[C@H]1C2=CC(C2)[C@@H](C)[C@H](C)S(=O)(=O)NC(=O)c2ccc3c(c2)N(C[C@@H]2CC[C@H]21)C[C@@]1(CCCc2cc(Cl)ccc21)CO3] | 4.8 | 17220 | >10000 |
| 12 (Isomer 2) | | 15 | 12330 | 4600 |
| 13 (mixture) | 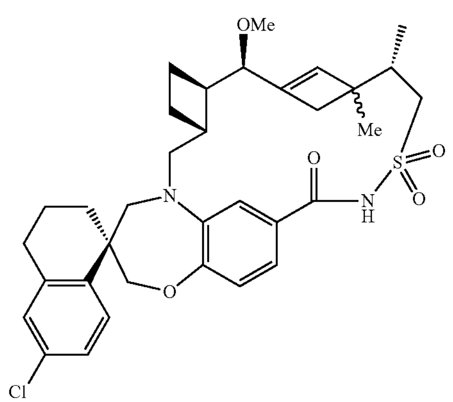 [SMILES: CO[C@H]1C2=CC(C)(C2)[C@H](C)CS(=O)(=O)NC(=O)c2ccc3c(c2)N(C[C@@H]2CC[C@H]21)C[C@@]1(CCCc2cc(Cl)ccc21)CO3] | 21 | 348 | 089 |

TABLE 2-continued

| Cpd. No. | Structure | Mcl-1 (FP, nM) | OPM-2 (5% FBS, nM) | H929 (5% FBS, nM) |
|---|---|---|---|---|
| 14 (Isomer 1) | 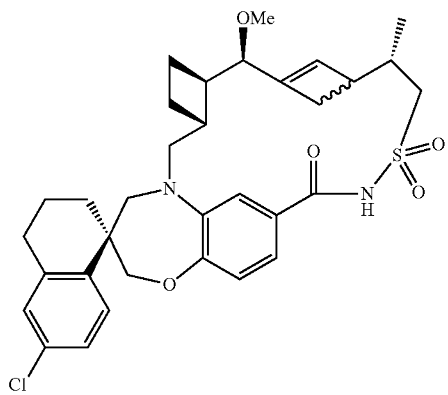 [SMILES: CO[C@H]1C2=CC(C2)[C@H](C)CS(=O)(=O)NC(=O)c2ccc3c(c2)N(C[C@@H]2CC[C@H]21)C[C@@]1(CCCc2cc(Cl)ccc21)CO3] | 4.7 | 208 | 26 |
| 14 (Isomer 2) | | 11 | 1313 | 150 |
| 15 (Isomer 1) | 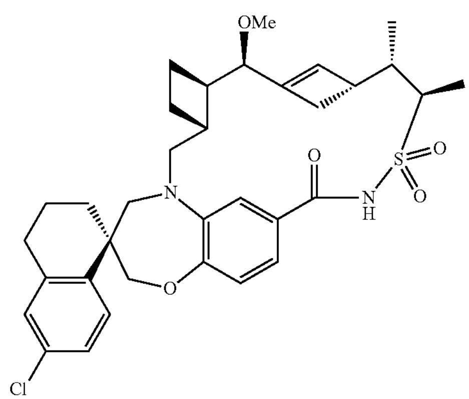 [SMILES: CO[C@H]1C2=C[C@@H](C2)[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | 9.7 | 84 | 18 |
| 15 (Isomer 2) | 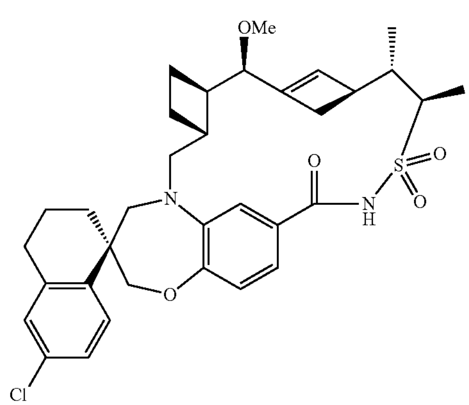 [SMILES: CO[C@H]1C2=C[C@H](C2)[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | 6.5 | 1002 | 230 |

TABLE 2-continued

| Cpd. No. | Structure | Mcl-1 (FP, nM) | OPM-2 (5% FBS, nM) | H929 (5% FBS, nM) |
|---|---|---|---|---|
| 16 (mixture) | 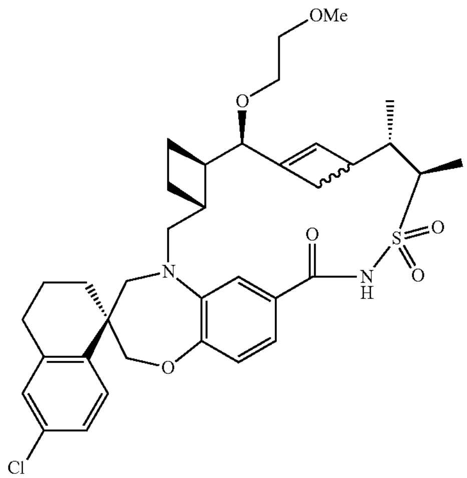 [SMILES: COCCO[C@H]1C2=CC(C2)[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | 9.0 | 136 | 37 |
| 17 (Isomer 1) | 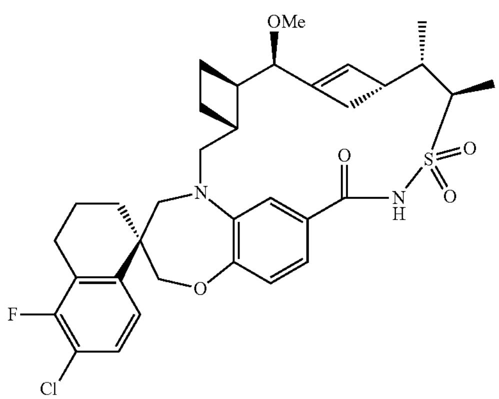 | 8.1 | 62 | 16 |
| 17 (Isomer 2) | 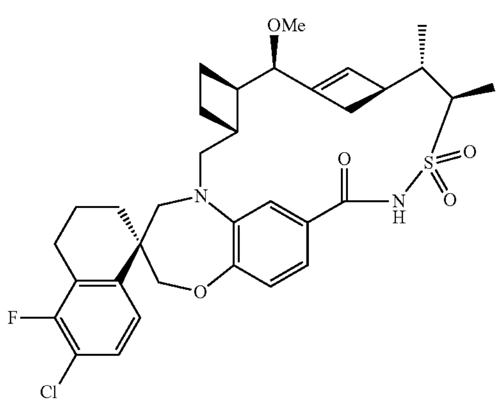 [SMILES: CO[C@H]1C2=C[C@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 12 | 601 | 310 |

TABLE 2-continued

| Cpd. No. | Structure | Mcl-1 (FP, nM) | OPM-2 (5% FBS, nM) | H929 (5% FBS, nM) |
|---|---|---|---|---|
| 18 (Isomer 1) | 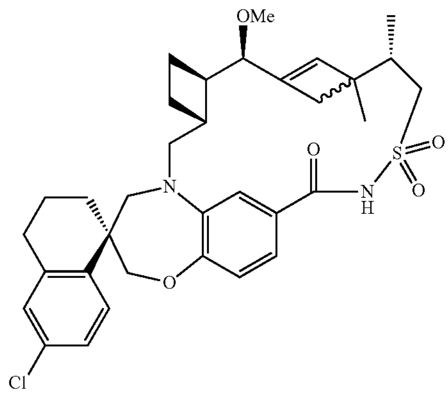 [SMILES: CO[C@H]1C2=CC(C)(C2)[C@H](C)CS(=O)(=O)NC(=O)c2ccc3c(c2)N(C[C@@H]2CC[C@H]21)C[C@@]1(CCCc2cc(Cl)ccc21)CO3] | 4.2 | 25 | 37 |
| 18 (Isomer 2) | | 4.9 | 1209 | 440 |
| 19 | 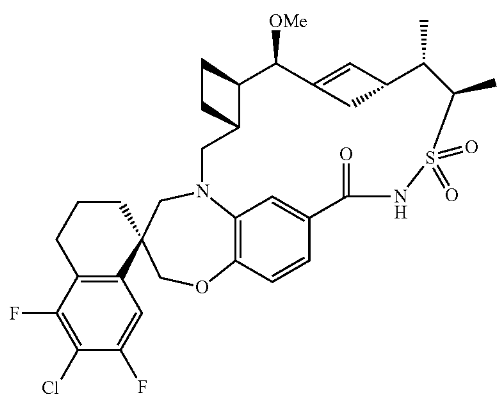 [SMILES: CO[C@H]1C2=C[C@@H](C2)[C@H](C)[C@@H](C)S(=O)(=O)NC(=O)c2ccc3c(c2)N(C[C@@H]2CC[C@H]21)C[C@@]1(CCCc2c1cc(F)c(Cl)c2F)CO3] | 19 | 802 | 670 |
| 20 (isomer 1) | 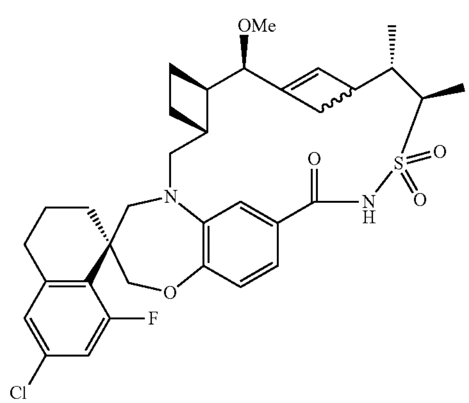 [SMILES: CO[C@H]1C2=CC(C2)[C@H](C)[C@@H](C)S(=O)(=O)NC(=O)c2ccc3c(c2)N(C[C@@H]2CC[C@H]21)C[C@@]1(CCCc2cc(Cl)cc(F)c21)CO3] | 12 | 2690 | 2000 |

TABLE 2-continued

| Cpd. No. | Structure | Mcl-1 (FP, nM) | OPM-2 (5% FBS, nM) | H929 (5% FBS, nM) |
| --- | --- | --- | --- | --- |
| 21 (isomer 1) | 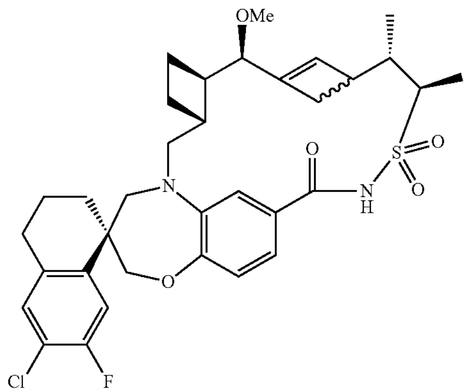 [SMILES: CO[C@H]1C2=CC(C2)[C@H](C)[C@@H](C)S(=O)(=O)NC(=O)c2ccc3c(c2)N(C[C@@H]2CC[C@H]21)C[C@@]1(CCCc2cc(Cl)c(F)cc21)CO3] | 6.6 | 1122 | 1000 |
| 22 (isomer 1) | 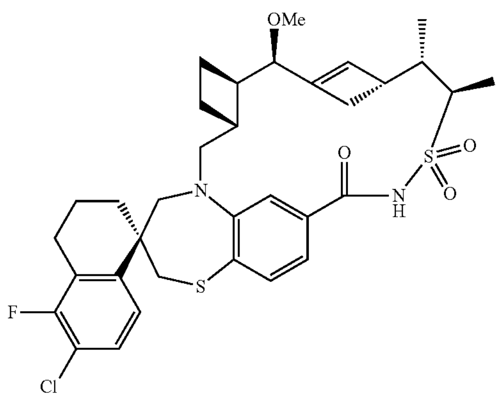 [SMILES: CO[C@H]1C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CS3] | 13 | 567 | 700 |
| 22 (isomer 2) | 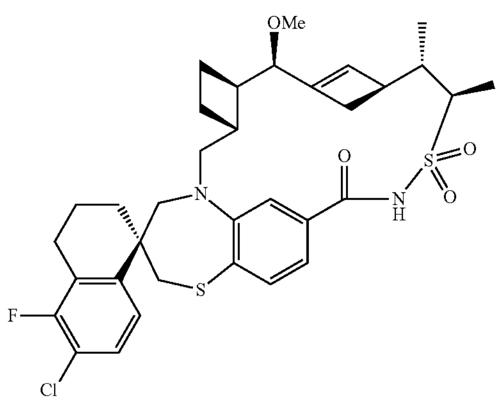 [SMILES: CO[C@H]1C2=C[C@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CS3] | | | |

TABLE 2-continued

| Cpd. No. | Structure | Mcl-1 (FP, nM) | OPM-2 (5% FBS, nM) | H929 (5% FBS, nM) |
| --- | --- | --- | --- | --- |
| 23 (isomer 1) | 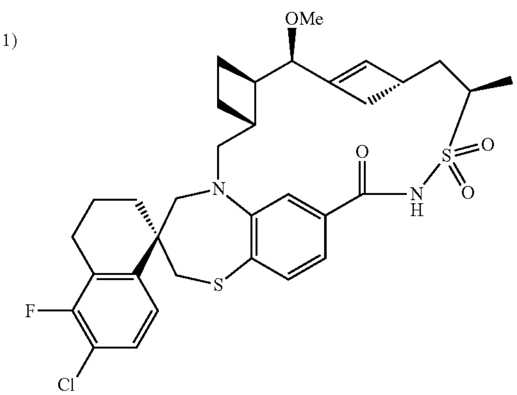 | | | |
| 23 (isomer 2) | 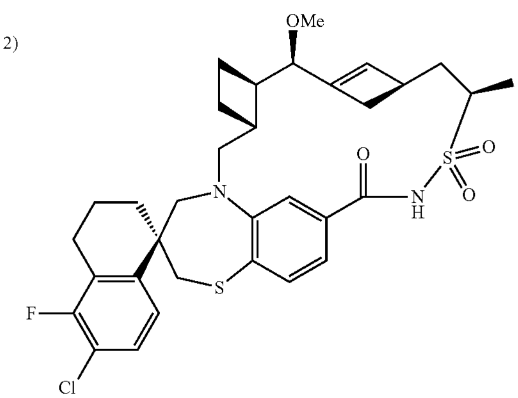 | | | |
| 24 (isomer 1) | 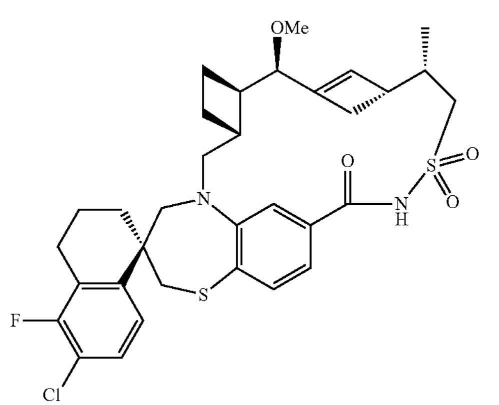 [SMILES: CO[C@H]1C2=C[C@@H](C2)[C@H](C)CS(=O)(=O)NC(=O)c2ccc3c(c2)N(C[C@@H]2CC[C@H]21)C[C@@]1(CCCc2c1ccc(Cl)c2F)CS3] | 6.4 | 670 | 660 |

TABLE 2-continued

| Cpd. No. | Structure | Mcl-1 (FP, nM) | OPM-2 (5% FBS, nM) | H929 (5% FBS, nM) |
|---|---|---|---|---|
| 24 (isomer 2) | 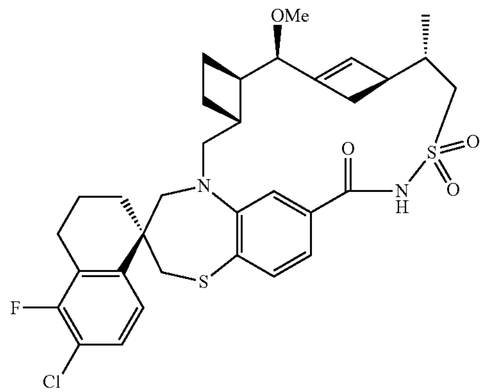 [SMILES: CO[C@H]1C2=C[C@H](C2)[C@H](C)CS(=O)(=O)NC(=O)c2ccc3c(c2)N(C[C@@H]2CC[C@H]21)C[C@@]1(CCCc2c1ccc(Cl)c2F)CS3] | 4.8 | 3300 | 4300 |
| 25 | 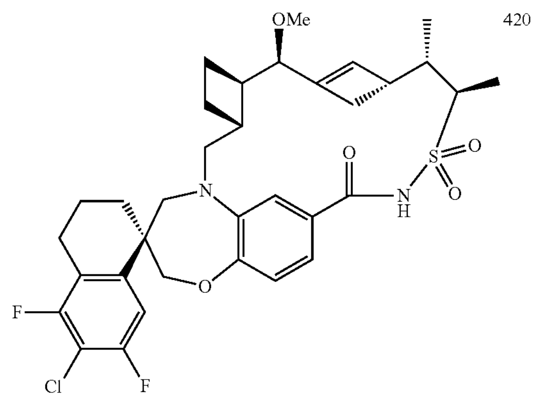 | 420 | 2500 | 3400 |
| AMG-176 | 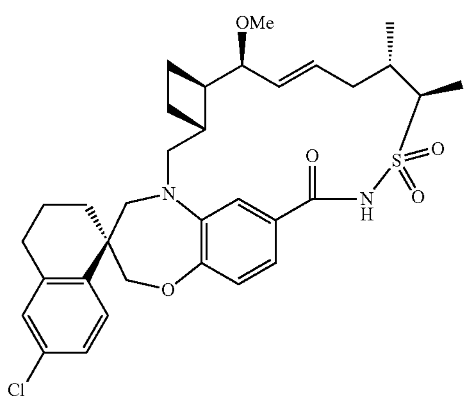 [SMILES: CO[C@H]1/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3] | 8.6 | 335 | 138 |

In another embodiment, Compounds of the Disclosure are compounds of Formula I-A selected from group consisting of the compounds of Table 2-A, or a pharmaceutically acceptable salt or solvate thereof.

TABLE 2-A

| Cpd. No. | Structure | Mcl-1 (FP, nM) | OPM-2 (5% FBS, nM) | H929 (5% FBS, nM) |
| --- | --- | --- | --- | --- |
| 26 (isomer 1) | 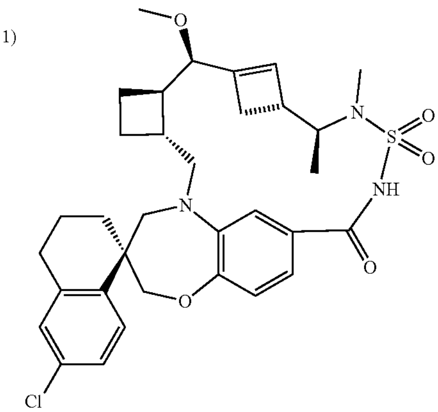 | 14 | 412 | 160 |
| 26 (isomer 2) | 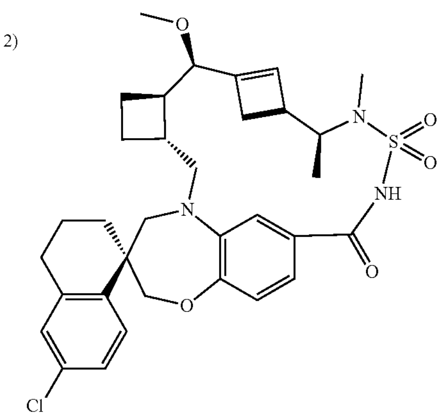 | 3.3 | 2241 | 2260 |
| 27 (isomer 1) | 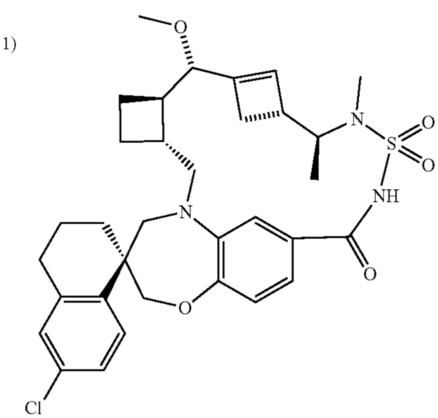 | 13 | 1441 | 1600 |

TABLE 2-A-continued

| Cpd. No. | Structure | Mcl-1 (FP, nM) | OPM-2 (5% FBS, nM) | H929 (5% FBS, nM) |
|---|---|---|---|---|
| 27 (isomer 2) | 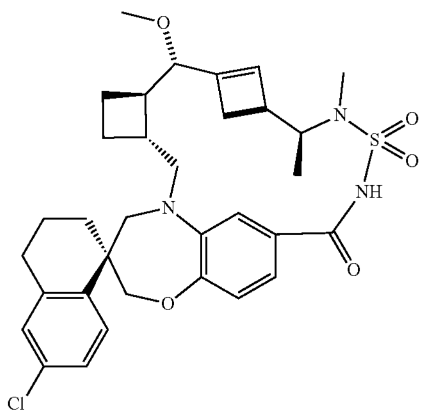 | 3.4 | 3607 | 5000 |
| 28 | 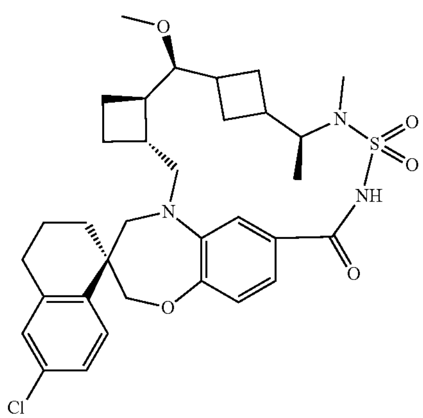 [SMILES: CO[C@H]1C2CC(C2)[C@H](C)N(C)S(=O)(=O)NC(=O)c2ccc3c(c2)N(C[C@@H]2CC[C@H]21)C[C@@]1(CCCc2cc(Cl)ccc21)CO3] | 14 | 1505 | 1300 |
| 29 | 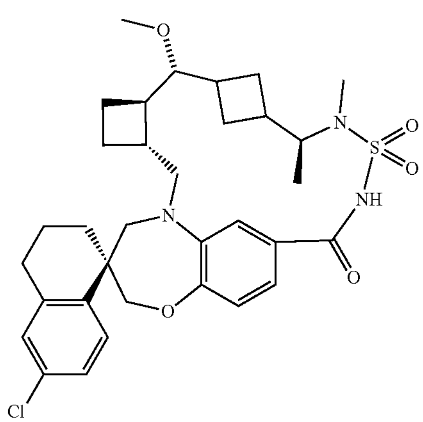 [SMILES: CO[C@@H]1C2CC(C2)[C@H](C)N(C)S(=O)(=O)NC(=O)c2ccc3c(c2)N(C[C@@H]2CC[C@H]21)C[C@@]1(CCCc2cc(Cl)ccc21)CO3] | 16 | 5208 | 5500 |

TABLE 2-A-continued

| Cpd. No. | Structure | Mcl-1 (FP, nM) | OPM-2 (5% FBS, nM) | H929 (5% FBS, nM) |
|---|---|---|---|---|
| 30 (isomer 1) | 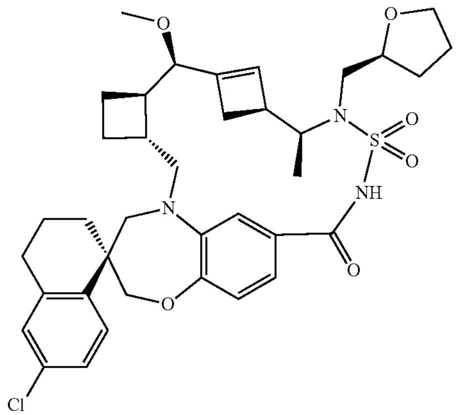 [SMILES: CO[C@H]1C2=C[C@H](C2)[C@H](C)N(C[C@@H]2CCCO2)S(=O)(=O)NC(=O)c2ccc3c(c2)N(C[C@@H]2CC[C@H]21)C[C@@]1(CCCc2cc(Cl)ccc21)CO3] | 6.2 | 2312 | 2900 |
| 30 (isomer 2) | 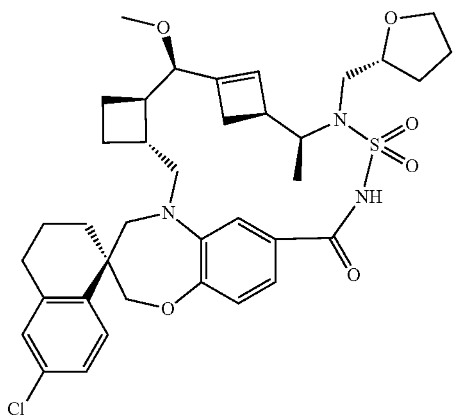 [SMILES: CO[C@H]1C2=C[C@H](C2)[C@H](C)N(C[C@H]2CCCO2)S(=O)(=O)NC(=O)c2ccc3c(c2)N(C[C@@H]2CC[C@H]21)C[C@@]1(CCCc2cc(Cl)ccc21)CO3] | 5.1 | 4768 | 4700 |
| 30 (isomer 3) | 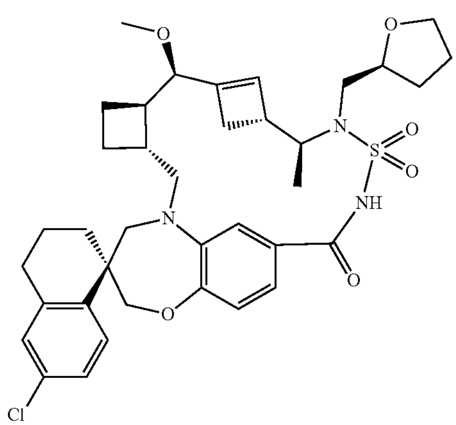 [SMILES: CO[C@H]1C2=C[C@@H](C2)[C@H](C)N(C[C@@H]2CCCO2)S(=O)(=O)NC(=O)c2ccc3c(c2)N(C[C@@H]2CC[C@H]21)C[C@@]1(CCCc2cc(Cl)ccc21)CO3] | 14 | 6097 | 5200 |

TABLE 2-A-continued
| Cpd. No. | Structure | Mcl-1 (FP, nM) | OPM-2 (5% FBS, nM) | H929 (5% FBS, nM) |
|---|---|---|---|---|
| 30 (isomer 4) | 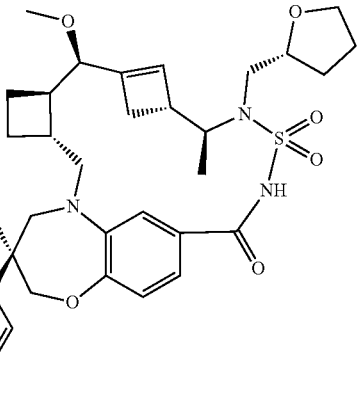 | 21 | >10000 | >10000 |
| 31 | 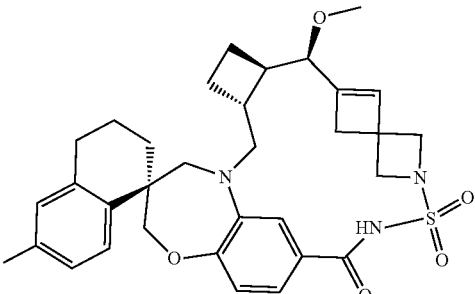 | 11 | 9284 | 9700 |
| 32 | 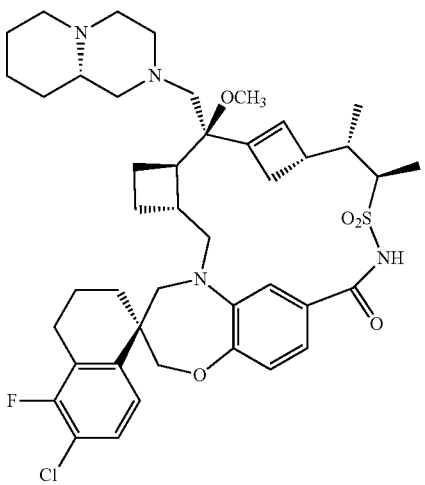 [SMILES: CO[C@@]1(CN2CCN3CCCC[C@H]3C2)C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 13 | 29 | 10 |

TABLE 2-A-continued

| Cpd. No. | Structure | Mcl-1 (FP, nM) | OPM-2 (5% FBS, nM) | H929 (5% FBS, nM) |
|---|---|---|---|---|
| 33 | 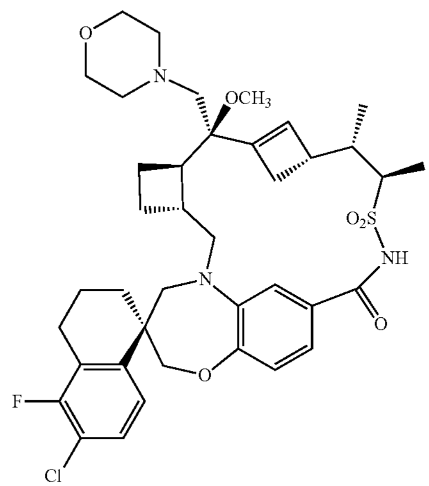 [SMILES: CO[C@@]1(CN2CCOCC2)C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 13 | 52 | 36 |
| 34 | 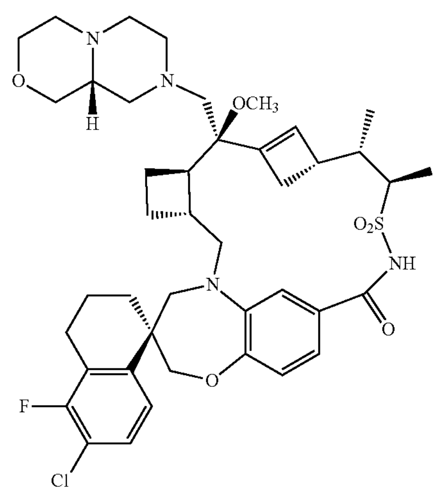 [SMILES: CO[C@@]1(CN2CCN3CCOC[C@H]3C2)C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 9.7 | 35 | 16 |
| 35 | 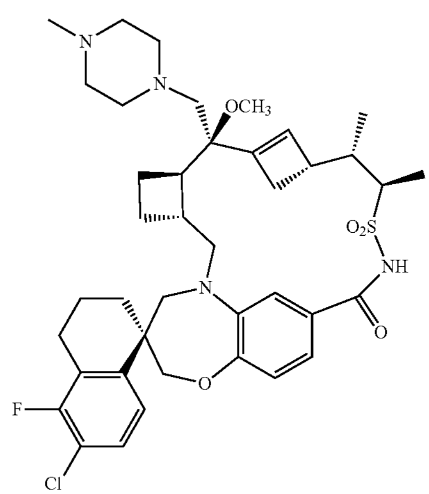 [SMILES: CO[C@@]1(CN2CCN(C)CC2)C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 14 | 32 | 2.4 |

TABLE 2-A-continued

| Cpd. No. | Structure | Mcl-1 (FP, nM) | OPM-2 (5% FBS, nM) | H929 (5% FBS, nM) |
|---|---|---|---|---|
| 36 | 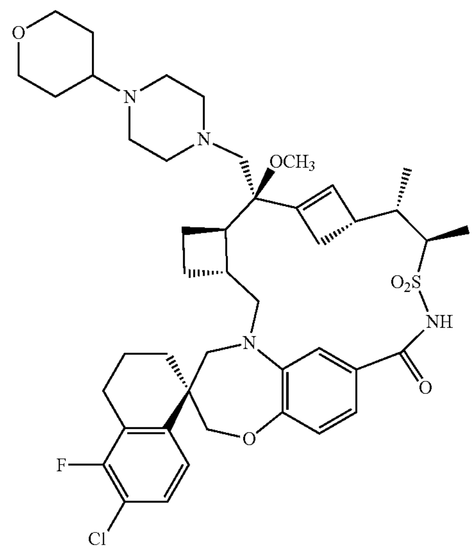 | 13 | 35 | 4.4 |
| 37 | 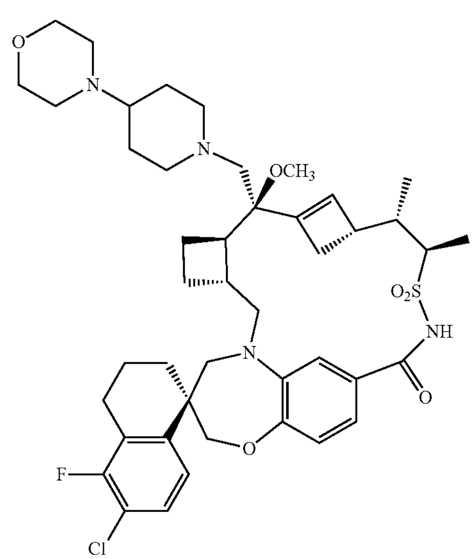 [SMILES: CO[C@@]1(CN2CCN(C3CCOCC3)CC2)C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 17 | 63 | 12 |

TABLE 2-A-continued

| Cpd. No. | Structure | Mcl-1 (FP, nM) | OPM-2 (5% FBS, nM) | H929 (5% FBS, nM) |
|---|---|---|---|---|
| 38 | 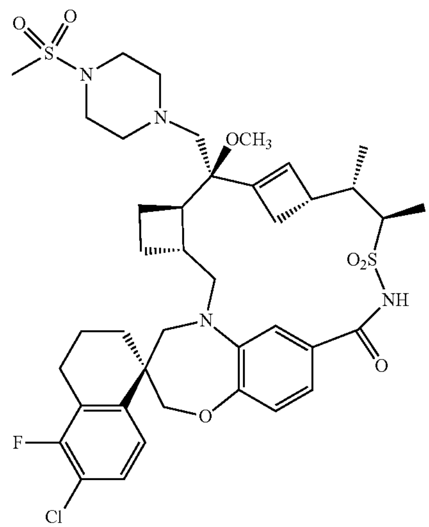 | 15 | 30 | 50 |
| 39 | 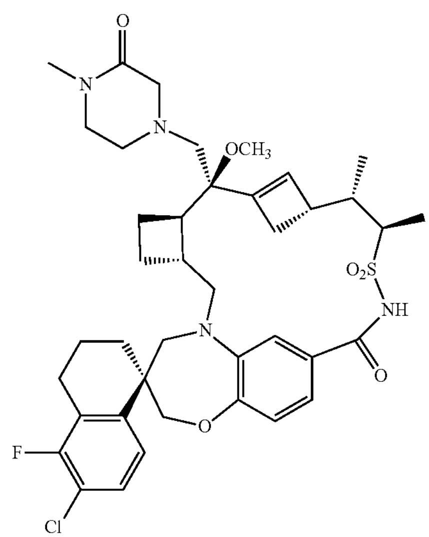 [SMILES: CO[C@@]1(CN2CCN(C)C(=O)C2)C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 14 | 62 | 7.7 |
| 40 | 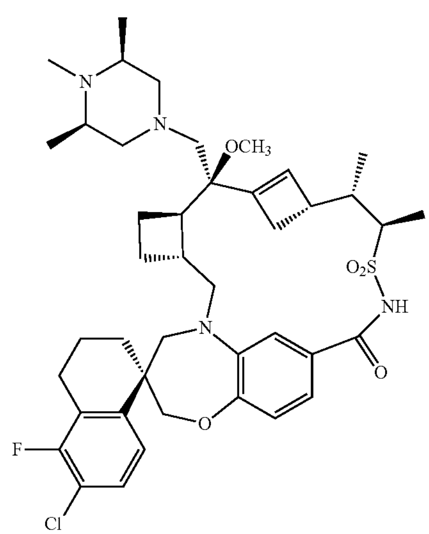 [SMILES: CO[C@@]1(CN2C[C@@H](C)N(C)[C@@H](C)C2)C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 17 | 55 | 2.6 |

TABLE 2-A-continued

| Cpd. No. | Structure | Mcl-1 (FP, nM) | OPM-2 (5% FBS, nM) | H929 (5% FBS, nM) |
|---|---|---|---|---|
| 41 | 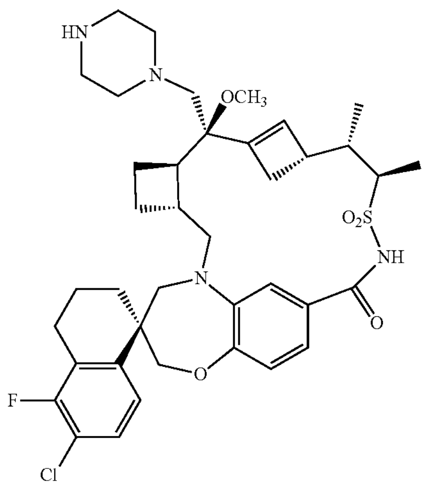 [SMILES: CO[C@@]1(CN2CCNCC2)C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 26 | 156 | 190 |
| 42 | 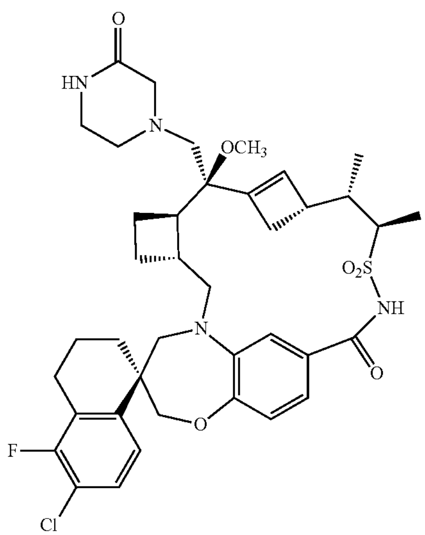 [SMILES: CO[C@@]1(CN2CCNC(=O)C2)C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 13 | 66 | 51 |
| 43 | 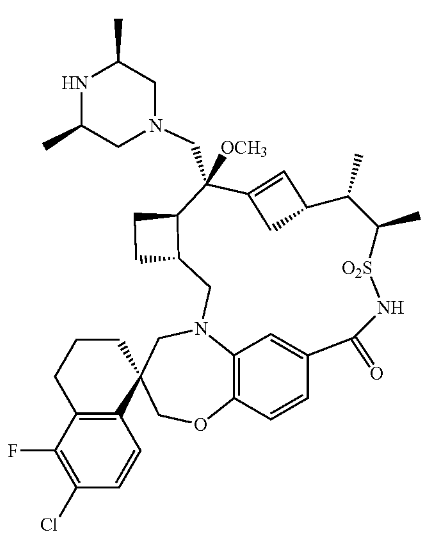 [SMILES: CO[C@@]1(CN2C[C@@H](C)N[C@@H](C)C2)C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 15 | 47 | 35 |

TABLE 2-A-continued

| Cpd. No. | Structure | Mcl-1 (FP, nM) | OPM-2 (5% FBS, nM) | H929 (5% FBS, nM) |
|---|---|---|---|---|
| 44 | 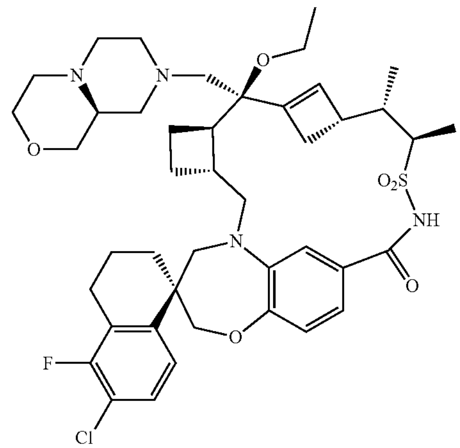 [SMILES: CCO[C@@]1(CN2CCN3CCOC[C@@H]3C2)C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 11 | 48 | 17 |
| 45 | 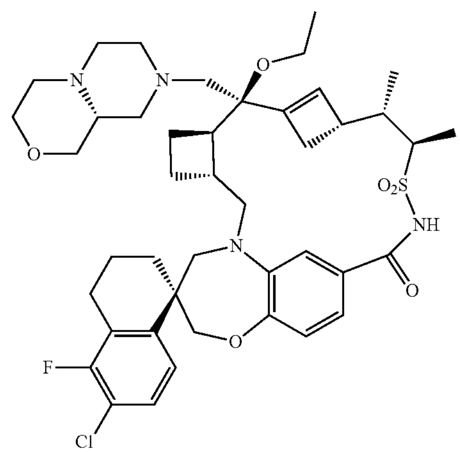 [SMILES: CCO[C@@]1(CN2CCN3CCOC[C@H]3C2)C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 15 | 105 | 46 |
| 46 | 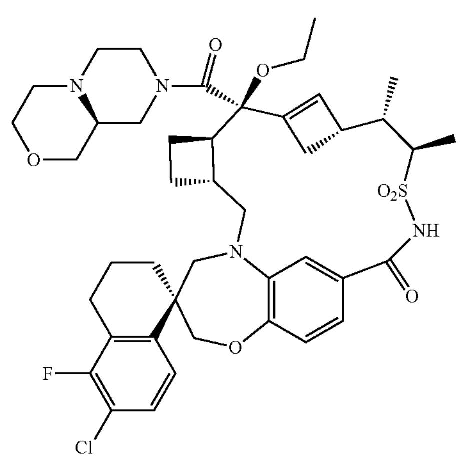 [SMILES: CCO[C@@]1(C(=O)N2CCN3CCOC[C@@H]3C2)C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 13 | 325 | 200 |

TABLE 2-A-continued

| Cpd. No. | Structure | Mcl-1 (FP, nM) | OPM-2 (5% FBS, nM) | H929 (5% FBS, nM) |
|---|---|---|---|---|
| 47 | 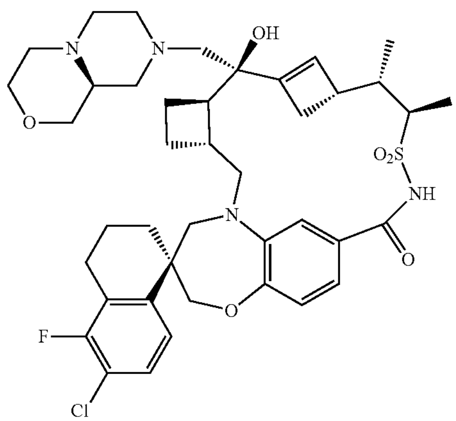 [SMILES: C[C@@H]1[C@@H](C)S(=O)(=O)NC(=O)c2ccc3c(c2)N(C[C@@H]2CC[C@H]2[C@](O)(CN2CCN4CCOC[C@@H]4C2)C2=C[C@H]1C2)C[C@@]1(CCCc2c1ccc(Cl)c2F)CO3] | 13 | 32 | 5.8 |
| 48 | 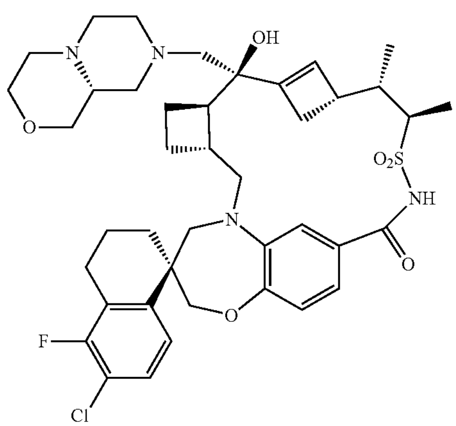 [SMILES: C[C@@H]1[C@@H](C)S(=O)(=O)NC(=O)c2ccc3c(c2)N(C[C@@H]2CC[C@H]2[C@](O)(CN2CCN4CCOC[C@H]4C2)C2=C[C@H]1C2)C[C@@]1(CCCc2c1ccc(Cl)c2F)CO3] | 18 | 69 | 28 |
| 49 | 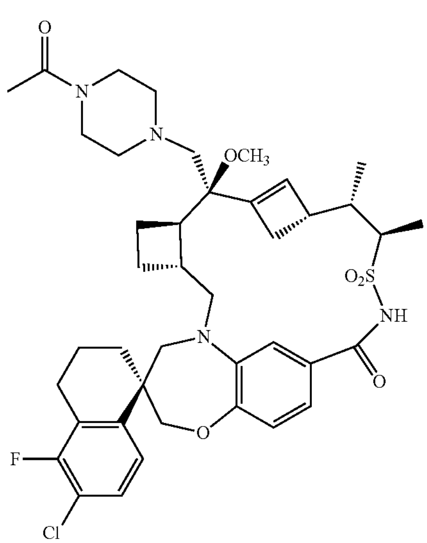 [SMILES: CO[C@@]1(CN2CCN(C(C)=O)CC2)C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 11 | 186 | 12 |

TABLE 2-A-continued

| Cpd. No. | Structure | Mcl-1 (FP, nM) | OPM-2 (5% FBS, nM) | H929 (5% FBS, nM) |
|---|---|---|---|---|
| 50 | 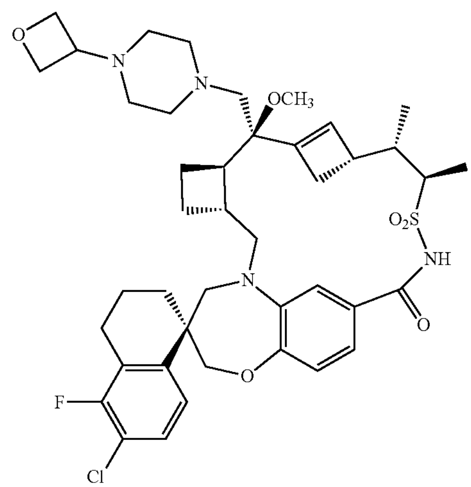 [SMILES: CO[C@@]1(CN2CCN(C3COC3)CC2)C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 11 | 28 | 11 |
| 51 | 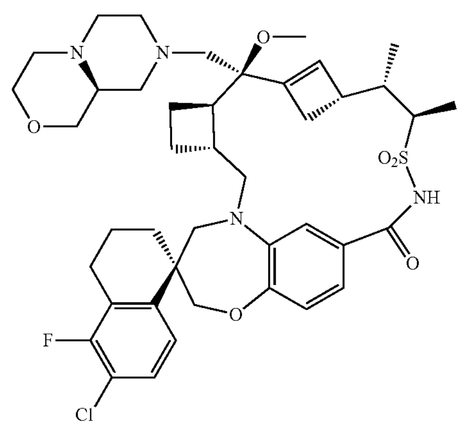 [SMILES: CO[C@@]1(CN2CCN3CCOC[C@@H]3C2)C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 7.4 | 14 | 6 |
| 52 | 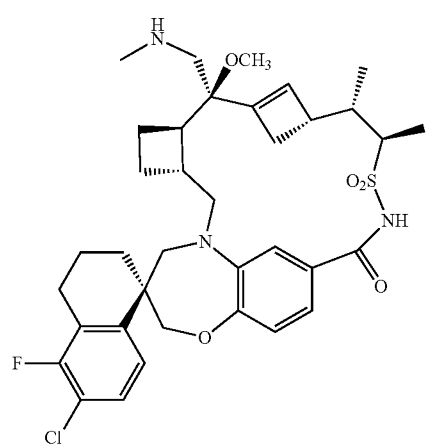 [SMILES: CNC[C@]1(OC)C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 7 | 23 | 19 |

TABLE 2-A-continued

| Cpd. No. | Structure | Mcl-1 (FP, nM) | OPM-2 (5% FBS, nM) | H929 (5% FBS, nM) |
|---|---|---|---|---|
| 53 | 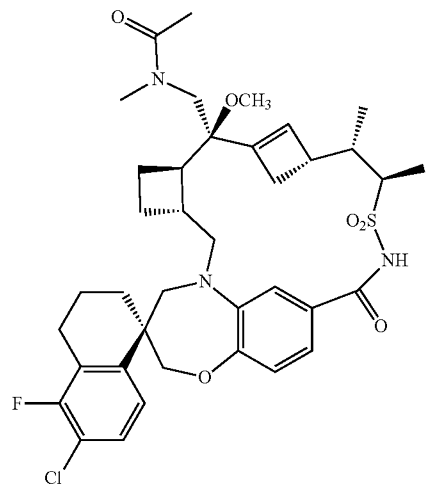 [SMILES: CO[C@@]1(CN(C)C(C)=O)C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 5.7 | 57 | 49 |
| 54 | 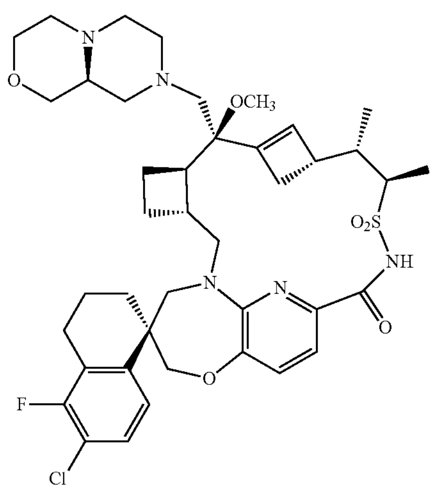 [SMILES: CO[C@@]1(CN2CCN3CCOC[C@@H]3C2)C2=C[C@@H](C2)[C@H](C)[C@@H](C)S(=O)(=O)NC(=O)c2ccc3c(n2)N(C[C@@H]2CC[C@H]21)C[C@@]1(CCCc2c1ccc(Cl)c2F)CO3] | 15 | 56 | 4.9 |
| 55 | 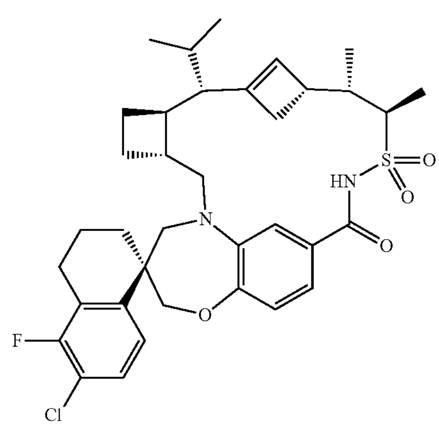 [SMILES: CC(C)[C@@H]1C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 13 | 1014 | 1000 |

TABLE 2-A-continued

| Cpd. No. | Structure | Mcl-1 (FP, nM) | OPM-2 (5% FBS, nM) | H929 (5% FBS, nM) |
| --- | --- | --- | --- | --- |
| 56 | 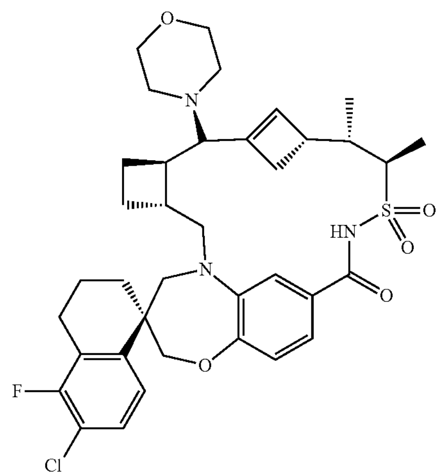 | 7.7 | 65 | 49 |
| 57 | 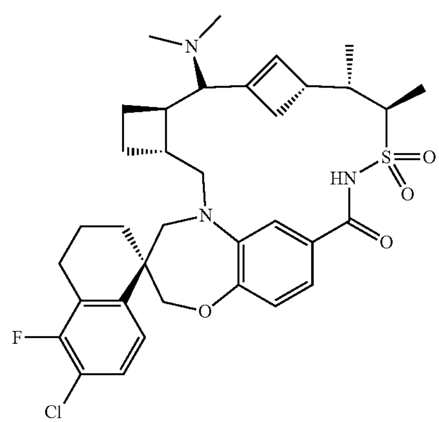 | 13 | 36 | 43 |
| 58 | 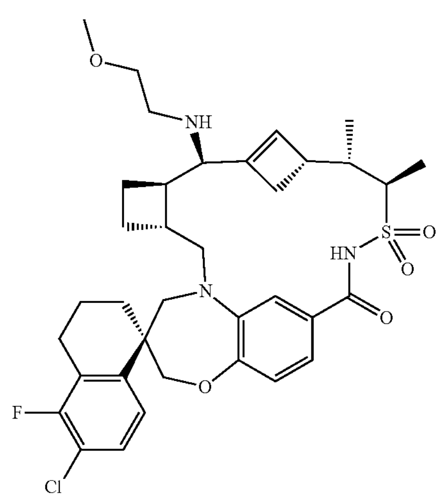 [SMILES: COCCN[C@H]1C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 19 | 57 | 18 |

TABLE 2-A-continued

| Cpd. No. | Structure | Mcl-1 (FP, nM) | OPM-2 (5% FBS, nM) | H929 (5% FBS, nM) |
|---|---|---|---|---|
| 59 | 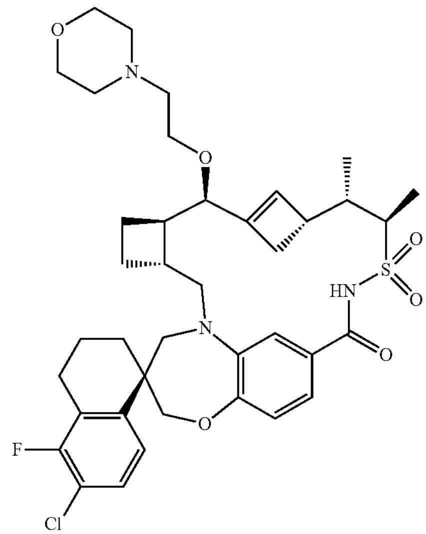 [SMILES: C[C@@H]1[C@@H](C)S(=O)(=O)NC(=O)c2ccc3c(c2)N(C[C@@H]2CC[C@H]2[C@@H](OCCN2CCOCC2)C2=C[C@H]1C2)C[C@@]1(CCCc2c1ccc(Cl)c2F)CO3] | 13 | 37 | 4.1 |
| 60 | 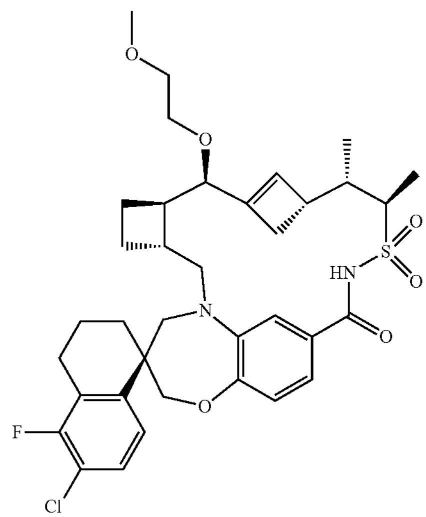 [SMILES: COCCO[C@H]1C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 15 | 66 | 19 |
| 61 | 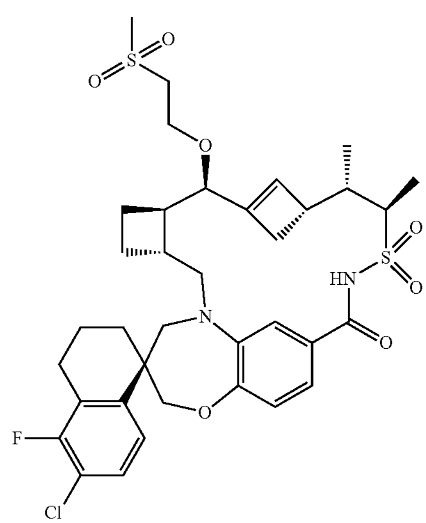 [SMILES: C[C@@H]1[C@@H](C)S(=O)(=O)NC(=O)c2ccc3c(c2)N(C[C@@H]2CC[C@H]2[C@@H](OCCS(C)(=O)=O)C2=C[C@H]1C2)C[C@@]1(CCCc2c1ccc(Cl)c2F)CO3] | 10 | 75 | 28 |

TABLE 2-A-continued
| Cpd. No. | Structure | Mcl-1 (FP, nM) | OPM-2 (5% FBS, nM) | H929 (5% FBS, nM) |
| --- | --- | --- | --- | --- |
| 62 | 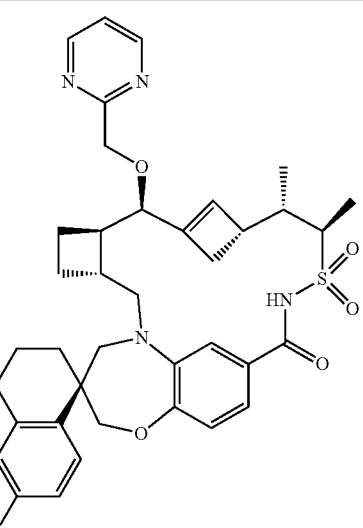 | 8.1 | 59 | 9.3 |
| 63 | 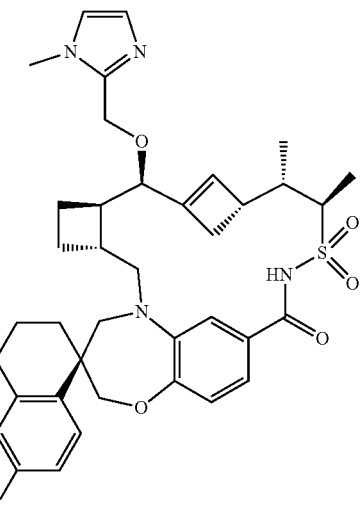 | 13 | 88 | 98 |
| 64 | 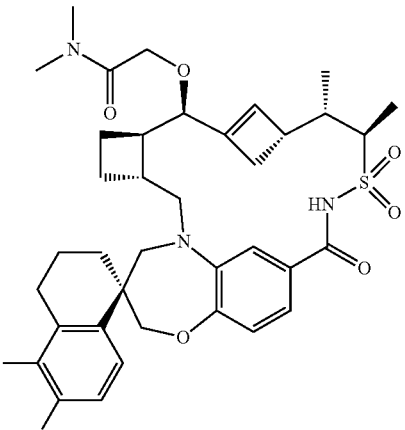 | 14 | 120 | 9.4 |

TABLE 2-A-continued

| Cpd. No. | Structure | Mcl-1 (FP, nM) | OPM-2 (5% FBS, nM) | H929 (5% FBS, nM) |
|---|---|---|---|---|
| 65 | 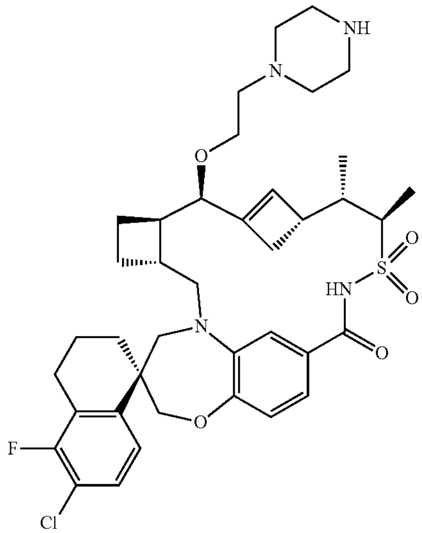 [SMILES: C[C@@H]1[C@@H](C)S(=O)(=O)NC(=O)c2ccc3c(c2)N(C[C@@H]2CC[C@H]2[C@@H](OCCN2CCNCC2)C2=C[C@H]1C2)C[C@@]1(CCCc2c1ccc(Cl)c2F)CO3] | 15 | 247 | 210 |
| 66 | 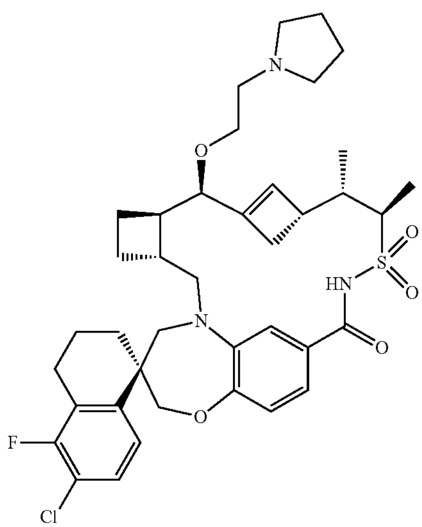 [SMILES: C[C@@H]1[C@@H](C)S(=O)(=O)NC(=O)c2ccc3c(c2)N(C[C@@H]2CC[C@H]2[C@@H](OCCN2CCCC2)C2=C[C@H]1C2)C[C@@]1(CCCc2c1ccc(Cl)c2F)CO3] | 15 | 31 | 7.7 |
| 67 | 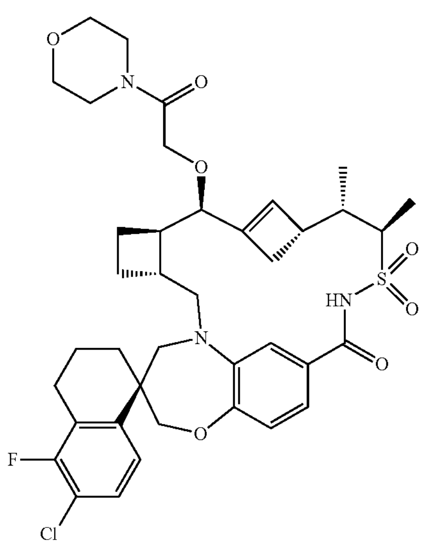 [SMILES: C[C@@H]1[C@@H](C)S(=O)(=O)NC(=O)c2ccc3c(c2)N(C[C@@H]2CC[C@H]2[C@@H](OCC(=O)N2CCOCC2)C2=C[C@H]1C2)C[C@@]1(CCCc2c1ccc(Cl)c2F)CO3] | 15 | 77 | 97 |

TABLE 2-A-continued
| Cpd. No. | Structure | Mcl-1 (FP, nM) | OPM-2 (5% FBS, nM) | H929 (5% FBS, nM) |
|---|---|---|---|---|
| 68 | 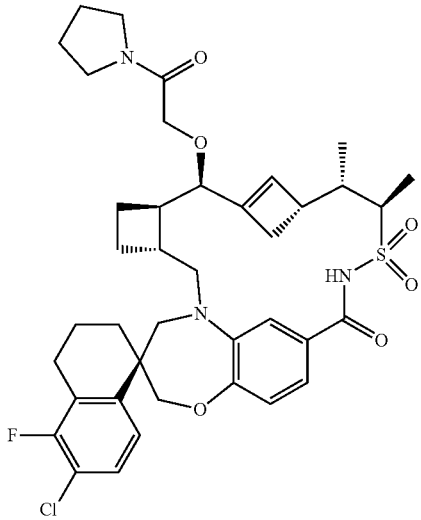 [SMILES: C[C@@H]1[C@@H](C)S(=O)(=O)NC(=O)c2ccc3c(c2)N(C[C@@H]2CC[C@H]2[C@@H](OCC(=O)N2CCCC2)C2=C[C@H]1C2)C[C@@]1(CCCc2c1ccc(Cl)c2F)CO3] | 15 | 47 | 43 |
| 69 | 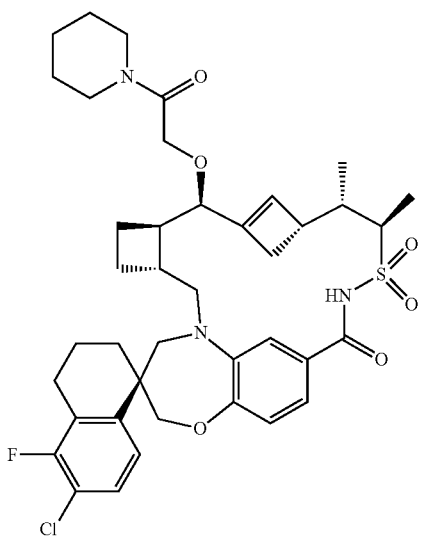 [SMILES: C[C@@H]1[C@@H](C)S(=O)(=O)NC(=O)c2ccc3c(c2)N(C[C@@H]2CC[C@H]2[C@@H](OCC(=O)N2CCCCC2)C2=C[C@H]1C2)C[C@@]1(CCCc2c1ccc(Cl)c2F)CO3] | 14 | 40 | 69 |

TABLE 2-A-continued

| Cpd. No. | Structure | Mcl-1 (FP, nM) | OPM-2 (5% FBS, nM) | H929 (5% FBS, nM) |
|---|---|---|---|---|
| 70 | 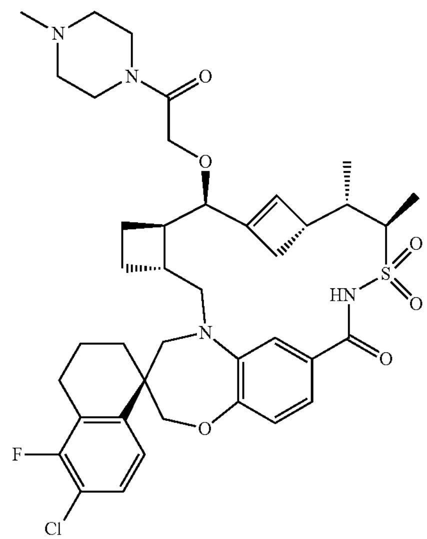 [SMILES: C[C@@H]1[C@@H](C)S(=O)(=O)NC(=O)c2ccc3c(c2)N(C[C@@H]2CC[C@H]2[C@@H](OCC(=O)N2CCN(C)CC2)C2=C[C@H]1C2)C[C@@]1(CCCc2c1ccc(Cl)c2F)CO3] | 14 | 35 | 81 |
| 71 | 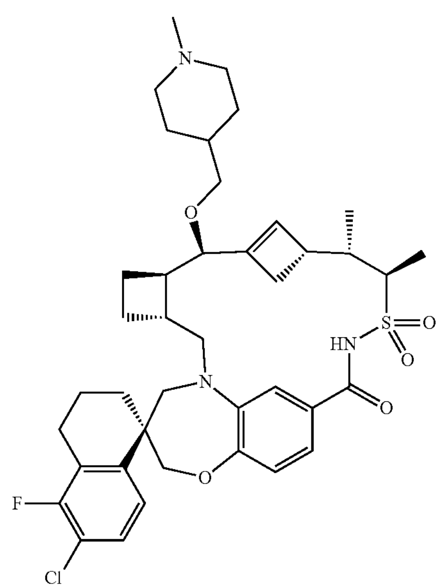 [SMILES: C[C@@H]1[C@@H](C)S(=O)(=O)NC(=O)c2ccc3c(c2)N(C[C@@H]2CC[C@H]2[C@@H](OCC2CCN(C)CC2)C2=C[C@H]1C2)C[C@@]1(CCCc2c1ccc(Cl)c2F)CO3] | 13 | 81 | 6 |

TABLE 2-A-continued
| Cpd. No. | Structure | Mcl-1 (FP, nM) | OPM-2 (5% FBS, nM) | H929 (5% FBS, nM) |
|---|---|---|---|---|
| 72 | 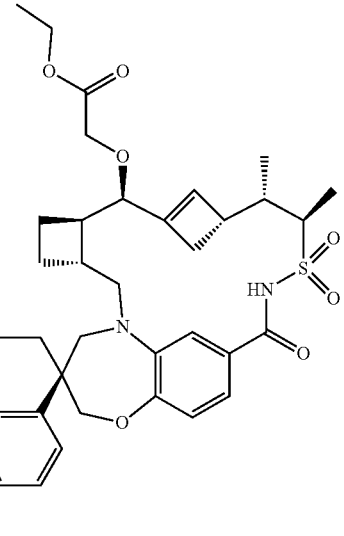 | 14 | 89 | 70 |
| 73 | 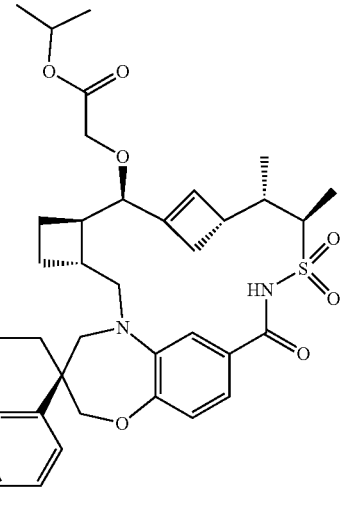 | 19 | 67 | 150 |
| 74 | 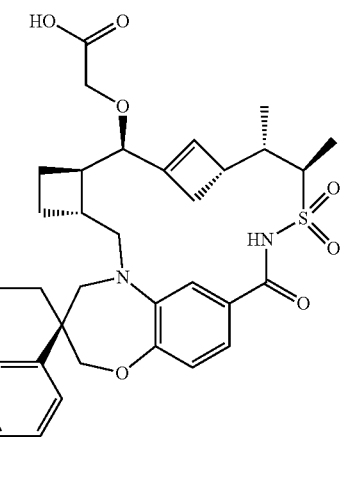 | 20 | 384 | 450 |

TABLE 2-A-continued

| Cpd. No. | Structure | Mcl-1 (FP, nM) | OPM-2 (5% FBS, nM) | H929 (5% FBS, nM) |
|---|---|---|---|---|
| 75 | 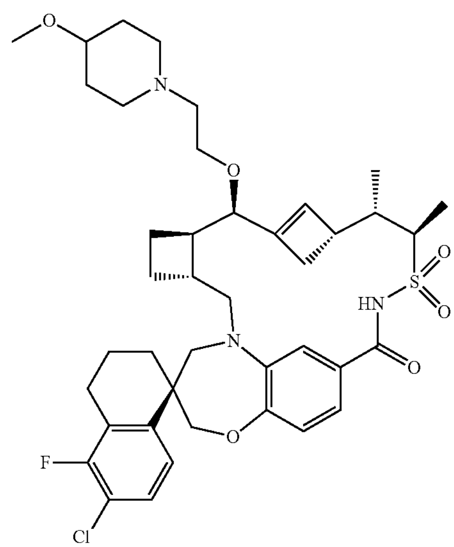 [SMILES: COC1CCN(CCO[C@H]2C3=C[C@@H](C3)[C@H](C)[C@@H](C)S(=O)(=O)NC(=O)c3ccc4c(c3)N(C[C@@H]3CC[C@H]32)C[C@@]2(CCCc3c2ccc(Cl)c3F)CO4)CC1] | 36 | 41 | 51 |
| 76 | 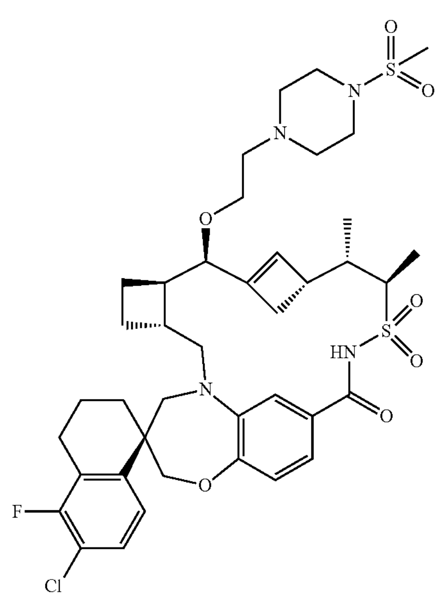 [SMILES: C[C@@H]1[C@@H](C)S(=O)(=O)NC(=O)c2ccc3c(c2)N(C[C@@H]2CC[C@H]2[C@@H](OCCN2CCN(S(C)(=O)=O)CC2)C2=C[C@H]1C2)C[C@@]1(CCCc2c1ccc(Cl)c2F)CO3] | 21 | 206 | 37 |

TABLE 2-A-continued

| Cpd. No. | Structure | Mcl-1 (FP, nM) | OPM-2 (5% FBS, nM) | H929 (5% FBS, nM) |
| --- | --- | --- | --- | --- |
| 77 | 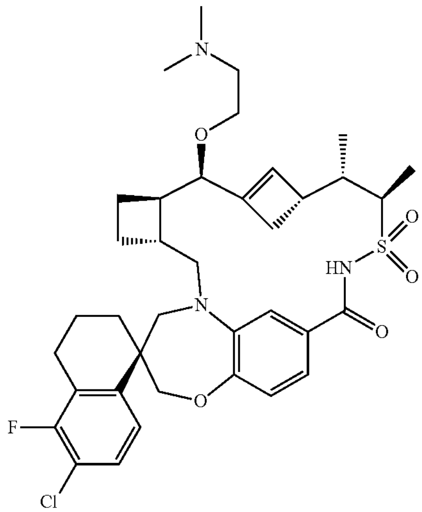 [SMILES: C[C@@H]1[C@@H](C)S(=O)(=O)NC(=O)c2ccc3c(c2)N(C[C@@H]2CC[C@H]2[C@@H](OCCN(C)C)C2=C[C@H]1C2)C[C@@]1(CCCc2c1ccc(Cl)c2F)CO3] | 8.5 | 68 | 5.3 |
| 78 | 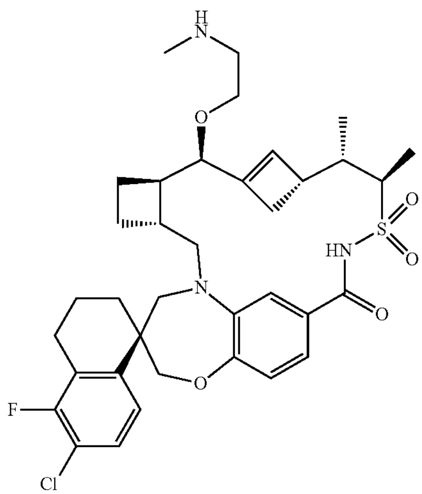 [SMILES: CNCCO[C@H]1C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 16 | 184 | 66 |
| 79 | 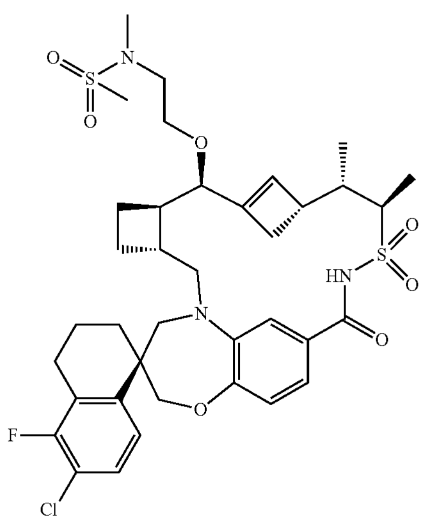 [SMILES: C[C@@H]1[C@@H](C)S(=O)(=O)NC(=O)c2ccc3c(c2)N(C[C@@H]2CC[C@H]2[C@@H](OCCN(C)S(C)(=O)=O)C2=C[C@H]1C2)C[C@@]1(CCCc2c1ccc(Cl)c2F)CO3] | 15 | 53 | 58 |

TABLE 2-A-continued
| Cpd. No. | Structure | Mcl-1 (FP, nM) | OPM-2 (5% FBS, nM) | H929 (5% FBS, nM) |
|---|---|---|---|---|
| 80 | 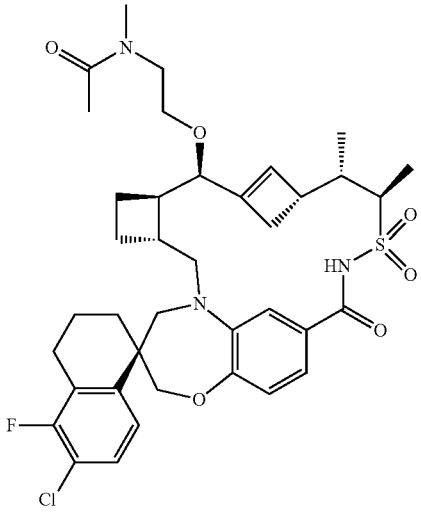 [SMILES: CC(=O)N(C)CCO[C@H]1C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3] | 13 | 158 | 62 |
| 81 | 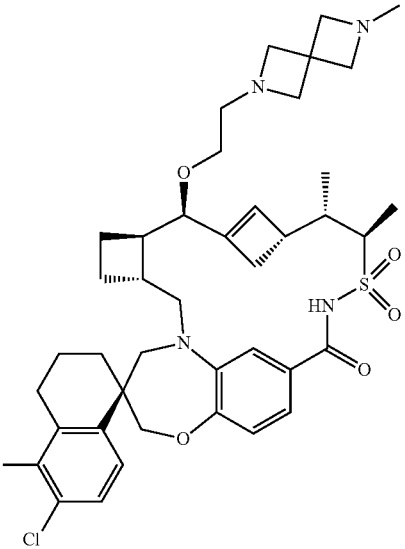 | 17 | 667 | 360 |

TABLE 2-A-continued

| Cpd. No. | Structure | Mcl-1 (FP, nM) | OPM-2 (5% FBS, nM) | H929 (5% FBS, nM) |
|---|---|---|---|---|
| 82 | 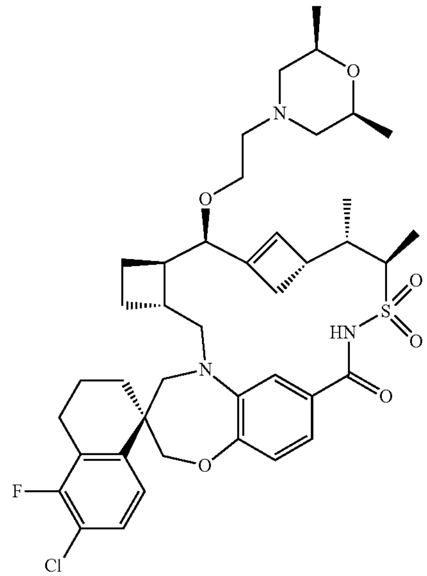 [SMILES: C[C@@H]1[C@@H](C)S(=O)(=O)NC(=O)c2ccc3c(c2)N(C[C@@H]2CC[C@H]2[C@@H](OCCN2C[C@@H](C)O[C@@H](C)C2)C2=C[C@H]1C2)C[C@@]1(CCCc2c1ccc(Cl)c2F)CO3] | 31 | 54 | 56 |
| 83 | 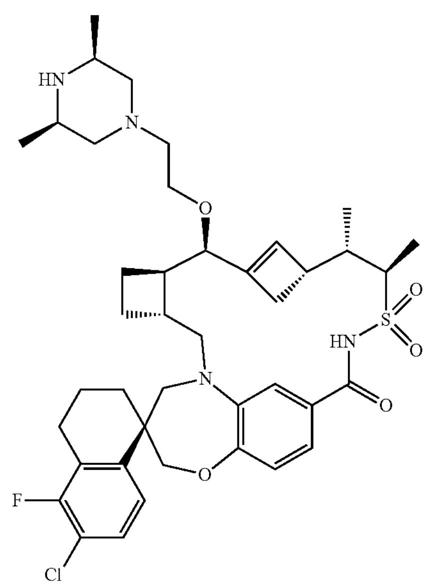 [SMILES: C[C@@H]1[C@@H](C)S(=O)(=O)NC(=O)c2ccc3c(c2)N(C[C@@H]2CC[C@H]2[C@@H](OCCN2C[C@@H](C)N[C@@H](C)C2)C2=C[C@H]1C2)C[C@@]1(CCCc2c1ccc(Cl)c2F)CO3] | 25 | 164 | 220 |

TABLE 2-A-continued

| Cpd. No. | Structure | Mcl-1 (FP, nM) | OPM-2 (5% FBS, nM) | H929 (5% FBS, nM) |
|---|---|---|---|---|
| 84 | 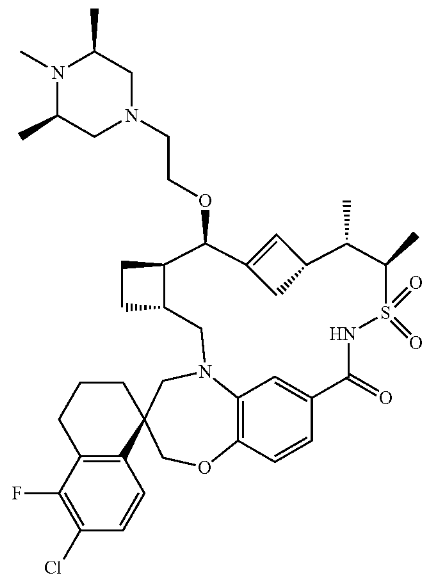 [SMILES: C[C@@H]1[C@@H](C)S(=O)(=O)NC(=O)c2ccc3c(c2)N(C[C@@H]2CC[C@H]2[C@@H](OCCN2C[C@@H](C)N(C)[C@@H](C)C2)C2=C[C@H]1C2)C[C@@]1(CCCc2c1ccc(Cl)c2F)CO3] | 20 | 65 | 76 |
| 85 | 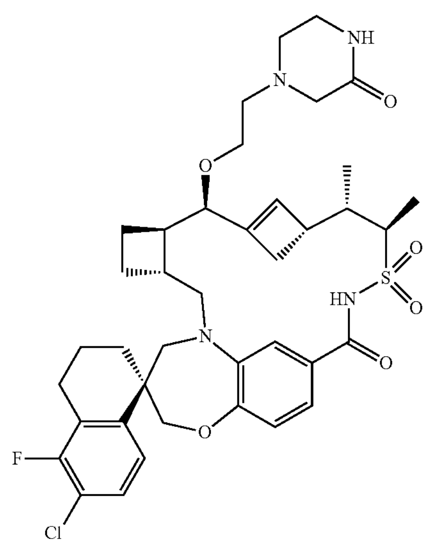 [SMILES: C[C@@H]1[C@@H](C)S(=O)(=O)NC(=O)c2ccc3c(c2)N(C[C@@H]2CC[C@H]2[C@@H](OCCN2CCNC(=O)C2)C2=C[C@H]1C2)C[C@@]1(CCCc2c1ccc(Cl)c2F)CO3] | 20 | 124 | 73 |

TABLE 2-A-continued

| Cpd. No. | Structure | Mcl-1 (FP, nM) | OPM-2 (5% FBS, nM) | H929 (5% FBS, nM) |
|---|---|---|---|---|
| 86 | 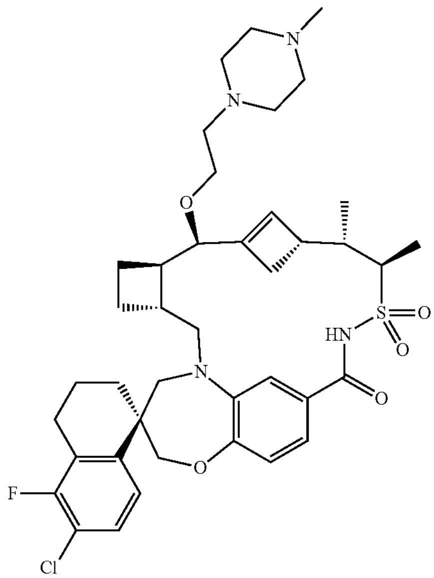 [SMILES: C[C@@H]1[C@@H](C)S(=O)(=O)NC(=O)c2ccc3c(c2)N(C[C@@H]2CC[C@H]2[C@@H](OCCN2CCN(C)CC2)C2=C[C@H]1C2)C[C@@]1(CCCc2c1ccc(Cl)c2F)CO3] | 10 | 64 | 3.8 |
| 87 | 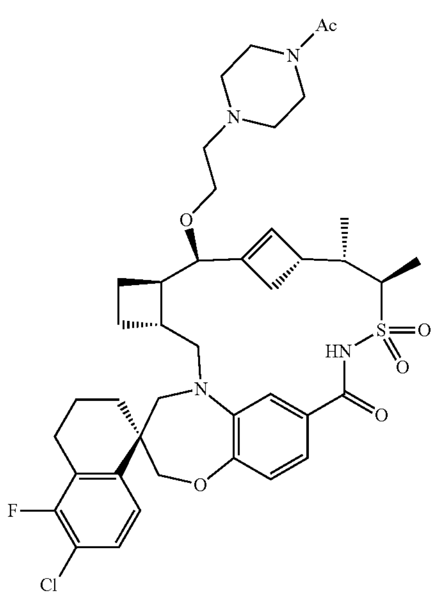 [SMILES: CC(=O)N1CCN(CCO[C@H]2C3=C[C@@H](C3)[C@H](C)[C@@H](C)S(=O)(=O)NC(=O)c3ccc4c(c3)N(C[C@@H]3CC[C@H]32)C[C@@]2(CCCc3c2ccc(Cl)c3F)CO4)CC1] | 8.5 | 369 | 27 |

TABLE 2-A-continued

| Cpd. No. | Structure | Mcl-1 (FP, nM) | OPM-2 (5% FBS, nM) | H929 (5% FBS, nM) |
|---|---|---|---|---|
| 88 | 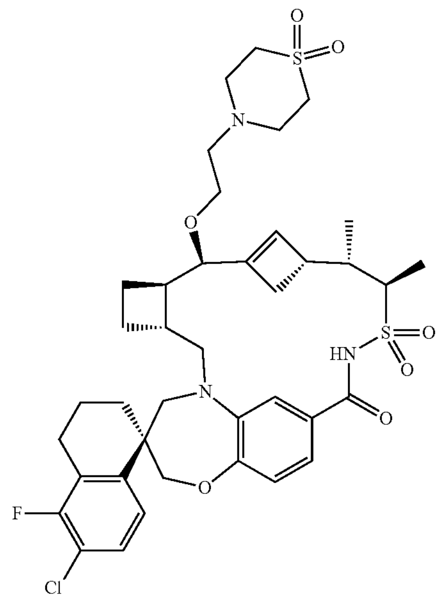 [SMILES: C[C@@H]1[C@@H](C)S(=O)(=O)NC(=O)c2ccc3c(c2)N(C[C@@H]2CC[C@H]2[C@@H](OCCN2CCS(=O)(=O)CC2)C2=C[C@H]1C2)C[C@@]1(CCCc2c1ccc(Cl)c2F)CO3] | 13 | 118 | 40 |
| 89 | 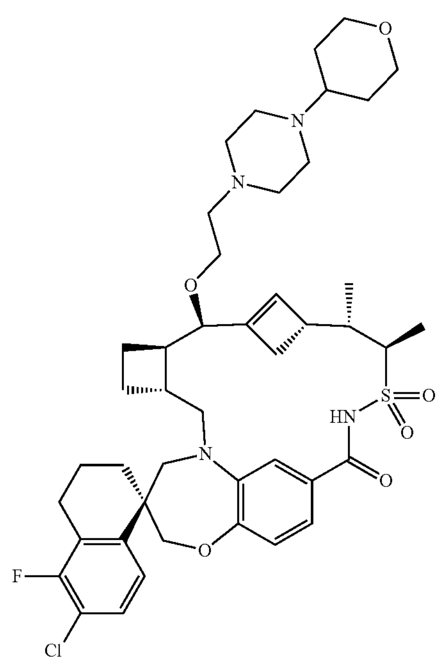 [SMILES: C[C@@H]1[C@@H](C)S(=O)(=O)NC(=O)c2ccc3c(c2)N(C[C@@H]2CC[C@H]2[C@@H](OCCN2CCN(C4CCOCC4)CC2)C2=C[C@H]1C2)C[C@@]1(CCCc2c1ccc(Cl)c2F)CO3] | 11 | 53 | 7.5 |

TABLE 2-A-continued

| Cpd. No. | Structure | Mcl-1 (FP, nM) | OPM-2 (5% FBS, nM) | H929 (5% FBS, nM) |
|---|---|---|---|---|
| 90 | 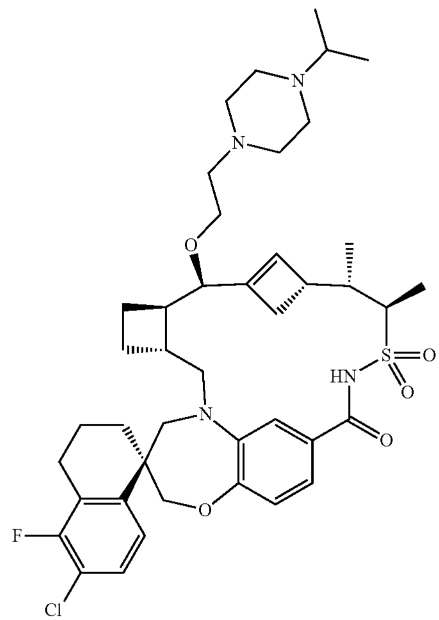 [SMILES: CC(C)N1CCN(CCO[C@H]2C3=C[C@@H](C3)[C@H](C)[C@@H](C)S(=O)(=O)NC(=O)c3ccc4c(c3)N(C[C@@H]3CC[C@H]32)C[C@@]2(CCCc3c2ccc(Cl)c3F)CO4)CC1] | 12 | 20 | 1.6 |
| 91 | 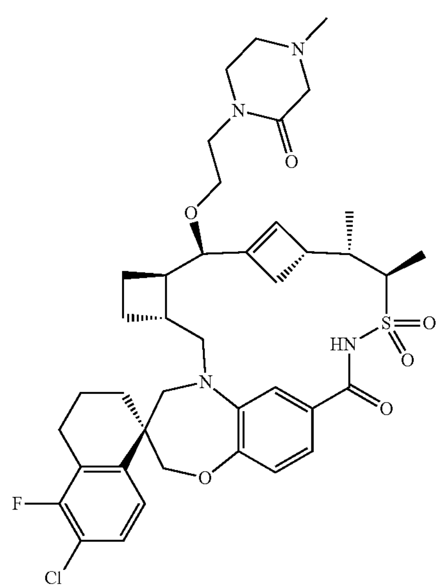 [SMILES: C[C@@H]1[C@@H](C)S(=O)(=O)NC(=O)c2ccc3c(c2)N(C[C@@H]2CC[C@H]2[C@@H](OCCN2CCN(C)CC2=O)C2=C[C@H]1C2)C[C@@]1(CCCc2c1ccc(Cl)c2F)CO3] | 15 | 59 | 16 |

TABLE 2-A-continued
| Cpd. No. | Structure | Mcl-1 (FP, nM) | OPM-2 (5% FBS, nM) | H929 (5% FBS, nM) |
|---|---|---|---|---|
| 92 | 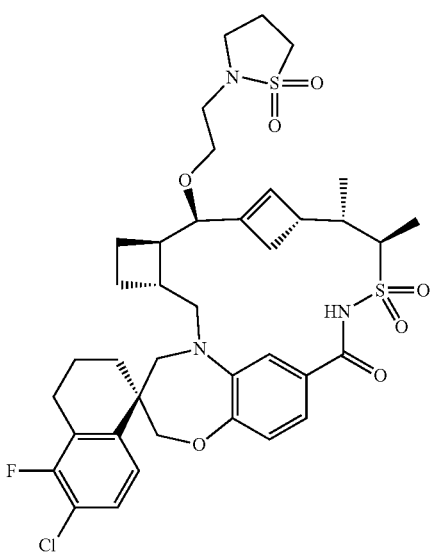 [SMILES: C[C@@H]1[C@@H](C)S(=O)(=O)NC(=O)c2ccc3c(c2)N(C[C@@H]2CC[C@H]2[C@@H](OCCN2CCCS2(=O)=O)C2=C[C@H]1C2)C[C@@]1(CCCc2c1ccc(Cl)c2F)CO3] | 14 | 44 | 59 |
| 93 | 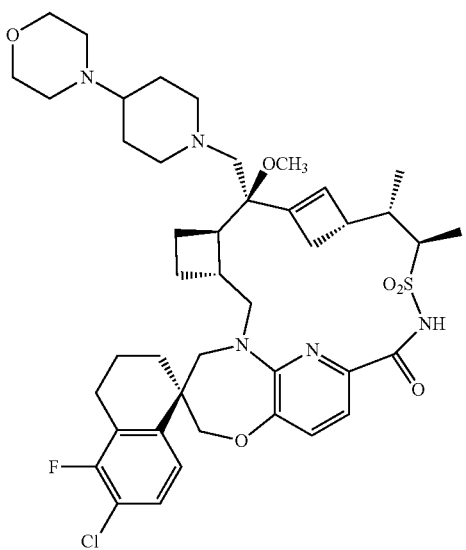 [SMILES: CO[C@@]1(CN2CCC(N3CCOCC3)CC2)C2=C[C@@H](C2)[C@H](C)[C@@H](C)S(=O)(=O)NC(=O)c2ccc3c(n2)N(C[C@@H]2CC[C@H]21)C[C@@]1(CCCc2c1ccc(Cl)c2F)CO3] | 19 | 71 | 11 |

TABLE 2-A-continued
| Cpd. No. | Structure | Mcl-1 (FP, nM) | OPM-2 (5% FBS, nM) | H929 (5% FBS, nM) |
| --- | --- | --- | --- | --- |
| 94 | 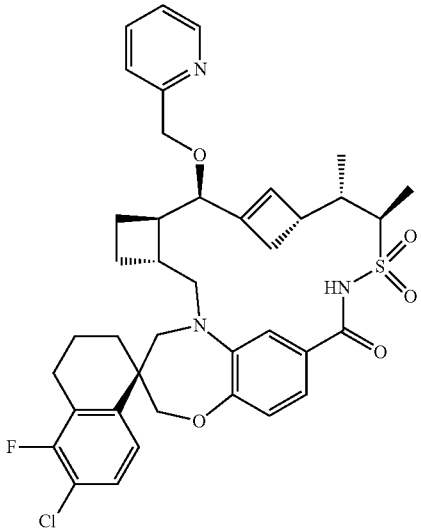 | 48 | 96 | 200 |
| 95 | 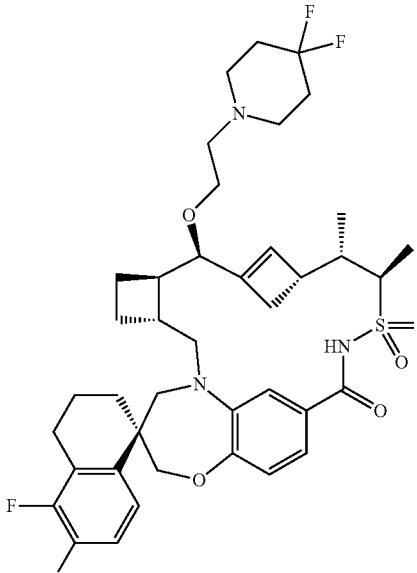 | 23 | 42 | 44 |

In another embodiment, Compounds of the Disclosure are selected from the group consisting of:

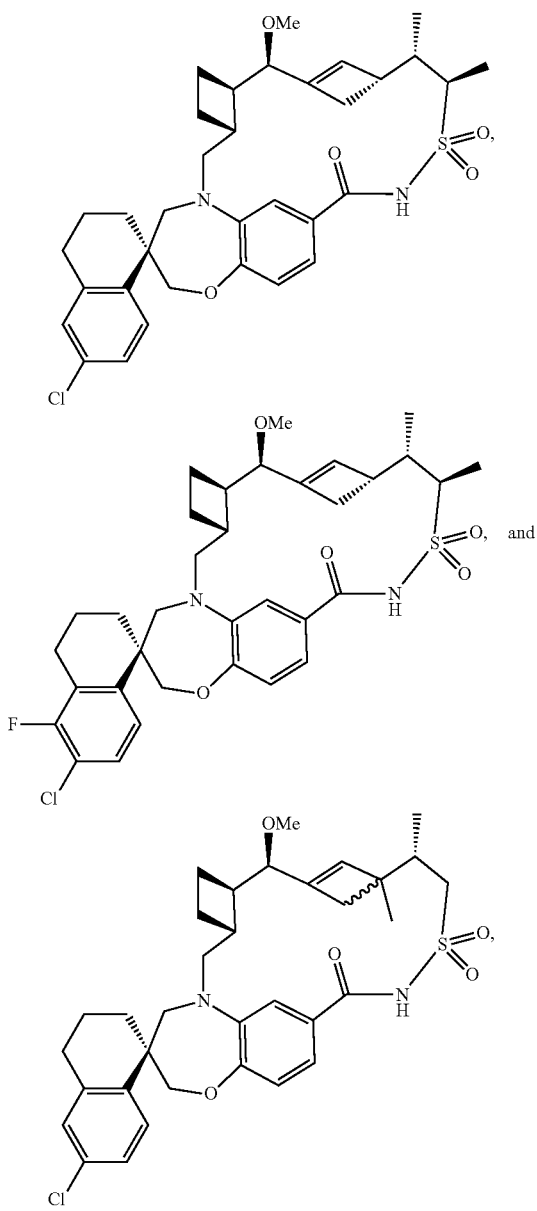

or a pharmaceutically acceptable salt or solvate thereof.

In another embodiment, the disclosure provides a pharmaceutical composition comprising a Compound of the Disclosure and a pharmaceutically acceptable carrier.

In another embodiment, Compounds of the Disclosure are enantiomerically enriched, e.g., the enantiomeric excess or "ee" of the compound is about 5% or more as measured by chiral HPLC. In another embodiment, the ee is about 10%. In another embodiment, the ee is about 20%. In another embodiment, the ee is about 30%. In another embodiment, the ee is about 40%. In another embodiment, the ee is about 50%. In another embodiment, the ee is about 60%. In another embodiment, the ee is about 70%. In another embodiment, the ee is about 80%. In another embodiment, the ee is about 85%. In another embodiment, the ee is about 90%. In another embodiment, the ee is about 91%. In another embodiment, the ee is about 92%. In another embodiment, the ee is about 93%. In another embodiment, the ee is about 94%. In another embodiment, the ee is about 95%. In another embodiment, the ee is about 96%. In another embodiment, the ee is about 97%. In another embodiment, the ee is about 98%. In another embodiment, the ee is about 99%.

The present disclosure encompasses the preparation and use of salts of Compounds of the Disclosure. As used herein, the pharmaceutical "pharmaceutically acceptable salt" refers to salts or zwitterionic forms of Compounds of the Disclosure. Salts of Compounds of the Disclosure can be prepared during the final isolation and purification of the compounds or separately by reacting the compound with a suitable acid. The pharmaceutically acceptable salts of Compounds of the Disclosure can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Non-limiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference Compounds of the Disclosure appearing herein is intended to include compounds of Compounds of the Disclosure as well as pharmaceutically acceptable salts, hydrates, or solvates thereof.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, and ethanol, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1):Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvate in a crystal of the solvate.

II. Intermediates of the Disclosure

The disclosure also provides synthetic intermediates, collectively referred to as "Intermediates of the Disclosure," that can be used to prepare Compounds of the Disclosure.

In one embodiment (referred to as "Embodiment 1"), Intermediates of the Disclosure are compounds of Formula XVIII-A:

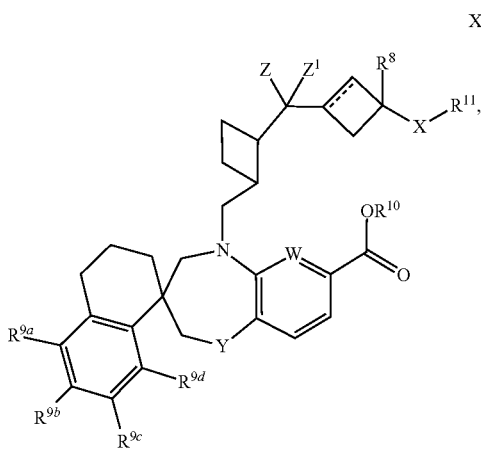

XVIII-A wherein:
X selected from the group consisting of:

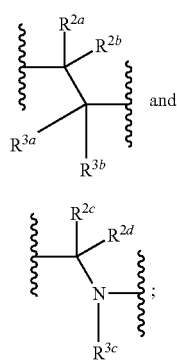

X-1 and

X-2 wherein the carbon atom bearing $R^{3a}$ and $R^{3b}$ of X-1 and the nitrogen atom of X-2 are attached to $R^{11}$;

$R^8$ is selected from the group consisting of hydrogen and $C_1$-$C_3$ alkyl; or X and $R^8$ taken together form a spirocycle of Formula X-3:

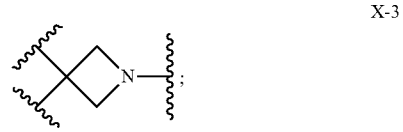 [SMILES: *N1CC(*)(*)C1]

X-3 wherein the nitrogen atom of X-3 is attached $R^{11}$;

Y is selected from the group consisting of —O— and —S—;

Z is selected from the group consisting of —R, —N($R^{1a}$)($R^{1b}$), and —OR$^1$;

$Z^1$ is selected from the group consisting of hydrogen, (hydroxy)$C_1$-$C_4$ alkyl, ($C_1$-$C_3$ alkoxy)$C_1$-$C_3$ alkyl, (heterocyclo)$C_1$-$C_4$ alkyl, (alkylsulfonyl)$C_1$-$C_4$ alkyl, (phenyl)$C_1$-$C_4$ alkyl, (heteroaryl) $C_1$-$C_4$ alkyl, (amino)$C_1$-$C_4$ alkyl, (amido)$C_1$-$C_4$ alkyl, (carboxy)$C_1$-$C_4$ alkyl, (alkoxycarbonyl)$C_1$-$C_4$ alkyl, (aminocarbonyl)$C_1$-$C_4$ alkyl, (aminosulfonyl)$C_1$-$C_4$ alkyl, and —C(=O)R$^{15}$;

R is selected from the group consisting of $C_1$-$C_6$ alkyl, $C_3$-$C_6$ cycloalkyl, and 4- to 10-membered heterocyclo;

$R^1$ is selected from the group consisting of hydrogen, —C(=O)CH$_3$, $C_1$-$C_6$ alkyl, (hydroxy)$C_1$-$C_4$ alkyl, ($C_1$-$C_3$ alkoxy)$C_1$-$C_3$ alkyl, (heterocyclo)$C_1$-$C_4$ alkyl, (alkylsulfonyl)$C_1$-$C_4$ alkyl, (phenyl)$C_1$-$C_4$ alkyl, (heteroaryl) $C_1$-$C_4$ alkyl, (amino)$C_1$-$C_4$ alkyl, (amido)$C_1$-$C_4$ alkyl, (carboxy) $C_1$-$C_4$ alkyl, (alkoxycarbonyl)$C_1$-$C_4$ alkyl, (aminocarbonyl) $C_1$-$C_4$ alkyl, and (aminosulfonyl)$C_1$-$C_4$ alkyl;

$R^{1a}$ is selected from the group consisting of hydrogen, $C_1$-$C_6$ alkyl, (hydroxy)$C_1$-$C_4$ alkyl, ($C_1$-$C_3$ alkoxy)$C_1$-$C_3$ alkyl, (heterocyclo)$C_1$-$C_4$ alkyl, (alkylsulfonyl)$C_1$-$C_4$ alkyl, (phenyl)$C_1$-$C_4$ alkyl, (heteroaryl)$C_1$-$C_4$ alkyl, (amino)$C_1$-$C_4$ alkyl, (amido)$C_1$-$C_4$ alkyl, (carboxy)$C_1$-$C_4$ alkyl, (alkoxycarbonyl)$C_1$-$C_4$ alkyl, (aminocarbonyl)$C_1$-$C_4$ alkyl, and (aminosulfonyl)$C_1$-$C_4$ alkyl;

$R^{1b}$ is selected from the group consisting of hydrogen and $C_1$-$C_3$ alkyl;

$R^{2a}$ is selected from the group consisting of hydrogen and $C_1$-$C_3$ alkyl;

$R^{3a}$ is selected from the group consisting of hydrogen and $C_1$-$C_3$ alkyl; or $R^{2a}$ and $R^{3a}$ taken together with the carbon atoms to which they are attached form a $C_3$-$C_6$ cycloalkyl or 4- to 10-membered heterocyclo;

$R^{2b}$ is selected from the group consisting of hydrogen and $C_1$-$C_3$ alkyl;

$R^{2c}$ is selected from the group consisting of hydrogen and $C_1$-$C_3$ alkyl;

$R^{2d}$ is selected from the group consisting of hydrogen and $C_1$-$C_3$ alkyl;

$R^{3b}$ is selected from the group consisting of hydrogen and $C_1$-$C_3$ alkyl;

$R^{3c}$ is selected from the group consisting of hydrogen, $C_1$-$C_6$ alkyl, (hydroxy)$C_1$-$C_4$ alkyl, ($C_1$-$C_3$ alkoxy)$C_1$-$C_3$ alkyl, (heterocyclo)$C_1$-$C_4$ alkyl, (alkylsulfonyl)$C_1$-$C_4$ alkyl, (phenyl)$C_1$-$C_4$ alkyl, (heteroaryl)$C_1$-$C_4$ alkyl, (amino)$C_1$-$C_4$ alkyl, (amido)$C_1$-$C_4$ alkyl, (carboxy)$C_1$-$C_4$ alkyl, (alkoxycarbonyl)$C_1$-$C_4$ alkyl, (aminocarbonyl)$C_1$-$C_4$ alkyl, and (aminosulfonyl)$C_1$-$C_4$ alkyl;

$R^{9a}$, $R^{9c}$, and $R^{9d}$ are independently selected from the group consisting of hydrogen and halo;

$R^{9b}$ is halo;

$R^{15}$ is 4- to 10-membered heterocyclo;

W is selected from the group consisting of —CH= and —N=;

=== represents a single or double bond;

$R^{10}$ is selected from the group consisting of hydrogen and $C_1$-$C_6$ alkyl;

when X is X-1, then $R^{11}$ is selected from the group consisting of —$OR^{12}$, —$SR^{14}$, —$S(=O)_2R^{14}$, and —$S(=O)$—$O^-M^+$;

$R^{12}$ is selected from the group consisting of hydrogen and —$C(=O)R^{13}$;

$R^{13}$ is selected from the group consisting of phenyl and naphthyl;

$R^{14}$ is selected from the group consisting of amino and 5- or 6-membered heteroaryl; and $M^+$ selected from the group consisting of $Li^+$, $Na^+$, and $K^+$; and when X is X-2, then $R^{11}$ is —$S(=O)_2NH_2$; and each $C_3$-$C_6$ cycloalkyl is unsubstituted or substituted with one, two, or three substituents independently selected from the group consisting of halo, hydroxy, amino, cyano, $C_1$-$C_6$ alkyl, $C_1$-$C_4$ alkoxy, $C_3$-$C_6$ cycloalkyl, 4- to 10-membered heterocyclo, alkylsulfonyl, alkylcarbonyl, and phenyl;

each 4- to 10-membered heterocyclo is unsubstituted or substituted with one, two, three, or four substituents independently selected from the group consisting of halo, hydroxy, amino, cyano, $C_1$-$C_6$ alkyl, $C_1$-$C_4$ alkoxy, $C_3$-$C_6$ cycloalkyl, 4- to 10-membered heterocyclo, alkylsulfonyl, alkylcarbonyl, and phenyl; and each phenyl is unsubstituted or substituted with one, two, three, or four substituents independently selected from the group consisting of halo, hydroxy, amino, cyano, $C_1$-$C_6$ alkyl, $C_1$-$C_4$ alkoxy, $C_3$-$C_6$ cycloalkyl, 4- to 10-membered heterocyclo, alkylsulfonyl, alkylcarbonyl, and phenyl, or a pharmaceutically acceptable salt or solvate thereof.

The following particular embodiments are also drawn to Intermediates of the Disclosure.

Embodiment 2. The compound of Embodiment 1 selected from the group consisting of:

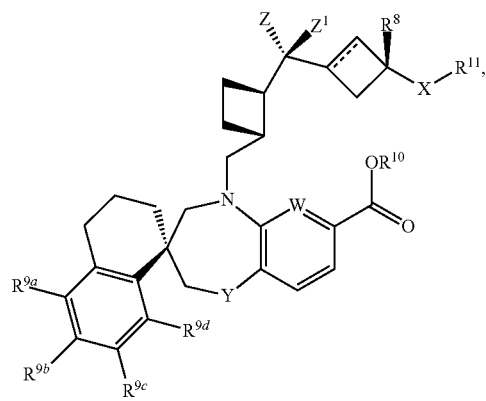

XX-A

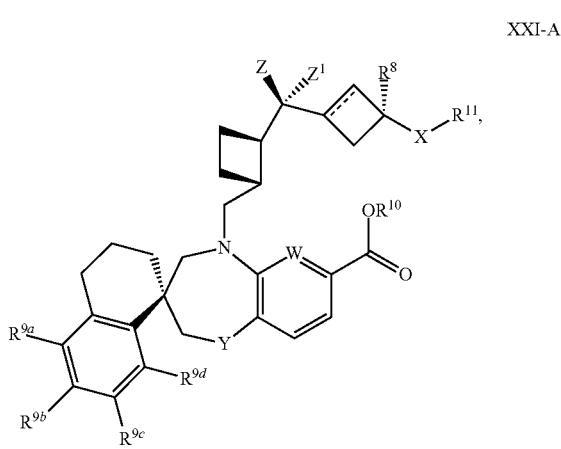

XXI-A

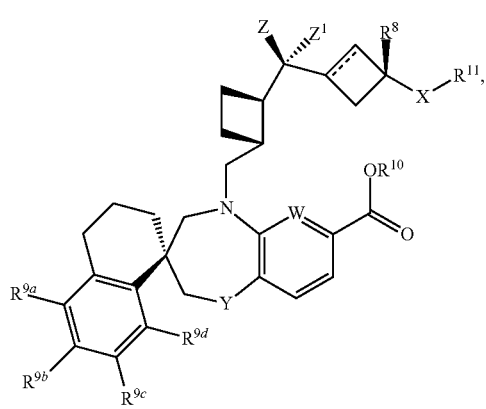

XIX-A

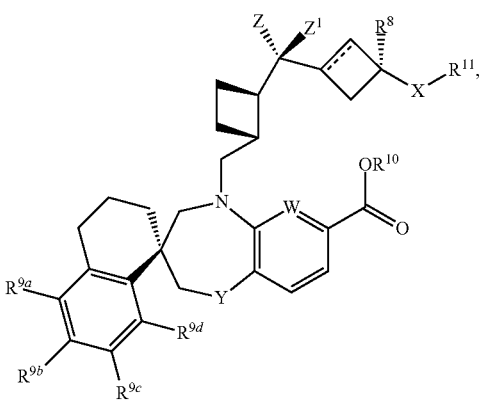

XXII-A

XXIII-A
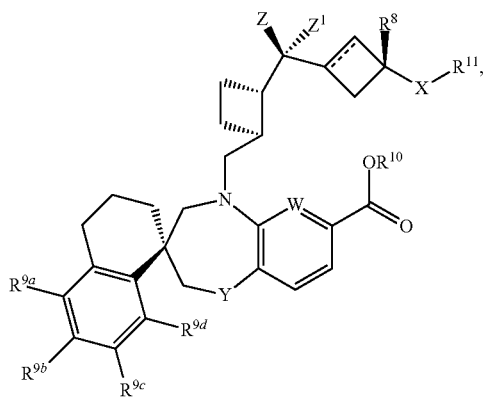
XXVI-A
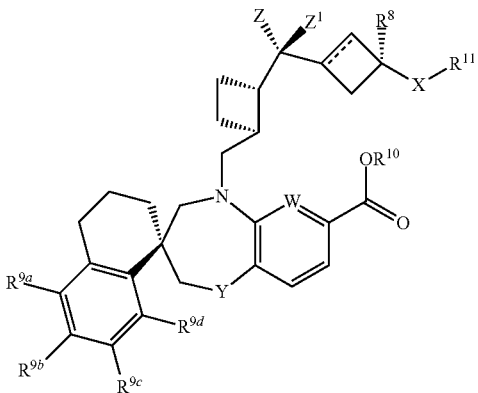
XXIV-A
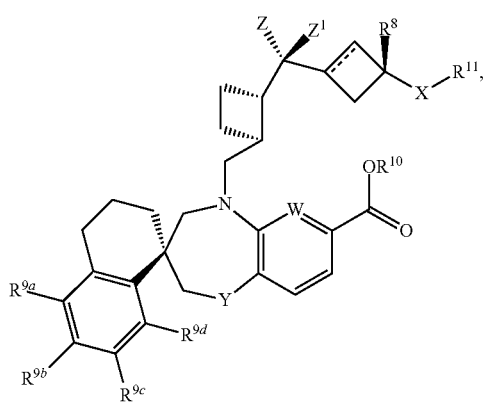
XXVII-A
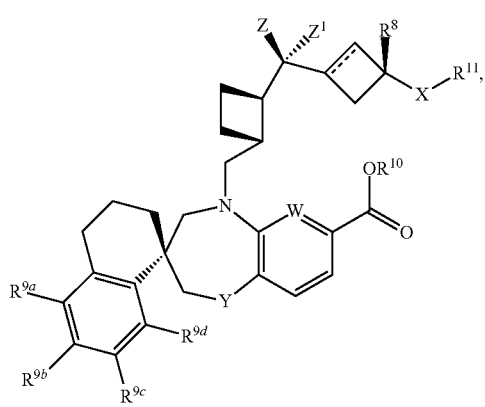
XXV-A
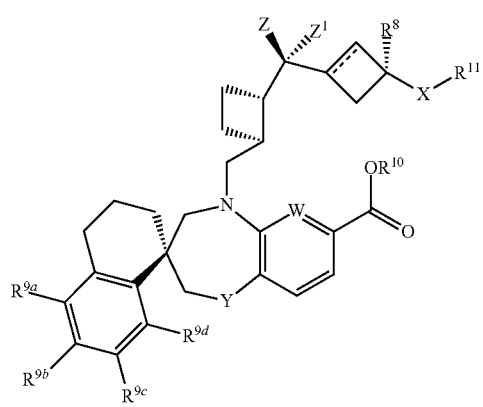
XXVIII-A
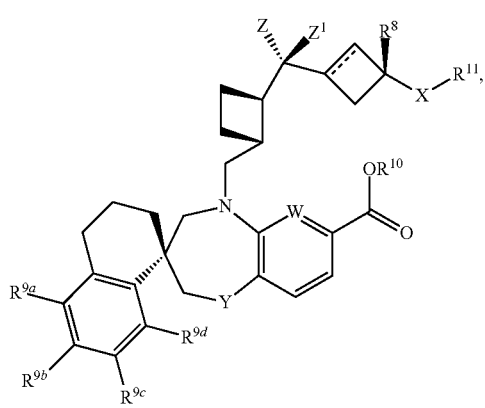

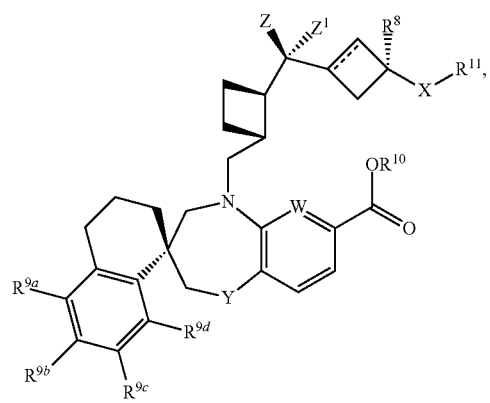
XXIX-A
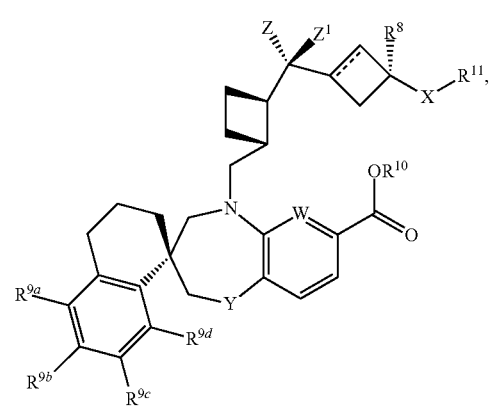
XXX-A
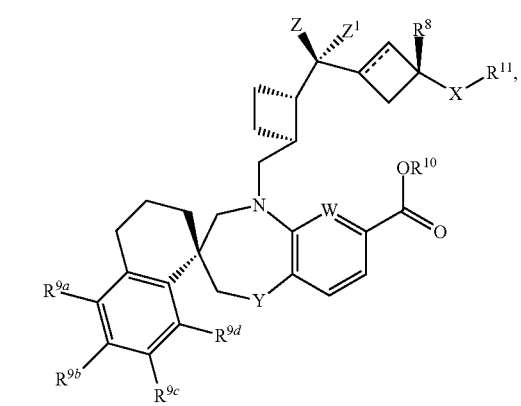
XXXI-A
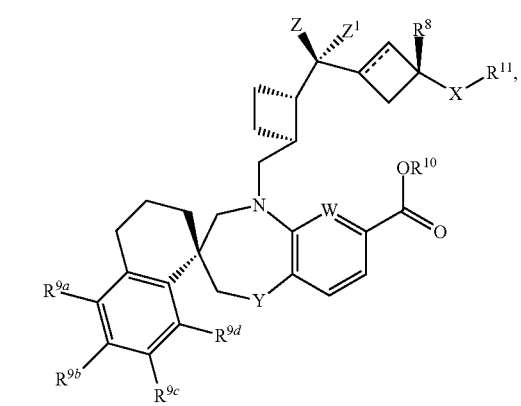
XXXII-A
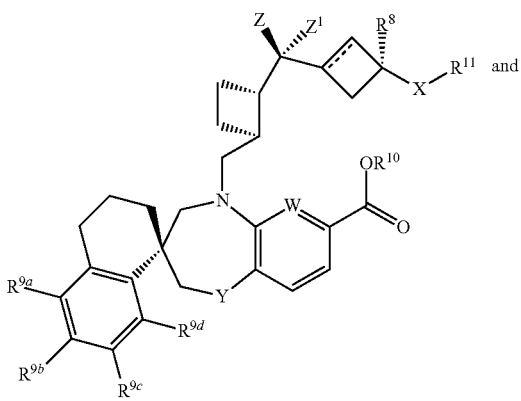
XXXIII-A
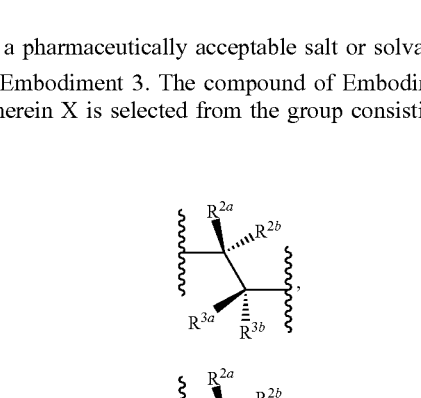
XXXIV-A
or a pharmaceutically acceptable salt or solvate thereof.
Embodiment 3. The compound of Embodiments 1 or 2, wherein X is selected from the group consisting of:
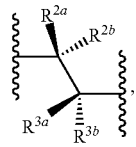
X-1-A
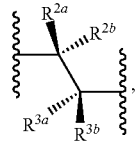
X-1-B
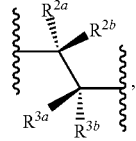
X-1-C
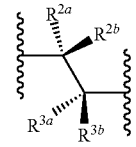
X-1-D -continued

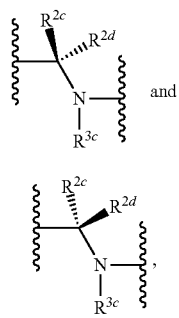

or a pharmaceutically acceptable salt or solvate thereof.

Embodiment 4. The compound of Embodiment 3 selected from any one or more compounds of Table 3-A, i.e., compounds of Formula XVIII-A having the specific combination of Formulae XIX-A, XX-A, XXI-A, XXII-A, XXIII-A, XXIV-A, XXV-A, XXVI-A, XXVII-A, XXVIII-A, XXIX-A, XXX-A, XXXI-A, XXXII-A, XXXIII-A, or XXXIV-A, and X, or a pharmaceutically acceptable salt or solvate thereof.

TABLE 3-A

| Formula | X | Formula | X |
|---|---|---|---|
| XIX-A | X-1-A | XX-A | X-1-A |
| XIX-A | X-1-B | XX-A | X-1-B |
| XIX-A | X-1-C | XX-A | X-1-C |
| XIX-A | X-1-D | XX-A | X-1-D |
| XIX-A | X-2-A | XX-A | X-2-A |
| XIX-A | X-2-B | XX-A | X-2-B |
| XXI-A | X-1-A | XXII-A | X-1-A |
| XXI-A | X-1-B | XXII-A | X-1-B |
| XXI-A | X-1-C | XXII-A | X-1-C |
| XXI-A | X-1-D | XXII-A | X-1-D |
| XXI-A | X-2-A | XXII-A | X-2-A |
| XXI-A | X-2-B | XXII-A | X-2-B |
| XXIII-A | X-1-A | XXIV-A | X-1-A |
| XXIII-A | X-1-B | XXIV-A | X-1-B |
| XXIII-A | X-1-C | XXIV-A | X-1-C |
| XXIII-A | X-1-D | XXIV-A | X-1-D |
| XXIII-A | X-2-A | XXIV-A | X-2-A |
| XXIII-A | X-2-B | XXIV-A | X-2-B |
| XXV-A | X-1-A | XXVI-A | X-1-A |
| XXV-A | X-1-B | XXVI-A | X-1-B |
| XXV-A | X-1-C | XXVI-A | X-1-C |
| XXV-A | X-1-D | XXVI-A | X-1-D |
| XXV-A | X-2-A | XXVI-A | X-2-A |
| XXV-A | X-2-B | XXVI-A | X-2-B |
| XXVII-A | X-1-A | XXVIII-A | X-1-A |
| XXVII-A | X-1-B | XXVIII-A | X-1-B |
| XXVII-A | X-1-C | XXVIII-A | X-1-C |
| XXVII-A | X-1-D | XXVIII-A | X-1-D |
| XXVII-A | X-2-A | XXVIII-A | X-2-A |
| XXVII-A | X-2-B | XXVIII-A | X-2-B |
| XXIX-A | X-1-A | XXX-A | X-1-A |
| XXIX-A | X-1-B | XXX-A | X-1-B |
| XXIX-A | X-1-C | XXX-A | X-1-C |
| XXIX-A | X-1-D | XXX-A | X-1-D |
| XXIX-A | X-2-A | XXX-A | X-2-A |
| XXIX-A | X-2-B | XXX-A | X-2-B |
| XXXI-A | X-1-A | XXXII-A | X-1-A |
| XXXI-A | X-1-B | XXXII-A | X-1-B |
| XXXI-A | X-1-C | XXXII-A | X-1-C |
| XXXI-A | X-1-D | XXXII-A | X-1-D |
| XXXI-A | X-2-A | XXXII-A | X-2-A |
| XXXI-A | X-2-B | XXXII-A | X-2-B |
| XXXIII-A | X-1-A | XXXIV-A | X-1-A |
| XXXIII-A | X-1-B | XXXIV-A | X-1-B |
| XXXIII-A | X-1-C | XXXIV-A | X-1-C |
| XXXIII-A | X-1-D | XXXIV-A | X-1-D |
| XXXIII-A | X-2-A | XXXIV-A | X-2-A |
| XXXIII-A | X-2-B | XXXIV-A | X-2-B |

Embodiment 5. The compound of Embodiments 3 or 4, wherein X is X-1-A, X-1-B, X-1-C, or X-1-D, or a pharmaceutically acceptable salt or solvate thereof.

Embodiment 6. The compound of Embodiments 3 or 4, wherein X is X-2-A or X-2-B, or a pharmaceutically acceptable salt or solvate thereof.

Embodiment 7. The compound of any one of Embodiments 1-6, wherein Z is —OR$^1$ and Z$^1$ is hydrogen, or a pharmaceutically acceptable salt or solvate thereof.

Embodiment 8. The compound of Embodiment 7, wherein R$^1$ is selected from the group consisting of (hydroxy)C$_1$-C$_4$ alkyl, (C$_1$-C$_3$ alkoxy)C$_1$-C$_3$ alkyl, (heterocyclo)C$_1$-C$_4$ alkyl, (alkylsulfonyl)C$_1$-C$_4$ alkyl, (phenyl)C$_1$-C$_4$ alkyl, (heteroaryl) C$_1$-C$_4$ alkyl, (amino)C$_1$-C$_4$ alkyl, (amido) C$_1$-C$_4$ alkyl, (carboxy)C$_1$-C$_4$ alkyl, (alkoxycarbonyl)C$_1$-C$_4$ alkyl, (aminocarbonyl)C$_1$-C$_4$ alkyl, (aminosulfonyl)C$_1$-C$_4$ alkyl, and —C(=O)R$^{15}$, or a pharmaceutically acceptable salt or solvate thereof.

Embodiment 9. The compound of any one of Embodiments 1-6, wherein Z is —R and Z$^1$ is hydrogen, or a pharmaceutically acceptable salt or solvate thereof.

Embodiment 10. The compound of any one of Embodiments 1-6, wherein Z is —N(R$^{1a}$)(R$^{1b}$) and Z$^1$ is hydrogen, or a pharmaceutically acceptable salt or solvate thereof.

Embodiment 11. The compound of any one of Embodiments 1-6, wherein:

Z is —OR$^1$;

R$^1$ is selected from the group consisting of hydrogen and C$_1$-C$_3$ alkyl; and Z$^1$ is selected from the group consisting of (hydroxy)C$_1$-C$_4$ alkyl, (C$_1$-C$_3$ alkoxy)C$_1$-C$_3$ alkyl, (heterocyclo)C$_1$-C$_4$ alkyl, (alkylsulfonyl)C$_1$-C$_4$ alkyl, (phenyl)C$_1$-C$_4$ alkyl, (heteroaryl) C$_1$-C$_4$ alkyl, (amino)C$_1$-C$_4$ alkyl, (amido)C$_1$-C$_4$ alkyl, (carboxy)C$_1$-C$_4$ alkyl, (alkoxycarbonyl)C$_1$-C$_4$ alkyl, (aminocarbonyl)C$_1$-C$_4$ alkyl, (aminosulfonyl)C$_1$-C$_4$ alkyl, and —C(=O)R$^{15}$, or a pharmaceutically acceptable salt or solvate thereof.

Embodiment 12. The compound of any one of Embodiments 1-11, wherein W is —CH=, or a pharmaceutically acceptable salt or solvate thereof.

Embodiment 13. The compound of any one of Embodiments 1-11, wherein W is —N=, or a pharmaceutically acceptable salt or solvate thereof.

Embodiment 14. The compound of any one of Embodiments 1-13, wherein R$^{3c}$ is selected from the group consisting of hydrogen, C$_1$-C$_4$ alkyl, and (heterocyclo)C$_1$-C$_4$ alkyl, or a pharmaceutically acceptable salt or solvate thereof.

Embodiment 15. The compound of any one of Embodiments 1-14, wherein R$^{10}$ is hydrogen, or a pharmaceutically acceptable salt or solvate thereof.

In another embodiment (referred to as "Embodiment 16"), Intermediates of the Disclosure are compounds of Formula XVIII:

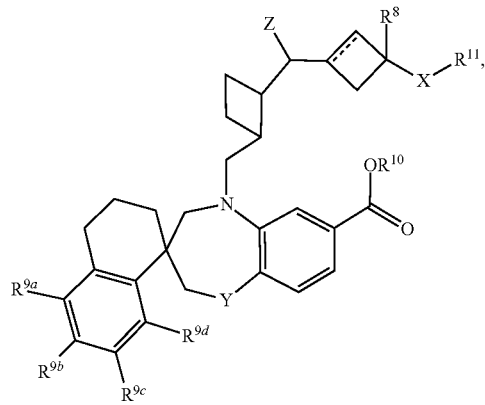

XVIII wherein:
X is:

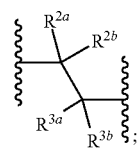

X-1 wherein the carbon atom bearing $R^{3a}$ and $R^{3b}$ is attached $R^{11}$,
Y is selected from the group consisting of —O— and —S—;
Z is —OR$^1$;
$R^1$ is selected from the group consisting of hydrogen, $C_1$-$C_3$ alkyl and ($C_1$-$C_3$ alkoxy)$C_1$-$C_3$ alkyl;
$R^{2a}$ is selected from the group consisting of hydrogen and $C_1$-$C_3$ alkyl;
$R^{3a}$ is selected from the group consisting of hydrogen and $C_1$-$C_3$ alkyl; or
$R^{2a}$ and $R^{3a}$ taken together with the carbon atoms to which they are attached form a $C_3$-$C_6$ cycloalkyl or 4- to 7-membered heterocyclo;
$R^{2b}$ is selected from the group consisting of hydrogen and $C_1$-$C_3$ alkyl;
$R^{3b}$ is selected from the group consisting of hydrogen and $C_1$-$C_3$ alkyl;
$R^8$ is selected from the group consisting of hydrogen and $C_1$-$C_3$ alkyl;
$R^{9a}$, $R^{9c}$, and $R^{9d}$ are independently selected from the group consisting of hydrogen and halo;
$R^{9b}$ is halo;
═══ represents a single or double bond,
$R^{10}$ is selected from the group consisting of hydrogen and $C_1$-$C_6$ alkyl;
$R^{11}$ is selected from the group consisting of —OR$^{12}$, —SR$^{14}$, —S(═O)$_2$R$^{14}$, and —S(═O)—O$^-$ M$^+$;
$R^{12}$ is selected from the group consisting of hydrogen and —C(═O)R$^{13}$;
$R^{13}$ is selected from the group consisting of phenyl and naphthyl;
$R^{14}$ is selected from the group consisting of amino and 5- or 6-membered heteroaryl; and
M$^+$ selected from the group consisting of Li$^+$, Na$^+$, and K$^+$, wherein each $C_3$-$C_6$ cycloalkyl, or 4- to 7-membered heterocyclo is unsubstituted or substituted with one, two, or three substituents independently selected from the group consisting of halo, $C_1$-$C_3$ alkyl, and $C_1$-$C_3$ alkoxy.

The following particular embodiments are also drawn to Intermediates of the Disclosure.

Embodiment 17. The compound of Embodiment 16 selected from the group consisting of:

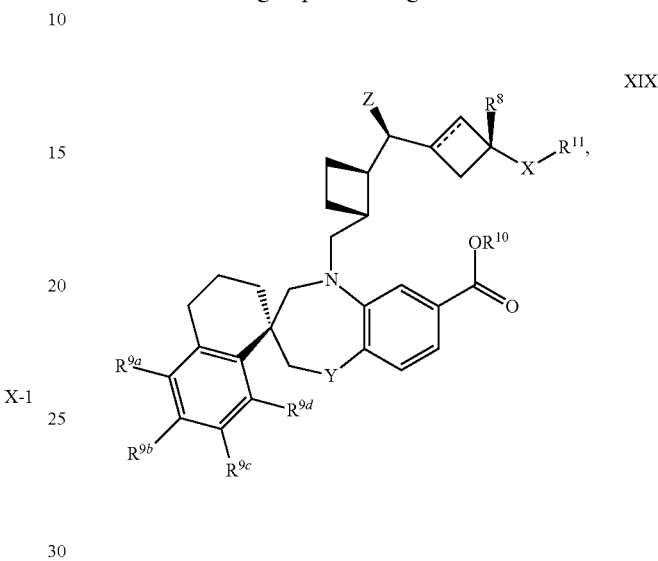

XIX

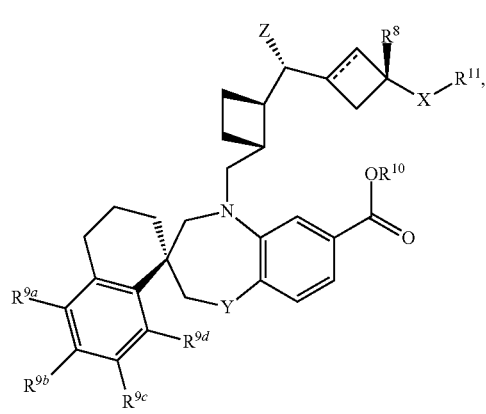

XX

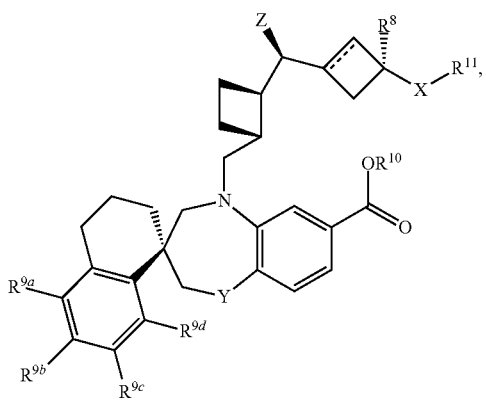

XXI

XXII
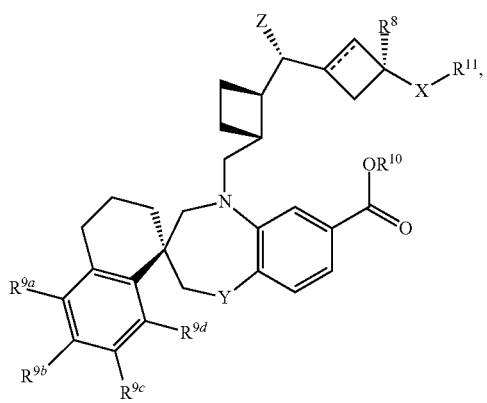
XXIII
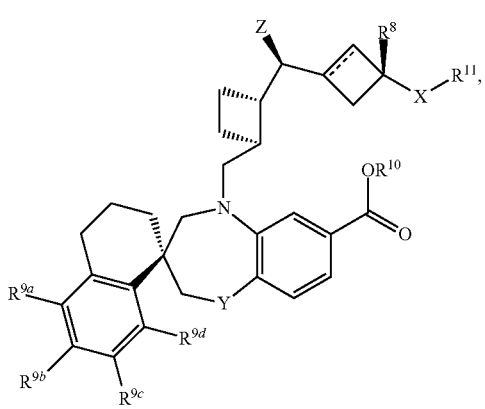
XXIV
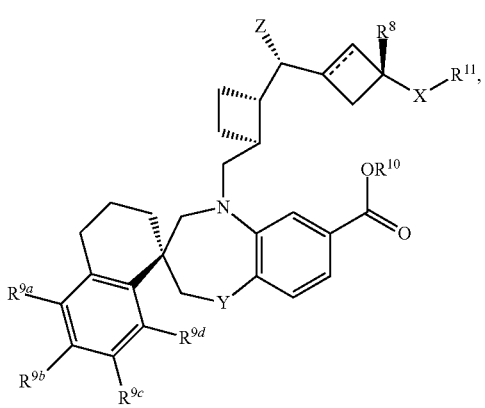
XXV
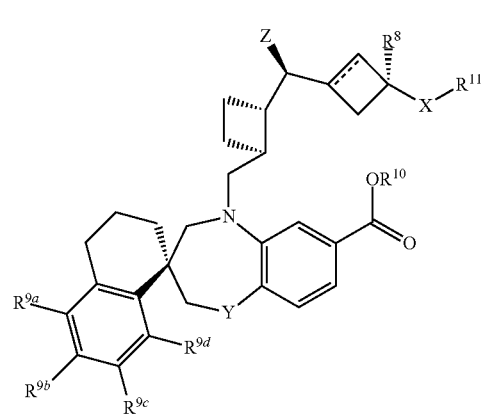
XXVI
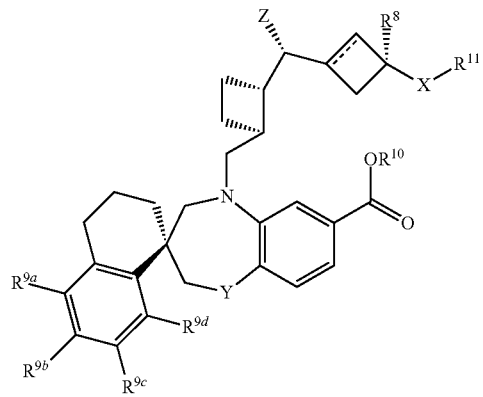
XXVII
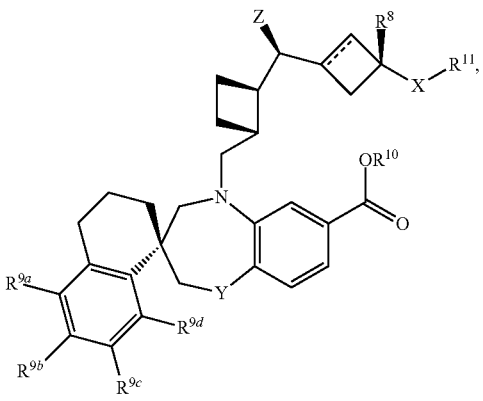
XXVIII
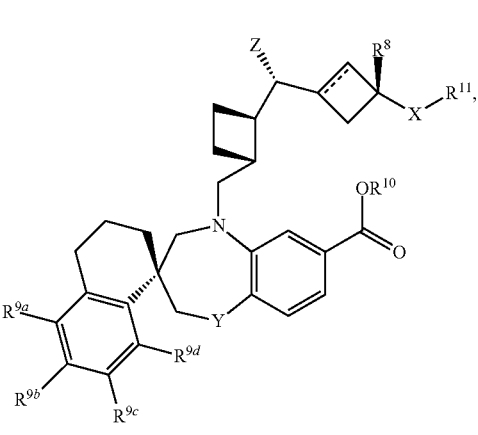
XXIX
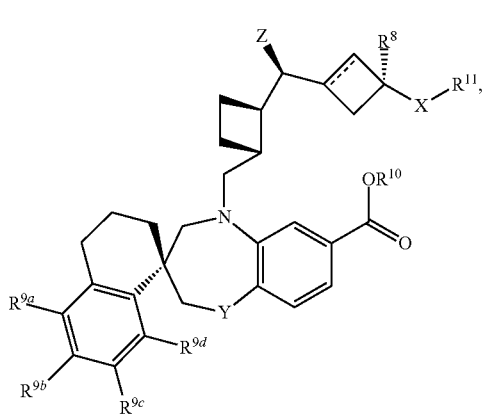

XXX

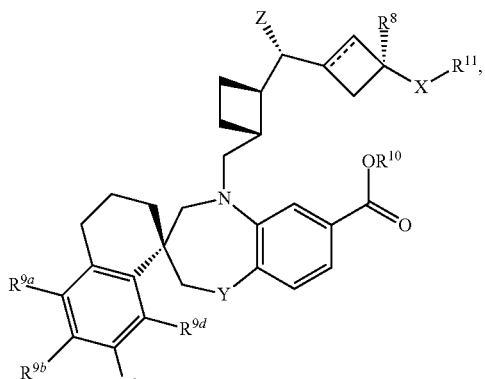

XXXI

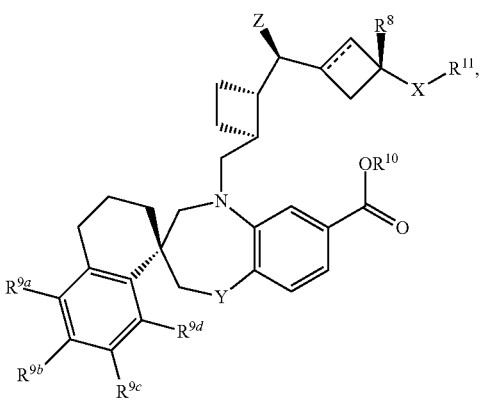

XXXII

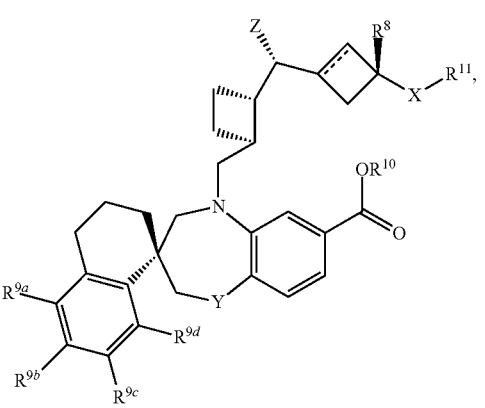

XXXIII

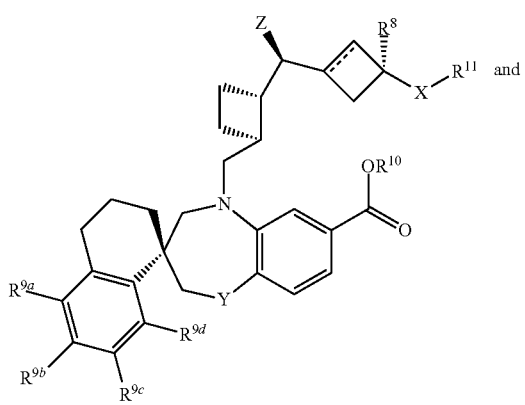

XXXIV

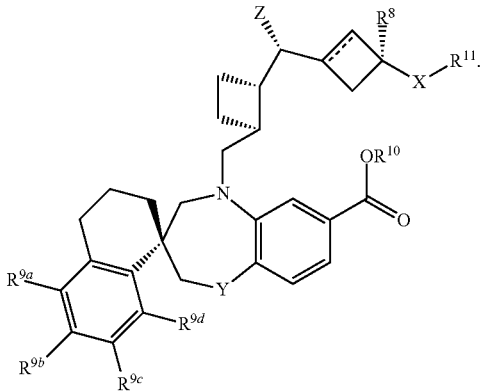

Embodiment 18. The compound of Embodiments 16 or 17, wherein X-1 is selected from the group consisting of:

X-1-A

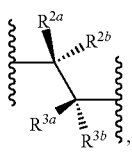

X-1-B

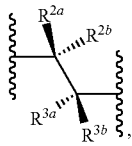

X-1-C

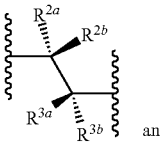

and

X-1-D

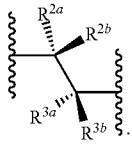

Embodiment 19. The compound of Embodiment 18 that is one or more of the compounds of Table 3:

TABLE 3

| Formula | X | Formula | X |
|---|---|---|---|
| XIX | X-1-A | XX | X-1-A |
| XIX | X-1-B | XX | X-1-B |
| XIX | X-1-C | XX | X-1-C |
| XIX | X-1-D | XX | X-1-D |
| XXI | X-1-A | XXII | X-1-A |
| XXI | X-1-B | XXII | X-1-B |
| XXI | X-1-C | XXII | X-1-C |
| XXI | X-1-D | XXII | X-1-D |
| XXIII | X-1-A | XXIV | X-1-A |
| XXIII | X-1-B | XXIV | X-1-B |
| XXIII | X-1-C | XXIV | X-1-C |
| XXIII | X-1-D | XXIV | X-1-D |
| XXV | X-1-A | XXVI | X-1-A |

TABLE 3-continued

| Formula | X | Formula | X |
|---|---|---|---|
| XXV | X-1-B | XXVI | X-1-B |
| XXV | X-1-C | XXVI | X-1-C |
| XXV | X-1-D | XXVI | X-1-D |
| XXVII | X-1-A | XXVIII | X-1-A |
| XXVII | X-1-B | XXVIII | X-1-B |
| XXVII | X-1-C | XXVIII | X-1-C |
| XXVII | X-1-D | XXVIII | X-1-D |
| XXIX | X-1-A | XXX | X-1-A |
| XXIX | X-1-B | XXX | X-1-B |
| XXIX | X-1-C | XXX | X-1-C |
| XXIX | X-1-D | XXX | X-1-D |
| XXXI | X-1-A | XXXII | X-1-A |
| XXXI | X-1-B | XXXII | X-1-B |
| XXXI | X-1-C | XXXII | X-1-C |
| XXXI | X-1-D | XXXII | X-1-D |
| XXXIII | X-1-A | XXXIV | X-1-A |
| XXXIII | X-1-B | XXXIV | X-1-B |
| XXXIII | X-1-C | XXXIV | X-1-C |
| XXXIII | X-1-D | XXXIV | X-1-D |

Embodiment 20. The compound of any one of Embodiments 1-19, wherein Z is —OR$^1$.

Embodiment 21. The compound of any one of Embodiments 1-20, wherein R$^1$ is methyl.

Embodiment 22. The compound of any one of Embodiments 1-20, wherein R$^1$ is —CH$_2$CH$_2$OCH$_3$.

Embodiment 23. The compound of any one of Embodiments 1-22, wherein R$^{2a}$ is hydrogen.

Embodiment 24. The compound of any one of Embodiments 1-22, wherein R$^{2a}$ is methyl.

Embodiment 25. The compound of any one of Embodiments 1-22, wherein R$^{2a}$ is ethyl.

Embodiment 26. The compound of any one of Embodiments 1-25, wherein R$^{2b}$ is hydrogen.

Embodiment 27. The compound of any one of Embodiments 1-25, wherein R$^{2b}$ is methyl.

Embodiment 28. The compound of any one of Embodiments 1-27, wherein R$^{1a}$ is hydrogen.

Embodiment 29. The compound of any one of Embodiments 1-27, wherein R$^{3a}$ is methyl.

Embodiment 30. The compound of any one of Embodiments 1-29, wherein R$^{3b}$ is hydrogen.

Embodiment 31. The compound of any one of Embodiments 1-29, wherein R$^{3b}$ is methyl.

Embodiment 32. The compound of any one of Embodiments 1-5 or 7-22, wherein R$^{2a}$ and R$^{3a}$ taken together with the carbon atoms to which they are attached form a C$_3$-C$_6$ cycloalkyl or 4- to 7-membered heterocyclo.

Embodiment 33. The compound of any one of Embodiments 1-32, wherein R$^8$ is hydrogen.

Embodiment 34. The compound of any one of Embodiments 1-32, wherein R$^8$ is methyl.

Embodiment 35. The compound of any one of Embodiments 1-34, wherein R$^{9b}$ is chloro.

Embodiment 36. The compound of any one of Embodiments 1-35, wherein R$^{9a}$ and R$^{9c}$ are independently selected from the group consisting of hydrogen and fluoro.

Embodiment 37. The compound of any one of Embodiments 1-36, wherein R$^{9d}$ is hydrogen.

Embodiment 38. The compound of any one of Embodiments 1-37, wherein ⚌ represents a single bond.

Embodiment 39. The compound of any one of Embodiments 1-37, wherein ⚌ represents a double bond.

Embodiment 40. The compound of any one of Embodiments 1-39, wherein Y is —O—.

Embodiment 41. The compound of any one of Embodiments 1-39, wherein Y is —S—.

Embodiment 42. The compound of any one of Embodiments 1-41, wherein R$^{10}$ is C$_1$-C$_6$ alkyl.

Embodiment 43. The compound of any one of Embodiments 16-42, wherein is —OR$^{12}$.

Embodiment 44. The compound of Embodiment 43, wherein R$^{12}$ is —C(=O)R$^{13}$ and R$^{13}$ is phenyl.

Embodiment 45. The compound of Embodiment 43, wherein R$^{12}$ is hydrogen.

Embodiment 36. The compound of any one of Embodiments 16-42, wherein R$^{11}$ is —SR$^{14}$.

Embodiment 37. The compound of any one of Embodiments 16-42, wherein R$^{11}$ is —S(=O)$_2$R$^{14}$.

Embodiment 38. The compound of Embodiments 36 or 37, wherein R$^{14}$ is 2-pyrimidyl.

Embodiment 39. The compound of Embodiment 37, wherein R$^{14}$ is —NH$_2$.

Embodiment 40. The compound of any one of Embodiments 16-42, wherein R$^{11}$ is —S(=O)—O$^-$Na$^+$.

Embodiment 41. The compound of Embodiment 39, wherein R$^{10}$ is hydrogen.

In another embodiment, Intermediates of the Disclosure are compounds of Formula XVIII selected from group consisting of the compounds of Table 4.

TABLE 4

| Int. No. | Structure |
|---|---|
| 41 | 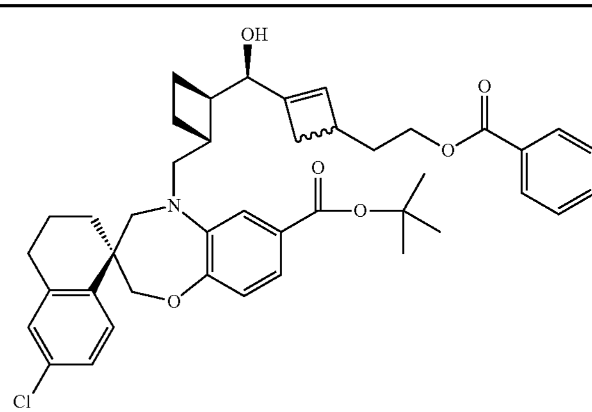 |

TABLE 4-continued
| Int. No. | Structure |
|---|---|
| 42 | 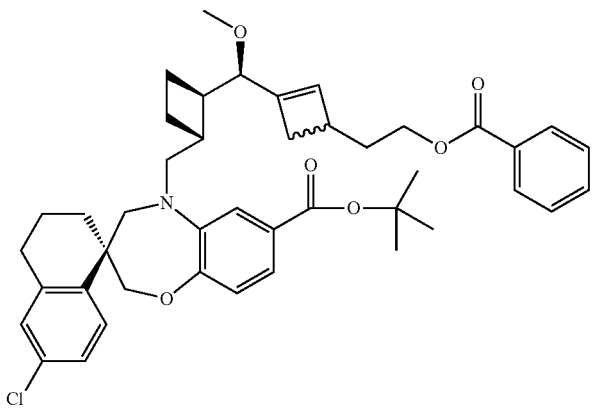 [SMILES: CO[C@@H](C1=CC(CCOC(=O)c2ccccc2)C1)[C@@H]1CC[C@H]1CN1C[C@@]2(CCCc3cc(Cl)ccc32)COc2ccc(C(=O)OC(C)(C)C)cc21] |
| 43 | 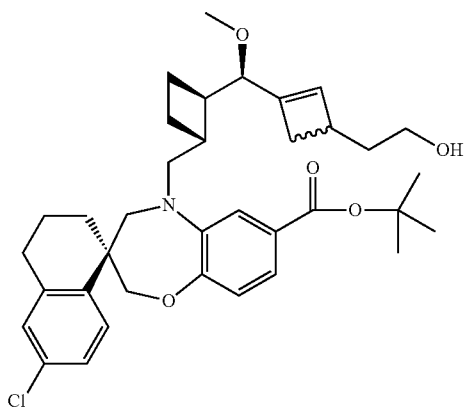 [SMILES: CO[C@@H](C1=CC(CCO)C1)[C@@H]1CC[C@H]1CN1C[C@@]2(CCCc3cc(Cl)ccc32)COc2ccc(C(=O)OC(C)(C)C)cc21] |
| 44 | 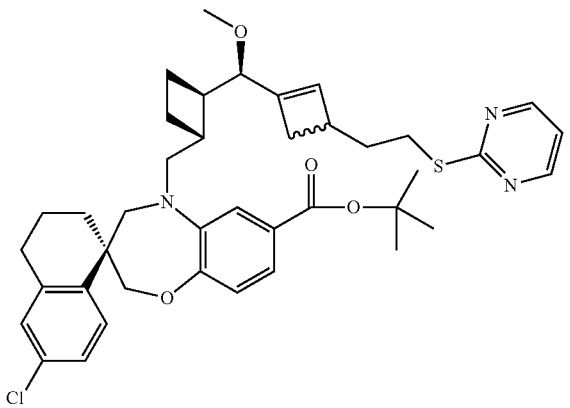 [SMILES: CO[C@@H](C1=CC(CCSc2ncccn2)C1)[C@@H]1CC[C@H]1CN1C[C@@]2(CCCc3cc(Cl)ccc32)COc2ccc(C(=O)OC(C)(C)C)cc21] |

TABLE 4-continued
| Int. No. | Structure |
| --- | --- |
| 45 | 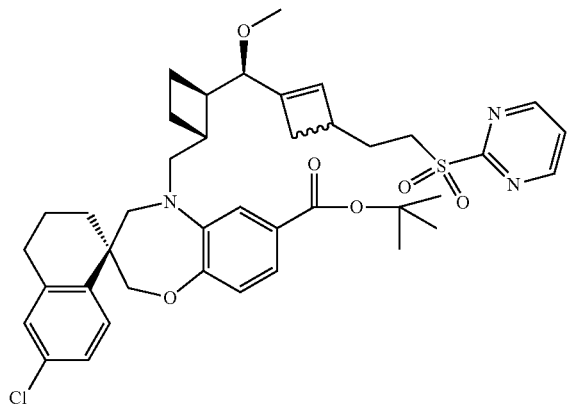 [SMILES: CO[C@@H](C1=CC(CCS(=O)(=O)c2ncccn2)C1)[C@@H]1CC[C@H]1CN1C[C@@]2(CCCc3cc(Cl)ccc32)COc2ccc(C(=O)OC(C)(C)C)cc21] |
| 46 | 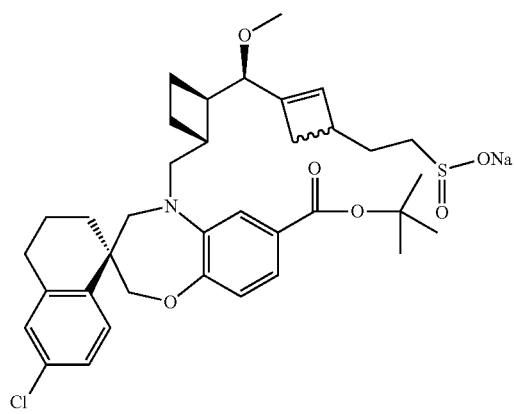 |
| 47 | 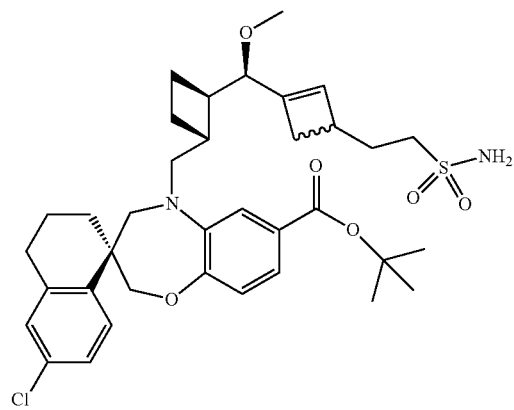 [SMILES: CO[C@@H](C1=CC(CCS(N)(=O)=O)C1)[C@@H]1CC[C@H]1CN1C[C@@]2(CCCc3cc(Cl)ccc32)COc2ccc(C(=O)OC(C)(C)C)cc21] |

TABLE 4-continued

| Int. No. | Structure |
|---|---|
| 48 | 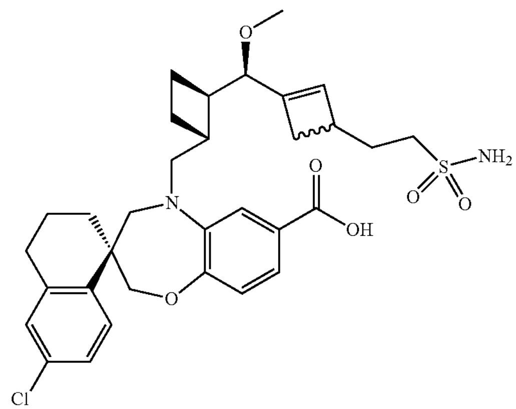 [SMILES: CO[C@@H](C1=CC(CCS(N)(=O)=O)C1)[C@@H]1CC[C@H]1CN1C[C@@]2(CCCc3cc(Cl)ccc32)COc2ccc(C(=O)O)cc21] |
| 49 | 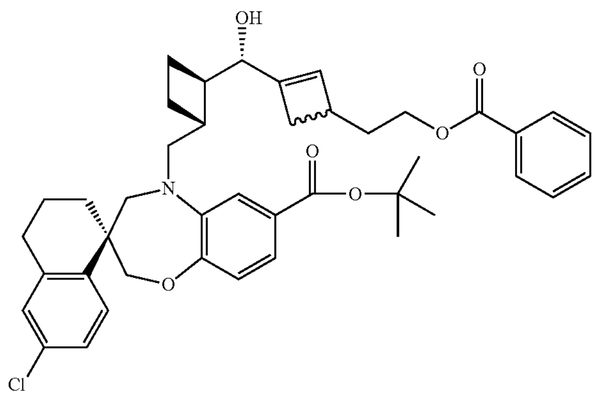 [SMILES: CC(C)(C)OC(=O)c1ccc2c(c1)N(C[C@@H]1CC[C@H]1[C@H](O)C1=CC(CCOC(=O)c3ccccc3)C1)C[C@@]1(CCCc3cc(Cl)ccc31)CO2] |
| 50 | 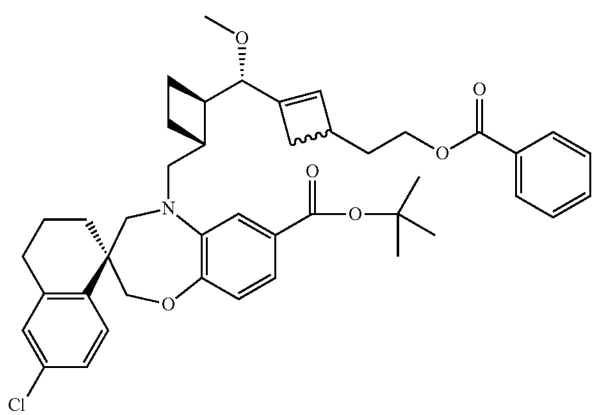 [SMILES: CO[C@H](C1=CC(CCOC(=O)c2ccccc2)C1)[C@@H]1CC[C@H]1CN1C[C@@]2(CCCc3cc(Cl)ccc32)COc2ccc(C(=O)OC(C)(C)C)cc21] |
| 51 | 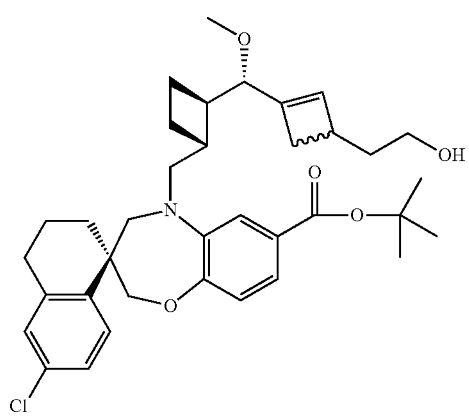 [SMILES: CO[C@H](C1=CC(CCO)C1)[C@@H]1CC[C@H]1CN1C[C@@]2(CCCc3cc(Cl)ccc32)COc2ccc(C(=O)OC(C)(C)C)cc21] |

TABLE 4-continued
| Int. No. | Structure |
|---|---|
| 52 | 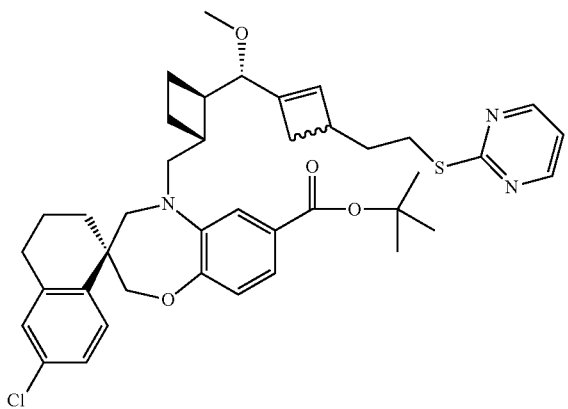 [SMILES: CO[C@H](C1=CC(CCSc2ncccn2)C1)[C@@H]1CC[C@H]1CN1C[C@@]2(CCCc3cc(Cl)ccc32)COc2ccc(C(=O)OC(C)(C)C)cc21] |
| 53 | 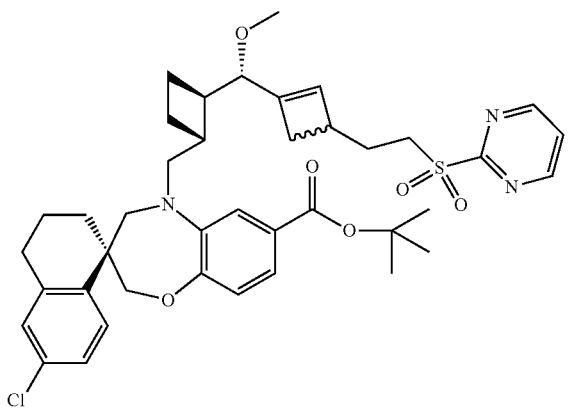 [SMILES: CO[C@H](C1=CC(CCS(=O)(=O)c2ncccn2)C1)[C@@H]1CC[C@H]1CN1C[C@@]2(CCCc3cc(Cl)ccc32)COc2ccc(C(=O)OC(C)(C)C)cc21] |
| 54 | 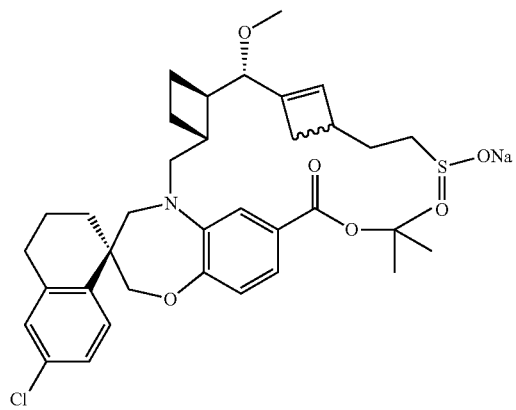 |

TABLE 4-continued
| Int. No. | Structure |
| --- | --- |
| 55 | 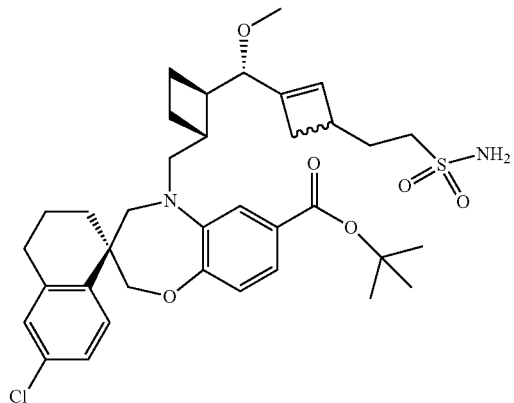 [SMILES: CO[C@H](C1=CC(CCS(N)(=O)=O)C1)[C@@H]1CC[C@H]1CN1C[C@@]2(CCCc3cc(Cl)ccc32)COc2ccc(C(=O)OC(C)(C)C)cc21] |
| 56 | 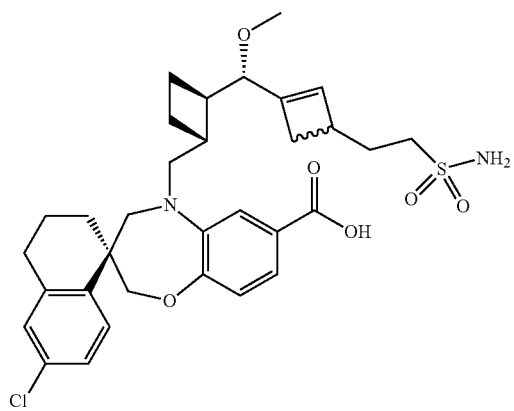 [SMILES: CO[C@H](C1=CC(CCS(N)(=O)=O)C1)[C@@H]1CC[C@H]1CN1C[C@@]2(CCCc3cc(Cl)ccc32)COc2ccc(C(=O)O)cc21] |
| 57 | 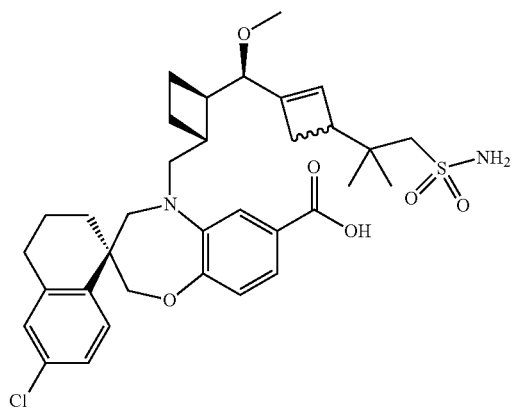 [SMILES: CO[C@@H](C1=CC(C(C)(C)CS(N)(=O)=O)C1)[C@@H]1CC[C@H]1CN1C[C@@]2(CCCc3cc(Cl)ccc32)COc2ccc(C(=O)O)cc21] |

TABLE 4-continued
| Int. No. | Structure |
| --- | --- |
| 58 | 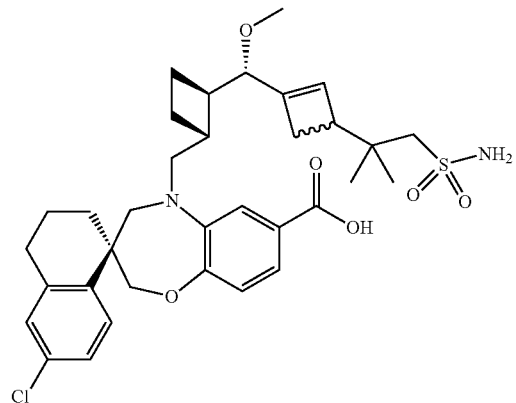 [SMILES: CO[C@H](C1=CC(C(C)(C)CS(N)(=O)=O)C1)[C@@H]1CC[C@H]1CN1C[C@@]2(CCCc3cc(Cl)ccc32)COc2ccc(C(=O)O)cc21] |
| 59 | 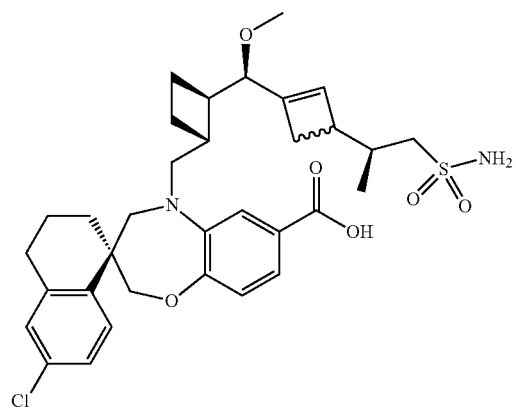 [SMILES: CO[C@@H](C1=CC([C@H](C)CS(N)(=O)=O)C1)[C@@H]1CC[C@H]1CN1C[C@@]2(CCCc3cc(Cl)ccc32)COc2ccc(C(=O)O)cc21] |
| 60 | 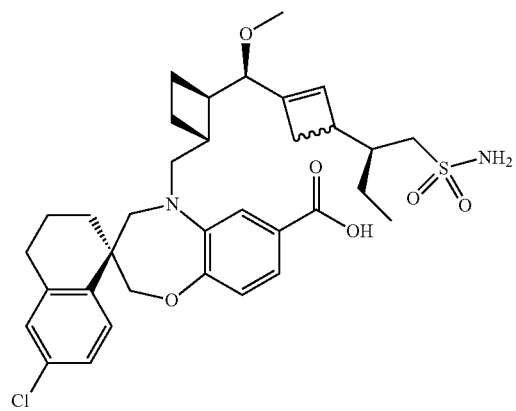 [SMILES: CC[C@H](CS(N)(=O)=O)C1C=C([C@H](OC)[C@@H]2CC[C@H]2CN2C[C@@]3(CCCc4cc(Cl)ccc43)COc3ccc(C(=O)O)cc32)C1] |

TABLE 4-continued
| Int. No. | Structure |
|---|---|
| 61 | 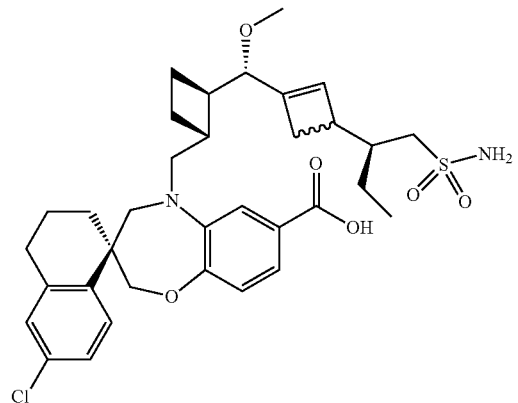 [SMILES: CC[C@H](CS(N)(=O)=O)C1C=C([C@@H](OC)[C@@H]2CC[C@H]2CN2C[C@@]3(CCCc4cc(Cl)ccc43)COc3ccc(C(=O)O)cc32)C1] |
| 62 | 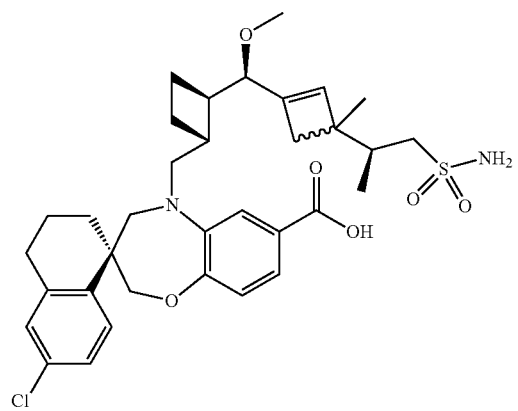 [SMILES: CO[C@@H](C1=CC(C)([C@H](C)CS(N)(=O)=O)C1)[C@@H]1CC[C@H]1CN1C[C@@]2(CCCc3cc(Cl)ccc32)COc2ccc(C(=O)O)cc21] |
| 63 | 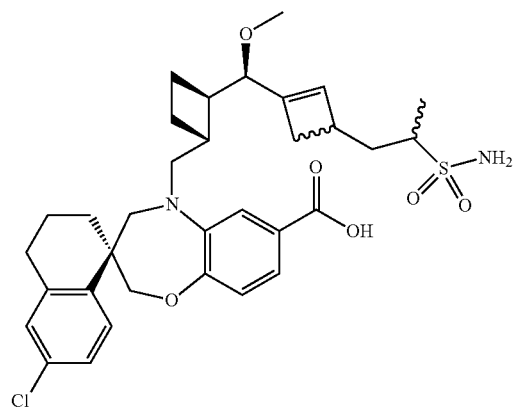 [SMILES: CO[C@@H](C1=CC(CC(C)S(N)(=O)=O)C1)[C@@H]1CC[C@H]1CN1C[C@@]2(CCCc3cc(Cl)ccc32)COc2ccc(C(=O)O)cc21] |

TABLE 4-continued
| Int. No. | Structure |
| --- | --- |
| 64 | 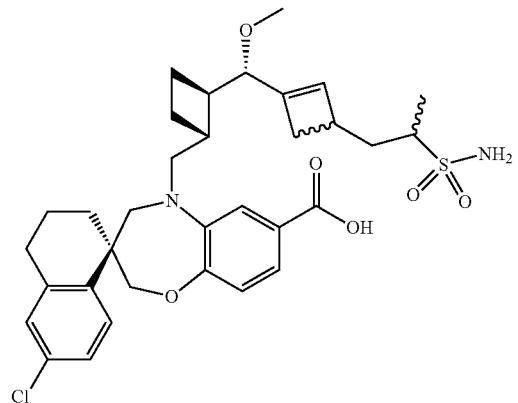 [SMILES: CO[C@H](C1=CC(CC(C)S(N)(=O)=O)C1)[C@@H]1CC[C@H]1CN1C[C@@]2(CCCc3cc(Cl)ccc32)COc2ccc(C(=O)O)cc21] |
| 65 (isomer 1) | 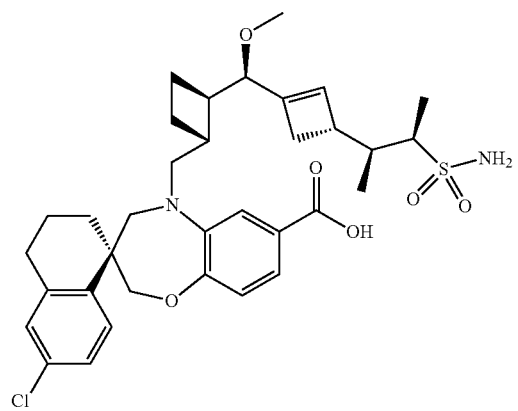 [SMILES: CO[C@@H](C1=C[C@H]([C@H](C)[C@@H](C)S(N)(=O)=O)C1)[C@@H]1CC[C@H]1CN1C[C@@]2(CCCc3cc(Cl)ccc32)COc2ccc(C(=O)O)cc21] |
| 65 (isomer 2) | 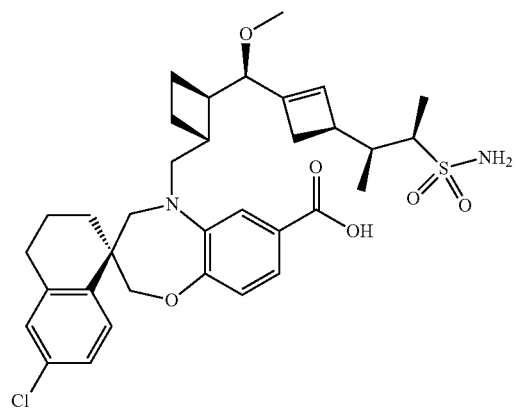 [SMILES: CO[C@@H](C1=C[C@@H]([C@H](C)[C@@H](C)S(N)(=O)=O)C1)[C@@H]1CC[C@H]1CN1C[C@@]2(CCCc3cc(Cl)ccc32)COc2ccc(C(=O)O)cc21] |

TABLE 4-continued
| Int. No. | Structure |
|---|---|
| 67 | 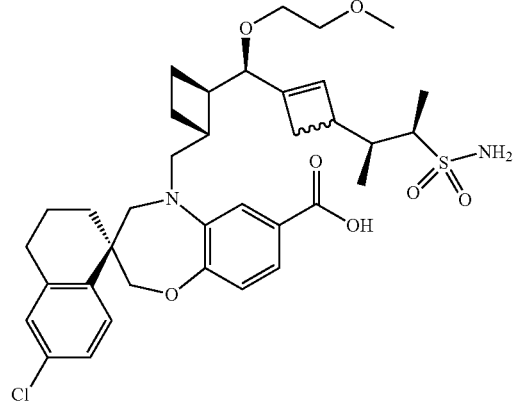 [SMILES: COCCO[C@@H](C1=CC([C@H](C)[C@@H](C)S(N)(=O)=O)C1)[C@@H]1CC[C@H]1CN1C[C@@]2(CCCc3cc(Cl)ccc32)COc2ccc(C(=O)O)cc21] |
| 68 (isomer 1) | 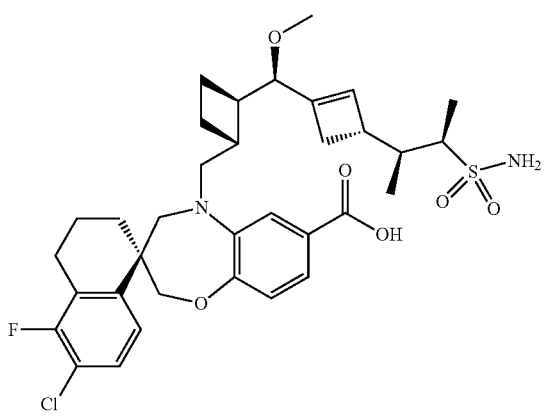 [SMILES: CO[C@@H](C1=C[C@H]([C@H](C)[C@@H](C)S(N)(=O)=O)C1)[C@@H]1CC[C@H]1CN1C[C@@]2(CCCc3c2ccc(Cl)c3F)COc2ccc(C(=O)O)cc21] |
| 68 (isomer 2) | 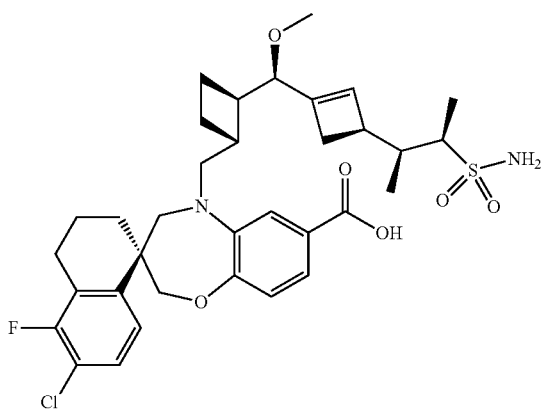 [SMILES: CO[C@@H](C1=C[C@@H]([C@H](C)[C@@H](C)S(N)(=O)=O)C1)[C@@H]1CC[C@H]1CN1C[C@@]2(CCCc3c2ccc(Cl)c3F)COc2ccc(C(=O)O)cc21] |

TABLE 4-continued
| Int. No. | Structure |
|---|---|
| 70 | 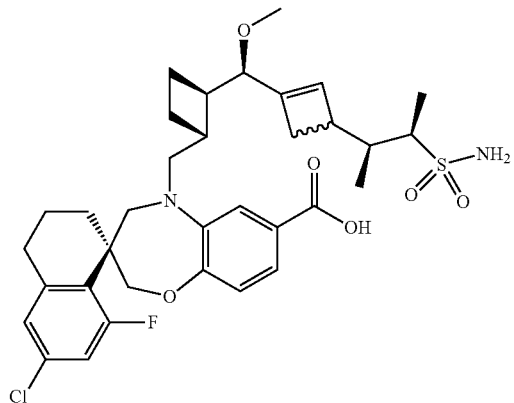 [SMILES: CO[C@@H](C1=CC([C@H](C)[C@@H](C)S(N)(=O)=O)C1)[C@@H]1CC[C@H]1CN1C[C@@]2(CCCc3cc(Cl)cc(F)c32)COc2ccc(C(=O)O)cc21] |
| 71 | 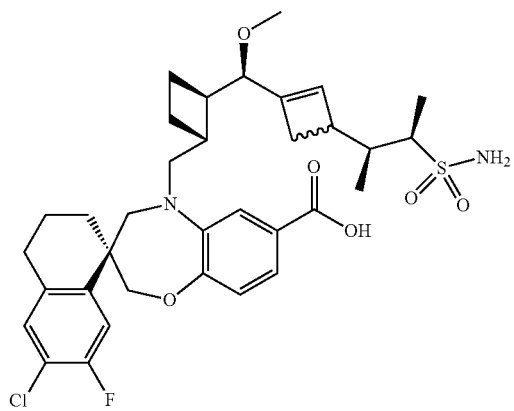 [SMILES: CO[C@@H](C1=CC([C@H](C)[C@@H](C)S(N)(=O)=O)C1)[C@@H]1CC[C@H]1CN1C[C@@]2(CCCc3cc(Cl)c(F)cc32)COc2ccc(C(=O)O)cc21] |
| 72 | 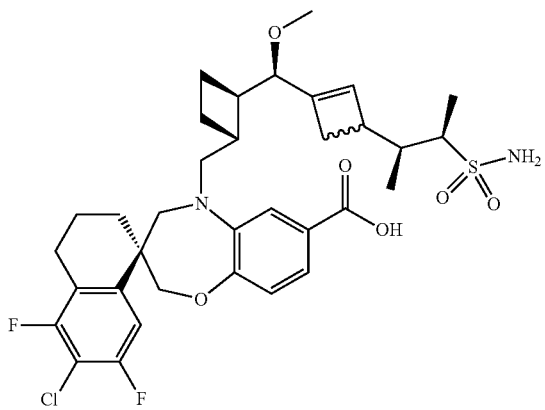 [SMILES: CO[C@@H](C1=CC([C@H](C)[C@@H](C)S(N)(=O)=O)C1)[C@@H]1CC[C@H]1CN1C[C@@]2(CCCc3c2cc(F)c(Cl)c3F)COc2ccc(C(=O)O)cc21] |

In another embodiment, Intermediates of the Disclosure are compounds of Formula XVIII-A selected from group consisting of the compounds of Table 4-A.

TABLE 4-A

| Int. No. | Structure |
|---|---|
| 73 | 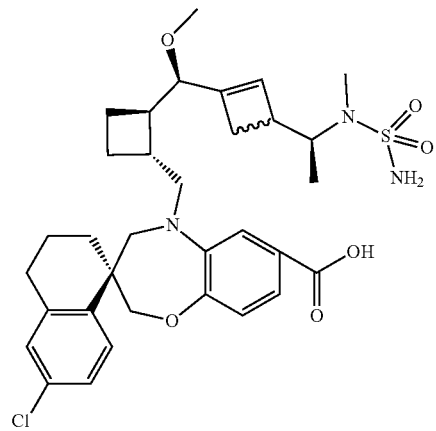 [SMILES: CO[C@@H](C1=CC([C@H](C)N(C)S(N)(=O)=O)C1)[C@@H]1CC[C@H]1CN1C[C@@]2(CCCc3cc(Cl)ccc32)COc2ccc(C(=O)O)cc21] |
| 74 | 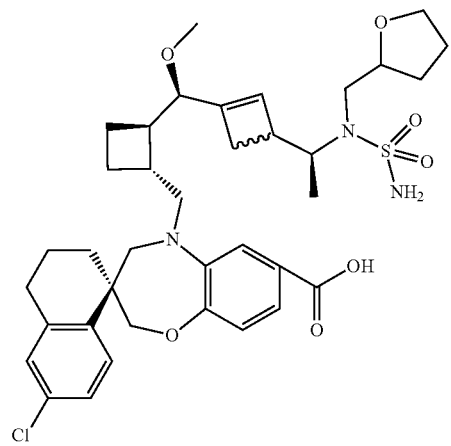 [SMILES: CO[C@@H](C1=CC([C@H](C)N(CC2CCCO2)S(N)(=O)=O)C1)[C@@H]1CC[C@H]1CN1C[C@@]2(CCCc3cc(Cl)ccc32)COc2ccc(C(=O)O)cc21] |
| 75 | 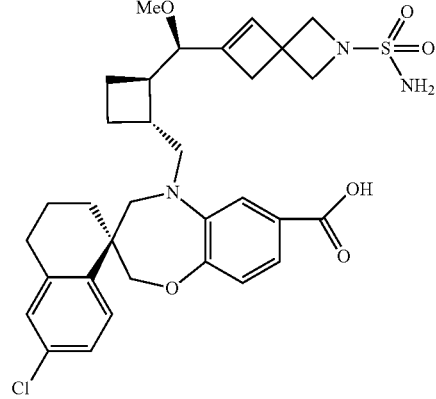 [SMILES: CO[C@@H](C1=CC2(C1)CN(S(N)(=O)=O)C2)[C@@H]1CC[C@H]1CN1C[C@@]2(CCCc3cc(Cl)ccc32)COc2ccc(C(=O)O)cc21] |

TABLE 4-A-continued

| Int. No. | Structure |
|---|---|
| 76 | 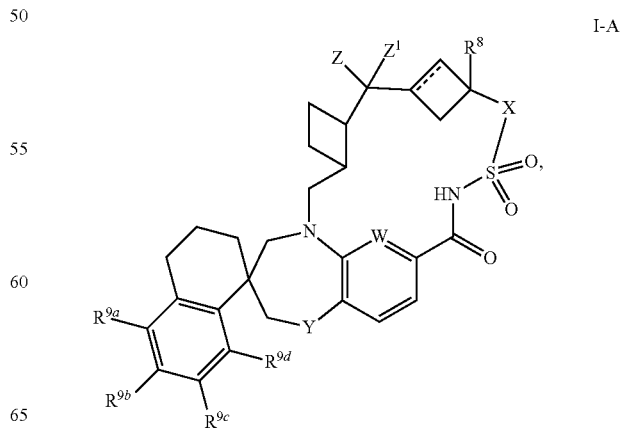 |
| 77 | 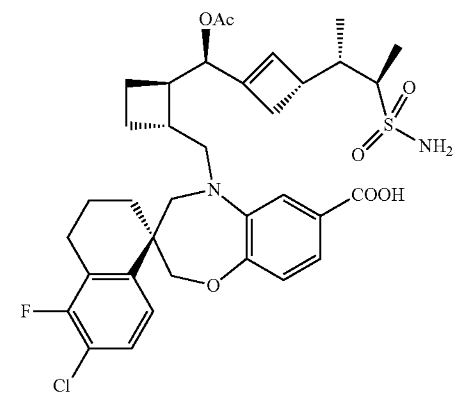 [SMILES: CC(=O)O[C@@H](C1=C[C@H]([C@H](C)[C@@H](C)S(N)(=O)=O)C1)[C@@H]1CC[C@H]1CN1C[C@@]2(CCCc3c2ccc(Cl)c3F)COc2ccc(C(=O)O)cc21] |

III. Methods of Preparing Compounds and Intermediates of the Disclosure

The disclosure also provides methods of preparing Compounds of the Disclosure and/or Intermediates of the Disclosure.

In one embodiment (referred to as process Embodiment I or "Embodiment (P) I"), the disclosure provides a method for preparing a compound of Formula I-A:

I-A wherein $R^8$, $R^{9a}$, $R^{9b}$, $R^{9c}$, $R^{9d}$, X, Y, W, Z, $Z^1$, and ⚌ are as defined above in connection with Embodiment 1, the method comprising cyclizing a compound of Formula XVIII-A:

XVIII-A wherein:

$R^{10}$ is hydrogen;

$R^{11}$ is —SO$_2$NH$_2$; and $R^8$, $R^{9a}$, $R^{9b}$, $R^{9c}$, $R^{9d}$, X, Y, W, Z, $Z^1$, and ⚌ are as defined above in connection with Embodiment 1, in a solvent to give the compound of Formula I-A.

In another embodiment, the method further comprises isolating the compound of Formula I-A.

The following particular embodiments are also drawn to methods of preparing Compounds of the Disclosure and/or Intermediates of the Disclosure.

Embodiment (P) II. The method of Embodiment (P) I, wherein the cyclizing is carried out in the presence of coupling agent, e.g., 2,4,6-tripropyl-1,3,5,2,4,6-trioxatriphosphinane 2,4,6-trioxide, triethylamine, and DMAP.

Embodiment (P) III. The method of Embodiments (P) I or II, the cyclizing is carried out at a temperature of about 0° C. to about 40° C.

Embodiment (P) IV. The method of any one of Embodiments (P) I-III, wherein the solvent is dichloromethane, 1,2-dichloroethane, or ethyl acetate, or a mixture thereof.

Embodiment (P) V. The method of any one of Embodiments (P) I-IV, wherein the compound of Formula XVII-A is selected from any one of Formulae XIX-A, XX-A, XXI-A, XXII-A, XXIII-A, XXIV-A, XXV-A, XXVI-A, XXVII-A, XXVIII-A, XXIX-A, XXX-A, XXXI-A, XXXII-A, XXXIII-A, or XXXIV-A.

Embodiment (P) VI. The method of any one of Embodiments (P) I-V, wherein X-1 is selected from the group consisting of X-1-A, X-1-B, X-1-C, and X-1-D.

Embodiment (P) VII. The method of any one of Embodiments (P) I-V, wherein X-1 is selected from the group consisting of X-2-A and X-2-B.

Embodiment (P) VIII. The compound of any one of Embodiments (P) wherein Z is —OR$^1$ and $Z^1$ is hydrogen, or a pharmaceutically acceptable salt or solvate thereof.

Embodiment (P) IX. The compound of Embodiment (P) VIII, wherein $R^1$ is selected from the group consisting of (hydroxy)C$_1$-C$_4$ alkyl, (C$_1$-C$_3$ alkoxy)C$_1$-C$_3$ alkyl, (heterocyclo)C$_1$-C$_4$ alkyl, (alkylsulfonyl)C$_1$-C$_4$ alkyl, (phenyl)C$_1$-C$_4$ alkyl, (hetero aryl) C$_1$-C$_4$ alkyl, (amino)C$_1$-C$_4$ alkyl, (amido)C$_1$-C$_4$ alkyl, (carboxy)C$_1$-C$_4$ alkyl, (alkoxycarbonyl)C$_1$-C$_4$ alkyl, (aminocarbonyl)C$_1$-C$_4$ alkyl, (aminosulfonyl)C$_1$-C$_4$ alkyl, and —C(=O)R$^{15}$, or a pharmaceutically acceptable salt or solvate thereof.

Embodiment (P) X. The compound of any one of Embodiments (P) wherein Z is —R and $Z^1$ is hydrogen, or a pharmaceutically acceptable salt or solvate thereof.

Embodiment (P) XI. The compound of any one of Embodiments (P) I-VII, wherein Z is —N(R$^{1a}$)(R$^{1b}$) and $Z^1$ is hydrogen, or a pharmaceutically acceptable salt or solvate thereof.

Embodiment (P) XII. The compound of any one of Embodiments (P) I-VII, wherein:

Z is —OR$^1$;

$R^1$ is selected from the group consisting of hydrogen and C$_1$-C$_3$ alkyl; and $Z^1$ is selected from the group consisting of (hydroxy)C$_1$-C$_4$ alkyl, (C$_1$-C$_3$ alkoxy)C$_1$-C$_3$ alkyl, (heterocyclo)C$_1$-C$_4$ alkyl, (alkylsulfonyl)C$_1$-C$_4$ alkyl, (phenyl)C$_1$-C$_4$ alkyl, (heteroaryl) C$_1$-C$_4$ alkyl, (amino)C$_1$-C$_4$ alkyl, (amido)C$_1$-C$_4$ alkyl, (carboxy)C$_1$-C$_4$ alkyl, (alkoxycarbonyl)C$_1$-C$_4$ alkyl, (aminocarbonyl)C$_1$-C$_4$ alkyl, (aminosulfonyl)C$_1$-C$_4$ alkyl, and —C(=O)R$^{15}$, or a pharmaceutically acceptable salt or solvate thereof.

Embodiment (P) XIII The compound of any one of Embodiments (P) wherein W is —CH=, or a pharmaceutically acceptable salt or solvate thereof.

Embodiment (P) XIV. The compound of any one of Embodiments (P) wherein W is —N=, or a pharmaceutically acceptable salt or solvate thereof.

Embodiment (P) XV. The compound of any one of Embodiments (P) I-XIV, wherein $R^{3c}$ is selected from the group consisting of hydrogen, C$_1$-C$_4$ alkyl, and (heterocyclo)C$_1$-C$_4$ alkyl, or a pharmaceutically acceptable salt or solvate thereof.

Embodiment (P) XVI. The compound of any one of Embodiments (P) I-XV, wherein $R^{10}$ is hydrogen, or a pharmaceutically acceptable salt or solvate thereof.

Embodiment (P) XVII. The method of Embodiment (P) I, wherein the compound of Formula XVIII-A is one or more of the compounds of Table 4-A.

In one embodiment (referred to as process Embodiment XVIII or "Embodiment (P) XVIII"), the disclosure provides a method for preparing a compound of Formula I:

I wherein $R^8$, $R^{9a}$, $R^{9b}$, $R^{9c}$, $R^{9d}$, X, Y, Z, and ⚌ are as defined above in connection with Embodiment 16, the method comprising cyclizing a compound of Formula XVIII:

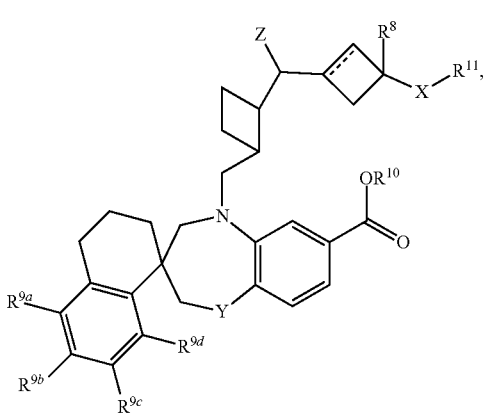

XVIII wherein:
R$^{10}$ is hydrogen;
R$^{11}$ is —SO$_2$NH$_2$; and
R$^8$, R$^{9a}$, R$^{9b}$, R$^{9c}$, R$^{9d}$, X, Y, Z, and ═══ are as defined above in connection with Embodiment 16,
in a solvent to give the compound of Formula I.

In another embodiment, the method further comprises isolating the compound of Formula I.

The following particular embodiments are also drawn to methods of preparing Compounds of the Disclosure and/or Intermediates of the Disclosure.

Embodiment (P) XIX. The method of Embodiment (P) XVIII, wherein the cyclizing is carried out in the presence of coupling agent, e.g., 2,4,6-tripropyl-1,3,5,2,4,6-trioxatriphosphinane 2,4,6-trioxide, triethylamine, and DMAP.

Embodiment (P) XX. The method of Embodiments (P) XVIII or XIX, the cyclizing is carried out at a temperature of about 0° C. to about 40° C.

Embodiment (P) XXI. The method of any one of Embodiments (P) XVIII-XX, wherein the solvent is dichloromethane, 1,2-dichloroethane, or ethyl acetate, or a mixture thereof.

Embodiment (P) XXII. The method of any one of Embodiments (P) XVIII-XXI, wherein the compound of Formula XVII is selected from the group consisting of Formula XIX-XXXIV.

Embodiment (P) XXIII The method of any one of Embodiments (P) XVIII-XXII, wherein X-1 is selected from the group consisting of X-1-A, X-1-B, X-1-C, and X-1-D.

Embodiment (P) XXIV. The method of Embodiment (P) XXIII, wherein the compound of Formula XVII is one or more of the compounds of Table 4.

Embodiment (P) XXV. The method of any one of Embodiments (P) XVIII-XXIV, wherein Z is —OR$^1$.

Embodiment (P) XXVI. The method of any one of Embodiments (P) XVIII-XXV, wherein R$^1$ is methyl.

Embodiment (P) XXVII. The method of any one of Embodiments (P) XVIII-XXV, wherein R$^1$ is —CH$_2$CH$_2$OCH$_3$.

Embodiment (P) XXVIII. The method of any one of Embodiments (P) XVIII-XXVII, wherein R$^{2a}$ is hydrogen.

Embodiment (P) XXIX. The method of any one of Embodiments (P) XVIII-XXVII, wherein R$^{2a}$ is methyl.

Embodiment (P) XXX. The method of any one of Embodiments (P) XVIII-XXVII, wherein R$^{2a}$ is ethyl.

Embodiment (P) XXXI. The method of any one of Embodiments (P) XVIII-XXX, wherein R$^{2b}$ is hydrogen.

Embodiment (P) XXXII. The method of any one of Embodiments (P) XVIII-XXX, wherein R$^{2b}$ is methyl.

Embodiment (P) XXXIII. The method of any one of Embodiments (P) XVIII-XXXII, wherein R$^{3a}$ is hydrogen.

Embodiment (P) XXXIV. The method of any one of Embodiments (P) XVIII-XXXII, wherein R$^{3a}$ is methyl.

Embodiment (P) XXXV. The method of any one of Embodiments (P) XVIII-XXXIV, wherein R$^{3b}$ is hydrogen.

Embodiment (P) XXXVI. The method of any one of Embodiments (P) XVIII-XXXIV, wherein R$^{3b}$ is methyl.

Embodiment (P) XXXVII. The method of any one of Embodiments (P) XVIII-XXIII, wherein R$^{2a}$ and R$^{3a}$ taken together with the carbon atoms to which they are attached form a C$_3$-C$_6$ cycloalkyl or 4- to 7-membered heterocyclo.

Embodiment (P) XXXVIII. The method of any one of Embodiments (P) XVIII-XXXVII, wherein R$^8$ is hydrogen.

Embodiment (P) XXXIX. The method of any one of Embodiments (P) XVIII-XXXVII, wherein R$^8$ is methyl.

Embodiment (P) XL. The method of any one of Embodiments (P) XVIII-XXXIX, wherein R$^{9b}$ is chloro.

Embodiment (P) XLI. The method of any one of Embodiments (P) XVIII-XL, wherein R$^{9a}$ and R$^{9c}$ are independently selected from the group consisting of hydrogen and fluoro.

Embodiment (P) XLII. The method of any one of Embodiments (P) IXVIII-XLI, wherein R$^{9d}$ is hydrogen.

Embodiment (P) XLIII. The method of any one of Embodiments (P) XVIII-XLII, wherein ═══ represents a single bond.

Embodiment (P) XLIV. The method of any one of Embodiments (P) XVIII-XLII, wherein ═══ represents a double bond.

Embodiment (P) XLV. The method of any one of Embodiments (P) XVIII-XLIV, wherein Y is —O—.

Embodiment (P) XLVI. The method of any one of Embodiments (P) XVIII-XLIV, wherein Y is —S—.

IV. Methods of Treating Disease with Compounds of the Disclosure

Compounds of the Disclosure inhibit Mcl-1 and are useful in the treatment or prevention of a variety of diseases and conditions. In particular, Compounds of the Disclosure are useful in methods of treating or preventing a disease or condition wherein inhibition of Mcl-1 provides a benefit, for example, cancers and proliferative diseases. In one embodiment, such a cancer is referred to as a "Mcl-1 mediated cancer." Cancers responsive to Mcl-1 inhibition are known in the art. The therapeutic methods of this disclosure comprise administering a therapeutically effective amount of a Compound of the Disclosure to a subject in need thereof. The present methods also encompass administering a second therapeutic agent to the subject in addition to the Compound of the Disclosure. The second therapeutic agent is selected from drugs known as useful in treating the disease or condition afflicting the subject in need thereof, e.g., a chemotherapeutic agent and/or radiation known as useful in treating a particular cancer.

The present disclosure provides Compounds of the Disclosure as Mcl-1 inhibitors for the treatment of diseases and conditions wherein inhibition of Mcl-1 has a beneficial effect. Compounds of the Disclosure typically have a half maximal inhibitory concentration (IC$_{50}$) for inhibiting Mcl-1 of less than 100 μM, e.g., less than 50 μM, less than 25 μM, and less than 5 μM, less than about 1 less than about 0.5 less than about 0.1 μM, less than about 0.05 μM, or less than about 0.01 µM. In one embodiment, the present disclosure relates to a method of treating an individual suffering from a disease or condition wherein inhibition of Mcl-1 provides a benefit comprising administering a therapeutically effective amount of a Compound of the Disclosure to an individual in need thereof.

Since Compounds of the Disclosure are inhibitors of Mcl-1 protein, a number of diseases and conditions mediated by Mcl-1 can be treated by employing these compounds. The present disclosure is thus directed generally to a method for treating a condition or disorder responsive to Mcl-1 inhibition in an animal, e.g., a human, suffering from, or at risk of suffering from, the condition or disorder, the method comprising administering to the animal an effective amount of one or more Compounds of the Disclosure.

The present disclosure is further directed to a method of inhibiting Mcl-1 in a subject in need thereof, said method comprising administering to the animal an effective amount of at least one Compound of the Disclosure.

The methods of the present disclosure can be accomplished by administering a Compound of the Disclosure as the neat compound or as a pharmaceutical composition. Administration of a pharmaceutical composition, or neat compound of a Compound of the Disclosure, can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a Compound of the Disclosure and, optionally, a second therapeutic agent, packaged separately or together, and an insert having instructions for using these active agents.

In one embodiment, a Compound of the Disclosure is administered in conjunction with a second therapeutic agent useful in the treatment of a disease or condition wherein inhibition of Mcl-1 provides a benefit. The second therapeutic agent is different from the Compound of the Disclosure. A Compound of the Disclosure and the second therapeutic agent can be administered simultaneously or sequentially to achieve the desired effect. In addition, the Compound of the Disclosure and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A Compound of the Disclosure and the second therapeutic agent can be administered together as a single-unit dose or separately as multi-unit doses, wherein the Compound of the Disclosure is administered before the second therapeutic agent or vice versa. One or more doses of the Compound of the Disclosure and/or one or more dose of the second therapeutic agent can be administered. The Compound of the Disclosure therefore can be used in conjunction with one or more second therapeutic agents, for example, but not limited to, anticancer agents.

Diseases and conditions treatable by the methods of the present disclosure include, but are not limited to, cancer and other proliferative disorders, inflammatory diseases, sepsis, autoimmune disease, and viral infection. In one embodiment, a human patient is treated with a Compound of the Disclosure, or a pharmaceutical composition comprising a Compound of the Disclosure, wherein the compound is administered in an amount sufficient to inhibit Mcl-1 activity in the patient.

In another aspect, the present disclosure provides a method of treating cancer in a subject comprising administering a therapeutically effective amount of a Compound of the Disclosure. While not being limited to a specific mechanism, in some embodiments, Compounds of the Disclosure treat cancer by inhibiting Mcl-1. Examples of treatable cancers include, but are not limited to, any one or more of the cancers of Table 5.

TABLE 5

| | | | |
|---|---|---|---|
| adrenal cancer | acinic cell carcinoma | acoustic neuroma | acral lentigious melanoma |
| acrospiroma | acute eosinophilic leukemia | acute erythroid leukemia | acute lymphoblastic leukemia |
| acute megakaryobiastic leukemia | acute monocytic leukemia | acute promyelocytic leukemia | adenocarcinoma |
| adenoid cystic carcinoma | adenoma | adenomatoid odontogenic tumor | adenosquamous carcinoma |
| adipose tissue neoplasm | adrenocortical carcinoma | adult T-cell leukemia/lymphoma | aggressive NK-cell leukemia |
| AIDS-related lymphoma | alveolar rhabdomyosarcoma | alveolar soft part sarcoma | ameloblastic fibroma |
| anaplastic large cell lymphoma | anaplastic thyroid cancer | angioimmunoblastic T-cell lymphoma | angiomyolipoma |
| angiosarcoma | astrocytoma | atypical teratoid rhabdoid tumor | B-cell chronic lymphocytic leukemia |
| B-cell prolymphocytic leukemia | B-cell lymphoma | basal cell carcinoma | biliary tract cancer |
| bladder cancer | blastoma | bone cancer | Brenner tumor |
| Brown tumor | Burkitt's lymphoma | breast cancer | brain cancer |
| carcinoma | carcinoma in situ | carcinosarcoma | cartilage tumor |
| cementoma | myeloid sarcoma | chondroma | chordoma |
| choriocarcinoma | choroid plexus papilloma | clear-cell sarcoma of the kidney | craniopharyngioma |
| cutaneous T-cell lymphoma | cervical cancer | colorectal cancer | Degos disease |

TABLE 5-continued

| | | | |
|---|---|---|---|
| desmoplastic small round cell tumor | diffuse large B-cell lymphoma | dysembryoplastic neuroepithelial tumor | dysgerminoma |
| embryonal carcinoma | endocrine gland neoplasm | endodermal sinus tumor | enteropathy-associated T-cell lymphoma |
| esophageal cancer | fetus in fetu | fibroma | fibrosarcoma |
| follicular lymphoma | follicular thyroid cancer | ganglioneuroma | gastrointestinal cancer |
| germ cell tumor | gestational choriocarcinoma | giant cell fibroblastoma | giant cell tumor of the bone |
| glial tumor | glioblastoma multiforme | glioma | gliomatosis cerebri |
| glucagonoma | gonadoblastoma | granulosa cell tumor | gynandroblastoma |
| gallbladder cancer | gastric cancer | hairy cell leukemia | hemangioblastoma |
| head and neck cancer | hemangiopericytoma | hematological cancer | hepatoblastoma |
| hepatosplenic T-cell lymphoma | Hodgkin's lymphoma | non-Hodgkin's lymphoma | invasive lobular carcinoma |
| intestinal cancer | kidney cancer | laryngeal cancer | lentigo maligna |
| lethal midline carcinoma | leukemia | leydig cell tumor | liposarcoma |
| lung cancer | lymphangioma | lymphangiosarcoma | lymphoepithelioma |
| lymphoma | acute lymphocytic leukemia | acute myelogeous leukemia | chronic lymphocytic leukemia |
| liver cancer | small cell lung cancer | non-small cell lung cancer | MALT lymphoma |
| malignant fibrous histiocytoma | malignant peripheral nerve sheath tumor | malignant triton tumor | mantle cell lymphoma |
| marginal zone B-cell lymphoma | mast cell leukemia | mediastinal germ cell tumor | medullary carcinoma of the breast |
| medullary thyroid cancer | medulloblastoma | melanoma | meningioma |
| merkel cell cancer | mesothelioma | metastatic urothelial carcinoma | mixed Mullerian tumor |
| mucinous tumor | multiple myeloma | muscle tissue neoplasm | mycosis fungoides |
| myxoid liposarcoma | myxoma | myxosarcoma | nasopharyngeal carcinoma |
| neurinoma | neuroblastoma | neurofibroma | neuroma |
| nodular melanoma | ocular cancer | oligoastrocytoma | oligodendroglioma |
| oncocytoma | optic nerve sheath meningioma | optic nerve tumor | oral cancer |
| osteosarcoma | ovarian cancer | Pancoast tumor | papillary thyroid cancer |
| paraganglioma | pinealoblastoma | pineocytoma | pituicytoma |
| pituitary adenoma | pituitary tumor | plasmacytoma | polyembryoma |
| precursor T-lymphoblastic lymphoma | primary central nervous system lymphoma | primary effusion lymphoma | preimary peritoneal cancer |
| prostate cancer | pancreatic cancer | pharyngeal cancer | pseudomyxoma periotonei |
| renal cell carcinoma | renal medullary carcinoma | retinoblastoma | rhabdomyoma |
| rhabdomyosarcoma | Richter's transformation | rectal cancer | sarcoma |
| Schwannomatosis | seminoma | Sertoli cell tumor | sex cord-gonadal stromal tumor |
| signet ring cell carcinoma | skin cancer | small blue round cell tumors | small cell carcinoma |
| soft tissue sarcoma | somatostatinoma | soot wart | spinal tumor |
| splenic marginal zone lymphoma | squamous cell carcinoma | synovial sarcoma | Sezary's disease |
| small intestine cancer | squamous carcinoma | stomach cancer | T-cell lymphoma |
| testicular cancer | thecoma | thyroid cancer | transitional cell carcinoma |
| throat cancer | urachal cancer | urogenital cancer | urothelial carcinoma |
| uveal melanoma | uterine cancer | verrucous carcinoma | visual pathway glioma |
| vulvar cancer | vaginal cancer | Waldenstrom's macroglobulinemia | Warthin's tumor |
| Wilms' tumor | | | |

In another embodiment, the cancer is a solid tumor. In another embodiment, the cancer a hematological cancer. Exemplary hematological cancers include, but are not limited to, the cancers listed in Table 6. In another embodiment, the hematological cancer is acute lymphocytic leukemia, chronic lymphocytic leukemia (including B-cell chronic lymphocytic leukemia), or acute myeloid leukemia.

TABLE 6

| | |
|---|---|
| acute lymphocytic leukemia (ALL) | acute eosinophilic leukemia |
| acute myeloid leukemia (AML) | acute erythroid leukemia |
| chronic lymphocytic leukemia (CLL) | acute lymphoblastic leukemia |
| small lymphocytic lymphoma (SLL) | acute megakaryoblastic leukemia |
| multiple myeloma (MM) | acute monocytic leukemia |
| Hodgkins lymphoma (HL) | acute promyelocytic leukemia |
| non-Hodgkin's lymphoma (NHL) | acute myelogeous leukemia |
| mantle cell lymphoma (MCL) | B-cell prolymphocytic leukemia |
| marginal zone B-cell lymphoma | B-cell lymphoma |
| splenic marginal zone lymphoma | MALT lymphoma |
| follicular lymphoma (FL) | precursor T-lymphoblastic lymphoma |
| Waldenstrom's macroglobulinemia (WM) | T-cell lymphoma |
| diffuse large B-cell lymphoma (DLBCL) | mast cell leukemia |
| marginal zone lymphoma (MZL) | adult T cell leukemia/lymphoma |
| hairy cell leukemia (HCL) | aggressive NK-cell leukemia |
| Burkitt's lymphoma (BL) | angioimmunoblastic T-cell lymphoma |
| Richter's transformation | |

In another embodiment, the cancer is a leukemia, for example a leukemia selected from acute monocytic leukemia, acute myelogenous leukemia, chronic myelogenous leukemia, chronic lymphocytic leukemia and mixed lineage leukemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is colorectal cancer. In another embodiment, the cancer is prostate cancer. In another embodiment, the cancer is breast cancer.

In another embodiment, the cancer is selected from the group consisting of acute monocytic leukemia, acute myelogenous leukemia, chronic myelogenous leukemia, chronic lymphocytic leukemia mixed lineage leukemia, NUT-midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

In another embodiment, the present disclosure provides a method of treating a benign proliferative disorder, such as, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

Compounds of the Disclosure can also treat infectious and noninfectious inflammatory events and autoimmune and other inflammatory diseases by administration of an effective amount of a present compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituatarism, Guillain-Barre syndrome, Behcet's disease, scleracierma, mycosis fungoides, acute inflammatory responses (such as acute respiratory distress syndrome and ischemia/reperfusion injury), and Graves' disease.

In another embodiment, the present disclosure provides a method of treating systemic inflammatory response syndromes, such as LPS-induced endotoxic shock and/or bacteria-induced sepsis by administration of an effective amount of a Compound of the Disclosure to a mammal, in particular a human in need of such treatment.

In another embodiment, the present disclosure provides a method for treating viral infections and diseases. Examples of viral infections and diseases treated using the compounds and methods described herein include episome-based DNA viruses including, but not limited to, human papillomavirus, Herpesvirus, Epstein-Barr virus, human immunodeficiency virus, hepatitis B virus, and hepatitis C virus.

In another embodiment, the present disclosure provides therapeutic method of modulating protein methylation, gene expression, cell proliferation, cell differentiation and/or apoptosis in vivo in diseases mentioned above, in particular cancer, inflammatory disease, and/or viral disease is provided by administering a therapeutically effective amount of a Compound of the Disclosure to a subject in need of such therapy.

In another embodiment, the present disclosure provides a method of regulating endogenous or heterologous promoter activity by contacting a cell with a Compound of the Disclosure.

In methods of the present disclosure, a therapeutically effective amount of a Compound of the Disclosure, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A Compound of the Disclosure can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a Compound of the Disclosure is administered in an effective amount to achieve its intended purpose. The exact formulation, route of administration, and dosage is determined by an individual physician in view of the diagnosed condition or disease. Dosage amount and interval can be adjusted individually to provide levels of a Compound of the Disclosure that is sufficient to maintain therapeutic effects.

Toxicity and therapeutic efficacy of the Compounds of the Disclosure can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a Compound of the Disclosure required for use in therapy varies with the nature of the condition being treated, the length of time that activity is desired, and the age and the condition of the patient, and ultimately is determined by the attendant physician. Dosage amounts and intervals can be adjusted individually to provide plasma levels of the Mcl-1 inhibitor that are sufficient to maintain the desired therapeutic effects. The desired dose can be administered in a single dose, or as multiple doses administered at appropriate intervals, for example as one, two, three, four or more subdoses per day. Multiple doses often are desired, or required. For example, a Compound of the Disclosure can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A Compound of the Disclosure used in a method of the present disclosure can be administered in an amount of about 0.005 to about 500 milligrams per dose, about 0.05 to about 250 milligrams per dose, or about 0.5 to about 100 milligrams per dose. For example, a Compound of the Disclosure can be administered, per dose, in an amount of about 0.005, about 0.05, about 0.5, about 5, about 10, about 20, about 30, about 40, about 50, about 100, about 150, about 200, about 250, about 300, about 350, about 400, about 450, or about 500 milligrams, including all doses between 0.005 and 500 milligrams.

The dosage of a composition containing a Compound of the Disclosure, or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, about 10 µg/kg, about 25 µg/kg, about 50 µg/kg, about 75 µg/kg, about 100 µg/kg, about 125 µg/kg, about 150 µg/kg, about 175 µg/kg, about 200 µg/kg, about 225 µg/kg, about 250 µg/kg, about 275 µg/kg, about 300 µg/kg, about 325 µg/kg, about 350 µg/kg, about 375 µg/kg, about 400 µg/kg, about 425 µg/kg, about 450 µg/kg, about 475 µg/kg, about 500 µg/kg, about 525 µg/kg, about 550 µg/kg, about 575 µg/kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. The above dosages are exemplary of the average case, but there can be individual instances in which higher or lower dosages are merited, and such are within the scope of this disclosure. In practice, the physician determines the actual dosing regimen that is most suitable for an individual patient, which can vary with the age, weight, and response of the particular patient.

As stated above, a Compound of the Disclosure can be administered in combination with a second therapeutically active agent. In some embodiments, the second therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

In another embodiment, chemotherapeutic agents or other anti-proliferative agents can be combined with Compound of the Disclosure to treat proliferative diseases and cancer. Examples of therapies and anticancer agents that can be used in combination with Compounds of the Disclosure include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effect (e.g., an antiemetic), and any other approved chemotherapeutic drug.

Examples of antiproliferative compounds include, but are not limited to, an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Nonlimiting exemplary aromatase inhibitors include, but are not limited to, steroids, such as atamestane, exemestane, and formestane, and non-steroids, such as aminoglutethimide, roglethimide, pyridoglutethimide, trilostane, testolactone, ketoconazole, vorozole, fadrozole, anastrozole, and letrozole.

Nonlimiting anti-estrogens include, but are not limited to, tamoxifen, fulvestrant, raloxifene, and raloxifene hydrochloride. Anti-androgens include, but are not limited to, bicalutamide. Gonadorelin agonists include, but are not limited to, abarelix, goserelin, and goserelin acetate.

Exemplary topoisomerase I inhibitors include, but are not limited to, topotecan, gimatecan, irinotecan, camptothecin and its analogues, 9-nitrocamptothecin, and the macromolecular camptothecin conjugate PNU-166148. Topoisomerase II inhibitors include, but are not limited to, anthracyclines, such as doxorubicin, daunorubicin, epirubicin, idarubicin, and nemorubicin; anthraquinones, such as mitoxantrone and losoxantrone; and podophillotoxines, such as etoposide and teniposide.

Microtubule active agents include microtubule stabilizing, microtubule destabilizing compounds, and microtubulin polymerization inhibitors including, but not limited to, taxanes, such as paclitaxel and docetaxel; vinca alkaloids, such as vinblastine, vinblastine sulfate, vincristine, and vincristine sulfate, and vinorelbine; discodermolides; cochicine and epothilones and derivatives thereof.

Exemplary nonlimiting alkylating agents include cyclophosphamide, ifosfamide, melphalan, and nitrosoureas, such as carmustine and lomustine.

Exemplary nonlimiting cyclooxygenase inhibitors include Cox-2 inhibitors, 5-alkyl substituted 2-arylaminophenylacetic acid and derivatives, such as celecoxib, rofecoxib, etoricoxib, valdecoxib, or a 5-alkyl-2-arylaminophenylacetic acid, such as lumiracoxib.

Exemplary nonlimiting matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Exemplary nonlimiting mTOR inhibitors include compounds that inhibit the mammalian target of rapamycin (mTOR) and possess antiproliferative activity such as sirolimus, everolimus, CCI-779, and ABT578.

Exemplary nonlimiting antimetabolites include 5-fluorouracil (5-FU), capecitabine, gemcitabine, DNA demethylating compounds, such as 5-azacytidine and decitabine, methotrexate and edatrexate, and folic acid antagonists, such as pemetrexed.

Exemplary nonlimiting platin compounds include carboplatin, cis-platin, cisplatinum, and oxaliplatin.

Exemplary nonlimiting methionine aminopeptidase inhibitors include bengamide or a derivative thereof and PPI-2458.

Exemplary nonlimiting bisphosphonates include etridonic acid, clodronic acid, tiludronic acid, pamidronic acid, alendronic acid, ibandronic acid, risedronic acid, and zoledronic acid.

Exemplary nonlimiting antiproliferative antibodies include trastuzumab, trastuzumab-DM1, cetuximab, bevacizumab, rituximab, PR064553, and 2C4. The term "antibody" is meant to include intact monoclonal antibodies, polyclonal antibodies, multispecific antibodies formed from at least two intact antibodies, and antibody fragments, so long as they exhibit the desired biological activity.

Exemplary nonlimiting heparanase inhibitors include compounds that target, decrease, or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras, for example, a farnesyl transferase inhibitor, such as L-744832, DK8G557, tipifarnib, and lonafarnib.

Exemplary nonlimiting telomerase inhibitors include compounds that target, decrease, or inhibit the activity of telomerase, such as compounds that inhibit the telomerase receptor, such as telomestatin.

Exemplary nonlimiting proteasome inhibitors include compounds that target, decrease, or inhibit the activity of the proteasome including, but not limited to, bortezomid.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, I-β-D-arabinofuransyl-cytosine (ara-c), and bisulfan; and ALK inhibitors, which are compounds which target, decrease, or inhibit anaplastic lymphoma kinase.

Exemplary nonlimiting Flt-3 inhibitors include PKC412, midostaurin, a staurosporine derivative, SU11248, and MLN518.

Exemplary nonlimiting HSP90 inhibitors include compounds targeting, decreasing, or inhibiting the intrinsic ATPase activity of HSP90; or degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins, or antibodies that inhibit the ATPase activity of HSP90, such as 17-allylamino,17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing, or inhibiting the activity of the platelet-derived growth factor-receptors (PDGFR), such as a compound that targets, decreases, or inhibits the activity of PDGFR, such as an N-phenyl-2-pyrimidine-amine derivatives, such as imatinib, SU101, SU6668, and GFB-111; b) a compound targeting, decreasing, or inhibiting the activity of the fibroblast growth factor-receptors (FGFR); c) a compound targeting, decreasing, or inhibiting the activity of the insulin-like growth factor receptor I (IGF-IR), such as a compound that targets, decreases, or inhibits the activity of IGF-IR; d) a compound targeting, decreasing, or inhibiting the activity of the Trk receptor tyrosine kinase family, or ephrin B4 inhibitors; e) a compound targeting, decreasing, or inhibiting the activity of the Axl receptor tyrosine kinase family; f) a compound targeting, decreasing, or inhibiting the activity of the Ret receptor tyrosine kinase; g) a compound targeting, decreasing, or inhibiting the activity of the Kit/SCFR receptor tyrosine kinase, such as imatinib; h) a compound targeting, decreasing, or inhibiting the activity of the c-Kit receptor tyrosine kinases, such as imatinib; i) a compound targeting, decreasing, or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing, or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; Isis 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin, such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) a compound targeting, decreasing, or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, Cl-1033, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; and m) a compound targeting, decreasing, or inhibiting the activity of the c-Met receptor.

Exemplary compounds that target, decrease, or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g., thalidomide and TNP-470.

Additional, nonlimiting, exemplary chemotherapeutic compounds, one or more of which may be used in combination with a Compound of the Disclosure, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, bevacizumab, porfimer sodium, anecortave, triamcinolone, hydrocortisone, 11-a-epihydrocotisol, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, and siRNA.

Other examples of second therapeutic agents, one or more of which a Compound of the Disclosure also can be combined, include, but are not limited to: a treatment for Alzheimer's Disease, such as donepezil and rivastigmine; a treatment for Parkinson's Disease, such as L-DOPA/carbidopa, entacapone, ropinrole, pramipexole, bromocriptine, pergolide, trihexephendyl, and amantadine; an agent for treating multiple sclerosis (MS) such as beta interferon (e.g., AVONEX® and REBIF®), glatiramer acetate, and mitoxantrone; a treatment for asthma, such as albuterol and montelukast; an agent for treating schizophrenia, such as zyprexa, risperdal, seroquel, and haloperidol; an anti-inflammatory agent, such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor, such as an acetylcholinesterase inhibitor, an MAO inhibitor, an interferon, an anti-convulsant, an ion channel blocker, riluzole, or an anti-Parkinson's agent; an agent for treating cardiovascular disease, such as a beta-blocker, an ACE inhibitor, a diuretic, a nitrate, a calcium channel blocker, or a statin; an agent for treating liver disease, such as a corticosteroid, cholestyramine, an interferon, and an anti-viral agent; an agent for treating blood disorders, such as a corticosteroid, an anti-leukemic agent, or a growth factor; or an agent for treating immunodeficiency disorders, such as gamma globulin.

The above-mentioned second therapeutically active agents, one or more of which can be used in combination with a Compound of the Disclosure, are prepared and administered as described in the art.

Compounds of the Disclosure typically are administered in admixture with a pharmaceutical carrier selected with regard to the intended route of administration and standard pharmaceutical practice. Pharmaceutical compositions for use in accordance with the present disclosure are formulated in a conventional manner using one or more physiologically acceptable carriers comprising excipients and/or auxiliaries that facilitate processing of Compound of the Disclosure.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the Compound of the Disclosure is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a Compound of the Disclosure. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a Compound of the Disclosure.

When a therapeutically effective amount of a Compound of the Disclosure is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of the Disclosure can be readily combined with pharmaceutically acceptable carriers well-known in the art. Standard pharmaceutical carriers are described in Remington's Pharmaceutical Sciences, Mack Publishing Co., Easton, Pa., 19th ed. 1995. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the Compound of the Disclosure to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

Compound of the Disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a Compound of the Disclosure can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the Disclosure also can be formulated in rectal compositions, such as suppositories or retention enemas, e.g., containing conventional suppository bases. In addition to the formulations described previously, the Compound of the Disclosure also can be formulated as a depot preparation. Such long-acting formulations can be administered by implantation (for example, subcutaneously or intramuscularly) or by intramuscular injection. Thus, for example, the Compound of the Disclosure can be formulated with suitable polymeric or hydrophobic materials (for example, as an emulsion in an acceptable oil) or ion exchange resins.

In particular, the Compounds of the Disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compound of the Disclosure also can be injected parenterally, for example, intravenously, intramuscularly, subcutaneously, or intracoronarily. For parenteral administration, the Compound of the Disclosure are typically used in the form of a sterile aqueous solution which can contain other substances, for example, salts or monosaccharides, such as mannitol or glucose, to make the solution isotonic with blood.

The disclosure provides the following particular embodiments in connection with treating a disease in a subject Embodiment I. A method of treating a subject, the method comprising administering to the subject a therapeutically effective amount of a Compound of the Disclosure, wherein the subject has cancer, a chronic autoimmune disorder, an inflammatory condition, a proliferative disorder, sepsis, or a viral infection.

Embodiment II. The method Embodiment I, wherein the subject has cancer.

Embodiment III. The method of Embodiment II, wherein the cancer is any one or more of the cancers of Table 5.

Embodiment IV. The method of Embodiment II, wherein the cancer is selected from the group consisting of acute monocytic leukemia, acute myelogenous leukemia, chronic myelogenous leukemia, chronic lymphocytic leukemia mixed lineage leukemia, NUT midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

Embodiment V. The method of Embodiment II, wherein the cancer is any one or more of the cancers of Table 6.

Embodiment VI. The method of any one of Embodiments I-V further comprising administering a therapeutically effective amount of a second therapeutic agent useful in the treatment of the disease or condition.

Embodiment VII. A pharmaceutical composition comprising a Compound of the Disclosure and a pharmaceutically acceptable excipient for use in treating cancer, a chronic autoimmune disorder, an inflammatory condition, a proliferative disorder, sepsis, or a viral infection.

Embodiment VIII. The pharmaceutical composition of Embodiment VII for use in treating cancer.

Embodiment IX. The pharmaceutical composition of Embodiment VIII, wherein the cancer is any one or more of the cancers of Table 5.

Embodiment X. The pharmaceutical composition of Embodiment IX, wherein the cancer is selected from the group consisting of acute monocytic leukemia, acute myelogenous leukemia, chronic myelogenous leukemia, chronic lymphocytic leukemia mixed lineage leukemia, NUT-midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

Embodiment XI. The pharmaceutical composition of Embodiment VIII, wherein the cancer is any one or more of the cancers of Table 6.

Embodiment XII. A Compound of the Disclosure for use in treatment of cancer, a chronic autoimmune disorder, an inflammatory condition, a proliferative disorder, sepsis, or a viral infection.

Embodiment XIII The compound of Embodiment XII for use in treating cancer.

Embodiment XIV. The compound of Embodiment XIII, wherein the cancer is any one or more of the cancers of Table 5.

Embodiment XV. The compound of Embodiment XIII, wherein the cancer is selected from the group consisting of acute monocytic leukemia, acute myelogenous leukemia, chronic myelogenous leukemia, chronic lymphocytic leukemia mixed lineage leukemia, NUT midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

Embodiment XVI. The compound of Embodiment XIII, wherein the cancer is any one or more of the cancers of Table 6.

Embodiment XVII. Use of a Compound of the Disclosure for the manufacture of a medicament for treatment of cancer, a chronic autoimmune disorder, an inflammatory condition, a proliferative disorder, sepsis, or a viral infection.

Embodiment XVIII. The use of Embodiment XVII for the treatment of cancer.

Embodiment XIX. The use of Embodiment XVIII, wherein the cancer is any one or more of the cancers of Table 5.

Embodiment XX. The use of Embodiment XVIII, wherein the cancer is selected from the group consisting of acute monocytic leukemia, acute myelogenous leukemia, chronic myelogenous leukemia, chronic lymphocytic leukemia mixed lineage leukemia, NUT midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

Embodiment XXI. The use of Embodiment XVIII, wherein the cancer is any one or more of the cancers of Table 6.

V. Kits of the Disclosure

In another embodiment, the present disclosure provides kits which comprise a Compound of the Disclosure (or a composition comprising a Compound of the Disclosure) packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label affixed to the container or included in the kit that describes use of the compound or composition to practice the method of the disclosure, e.g., the method of any one of Embodiments I-VI. In one embodiment, the compound or composition is packaged in a unit dosage form. The kit further can include a device suitable for administering the composition according to the intended route of administration.

VI. Definitions

The term "a disease or condition wherein inhibition of Mcl-1 provides a benefit" pertains to a disease or condition in which Mcl-1 is important or necessary, e.g., for the onset, progress, expression of that disease or condition, or a disease or a condition which is known to be treated by an Mcl-1 inhibitor. Examples of such conditions include, but are not limited to, a cancer, a chronic autoimmune disease, an inflammatory disease, a proliferative disease, sepsis, and a viral infection. One of ordinary skill in the art is readily able to determine whether a compound treats a disease or condition mediated by a Mcl-1 inhibitor for any particular cell type, for example, by assays which conveniently can be used to assess the activity of particular compounds.

The terms "Mcl-1" or "Myeloid Cell Leukemia Sequence 1" refer to a protein encoded by the MCL1 gene. The term Mcl-1 includes isoforms and mutants of Mcl-1. Mcl-1 belongs to the Bcl-2 family. Alternative splicing occurs at this locus and two transcript variants encoding distinct isoforms have been identified. The longer gene product (isoform 1) enhances cell survival by inhibiting apoptosis while the alternatively spliced shorter gene product (isoform 2) promotes apoptosis and is death-inducing.

The term "second therapeutic agent" refers to a therapeutic agent different from a Compound of the Disclosure and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. As demonstrated below, Compounds of the Disclosure are inhibitors of Mcl-1 and can be used in treating or preventing diseases and conditions wherein inhibition of Mcl-1 provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. The term "treat" and synonyms contemplate administering a therapeutically effective amount of a Compound of the Disclosure to a subject in need of such treatment. The treatment can be orientated symptomatically, for example, to suppress symptoms. It can be effected over a short period, be oriented over a medium term, or can be a long-term treatment, for example within the context of a maintenance therapy.

As used herein, the terms "prevent," "preventing," and "prevention" refer to a method of preventing the onset of a disease or condition and/or its attendant symptoms or barring a subject from acquiring a disease. As used herein, "prevent," "preventing," and "prevention" also include delaying the onset of a disease and/or its attendant symptoms and reducing a subject's risk of acquiring a disease. The terms "prevent," "preventing" and "prevention" may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition.

The term "therapeutically effective amount" or "effective dose" as used herein refers to an amount of the active ingredient(s) that is(are) sufficient, when administered by a method of the disclosure, to efficaciously deliver the active ingredient(s) for the treatment of condition or disease of interest to a subject in need thereof. In the case of a cancer or other proliferation disorder, the therapeutically effective amount of the agent may reduce (i.e., retard to some extent or stop) unwanted cellular proliferation; reduce the number of cancer cells; reduce the tumor size; inhibit (i.e., retard to some extent or stop) cancer cell infiltration into peripheral organs; inhibit (i.e., retard to some extent or stop) tumor metastasis; inhibit, to some extent, tumor growth; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to a subject in a sequence and sufficiently close in time so as to provide the desired therapeutic effect and can act in concert. For example, a Compound of the Disclosure can be administered at the same time or sequentially in any order at different points in time as a second therapeutic agent. A Compound of the Disclosure and the second therapeutic agent can be administered separately, in any appropriate form and by any suitable route. When a Compound of the Disclosure and the second therapeutic agent are not administered concurrently, it is understood that they can be administered in any order to a subject in need thereof. For example, a Compound of the Disclosure can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to a subject in need thereof. In various embodiments, a Compound of the Disclosure and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at about 1 minute to about 24 hours apart.

The use of the terms "a", "an", "the", and similar referents in the context of describing the disclosure (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein is intended to better illustrate the disclosure and is not a limitation on the scope of the disclosure unless otherwise claimed. No language in the specification should be construed as indicating any non-claimed element as essential to the practice of the disclosure.

The term "$C_1$-$C_6$ alkyl" as used by itself or as part of another group refers to unsubstituted straight- or branched-chain aliphatic hydrocarbons containing from one to six carbon atoms. The term "$C_1$-$C_4$ alkyl" as used herein by itself or part of another group refers to methyl, ethyl, n-propyl, isopropyl, n-butyl, sec-butyl, or tert-butyl. The term "$C_1$-$C_3$ alkyl" as used herein by itself or part of another group refers to methyl, ethyl, n-propyl, or isopropyl. The term "$C_2$-$C_3$ alkyl" as used herein by itself or part of another group refers to ethyl, n-propyl, or isopropyl The term "$C_1$-$C_6$ alkoxy" as used herein by itself or part of another group refers to a $C_1$-$C_6$ alkyl group attached to a terminal oxygen atom. Exemplary non-limiting $C_1$-$C_6$ alkoxy groups include —$OCH_3$, —$OCH_2CH_3$, —$OCH_2CH_2CH_3$, —$OCH(CH_3)_2$, —$O(CH_2)_3CH_3$, and —$OC(CH_3)_3$.

The term "$C_1$-$C_3$ alkoxy" as used herein by itself or part of another group refers to —$OCH_3$, —$OCH_2CH_3$, —$OCH_2CH_2CH_3$, or —$OCH(CH_3)_2$.

The term "($C_1$-$C_3$ alkoxy)$C_2$-$C_3$ alkyl" as used herein by itself or part of another group refers to a $C_2$-$C_3$ alkyl substituted with one $C_1$-$C_3$ alkoxy group. Exemplary non-limiting ($C_1$-$C_3$ alkoxy)$C_2$-$C_3$ alkyl groups include —$CH_2CH_2OCH_3$ and —$CH_2CH_2CH_2OCH_3$.

The term "halo" as used herein by itself or part of another group refers to fluoro, chloro, bromo, or iodo.

The term "$C_3$-$C_6$ cycloalkyl" as used herein by itself or part of another group refers to cyclopropyl, cyclobutyl, cyclopentyl, or cyclohexyl. The $C_3$-$C_6$ cycloalkyl can be either unsubstituted or substituted with one, two, three, or four substituents independently selected from the group consisting of halo, $C_1$-$C_3$ alkyl, and $C_1$-$C_3$ alkoxy.

The term "4- to 7-membered heterocyclo" as used herein by itself or part of another group refers to saturated and partially unsaturated, e.g., containing a double bond, monocyclic or bicyclic, groups containing four to seven ring members comprising carbon atoms and one or two heteroatoms. Each heteroatom is independently oxygen, sulfur, or nitrogen. Each sulfur atom is independently oxidized to give a sulfoxide, i.e., S(=O), or sulfone, i.e., S(=O)$_2$. The 4- to 7-membered heterocyclo can be either unsubstituted or substituted with one, two, three, or four substituents independently selected from the group consisting of halo, $C_1$-$C_3$ alkyl, and $C_1$-$C_3$ alkoxy.

The term "amino" as used herein by itself or part of another group refers to a radical of the formula —$NR^{30a}R^{30b}$, wherein $R^{30a}$ and $R^{30b}$ are independently hydrogen, $C_1$-$C_3$ alkyl, or benzyl, wherein the benzyl is unsubstituted or substituted with one or two groups selected from the group consisting of $C_1$-$C_3$ alkyl and $C_1$-$C_3$ alkoxy.

The term "5- or 6-membered heteroaryl" as used herein by itself or part of another group refers to monocyclic aromatic ring systems having 5 or 6 ring atoms, wherein at least one carbon atom of one the ring is replaced with a heteroatom independently selected from the group consisting of oxygen, nitrogen and sulfur. Non-limiting exemplary 5- or 6-membered heteroaryl groups include thienyl, furyl, pyrrolyl, oxazolyl, pyrazolyl, imidazolyl, thiazolyl, isothiazolyl, isoxazolyl, pyridyl, pyrazinyl, pyrimidinyl, and pyridazinyl.

The term "coupling agent" as used herein refers to the reagent, e.g., activator, or combination of reagents, e.g., activator and base, or activator, base, and additive(s), used to form an between a —C(=O)OH group and a $H_2N$—S(=O)$_2$— group. Coupling agents for this transformation are known in the art. Any coupling agent known in art can be used in the cyclization of Formula XVIII to give Formula I.

The term "halo" as used by itself or as part of another group refers to —Cl, —F, —Br, or —I.

The term "cyano" as used by itself or as part of another group refers to —CN.

The term "hydroxy" as used by itself or as part of another group refers to —OH.

The term "4- to 10-membered heterocyclo" as used herein by itself or part of another group refers to saturated and partially unsaturated, e.g., containing a double bond, monocyclic or bicyclic, groups containing four to ten ring members comprising carbon atoms and one, two or three heteroatoms. Each heteroatom is independently oxygen, sulfur, or nitrogen. Each sulfur atom is independently oxidized to give a sulfoxide, i.e., S(=O), or sulfone, i.e., S(=O)$_2$. The term 4- to 10-membered heterocyclo includes groups wherein one or more —CH$_2$— groups is replaced with one or more —C(=O)— groups, including cyclic ureido groups such as imidazolidinyl-2-one, cyclic amide groups such as pyrrolidin-2-one or piperidin-2-one, and cyclic carbamate groups such as oxazolidinyl-2-one. The term 4- to 10-membered heterocyclo also includes groups having fused optionally substituted aryl or optionally substituted heteroaryl groups such as indoline, indolin-2-one, 2,3-dihydro-1H-pyrrolo[2,3-c]pyridine, 2,3,4,5-tetrahydro-1H-benzo[d]azepine, or 1,3,4,5-tetrahydro-2H-benzo[d]azepin-2-one. The 4- to 10-membered heterocyclo can be either unsubstituted or substituted with one, two, three, or four substituents independently selected from the group consisting of halo, hydroxy, amino, cyano, $C_1$-$C_6$ alkyl, $C_1$-$C_4$ alkoxy, $C_3$-$C_6$ cycloalkyl, 4- to 7-membered heterocyclo, alkylsulfonyl, alkylcarbonyl, and phenyl. Non-limiting exemplary heterocyclo groups include:

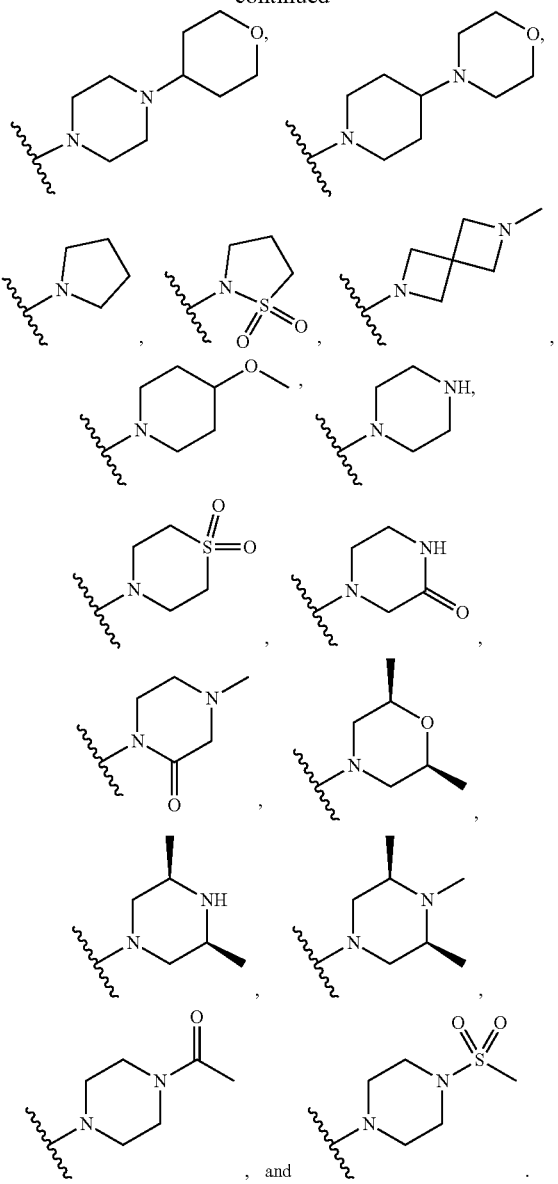

The term "(heterocyclo)$C_1$-$C_4$ alkyl" as used herein by itself or as part of another group refers to a $C_1$-$C_4$ alkyl substituted with a 4- to 10-membered heterocyclo group. In another embodiment, alkyl is a $C_1$-$C_3$ alkyl. In another embodiment, the alkyl is a $C_1$ or $C_2$ alkyl. The heterocyclo group can be linked to the alkyl group through a carbon or nitrogen atom. Non-limiting exemplary (heterocyclo)$C_1$-$C_4$ alkyl groups include:

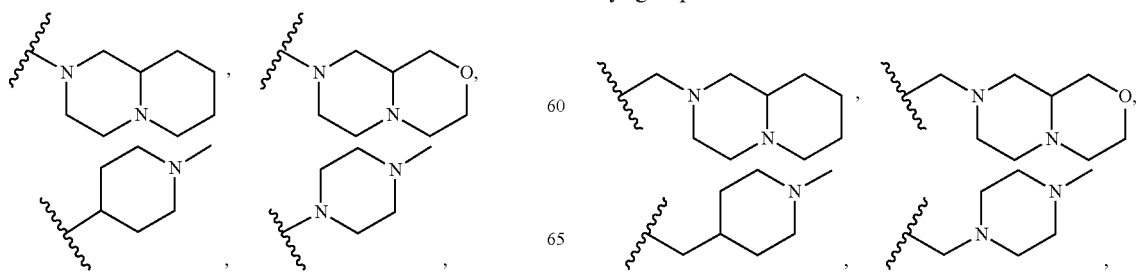

-continued

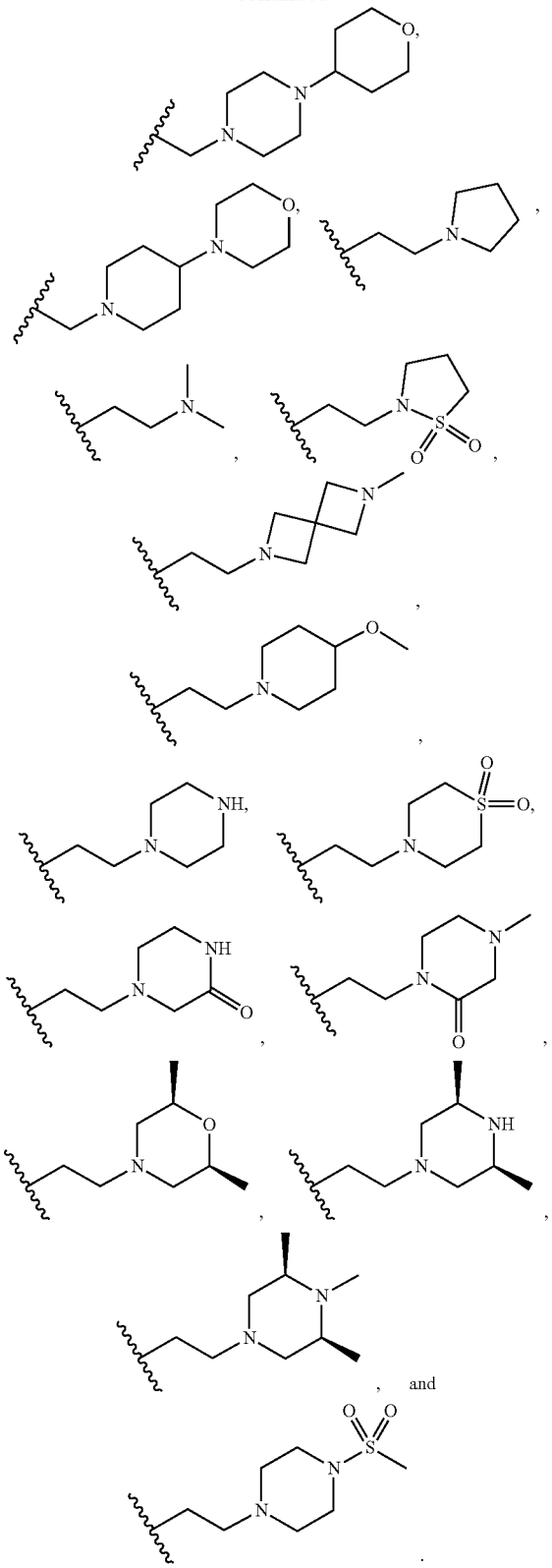

The term "alkylcarbonyl" as used herein by itself or as part of another group refers to a carbonyl group, i.e., —C(=O)—, substituted by a $C_1$-$C_3$ alkyl group. A non-limiting exemplary alkylcarbonyl group is —C(=O)$CH_3$.

The term "alkylsulfonyl" as used herein by itself or as part of another group refers to a sulfonyl group, i.e., —$SO_2$—, substituted by a $C_1$-$C_3$ alkyl group. A non-limiting exemplary alkylsulfonyl group is —S(=O)$_2$$CH_3$.

The term "(alkylsulfonyl)$C_1$-$C_4$ alkyl" as used herein by itself or as part of another group refers to a $C_1$-$C_4$ alkyl substituted with an alkylsulfonyl group. In one embodiment, alkyl is a $C_2$ alkyl. A non-limiting exemplary (alkylsulfonyl) $C_1$-$C_4$ alkyl group is —$CH_2$$CH_2$S(=O)$_2$$CH_3$.

The term "(amino)$C_1$-$C_4$ alkyl" as used herein by itself or as part of another group refers to an to a $C_1$-$C_4$ alkyl substituted with an amino group. Non-limiting exemplary (amino)$C_1$-$C_4$ alkyl groups include —$CH_2$$NH_2$, —$CH_2$N(H)$CH_3$, and —$CH_2$N($CH_3$)$_2$.

The term "(phenyl)$C_1$-$C_4$ alkyl" as used herein by itself or as part of another group refers to a $C_1$-$C_4$ alkyl substituted with a phenyl group. In one embodiment, the alkyl is a $C_1$ or $C_2$ alkyl. The phenyl group (abbreviated "Ph") as used in this or any other group can be either unsubstituted or substituted with one, two, three, or four substituents independently selected from the group consisting of halo, hydroxy, amino, cyano, $C_1$-$C_6$ alkyl, $C_1$-$C_4$ alkoxy, $C_3$-$C_6$ cycloalkyl, 4- to 7-membered heterocyclo, alkylsulfonyl, alkylcarbonyl, and phenyl. Non-limiting exemplary (phenyl) $C_1$-$C_4$ alkyl groups include —$CH_2$Ph, —$CH_2$$CH_2$Ph, and —$CH_2$(4-F-Ph).

The term "(heteroaryl)$C_1$-$C_4$ alkyl" as used herein by itself or as part of another group refers to a $C_1$-$C_4$ alkyl substituted with a 5- or 6-membered heteroaryl group. The 5- or 6-membered heteroaryl can be either unsubstituted or substituted with one, two, or three substituents independently selected from the group consisting of halo, hydroxy, amino, cyano, $C_1$-$C_6$ alkyl, $C_1$-$C_4$ alkoxy, $C_3$-$C_6$ cycloalkyl, 4- to 10-membered heterocyclo, alkylsulfonyl, alkylcarbonyl, and phenyl. Non-limiting exemplary (heteroaryl)$C_1$-$C_4$ alkyl groups include:

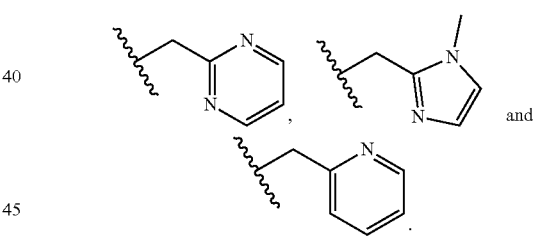

and

The term "amido" as used herein by itself or as part of another group refers to a radical of formula —C(=O) NR$^{40a}$R$^{40b}$, wherein R$^{40a}$ and R$^{40b}$ are each independently selected from group consisting of hydrogen and $C_1$-$C_4$ alkyl, or R$^{40a}$ and R$^{40b}$ taken together form a 4- to 10-membered heterocyclo group. Non-limiting exemplary amido groups include:

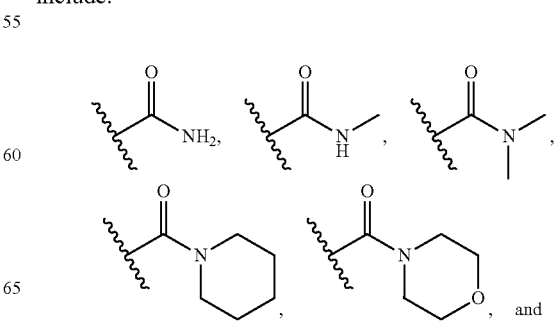

and

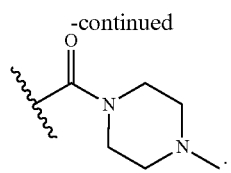

The term "(amido)$C_1$-$C_4$ alkyl" as used herein by itself or as part of another group refers to a $C_1$-$C_4$ alkyl substituted with an amido group. In one embodiment, the alkyl is a $C_1$ or $C_2$ alkyl. Non-limiting exemplary (amido)$C_1$-$C_4$ alkyl groups include:

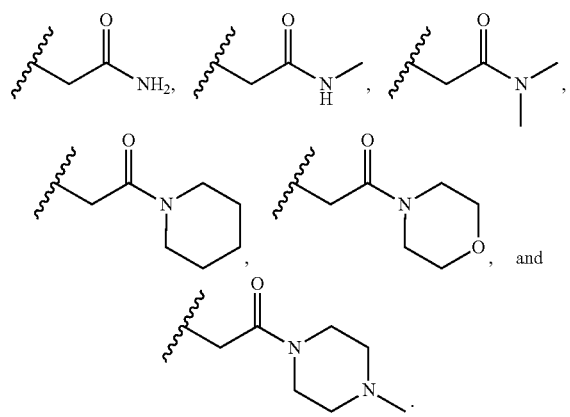

The term "carboxy" as used by itself or as part of another group refers to a radical of the formula —C(=O)OH.

The term "(carboxy)$C_1$-$C_4$ alkyl" as used herein by itself or as part of another group refers to a $C_1$-$C_4$ alkyl substituted with an carboxy group. In one embodiment, the alkyl is a $C_1$ or $C_2$ alkyl. A non-limiting exemplary (carboxy)$C_1$-$C_4$ alkyl group is —$CH_2$C(=O)OH.

the term "alkoxycarbonyl" as used by itself or as part of another group refers to a carbonyl group, i.e., —C(=O)—, substituted with a $C_1$-$C_6$ alkoxy. In one embodiment, the alkoxy is a $C_{1-3}$ alkoxy. Non-limiting exemplary alkoxycarbonyl groups include —C(=O)$OCH_3$, —C(=O)$OCH_2CH_3$, and —C(=O)$OCH(CH_3)_2$.

The term "(alkoxycarbonyl)$C_1$-$C_4$ alkyl" as used herein by itself or as part of another group refers to a $C_1$-$C_4$ alkyl substituted with an alkoxycarbonyl group. In one embodiment, the alkyl is a $C_1$ or $C_2$ alkyl. Non-limiting exemplary (alkoxycarbonyl)$C_1$-$C_4$ alkyl groups include —$CH_2$C(=O)$OCH_3$, —$CH_2$C(=O)$OCH_2CH_3$, and —$CH_2$C(=O)$OCH(CH_3)_2$.

The term "aminocarbonyl" as used herein by itself or as part of another group refers to a radical of formula —N($R^{70a}$)C(=O)$R^{70b}$, wherein $R^{70a}$ is selected from the group consisting of hydrogen and $C_1$-$C_3$ alkyl; and $R^{70b}$ is $C_1$-$C_6$ alkyl, Non-limiting exemplary aminocarbonyl groups include —N(H)C(=O)$CH_3$ and —N($CH_3$)C(=O)$CH_3$.

The term "(aminocarbonyl)$C_1$-$C_4$ alkyl" as used herein by itself or as part of another group refers to a $C_1$-$C_4$ alkyl substituted with an aminocarbonyl group. In one embodiment, the alkyl is a $C_1$ or $C_2$ alkyl. Non-limiting exemplary (aminocarbonyl)$C_1$-$C_4$ alkyl groups include —$CH_2CH_2$N(H)C(=O)$CH_3$ and —$CH_2CH_2$N($CH_3$)C(=O)$CH_3$.

The term "aminosulfonyl" as used herein by itself or as part of another group refers to a radical of formula —N($R^{80a}$)S(=O)$_2R^{80b}$, wherein $R^{80a}$ is selected from the group consisting of hydrogen and $C_1$-$C_3$ alkyl; and $R^{80b}$ is $C_1$-$C_6$ alkyl, Non-limiting exemplary aminosulfonyl groups include —N(H)S(=O)$_2CH_3$ and —N($CH_3$)S(=O)$_2CH_3$.

The term "(aminosulfonyl)$C_1$-$C_4$ alkyl" as used herein by itself or as part of another group refers to a $C_1$-$C_4$ alkyl substituted with an aminosulfonyl group. In one embodiment, the alkyl is a $C_1$ or $C_2$ alkyl. Non-limiting exemplary (aminosulfonyl)$C_1$-$C_4$ alkyl groups include —$CH_2CH_2$N(H)S(=O)$_2CH_3$ and —$CH_2CH_2$N($CH_3$)S(=O)$_2CH_3$.

The term "(hydroxy)$C_1$-$C_4$ alkyl" as used herein by itself or as part of another group refers to a $C_1$-$C_4$ alkyl substituted with one or two hydroxy groups. In one embodiment, the alkyl is a $C_1$ or $C_2$ alkyl. Non-limiting exemplary (hydroxy)$C_1$-$C_4$ alkyl groups include —$CH_2$OH, —$CH_2CH_2$OH, and —$CH_2$CH(OH)$CH_2$OH.

The term "$C_3$-$C_7$ cycloalkyl" as used herein by itself or part of another group refers to cyclopropyl, cyclobutyl, cyclopentyl, cyclohexyl, or cycloheptyl. The $C_3$-$C_7$ cycloalkyl can be either unsubstituted or substituted with one, two, three, or four substituents independently selected from the group consisting of halo, hydroxy, amino, cyano, $C_1$-$C_6$ alkyl, $C_1$-$C_4$ alkoxy, $C_3$-$C_6$ cycloalkyl, 4- to 7-membered heterocyclo, alkylsulfonyl, alkylcarbonyl, and phenyl.

Compounds of the Disclosure and Intermediates of the Disclosure have asymmetric centers and may thus give rise to enantiomers, diastereomers, and other stereoisomeric forms. The present disclosure encompasses the preparation and use of all such possible stereoisomeric forms, as well as their racemic and resolved forms, and mixtures thereof. The enantiomers and diastereomers can be separated according to methods known in the art in view of the present disclosure. When the compounds described herein contain olefinic double bonds or other centers of geometric asymmetry, and unless specified otherwise, it is intended that they include both E and Z geometric isomers. All tautomers are also encompassed by the present disclosure.

As used herein, the term "stereoisomers" is a general term for all isomers of individual molecules that differ only in the orientation of their atoms in space. It includes enantiomers, atropisomers, and isomers of compounds with more than one chiral center that are not mirror images of one another (diastereomers).

The term "chiral center" or "asymmetric carbon atom" refers to a carbon atom to which four different groups are attached. In Formula I, the phrase "the asymmetric carbon atom of the cyclobutene ring" refers to the carbon atom to which $R^8$ and X is attached.

The term "atropisomer" refers to a stereoisomer arising because of hindered rotation about a single bond. Atropisomers display axial chirality.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction. Enantiomers may be separated by chiral chromatography using methods well known in the art.

The term "racemic" or "racemate" refers to a mixture of equal parts of enantiomers and which mixture is optically inactive.

The term "absolute configuration" refers to the spatial arrangement of the atoms of a chiral molecular entity (or group) and its stereochemical description, e.g., R or S.

The stereochemical terms and conventions used in the specification are meant to be consistent with those described in *Pure & Appl. Chem* 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as $([\alpha]_{obs}/[\alpha]_{max})*100$ where $[\alpha]_{obs}$ is the optical rotation of the mixture of ax, enantiomers and $[\alpha]_{max}$ is the optical rotation of the pure enantiomer. Determination of enantiomeric excess is possible using a variety of analytical techniques, including NMR spectroscopy, chiral column chromatography, or optical polarimetry. Compounds of the Disclosure or Intermediates of the Disclosure that are racemic can be separated by chiral HPLC, e.g., using a CHIRALPAK IE column. In one embodiment, Compounds of the Disclosure or Intermediates of the Disclosure have an ee of about 70% or more, e.g., about 80% or more, about 90% or more, about 91% or more, about 92% or more, about 93% or more, about 94% or more, about 95% or more, about 96% or more, about 97% or more, about 98% or more, or about 99% or more.

The terms "enantiomerically pure" or "enantiopure" refer to a sample of a chiral substance all of whose molecules (within the limits of detection) have the same chirality sense.

The terms "enantiomerically enriched" or "enantioenriched" refer to a sample of a chiral substance whose enantiomeric ratio is greater than 50:50. Enantiomerically enriched compounds may be enantiomerically pure. Certain compounds of the Disclosure are enantioenriched.

The term "diastereomeric excess" or "de" refers to a measure for how much of one diastereomer is present compared to another, and is defined by analogy to enantiomeric excess. Determination of diastereomeric excess is possible using a variety of analytical techniques, including NMR spectroscopy and column chromatography.

The term "about," as used herein, includes the recited number ±10%. Thus, "about 10" means 9 to 11.

EXAMPLES

General Schemes

Compounds of the Disclosure and Intermediates of the Disclosure can be prepared according to the following General Schemes.

General Scheme 1

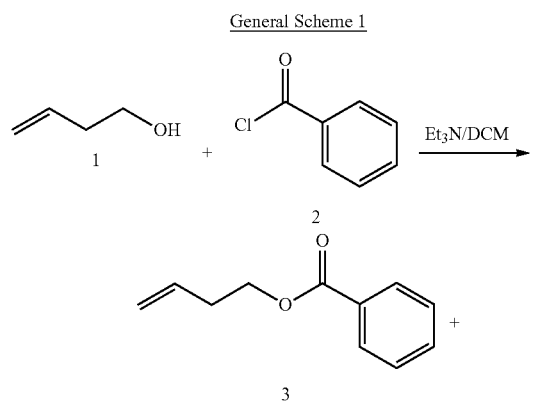

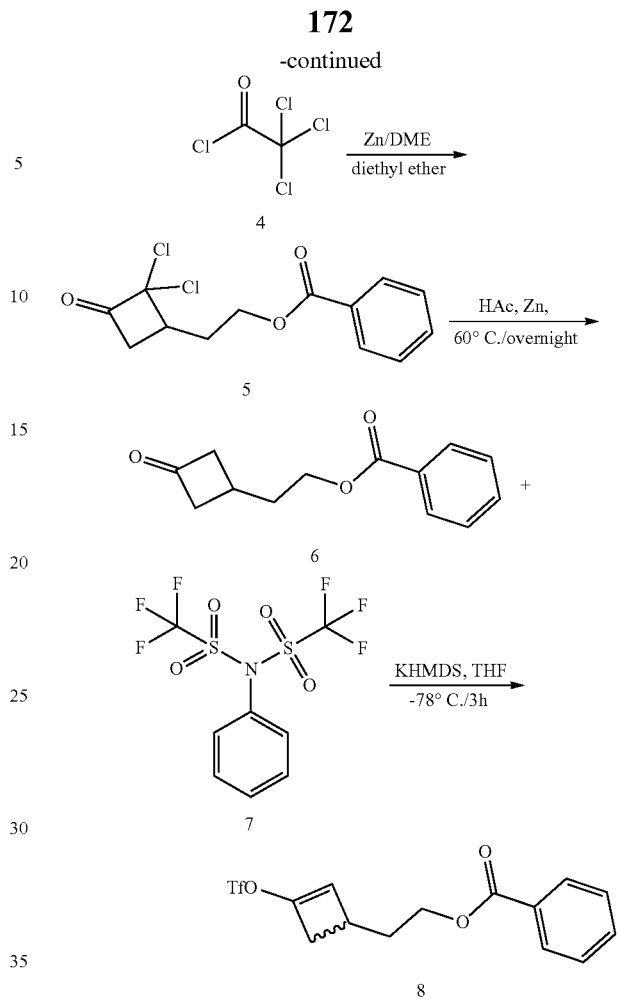

In General Scheme 1, the cyclobutenyl triflate (compound 8) is prepared as a racemic form from but-3-en-1-ol (compound 1). The benzoate 3 is prepared from alcohol 1 and benzoyl chloride 2. Cyclic addition reaction followed by dechloration under zinc affords cyclobutanone 6, which is reacted with 1,1,1-trifluoro-N-phenyl-N-((tri-fluoromethyl)sulfonyl)methanesulfonamide 7 affords cyclobutenyl triflate 8.

General Scheme 2

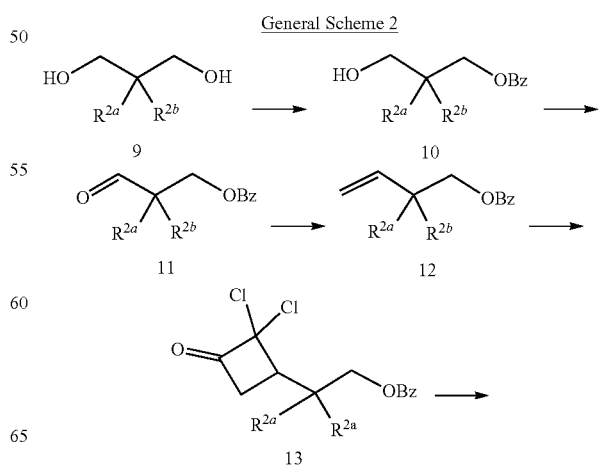

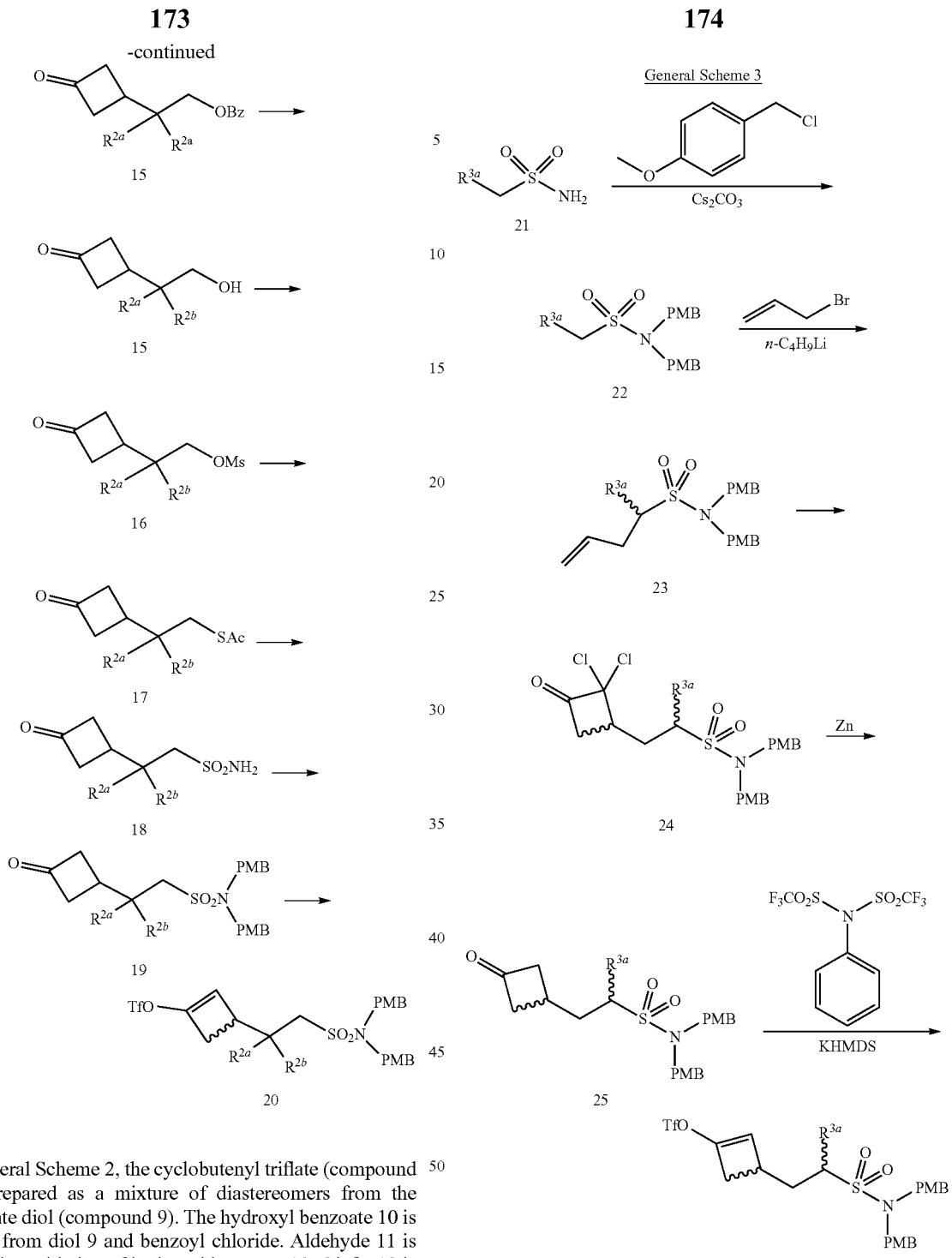

In General Scheme 2, the cyclobutenyl triflate (compound 20) is prepared as a mixture of diastereomers from the appropriate diol (compound 9). The hydroxyl benzoate 10 is prepared from diol 9 and benzoyl chloride. Aldehyde 11 is obtained by oxidation of hydroxyl benzoate 10. Olefin 12 is obtained by Wittig reaction. Cyclic addition reaction olefin 12 and 2,2,2-trichloroacetyl chloride followed by dechloration affords cyclobutanone 14. Hydrolysis of benzoate 14 affords alcohol 15. Treatment of alcohol 15 with mesyl chloride affords methanesulfonate 16. Substitution reaction of 16 with potassium thioacetate gives ethanethioate 17. Treatment of 17 with NCS followed by ammonium hydroxide gives sulfonamide 18. DiPMB protected sulfonamide 19 is obtained by treatment of sulfonamide 18 with PMB-Cl. Compound 19 is treated with KHMDS followed by 1,1,1-trifluoro-N-phenyl-N-((tri-fluoromethyl)sulfonyl)methanesulfonamide affords the cyclobutenyl triflate 20.

In General Scheme 3, the cyclobutenyl triflate (compound 26) is prepared as a mixture of diastereomers from the appropriate sulfonamide (compound 21). Sulfonamide 21 is protected by PMB to give di-PMB protected sulfonamide 22. Sulfonamide 22 is treated with n-BuLi followed by 3-bromoprop-1-ene to give olefin 23. Cyclic addition reaction followed by dechloration affords cyclobutanone 25. Cyclobutanone 25 is treated with KHMDS followed by 1,1,1-trifluoro-N-phenyl-N-((tri-fluoromethyl)sulfonyl) methanesulfonamide affords the cyclobutenyl triflate 26.

General Scheme 4

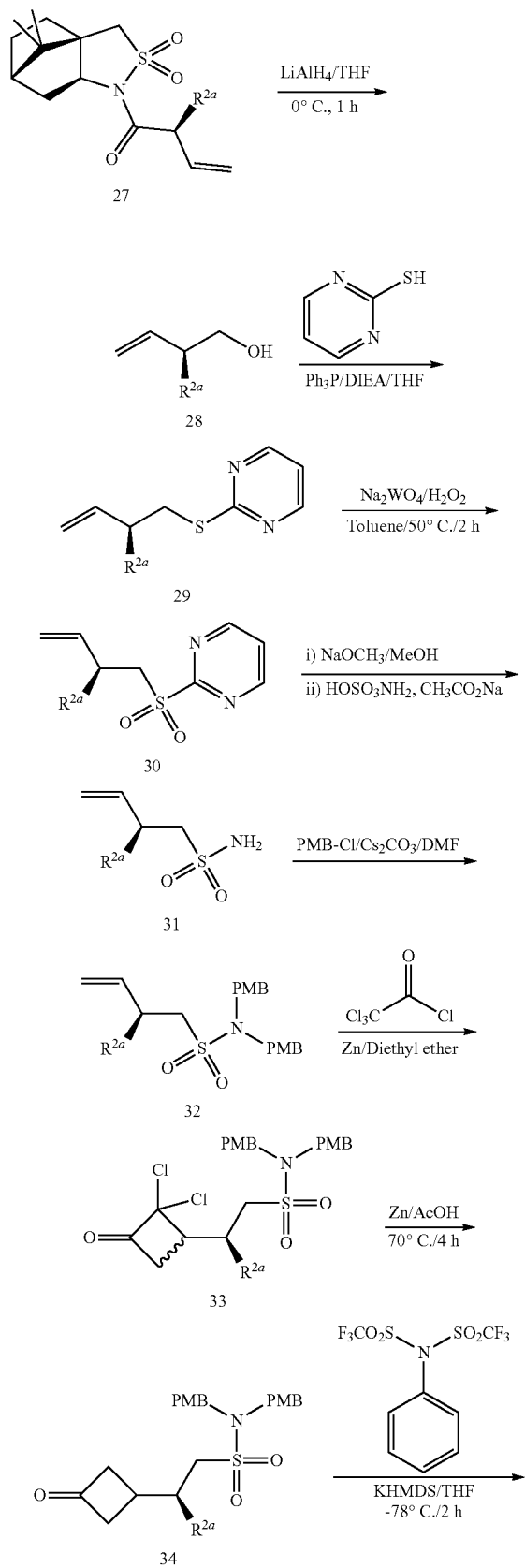

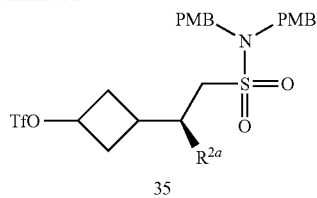

In General Scheme 4, the cyclobutenyl triflate (compound 35) is prepared as a mixture of diastereomers from the acyl substituted camphorsultamsulfonamide 27. Reduction of 27 using LiAlH$_4$ gives alcohol 28. Mitsunobu reaction affords pyrimidine-2-thioether 29. Oxidation of thioether 29 followed by treatment with sodium methoxide and aminooxysulfonic acid affords sulfonamide 31. Di-PMB protected sulfonamide 32 is obtained by treatment of 31 with PMB chloride under Cs$_2$CO$_3$ in DMF. Cyclic addition reaction followed by dechloration affords cyclobutanone 34. Cyclobutanone 34 is treated with KHMDS followed by 1,1,1-trifluoro-N-phenyl-N-((tri-fluoromethyl)sulfonyl) methanesulfonamide affords the cyclobutenyl triflate 35 as a mixture of diastereomers.

General Scheme 5

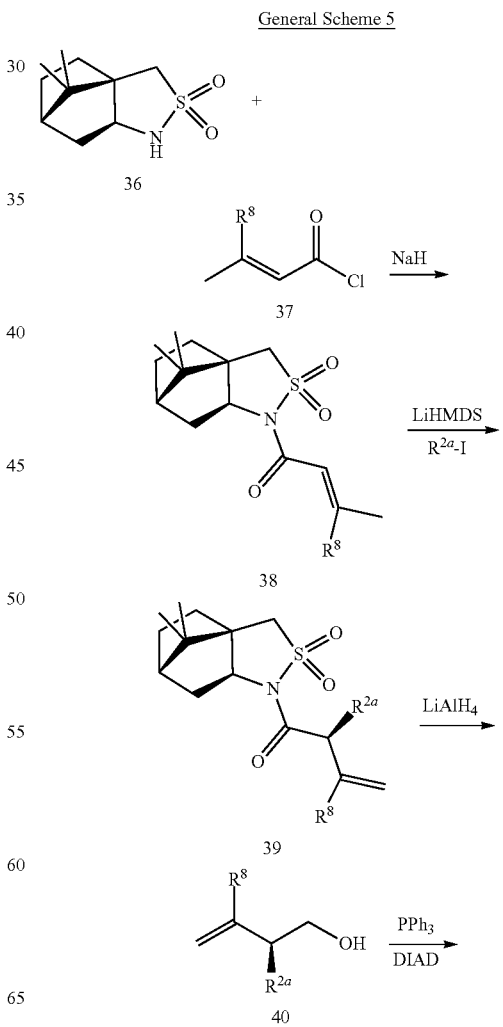

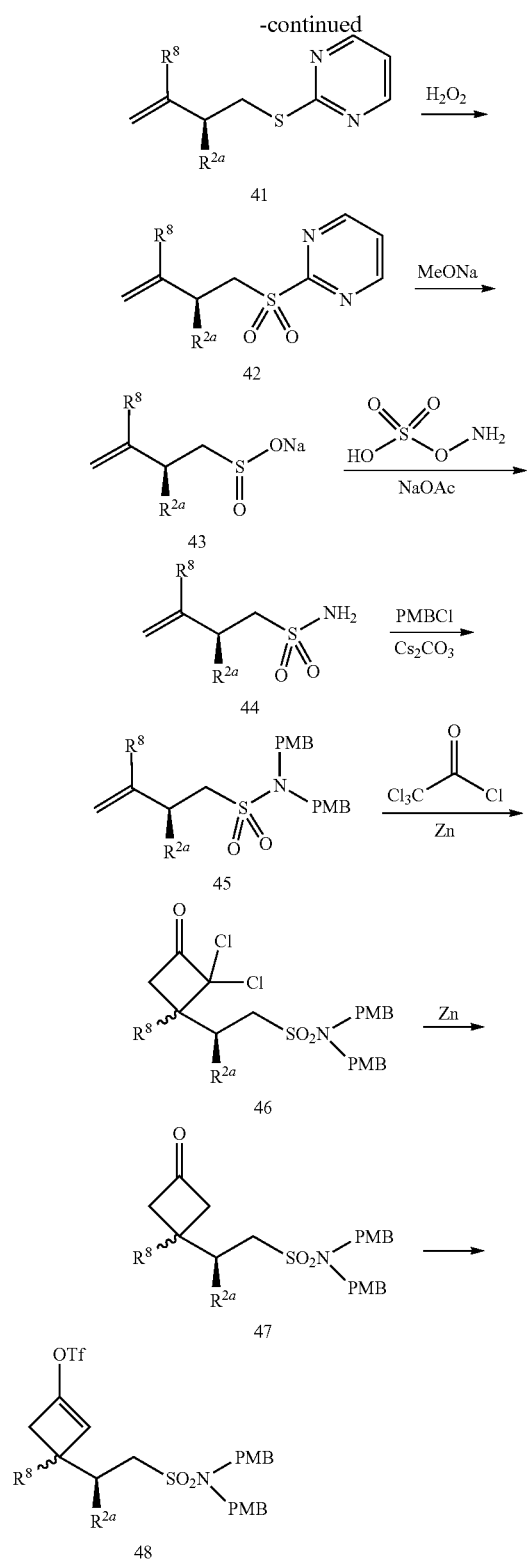

affords the appropriate substituted acyl camphorsultamsulfonamide 39. Reduction of 39 using LiAlH$_4$ gives alcohol 40. Mitsunobu reaction affords pyrimidine-2-thioether 41. Oxidation of thioether 41 followed by treatment with sodium methoxide and aminooxysulfonic acid affords sulfonamide 44. Di-PMB protected sulfonamide 45 is obtained by treatment of 44 with PMB chloride in the presence of Cs$_2$CO$_3$ in DMF. Cyclic addition reaction followed by dechloration affords cyclobutanone 47. The cyclobutanone 47 is treated with KHMDS followed by 1,1,1-trifluoro-N-phenyl-N-((tri-fluoromethyl)sulfonyl)methanesulfonamide affords the cyclobutenyl triflate 48 as a mixture of diastereomers.

General Scheme 6

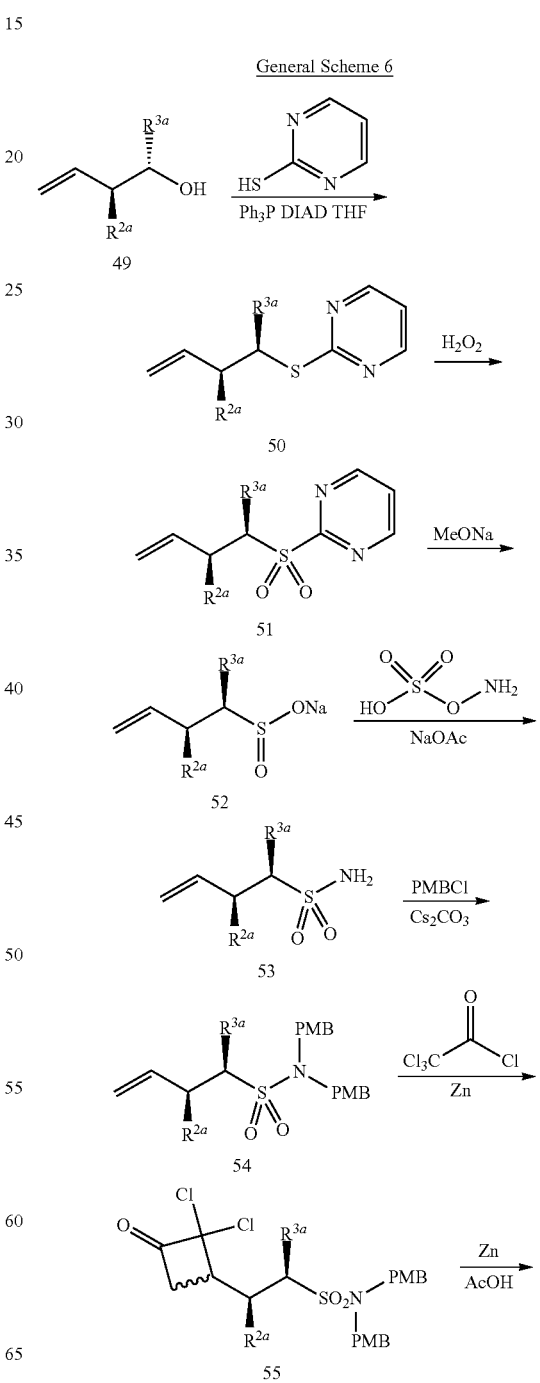

In General Scheme 5, the cyclobutenyl triflate (compound 48) is prepared as a mixture of diastereomers from the chiral auxiliary (compound 36) and appropriate chloride (compound 37). The acyl camphorsultamsulfonamide 38 is obtained from acylation of camphorsultamsulfonamide. Compound 38 is treated with KHMDS followed by Iodide -continued

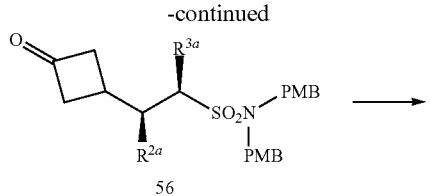
56

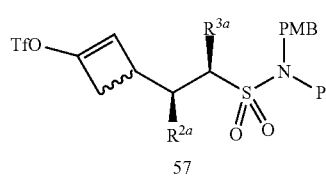
57

In General Scheme 6, the cyclobutenyl triflate (compound 58) is prepared as a mixture of diastereomers from the appropriate chiral alcohol. Mitsunobu reaction of chiral alcohol 49 with pyrimidine-2-thiol affords pyrimidine-2-thioether 50. Oxidation of thioether 50 followed by treatment with sodium methoxide and aminooxysulfonic acid affords sulfonamide 53. Di-PMB protected sulfonamide 54 is obtained by treatment of 53 with PMB chloride in the presence of $Cs_2CO_3$ in DMF. Cyclic addition reaction followed by dechloration affords cyclobutanone 56. Cyclobutanone 56 is treated with KHMDS followed by 1,1,1-trifluoro-N-phenyl-N-((tri-fluoromethyl)sulfonyl)methanesulfonamide affords the cyclobutenyl triflate 57 as a mixture of diastereomers.

General Scheme 7

-continued

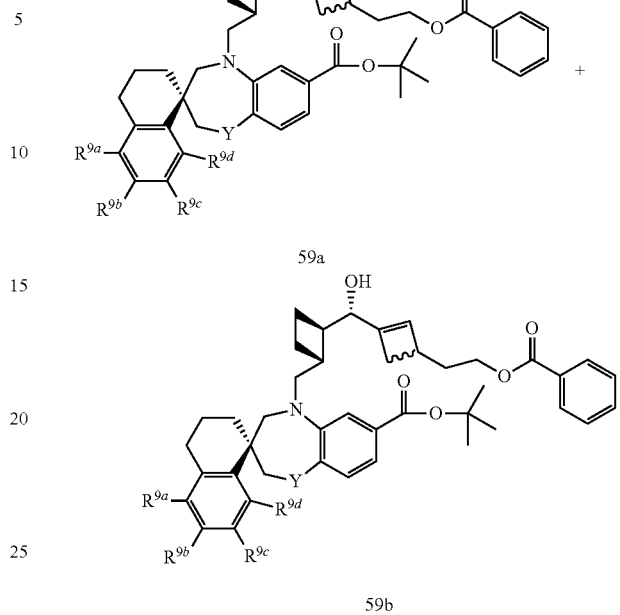

In General Scheme 7, the cyclobutenyl triflate (compound 8) is reacted with the aldehyde of compound 58 to give four stereoisomers: compound 59a (as a mixture of diastereomers) and compound 59b (as a mixture of diastereomers). Compounds 59a and 59b are separated by silica gel chromatography.

General Scheme 8

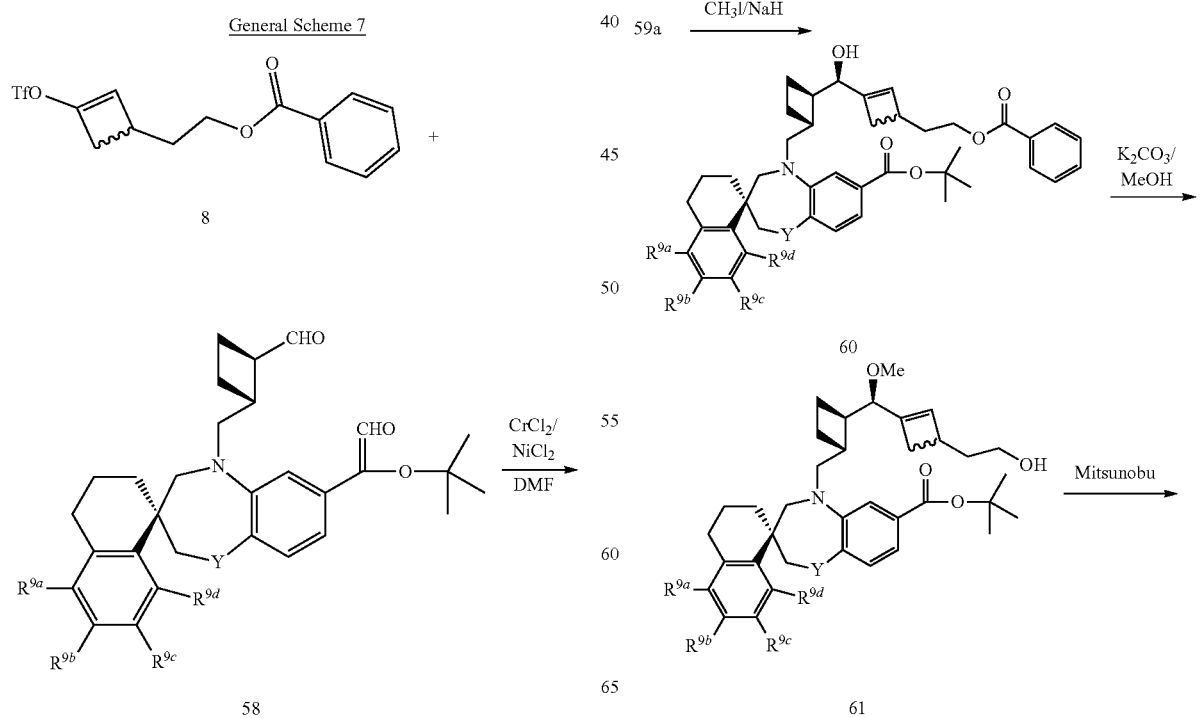

181
-continued

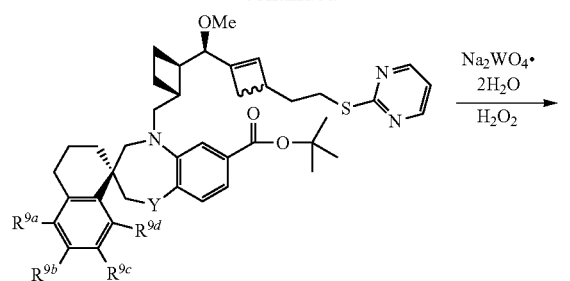
62

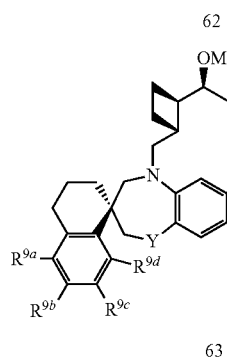
63

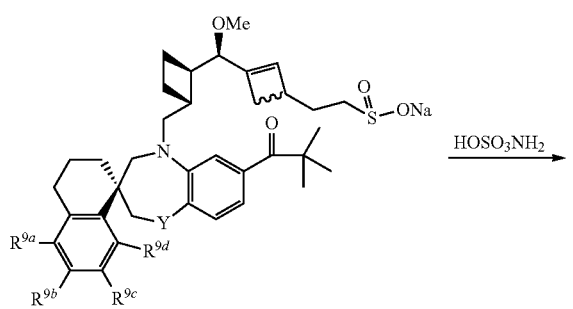
64

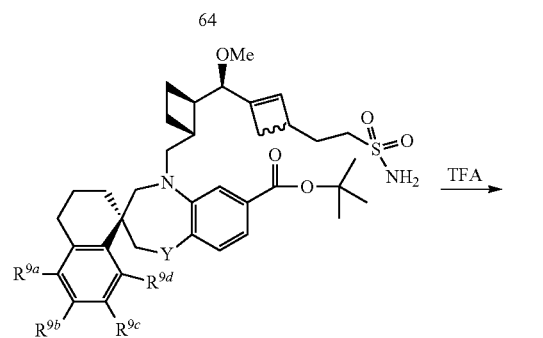
65

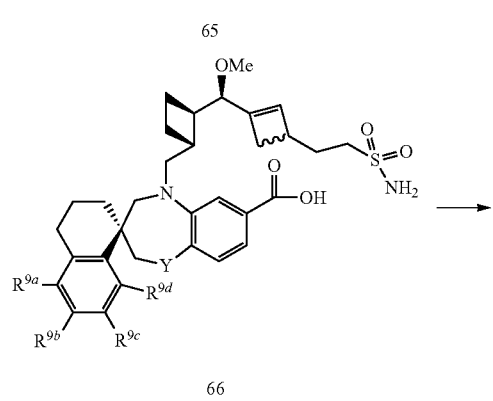
66

182
-continued

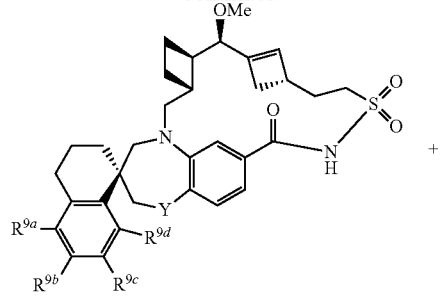
67a

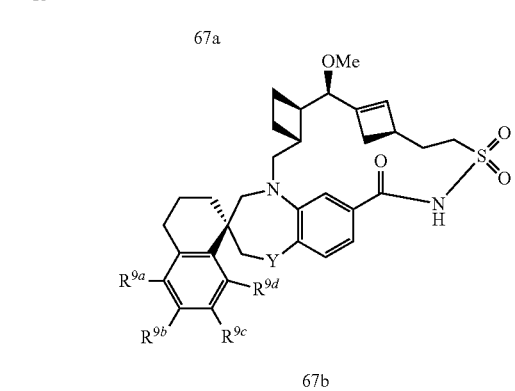
67b

In General Scheme 8, compound 59a is converted to compound 65 using the similar method as described previously. The hydroxy group of compound 59a is methylated to give compound 60, and compound 60 is deprotected to give alcohol 61. Mitsunobu reaction of alcohol 61 with pyrimidine-2-thiol affords pyrimidine-2-thioether 62. Oxidation of thioether 62 followed by treatment with sodium methoxide and aminooxysulfonic acid affords sulfonamide 65. Sulfonamide 65 is deprotected to give carboxylic acid 66. Intramolecular cyclization of 66 gives compounds 67a and 67b as a mixture of diastereoisomers that can be separated by column chromatography or preparative HPLC. The same process can be applied to compound 59b.

General Scheme 9

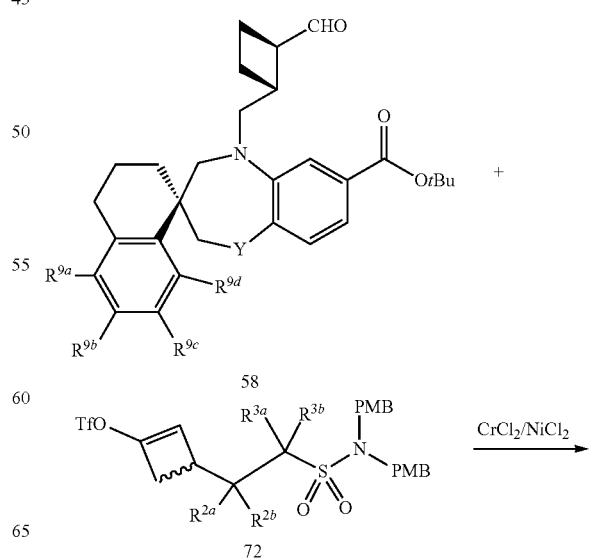
58
72

-continued

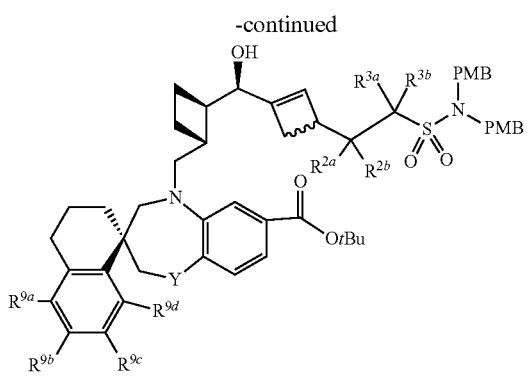

68a

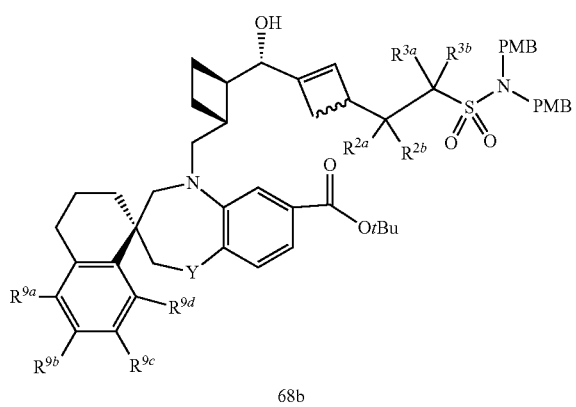

68b

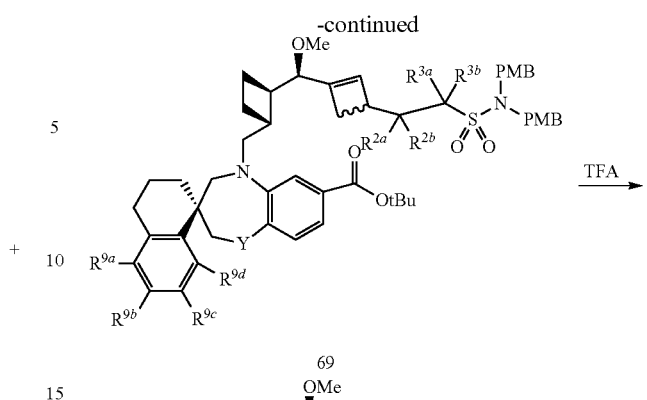

69

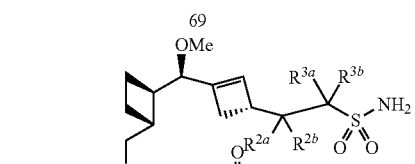 TFA

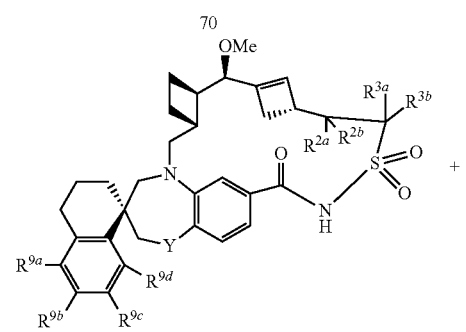

70

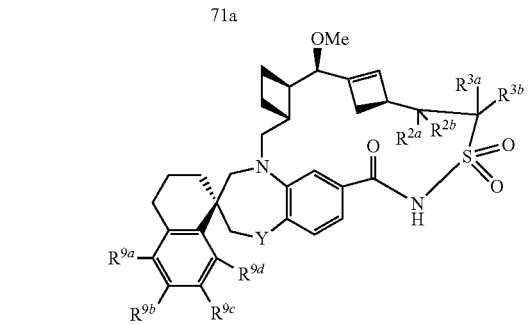

71a

In General Scheme 9, the cyclobutenyl triflate (compound 72) is reacted with the aldehyde of compound 58 to give four stereoisomers: compound 68a (as a mixture of diastereomers) and compound 68b (as a mixture of diastereomers). Compounds 68a and 68b are separated by silica gel chromatography.

General Scheme 10

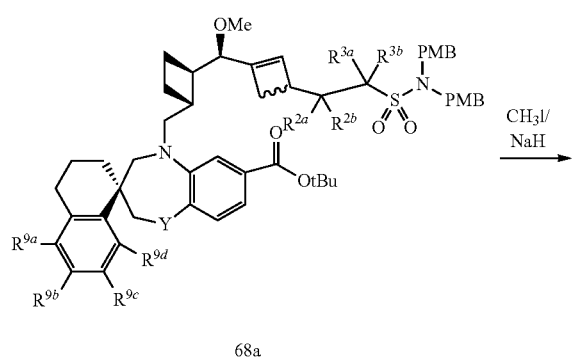

68a

CH$_3$I/ NaH →

In General Scheme 10, the hydroxy group of compound 68a is methylated to give compound 69, and compound 69 is deprotected to give compound 70. The diastereomers of compound 70 can be separated, e.g., by column chromatography or preparative HPLC, and the pure stereoisomers of compound 70 can be cyclized to give compounds 71a and 71b. In the alternative, compound 70 as a mixture of diastereomers can be cyclized to give a mixture of compounds 71a and 71b. After cyclication, the mixture of compounds 71a and 71b can be separated to give pure stereoisomers. The same process can be applied to compound 68b.

General Scheme 11

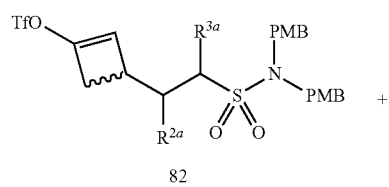

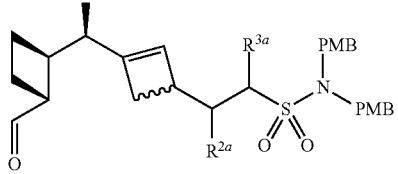

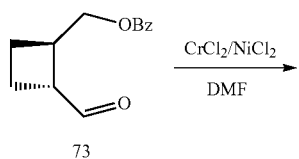

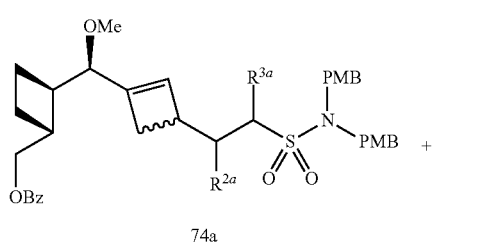

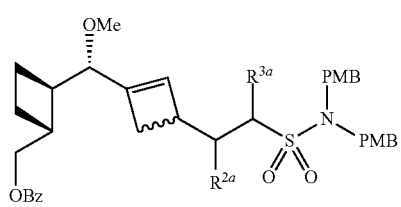

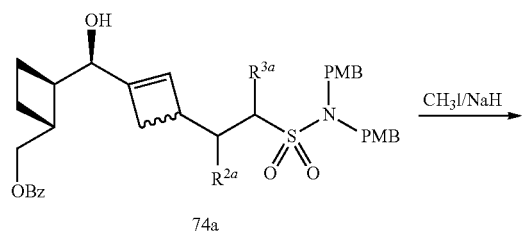

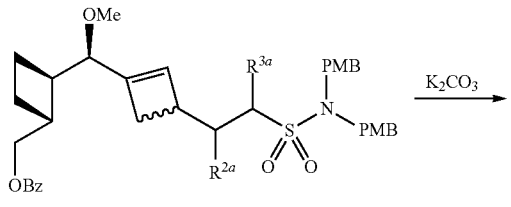

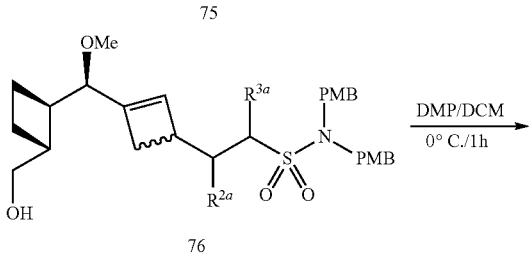

In General Scheme 11, the cyclobutenyl triflate (compound 82) is reacted with ((1R,2R)-2-formylcyclobutyl) methyl benzoate to give a mixture of compounds 74a and 74b. Compounds 74a and 74b are separated by silica gel chromatography. The hydroxy group of compound 74a is methylated to give compound 75, and compound 75 is deprotected to give 76. The hydroxy group of compound 76 is oxidized to give aldehyde 77. The same process can be applied to compound 74b.

General Scheme 12

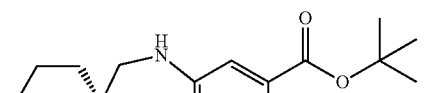

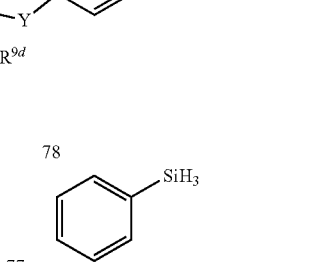

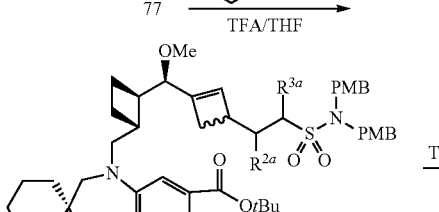

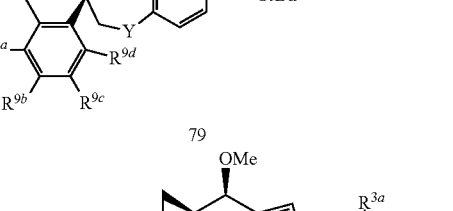

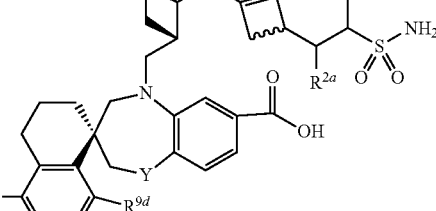

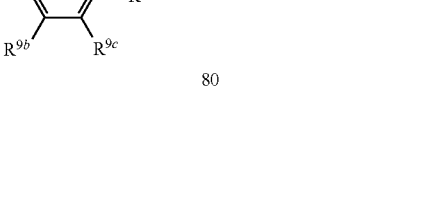

-continued

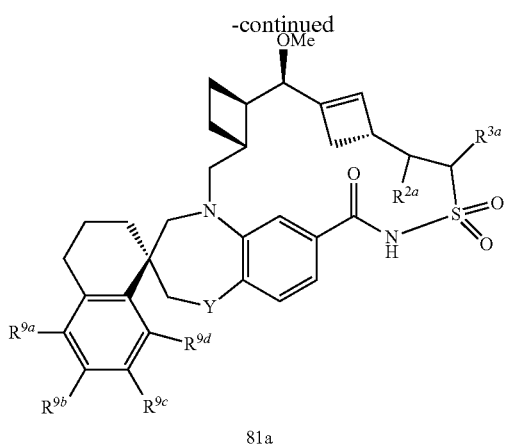

81a

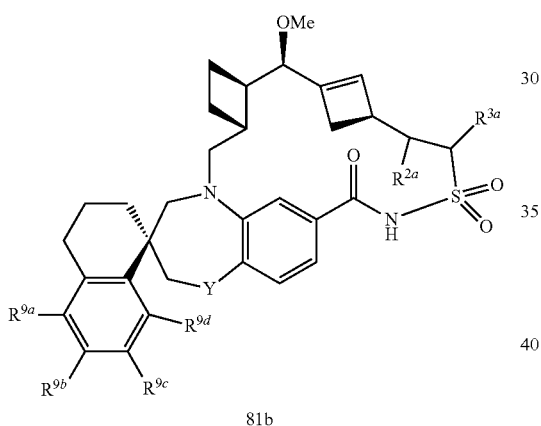

81b

In General Scheme 12, compound 77 is reacted with compound 78 to give compound 79 (as a mixture of diastereomers). Deprotection of compound 79 gives compound 80 (as a mixture of diastereomers). The diastereomers of compound 80 can be separated, e.g., by column chromatography or preparative HPLC, and the pure stereoisomers of compound 80 can be cyclized to give compounds 81a and 81b. In the alternative, compound 80 as a mixture of diastereomers can be cyclized to give a mixture of compounds 81a and 81b. After cyclication, the mixture of compounds 81a and 81b can be separated to give pure stereoisomers.

Example 1

Synthesis of Cpd. No. 1 (Isomer 1) and Cpd. No. 1 (Isomer 2)

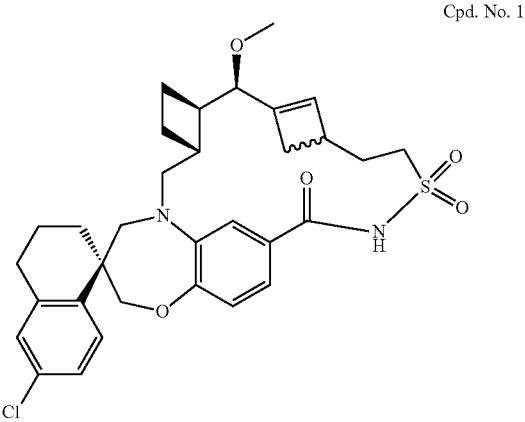 [SMILES: CO[C@H]1C2=CC(CCS(=O)(=O)NC(=O)c3ccc4c(c3)N(C[C@@H]3CC[C@H]31)C[C@@]1(CCCc3cc(Cl)ccc31)CO4)C2]

Cpd. No. 1

Step 1: but-3-en-1-yl benzoate

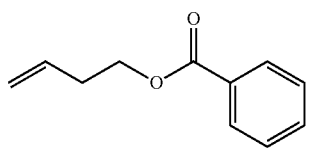

In a 100 mL three-necked round-bottomed flask, but-3-en-1-ol (2.4 g, 33.3 mmol) and triethylamine (5.8 g, 57.3 mmol) were dissolved in $CH_2Cl_2$ (60 mL) and the reaction mixture was cooled to 0° C. with an ice/water bath. Benzoyl chloride (4.5 g, 32.0 mmol) was added and the reaction mixture was warmed to room temperature and stirred overnight. The reaction was quenched with water. The organic layer was separated and the aqueous phase was extracted with DCM. The organic layers were combined, washed with saturated NaCl, and concentrated. The residue was purified with silica gel column chromatography (ethyl acetate/hexane, 1/50-1/10, v/v) to give the title compound (5.0 g, yield: 85.0%). MS m/z 177.1[M+H]$^+$. 1H NMR (400 MHz, CDCl$_3$) δ 8.10-8.03 (m, 2H), 7.62-7.53 (m, 1H), 7.46 (t, J=7.7 Hz, 2H), 5.98-5.83 (m, 1H), 5.24-5.17 (m, 1H), 5.16-5.11 (m, 1H), 4.40 (t, J=6.7 Hz, 2H), 2.55-2.52 (m, 2H).

Step 2: 2-(2,2-dichloro-3-oxocyclobutyl)ethyl benzoate

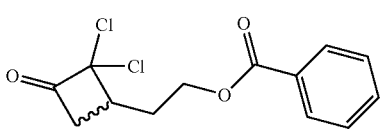 [SMILES: O=C(OCCC1CC(=O)C1(Cl)Cl)c1ccccc1]

In a dried 100 mL three-necked round-bottomed flask, but-3-en-1-yl benzoate (2.0 g, 11.35 mmol) and zinc (2.97 g, 45.4 mmol) were added in diethyl ether (25 mL) under nitrogen. 2,2,2-Trichloroacetyl chloride (4.13 g, 22.70 mmol) and DME (2.05 g, 22.70 mmol), as a solution in diethyl ether (25 mL) were added dropwise to the reaction mixture over 20 min and the mixture was stirred overnight. Heptane (50 mL) was added to the reaction. Zn was precipitated and removed through filtration. The organic layer was washed with H$_2$O, saturated NaHCO$_3$, saturated NaCl, dried over Na$_2$SO$_4$, and concentrated. The residue was added to a Biotage column and eluted with ethyl acetate/hexane from 10% to 35% to give the title compound (1.57 g, 48.2%) as a yellow oil. MS m/z 288.0 [M+H]$^+$; $^1$H NMR (400 MHz, CDCl$_3$) δ8.12-8.00 (m, 2H), 7.67-7.55 (m, 1H), 7.52-7.44 (m, 2H), 4.55-4.50 (m, 2H), 3.54-3.38 (m, 1H), 3.21-3.06 (m, 2H), 2.52-2.39 (m, 1H), 2.20-2.08 (m, 1H).

Step 3: 2-(3-oxocyclobutyl)ethyl benzoate

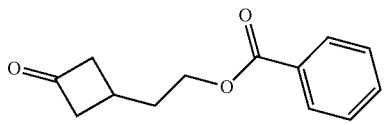 [SMILES: O=C1CC(CCOC(=O)c2ccccc2)C1]

In a dried 25 mL round-bottomed flask, 2-(2,2-dichloro-3-oxocyclobutyl)ethyl benzoate (1.5 g, 5.22 mmol) was dissolved in acetic acid (10 mL). Zinc (1.0 g, 15.66 mmol) was added and the reaction mixture was stirred at 60° C. for 3 h. Acetic acid was removed under reduced pressure and the residue was purified by chromatography and eluted with ethyl acetate/hexane from 5% to 35% to give the title compound (1.0 g, 88.0%) as a colorless oil. MS m/z 218.1 [M+H]$^+$; $^1$H NMR (400 MHz, CDCl$_3$) δ8.09-8.02 (m, 2H), 7.63-7.54 (m, 1H), 7.47 (t, J=7.6 Hz, 2H), 4.50-4.35 (m, 2H), 3.33-3.20 (m, 2H), 2.91-2.79 (m, 2H), 2.67-2.52 (m, 1H), 2.21-2.04 (m, 2H).

Step 4: 2-(3-(((trifluoromethyl)sulfonyl)oxy)cyclobut-2-en-1-yl)ethyl benzoate

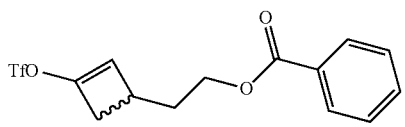 [SMILES: O=C(OCCC1C=C(OS(=O)(=O)C(F)(F)F)C1)c1ccccc1]

In a dried 50 mL two-necked round-bottomed flask 2-(3-oxocyclobutyl)ethyl benzoate (500 mg, 2.29 mmol) was dissolved in tetrahydrofuran (5 mL) under nitrogen. The reaction mixture was cooled to −78° C. 1M potassium bis(trimethylsilyl)amide (5.0 mL, 5.0 mmol) in THF was added slowly to the reaction and the mixture was stirred for 15 min. 1,1,1-Trifluoro-N-phenyl-N-((tri-fluoromethyl)sulfonyl)methanesulfonamide (859 mg, 2.40 mmol) in THF (5 mL) was added dropwise over 15 min and the reaction mixture was stirred at −78° C. for 1.5 h. H$_2$O was added to quench the reaction. The reaction mixture was extracted with ethyl acetate (30 mL×3). The organic layers were combined and concentrated. The residue was purified with ethyl acetate/hexane from 5% to 20% to give the title compound (350 mg, 43.6%) as a colorless oil. MS m/z 351.1 [M+H]$^+$; $^1$H NMR (400 MHz, CDCl$_3$) δ 8.05 (dd, J=8.1, 1.4 Hz, 2H), 7.64-7.56 (m, 1H), 7.51-7.45 (m, 2H), 5.58 (s, 1H), 4.44-4.35 (m, 2H), 3.14 (dd, J=13.5, 4.2 Hz, 1H), 2.82-2.72 (m, 1H), 2.59 (dd, J=13.5, 1.3 Hz, 1H), 2.04-1.97 (m, 2H).

Step 5: tert-butyl (S)-5-(((1R,2R)-2-((R)—((S)-3-(2-(benzoyloxy)ethyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—((R)-3-(2-(benzoyloxy)ethyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate

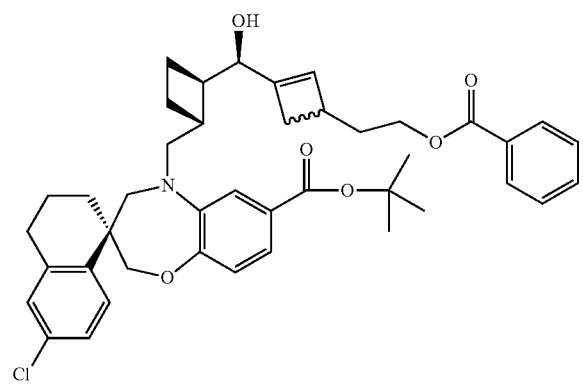 [SMILES: CC(C)(C)OC(=O)c1ccc2c(c1)N(C[C@@H]1CC[C@H]1[C@@H](O)C1=CC(CCOC(=O)c3ccccc3)C1)C[C@@]1(CCCc3cc(Cl)ccc31)CO2]

In a dried 25 mL two-necked round-bottomed flask chromium (II) chloride (951 mg, 7.74 mmol) and nickel (II) chloride (5.02 mg, 0.04 mmol) were added in DMF (5 mL) under nitrogen. The mixture was stirred for 15 min. A solution of tert-butyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (960 mg, 1.935 mmol) in DMF (5 mL) and a solution of 2-(3-(((trifluoromethyl)sulfonyl) oxy)cyclobut-2-en-1-yl)ethyl benzoate (1.08 g, 3097 mmol) in DMF (5 mL) were added and the reaction mixture was stirred at 70° C. for 3 h. H$_2$O was added to the reaction mixture followed by extraction with ethyl acetate. The organic layer was washed with saturated NaCl, dried over Na$_2$SO$_4$, and concentrated to give a mixture of four stereoisomers. The residue was added to a Biotage column and eluted with ethyl acetate/hexane from 0 to 30% to give the title compound (400 mg, 29.6%) as a mixture of the first eluting diastereomers. MS m/z 699.3 [M+H]$^+$.

191

Step 6: tert-butyl (S)-5-(((1R,2R)-2-((R)—((S)-3-(2-(benzoyloxy)ethyl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—((R)-3-(2-(benzoyloxy)ethyl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate

192

Step 7: tert-butyl (S)-6'-chloro-5-(((1R,2R)-2-((R)—((S)-3-(2-hydroxyethyl)cyclobut-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate and tert-butyl (S)-6'-chloro-5-(((1R,2R)-2-((R)—((R)-3-(2-hydroxyethyl)cyclobut-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate

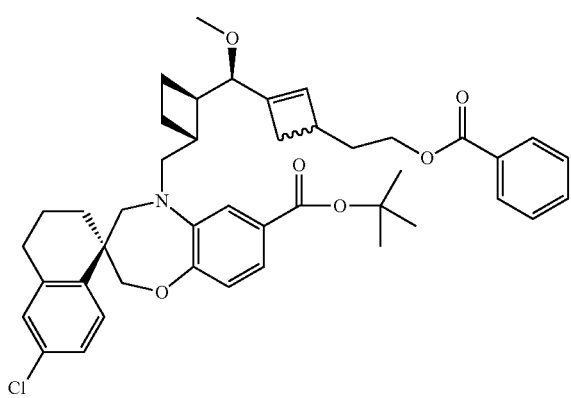 [SMILES: CO[C@@H](C1=CC(CCOC(=O)c2ccccc2)C1)[C@@H]1CC[C@H]1CN1C[C@@]2(CCCc3cc(Cl)ccc32)COc2ccc(C(=O)OC(C)(C)C)cc21]

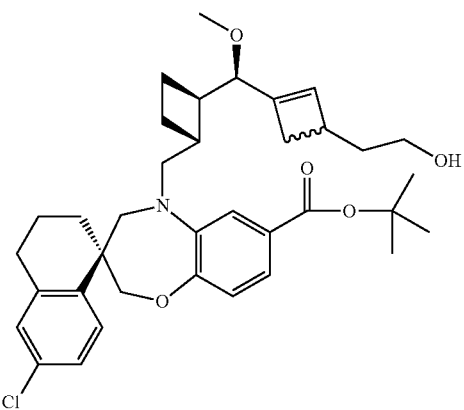 [SMILES: CO[C@@H](C1=CC(CCO)C1)[C@@H]1CC[C@H]1CN1C[C@@]2(CCCc3cc(Cl)ccc32)COc2ccc(C(=O)OC(C)(C)C)cc21]

In a 100 mL round-bottomed flask, NaH (19.25 mg, 0.80 mmol) was added in tetrahydrofuran (10 mL) and the mixture was stirred for 30 min. A mixture of tert-butyl (S)-5-(((1R,2R)-2-((R)—((S)-3-(2-(benzoyloxy)ethyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—((R)-3-(2-(benzoyloxy)ethyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate (280 mg, 0.40 mmol) in THF (4 mL) was added, followed by DMAP (0.98 mg, 8.02 µmol) and $CH_3I$ (114 mg, 0.80 mmol). The mixture was stirred at 30° C. for 3 h. The reaction was quenched with aq. $NH_4Cl$ (10 mL), followed by extraction with ethyl acetate. The combined organic layers were dried over $Na_2SO_4$, filtered and concentrated to give Cpd. No. 42 as a mixture of the title compounds as a yellow oil (260 mg) which was used directly in the next step without further purification.

In a 50 mL round-bottomed flask, a mixture of tert-butyl (S)-5-(((1R,2R)-2-((R)—((S)-3-(2-(benzoyloxy)ethyl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—((R)-3-(2-(benzoyloxy)ethyl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate (200 mg, 0.28 mmol) was dissolved in MeOH (10 mL) and DCM (5 mL). $K_2CO_3$ (156 mg, 1.12 mmol) was added and the reaction mixture was stirred for 3 h. $K_2CO_3$ was removed by filtration and solvent was removed under reduced pressure. The residue was added to a Biotage column and eluted with ethyl acetate/hexane from 10% to 50% to give the title compound as a mixture of two diastereomers (100 mg, 58.6%). MS m/z 609.4 $[M+H]^+$.

Step 8: tert-butyl (S)-6'-chloro-5-(((1R,2R)-2-((R)-methoxy((S)-3-(2-(pyrimidin-2-ylthio)ethyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylate and tert-butyl (S)-6'-chloro-5-(((1R,2R)-2-((R)-methoxy((R)-3-(2-(pyrimidin-2-ylthio)ethyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylate

Step 9: tert-butyl (S)-6'-chloro-5-(((1R,2R)-2-((R)-methoxy((S)-3-(2-(pyrimidin-2-ylsulfonyl)ethyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylate and tert-butyl (S)-6'-chloro-5-(((1R,2R)-2-((R)-methoxy((R)-3-(2-(pyrimidin-2-ylsulfonyl)ethyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylate

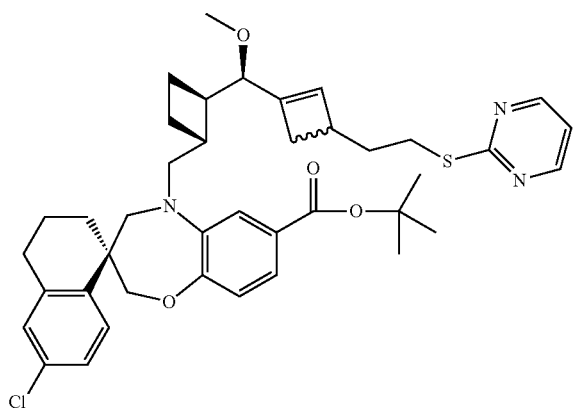 [SMILES: CO[C@@H](C1=CC(CCSc2ncccn2)C1)[C@@H]1CC[C@H]1CN1C[C@@]2(CCCc3cc(Cl)ccc32)COc2ccc(C(=O)OC(C)(C)C)cc21]

In a 50 mL two-necked round-bottomed flask, triphenylphosphane (110 mg, 0.42 mmol) was dissolved in toluene (3 mL) under nitrogen and the reaction mixture was cooled to 0° C. A solution of DIAD (82 mg, 0.41 mmol) in toluene (3 mL) was added and the reaction mixture was stirred for 10 min. A mixture of tert-butyl (S)-6'-chloro-5-(((1R,2R)-2-((R)—(S)-3-(2-hydroxyethyl)cyclobut-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate and tert-butyl (S)-6'-chloro-5-(((1R,2R)-2-((R)—(R)-3-(2-hydroxyethyl)cyclobut-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate (165 mg, 0.27 mmol) in toluene (6 mL) was added and the reaction mixture was stirred for 1 h. Then pyrimidine-2-thiol (10.0 mg, 0.09 mmol) was added and the reaction mixture was stirred overnight. Solvent was removed under vacuum and the residue was added to a Biotage column to give the title compound as a mixture of two diastereomers (90 mg, 47.2%). MS m/z 703.3 [M+H]$^+$.

In a 25 mL two-necked round-bottomed flask, sodium tungstate dihydrate (122.1 mg, 0.37 mmol), phenylphosphonic acid (60 mg, 0.38 mmol), and bis(tetrabutylammonium) sulphate (215 mg, 0.37 mmol) were mixed, then hydrogen peroxide (15.74 mg, 0.46 mmol) was added to the reaction mixture. A mixture of tert-butyl (S)-6'-chloro-5-(((1R,2R)-2-((R)-methoxy((S)-3-(2-(pyrimidin-2-ylthio)ethyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylate and tert-butyl (S)-6'-chloro-5-(((1R,2R)-2-((R)-methoxy((R)-3-(2-(pyrimidin-2-ylthio)ethyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylate (130 mg, 0.18 mmol) in toluene (5 mL) was added and the reaction mixture was stirred at 75° C. overnight. H$_2$O (15 mL) was added to the reaction mixture followed by extraction with ethyl acetate (20 mL×3). The combined organic layers were dried over Na$_2$SO$_4$, filtered and concentrated. The residue was added to a Biotage column and eluted with ethyl acetate/hexane from 10% to 50% to give the title compound as a mixture of two diastereomers (90 mg, 66.2%). MS m/z 734.3 [M+H]$^+$.

Step 10: sodium 2-((S)-3-((R)-((1R,2R)-2-((S)-7-(tert-butoxycarbonyl)-6'-chloro-3',4'-dihydro-2H,2'H-spiro[benzo[b][1,4]oxazepine-3,1'-naphthalen]-5(4H)-yl)methyl)cyclobutyl)(methoxy)methyl)cyclobutan-1-yl)ethane-1-sulfinate and sodium 2-((R)-3-((R)-((1R,2R)-2-((S)-7-(tert-butoxycarbonyl)-6'-chloro-3',4'-dihydro-2H,2'H-spiro[benzo[b][1,4]oxazepine-3,1'-naphthalen]-5(4H)-yl)methyl)cyclobutyl)(methoxy)methyl)cyclobutan-1-yl)ethane-1-sulfinate

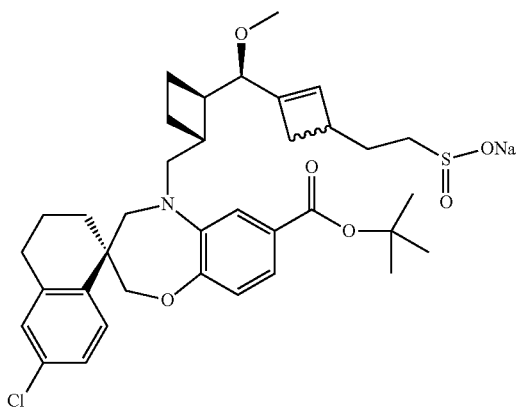

In a 25 mL round-bottomed flask, a mixture of tert-butyl (S)-6'-chloro-5-(((1R,2R)-2-((R)-methoxy((S)-3-(2-(pyrimidin-2-ylsulfonyl)ethyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylate and tert-butyl (S)-6'-chloro-5-(((1R,2R)-2-((R)-methoxy((R)-3-(2-(pyrimidin-2-ylsulfonyl)ethyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylate (95 mg, 0.13 mmol) was dissolved in methanol (3 mL) and the reaction mixture was cooled to 0° C. with an ice/water bath. CH$_3$ONa in CH$_3$OH (28 mg, 0.131 mmol) was added and the reaction mixture was stirred for 15 min. Solvent was removed under vacuum and diethyl ether was added to the residue and the mixture was stirred for 5 min and concentrated to give the title compound as a mixture of two diastereomers (60 mg). The crude product was used directly for the next step without further purification.

Step 11: tert-butyl (S)-6'-chloro-5-(((1R,2R)-2-((R)-methoxy((S)-3-(2-sulfamoylethyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylate and tert-butyl (S)-6'-chloro-5-(((1R,2R)-2-((R)-methoxy((R)-3-(2-sulfamoyl ethyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylate

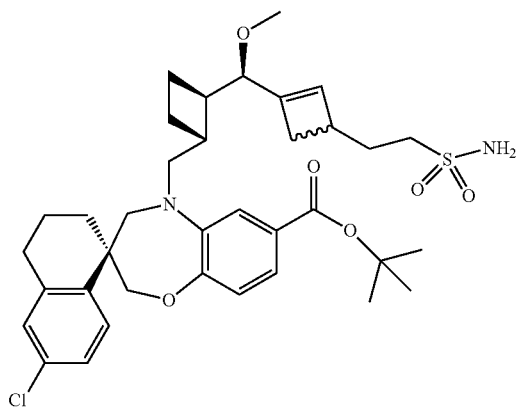 [SMILES: CO[C@@H](C1=CC(CCS(N)(=O)=O)C1)[C@@H]1CC[C@H]1CN1C[C@@]2(CCCc3cc(Cl)ccc32)COc2ccc(C(=O)OC(C)(C)C)cc21]

In a 25 mL round-bottomed flask, a mixture of sodium 2-((S)-3-((R)-((1R,2R)-2-(((S)-7-(tert-butoxycarbonyl)-6'-chloro-3',4'-dihydro-2H,2'H-spiro[benzo[b][1,4]oxazepine-3,1'-naphthalen]-5(4H)-yl)methyl)cyclobutyl)(methoxy)methyl)cyclobutan-1-yl)ethane-1-sulfinate and sodium 2-((R)-3-((R)-((1R,2R)-2-(((S)-7-(tert-butoxycarbonyl)-6'-chloro-3',4'-dihydro-2H,2'H-spiro[benzo[b][1,4]oxazepine-3,1'-naphthalen]-5(4H)-yl)methyl)cyclobutyl)(methoxy)methyl)cyclobutan-1-yl)ethane-1-sulfinate (90 mg, 0.13 mmol) was dissolved in water (2 mL). Acetylsodium (13.1 mg, 0.20 mmol) and 1-nitroso-3-(14-sulfanyl)trioxidane (22.5 mg, 0.20 mmol) were added and the reaction-mixture was stirred overnight. Solvent was removed under vacuum and the residue was purified with column chromatography (DCM/MeOH, 50/1-10/1, v/v) to give the title compound as a mixture of two diastereomers (55 mg, 61.7%). MS m/z 671.4 [M+H]$^+$.

Step 12: (S)-6'-chloro-5-((((1R,2R)-2-((R)-methoxy ((S)-3-(2-sulfamoylethyl)cyclobut-1-en-1-yl)methyl) cyclobutyl)methyl)-3',4,4',5-tetrahydro-2H,2'H-spiro [benzo[b][1,4]oxazepine-3,1'-naphthalene]-7-carboxylic acid and (S)-6'-chloro-5-(((1R,2R)-2-((R)-methoxy((S)-3-(2-sulfamoylethyl)cyclobut-1-en-1-yl)methyl)cyclobutyl)methyl)-3',4,4',5-tetrahydro-2H,2'H-spiro[benzo[b][1,4]oxazepine-3, 1'-naphthalene]-7-carboxylic acid

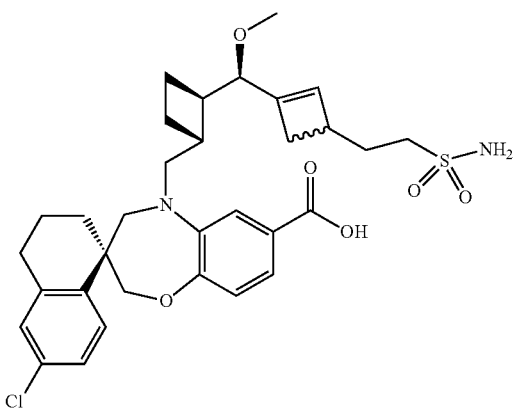 [SMILES: CO[C@@H](C1=CC(CCS(N)(=O)=O)C1)[C@@H]1CC[C@H]1CN1C[C@@]2(CCCc3cc(Cl)ccc32)COc2ccc(C(=O)O)cc21]

In a 25 mL round-bottomed flask, a mixture of tert-butyl (S)-6'-chloro-5-((((1R,2R)-2-((R)-methoxy((S)-3-(2-sulfamoylethyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylate and tert-butyl (S)-6'-chloro-5-((((1R,2R)-2-((R)-methoxy((R)-3-(2-sulfamoyl ethyl) cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylate (55 mg, 0.082 mmol) was dissolved in $CH_2Cl_2$ (5 mL). TFA (3 mL) was added and the reaction mixture was stirred at room temperature for 2 h. Solvent was removed under vacuum and the residue was purified with column chromatography (DCM/MeOH, 50/1-5/1, v/v) to give the title compound as a mixture of two diastereomers (50 mg, 99%) that was used directly in the next step without further purification. MS m/z 615.3 $[M+H]^+$.

Step 13: Cpd. No. 1 (Isomer 1) and Cpd. No. 1 (Isomer 2)

In a 25 mL round-bottomed flask, a mixture of (S)-6'-chloro-5-((((1R,2R)-2-((R)-methoxy((S)-3-(2-sulfamoylethyl)cyclobut-1-en-1-yl)methyl)cyclobutyl)methyl)-3',4,4', 5-tetrahydro-2H,2'H-spiro[benzo[b][1,4]oxazepine-3,1'-naphthalene]-7-carboxylic acid and (S)-6'-chloro-5-((((1R, 2R)-2-((R)-methoxy((R)-3-(2-sulfamoyl ethyl)cyclobut-1-en-1-yl)methyl)cyclobutyl)methyl)-3',4,4',5-tetrahydro-2H, 2'H-spiro[benzo[b][1,4]oxazepine-3,1'-naphthalene]-7-carboxylic acid (50 mg, 0.081 mmol) was dissolved in 1,2-dichloroethane (10 mL). The reaction mixture was cooled to 0° C. with ice/water bath, then triethylamine (24.7 mg), $T_3P$ (51.7 mg, 50% solution in EA), and DMAP (20.0 mg) were added and the reaction mixture was stirred at room temperature for 3 h. The solvent was removed under reduced pressure and the residue was purified by preparative HPLC.

The first-eluting diastereomer (9.7 mg) was designated as Cpd. No. 1 (isomer 1). The stereochemistry of the asymmetric carbon atom of the cyclobutene ring has not been determined. $^1$H NMR (500 MHz, DMSO-$d_6$) δ 11.89 (s, 1H), 7.69 (d, J=8.5 Hz, 1H), 7.31 (dd, J=8.5, 1.8 Hz, 1H), 7.23 (d, J=1.8 Hz, 1H), 6.95 (d, J=8.1 Hz, 1H), 6.91 (d, J=8.1 Hz, 1H), 6.87 (s, 1H), 6.10 (s, 1H), 4.13 (d, J=12.3 Hz, 1H), 3.94 (d, J=12.3 Hz, 1H), 3.78 (dd, J=15.6, 4.3 Hz, 1H), 3.71 (d, J=14.4 Hz, 1H), 3.68-3.58 (m, 1H), 3.56-3.49 (m, 3H), 3.21-3.18 (m, 1H), 3.19 (s, 3H), 2.87-2.79 (m, 1H), 2.79-2.73 (m, 2H), 2.64-2.59 (m, 1H), 2.47-2.38 (m, 1H), 2.30-2.22 (m, 1H), 2.08-1.79 (m, 8H), 1.76-1.71 (m, 1H), 1.68-1.63 (m, 1H), 1.47-1.39 (m, 1H).

The second-eluting diastereomer (12.4 mg) was designated as Cpd. No. 1 (isomer 2). The stereochemistry of the asymmetric carbon atom of the cyclobutene ring has not been determined. $^1$H NMR (500 MHz, DMSO-$d_6$) δ 11.84 (s, 1H), 7.68 (d, J=8.5 Hz, 1H), 7.31 (dd, J=8.5, 2.2 Hz, 1H), 7.21 (d, J=2.2 Hz, 1H), 6.93 (d, J=8.0 Hz, 1H), 6.89-6.85 (m, 1H), 6.83 (s, 1H), 6.21 (s, 1H), 4.10 (d, J=12.4 Hz, 1H), 3.92 (d, J=12.4 Hz, 1H), 3.73-3.32 (m, 6H), 3.29 (s, 3H), 3.11-3.02 (m, 1H), 2.93-2.80 (m, 2H), 2.77-2.66 (m, 2H), 2.34-2.28 (m, 1H), 2.23-2.14 (m, 1H), 2.06-1.73 (m, 8H), 1.64-1.55 (m, 1H), 1.46-1.35 (m, 2H).

Example 2

Synthesis of Cpd. No. 4 (Isomer 1) and Cpd. No. 4 (Isomer 2)

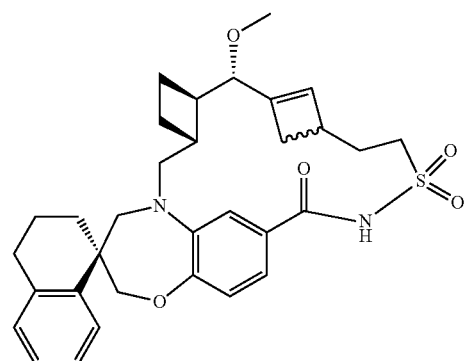

Step 1: tert-butyl (S)-5-(((1R,2R)-2-((S)—((S)-3-(2-(benzoyloxy)ethyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((S)—((R)-3-(2-(benzoyloxy)ethyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate

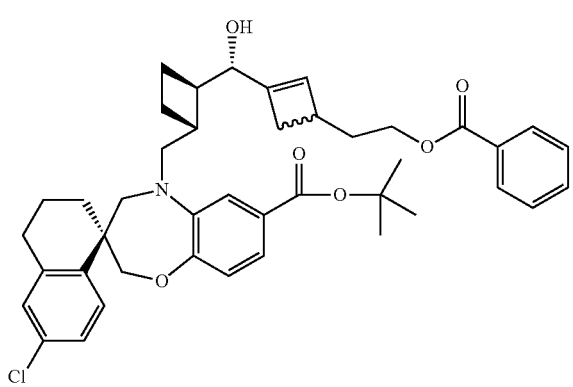 [SMILES: CC(C)(C)OC(=O)c1ccc2c(c1)N(C[C@@H]1CC[C@H]1[C@H](O)C1=CC(CCOC(=O)c3ccccc3)C1)C[C@@]1(CCCc3cc(Cl)ccc31)CO2]

The title compounds (350 mg, 25.9%) were obtained as a mixture of the second eluting diastereomers described in Example 1, Step 5. MS m/z 699.3 [M+H]+.

Step 2: Cpd. No. 4 (Isomer 1) and Cpd. No. 4 (Isomer 2)

Cpd. No. 4 (isomer 1) and Cpd. No. 4 (isomer 2) were prepared from a mixture of tert-butyl (S)-5-(((1R,2R)-2-((S)—((S)-3-(2-(benzoyloxy)ethyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((S)—((R)-3-(2-(benzoyl oxy)ethyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate (from step 1), following a similar procedure described in Example 1, Steps 6 through 13.

The first-eluting diastereomer (3.1 mg, 9.12%) was designated as Cpd. No. 4 (isomer 1). The stereochemistry of the asymmetric carbon atom of the cyclobutene ring has not been determined. MS m/z 597 [M+H]+.

The second-eluting diastereomer (6.1 mg, 18.0%) was designated as Cpd. No. 4 (isomer 2). The stereochemistry of the asymmetric carbon atom of the cyclobutene ring has not been determined. MS m/z 597 [M+H]+.

Example 3

Synthesis of Cpd. No. 5 (Isomer 1) and Cpd. No. 5 (Isomer 2)

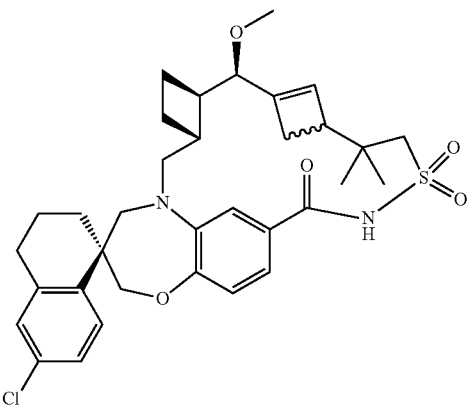 [SMILES: CO[C@H]1C2=CC(C2)C(C)(C)CS(=O)(=O)NC(=O)c2ccc3c(c2)N(C[C@@H]2CC[C@H]21)C[C@@]1(CCCc2cc(Cl)ccc21)CO3]

Step 1: 3-hydroxy-2,2-dimethylpropyl benzoate

In a round-bottomed flask 2,2-dimethylpropane-1,3-diol (10 g, 96 mmol), DMAP (0.587 g, 4.80 mmol), and DIPEA (24.82 g, 192 mmol) were dissolved in DCM (400 mL) and the reaction mixture was cooled to 0° C. A solution of benzoyl chloride (14.85 g, 106 mmol) in DCM (60 mL) was added dropwise and the reaction mixture was stirred at room temperature for 1.5 h. Saturated NaCl was added to the reaction mixture followed by extraction with dichloromethane. The combined organic layers were dried over Na₂SO₄, filtered and concentrated. The residue was added to a silica gel column and eluted with ethyl acetate/hexane from 0 to 30% to give the title compound (13 g, 65.0%). MS m/z 209.2 (M+H)+.

Step 2: 2,2-dimethyl-3-oxopropyl benzoate

In a round-bottomed flask 3-hydroxy-2,2-dimethylpropyl benzoate (13 g, 62.4 mmol), Silica gel (26 g), and PCC (26.9 g, 125 mmol) were added in DCM (150 mL) and the mixture was stirred for 3 h. The reaction mixture was filtered through a silica gel and the filter cake was rinsed with dichloromethane. The solvent was removed in vacuo to give the title compound (8 g, 62.1%).

Step 3: 2,2-dimethylbut-3-en-1-yl benzoate

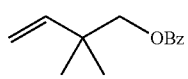

In a round-bottomed flask bromo(methyl)triphenylphosphane (20.79 g, 58.2 mmol) was dissolved in THF (200 mL) under argon. The mixture was cooled to 0° C. and potassium 2-methylpropan-2-olate (6.53 g, 58.2 mmol) was added slowly and the reaction mixture was stirred at room temperature for 4 h. The mixture was cooled to −50° C. 2,2-Dimethyl-3-oxopropyl benzoate (8 g, 38.8 mmol) was added dropwise to the reaction mixture. The mixture was warmed to room temperature and stirred for 1 h. Saturated NH$_4$Cl was added to the reaction mixture followed by extraction with ethyl acetate. The combined organic layers were dried over Na$_2$SO$_4$, filtered and concentrated. The crude product was added to a silica gel column and eluted with ethyl acetate/hexane from 0 to 5% to give the title compound (6.2 g, 78%).

Step 4: 2-methyl-2-(3-oxocyclobutyl)propyl benzoate

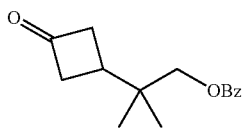

In a round-bottomed flask 2,2-dimethylbut-3-en-1-yl benzoate (6.2 g, 30.4 mmol) and zinc (7.94 g, 121 mmol) were added in diethyl ether (15 ml) under argon. 2,2,2-Trichloroacetyl chloride (11.04 g, 60.7 mmol) and DME (5.47 g, 60.7 mmol), as a solution in diethyl ether (30 mL) were added and the reaction mixture was heated to 40° C. and stirred overnight. Hexane (50 mL) was added and the suspension stirred for 20 min to precipitate the zinc salts. The solution was washed with H$_2$O, saturated NaHCO$_3$ and saturated NaCl and concentrated. The residue was dissolved in acetic acid (100 mL) and zinc (5.95 g, 91.2 mmol) was then added. The mixture was heated to 70° C. and stirred for 8 h. The reaction mixture was filtered through a celite and the solvent was removed in vacuo. The residue was added to a silica gel column and eluted with ethyl acetate/hexane from 0 to 10% to give the title compound (5.5 g, 73.3%). MS m/z 247.2 (M+H)$^+$.

Step 5: 3-(1-hydroxy-2-methylpropan-2-yl)cyclobutan-1-one

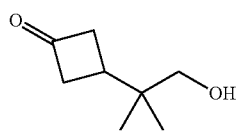

In a round-bottomed flask K$_2$CO$_3$ (9.26 g, 67.0 mmol) and 2-methyl-2-(3-oxocyclobutyl)propyl benzoate (5.5 g, 22.33 mmol) were dissolved in MeOH (100 mL). The mixture was heated to 35° C. and stirred for 3 h. The reaction mixture was filtered through a celite and concentrated. The residue was added to a silica gel column and eluted with ethyl acetate/hexane from 0 to 50% to give the title compound (1.9 g, 59.8%). $^1$H NMR (500 MHz, CDCl$_3$) δ 3.41 (s, 2H), 2.93 (d, J=8.4 Hz, 4H), 2.51-2.43 (m, 1H), 0.93 (s, 6H).

Step 6: 2-methyl-2-(3-oxocyclobutyl)propyl methanesulfonate

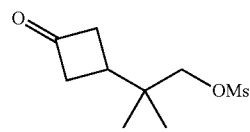

In a round-bottomed flask 3-(1-hydroxy-2-methylpropan-2-yl)cyclobutan-1-one (1.9 g, 13.36 mmol) and triethylamine (2.028 g, 20.04 mmol) were dissolved in DCM (15 mL) and the mixture was cooled to 0° C. Mesyl chloride (1.837 g, 16.03 mmol) was added dropwise and the reaction mixture was stirred for 30 min. H$_2$O was added to the reaction mixture followed by extraction with ethyl acetate. The combined organic layers were dried over Na$_2$SO$_4$, filtered and concentrated. The residue was added to a silica gel column and eluted with ethyl acetate/hexane from 0 to 40% to give the title compound (2.5 g, 85%). $^1$H NMR (500 MHz, CDCl$_3$) δ 3.97 (s, 2H), 3.02 (s, 3H), 3.01-2.88 (m, 4H), 2.55-2.46 (m, 1H), 1.02 (s, 6H). MS m/z (ESI) 221.4 (M+H)$^+$.

Step 7: S-(2-methyl-2-(3-oxocyclobutyl)propyl) ethanethioate

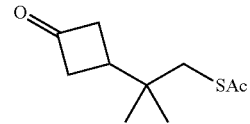

In a round-bottomed flask 2-methyl-2-(3-oxocyclobutyl) propyl methanesulfonate (2 g, 9.08 mmol) and potassium thioacetate (4.15 g, 36.3 mmol) were dissolved in DMF (20 mL) under argon. The mixture was stirred at 100° C. for 3 h. Saturated NaCl was added to the reaction mixture followed by extraction with ethyl acetate. The combined organic layers were dried over Na$_2$SO$_4$, filtered and concentrated. The residue was added to a silica gel column and eluted with ethyl acetate/hexane from 0 to 20% to give the title compound (850 mg, 46.7%). $^1$H NMR (500 MHz, CDCl$_3$) δ 2.96-2.88 (m, 6H), 2.49-2.39 (m, 1H), 2.36 (s, 3H), 0.96 (s, 6H). MS m/z 201.1 (M+H)$^+$.

Step 8: 2-Methyl-2-(3-oxocyclobutyl)propane-1-sulfonamide

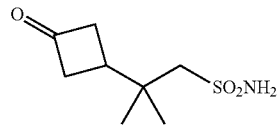

In a round-bottomed flask S-(2-methyl-2-(3-oxocyclobutyl)propyl) ethanethioate (950 mg, 4.74 mmol) and 2M HCl (8 mL, 16.00 mmol) were dissolved in acetonitrile (4 mL) and the solution was cooled to 0° C. NCS (2533 mg, 18.97 mmol) was added and the mixture was warmed to room temperature and stirred for 30 min. The solvent was removed in vacuo to give sulfuryl chloride. In a round-bottomed flask ammonium hydroxide (9 g, 71.9 mmol) was dissolved in THF (4.00 mL) and the mixture was cooled to 0° C. Sulfuryl chloride, as a solution in THF (4.00 mL), was added dropwise and the reaction mixture was stirred for 10 min. TLC showed the reaction was complete. H₂O was added to the reaction mixture followed by extraction with ethyl acetate. The combined organic layers were dried over Na₂SO₄, filtered and concentrated to give the title compound (920 mg, 94%). ¹H NMR (500 MHz, DMSO-d₆) δ 6.83 (s, 2H), 3.01 (s, 1H), 2.90 (d, J=8.2 Hz, 4H), 2.67-2.58 (m, 1H), 1.09 (s, 6H). MS m/z 204.1 (M−H)⁻.

Step 9: N,N-Bis(4-methoxybenzyl)-2-methyl-2-(3-oxocyclobutyl)propane-1-sulfonamide

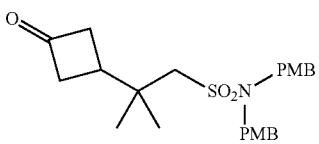

In a round-bottomed flask 2-methyl-2-(3-oxocyclobutyl)propane-1-sulfonamide (920 mg, 4.48 mmol), Cs₂CO₃ (4.381 g, 13.45 mmol), and 4-methoxybenzyl chloride (2.106 g, 13.45 mmol) were added in DMF (15 mL) and the mixture was stirred at 50° C. for 2 h. Saturated NaCl was added to the reaction mixture followed by extraction with ethyl acetate. The combined organic layers were dried over Na₂SO₄, filtered and concentrated. The residue was added to a silica gel column and eluted with ethyl acetate/hexane from 0 to 25% to give the title compound (810 mg, 40.6%). MS m/z 468.5 (M+Na)⁺.

Step 10: (R)-3-(1-(N,N-bis(4-methoxybenzyl)sulfamoyl)-2-methylpropan-2-yl)cyclobut-1-en-1-yl trifluoromethanesulfonate and (S)-3-(1-(N,N-bis(4-methoxybenzyl)sulfamoyl)-2-methylpropan-2-yl)cyclobut-1-en-1-yl trifluoromethanesulfonate

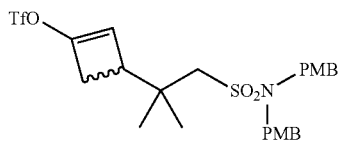

In an oven-dried round-bottomed flask N,N-bis(4-methoxybenzyl)-2-methyl-2-(3-oxocyclobutyl)propane-1-sulfonamide (810 mg, 1.818 mmol) and 1,1,1-trifluoro-N-phenyl-N-((trifluoromethyl)sulfonyl)methanesulfonamide (974 mg, 2.73 mmol) were dissolved in THF (15 mL) under argon and cooled to −78° C. 1M KHMDS (435 mg, 2.181 mmol) in THF was added to the reaction mixture dropwise. The mixture was stirred for 2 h. Saturated NH₄Cl was added to the reaction mixture followed by extraction with ethyl acetate. The combined organic layers were dried over Na₂SO₄, filtered and concentrated. The residue was added to a silica gel column and eluted with ethyl acetate/hexane from 0 to 15% to give a mixture of the title compounds (500 mg, 47.6%). MS m/z 600.3 (M+Na)⁺.

Step 11: tert-butyl (S)-5 #(1R,2R)-2-((R)—((R)-3-(1-(N,N-bis(4-methoxybenzyl)sulfamoyl)-2-methylpropan-2-yl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—((S)-3-(1-(N,N-bis(4-methoxybenzyl)sulfamoyl)-2-methylpropan-2-yl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate

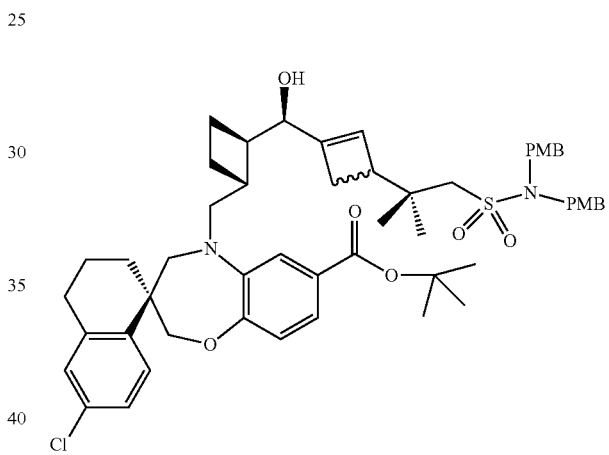

In an oven-dried three-necked round-bottomed flask, chromium (II) chloride (400 mg, 3.25 mmol) and nickel (II) chloride (20 mg, 0.154 mmol) were added in DMF (10 mL) under argon. tert-Butyl (S)-6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (200 mg, 0.403 mmol) and a mixture of (R)-3-(1-(N,N-bis(4-methoxybenzyl)sulfamoyl)-2-methylpropan-2-yl)cyclobut-1-en-1-yl trifluoromethanesulfonate and (S)-3-(1-(N,N-bis(4-methoxybenzyl)sulfamoyl)-2-methylpropan-2-yl)cyclobut-1-en-1-yl trifluoromethanesulfonate (256 mg, 0.444 mmol), as a solution in DMF (10 mL) were added and the reaction mixture was stirred at 70° C. for 3 h. Saturated NaCl was added to the reaction mixture followed by extraction with ethyl acetate. The combined organic layers were dried over Na₂SO₄, filtered and concentrated to give a mixture of four isomers. The residue was added to a silica gel column and eluted with ethyl acetate/hexane from 0 to 15% to give the title compounds as the first eluting isomers as a mixture (100 mg, 26.8%). MS m/z 926.2 (M+H)⁺.

Step 12: (S)-6'-chloro-5-((((1R,2R)-2-((R)-methoxy((R)-3-(2-methyl-1-sulfamoylpropan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-((((1R,2R)-2-((R)-methoxy((S)-3-(2-methyl-1-sulfamoylpropan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid

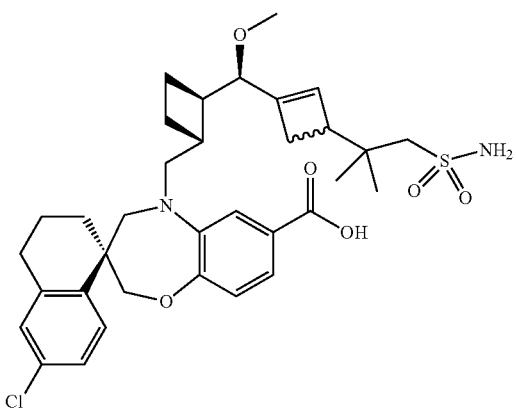 [SMILES: CO[C@@H](C1=CC(C(C)(C)CS(N)(=O)=O)C1)[C@@H]1CC[C@H]1CN1C[C@@]2(CCCc3cc(Cl)ccc32)COc2ccc(C(=O)O)cc21]

In a round-bottomed flask a mixture of tert-butyl (S)-5-((((1R,2R)-2-((R)—((R)-3-(1-(N,N-bis(4-methoxybenzyl)sulfamoyl)-2-methylpropan-2-yl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—((S)-3-(1-(N,N-bis(4-methoxybenzyl)sulfamoyl)-2-methylpropan-2-yl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate (100 mg, 0.108 mmol), DMAP (26.4 mg, 0.216 mmol), and iodomethane (77 mg, 0.540 mmol) were dissolved in THF (10 ml). NaH (51.9 mg, 2.161 mmol) was added at 0° C. and the mixture was stirred for 4 h. H$_2$O was added to the reaction mixture followed by extraction with ethyl acetate. The combined organic layers were dried over Na$_2$SO$_4$, filtered and concentrated. The residue was dissolved in DCM (5 mL) and TFA (5.00 mL) and the mixture was stirred overnight. The solvent was removed in vacuo and the residue was added to a silica gel column and eluted with methanol/dichloromethane from 0 to 10% to give the title compounds as a mixture of two diastereomers (80 mg, 115%). MS m/z 643.4 (M+H)$^+$.

Step 13: Cpd. No. 5 (Isomer 1) and Cpd. No. 5 (Isomer 2)

In a round-bottomed flask a mixture of (S)-6'-chloro-5-((((1R,2R)-2-((R)-methoxy((R)-3-(2-methyl-1-sulfamoylpropan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-((((1R,2R)-2-((R)-methoxy((S)-3-(2-methyl-1-sulfamoylpropan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid (80 mg, 0.124 mmol), triethylamine (62.9 mg, 0.622 mmol), and DMAP (15.19 mg, 0.124 mmol) were dissolved in DCM (20 mL) under argon. The mixture was cooled to 0° C. and 2,4,6-tripropyl-1,3,5,2,4,6-trioxatriphosphinane 2,4,6-trioxide (119 mg, 0.373 mmol) was added. The mixture was stirred for 30 min. H$_2$O was added to the reaction mixture followed by extraction with ethyl acetate. The combined organic layers were dried over Na$_2$SO$_4$, filtered and concentrated. The residue was purified with preparative HPLC to give the title compounds.

The first-eluting diastereomer (10.7 mg, 13.76%) was designated as Cpd. No. 5 (isomer 1). The stereochemistry of the asymmetric carbon atom of the cyclobutene ring has not been determined. $^1$H NMR (500 MHz, DMSO-d$_6$) δ 11.93 (s, 1H), 7.65 (d, J=8.4 Hz, 1H), 7.28 (d, J=8.4 Hz, 1H), 7.18 (s, 1H), 6.93 (d, J=8.2 Hz, 1H), 6.89 (d, J=8.2 Hz, 1H), 6.78 (s, 1H), 6.42 (s, 1H), 4.06 (d, J=12.4 Hz, 1H), 3.89 (d, J=12.4 Hz, 1H), 3.85 (d, J=6.5 Hz, 1H), 3.77 (d, J=14.2 Hz, 1H), 3.69-3.60 (m, 2H), 3.50 (d, J=15.5 Hz, 1H), 3.36-3.31 (m, 1H), 3.26 (d, J=14.2 Hz, 1H), 3.18 (s, 3H), 2.99-2.90 (m, 2H), 2.84-2.60 (m, 2H), 2.46-2.26 (m, 3H), 2.02-1.93 (m, 1H), 1.92-1.80 (m, 2H), 1.71-1.54 (m, 4H), 1.42-1.32 (m, 1H), 1.01 (s, 3H), 1.00 (s, 3H). MS m/z 625.2 [M+H]$^+$.

The second-eluting diastereomer (12.3 mg, 15.8%) was designated as Cpd. No. 5 (isomer 2). The stereochemistry of the asymmetric carbon atom of the cyclobutene ring has not been determined. $^1$H NMR (500 MHz, DMSO-d$_6$) δ 11.80 (s, 1H), 7.66 (d, J=8.5 Hz, 1H), 7.27 (d, J=8.3 Hz, 1H), 7.17 (s, 1H), 6.91 (d, J=8.4 Hz, 1H), 6.81-6.78 (m, 2H), 5.93 (s, 1H), 4.09 (d, J=12.2 Hz, 1H), 3.80 (d, J=12.2 Hz, 1H), 3.69 (d, J=14.4 Hz, 1H), 3.57-3.51 (m, 3H), 3.43-3.38 (m, 1H), 3.29-3.22 (m, 2H), 3.26 (s, 3H), 3.14-3.06 (m, 1H), 2.84-2.77 (m, 1H), 2.75-2.63 (m, 1H), 2.47-2.41 (m, 1H), 2.40-2.34 (m, 1H), 2.28-2.17 (m, 2H), 2.01-1.94 (m, 1H), 1.92-1.78 (m, 5H), 1.76-1.66 (m, 1H), 1.43-1.35 (m, 1H), 1.12 (s, 3H), 0.95 (s, 3H). MS m/z 625.2 [M+H]$^+$.

Example 4

Synthesis of Cpd. No. 6 (Isomer 1) and Cpd. No. 6 (Isomer 2)

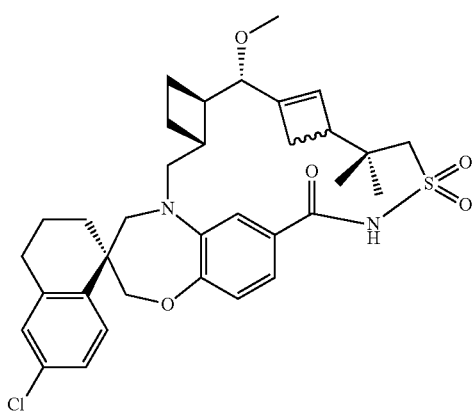

Step 1: tert-butyl (S)-5-(((1R,2R)-2-((S)—((R)-3-(1-(N,N-bis(4-methoxybenzyl)sulfamoyl)-2-methylpropan-2-yl)cyclobut-1-en-1-yl)(hydroxy)methyl)cyclobutyl)methyl)-6'-chloro-3',4',5-tetrahydro-2H,2'H-spiro[benzo[b][1,4]oxazepine-3,1'-naphthalene]-7-carboxylate and tert-butyl (S)-5-(((1R,2R)-2-((S)—((S)-3-(1-(N,N-bis(4-methoxybenzyl)sulfamoyl)-2-methylpropan-2-yl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate

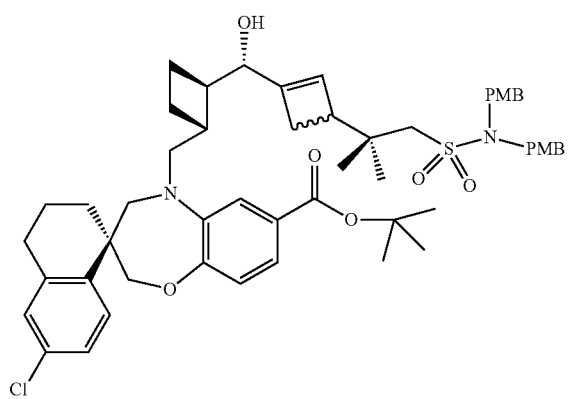

The title compounds were obtained as a mixture of the second eluting diastereomers (90 mg, 24.12%) as described in Example 3, Step 11. MS m/z 926.2 (M+H)+.

Step 2: (S)-6'-chloro-5-(((1R,2R)-2-((S)-methoxy((R)-3-(2-methyl-1-sulfamoylpropan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S)-methoxy((S)-3-(2-methyl-1-sulfamoylpropan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid

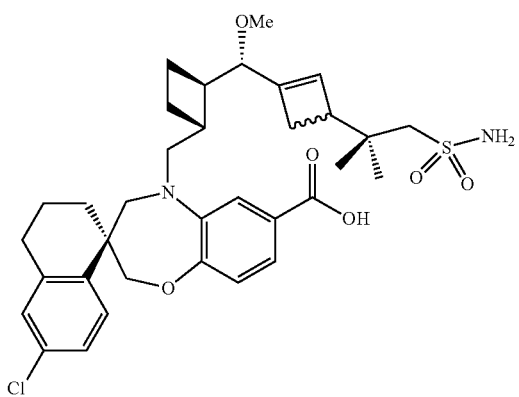

In a round-bottomed flask a mixture of tert-butyl (S)-5-(((1R,2R)-2-((S)—((R)-3-(1-(N,N-bis(4-methoxybenzyl)sulfamoyl)-2-methylpropan-2-yl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((S)—((S)-3-(1-(N,N-bis(4-methoxybenzyl)sulfamoyl)-2-methylpropan-2-yl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate (90 mg, 0.097 mmol), N,N-dimethylpyridin-4-amine (23.76 mg, 0.194 mmol), and iodomethane (69.0 mg, 0.486 mmol) were dissolved in THF (10 mL). The mixture was cooled to 0° C. and sodium hydride (46.7 mg, 1.945 mmol) was added and the mixture was stirred for 4 h. $H_2O$ was added to the reaction mixture followed by extraction with ethyl acetate. The combined organic layers were dried over $Na_2SO_4$, filtered and concentrated. The residue was dissolved in DCM (4 mL) and TFA (4.00 mL), and the mixture was stirred overnight. The solvent was removed in vacuo and the residue was added to a silica gel column and eluted with methanol/dichloromethane from 0 to 10% to give Cpd. No. 58 as a mixture of the title compounds (80 mg, 128%). MS m/z 643.4 (M+H)+.

Step 3: Cpd. No. 6 (Isomer 1) and Cpd. No. 6 (Isomer 2)

In a round-bottomed flask a mixture of (S)-6'-chloro-5-(((1R,2R)-2-((S)-methoxy((R)-3-(2-methyl-1-sulfamoylpropan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S)-methoxy((S)-3-(2-methyl-1-sulfamoylpropan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid (80 mg, 0.124 mmol), TEA (62.9 mg, 0.622 mmol), and DMAP (15.19 mg, 0.124 mmol) were dissolved in DCM (20 mL) under argon. The mixture was cooled to 0° C. and 2,4,6-tripropyl-1,3,5,2,4,6-trioxatriphosphinane 2,4,6-trioxide (119 mg, 0.373 mmol) was added. The mixture was stirred for 30 min. $H_2O$ was added to the reaction mixture followed by extraction with ethyl acetate. The combined organic layers were dried over $Na_2SO_4$, filtered and concentrated. The residue was purified with preparative HPLC.

The first-eluting diastereomer (13.5 mg, 17.36%) was designated as Cpd. No. 6 (isomer 1). The stereochemistry of the asymmetric carbon atom of the cyclobutene ring has not been determined. $^1$H NMR (500 MHz, DMSO-$d_6$) δ 11.82 (s, 1H), 7.66 (d, J=8.4 Hz, 1H), 7.27 (d, J=8.4 Hz, 1H), 7.17 (s, 1H), 6.92 (d, J=7.9 Hz, 1H), 6.83-6.73 (m, 2H), 6.15 (s, 1H), 4.09 (d, J=12.3 Hz, 1H), 3.82 (d, J=12.3 Hz, 1H), 3.69 (d, J=14.1 Hz, 1H), 3.60 (d, J=8.9 Hz, 1H), 3.55-3.45 (m, 2H), 3.31-3.23 (m, 2H), 3.14 (s, 3H), 3.13-3.10 (m, 1H), 2.84-2.76 (m, 1H), 2.75-2.65 (m, 1H), 2.54-2.47 (m, 1H), 2.40-2.33 (m, 1H), 2.21 (d, J=13.2 Hz, 1H), 2.17-2.09 (m, 1H), 2.06-1.93 (m, 4H), 1.89-1.74 (m, 3H), 1.65-1.56 (m, 1H), 1.43-1.33 (m, 1H), 1.10 (s, 3H), 0.96 (s, 3H). MS m/z 625.2 [M+H]+.

The second-eluting diastereomer (8.4 mg, 10.80%) was designated as Cpd. No. 6. (isomer 2). The stereochemistry of the asymmetric carbon atom of the cyclobutene ring has not been determined. $^1$H NMR (500 MHz, DMSO-$d_6$) δ 11.97 (s, 1H), 7.64 (d, J=8.5 Hz, 1H), 7.27 (d, J=8.5 Hz, 1H), 7.17 (s, 1H), 6.92 (d, J=8.0 Hz, 1H), 6.88 (d, J=8.0 Hz, 1H), 6.82 (s, 1H), 6.29 (s, 1H), 4.05 (d, J=12.3 Hz, 1H), 3.90 (d, J=12.3 Hz, 1H), 3.77 (d, J=14.4 Hz, 1H), 3.67-3.58 (m, 2H), 3.57-3.47 (m, 2H), 3.29-3.24 (m, 1H) 3.27 (s, 3H), 3.02-2.93 (m, 1H), 2.91-2.88 (m, 1H), 2.83-2.75 (m, 1H), 2.74-2.65 (m, 1H), 2.43-2.24 (m, 4H), 2.02-1.95 (m, 1H), 1.91-1.77

(m, 3H), 1.76-1.62 (m, 2H), 1.55-1.46 (m, 1H), 1.41-1.33 (m, 1H), 1.03 (s, 3H), 1.00 (s, 3H). MS m/z 625.2 [M+H]⁺.

Example 5

Synthesis of Cpd. No. 14 (Isomer 1) and Cpd. No. 14 (Isomer 2)

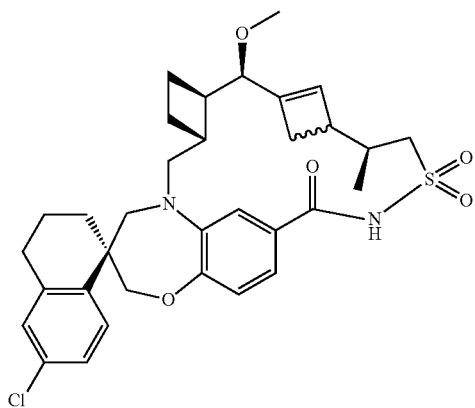 [SMILES: CO[C@H]1C2=CC(C2)[C@H](C)CS(=O)(=O)NC(=O)c2ccc3c(c2)N(C[C@@H]2CC[C@H]21)C[C@@]1(CCCc2cc(Cl)ccc21)CO3]

Step 1: (E)-1-((3aR,6S,7aS)-8,8-dimethyl-2,2-dioxidotetrahydro-3H-3a,6-methanobenzo[c]isothiazol-1 (4H)-yl)but-2-en-1-one

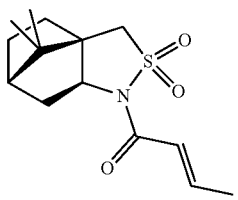 [SMILES: C/C=C/C(=O)N1[C@H]2C[C@@H]3CC[C@@]2(CS1(=O)=O)C3(C)C]

In an argon flushed round-bottomed flask (3aR,6S,7aS)-8,8-dimethylhexahydro-3H-3a,6-methanobenzo[c]isothiazole 2,2-dioxide (25 g, 116 mmol) was dissolved in toluene (400 mL) under argon. The mixture was cooled to 0° C. NaH (6.97 g, 174 mmol) was added slowly to the reaction mixture. The mixture was allowed to warm to room temperature and stirred for 1.5 h. (E)-But-2-enoyl chloride (14.83 g, 128 mmol) was added dropwise and the mixture was stirred for 3 h. TLC showed the reaction was complete. Saturated NaCl was added to the reaction mixture followed by extraction with ethyl acetate. The combined organic layers were dried over Na₂SO₄, filtered and concentrated. The residue was triturated with MeOH. The resulting solid was filtered through a Buchner Funnel, rinsed with MeOH, and collected to give the title compound (28 g, 85%). MS m/z 284.4 (M+H)⁺.

Step 2: (S)-1-((3 aR,6S,7aS)-8,8-dimethyl-2,2-dioxidotetrahydro-3H-3a,6-methanobenzo[c]isothiazol-1(4H)-yl)-2-m ethylbut-3-en-1-one

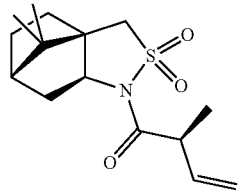 [SMILES: C=C[C@H](C)C(=O)N1[C@H]2C[C@@H]3CC[C@@]2(CS1(=O)=O)C3(C)C]

HMPA (52 mL) was added to 1M LiHMDS (17.36 g, 104 mmol) in THF and the mixture was cooled to −78° C. under argon. (E)-1-((3aR,6S,7aS)-8,8-Dimethyl-2,2-dioxidotetrahydro-3H-3a,6-methanobenzo[c]isothiazol-1(4H)-yl)but-2-en-1-one (28 g, 99 mmol) as a solution in THF (200 mL) was added and the mixture was stirred for 1.5 h. Iodomethane (56.1 g, 395 mmol) was added dropwise and the reaction mixture was stirred for 3 h. 1M HCl was added to the reaction mixture followed by extraction with ethyl acetate. The combined organic layers were dried over Na₂SO₄. Solvent was removed under reduced pressure and the residue was crystallized from MeOH to give the title compound (23 g, 78%). ¹H NMR (500 MHz, CDCl₃) δ 5.97 (ddd, J=17.4, 10.2, 7.5 Hz, 1H), 5.20 (d, J=17.4 Hz, 1H), 5.14 (d, J=10.2 Hz, 1H), 3.88 (t, J=6.3 Hz, 1H), 3.83-3.75 (m, 1H), 3.51 (d, J=13.8, 1H), 3.44 (d, J=13.8, 1H), 2.09-2.03 (m, 2H), 1.95-1.83 (m, 3H), 1.43-1.35 (m, 2H), 1.33 (d, J=7.0 Hz, 3H), 1.16 (s, 3H), 0.97 (s, 3H). MS m/z (ESI) 298.4 (M+H)⁺.

Step 3: (S)-2-methylbut-3-en-1-ol

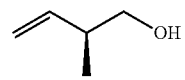

In a flame-dried 500 mL three-necked round-bottomed flask LiAlH₄ (3.06 g, 81 mmol) was added in THF (100 mL) under argon. The reaction mixture was cooled to 0° C. with an ice/water bath. (S)-1-((3aR,6S,7aS)-8,8-Dimethyl-2,2-dioxidotetrahydro-3H-3a,6-methanobenzo[c]isothiazol-1 (4H)-yl)-2-methylbut-3-en-1-one (20 g, 67.2 mmol) in THF (50 mL) was added dropwise over 30 min and the reaction mixture was stirred at 0° C. for 1 h. The crude material was distilled to give the title compound (5 g, 86%) as a colorless oil.

Step 4: (S)-2-((2-methylbut-3-en-1-yl)thio)pyrimidine

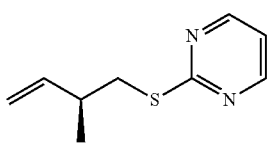

In a flame-dried 100 mL three-necked round-bottomed flask triphenylphosphine (45.7 g, 174 mmol), pyrimidine-2-thiol (19.53 g, 174 mmol), and (S)-2-methylbut-3-en-1-ol (10 g, 116 mmol) were dissolved in THF (20 mL) under argon. The reaction mixture was cooled to 0° C. with an ice/water bath. DIAD (35.2 g, 174 mmol) was added dropwise over 20 min and the reaction mixture was stirred at room temperature for 16 h. Saturated NaCl (30 mL) was added to the reaction mixture followed by extraction with ethyl acetate (30 mL×2). The combined organic layers were dried over $Na_2SO_4$, filtered and concentrated. The residue was added to a silica gel column and was eluted with ethyl acetate/hexane from 0% to 10% to give the title compound (11.86 g, 56.7%) as a colorless oil. $^1$H NMR (500 MHz, $CDCl_3$) δ 8.49 (d, J=4.8 Hz, 2H), 6.94 (t, J=4.8 Hz, 1H), 5.83 (ddd, J=17.3, 10.2, 7.2 Hz, 1H), 5.08 (d, J=17.3 Hz, 1H), 5.02 (d, J=10.2 Hz, 1H), 3.22 (dd, J=13.1, 6.9 Hz, 1H), 3.12 (dd, J=13.1, 6.9 Hz, 1H), 2.62-2.49 (m, 1H), 1.16 (d, J=6.7 Hz, 3H). MS m/z (ESI) 181.4 (M+H)$^+$ Step 5: (S)-2-((2-methylbut-3-en-1-yl)sulfonyl)pyrimidine

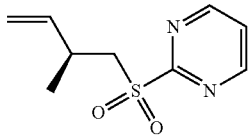

In a 50 mL round-bottomed flask hydroxydioxo(phenyl)phosphane (0.253 g, 1.609 mmol), bis(tetrabutylammonium) sulfate (0.253 g, 1.609 mmol), $Na_2SO_4$ (0.473 g, 1.609 mmol), (S)-2-((2-methylbut-3-en-1-yl)thio)pyrimidine (2.9 g, 16.09 mmol), and hydrogen peroxide (7.30 g, 64.3 mmol) were added in toluene (3 mL). The reaction mixture was stirred at 50° C. for 1 h. Saturated NaCl (10 mL) was added to the reaction mixture followed by extraction with ethyl acetate (20 mL×2). The combined organic layers were dried $Na_2SO_4$, filtered and concentrated. The residue was added to a silica gel column and was eluted with ethyl acetate/hexane from 0% to 50% to give the title compound (2.6 g, 76%) as a colorless liquid. $^1$H NMR (500 MHz, $CDCl_3$) δ 8.95 (d, J=4.8 Hz, 2H), 7.55 (t, J=4.8 Hz, 1H), 5.68 (ddd, J=17.5, 10.2, 7.5 Hz, 1H), 5.03 (d, J=17.5 Hz, 1H), 4.89 (d, J=10.2 Hz, 1H), 3.73 (dd, J=14.4, 6.7 Hz, 1H), 3.42 (dd, J=14.4, 6.7 Hz, 1H), 2.98 (dt, J=13.8, 6.9 Hz, 1H), 1.22 (d, J=6.9 Hz, 3H). MS m/z 213.1 (M+H)$^+$.

Step 6: (S)-2-methylbut-3-ene-1-sulfonamide

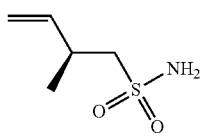

In a 200 mL round-bottomed flask (S)-2-(2-methylbut-3-en-1-yl)sulfonyl)pyrimidine (4.92 g, 23.18 mmol) was dissolved in MeOH (30 mL). The reaction mixture was cooled to 0° C. with an ice/water bath. Sodium methanolate (1.628 g, 30.1 mmol) as a solution in MeOH (10 mL) was added dropwise over 10 min. The reaction mixture was stirred at room temperature for 4 h and concentrated. The residue was triturated with diethyl ether. The resulting solid was filtered through a Buchner Funnel, rinsed with diethyl ether, and collected. The solid was dissolved in $H_2O$ (30 mL), sodium acetate (3.8 g, 46.4 mmol) and (aminooxy)sulfonic acid (5.24 g, 46.4 mmol) were added. The reaction mixture was stirred at room temperature for 16 h. $H_2O$ (40 mL) was added to the reaction mixture followed by extraction with ethyl acetate (60 mL×2). The combined organic layers were dried $Na_2SO_4$, filtered and concentrated to afford the title compound (3.6 g, 104%) as a yellow oil. This product was used directly in the next step without further purification.

Step 7: (S)—N,N-bis(4-Methoxybenzyl)-2-m ethyl-but-3-ene-1-sulfonamide

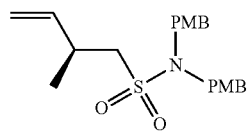

In a 200 mL round-bottomed flask (S)-2-methylbut-3-ene-1-sulfonamide (1.9 g, 12.73 mmol), 1-(chloromethyl)-4-methoxybenzene (3.99 g, 25.5 mmol), and $Cs_2CO_3$ (8.30 g, 25.5 mmol) were added in DMF (30 mL) under argon. The reaction mixture was stirred at 50° C. for 2 h. Saturated NaCl (50 mL) was added to the reaction mixture followed by extraction with ethyl acetate (60 mL×2). The combined organic layers were dried $Na_2SO_4$, filtered and concentrated. The residue was added to a silica gel column and eluted with ethyl acetate/hexane from 0% to 15% to give the title compound (3.5 g, 70.6%) as a colorless oil. $^1$H NMR (500 MHz, $CDCl_3$) δ 7.22 (d, J=8.5 Hz, 4H), 6.88 (d, J=8.5 Hz, 4H), 5.76 (ddd, J=17.2, 10.3, 6.9 Hz, 1H), 5.13-4.97 (m, 2H), 4.28 (d, J=15.0 Hz, 2H), 4.23 (d, J=15.0 Hz, 2H), 3.81 (s, 6H), 2.95-2.69 (m, 3H), 1.18 (d, J=6.6 Hz, 3H). MS m/z (ESI) 412.6 (M+Na)$^+$.

Step 8: (2S)-2-(2,2-dichloro-3-oxocyclobutyl)-N,N-bis(4-methoxybenzyl) propane-1-sulfonamide

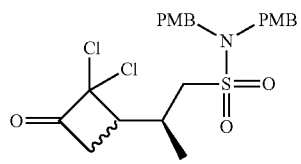

In a 250 mL round-bottomed flask (S)—N,N-bis(4-methoxybenzyl)-2-methylbut-3-ene-1-sulfonamide (3.5 g, 8.99 mmol) and zinc (2.350 g, 35.9 mmol) were added in diethyl ether (30 mL) under argon. 2,2,2-Trichloroacetyl chloride (3.27 g, 17.97 mmol) and 1,2-dimethoxyethane (1.620 g, 17.97 mmol) were added dropwise over 30 min and the reaction mixture was stirred at 40° C. for 16 h. The reaction mixture was filtered through a celite and the filter cake was rinsed with hexane. The filtrate was washed with $H_2O$ (100 mL), saturated $NaHCO_3$ (100 mL), and saturated NaCl (100 mL). The organic layer was dried over $Na_2SO_4$, filtered and concentrated to afford the title compound (5.2 g)

as a yellow oil. This product was used directly in the next step without further purification.

Step 9: (S)—N,N-bis(4-methoxybenzyl)-2-(3-oxocyclobutyl)propane-1-sulfonamide

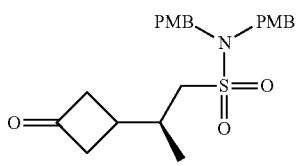

In a 200 mL round-bottomed flask (2S)-2-(2,2-dichloro-3-oxocyclobutyl)-N,N-bis(4-methoxybenzyl)propane-1-sulfonamide (4.5 g, 8.99 mmol) and zinc (1.764 g, 27.0 mmol) were added in acetic acid (30 mL). The reaction mixture was stirred at 70° C. for 8 h. The reaction mixture was filtered through a celite and the filter cake was rinsed with ethyl acetate (50 mL×2). Saturated NaCl (50 mL) was added to the reaction mixture followed by extraction with ethyl acetate (50 mL×2). The combined organic layers were dried over Na$_2$SO$_4$, filtered and concentrated. The residue was added to a silica gel column and eluted with ethyl acetate/hexane from 0% to 30% to give the title compound (1.7 g, 43.8%) as a yellow oil. $^1$H NMR (500 MHz, CDCl$_3$) δ 7.24 (d, J=8.6 Hz, 4H), 6.89 (d, J=8.6 Hz, 4H), 4.30 (d, J=15.0 Hz, 2H), 4.23 (d, J=15.0 Hz, 2H), 3.82 (s, 6H), 3.12-3.01 (m, 1H), 3.01-2.89 (m, 1H), 2.79-2.60 (m, 4H), 2.29-2.13 (m, 2H), 1.18 (d, J=6.5 Hz, 3H). MS m/z (ESI) 454.7 (M+Na)$^+$.

Step 10: (R)-3-((S)-1-(N,N-bis(4-methoxybenzyl)sulfamoyl)propan-2-yl)cyclobut-1-en-1-yl trifluoromethanesulfonate and (S)-3-((S)-1-(N,N-bis(4-methoxybenzyl)sulfamoyl)propan-2-yl)cyclobut-1-en-1-yl trifluoromethanesulfonate

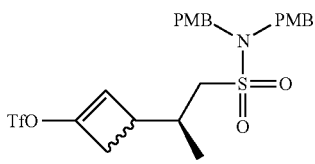

In a flame-dried 100 mL three-necked round-bottomed flask 1,1,1-trifluoro-N-phenyl-N-((trifluoromethyl)sulfonyl)methanesulfonamide (0.646 g, 1.807 mmol) and (S)—N,N-bis(4-methoxybenzyl)-2-(3-oxocyclobutyl)propane-1-sulfonamide (0.6 g, 1.390 mmol) were dissolved in THF (15 mL) under argon. The reaction mixture was cooled to −78° C. with a dry ice/acetone bath. KHMDS (0.416 g, 2.085 mmol) was added dropwise over 10 min and the reaction mixture was stirred at −78° C. for 2 h. Saturated NH$_4$Cl (20 mL) was added to the reaction mixture followed by extraction with diethyl ether (30 mL×2). The combined organic layers were dried over Na$_2$SO$_4$, filtered and concentrated. The residue was added to a silica gel column and eluted with ethyl acetate/hexane from 0% to 20% to give the title compounds (0.66 g, 84%) as a mixture of two diastereomers. MS m/z 586.1 (M+Na)$^+$.

Step 11: ((1R,2R)-2-((R)—((R)-3-((S)-1-(N,N-bis(4-methoxybenzyl)sulfamoyl)propan-2-yl)cyclobut-1-en-1-yl)(hydroxy)methyl)cyclobutyl)methyl benzoate and ((1R,2R)-2-((R)—((S)-3-((S)-1-(N,N-bis(4-methoxybenzyl)sulfamoyl)propan-2-yl)cyclobut-1-en-1-yl)(hydroxy)methyl)cyclobutyl)methyl benzoate

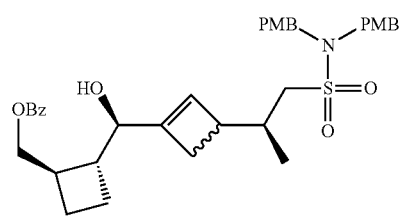

In a flame-dried 100 mL three-necked round-bottomed flask chromium (II) chloride (0.717 g, 5.83 mmol) and nickel (II) chloride (0.030 g, 0.233 mmol) were added in DMF (10 mL) under argon. A mixture of (R)-3-((S)-1-(N,N-bis(4-methoxybenzyl)sulfamoyl)propan-2-yl)cyclobut-1-en-1-yl trifluoromethanesulfonate and (S)-3-((S)-1-(N,N-bis(4-methoxybenzyl)sulfamoyl)propan-2-yl)cyclobut-1-en-1-yl trifluoromethanesulfonate (0.66 g, 1.167 mmol) and ((1R,2R)-2-formylcyclobutyl)methyl benzoate (0.306 g, 1.400 mmol), as a solution in DMF (10 mL) were added to the reaction mixture in one portion. The reaction mixture was stirred at 70° C. for 16 h. H$_2$O (80 mL) was added to the reaction mixture followed by extraction with ethyl acetate (50 mL×3). The combined organic layers were dried over Na$_2$SO$_4$, filtered and concentrated. The residue was added to a silica gel column and eluted with ethyl acetate/hexane from 0% to 25% to give the title compounds (0.26 g, 35.2%) as a mixture. MS m/z 657.0 (M+Na)$^+$.

Step 12: ((1R,2R)-2-((R)—((R)-3-((S)-1-(N,N-bis(4-methoxybenzyl)sulfamoyl) propan-2-yl)cyclobut-1-en-1-yl)(methoxy)methyl)cyclobutyl)methyl benzoate and ((1R,2R)-2-((R)—((S)-3-((S)-1-(N,N-bis(4-methoxybenzyl)sulfamoyl)propan-2-yl)cyclobut-1-en-1-yl)(methoxy)methyl)cyclobutyl)methyl benzoate

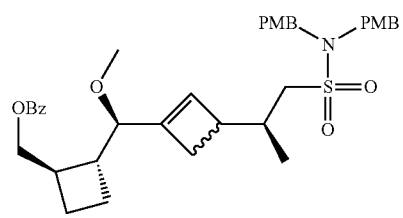

In a 100 mL round-bottomed flask a mixture of ((1R,2R)-2-((R)—((R)-3-((S)-1-(N,N-bis(4-methoxybenzyl)sulfamoyl)propan-2-yl)cyclobut-1-en-1-yl)(hydroxy)methyl)cyclobutyl)methyl benzoate and ((1R,2R)-2-((R)—((S)-3-((S)-1-(N,N-bis(4-methoxybenzyl)sulfamoyl)propan-2-yl)cyclobut-1-en-1-yl)(hydroxy)methyl)cyclobutyl) methyl benzoate (0.24 g, 0.379 mmol), iodomethane (0.161 g, 1.136 mmol), and DMAP (9.25 mg, 0.076 mmol) were dissolved in DMF (5 mL) under argon. The reaction mixture was cooled to 0° C. with an ice/water bath. Sodium hydride (1.060 g, 26.5 mmol) was added to the reaction mixture in one portion. The reaction mixture was stirred at 0° C. for 30 min. H₂O (30 mL) was added to the reaction mixture followed by extraction with ethyl acetate (40 mL×2). The combined organic layers were dried over Na₂SO₄, filtered, and concentrated to afford the title compounds (0.245 g, 100%) as a mixture of two diastereomers. MS m/z 671.0 (M+Na)⁺.

Step 13: (S)-2-((R)-3-((R)-((1R,2R)-2-(hydroxymethyl)cyclobutyl) (methoxy)methyl)cyclobut-2-en-1-yl)-N,N-bis(4-methoxybenzyl)propane-1-sulfonamide and (S)-2-((S)-3-((R)-((1R,2R)-2-(hydroxymethyl)cyclobutyl)(methoxy)methyl) cyclobut-2-en-1-yl)-N,N-bis(4-methoxybenzyl) propane-1-sulfonamide

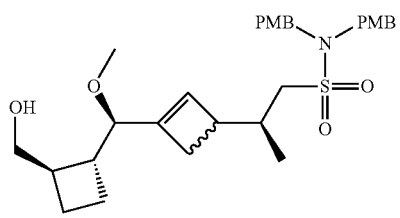

In a 100 mL round-bottomed flask a mixture of ((1R,2R)-2-((R)—((R)-3-((S)-1-(N,N-bis(4-methoxybenzyl)sulfamoyl)propan-2-yl)cyclobut-1-en-1-yl)(methoxy)methyl)cyclobutyl)methyl benzoate and ((1R,2R)-2-((R)—((S)-3-((S)-1-(N,N-bis(4-methoxybenzyl)sulfamoyl)propan-2-yl)cyclobut-1-en-1-yl)(methoxy)methyl)cyclobutyl)methyl benzoate (0.24 g, 0.370 mmol) and K₂CO₃ (0.256 g, 1.852 mmol) were added in MeOH (10 mL). The reaction mixture was stirred at 35° C. for 16 h and concentrated. The residue was added to a silica gel column and eluted with ethyl acetate/hexane from 0% to 40% to give the title compounds (0.22 g, 109%) as a mixture of two diastereomers. MS m/z 566.8 (M+Na)⁺.

Step 14: (S)-2-((R)-3-((R)-((1R,2R)-2-formylcyclobutyl)(methoxy) methyl)cyclobut-2-en-1-yl)-N,N-bis(4-methoxybenzyl)propane-1-sulfonamide and (S)-2-((S)-3-((R)-((1R,2R)-2-formylcyclobutyl)(methoxy)methyl)cyclobut-2-en-1-yl)-N,N-bis(4-methoxybenzyl)propane-1-sulfonamide

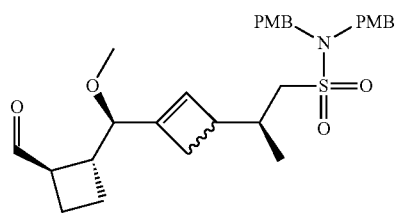

In a 100 mL round-bottomed flask a mixture of (S)-2-((R)-3-((R)-((1R,2R)-2-(hydroxymethyl)cyclobutyl)(methoxy)methyl)cyclobut-2-en-1-yl)-N,N-bis(4-methoxybenzyl)propane-1-sulfonamide and (S)-2-((S)-3-((R)-((1R,2R)-2-(hydroxymethyl)cyclobutyl)(methoxy)methyl)cyclobut-2-en-1-yl)-N,N-bis(4-methoxybenzyl)propane-1-sulfonamide (0.28 g, 0.515 mmol) was dissolved in DCM (5 mL). The reaction mixture was cooled to 0° C. with an ice/water bath. Dess-Martinperiodinane (0.328 g, 0.772 mmol) was added to the reaction mixture in one portion. The reaction mixture was stirred at 0° C. for 1 h. Saturated NaHCO₃ (20 mL) was added to the reaction mixture followed by extraction with ethyl acetate (30 mL×2). The combined organic layers were dried over Na₂SO₄, filtered and concentrated to afford the title compounds (0.279 g, 100%) as a mixture of two diastereomers.

Step 15: tert-butyl (S)-5-(((1R,2R)-2-((R)—((R)-3-((S)-1-(N,N-bis(4-methoxybenzyl)sulfamoyl)propan-2-yl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—((S)-3-((S)-1-(N,N-bis(4-methoxybenzyl)sulfamoyl)propan-2-yl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate

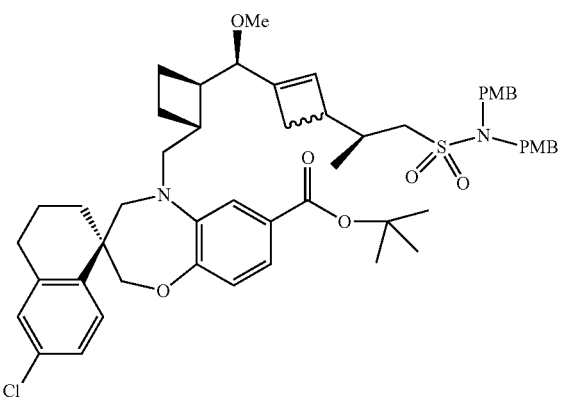

In a 100 mL round-bottomed flask a mixture of (S)-2-((R)-3-((R)-((1R,2R)-2-formylcyclobutyl)(methoxy)methyl)cyclobut-2-en-1-yl)-N,N-bis(4-methoxybenzyl)propane-1-sulfonamide and (S)-2-((S)-3-((R)-((1R,2R)-2-formylcyclobutyl)(methoxy)methyl)cyclobut-2-en-1-yl)-N,N-bis(4-methoxybenzyl)propane-1-sulfonamide (0.279 g, 0.515 mmol) and tert-butyl (S)-6'-chloro-3',4,4',5-tetrahydro-2H,2'H-spiro[benzo[b][1,4]oxazepine-3,1'-naphthalene]-7-carboxylate (0.247 g, 0.618 mmol) were dissolved in TFA (2 mL) and THF (6.00 mL). Phenylsilane (0.111 g, 1.030 mmol) was added to the reaction mixture in one portion. The reaction mixture was stirred at room temperature for 2 h. Saturated NaHCO₃ (20 mL) was added to the reaction mixture followed by extraction with ethyl acetate (30 mL×2). The combined organic layers were dried over Na₂SO₄, filtered and concentrated. The residue was added to a silica gel column and eluted with ethyl acetate/hexane from 0% to 25% to give the title compounds (0.25 g, 52.4%) as a mixture of two diastereomers. MS m/z 926.8 (M+H)⁺.

Step 16: (S)-6'-chloro-5-(((1R,2R)-2-((R)-methoxy((R)-3-((S)-1-sulfamoyl propan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((R)-methoxy((S)-3-((S)-1-sulfamoylpropan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid

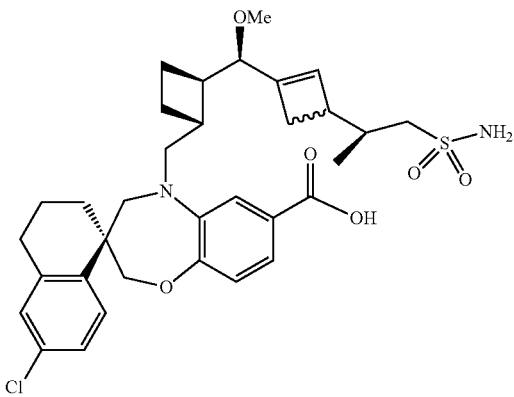 [SMILES: CO[C@@H](C1=CC([C@H](C)CS(N)(=O)=O)C1)[C@@H]1CC[C@H]1CN1C[C@@]2(CCCc3cc(Cl)ccc32)COc2ccc(C(=O)O)cc21]

In a 100 mL round-bottomed flask a mixture of tert-butyl (S)-5-(((1R,2R)-2-((R)—((R)-3-((S)-1-(N  N-bis(4-methoxybenzyl)sulfamoyl)propan-2-yl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—((S)-3-((S)-1-(N,N-bis(4-methoxybenzyl)sulfamoyl)propan-2-yl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate (0.25 g, 0.270 mmol) was dissolved in TFA (2 mL) and DCM (2.000 mL). The reaction mixture was stirred at room temperature for 16 h and concentrated. The residue was purified by reverse-phase preparative HPLC to give the title compounds as a mixture of two diastereomers (0.06 g, 35.34%). MS m/z 629.6 (M+H)+.

Step 17: Cpd. No. 14 (Isomer 1) and Cpd. No. 14 (Isomer 2)

In a 100 mL round-bottomed flask a mixture of (S)-6'-chloro-5-(((1R,2R)-2-((R)-methoxy((R)-3-((S)-1-sulfamoylpropan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((R)-methoxy((S)-3-((S)-1-sulfamoylpropan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid (0.025 g, 0.040 mmol), triethylamine (0.012 g, 0.119 mmol), and DMAP (4.85 mg, 0.040 mmol) were dissolved in DCM (20 mL) under argon. The reaction mixture was cooled to 0° C. with an ice/water bath. T3P (0.038 g, 0.060 mmol) was added to the reaction mixture in one portion. The reaction mixture was stirred at 0° C. for 30 min. Saturated NaCl (20 mL) was added to the reaction mixture followed by extraction with ethyl acetate (20 mL×2). The combined organic layers were dried over Na2SO4, filtered and concentrated. The residue was purified by reverse-phase preparative HPLC.

The first-eluting diastereomer (8.6 mg, 35.4%) was obtained as a white solid and designated as Cpd. No. 14 (isomer 1). The stereochemistry of the asymmetric carbon atom of the cyclobutene ring has not been determined. 1H NMR (500 MHz, DMSO-d6) δ 11.78 (s, 1H), 7.64 (d, J=8.5 Hz, 1H), 7.27 (d, J=8.5 Hz, 1H), 7.18 (s, 1H), 6.94-6.88 (m, 2H), 6.77 (s, 1H), 6.29 (s, 1H), 4.06 (d, J=12.2 Hz, 1H), 3.88 (d, J=14.3 Hz, 1H), 3.73 (d, J=13.2 Hz, 1H), 3.66 (d, J=4.9 Hz, 1H), 3.62 (d, J=14.3 Hz, 1H), 3.36-3.29 (m, 1H), 3.25-3.17 (m, 1H), 3.09 (s, 3H), 3.07-2.99 (m, 1H), 2.84-2.76 (m, 1H), 2.74-2.35 (m, 5H), 2.12 (d, J=13.2 Hz, 1H), 2.02-1.63 (m, 7H), 1.52-1.35 (m, 2H), 1.08 (d, J=6.4 Hz, 3H). MS m/z 611.1 [M+H]+.

The second-eluting diastereomer was obtained as a white solid and designated as Cpd. No. 14 (isomer 2). The stereochemistry of the asymmetric carbon atom of the cyclobutene ring has not been determined.
1H NMR (500 MHz, DMSO-d6) δ 11.89 (s, 1H), 7.65 (d, J=8.5 Hz, 1H), 7.27 (d, J=9.1 Hz, 1H), 7.18 (s, 1H), 6.91 (d, J=8.2 Hz, 1H), 6.88 (d, J=8.2 Hz, 1H), 6.76 (s, 1H), 6.07 (s, 1H), 4.08 (d, J=12.2 Hz, 1H), 3.93 (d, J=12.2 Hz, 1H), 3.80 (d, J=14.6 Hz, 1H), 3.75-3.69 (m, 2H), 3.63 (d, J=14.1 Hz, 1H), 3.33-3.19 (m, 3H), 3.17 (s, 3H), 3.06-2.97 (m, 1H), 2.83-2.61 (m, 3H), 2.57-2.43 (m, 2H), 2.18 (d, J=13.6 Hz, 1H), 2.03-1.78 (m, 3H), 1.75-1.55 (m, 5H), 1.43-1.35 (m, 1H), 1.10 (d, J=6.6 Hz, 3H). MS m/z 611.1 [M+H]+.

Example 6

Synthesis of Cpd. No. 9 (Isomer 1) and Cpd. No. 9 (Isomer 2)

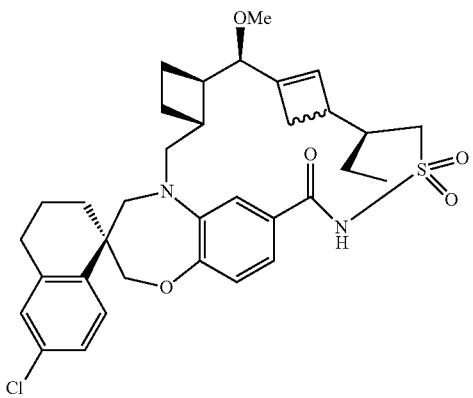

Step 1: (2S)-2-(2,2-dichloro-3-oxocyclobutyl)-N,N-bis(4-methoxybenzyl)butane-1-sulfonamide

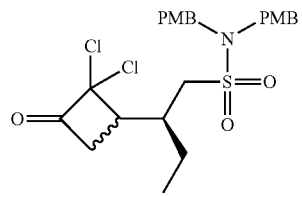

The title compound was prepared from (S)-1-((3 aR,6S,7aS)-8,8-dimethyl-2,2-dioxidotetrahydro-3H-3a,6-methanobenzo[c]isothiazol-1(4H)-yl)-2-methylbut-3-en-1-one and iodoethane, following a similar procedure described in Example 5, Steps 2 through 8.

Step 2: (S)—N,N-bis(4-methoxybenzyl)-2-(3-oxocyclobutyl)butane-1-sulfonamide

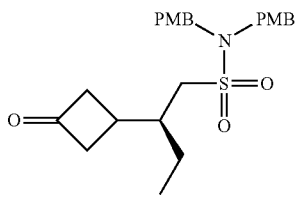

In a dried 25 mL round-bottomed flask, (2S)-2-(2,2-dichloro-3-oxocyclobutyl)-N,N-bis(4-methoxybenzyl)butane-1-sulfonamide (4.2 g, 8.16 mmol) was dissolved in AcOH (30 mL). Zinc (1.60 g, 24.50 mmol) was added and the reaction mixture was stirred at 60° C. for 3 h. AcOH was removed under reduced pressure and the residue was purified by chromatography and eluted with ethyl acetate/heptane from 5% to 35% to give the title compound (1.26 g, 34.6%) as a colorless oil. MS m/z 468.2 [M+Na]+.

Step 3: (R)-3-((S)-1-(N,N-bis(4-methoxybenzyl)sulfamoyl)butan-2-yl)cyclobut-1-en-1-yl trifluoromethanesulfonate and (S)-3-((S)-1-(N,N-bis(4-methoxybenzyl)sulfamoyl)butan-2-yl)cyclobut-1-en-1-yl trifluoromethanesulfonate

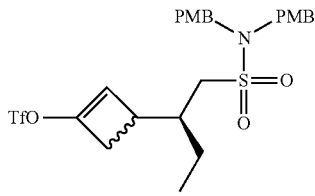

In a dried 50 mL two-necked round-bottomed flask (S)—N,N-bis (4-methoxy benzyl)-2-(3-oxocyclobutyl)butane-1-sulfonamide (1.26 g, 2.83 mmol) was dissolved in tetrahydrofuran (15 mL) under nitrogen. The reaction mixture was cooled to −78° C. 1M potassium bis(trimethylsilyl)amide in THF (5.66 mL, 5.66 mmol) was added slowly and the reaction mixture was stirred for 15 min. 1,1,1-Trifluoro-N-phenyl-N-((tri-fluoromethyl)sulfonyl)methanesulfonamide (1.06 g, 2.97 mmol) in THF (10 mL) was added dropwise over 15 min and the reaction mixture was stirred at −78° C. for 1.5 h. H2O was added and the reaction mixture was extracted with ethyl acetate (30 mL×3). The organic layers were combined and concentrated. The residue was purified with ethyl acetate/heptane from 5% to 20% to give the title compounds (500 mg, 30.6%) as a mixture of two diastereomers. MS m/z 600.1[M+Na]+.

Step 4: tert-butyl (S)-5-(((1R,2R)-2-((R)—((R)-3-((S)-1-(N,N-bis(4-methoxybenzyl)sulfamoyl)butan-2-yl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—((S)-3-((S)-1-(N,N-bis(4-methoxybenzyl)sulfamoyl)butan-2-yl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate

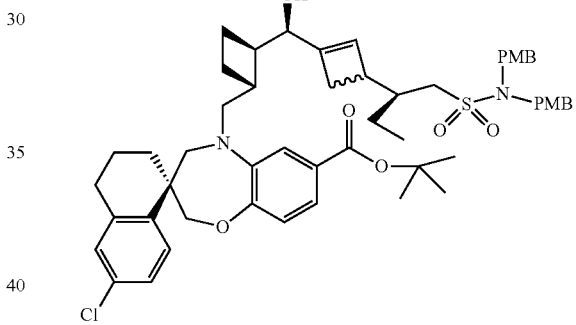

In a 100 mL two-necked round-bottomed flask, chromium (II) chloride (208 mg, 1.69 mmol) and nickel (II) chloride (5.49 mg, 0.042 mmol) were dissolved in DMF (15 mL). tert-Butyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (210 mg, 0.423 mmol) in DMF (6 mL) and a mixture of (R)-3-((S)-1-(N,N-bis(4-methoxybenzyl)sulfamoyl)butan-2-yl)cyclobut-1-en-1-yl trifluoromethanesulfonate and (S)-3-((S)-1-(N,N-bis(4-methoxybenzyl)sulfamoyl)butan-2-yl)cyclobut-1-en-1-yl trifluoromethanesulfonate (489 mg, 0.85 mmol) in DMF (6 mL) were added to the reaction mixture. The reaction mixture was degassed and stirred at 70° C. overnight. H2O was added to the reaction mixture followed by extraction with ethyl acetate. The organic layer was washed with saturated NaCl. dried over Na2SO4, filtered and concentrated. The residue was added to a Biotage column and eluted with ethyl acetate/hexane from 0 to 30% to give the title compounds (150 mg, 38.3%) as a mixture of two diastereomers.

Step 5: tert-butyl (S)-5-(((1R,2R)-2-((R)—((R)-3-((S)-1-(N,N-bis(4-methoxybenzyl)sulfamoyl)butan-2-yl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—((S)-3-((S)-1-(N,N-bis(4-methoxybenzyl)sulfamoyl)butan-2-yl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate

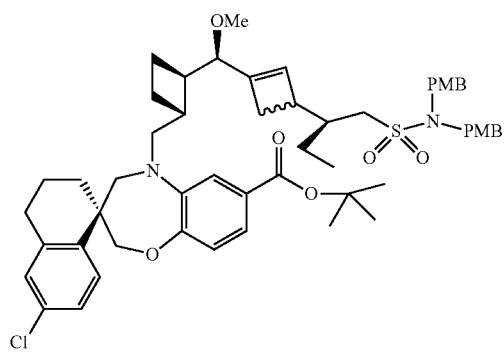

In a 100 mL round-bottomed flask, NaH (60%) (13.0 mg, 0.324 mmol) was added in tetrahydrofuran (5 mL) and the mixture was stirred for 30 min. A mixture of tert-butyl (S)-5-(((1R,2R)-2-((R)—((R)-3-((S)-1-(N,N-bis(4-methoxybenzyl)sulfamoyl)butan-2-yl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—((S)-3-((S)-1-(N,N-bis(4-methoxybenzyl)sulfamoyl)butan-2-yl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate (150 mg, 0.162 mmol) in THF (1 mL), DMAP (0.79 mg, 6.48 µmol) and CH₃I (46 mg, 0.324 mmol) were added and the reaction mixture was stirred at 30° C. for 3 h. The reaction was quenched with aqueous NH₄Cl (10 mL), followed by extraction with ethyl acetate. The combined organic layers were dried over Na₂SO₄, filtered and concentrated to give the title compounds as a mixture of two diastereomers (140 mg).

Step 6: (S)-6'-chloro-5-(((1R,2R)-2-((R)-methoxy((R)-3-((S)-1-sulfamoylbutan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((R)-methoxy((S)-3-((S)-1-sulfamoylbutan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid

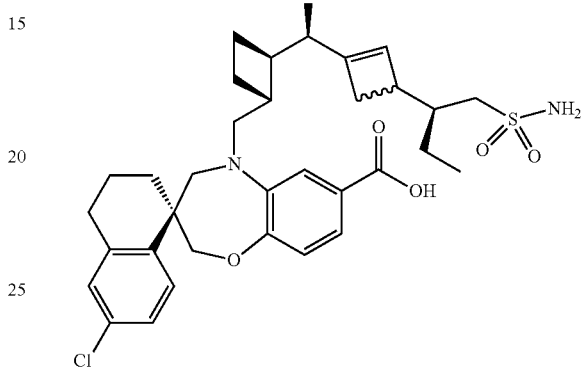

In a 25 mL round-bottomed flask, a mixture of tert-butyl (S)-5-(((1R,2R)-2-((R)—((R)-345)-1-(N,N-bis(4-methoxybenzyl)sulfamoyl)butan-2-yl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—((S)-3-((S)-1-(N,N-bis(4-methoxybenzyl)sulfamoyl)butan-2-yl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate (140 mg, 0.15 mmol) was dissolved in DCM (5 mL). TFA (5 mL) was added and the reaction mixture was stirred for 2 h. Solvent was removed under vacuum and the residue was added to a Biotage column and eluted with ethyl acetate/hexane from 20% to 100% to give the title compounds as a mixture of two diastereomers (92 mg, 90.0%).

Step 7: Cpd. No. 9 (Isomer 1) and Cpd. No. 9 (Isomer 2)

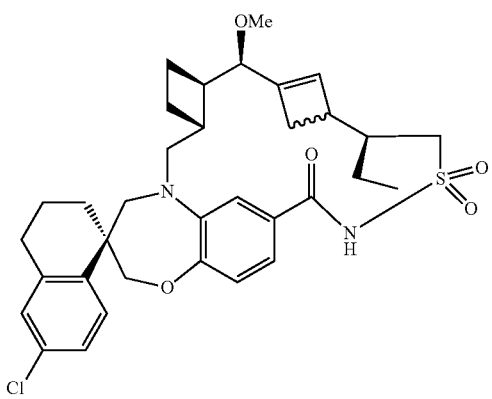 [SMILES: CC[C@@H]1CS(=O)(=O)NC(=O)c2ccc3c(c2)N(C[C@@H]2CC[C@H]2[C@@H](OC)C2=CC1C2)C[C@@]1(CCCc2cc(Cl)ccc21)CO3]

In a 25 mL round-bottomed flask, a mixture of (S)-6'-chloro-5-(((1R,2R)-2-((R)-methoxy((R)-3-((S)-1-sulfamoylbutan-2-yl)cyclobut-1-en-1-yl)methyl)cyclobutyl)methyl)-3',4',4',5-tetrahydro-2H,2'H-spiro[benzo[b][1,4]oxazepine-3,1'-naphthalene]-7-carboxylic acid and (S)-6'-chloro-5-(((1R,2R)-2-((R)-methoxy((S)-3-((S)-1-sulfamoylbutan-2-yl)cyclobut-1-en-1-yl)methyl)cyclobutyl)methyl)-3',4',4',5-tetrahydro-2H,2'H-spiro[benzo[b][1,4]oxazepine-3,1'-naphthalene]-7-carboxylic acid (90 mg, 0.14 mmol) was dissolved in 1,2-dichloroethane (10 mL). The reaction mixture was cooled to 0° C. Triethylamine (42.5 mg, 0.42 mmol), T₃P (178.0 mg, 0.28 mmol, 50% in ethyl acetate), and DMAP (34.2 mg, 0.28 mmol) were added and the reaction mixture was stirred at room temperature for 3 h. Solvent was removed and the residue was purified by preparative HPLC.

The first-eluting diastereomer (7.4 mg) was designated as Cpd. No. 9 (isomer 1).

The stereochemistry of the asymmetric carbon atom of the cyclobutene ring has not been determined. ¹H NMR (500 MHz, DMSO-d₆) δ 11.84 (s, 1H), 7.68 (dd, J=8.5, 2.1 Hz, 1H), 7.32-7.28 (m, 1H), 7.21 (s, 1H), 7.00-6.91 (m, 2H), 6.85 (s, 1H), 6.30 (s, 1H), 4.09 (d, J=11.5 Hz, 1H), 4.02-3.97 (m, 1H), 3.84-3.70 (m, 2H), 3.67-3.61 (m, 2H), 3.35-3.25 (m, 2H), 3.12 (m, 3H), 3.10-3.05 (m, 1H), 2.86-2.42 (m, 5H), 2.21 (d, J=13.4 Hz, 1H), 2.03-1.51 (m, 11H), 1.47-1.39 (m, 1H), 0.90-0.85 (m, 3H).

The second-eluting diastereomer (24.5 mg) was obtained as a white solid and designated Cpd. No. 9 (isomer 2). The stereochemistry of the asymmetric carbon atom of the cyclobutene ring has not been determined. ¹H NMR (500 MHz, DMSO-d₆) δ 11.92 (s, 1H), 7.69 (dd, J=8.6, 2.3 Hz, 1H), 7.32-7.28 (m, 1H), 7.24-7.19 (m, 1H), 6.98-6.93 (m, 2H), 6.82 (s, 1H), 5.91 (s, 1H), 4.11 (d, J=12.9 Hz, 1H), 3.99 (d, J=12.9 Hz, 1H), 3.85-3.79 (m, 2H), 3.64 (d, J=14.4 Hz, 2H), 3.31-3.26 (m, 2H), 3.24 (d, J=2.4 Hz, 3H), 3.11-3.03 (m, 1H), 2.86-2.71 (m, 3H), 2.57-2.45 (m, 2H), 2.18 (d, J=13.8 Hz, 1H), 1.99 (d, J=13.8 Hz, 1H), 1.95-1.51 (m, 10H), 1.47-1.40 (m, 1H), 0.92 (t, J=7.5 Hz, 3H).

Example 7

Synthesis of Cpd. No. 10 (Isomer 1) and Cpd. No. 10 (Isomer 2)

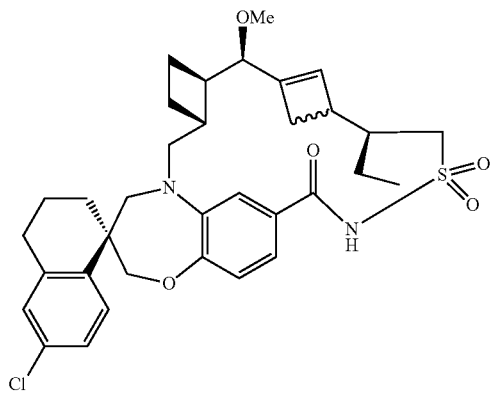 [SMILES: CC[C@@H]1CS(=O)(=O)NC(=O)c2ccc3c(c2)N(C[C@@H]2CC[C@H]2[C@@H](OC)C2=CC1C2)C[C@@]1(CCCc2cc(Cl)ccc21)CO3]

Step 1: tert-butyl (S)-5-(((1R,2R)-2-((S)—((R)-3-((S)-1-(N,N-bis(4-methoxybenzyl)sulfamoyl)butan-2-yl)cyclobut-1-en-1-yl)(hydroxy)methyl)cyclobutyl)methyl)-6'-chloro-3',4',4',5-tetrahydro-2H,2'H-spiro[benzo[b][1,4]oxazepine-3,1'-naphthalene]-7-carboxylate and tert-butyl (S)-5-(((1R,2R)-2-((S)—((S)-3-((S)-1-(N,N-bis(4-methoxybenzyl)sulfamoyl)butan-2-yl)cyclobut-1-en-1-yl)(hydroxy)methyl)cyclobutyl)methyl)-6'-chloro-3',4',4',5-tetrahydro-2H,2'H-spiro[benzo[b][1,4]oxazepine-3,1'-naphthalene]-7-carboxylate

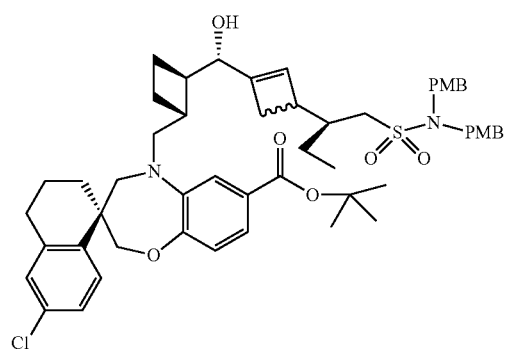

The title compounds were obtained as a mixture of the second eluting diastereomers as described in Example 6, Step 4.

Step 2: tert-butyl (S)-5-(((1R,2R)-2-((S)—((R)-3-((S)-1-(N,N-bis(4-methoxybenzyl)sulfamoyl)butan-2-yl)cyclobut-1-en-1-yl)(methoxy)methyl)cyclobutyl)methyl)-6'-chloro-3',4',4',5-tetrahydro-2H,2'H-spiro[benzo[b][1,4]oxazepine-3,1'-naphthalene]-7-carboxylate and tert-butyl (S)-5-(((1R,2R)-2-((S)—((S)-3-((S)-1-(N,N-bis(4-methoxybenzyl)sulfamoyl)butan-2-yl)cyclobut-1-en-1-yl)(methoxy)methyl)cyclobutyl)methyl)-6'-chloro-3',4',4',5-tetrahydro-2H,2'H-spiro[benzo[b][1,4]oxazepine-3,1'-naphthalene]-7-carboxylate

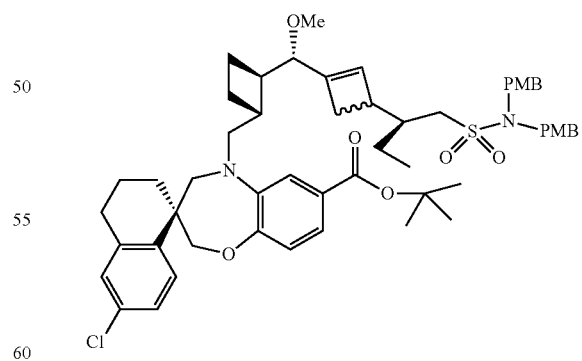

In a 100 mL round-bottomed flask, NaH (60%) (9.5 mg, 0.238 mmol) was added in tetrahydrofuran (5 mL) and the mixture was stirred for 30 min. A mixture of tert-butyl (S)-5-(((1R,2R)-2-((S)—((R)-3-((S)-1-(N,N-bis(4-methoxybenzyl)sulfamoyl)butan-2-yl)cyclobut-1-en-1-yl)(hydroxy)methyl)cyclobutyl)methyl)-6'-chloro-3',4',4',5-tetrahydro-2H,2'H-spiro[benzo[b][1,4]oxazepine-3,1'-naphthalene]-7-carboxylate and tert-butyl (S)-5-(((1R,2R)-2-((S)—(S)-3-((S)-1-(N,N-bis(4-methoxybenzyl)sulfamoyl)butan-2-yl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate (110 mg, 0.12 mmol) in THF (1 mL), DMAP (0.3 mg, 2.40 μmol) and CH$_3$I (33.7 mg, 0.238 mmol) were added and the reaction mixture was stirred at 30° C. for 3 h. The reaction was quenched with aqueous NH$_4$Cl (110 mL), followed by extraction with ethyl acetate. The combined organic layers were dried over Na$_2$SO$_4$, filtered and concentrated to give the title compounds (110 mg) as a mixture of two diastereomers.

Step 3: (S)-6'-chloro-5-(((1R,2R)-2-((S)-methoxy((R)-3-((S)-1-sulfamoylbutan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S)-methoxy((S)-3-((S)-1-sulfamoylbutan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid

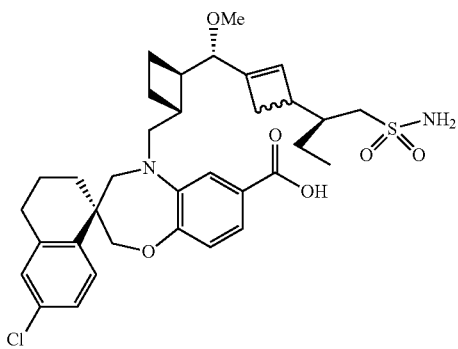 [SMILES: CC[C@H](CS(N)(=O)=O)C1C=C([C@@H](OC)[C@@H]2CC[C@H]2CN2C[C@@]3(CCCc4cc(Cl)ccc43)COc3ccc(C(=O)O)cc32)C1]

In a 25 mL round-bottomed flask a mixture of tert-butyl (S)-5-(((1R,2R)-2-((S)—(R)-3-((S)-1-(N,N-bis(4-methoxybenzyl)sulfamoyl)butan-2-yl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((S)—(S)-3-((S)-1-(N,N-bis(4-methoxybenzyl)sulfamoyl)butan-2-yl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate (110 mg, 0.117 mmol) was dissolved in DCM (5 mL). TFA (5 mL) was added and the reaction mixture was stirred for 2 h. Solvent was removed under vacuum and the residue was added to a Biotage column and eluted with ethyl acetate/hexane from 20% to 100% to give the title compounds as a mixture of two diastereomers (55 mg, 73%).

Step 4: Cpd. No. 10 (Isomer 1) and Cpd. No. 10 (Isomer 2)

In a 25 mL round-bottomed flask, a mixture of (S)-6'-chloro-5-(((1R,2R)-2-((S)-methoxy((R)-3-((S)-1-sulfamoylbutan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S)-methoxy((S)-3-((S)-1-sulfamoylbutan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid (50 mg, 0.078 mmol) was dissolved in 1,2-dichloroethane (10 mL). The reaction mixture was cooled to 0° C. Triethylamine (23.6 mg, 0.23 mmol), T$_3$P (99.0 mg, 0.23 mmol, 50% in ethyl acetate), and DMAP (28.1 mg, 0.23 mmol) were added and the reaction mixture was stirred at room temperature for 3 h. The solvent was removed under vacuum and the residue was purified by preparative HPLC.

The first-eluting diastereomer (1.5 mg) was designated as Cpd. No. 10 (isomer 1). The stereochemistry of the asymmetric carbon atom of the cyclobutene ring has not been determined. $^1$H NMR (500 MHz, DMSO-d$_6$) δ 11.84 (d, J=2.2 Hz, 1H), 7.68 (dd, J=8.6, 2.2 Hz, 1H), 7.32-7.29 (m, 1H), 7.21 (s, 1H), 6.95-6.90 (m, 3H), 6.15 (s, 1H), 4.11-4.06 (m, 1H), 3.98 (dd, J=12.3, 2.1 Hz, 1H), 3.79-3.72 (m, 2H), 3.63 (d, J=14.3 Hz, 1H), 3.55-3.52 (m, 1H), 3.36-3.27 (m, 2H), 3.31 (s, 3H), 3.08-2.99 (m, 1H), 2.86-2.38 (m, 5H), 2.18-2.13 (m, 1H), 2.05-1.98 (m, 1H), 1.93-1.56 (m, 10H), 1.45-1.38 (m, 1H), 0.88 (t, J=7.5 Hz, 3H).

The second-eluting diastereomer (10.6 mg) was obtained as a white solid and designated as Cpd. No. 10 (isomer 2). The stereochemistry of the asymmetric carbon atom of the cyclobutene ring has not been determined. $^1$H NMR (500 MHz, DMSO-d$_6$) δ 11.91 (s, 1H), 7.68 (dd, J=8.6, 2.0 Hz, 1H), 7.30 (dd, J=8.5, 2.5 Hz, 1H), 7.21 (s, 1H), 6.99-6.91 (m, 3H), 6.02 (s, 1H), 4.10 (d, J=12.3 Hz, 1H), 3.98 (d, J=12.3 Hz, 1H), 3.84 (d, J=14.2 Hz, 1H), 3.64 (t, J=14.2 Hz, 2H), 3.54-3.51 (m, 1H), 3.39-3.27 (m, 2H), 3.25 (s, 3H), 3.17-3.08 (m, 1H), 2.86-2.79 (m, 1H), 2.78-2.71 (m, 1H), 2.69-2.57 (m, 2H), 2.41-2.35 (m, 1H), 2.22-2.17 (m, 1H), 2.06-1.98 (m, 1H), 1.94-1.53 (m, 10H), 1.46-1.38 (m, 1H), 0.90 (t, J=7.4 Hz, 3H).

Example 8

Synthesis of Cpd. No. 18 (Isomer 1) and Cpd. No. 18 (Isomer 2)

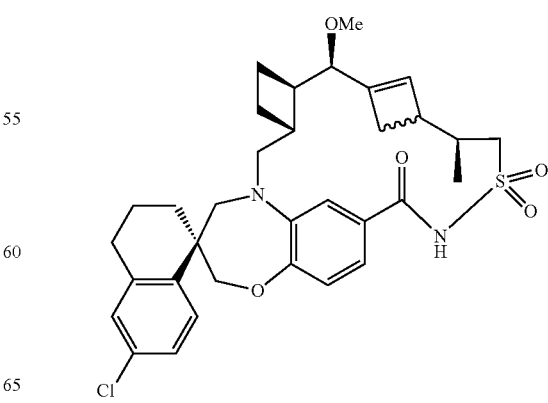

Step 1: 1-((3aR,6S,7aS)-8,8-dimethyl-2,2-dioxido-tetrahydro-3H-3a,6-methanobenzo[c]isothiazol-1(4H)-yl)-3-methylbut-2-en-1-one

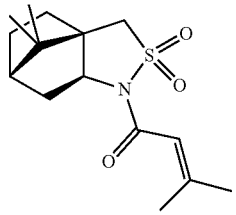 [SMILES: CC(C)=CC(=O)N1[C@H]2C[C@@H]3CC[C@@]2(CS1(=O)=O)C3(C)C]

In an argon flushed round-bottomed flask (3aR,6S,7aS)-8,8-dimethylhexahydro-3H-3a,6-methanobenzo[c]isothiazole 2,2-dioxide (20 g, 93 mmol) was dissolved in toluene (300 mL) under argon. The mixture was cooled to 0° C. NaH (5.57 g, 139 mmol) was added slowly and the reaction mixture was allowed to warm to room temperature and stirred for 1.5 h. 3-Methylbut-2-enoyl chloride (12.11 g, 102 mmol) was added dropwise and the mixture was stirred for 3 h. Saturated NaCl was added followed by extraction with ethyl acetate. The combined organic layers were dried over Na$_2$SO$_4$, filtered and concentrated. The residue was triturated with MeOH. The resulting solid was filtered through a Buchner Funnel, rinsed with MeOH, and collected to give the title compound (28 g, 101%). MS m/z 298.4 (M+H)$^+$.

Step 2: 1-((3 aR,6S,7aS)-8,8-dimethyl-2,2-dioxido-tetrahydro-3H-3a,6-methanobenzo[c]isothiazol-1(4H)-yl)-3-m ethylbut-2-en-1-one

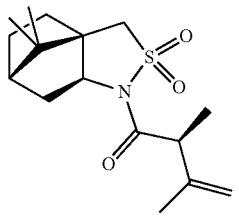 [SMILES: C=C(C)[C@H](C)C(=O)N1[C@H]2C[C@@H]3CC[C@@]2(CS1(=O)=O)C3(C)C]

HMPA (46 mL) was added to 1 M LiHMDS (15.36 g, 92 mmol) in THF, and the mixture was cooled to −78° C. under argon. 1-((3aR,6S,7aS)-8,8-Dimethyl-2,2-dioxidotetrahydro-3H-3a,6-methanobenzo[c]isothiazol-1(4H)-yl)-3-m ethylbut-2-en-1-one (26 g, 87 mmol), as a solution in THF (150 mL), was added to the reaction mixture dropwise and stirred for 1 h. Iodomethane (49.6 g, 350 mmol), as a solution in THF (50 mL), was added to the reaction mixture dropwise. The mixture was stirred at −78° C. for 3 h. 1M HCl was added to the reaction mixture followed by extraction with ethyl acetate. The combined organic layers were dried over Na$_2$SO$_4$. The residue was triturated with MeOH. The resulting solid was filtered through a Buchner Funnel, rinsed with MeOH, and collected to give the title compound (20.3 g, 74.6%). $^1$H NMR (500 MHz, DMSO-d$_6$) δ 4.89 (s, 1H), 4.83 (s, 1H), 3.90-3.82 (m, 2H), 3.67 (d, J=14.2 Hz, 1H), 3.59 (q, J=6.8 Hz, 1H), 1.96-1.85 (m, 2H), 1.84-1.73 (m, 3H), 1.71 (s, 3H), 1.51-1.42 (m, 1H), 1.30-1.21 (m, 4H), 1.06 (s, 3H), 0.94 (s, 3H). MS m/z 312.4 (M+H)$^+$.

Step 3: (S)-2,3-dimethylbut-3-en-1-ol

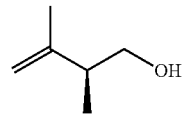

In a round-bottomed flask aluminum (III) lithium hydride (2.92 g, 77 mmol) was dissolved in THF (300 mL). (S)-1-((3aR,6S,7aS)-8,8-Dimethyl-2,2-dioxidotetrahydro-3H-3a,6-methanobenzo[c]isothiazol-1(4H)-yl)-2,3-dimethylbut-3-en-1-one (20 g, 64.2 mmol), as a solution in THF (100 mL), was added dropwise to the reaction mixture under 0° C. and the mixture was stirred for 30 min. H$_2$O (2.92 mL), 2.92 g 15% NaOH and 8.76 g H$_2$O was added. The reaction mixture was filtered through a celite and the filter cake was rinsed with ethyl acetate. The crude material was distilled to give the title compound (4.67 g, 72.6%). $^1$H NMR (500 MHz, CDCl$_3$) δ 4.87 (s, 1H), 4.79 (s, 1H), 3.52-3.47 (m, 2H), 2.43-2.30 (m, 1H), 1.70 (s, 3H), 1.02 (d, J=7.0 Hz, 3H).

Step 4: (S)-2-((2,3-Dim ethylbut-3-en-1-yl)thio)pyrimidine

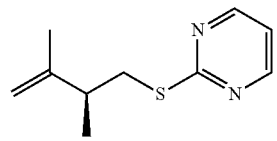

In a three-necked round-bottomed flask (S)-2,3-dimethylbut-3-en-1-ol (4.47 g, 44.6 mmol), pyrimidine-2-thiol (7.51 g, 66.9 mmol), and Ph$_3$P (29.3 g, 112 mmol) were dissolved in THF (300 mL) under argon. The mixture was cooled to 0° C. DIAD (22.56 g, 112 mmol), as a solution in THF (50 mL), was added to the reaction mixture dropwise. The mixture was stirred overnight. Saturated NaCl was added to the reaction mixture followed by extraction with ethyl acetate. The combined organic layers were dried over Na$_2$SO$_4$, filtered and concentrated. The residue was added to a silica gel column and eluted with ethyl acetate/hexane from 0 to 10% to give the title compound (6.1 g, 70.3%). MS m/z 195.2 (M+H)$^+$.

Step 5: (S)-2-((2,3-dimethylbut-3-en-1-yl)sulfonyl)pyrimidine

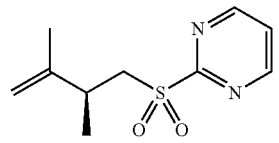

Bis(tetrabutylammonium) sulphate (3.77 g, 3.24 mmol), sodium tungstate dihydrate (1.070 g, 3.24 mmol), and phenylphosphonic acid (0.513 g, 3.24 mmol) were added to hydrogen peroxide (11.03 g, 97 mmol) and cooled to 0° C. (S)-2-((2,3-Dimethylbut-3-en-1-yl)thio)pyrimidine (6.3 g, 32.4 mmol), as a solution in toluene (20 mL), was added and Step 6: (S)-2,3-dimethylbut-3-ene-1-sulfonamide

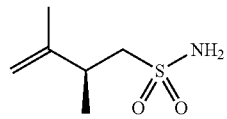

In a round-bottomed flask (S)-2-((2,3-dimethylbut-3-en-1-yl)sulfonyl)pyrimidine (4.9 g, 21.65 mmol) was dissolved in MeOH (30 mL) under argon. The mixture was cooled to 0° C. 5M sodium methoxide (1.287 g, 23.82 mmol) in MeOH was added dropwise and the reaction mixture was stirred for 1 h. The solvent was removed in vacuo and the residue was triturated with diethyl ether to give the sodium salt. The sodium salt was dissolved in water (20 mL). Sodium acetate (3.55 g, 43.3 mmol) and (aminooxy)sulfonic acid (4.90 g, 43.3 mmol) were added and the reaction mixture was stirred overnight. Saturated NaCl was added to the reaction mixture followed by extraction with ethyl acetate. The combined organic layers were dried over Na$_2$SO$_4$, filtered and concentrated to give the title compound (4 g, 113%). MS m/z (ESI) 164.0 (M+H)$^+$.

Step 7: (S)—N,N-Bis(4-methoxybenzyl)-2,3-dimethylbut-3-ene-1-sulfonamide

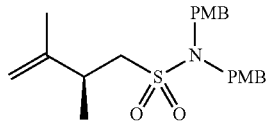

In a round-bottomed flask (S)-2,3-dimethylbut-3-ene-1-sulfonamide (4 g, 24.50 mmol), Cs$_2$CO$_3$ (15.97 g, 49.0 mmol), and 4-methoxybenzyl chloride (7.68 g, 49.0 mmol) were added in DMF (50 mL). The mixture was stirred at 50° C. for 2 h. H$_2$O was added to the reaction mixture followed by extraction with ethyl acetate. The combined organic layers were dried over Na$_2$SO$_4$, filtered and concentrated. The residue was added to a silica gel column and eluted with ethyl acetate/hexane from 0 to 20% to give the title compound (6.4 g, 64.7%). $^1$H NMR (500 MHz, CDCl$_3$) δ 7.22 (d, J=8.5 Hz, 4H), 6.87 (d, J=8.5 Hz, 4H), 4.75 (s, 1H), 4.73 (s, 1H), 4.25 (s, 4H), 3.81 (s, 6H), 2.94 (dd, J=12.8, 3.9 Hz, 1H), 2.84-2.70 (m, 2H), 1.67 (s, 3H), 1.21 (d, J=6.6 Hz, 3H). MS m/z 426.4 (M+Na)$^+$.

Step 8: (S)—N,N-bis(4-methoxybenzyl)-2-(1-methyl-3-oxocyclobutyl)propane-1-sulfonamide

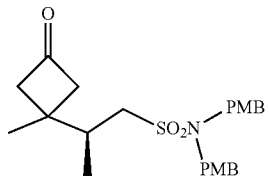

In a round-bottomed flask zinc (4.37 g, 66.9 mmol) and (S)—N,N-bis(4-methoxybenzyl)-2,3-dimethylbut-3-ene-1-sulfonamide (4.5 g, 11.15 mmol) were added in diethyl ether (8 mL) under argon. 2,2,2-Trichloroacetyl chloride (4.06 g, 22.30 mmol) and 1,2-dimethoxyethane (2.010 g, 22.30 mmol), as a solution in diethyl ether (8.00 mL) were added dropwise and the reaction mixture was stirred at 40° C. for 20 h. Hexane (20 mL) was added and then filtered. The filtrate was washed with H$_2$O and saturated NaHCO$_3$ and then concentrated. The residue was dissolved in acetic acid (20 mL). Zinc (2.187 g, 33.5 mmol) was then added. The mixture was stirred at 60° C. for 8 h. The reaction mixture was filtered through a celite and then concentrated. The residue was added to a silica gel column and was eluted with ethyl acetate/hexane from 0 to 20% to give the title compound (1.7 g, 34.2%). $^1$H NMR (500 MHz, CDCl$_3$) δ 7.25 (d, J=8.7 Hz, 4H), 6.89 (d, J=8.7 Hz, 4H), 4.33 (d, J=15.0 Hz, 2H), 4.22 (d, J=15.0 Hz, 2H), 3.81 (s, 6H), 2.84 (d, J=17.1 Hz, 1H), 2.75 (d, J=17.1 Hz, 1H), 2.68-2.57 (m, 3H), 2.55-2.47 (m, 1H), 2.34-2.26 (m, 1H), 1.17 (d, J=6.8 Hz, 3H), 1.04 (s, 3H). MS m/z 468.5 (M+Na)$^+$.

Step 9: 3-((S)-1-(N,N-bis(4-methoxybenzyl)sulfamoyl)propan-2-yl)-3-methylcyclobut-1-en-1-yl trifluoromethanesulfonate

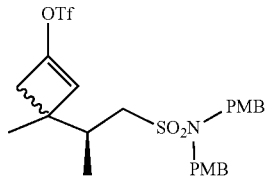

In a round-bottomed flask 1,1,1-trifluoro-N-phenyl-N-((trifluoromethyl)sulfonyl)methanesulfonamide (1.203 g, 3.37 mmol) and (S)—N,N-bis(4-methoxybenzyl)-2-(1-methyl-3-oxocyclobutyl)propane-1-sulfonamide (1 g, 2.244 mmol) were dissolved in THF (20 mL) under argon. The mixture was cooled to −78° C. 1M KHMDS in THF (0.537 g, 2.69 mmol) was added and the reaction mixture was stirred for 2 h. Saturated NH$_4$Cl was added to the reaction mixture followed by extraction with ethyl acetate. The combined organic layers were dried over Na$_2$SO$_4$, filtered and concentrated. The residue was added to a silica gel column and eluted with ethyl acetate/hexane from 0 to 15% to give the title compound (1 g, 77%). MS m/z 600.5 (M+Na)$^+$.

Step 10: ((1R,2R)-2-((R)—((R)-3-((S)-1-(N,N-bis (4-methoxybenzyl)sulfamoyl) propan-2-yl)-3-methylcyclobut-1-en-1-yl)(hydroxy)methyl)cyclobutyl) methyl benzoate and ((1R,2R)-2-((R)—((S)-3-((S)-1-(N,N-bis(4-methoxybenzyl)sulfamoyl)propan-2-yl)-3-methylcyclobut-1-en-1-yl)(hydroxy)methyl) cyclobutyl)methyl benzoate

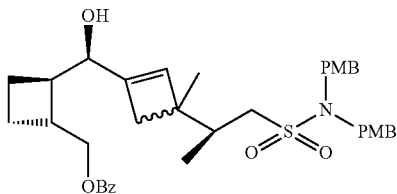

In an argon flushed three-necked round-bottomed flask chromium (II) chloride (532 mg, 4.33 mmol) and nickel (II) chloride (22.44 mg, 0.173 mmol) were added in DMF (10 mL) under argon. The mixture was heated to 70° C. ((1R,2R)-2-formylcyclobutyl)methyl benzoate (200 mg, 0.916 mmol) and 3-((S)-1-(N,N-bis(4-methoxybenzyl)sulfamoyl) propan-2-yl)-3-methylcyclobut-1-en-1-yl trifluoromethanesulfonate (500 mg, 0.866 mmol), as a solution in DMF (10 mL) were added to the reaction mixture. The mixture was stirred at 70° C. overnight. Saturated NaCl was added to the reaction mixture followed by extraction with ethyl acetate. The combined organic layers were dried over Na$_2$SO$_4$, filtered and concentrated. The residue was added to a silica gel column and eluted with ethyl acetate/hexane from 0 to 25% to give the title compounds (120 mg, 21.40%) as a mixture of two diastereomers.

Step 11: (S)-2-((R)-3-((R)-((1R,2R)-2-(hydroxymethyl)cyclobutyl)(methoxy) methyl)-1-methylcyclobut-2-en-1-yl)-N,N-bis(4-methoxybenzyl)propane-1-sulfonamide and (S)-2-((S)-3-((R)-((1R,2R)-2-(hydroxymethyl)cyclobutyl)(methoxy)methyl)-1-methylcyclobut-2-en-1-yl)-N,N-bis(4-methoxybenzyl)propane-1-sulfonamide

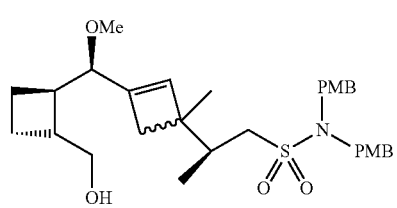

In a round-bottomed flask a mixture of ((1R,2R)-2-((R)—((R)-3-((S)-1-(N,N-bis(4-methoxybenzyl)sulfamoyl)propan-2-yl)-3-methylcyclobut-1-en-1-yl)(hydroxy)methyl)cyclobutyl)methyl benzoate and ((1R,2R)-2-((R)—((S)-3-((S)-1-(N,N-bis(4-methoxybenzyl)sulfamoyl)propan-2-yl)-3-methylcyclobut-1-en-1-yl)(hydroxy)methyl)cyclobutyl) methyl benzoate (120 mg, 0.185 mmol), DMAP (22.63 mg, 0.185 mmol), and iodomethane (79 mg, 0.556 mmol) were dissolved in DMF (5 mL) under argon. The mixture was cooled to 0° C. NaH (370 mg, 9.26 mmol) was added and the reaction mixture was stirred for 30 min. H$_2$O was added to the reaction mixture followed by extraction with ethyl acetate. The combined organic layers were dried over Na$_2$SO$_4$, filtered and concentrated. The residue was dissolved in MeOH (5.00 ml). K$_2$CO$_3$ (128 mg, 0.926 mmol) was added and the mixture was stirred at 35° C. for 4 h. The solvent was removed in vacuo and the residue was added to a silica gel column and eluted with ethyl acetate/hexane from 0 to 50% to give the title compounds (95 mg, 92%) as a mixture of two diastereomers. MS m/z 580.7 (M+Na)$^+$.

Step 12: (S)-2-((R)-3-((R)-((1R,2R)-2-formylcyclobutyl)(methoxy)methyl)-1-methylcyclobut-2-en-1-yl)-N,N-bis(4-methoxybenzyl)propane-1-sulfonamide and (S)-2-((S)-3-((R)-((1R,2R)-2-formylcyclobutyl)(methoxy)methyl)-1-methylcyclobut-2-en-1-yl)-N,N-bis(4-methoxybenzyl)propane-1-sulfonamide

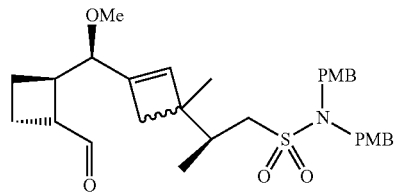

In a round-bottomed flask a mixture of (S)-2-((R)-3-((R)-((1R,2R)-2-(hydroxymethyl)cyclobutyl)(methoxy)methyl)-1-methylcyclobut-2-en-1-yl)-N,N-bis(4-methoxybenzyl) propane-1-sulfonamide and (S)-2-((S)-3-((R)-((1R,2R)-2-(hydroxymethyl)cyclobutyl)(methoxy)methyl)-1-methylcyclobut-2-en-1-yl)-N,N-bis(4-methoxybenzyl) propane-1-sulfonamide (95 mg, 0.170 mmol) were dissolved in DCM (5 mL). The mixture was cooled to 0° C. DMP (108 mg, 0.255 mmol) was added and the reaction mixture was stirred for 30 min. Saturated NaHCO$_3$ was added to the reaction mixture followed by extraction with ethyl acetate. The combined organic layers were dried over Na$_2$SO$_4$, filtered and concentrated to give the title compounds (85 mg, 90%) as a mixture of two diastereomers. MS m/z 578.4 (M+Na)$^+$.

Step 13: tert-butyl (S)-5-(((1R,2R)-2-((R)—(R)-3-((S)-1-(N,N-bis(4-methoxybenzyl)sulfamoyl)propan-2-yl)-3-methylcyclobut-1-en-1-yl)(methoxy)methyl) cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—(S)-3-((S)-1-(N,N-bis(4-methoxybenzyl)sulfamoyl)propan-2-yl)-3-methylcyclobut-1-en-1-yl)(methoxy)methyl) cyclobutyl)methyl)-6'-chloro-3',4,4',5-tetrahydro-2H,2'H-spiro[benzo[b][1,4]oxazepine-3,1'-naphthalene]-7-carboxylate Step 14: (S)-6'-chloro-5-(((1R,2R)-2-((R)-methoxy((R)-3-methyl-3-((S)-1-sulfamoylpropan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((R)-methoxy((S)-3-methyl-3-((S)-1-sulfamoylpropan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid

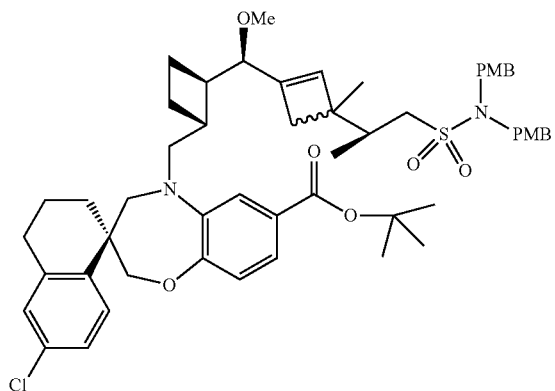

In a round-bottomed flask a mixture of tert-butyl (S)-5-(((1R,2R)-2-((R)—(R)-3-((S)-1-(N,N-bis(4-methoxybenzyl)sulfamoyl)propan-2-yl)-3-methylcyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—(S)-3-((S)-1-(N,N-bis(4-methoxybenzyl)sulfamoyl)propan-2-yl)-3-methylcyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate (150 mg, 0.160 mmol) was dissolved in a solution of DCM (5 mL)/TFA (5 mL). The mixture was stirred overnight. The solvent was removed in vacuo and the residue was added to a silica gel column and eluted with methanol/dichloromethane from 0 to 15% to give the title compounds as a mixture of two diastereomers (90 mg, 88%). MS m/z 643.4 (M+H)⁺.

Step 15: Cpd. No. 18 (Isomer 1) and Cpd. No. 18 (Isomer 2)

TFA (2 ml) was added to THF (6 mL) and stirred for 5 min. A mixture of (S)-2-((R)-3-((R)-((1R,2R)-2-formylcyclobutyl)(methoxy)methyl)-1-methylcyclobut-2-en-1-yl)-N,N-bis(4-methoxybenzyl)propane-1-sulfonamide and (S)-2-((S)-3-((R)-((1R,2R)-2-formylcyclobutyl)(methoxy)methyl)-1-methylcyclobut-2-en-1-yl)-N,N-bis(4-methoxybenzyl)propane-1-sulfonamide (85 mg, 0.153 mmol), tert-butyl (S)-6'-chloro-3',4,4',5-tetrahydro-2H,2'H-spiro[benzo[b][1,4]oxazepine-3,1'-naphthalene]-7-carboxylate (61.2 mg, 0.153 mmol) and phenylsilane (33.1 mg, 0.306 mmol) were added and the mixture was stirred for 3 h. H₂O was added to the reaction mixture followed by extraction with ethyl acetate. The combined organic layers were dried over Na₂SO₄, filtered and concentrated. The residue was added to a silica gel column and eluted with ethyl acetate/hexane from 0 to 30% to give the title compounds (60 mg, 41.7%) as a mixture of two diastereomers. MS m/z 940.5 (M+H)⁺.

In an argon flushed round-bottomed flask a mixture of (S)-6'-chloro-5-(((1R,2R)-2-((R)-methoxy((R)-3-methyl-3-((S)-1-sulfamoylpropan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((R)-methoxy((S)-3-methyl-3-((S)-1-sulfamoylpropan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid (90 mg, 0.140 mmol), DMAP (17.09 mg, 0.140 mmol), and triethylamine (70.8 mg, 0.700 mmol) were dissolved in DCM (20 mL) under argon. The mixture was cooled to 0° C. 2,4,6-Tripropyl-1,3,5,2,4,6-trioxatriphosphinane 2,4,6-trioxide (134 mg, 0.420 mmol) was added and the mixture was stirred for 1 h. Saturated NaCl was added to the reaction mixture followed by extraction with ethyl acetate. The combined organic layers were dried over Na$_2$SO$_4$, filtered and concentrated. The residue was purified with preparative HPLC.

The first-eluting diastereomer (29.3 mg, 33.5%) was designated Cpd. No. 18 (isomer 1). The stereochemistry of the asymmetric carbon atom of the cyclobutene ring has not been determined. MS m/z (ESI) 625.2 (M+H)$^+$. $^1$H NMR (500 MHz, DMSO-d6) δ 11.79 (s, 1H), 7.64 (d, J=8.5 Hz, 1H), 7.27 (dd, J=8.5, 2.1 Hz, 1H), 7.18 (d, J=2.1 Hz, 1H), 6.95 (d, J=8.1 Hz, 1H), 6.90 (d, J=8.1 Hz, 1H), 6.82 (s, 1H), 6.31 (s, 1H), 4.06 (d, J=12.2 Hz, 1H), 3.98 (d, J=12.2 Hz, 1H), 3.76 (d, J=13.8 Hz, 1H), 3.70-3.65 (m, 3H), 3.31-3.28 (m, 1H), 3.22-3.15 (m, 1H), 3.14-3.07 (m, 1H), 3.09 (s, 3H), 2.83-2.41 (m, 8H), 2.30 (d, J=13.1 Hz, 1H), 2.19 (d, J=13.1 Hz, 1H), 2.02-1.64 (m, 8H), 1.47-1.38 (m, 1H), 1.06 (d, J=6.7 Hz, 3H), 1.04 (s, 3H).

The second-eluting diastereomer was obtained as a white solid and designated Cpd. No. 18 (isomer 2). The stereochemistry of the asymmetric carbon atom of the cyclobutene ring has not been determined. $^1$H NMR (500 MHz, DMSO-d6) δ 11.87 (s, 1H), 7.65 (d, J=8.5 Hz, 1H), 7.26 (d, J=8.5 Hz, 1H), 7.18 (s, 1H), 6.94 (d, J=8.1 Hz, 1H), 6.91 (d, J=8.1 Hz, 1H), 6.80 (s, 1H), 6.13 (s, 1H), 4.08 (d, J=12.2 Hz, 1H), 3.96 (d, J=12.2 Hz, 1H), 3.78-3.58 (m, 5H), 3.33-3.26 (m, 1H), 3.20-3.13 (m, 1H), 3.18 (s, 3H), 3.11-3.04 (m, 1H), 2.83-2.65 (m, 2H), 2.55-2.44 (m, 1H), 2.28 (d, J=13.4 Hz, 1H), 2.10 (d, J=13.4 Hz, 1H), 2.01-1.79 (m, 3H), 1.77-1.59 (m, 5H), 1.46-1.38 (m, 1H), 1.09 (d, J=6.7 Hz, 3H), 1.06 (s, 3H).

Example 9

Synthesis of Cpd. No. 11 as a Mixture of Stereoisomers

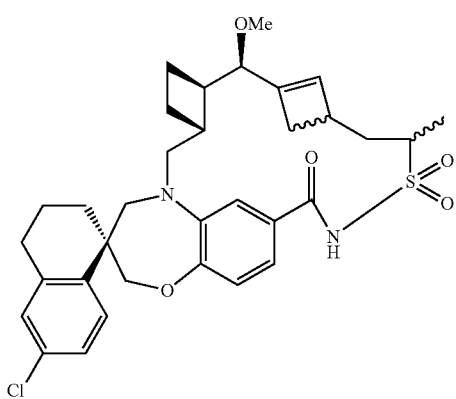 [SMILES: CO[C@H]1C2=CC(C2)CC(C)S(=O)(=O)NC(=O)c2ccc3c(c2)N(C[C@@H]2CC[C@H]21)C[C@@]1(CCCc2cc(Cl)ccc21)CO3]

Step 1:
N,N-bis(4-methoxybenzyl)ethanesulfonamide

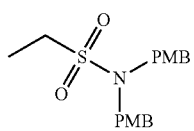

In a 100 mL round-bottomed flask ethanesulfonamide (2 g, 18.32 mmol), 1-(chloromethyl)-4-methoxybenzene (7.17 g, 45.8 mmol), and K$_2$CO$_3$ (10.13 g, 73.3 mmol) were added in DMF (20 mL). The reaction mixture was stirred at 50° C. for 16 h. H$_2$O (60 mL) was added to the reaction mixture followed by extraction with ethyl acetate (60 mL×2). The combined organic layers were dried over Na$_2$SO$_4$, filtered and concentrated. The residue was added to a silica gel column and eluted with ethyl acetate/hexane from 0% to 30% to give the title compound (6 g, 94%) as a white solid. $^1$H NMR (500 MHz, DMSO-d6) δ 7.17 (d, J=8.5 Hz, 4H), 6.89 (d, J=8.5 Hz, 4H), 4.20 (s, 4H), 3.74 (s, 6H), 3.04 (q, J=7.3 Hz, 2H), 1.17 (t, J=7.3 Hz, 3H). MS m/z (ESI) 361.5 (M+Na)$^+$.

Step 2:
N,N-bis(4-Methoxybenzyl)pent-4-ene-2-sulfonamide

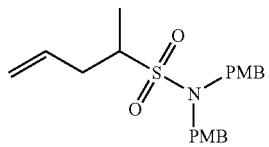

In a flame-dried 100 mL three-necked round-bottomed flask N,N-bis(4-methoxybenzyl)ethanesulfonamide (4.8 g, 13.74 mmol) was dissolved in THF (60 mL) under argon. The reaction mixture was cooled to −78° C. with a dry ice/acetone bath. Butyllithium (1.055 g, 16.47 mmol) was added dropwise over 20 min. The reaction mixture was stirred at −78° C. for 1 h. 3-bromoprop-1-ene (6.65 g, 54.9 mmol) was added and the reaction mixture was stirred at −78° C. for 1 h. Saturated NH$_4$Cl (40 mL) was added to the reaction mixture followed by extraction with ethyl acetate (50 mL×2). The combined organic layers were dried over Na$_2$SO$_4$, filtered and concentrated. The residue was added to a silica gel column and eluted with ethyl acetate/hexane from 0% to 10% to give the title compound (4.5 g, 84%) as a white solid. MS m/z 412.3 (M+Na)$^+$.

Step 3: 1-(2,2-diChloro-3-oxocyclobutyl)-N,N-bis (4-methoxybenzyl)propane-2-sulfonamide

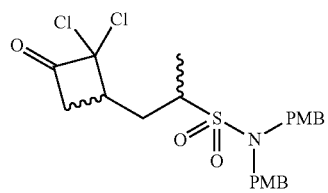

In a flame-dried 250 mL three-necked round-bottomed flask N,N-bis(4-methoxybenzyl)pent-4-ene-2-sulfonamide (4.5 g, 11.55 mmol) and zinc (3.02 g, 46.2 mmol) were added in diethyl ether (20 mL) under argon. 2,2,2-Trichloroacetyl chloride (4.20 g, 23.11 mmol) and 1,2-dimethoxyethane (2.08 g, 23.11 mmol) in diethyl ether (40.0 mL) were added dropwise to the reaction mixture over 20 min. The reaction mixture was stirred at 40° C. for 16 h. The reaction mixture was diluted with hexane (60 mL) and filtered through a celite and the filter cake was rinsed with hexane (30 mL×2). The filtrate was washed with H$_2$O (100 mL), saturated NaHCO$_3$ (100 mL), and saturated NaCl (100 mL). The organic layer was dried over Na$_2$SO$_4$, filtered and concentrated to afford the title compound (4 g, 69.2%) as a yellow oil. This product was used directly in the next step without further purification.

Step 4: N,N-bis(4-Methoxybenzyl)-1-(3-oxocyclobutyl)propane-2-sulfonamide

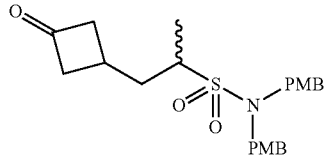

In a 250 mL round-bottomed flask 1-(2,2-dichloro-3-oxocyclobutyl)-N,N-bis(4-methoxybenzyl)propane-2-sulfonamide (4 g, 7.99 mmol) and zinc (1.568 g, 23.98 mmol) were added in acetic acid (50 mL) under argon. The reaction mixture was stirred at 70° C. for 4 h. The reaction mixture was filtered through a celite and the filter cake was rinsed with ethyl acetate (30 mL×2) and concentrated. H$_2$O (100 mL) was added to the reaction mixture followed by extraction with ethyl acetate (50 mL×2). The combined organic layers were dried over Na$_2$SO$_4$, filtered and concentrated. The residue was added to a silica gel column and eluted with ethyl acetate/hexane from 0% to 30% to give the title compound (1.67 g, 48.4%) as a yellow oil.

$^1$H NMR (500 MHz, DMSO-d6) δ 7.19 (d, J=8.5 Hz, 4H), 6.88 (d, J=8.5 Hz, 4H), 4.28 (d, J=15.2 Hz, 2H), 4.21 (d, J=15.2 Hz, 2H), 3.73 (s, 6H), 3.16-3.07 (m, 1H), 3.05-2.96 (m, 2H), 2.78-2.69 (m, 1H), 2.53 (dd, J=6.2, 3.1 Hz, 1H), 2.42 (dt, J=12.9, 6.4 Hz, 1H), 1.94 (ddd, J=13.2, 9.2, 3.8 Hz, 1H), 1.76 (ddd, J=13.6, 10.0, 6.2 Hz, 1H), 1.20 (d, J=6.8 Hz, 3H). MS m/z 454.6 (M+Na)$^+$.

Step 5: (S)-3-((R)-2-(N,N-bis(4-methoxybenzyl)sulfamoyl)propyl)cyclobut-1-en-1-yl trifluoromethanesulfonate and (R)-3-((R)-2-(N,N-bis(4-methoxybenzyl)sulfamoyl)propyl)cyclobut-1-en-1-yl trifluoromethanesulfonate and (S)-3-((S)-2-(N,N-bis(4-methoxybenzyl)sulfamoyl)propyl)cyclobut-1-en-1-yl trifluoromethanesulfonate and (R)-3-((S)-2-(N, N-bis(4-methoxybenzyl)sulfamoyl)propyl)cyclobut-1-en-1-yl trifluoromethanesulfonate

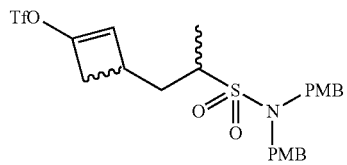

In a flame-dried 250 mL round-bottomed flask N,N-bis(4-methoxybenzyl)-1-(3-oxocyclobutyl)propane-2-sulfonamide (1.67 g, 3.87 mmol) and 1,1,1-trifluoro-N-phenyl-N-((trifluoromethyl)sulfonyl)methanesulfonamide (1.797 g, 5.03 mmol) were dissolved in THF (30 ml) under argon. The reaction mixture was cooled to −78° C. with a dry ice/acetone bath. KHMDS (1.158 g, 5.80 mmol) was added dropwise to the reaction mixture over 20 min. The reaction mixture was stirred at −78° C. for 2 h. Saturated NH$_4$Cl (30 mL) was added to the reaction mixture followed by extraction with ethyl acetate (40 mL×2). The combined organic layers were dried over Na$_2$SO$_4$, filtered and concentrated. The residue was added to a silica gel column and eluted with ethyl acetate/hexane from 0% to 20% to give a mixture of the title compounds (1.7 g, 78%) as a colorless oil. MS m/z 586.1 (M+Na)$^+$.

Step 6: tert-butyl (S)-5-(((1R,2R)-2-((R)—((S)-3-((R)-2-(N,N-bis(4-methoxybenzyl)sulfamoyl)propyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—((R)-3-((R)-2-(N,N-bis(4-methoxybenzyl)sulfamoyl)propyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—((S)-3-((S)-2-(N,N-bis(4-methoxybenzyl)sulfamoyl)propyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—((R)-3-((S)-2-(N,N-bis(4-methoxybenzyl)sulfamoyl)propyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate

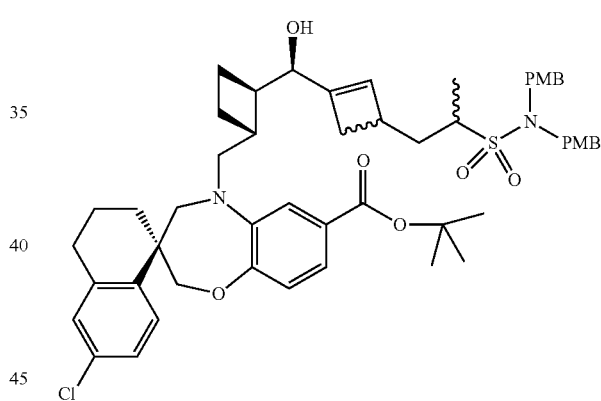

In a flame-dried 100 mL three-necked round-bottomed flask chromium (II) chloride (0.446 g, 3.63 mmol) and nickel (II) chloride (0.016 g, 0.121 mmol) were added in DMF (10 mL) under argon. tert-Butyl (S)-6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (0.3 g, 0.605 mmol) and a mixture of (S)-3-((R)-2-(N,N-bis(4-methoxybenzyl)sulfamoyl)propyl)cyclobut-1-en-1-yl trifluoromethanesulfonate and (R)-3-((R)-2-(N,N-bis(4-methoxybenzyl)sulfamoyl)propyl)cyclobut-1-en-1-yl trifluoromethanesulfonate and (S)-3-((S)-2-(N,N-bis(4-methoxybenzyl)sulfamoyl)propyl)cyclobut-1-en-1-yl trifluoromethanesulfonate and (R)-3-((S)-2-(N,N-bis(4-methoxybenzyl)sulfamoyl)propyl)cyclobut-1-en-1-yl trifluoromethanesulfonate (0.375 g, 0.665 mmol) were dissolved in DMF (10 mL) and the solution was added to the reaction mixture in one portion. The reaction mixture was stirred at 70° C. for 3 h. H$_2$O (50 mL) was added to the reaction mixture followed by extraction with ethyl acetate (50 mL×2). The combined organic layers were dried over Na$_2$SO$_4$, filtered and concentrated. The residue was added to a silica gel column and eluted with ethyl acetate/hexane from 0% to 20% to give the title compounds (0.2 g, 36.3%) as a mixture of diastereomers. MS m/z 911.7 (M+H)$^+$.

Step 7: tert-butyl (S)-5-(((1R,2R)-2-((R)—(S)-3-((R)-2-(N,N-bis(4-methoxybenzyl)sulfamoyl)propyl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—((R)-3-((R)-2-(N,N-bis(4-methoxybenzyl)sulfamoyl)propyl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—((S)-3-((S)-2-(N,N-bis(4-methoxybenzyl)sulfamoyl)propyl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—(R)-3-((S)-2-(N,N-bis(4-methoxybenzyl)sulfamoyl)propyl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate

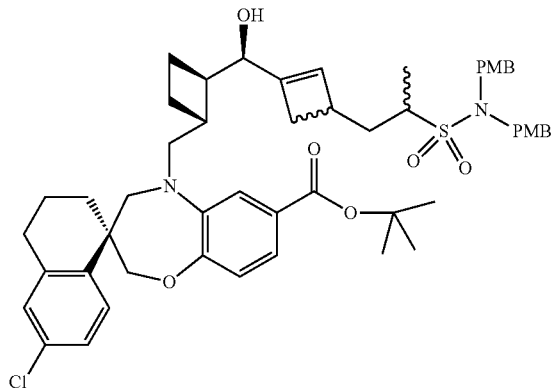

In a 100 mL round-bottomed flask a mixture of tert-butyl (S)-5-(((1R,2R)-2-((R)—(S)-3-((R)-2-(N,N-bis(4-methoxybenzyl)sulfamoyl)propyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—((R)-3-((R)-2-(N,N-bis(4-methoxybenzyl)sulfamoyl)propyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—(S)-3-((S)-2-(N,N-bis(4-methoxybenzyl)sulfamoyl)propyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—(R)-3-((S)-2-(N,N-bis(4-methoxybenzyl)sulfamoyl)propyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate (0.2 g, 0.219 mmol), DMAP (0.027 g, 0.219 mmol), and iodomethane (0.311 g, 2.194 mmol) were dissolved in THF (5 mL) under argon. The reaction mixture was cooled to 0° C. with an ice/water bath. Sodium hydride (0.263 g, 6.58 mmol) was added to the reaction mixture in one portion. The reaction mixture was stirred at room temperature for 4 h. H$_2$O (10 mL) was added to the reaction mixture followed by extraction with ethyl acetate (30 mL×2). The combined organic layers were dried over Na$_2$SO$_4$, filtered and concentrated to afford the title compounds (0.2 g, 98%) as a mixture of diastereomers. MS m/z 926.7 (M+H)$^+$.

Step 8: (S)-6'-chloro-5-(((1R,2R)-2-((R)-methoxy((S)-3-((R)-2-sulfamoylpropyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((R)-methoxy((R)-3-((R)-2-sulfamoylpropyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((R)-methoxy((S)-3-((S)-2-sulfamoylpropyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((R)-methoxy((R)-3-((S)-2-sulfamoylpropyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid

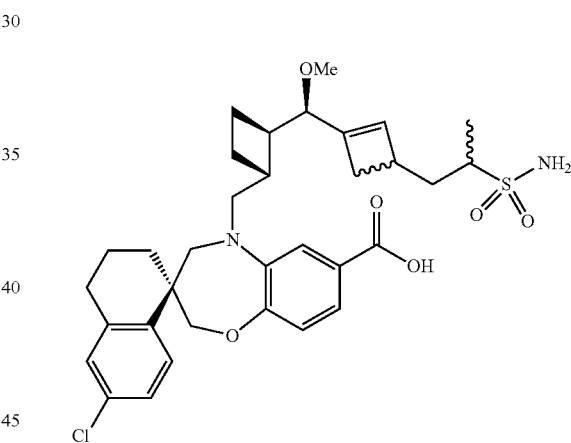

In a 100 mL round-bottomed flask a mixture of tert-butyl (S)-5-(((1R,2R)-2-((R)—(S)-3-((R)-2-(N,N-bis(4-methoxybenzyl)sulfamoyl)propyl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—(R)-3-((R)-2-(N,N-bis(4-methoxybenzyl)sulfamoyl)propyl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—(S)-3-((S)-2-(N,N-bis(4-methoxybenzyl)sulfamoyl)propyl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—(R)-3-((S)-2-(N,N-bis(4-methoxybenzyl)sulfamoyl)propyl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate (0.2 g, 0.216 mmol) was dissolved in DCM (3.00 ml) and TFA (3 ml). The reaction mixture was stirred at room temperature for 16 h. Solvent was removed under vacuum and the residue was added to a silica gel column and eluted with methanol/dichloromethane from 0% to 10% to give the title compounds as a mixture of diastereomers (0.130 g, 96%). MS m/z 629.2 (M+H)$^+$.

Step 9: Cpd. No. 11

In a 100 mL round-bottomed flask a mixture of (S)-6'-chloro-5-(((1R,2R)-2-((R)-methoxy((S)-3-((R)-2-sulfamoylpropyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((R)-methoxy((R)-3-((R)-2-sulfamoylpropyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((R)-methoxy((S)-3-((S)-2-sulfamoylpropyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((R)-methoxy((R)-3-((S)-2-sulfamoylpropyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid (0.130 g, 0.207 mmol), DMAP (0.025 g, 0.207 mmol), and triethylamine (0.063 g, 0.620 mmol) were dissolved in DCM (30 mL) under argon. The reaction mixture was cooled to 0° C. with an ice/water bath. T$_3$P (0.197 g, 0.310 mmol) was added dropwise and the reaction mixture was stirred at room temperature for 2 h. H$_2$O (20 mL) was added to the reaction mixture followed by extraction with ethyl acetate (30 mL×2). The combined organic layers were dried over Na$_2$SO$_4$, filtered and concentrated. The residue was purified by reverse-phase preparative HPLC to give two isomers that were isolated in pure form. The other two isomers were obtained as a mixture. MS m/z 611.2 (M+H)$^+$.

Example 10

Synthesis of Cpd. No. 7 as a Mixture of Stereoisomers

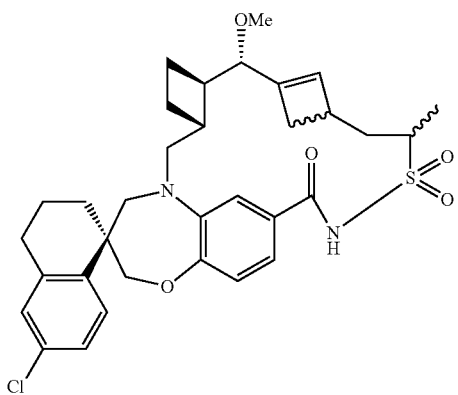 [SMILES: CO[C@@H]1C2=CC(C2)CC(C)S(=O)(=O)NC(=O)c2ccc3c(c2)N(C[C@@H]2CC[C@H]21)C[C@@]1(CCCc2cc(Cl)ccc21)CO3]

Step 1: tert-butyl (S)-5-(((1R,2R)-2-((S)—((S)-3-((R)-2-(N,N-bis(4-methoxybenzyl)sulfamoyl)propyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((S)—((R)-3-((R)-2-(N,N-bis(4-methoxybenzyl)sulfamoyl)propyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((S)—((S)-3-((S)-2-(N,N-bis(4-methoxybenzyl)sulfamoyl)propyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((S)—((R)-3-((S)-2-(N,N-bis(4-methoxybenzyl)sulfamoyl)propyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate

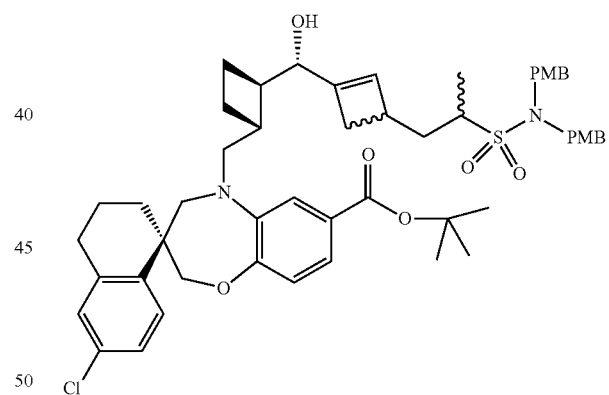

The title compounds were obtained as a mixture of the second eluting isomers (0.16 g, 29.0%) as described in Example 9, Step 6. MS m/z 911.7 (M+H)$^+$.

Step 2: tert-butyl (S)-5-(((1R,2R)-2-((S)—((S)-3-((R)-2-(N,N-bis(4-methoxybenzyl)sulfamoyl)propyl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((S)—((R)-3-((R)-2-(N,N-bis(4-methoxybenzyl)sulfamoyl)propyl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((S)—((S)-3-((S)-2-(N,N-bis(4-methoxybenzyl)sulfamoyl)propyl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((S)—((R)-3-((S)-2-(N,N-bis(4-methoxybenzyl)sulfamoyl)propyl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate

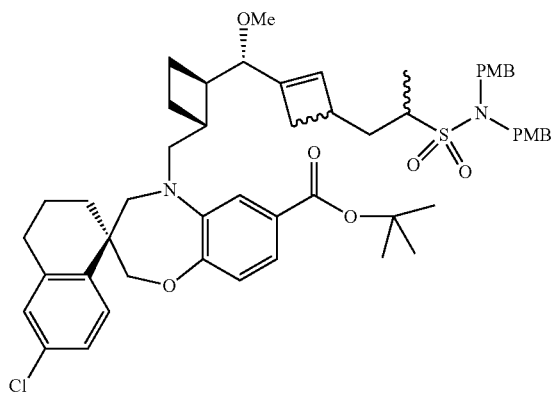

In a 100 mL round-bottomed flask a mixture of tert-butyl (S)-5-(((1R,2R)-2-((S)—((S)-3-((R)-2-(N,N-bis(4-methoxybenzyl)sulfamoyl)propyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((S)—((R)-3-((R)-2-(N,N-bis(4-methoxybenzyl)sulfamoyl)propyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((S)—((S)-3-((S)-2-(N,N-bis(4-methoxybenzyl)sulfamoyl)propyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((S)—((R)-3-((S)-2-(N,N-bis(4-methoxybenzyl)sulfamoyl)propyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate (0.16 g, 0.176 mmol), iodomethane (0.249 g, 1.755 mmol), and DMAP (0.021 g, 0.176 mmol) were dissolved in THF (5 mL) under argon. The reaction mixture was cooled to 0° C. with an ice/water bath. Sodium hydride (0.211 g, 5.27 mmol) was added to the reaction mixture in one portion. The reaction mixture was stirred at room temperature for 4 h. H$_2$O (10 mL) was added to the reaction mixture followed by extraction with ethyl acetate (30 mL×2). The combined organic layers were dried over Na$_2$SO$_4$, filtered and concentrated to afford the title compounds (0.16 g, 98%) as a mixture. MS m/z 926.6 (M+H)$^+$.

Step 3: (S)-6'-chloro-5-(((1R,2R)-2-((S)-methoxy((S)-3-((R)-2-sulfamoylpropyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S)-methoxy((R)-3-((R)-2-sulfamoylpropyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S)-methoxy((S)-3-((S)-2-sulfamoylpropyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S)-methoxy((R)-3-((S)-2-sulfamoylpropyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid

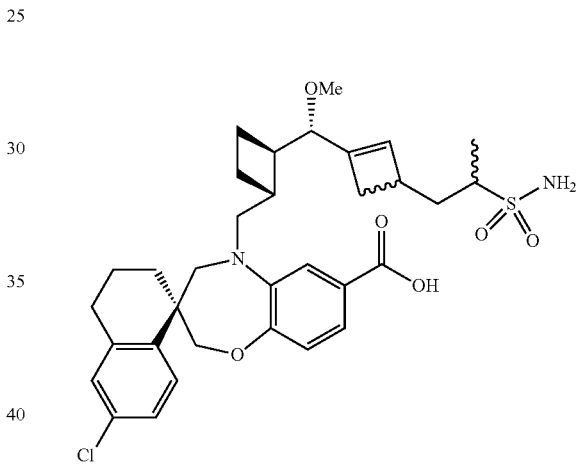

In a 100 mL round-bottomed flask a mixture of tert-butyl (S)-5-(((1R,2R)-2-((S)—((S)-3-((R)-2-(N,N-bis(4-methoxybenzyl)sulfamoyl)propyl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((S)—((R)-3-((R)-2-(N,N-bis(4-methoxybenzyl)sulfamoyl)propyl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((S)—((S)-3-((S)-2-(N,N-bis(4-methoxybenzyl)sulfamoyl)propyl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((S)—((R)-3-((S)-2-(N,N-bis(4-methoxybenzyl)sulfamoyl)propyl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate (0.16 g, 0.173 mmol) was dissolved in DCM (3.00 mL) and TFA (3 mL). The reaction mixture was stirred at room temperature for 16 h. Solvent was removed under vacuum and the residue was added to a silica gel column and eluted with methanol/dichloromethane from 0% to 10% to give the title compounds (0.108 g, 99%) as a brown oil. MS m/z 629.3 (M+H)⁺.

Step 4: Cpd. No. 7

In a 100 mL round-bottomed flask a mixture of (S)-6'-chloro-5-(((1R,2R)-2-((S)-methoxy((S)-3-((R)-2-sulfamoylpropyl)cyclobut-1-en-1-yl)methyl)cyclobutyl)methyl)-3',4,4',5-tetrahydro-2H,2'H-spiro[benzo[b][1,4]oxazepine-3,1'-naphth al ene]-7-carboxylic acid and (S)-6'-chloro-5-(((1R,2R)-2-((S)-methoxy((R)-3-((R)-2-sulfamoylpropyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S)-methoxy((S)-3-((S)-2-sulfamoylpropyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S)-methoxy((R)-3-((S)-2-sulfamoylpropyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid (0.108 g, 0.172 mmol), DMAP (0.021 g, 0.172 mmol), and triethylamine (0.052 g, 0.515 mmol) were dissolved in DCM (30 mL) under argon. The reaction mixture was cooled to 0° C. with an ice/water bath. T₃P (0.164 g, 0.257 mmol) was added to the reaction mixture dropwise. The reaction mixture was stirred at room temperature for 2 h. H₂O (20 mL) was added to the reaction mixture followed by extraction with ethyl acetate (30 mL×2). The combined organic layers were dried over Na₂SO₄, filtered and concentrated. The crude material was purified by reverse-phase preparative HPLC to give two isomers that were isolated in pure form. The other two isomers were obtained as a mixture. MS m/z 611.2 (M+H)⁺.

Example 11

Synthesis of Cpd. No. 15 (Isomer 1) and Cpd. No. 15 (Isomer 2)

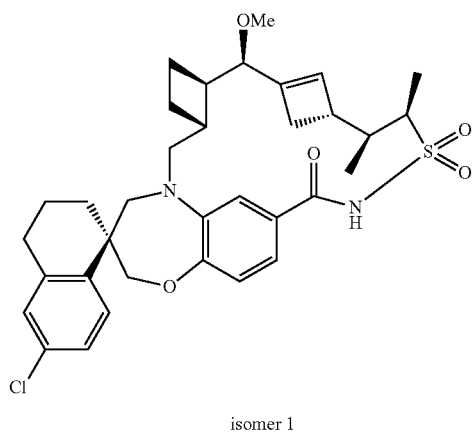

isomer 1

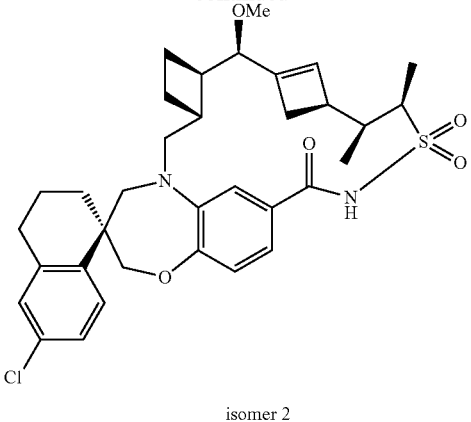

isomer 2

Step 1: 2-(((2S,3R)-3-methylpent-4-en-2-yl)thio)pyrimidine

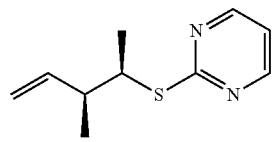

In an argon flushed three-necked round-bottomed flask (2S,3S)-3-methylpent-4-en-2-ol (9.2 g, 92 mmol), pyrimidine-2-thiol (15.45 g, 138 mmol) and Ph₃P (48.2 g, 184 mmol) were dissolved in THF (300 mL) under argon. The mixture was cooled to 0° C. DIAD (37.1 g, 184 mmol) as a solution in THF (50 mL) was added dropwise. The mixture was stirred overnight. Saturated NaCl was added to the reaction mixture followed by extraction with ethyl acetate. The combined organic layers were dried over Na₂SO₄, filtered and concentrated. The resin was added to a silica gel column and eluted with ethyl acetate/hexane from 0 to 10% to give the title compound (7.9 g, 44.3%). MS m/z 195.2 (M+H)⁺.

Step 2: 2-(((2R,3S)-3-methylpent-4-en-2-yl)sulfonyl)pyrimidine

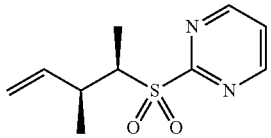

Bis(tetrabutylammonium) sulphate (4.72 g, 4.07 mmol), sodium tungstate dihydrate (1.341 g, 4.07 mmol), and phenylphosphonic acid (0.643 g, 4.07 mmol) were added in hydrogen peroxide (13.83 g, 122 mmol) and the mixture was cooled to 0° C. 2-(((2R,3S)-3-Methylpent-4-en-2-yl)thio)pyrimidine (7.9 g, 40.7 mmol), as a solution in toluene (40 mL), was added and the reaction mixture was stirred at 50° C. for 2 h. Saturated NaCl was added to the reaction mixture followed by extraction with ethyl acetate. The combined organic layers were dried over Na₂SO₄, filtered and concentrated. The residue was added to a silica gel column and eluted with ethyl acetate/hexane from 70% to 90% to give the title compound (8 g, 87%). MS m/z 227.1 (M+H)⁺.

Step 3: (2R,3S)-3-Methylpent-4-ene-2-sulfonamide

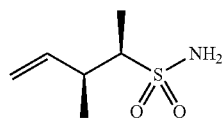

In a round-bottomed flask 2-(((2R,3S)-3-methylpent-4-en-2-yl)sulfonyl)pyrimidine (8 g, 35.4 mmol) was dissolved in MeOH (50 ml) under argon. The mixture was cooled to 0° C. and 5M sodium methoxide (2.483 g, 46.0 mmol) in MeOH was added dropwise and the reaction mixture was stirred for 1 h. Solvent was removed in vacuo and the residue was triturated with diethyl ether to give the sodium salt. The sodium salt was dissolved in water (20 mL), sodium acetate (5.80 g, 70.7 mmol) and (aminooxy)sulfonic acid (8.00 g, 70.7 mmol) were added and the reaction mixture was stirred overnight. Saturated NaCl was added to the reaction mixture followed by extraction with ethyl acetate. The combined organic layers were dried over Na₂SO₄, filtered and concentrated to give the title compound (4 g, 69.3%). MS m/z 164.0 (M+H)⁺.

Step 4: (2R,3S)—N,N-bis(4-methoxybenzyl)-3-methylpent-4-ene-2-sulfonamide

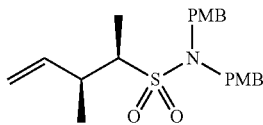

In a round-bottomed flask (2R,3S)-3-methylpent-4-ene-2-sulfonamide (4 g, 24.50 mmol), Cs₂CO₃ (19.96 g, 61.3 mmol) were added in DMF (40 mL) under argon. 4-Methoxybenzyl chloride (9.59 g, 61.3 mmol) was added and the mixture was stirred at 50° C. for 2 h. Saturated NaCl was added to the reaction mixture followed by extraction with ethyl acetate. The combined organic layers were dried over Na₂SO₄, filtered and concentrated. The residue was added to a silica gel column and eluted with ethyl acetate/hexane from 0 to 20% to give the title compound (4.5 g, 45.5%). MS m/z 426.4 (M+Na)⁺.

Step 5: (2R,3S)—N,N-Bis(4-methoxybenzyl)-3-(3-oxocyclobutyl)butane-2-sulfonamide

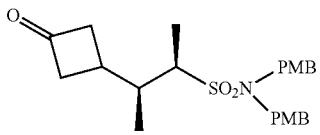

In a round-bottomed flask (2R,3S)—N,N-bis(4-methoxybenzyl)-3-methylpent-4-ene-2-sulfonamide (4.5 g, 11.15 mmol) and zinc (3.65 g, 55.8 mmol) were added in diethyl ether (15 mL) under argon. 2,2,2-Trichloroacetyl chloride (4.06 g, 22.30 mmol) and DME (2.010 g, 22.30 mmol), as a solution in diethyl ether (15.00 mL) were added to the reaction mixture. The mixture was stirred at 40° C. for 20 h. Hexane (30 mL) was added and then the mixture was filtered through a celite. The filtrate was washed with saturated NaHCO₃, saturated NaCl, and concentrated. The residue was dissolved in acetic acid (50 mL). Zinc (1.21 g, 33.5 mmol) was added and the mixture was stirred at 70° C. for 8 h. The mixture was filtered through a celite and then concentrated. The residue was added to a silica gel column and eluted with ethyl acetate/hexane from 0 to 30% to give the title compound (1.7 g, 34.2%). ¹H NMR (500 MHz, DMSO-d₆) δ 7.20 (d, J=8.5 Hz, 4H), 6.88 (d, J=8.5 Hz, 4H), 4.36 (d, J=15.2 Hz, 2H), 4.17 (d, J=15.2 Hz, 2H), 3.73 (s, 6H), 3.03-2.95 (m, 1H), 2.92-2.85 (m, 1H), 2.84-2.73 (m, 2H), 2.47-2.41 (m, 1H), 2.17-2.06 (m, 2H), 1.10 (d, J=7.0 Hz, 3H), 0.96 (d, J=5.8 Hz, 3H). MS m/z 468.5 (M+Na)⁺.

Step 6: (R)-3-((2S,3R)-3-(N,N-bis(4-methoxybenzyl)sulfamoyl)butan-2-yl)cyclobut-1-en-1-yl trifluoromethanesulfonate and (S)-3-((2S,3R)-3-(N,N-bis(4-methoxybenzyl)sulfamoyl)butan-2-yl)cyclobut-1-en-1-yl trifluoromethanesulfonate

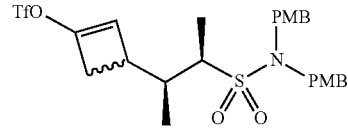

In an argon flushed round-bottomed flask (2R,3S)—N,N-bis(4-methoxybenzyl)-3-(3-oxocyclobutyl)butane-2-sulfonamide (1.7 g, 3.82 mmol) and 1,1,1-trifluoro-N-phenyl-N-((trifluoromethyl)sulfonyl)methanesulfonamide (2.044 g, 5.72 mmol) were dissolved in THF (20 mL) under argon. The mixture was cooled to −78° C. 1M KHMDS (0.913 g, 4.58 mmol) in THF was added dropwise. The mixture was stirred for 2 h. Saturated NH₄Cl was added to the reaction mixture followed by extraction with ethyl acetate. The combined organic layers were dried over Na₂SO₄, filtered and concentrated. The residue was added to a silica gel column and eluted with ethyl acetate/hexane from 0 to 20% to give the title compounds (1.8 g, 82%) as a mixture. MS m/z (ESI) 600.5 (M+Na)⁺.

Step 7: ((1R,2R)-2-((tert-Butyldiphenylsilyl)oxy)methyl)cyclobutyl)methanol

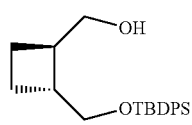

In a round-bottomed flask ((1R,2R)-2-(hydroxymethyl)cyclobutyl)methyl benzoate (2 g, 9.08 mmol), imidazole (0.927 g, 13.62 mmol), and TBDPS-Cl (2.99 g, 10.90 mmol) were dissolved in DMF (10 mL) under argon. The mixture was stirred at room temperature overnight. Saturated NaCl was added to the reaction mixture followed by extraction with ethyl acetate. The combined organic layers were dried over Na₂SO₄, filtered and concentrated. The residue was dissolved in MeOH (20 mL) and K₂CO₃ (6.27 g, 45.4 mmol) was added. The mixture was stirred at 35° C. for 3 h. Saturated NaCl was added to the reaction mixture followed by extraction with ethyl acetate. The combined organic layers were dried over Na₂SO₄, filtered and concentrated. The residue was added to a silica gel column and eluted with ethyl acetate/hexane from 0 to 50% to give the title compound (3.5 g). MS m/z (ESI) 355.4 (M+H)⁺.

Step 8: (1R,2R)-2-(((tert-butyldiphenylsilyl)oxy) methyl)cyclobutane-1-carbaldehyde

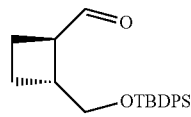

In a round-bottomed flask ((1R,2R)-2-(((tert-butyldiphenylsilyl)oxy)methyl) cyclobutyl)methanol (1.5 g, 4.23 mmol) was dissolved in DCM (20 mL). The mixture was cooled to 0° C. and DMP (2.153 g, 5.08 mmol) was added slowly to the reaction mixture. The mixture was stirred for 30 min. Saturated NaHCO₃ was added to the reaction mixture followed by extraction with ethyl acetate and washed with saturated Na₂S₂O₃. The combined organic layers were dried over Na₂SO₄, filtered and concentrated. The residue was added to a silica gel column and eluted with ethyl acetate/hexane from 0 to 20% to give the title compound (1.05 g, 70.4%).

Step 9: (2R,3S)-3-((R)-3-((R)-((1R,2R)-2-(((tert-butyldiphenylsilyl)oxy)methyl) cyclobutyl)(hydroxy)methyl)cyclobut-2-en-1-yl)-N,N-bis(4-methoxybenzyl)butane-2-sulfonamide and (2R,3S)-3-((S)-3-((R)-((1R,2R)-2-(((tert-butyldiphenylsilyl) oxy) methyl)cyclobutyl)(hydroxy)methyl)cyclobut-2-en-1-yl)-N,N-bis(4-methoxybenzyl) butane-2-sulfonamide

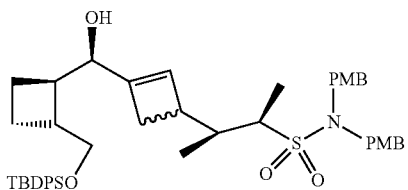

In an argon flushed three-necked round-bottomed flask chromium (II) chloride (1.106 g, 9.00 mmol) and nickel (II) chloride (0.058 g, 0.450 mmol) were dissolved in DMF (20 ml) under argon. The mixture was heated to 70° C. (1R, 2R)-2-(((tert-butyldiphenylsilyl)oxy)methyl)cyclobutane-1-carbaldehyde (0.952 g, 2.70 mmol) and a mixture of (R)-3-((2S,3R)-3-(N,N-bis(4-methoxybenzyl)sulfamoyl)butan-2-yl)cyclobut-1-en-1-yl trifluoromethanesulfonate and (S)-3-((2S,3R)-3-(N,N-bis(4-methoxybenzyl)sulfamoyl)butan-2-yl)cyclobut-1-en-1-yl trifluoromethanesulfonate (1.3 g, 2.251 mmol), as a solution in DMF (20.00 mL) were added to the reaction mixture. The mixture was stirred for 6 h. Saturated NaCl was added to the reaction mixture followed by extraction with ethyl acetate. The combined organic layers were dried over Na₂SO₄, filtered and concentrated. The residue was added to a silica gel column and eluted with ethyl acetate/hexane from 0 to 25% to give the title compounds (700 mg, 39.8%) as a mixture. MS m/z (ESI) 805.2 (M+Na)⁺.

Step 10: (2R,3S)-3-((R)-3-((R)-((1R,2R)-2-(hydroxymethyl)cyclobutyl) (methoxy)methyl)cyclobut-2-en-1-yl)-N,N-bis(4-methoxybenzyl)butane-2-sulfonamide and (2R,3S)-3-((S)-3-((R)-((1R,2R)-2-(hydroxymethyl)cyclobutyl)(methoxy)methyl) cyclobut-2-en-1-yl)-N,N-bis(4-methoxybenzyl)butane-2-sulfonamide

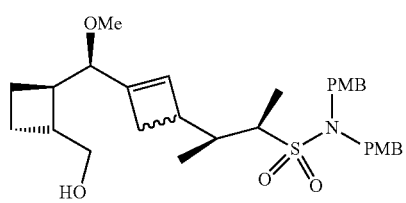

In an argon flushed round-bottomed flask a mixture of (2R,3S)-3-((R)-3-((R)-((1R,2R)-2-(((tert-butyldiphenylsilyl)oxy)methyl)cyclobutyl)(hydroxy)methyl)cyclobut-2-en-1-yl)-N,N-bis(4-methoxybenzyl)butane-2-sulfonamide and (2R,3S)-3-((S)-3-((R)-((1R,2R)-2-(((tert-butyldiphenylsilyl)oxy)methyl)cyclobutyl)(hydroxy)methyl)cyclobut-2-en-1-yl)-N,N-bis(4-methoxybenzyl)butane-2-sulfonamide (500 mg, 0.639 mmol), DMAP (15.62 mg, 0.128 mmol), and MeI (272 mg, 1.918 mmol) were dissolved in DMF (10 mL) under argon and the mixture was cooled to 0° C. NaH (767 mg, 19.18 mmol) was added and the mixture was stirred for 30 min. H₂O was added to the reaction mixture followed by extraction with ethyl acetate. The combined organic layers were dried over Na₂SO₄, filtered, and concentrated.

The residue was dissolved in THF (10.00 mL) and 1M TBAF (251 mg, 0.959 mmol) in THF was added and the mixture was stirred overnight. Saturated NaCl was added to the reaction mixture followed by extraction with ethyl acetate. The combined organic layers were dried over Na₂SO₄, filtered and concentrated. The residue was added to a silica gel column and eluted with ethyl acetate/hexane from 0 to 50% to give the title compounds (350 mg, 98%) as a mixture. MS m/z (ESI) 580.7 (M+Na)⁺.

Step 11: (2R,3S)-3-((R)-3-((R)-((1R,2R)-2-formylcyclobutyl)(methoxy)methyl) cyclobut-2-en-1-yl)-N,N-bis(4-methoxybenzyl)butane-2-sulfonamide and (2R,3S)-3-((S)-3-((R)-((1R,2R)-2-formylcyclobutyl)(methoxy)methyl)cyclobut-2-en-1-yl)-N,N-bis(4-methoxybenzyl)butane-2-sulfonamide

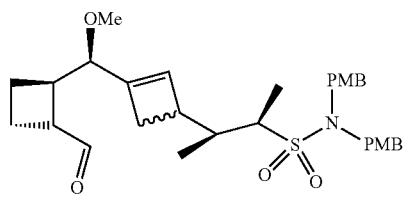

In a round-bottomed flask a mixture of (2R,3S)-3-((R)-3-((R)-((1R,2R)-2-(hydroxymethyl)cyclobutyl)(methoxy)

methyl)cyclobut-2-en-1-yl)-N,N-bis(4-methoxybenzyl)bu-tane-2-sulfonamide and (2R,3S)-3-((S)-3-((R)-((1R,2R)-2-(hydroxymethyl)cyclobutyl)(methoxy)methyl)cyclobut-2-en-1-yl)-N,N-bis(4-methoxybenzyl)butane-2-sulfonamide (350 mg, 0.628 mmol) was dissolved in DCM (10 mL). The mixture was cooled to 0° C. and DMP (319 mg, 0.753 mmol) was added. The mixture was stirred for 30 min. Saturated NaHCO₃ was added to the reaction mixture followed by extraction with ethyl acetate. The combined organic layers were dried over Na₂SO₄, filtered and concentrated to the title compounds as a mixture (330 mg, 95%). MS m/z (ESI) 578.4 (M+Na)⁺.

Step 12: tert-butyl (S)-5-(((1R,2R)-2-((R)—(R)-3-((2S,3R)-3-(N,N-bis(4-methoxybenzyl)sulfamoyl)butan-2-yl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—(S)-3-((2S,3R)-3-(N,N-bis(4-methoxybenzyl)sulfamoyl)butan-2-yl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate

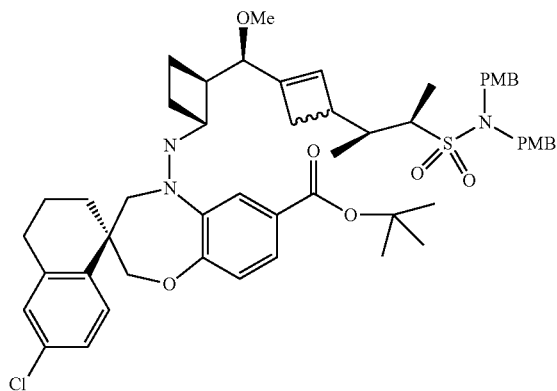

TFA (2 mL) was added to THF (6 mL) and the mixture was stirred for 5 min. tert-Butyl (S)-6'-chloro-3',4,4',5-tet-rahydro-2H,2'H-spiro[benzo[b][1,4]oxazepine-3,1'-naph-thalene]-7-carboxylate (230 mg, 0.576 mmol), a mixture of (2R,3S)-3-((R)-3-((R)-((1R,2R)-2-formylcyclobutyl)(methoxy)methyl)cyclobut-2-en-1-yl)-N,N-bis(4-methoxy-benzyl)butane-2-sulfonamide and (2R,3S)-3-((S)-3-((R)-((1R,2R)-2-formylcyclobutyl)(methoxy)methyl)cyclobut-2-en-1-yl)-N,N-bis(4-methoxybenzyl)butane-2-sulfonamide (320 mg, 0.576 mmol), and phenylsilane (93 mg, 0.864 mmol) were added and the reaction mixture was stirred for 2 h. H₂O was added to the reaction mixture followed by extraction with ethyl acetate and washed with saturated NaHCO₃. The combined organic layers were dried over Na₂SO₄, filtered and concentrated. The residue was added to a silica gel column and eluted with ethyl acetate/hexane from 0 to 30% to give the title compounds (540 mg, 100%) as a mixture. MS m/z (ESI) 940.5 (M+H)⁺.

Step 13: (S)-6'-chloro-5-(((1R,2R)-2-((R)-methoxy((R)-3-((2S,3R)-3-sulfamoylbutan-2-yl)cyclobut-1-en-1-yl)methyl)cyclobutyl)methyl)-3',4,4',5-tetra-hydro-2H,2'H-spiro[benzo[b][1,4]oxazepine-3,1'-naphthalene]-7-carboxylic acid and (S)-6'-chloro-5-(((1R,2R)-2-((R)-methoxy((S)-3-((2S,3R)-3-sulfamoylbutan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid

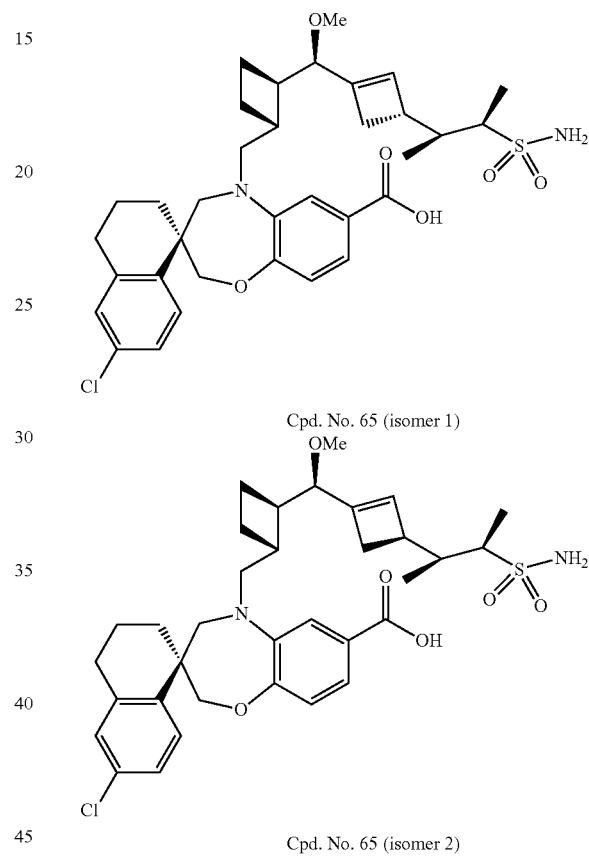

In a round-bottomed flask tert-butyl a mixture of tert-butyl (S)-5-(((1R,2R)-2-((R)—(R)-3-((2S,3R)-3-(N,N-bis(4-methoxybenzyl)sulfamoyl)butan-2-yl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—(S)-3-((2S,3R)-3-(N,N-bis(4-methoxybenzyl)sulfamoyl)butan-2-yl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate (540 mg, 0.575 mmol) was dissolved in DCM (5 mL)/TFA (5 mL). The mixture was stirred overnight. The solvent was removed in vacuo and the residue was purified with preparative HPLC to give the title compounds (90 mg, 24.35%) as a mixture. MS m/z (ESI) 643.4 (M+H)⁺.

Step 14: Cpd. No. 15

In an argon flushed round-bottomed flask a mixture of (S)-6'-chloro-5-(((1R,2R)-2-((R)-methoxy((R)-3-((2S,3R)-

3-sulfamoylbutan-2-yl)cyclobut-1-en-1-yl)methyl)cy-clobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((R)-methoxy((S)-3-((2S,3R)-3-sulfamoylbutan-2-yl)cyclobut-1-en-1-yl)methyl)cy-clobutyl)methyl)-3',4,4',5-tetrahydro-2H,2'H-spiro[benzo[b][1,4]oxazepine-3,1'-naphthalene]-7-carboxylic acid (90 mg, 0.140 mmol), DMAP (17.09 mg, 0.140 mmol), and triethylamine (70.8 mg, 0.700 mmol) were dissolved in DCM (40 mL) under argon. The mixture was cooled to 0° C. and 2,4,6-tripropyl-1,3,5,2,4,6-trioxatriphosphinane 2,4,6-trioxide (134 mg, 0.420 mmol) was added. The mixture was stirred for 30 min. Saturated NaCl was added to the reaction mixture followed by extraction with ethyl acetate. The combined organic layers were dried over $Na_2SO_4$, filtered and concentrated. The residue was purified with preparative HPLC.

The first-eluting diastereomer (25.4 mg, 29.0%) was designated as Cpd. No. 15 (isomer 1). $^1$H NMR (500 MHz, DMSO-$d_6$) δ 11.72 (s, 1H), 7.64 (d, J=8.6 Hz, 1H), 7.27 (dd, J=8.6, 2.2 Hz, 1H), 7.18 (d, J=2.2 Hz, 1H), 6.91-6.87 (m, 2H), 6.72 (s, 1H), 6.26 (s, 1H), 4.09-4.02 (m, 2H), 3.95 (d, J=12.3 Hz, 1H), 3.78-3.72 (m, 1H), 3.68 (d, J=5.1 Hz, 1H), 3.61 (d, J=14.0 Hz, 1H), 3.33-3.27 (m, 1H), 3.08 (s, 3H), 3.04-2.97 (m, 1H), 2.83-2.38 (m, 6H), 2.13 (d, J=13.1 Hz, 1H), 2.01-1.94 (m, 1H), 1.93-1.79 (m, 2H), 1.77-1.62 (m, 5H), 1.42-1.34 (m, 1H), 1.32 (d, J=7.1 Hz, 3H), 0.92 (d, J=6.7 Hz, 3H). MS m/z 625.2 [M+H]$^+$.

The second-eluting diastereomer was designated as Cpd. No. 15 (isomer 2). $^1$H NMR (500 MHz, DMSO-$d_6$) δ 11.82 (s, 1H), 7.64 (d, J=8.5 Hz, 1H), 7.27 (dd, J=8.5, 1.8 Hz, 1H), 7.18 (d, J=1.8 Hz, 1H), 6.93-6.87 (m, 2H), 6.75 (s, 1H), 6.15 (s, 1H), 4.08 (d, J=12.3 Hz, 1H), 3.93 (d, J=12.3 Hz, 1H), 3.84-3.76 (m, 2H), 3.66-3.59 (m, 2H), 3.34-3.28 (m, 1H), 3.16 (s, 3H), 3.07-2.97 (m, 1H), 2.84-2.75 (m, 1H), 2.74-2.65 (m, 1H), 2.63-2.53 (m, 3H), 2.48-2.40 (m, 1H), 2.16 (d, J=13.2 Hz, 1H), 2.01-1.95 (m, 1H), 1.92-1.79 (m, 2H), 1.74-1.56 (m, 5H), 1.45-1.36 (m, 1H), 1.30 (d, J=6.1 Hz, 3H), 0.99 (d, J=6.6 Hz, 3H). MS m/z 625.2 [M+H]$^+$.

Example 12

Synthesis of Cpd. No. 16 as a Mixture of Stereoisomers

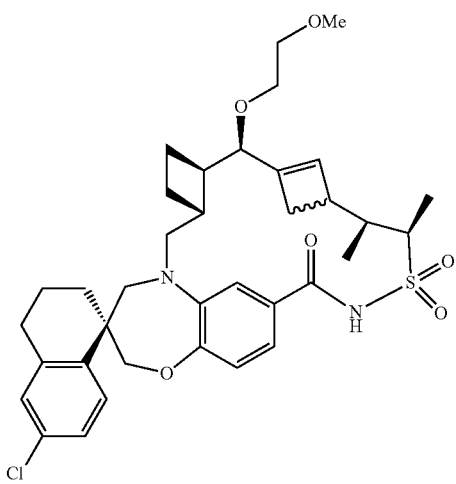

Cpd. No. 16

Step 1: (2R,3S)-3-((R)-3-((R)-((1R,2R)-2-(hy-droxymethyl)cyclobutyl)(2-methoxyethoxy)methyl)cyclobut-2-en-1-yl)-N,N-bis(4-methoxybenzyl)bu-tane-2-sulfonamide and (2R,3S)-3-((S)-3-((R)-((1R,2R)-2-(hydroxymethyl)cyclobutyl)(2-methoxyethoxy)methyl)cyclobut-2-en-1-yl)-N,N-bis(4-methoxybenzyl)butane-2-sulfonamide

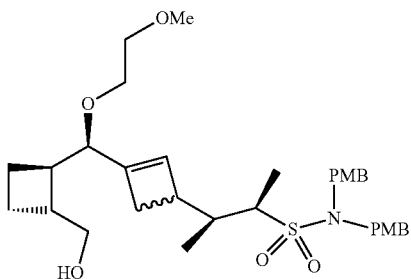

In an argon flushed round-bottomed flask a mixture of (2R,3S)-3-((R)-3-((R)-((1R,2R)-2-(((tert-butyldiphenylsi-lyl)oxy)methyl)cyclobutyl)(hydroxy)methyl)cyclobut-2-en-1-yl)-N,N-bis(4-methoxybenzyl)butane-2-sulfonamide and (2R,3S)-3-((S)-3-((R)-((1R,2R)-2-(((tert-butyldiphenylsi-lyl)oxy)methyl)cyclobutyl)(hydroxy)methyl)cyclobut-2-en-1-yl)-N,N-bis(4-methoxybenzyl)butane-2-sulfonamide (500 mg, 0.639 mmol) (from Example 23, Step 9), DMAP (15.62 mg, 0.128 mmol), and 1-iodo-2-methoxyethane (392 mg, 2.110 mmol) were dissolved in DMF (10 mL) under argon and the mixture was cooled to 0° C. NaH (767 mg, 19.18 mmol) was added and the mixture was stirred for 2.5 h. $H_2O$ was added to the reaction mixture followed by extraction with ethyl acetate. The combined organic layers were dried over $Na_2SO_4$, filtered and concentrated. The residue was dissolved in THF (10.00 mL) and 1M TBAF (251 mg, 0.959 mmol) in THF was added. The mixture was stirred overnight. Saturated NaCl was added to the reaction mixture followed by extraction with ethyl acetate. The combined organic layers were dried over $Na_2SO_4$, filtered and concentrated. The residue was added to a silica gel column and eluted with ethyl acetate/hexane from 0 to 50% to give the title compounds as a mixture (65 mg, 15.36%). MS m/z (ESI) 624.5 (M+Na)$^+$.

Step 2: (2R,3S)-3-((R)-3-((R)-((1R,2R)-2-formylcy-clobutyl)(2-methoxyethoxy)methyl)cyclobut-2-en-1-yl)-N,N-bis(4-methoxybenzyl)butane-2-sulfonamide and (2R,3S)-3-((S)-3-((R)-((1R,2R)-2-formylcy-clobutyl)(2-methoxyethoxy)methyl)cyclobut-2-en-1-yl)-N,N-bis(4-methoxybenzyl)butane-2-sulfonamide

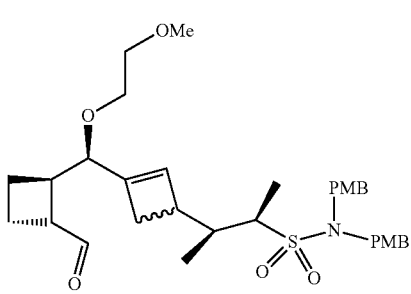

In a round-bottomed flask a mixture of (2R,3S)-3-((R)-3-((R)-((1R,2R)-2-(hydroxymethyl)cyclobutyl)(2-methoxyethoxy)methyl)cyclobut-2-en-1-yl)-N,N-bis(4-methoxybenzyl)butane-2-sulfonamide and (2R,3S)-3-((S)-3-((R)-((1R,2R)-2-(hydroxymethyl)cyclobutyl)(2-methoxyethoxy)methyl)cyclobut-2-en-1-yl)-N,N-bis(4-methoxybenzyl)butane-2-sulfonamide (65 mg, 0.108 mmol) was dissolved in DCM (5 mL). The mixture was cooled to 0° C. and DMP (68.7 mg, 0.162 mmol) was added. The mixture was stirred for 30 min. Saturated NaHCO₃ was added to the reaction mixture followed by extraction with ethyl acetate. The combined organic layers were dried over Na₂SO₄, filtered and concentrated to give the title compounds (50 mg, 77%) as a mixture. MS m/z (ESI) 622.5 (M+Na)⁺.

Step 3: tert-butyl (S)-5-(((1R,2R)-2-((R)—((R)-3-((2S,3R)-3-(N,N-bis(4-methoxybenzyl)sulfamoyl)butan-2-yl)cyclobut-1-en-1-yl)(2-methoxyethoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—((S)-3-((2S,3R)-3-(N,N-bis(4-methoxybenzyl)sulfamoyl)butan-2-yl)cyclobut-1-en-1-yl)(2-methoxyethoxy)methyl)cyclobutyl)methyl)-6'-chloro-3',4,4',5-tetrahydro-2H,2'H-spiro[benzo[b][1,4]oxazepine-3,1'-naphthalene]-7-carboxylate

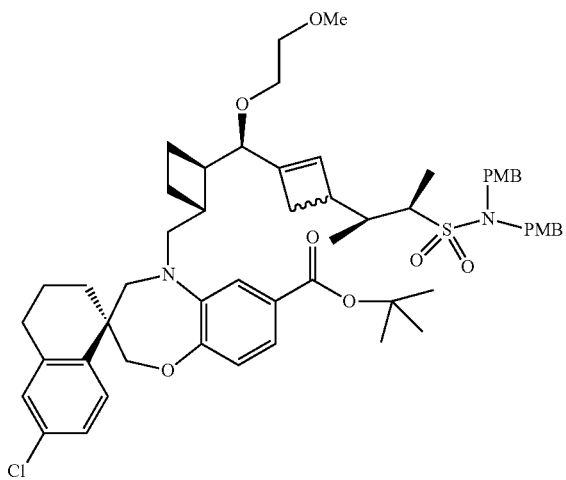

TFA (1 mL) was added to THF (3 mL) and the mixture was stirred for 5 min. tert-Butyl (S)-6'-chloro-3',4,4',5-tetrahydro-2H,2'H-spiro[benzo[b][1,4]oxazepine-3,1'-naphthalene]-7-carboxylate (33.3 mg, 0.083 mmol), a mixture of (2R,3S)-3-((R)-3-((R)-((1R,2R)-2-formylcyclobutyl)(2-methoxyethoxy)methyl)cyclobut-2-en-1-yl)-N,N-bis(4-methoxybenzyl)butane-2-sulfonamide and (2R,3S)-3-((S)-3-((R)-((1R,2R)-2-formylcyclobutyl)(2-methoxyethoxy)methyl)cyclobut-2-en-1-yl)-N,N-bis(4-methoxybenzyl)butane-2-sulfonamide (50 mg, 0.083 mmol) and phenylsilane (18.04 mg, 0.167 mmol) were added and the reaction mixture was stirred for 2 h. Saturated NaCl was added to the reaction mixture followed by extraction with ethyl acetate and washed with saturated NaHCO₃. The combined organic layers were dried over Na₂SO₄, filtered and concentrated. The residue was added to a silica gel column and eluted with ethyl acetate/hexane from 0 to 30% to give the title compounds as a mixture (80 mg, 98%). MS m/z (ESI) 984.0 (M+H)⁺.

Step 4: (S)-6'-chloro-5-(((1R,2R)-2-((R)-(2-methoxyethoxy)((R)-3-((2S,3R)-3-sulfamoylbutan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((R)-(2-methoxyethoxy)((S)-3-((2S,3R)-3-sulfamoylbutan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid

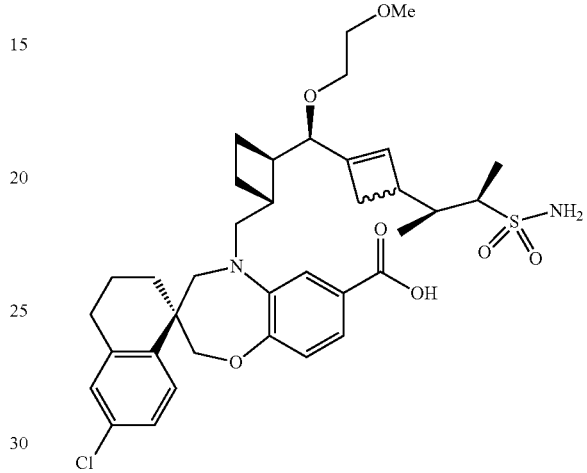

In a round-bottomed flask a mixture of tert-butyl (S)-5-(((1R,2R)-2-((R)—((R)-3-((2S,3R)-3-(N,N-bis(4-methoxybenzyl)sulfamoyl)butan-2-yl)cyclobut-1-en-1-yl)(2-methoxyethoxy)methyl)cyclobutyl)methyl)-6'-chloro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—((S)-3-((2S,3R)-3-(N,N-bis(4-methoxybenzyl)sulfamoyl)butan-2-yl)cyclobut-1-en-1-yl)(2-methoxyethoxy)methyl)cyclobutyl)methyl)-6'-chloro-3',4,4',5-tetrahydro-2H,2'H-spiro[benzo[b][1,4]oxazepine-3,1'-naphthalene]-7-carboxylat (80 mg, 0.081 mmol) was dissolved in DCM (5 mL)/TFA (5 mL). The mixture was stirred overnight. The solvent was removed in vacuo and the residue was added to a silica gel column and eluted with methanol/dichloromethane from 0 to 10% to give the title compounds as a mixture of two diastereomers (50 mg, 89%). MS m/z (ESI) 687.6 (M+H)⁺.

Step 5: Cpd. No. 16

In an argon flushed round-bottomed flask a mixture of (S)-6'-chloro-5-(((1R,2R)-2-((R)-(2-methoxyethoxy)((R)-3-((2S,3R)-3-sulfamoylbutan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((R)-(2-methoxyethoxy)((S)-3-((2S,3R)-3-sulfamoylbutan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid (50 mg, 0.073 mmol), N,N-dimethylpyridin-4-amine (44.4 mg, 0.364 mmol), and triethylamine (7.36 mg, 0.073 mmol) were dissolved in DCM (15 mL) under argon. The mixture was cooled to 0° C. and 2,4,6-tripropyl-1,3,5,2,4,6-trioxatriphosphinane 2,4,6-trioxide (69.4 mg, 0.218 mmol) was added and the mixture was stirred for 1 h. Saturated NaCl was added to the reaction mixture followed by extraction with ethyl acetate. The combined organic layers were dried over Na₂SO₄, filtered and concentrated. The residue was purified with preparative HPLC to give the title compounds (13.6 mg, 27.9%) as a mixture of stereoisomers. MS m/z (ESI) 669.6 (M+H)⁺.

Example 12

Synthesis of Cpd. No. 17 (Isomer 1) and Cpd. No. 17 (Isomer 2)

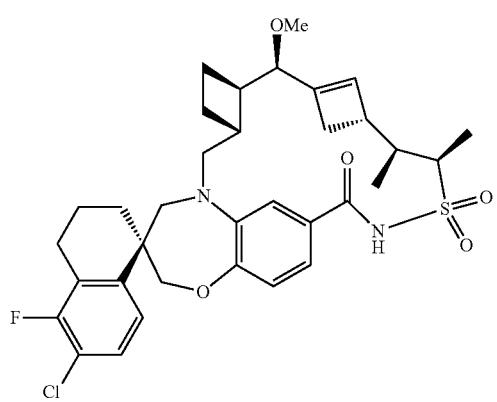

Cpd. No. 17 (isomer 1)

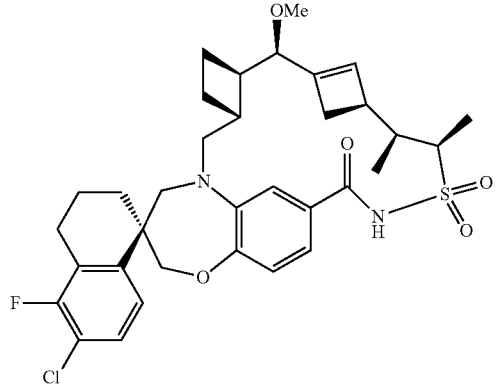

Cpd. No. 17 (isomer 2)

Step 1: (E)-4-(3-chloro-2-fluorophenyl)but-3-enoic acid

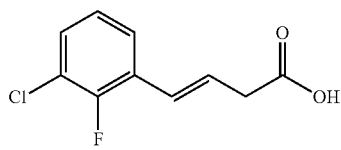 [SMILES: O=C(O)C/C=C/c1cccc(Cl)c1F]

In a argon flushed 1 L three-necked round-bottomed flask (2-carboxyethyl)triphenylphosphonium bromide (144 g, 347 mmol) was dissolved in THF (300 mL)/DMSO (300 mL) under argon. The mixture was cooled to −15° C. and 60% sodium hydride (29.0 g, 725 mmol) was added. The mixture was allowed to warm to room temperature and stirred for 30 min. The mixture was cooled to −10° C. and 3-chloro-2-fluorobenzaldehyde (50 g, 315 mmol) was added. The mixture was stirred for 30 min and then warmed to room temperature and stirred overnight. Water was added to quench the reaction. The mixture was extracted with ethyl acetate. Then conc. HCl was added to the reaction mixture to adjust pH to 3, followed by extraction with ethyl acetate.

The combined organic layers were dried over Na₂SO₄, filtered and concentrated. The residue was added to a Biotage column and eluted with MeOH/DCM from 0 to 0.5% to give the title compound (40 g, 59.1%) as a white solid. MS m/z (ESI) 215.1 (M+H)⁺. ¹H NMR (400 MHz, CDCl₃) δ 7.38 (td, J=7.1, 6.3, 1.6 Hz, 1H), 7.30 (d, J=8.2 Hz, 1H), 7.05 (td, J=7.9, 1.2 Hz, 1H), 6.68 (d, J=15.8 Hz, 1H), 6.43 (dt, J=15.8, 7.0 Hz, 1H), 3.37 (d, J=7.0 Hz, 2H).

Step 2: 4-(3-chloro-2-fluorophenyl)butanoic acid

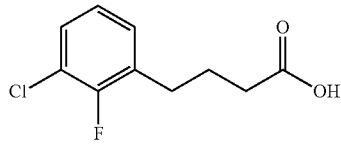 [SMILES: O=C(O)CCCc1cccc(Cl)c1F]

In a 250 mL round-bottomed flask (E)-4-(3-chloro-4-fluorophenyl)but-3-enoic acid (47 g, 219 mmol) and platinum (IV) oxide (1.492 g, 6.57 mmol) were added in ethyl acetate (100 mL). The reaction mixture was hydrogenated at room temperature for 16 h. The reaction mixture was filtered through a celite and the filter cake was rinsed with ethyl acetate. The filtrate was concentrated to give the title compound (47 g, 99%). MS m/z (ESI) 215.1 (M−H)⁻. ¹H NMR (400 MHz, CDCl₃) δ 7.26 (t, J=7.4 Hz, 1H), 7.09 (t, J=7.2 Hz, 1H), 7.01 (t, J=7.7 Hz, 1H), 2.75-2.72 (m, 2H), 2.41-2.35 (m, 2H), 1.98-1.94 (m, 2H).

Step 3: 6-chloro-5-fluoro-3,4-dihydronaphthalen-1(2H)-one

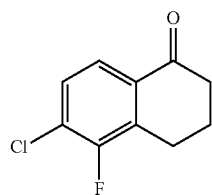 [SMILES: O=C1CCCc2c1ccc(Cl)c2F]

In a 100 mL round-bottomed flask 4-(3-chloro-4-fluorophenyl)butanoic acid (47 g, 217 mmol) was dissolved in TfOH (80 mL) under argon. The reaction mixture was stirred at 80° C. for 3 h. The reaction mixture was dropped into ice water followed by extraction with ethyl acetate (300 mL×2). The combined organic layers were dried over Na₂SO₄, filtered and concentrated. The residue was added to a silica gel column and eluted with ethyl acetate/hexane from 0% to 10% to give the title compound (31 g, 71.9%) as a brown solid. ¹H NMR (500 MHz, DMSO-d₆) δ 7.72 (d, J=8.4 Hz, 1H), 7.58 (t, J=7.7 Hz, 1H), 2.95 (t, J=5.9 Hz, 2H), 2.62 (t, J=6.1 Hz, 2H), 2.13-2.04 (m, 2H). MS m/z (ESI) 199.1 (M+H)⁺.

Step 4: (6-chloro-5-fluoro-1,2,3,4-tetrahydronaphthalene-1,1-diyl)dimethanol

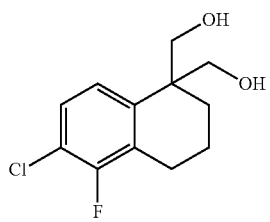 [SMILES: OCC1(CO)CCCc2c1ccc(Cl)c2F]

In a nitrogen flushed 100 mL two-necked round-bottomed flask sodium hydride (1.0 g, 24.95 mmol) was added in DMSO (30 mL) under nitrogen. The reaction mixture was cooled in a water bath at room temperature. Trimethylsulfoxonium iodide (5.92 g, 26.86 mmol) was added in one portion and the reaction mixture was stirred at room temperature for 30 min. 6-Chloro-5-fluoro-3,4-dihydronaphthalen-1(2H)-one (3.81 g, 19.23 mmol), as a solution in DMSO, was added and the reaction mixture was stirred at room temperature for 2 h. H$_2$O (10 mL) was added to the reaction mixture followed by extraction with dichloromethane (80 ml×3). The combined organic layers were washed with water (20 ml×3), dried over Na$_2$SO$_4$, filtered and concentrated. In a nitrogen flushed 100 mL two-necked round-bottomed flask the above crude product was dissolved in THF (60 mL) under nitrogen. The reaction mixture was cooled to −15° C. Boron trifluoride etherate (44.09 mg, 0.312 mmol) was added dropwise to the reaction mixture over 10 min and the mixture was stirred at −5° C. for 2 h. The reaction mixture was concentrated to provide an oil. In a nitrogen flushed 100 mL round-bottomed flask the above oil was dissolved in dioxane and the solution was cooled to 5° C. Formaldehyde (37% solution in H$_2$O, 3.316 g, 40.9 mmol) was added. Then KOH (45% solution in H$_2$O, 2.036 g, 16.36 mmol) was added dropwise to the reaction mixture over 10 min and the mixture was stirred at 45° C. for 2 h. The reaction mixture was cooled to room temperature. H$_2$O (10 mL) was added to the reaction mixture followed by extraction with dichloromethane. The combined organic layers were dried over Na$_2$SO$_4$, filtered and concentrated. The residue was added to a Biotage column and eluted with ethyl acetate/hexane from 0% to 35% to give the title compound (0.86 g) as an oil.

Step 5: tert-butyl 4-fluoro-3-nitrobenzoate

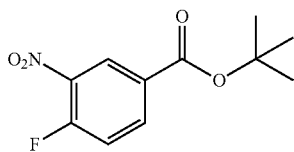 [SMILES: CC(C)(C)OC(=O)c1ccc(F)c([N+](=O)[O-])c1]

In a round-bottomed flask 4-fluoro-3-nitrobenzoic acid (10 g, 54.0 mmol) was added in t-BuOH (100 mL) under nitrogen. DMAP (1.320 g, 10.80 mmol) and (Boc)2O (23.58 g, 108 mmol) were added and the reaction mixture was stirred at 45° C. for 20 h. H$_2$O was added to the reaction mixture followed by extraction with ethyl acetate. The combined organic layers were dried over Na$_2$SO$_4$, filtered and concentrated. The residue was added to a silica gel column and eluted with ethyl acetate/hexane from 0 to 5% to give the title compound (10.1 g, 78%) as a white solid. $^1$H NMR (500 MHz, DMSO-d$_6$) δ 8.51 (dd, J=7.3, 2.1 Hz, 1H), 8.27 (ddd, J=8.8, 4.2, 2.1 Hz, 1H), 7.72 (dd, J=11.0, 8.8 Hz, 1H), 1.57 (s, 9H).

Step 6: tert-butyl 4-((6-chloro-5-fluoro-1-(hydroxymethyl)-1,2,3,4-tetrahydronaphthalen-1-yl)methoxy)-3-nitrobenzoate

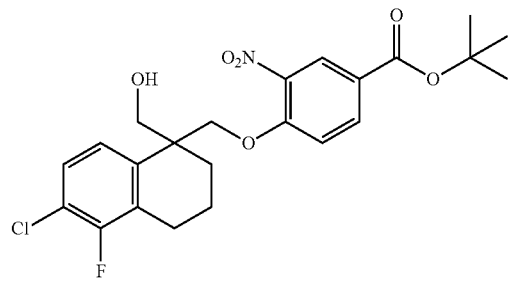 [SMILES: CC(C)(C)OC(=O)c1ccc(OCC2(CO)CCCc3c2ccc(Cl)c3F)c([N+](=O)[O-])c1]

In a 100 mL two-necked round-bottomed flask (6-chloro-5-fluoro-1,2,3,4-tetrahydronaphthalene-1,1-diyl)dimethanol (3.8 g, 15.53 mmol) was dissolved in DMF (40 mL) under nitrogen. The reaction mixture was cooled to −15° C. Potassium tert-butoxide (1.830 g, 16.31 mmol) was added and the reaction mixture was stirred for 30 min. tert-Butyl 4-fluoro-3-nitrobenzoate (4.50 g, 18.64 mmol) was added and the reaction mixture was stirred at 0° C. for 4 h. The reaction mixture was diluted with H$_2$O (50 mL). The reaction mixture was extracted with dichloromethane (50 ml×2). The organic layer was washed with saturated NaCl (30 mL×2), dried over Na$_2$SO$_4$, filtered through a glass fiber paper and concentrated. The residue was added to a silica gel column and eluted with ethyl acetate/Hexane (1/2, v/v) to give the title compound (2.05 g, 28.3%) as an oil. MS m/z (ESI) 488.2 (M+Na)$^+$.

Step 7: tert-butyl 4-((6-chloro-5-fluoro-1-formyl-1,2,3,4-tetrahydronaphthalen-1-yl)methoxy)-3-nitrobenzoate

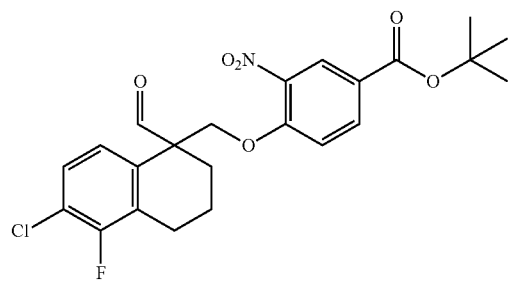 [SMILES: CC(C)(C)OC(=O)c1ccc(OCC2(C=O)CCCc3c2ccc(Cl)c3F)c([N+](=O)[O-])c1]

In a 100 mL two-necked round-bottomed flask tert-butyl 4-((6-chloro-5-fluoro-1-(hydroxymethyl)-1,2,3,4-tetrahydronaphthalen-1-yl)methoxy)-3-nitrobenzoate (2.2 g, 4.72 mmol) was dissolved in DCM (40 mL) under nitrogen. The reaction mixture was cooled to 0° C. in ice/water bath. DMP (4.01 g, 9.44 mmol) was added and the reaction mixture was stirred for 1 h. Solvent was removed under vacuum and the residue was added to a silica gel column and eluted with ethyl acetate/hexane (1/4, v/v) to give the title compound (1.8 g, 82%) as an oil. MS m/z (ESI) 486.1 (M+Na)⁺.

Step 8: tert-butyl (S)-6'-chloro-5'-fluoro-3',4,4',5-tetrahydro-2H,2'H-spiro[benzo[b][1,4]oxazepine-3,1'-naphthalene]-7-carboxylate Step 9: tert-butyl (S)-5-(((1R,2R)-2-((R)—((R)-3-((2S,3R)-3-(N,N-bis(4-methoxybenzyl)sulfamoyl)butan-2-yl)cyclobut-1-en-1-yl)(methoxy)methyl)cyclobutyl)methyl)-6'-chloro-5'-fluoro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—((S)-3-((2S,3R)-3-(N,N-bis(4-methoxybenzyl)sulfamoyl)butan-2-yl)cyclobut-1-en-1-yl)(methoxy)methyl)cyclobutyl)methyl)-6'-chloro-5'-fluoro-3',4,4',5-tetrahydro-2H,2'H-spiro[benzo[b][1,4]oxazepine-3,1'-naphthalene]-7-carboxylate

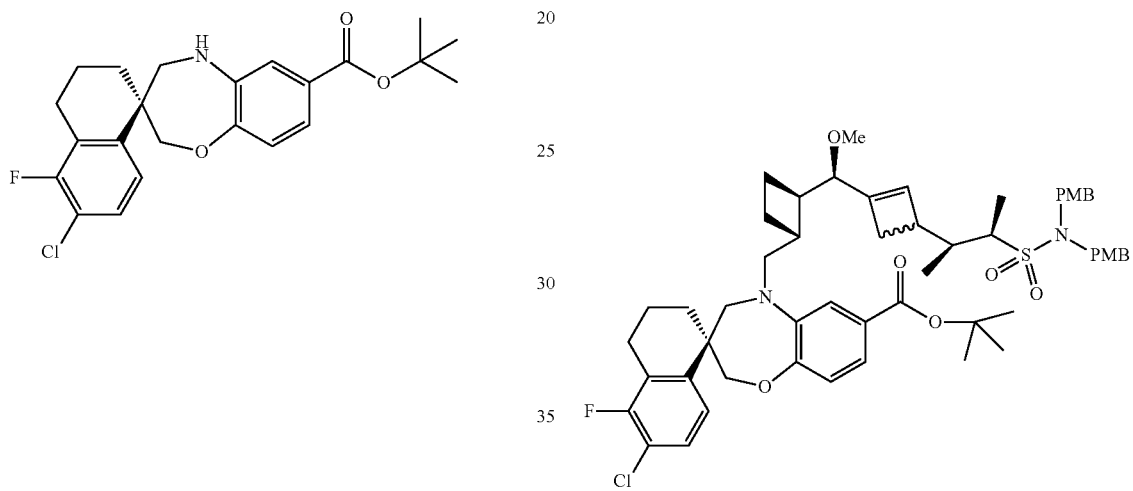

In a 250 mL round-bottomed flask tert-butyl 4-((6-chloro-5-fluoro-1-formyl-1,2,3,4-tetrahydronaphthalen-1-yl)methoxy)-3-nitrobenzoate (2.0 g, 4.31 mmol) was dissolved in acetic acid (40 mL). Iron powder (2.408 g, 43.1 mmol) was added to the reaction mixture in one portion. The reaction mixture was stirred at 75° C. for 3 h. The reaction mixture was cooled to 25° C., diluted with dichloromethane (100 mL), and filtered through a glass fiber paper. The filter cake was rinsed with dichloromethane (10 mL). The filtrate was concentrated and dissolved in THF (40 mL). Phenylsilane (4.67 g, 43.1 mmol) and TFA (2.458 g, 21.56 mmol) were added and the reaction mixture was stirred at 60° C. for 12 h and concentrated. The residue was added to a silica gel column and eluted with ethyl acetate/Hexane (1/10, v/v) to give the title compound (970 mg, 53.8%) as a racemic form. SFC chiral separation gave title compound in optically active form. ¹H NMR (500 MHz, DMSO-d₆) δ 7.69 (d, J=8.6 Hz, 1H), 7.46-7.39 (m, 1H), 7.32 (s, 1H), 7.14 (d, J=8.2 Hz, 1H), 6.85 (d, J=8.2 Hz, 1H), 6.06 (m, 1H), 4.16-4.04 (m, 2H), 3.30-3.18 (m, 2H), 2.80-2.58 (m, 2H), 1.89-1.78 (m, 2H), 1.78-1.67 (m, 1H), 1.60-1.53 (m, 1H), 1.51 (s, 9H).

In a round-bottomed flask tert-butyl (S)-6'-chloro-5'-fluoro-3',4,4',5-tetrahydro-2H,2'H-spiro[benzo[b][1,4]oxazepine-3,1'-naphthalene]-7-carboxylate (1.504 g, 3.60 mmol) and a mixture of (2R,3S)-3-((R)-3-((R)-((1R,2R)-2-formylcyclobutyl)(methoxy)methyl)cyclobut-2-en-1-yl)-N,N-bis(4-methoxybenzyl)butane-2-sulfonamide and (2R,3S)-3-((S)-3-((R)-((1R,2R)-2-formylcyclobutyl)(methoxy)methyl)cyclobut-2-en-1-yl)-N,N-bis(4-methoxybenzyl)butane-2-sulfonamide (2 g, 3.60 mmol) (from Example 23, Step 11) were dissolved in THF (12 mL)/TFA (4 mL). Phenylsilane (1.168 g, 10.80 mmol) was added. The mixture was stirred for 1 h. Saturated NaCl was added to the reaction mixture followed by extraction with ethyl acetate and washed with saturated NaHCO₃. The combined organic layers were dried over Na₂SO₄, filtered and concentrated to give the title compounds as a mixture (3.4 g, 99%). MS m/z (ESI) 958.9 (M+H)⁺.

Step 10: (S)-6'-chloro-5'-fluoro-5-(((1R,2R)-2-((R)-methoxy((R)-3-((2S,3R)-3-sulfamoylbutan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5'-fluoro-5-(((1R,2R)-2-((R)-methoxy((S)-3-((2S,3R)-3-sulfamoylbutan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid

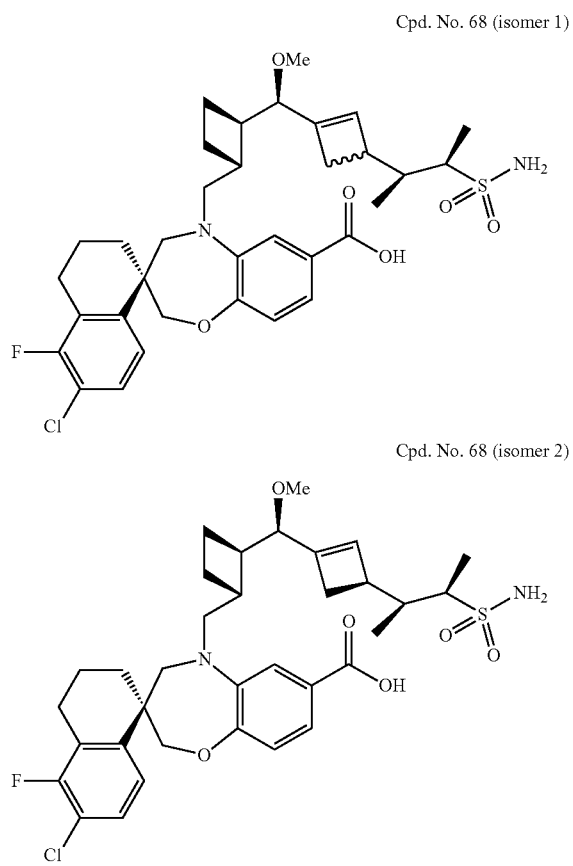

Cpd. No. 68 (isomer 1)

Cpd. No. 68 (isomer 2)

In a 100 mL round-bottomed flask a mixture of tert-butyl (S)-5-(((1R,2R)-2-((R)—(R)-342S,3R)-3-(N,N-bis(4-methoxybenzyl)sulfamoyl)butan-2-yl)cyclobut-1-en-1-yl)(methoxy)methyl)cyclobutyl)methyl)-6'-chloro-5'-fluoro-3',4,4',5-tetrahydro-2H,2'H-spiro[benzo[b][1,4]oxazepine-3,1'-naphthalene]-7-carboxylate and tert-butyl (S)-5-(((1R,2R)-2-((R)—((S)-3-((2S,3R)-3-(N,N-bis(4-methoxybenzyl)sulfamoyl)butan-2-yl)cyclobut-1-en-1-yl)(methoxy)methyl)cyclobutyl)methyl)-6'-chloro-5'-fluoro-3',4,4',5-tetrahydro-2H,2'H-spiro[benzo[b][1,4]oxazepine-3,1'-naphthalene]-7-carboxylate (0.185 g, 0.193 mmol) was dissolved in DCM (2.000 mL) and TFA (2 mL) under argon. The reaction mixture was stirred at room temperature for 16 h. The crude material was purified by reverse-phase preparative HPLC to give Cpd. 68 (isomer 1) (0.03 g, 23.49%) as a white solid as the first-eluting isomer. The stereochemistry of this isomer was determined by x-ray crystallography. MS m/z (ESI) 661.5 (M+H)$^+$. Cpd. No. 68 (isomer 2) (0.025 g, 19.57%) was obtained as the second-eluting isomer. MS m/z (ESI) 661.5 (M+H)$^+$.

Step 11: Cpd. No. 17 (Isomer 1) and Cpd. No. 17 (Isomer 2)

In a 100 mL round-bottomed flask (S)-6'-chloro-5'-fluoro-5-(((1R,2R)-2-((R)-methoxy((R)-3-((2S,3R)-3-sulfamoylbutan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid (0.030 g, 0.045 mmol), triethylamine (0.014 g, 0.136 mmol), and DMAP (5.54 mg, 0.045 mmol) were dissolved in DCM (20 ml) under argon. The reaction mixture was cooled to 0° C. with an ice/water bath. T$_3$P (0.043 g, 0.068 mmol) was added to the reaction mixture in one portion. The reaction mixture was stirred at 0° C. for 30 min. Saturated NaCl (20 mL) was added to the reaction mixture followed by extraction with ethyl acetate (20 mL×2). The combined organic layers were dried over Na$_2$SO$_4$, filtered and concentrated. The residue was purified by reverse-phase preparative HPLC. The same procedure was used starting with (S)-6'-chloro-5'-fluoro-5-(((1R,2R)-2-((R)-methoxy((S)-3-((2S,3R)-3-sulfamoylbutan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid.

Cpd. No. 17 (isomer 1) (8 mg, 27.4%) was obtained as a white solid. $^1$H NMR (500 MHz, DMSO-d$_6$) δ 11.73 (s, 1H), 7.51 (d, J=8.8 Hz, 1H), 7.48-7.42 (m, 1H), 6.94-6.88 (m, 2H), 6.73 (s, 1H), 6.27 (s, 1H), 4.12-4.01 (m, 2H), 3.97 (d, J=12.5 Hz, 1H), 3.80-3.72 (m, 1H), 3.68 (d, J=4.9 Hz, 1H), 3.63 (d, J=14.0 Hz, 1H), 3.38-3.34 (m, 1H), 3.09 (s, 3H), 3.05-2.95 (m, 1H), 2.91-2.83 (m, 1H), 2.75-2.66 (m, 1H), 2.63-2.53 (m, 3H), 2.46-2.38 (m, 1H), 2.13 (d, J=13.1 Hz, 1H), 2.02-1.94 (m, 1H), 1.93-1.86 (m, 2H), 1.77-1.62 (m, 5H), 1.44-1.35 (m, 1H), 1.33 (d, J=7.2 Hz, 3H), 0.92 (d, J=6.5 Hz, 3H).

Cpd. No. 17 (isomer 2). $^1$H NMR (500 MHz, DMSO-d6) δ 11.83 (s, 1H), 7.57-7.41 (m, 2H), 6.94-6.87 (m, 2H), 6.75 (s, 1H), 6.15 (s, 1H), 4.10 (d, J=12.4 Hz, 1H), 3.94 (d, J=12.4 Hz, 1H), 3.84-3.77 (m, 2H), 3.74-3.61 (m, 3H), 3.16 (s, 3H), 3.09-2.81 (m, 2H), 2.64-2.42 (m, 5H), 2.16 (d, J=13.2 Hz, 1H), 2.01-1.87 (m, 3H), 1.73-1.58 (m, 5H), 1.44-1.35 (m, 1H), 1.31 (d, J=7.2 Hz, 3H), 0.99 (d, J=6.7 Hz, 3H). MS m/z (ESI) 643.5 (M+H)$^+$.

Example 13

Synthesis of Cpd. No. 20 (Isomer 1)

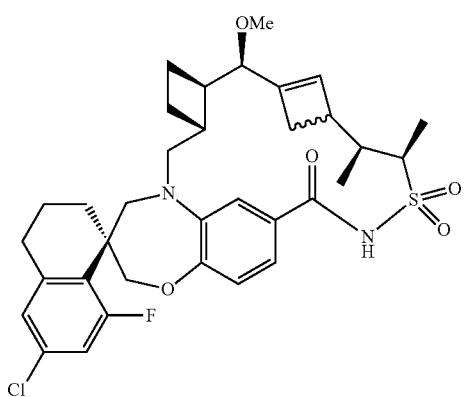 [SMILES: CO[C@H]1C2=CC(C2)[C@H](C)[C@@H](C)S(=O)(=O)NC(=O)c2ccc3c(c2)N(C[C@@H]2CC[C@H]21)C[C@@]1(CCCc2cc(Cl)cc(F)c21)CO3]

One of the diastereomers of Cpd. No. 20 was prepared from 3-chloro-5-fluorobenzaldehyde and (2-carboxyethyl)

triphenylphosphonium bromide, following a similar procedure described in Example 12, Steps 1 through 11. The stereochemistry of the asymmetric carbon atom of the cyclobutene ring has not been determined. $^1$H NMR (500 MHz, DMSO-d6) δ 11.70 (s, 1H), 7.22-7.15 (m, 1H), 7.11 (s, 1H), 6.87-6.80 (m, 2H), 6.70 (s, 1H), 6.22 (s, 1H), 4.30 (d, J=12.5 Hz, 1H), 4.17 (d, J=13.7 Hz, 1H), 4.03 (q, J=7.1 Hz, 1H), 3.94 (d, J=12.7 Hz, 1H), 3.74-3.66 (m, 1H), 3.64 (d, J=5.2 Hz, 1H), 3.18 (d, J=13.8 Hz, 1H), 3.07 (s, 3H), 3.06-2.97 (m, 1H), 2.87-2.67 (m, 3H), 2.65-2.53 (m, 2H), 2.45-2.35 (m, 1H), 2.17-2.12 (m, 2H), 1.90-1.56 (m, 8H), 1.32 (d, J=7.2 Hz, 3H), 0.93 (d, J=6.7 Hz, 3H).

Example 13

Synthesis of Cpd. No. 21 (Isomer 1)

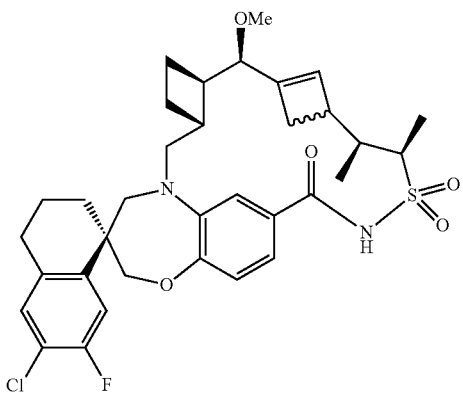 [SMILES: CO[C@H]1C2=CC(C2)[C@H](C)[C@@H](C)S(=O)(=O)NC(=O)c2ccc3c(c2)N(C[C@@H]2CC[C@H]21)C[C@@]1(CCCc2cc(Cl)c(F)cc21)CO3]

One of the diastereomers of Cpd. No. 21 was prepared from 3-chloro-4-fluorobenzaldehyde and (2-carboxyethyl)triphenylphosphonium bromide, following a similar procedure described in Example 12, Steps 1 through 11. The stereochemistry of the asymmetric carbon atom of the cyclobutene ring has not been determined. $^1$H NMR (500 MHz, DMSO-d6) δ 11.76 (s, 1H), 7.55 (d, J=11.3 Hz, 1H), 7.35 (d, J=7.8 Hz, 1H), 6.96-6.89 (m, 2H), 6.74 (s, 1H), 6.26 (s, 1H), 4.12-4.02 (m, 2H), 3.95 (d, J=12.3 Hz, 1H), 3.74 (d, J=13.4 Hz, 1H), 3.68 (d, J=5.1 Hz, 1H), 3.59 (d, J=14.1 Hz, 1H), 3.30 (d, J=14.1 Hz, 1H), 3.08 (s, 3H), 3.03-2.95 (m, 1H), 2.83-2.76 (m, 1H), 2.75-2.61 (m, 2H), 2.61-2.53 (m, 2H), 2.46-2.37 (m, 1H), 2.13 (d, J=13.2 Hz, 1H), 1.97-1.79 (m, 3H), 1.78-1.60 (m, 5H), 1.41-1.35 (m, 1H), 1.32 (d, J=7.2 Hz, 3H), 0.92 (d, J=6.7 Hz, 3H).

Example 14

Synthesis of Cpd. No. 19 (Isomer 1)

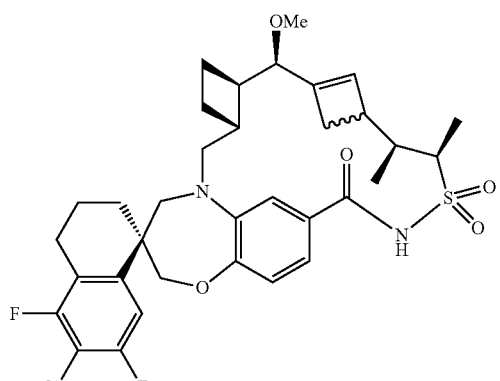

One of the diastereomers of Cpd. No. 19 was prepared from 3-chloro-2,4-difluorobenzaldehyde and (2-carboxyethyl)triphenylphosphonium bromide, following a similar procedure described in Example 12, Steps 1 through 11. The stereochemistry of the asymmetric carbon atom of the cyclobutene ring has not been determined. $^1$H NMR (500 MHz, DMSO-d$_6$) δ 11.75 (s, 1H), 7.48 (d, J=10.6 Hz, 1H), 6.95-6.88 (m, 2H), 6.74 (s, 1H), 6.26 (s, 1H), 4.14-4.02 (m, 2H), 3.95 (d, J=12.1 Hz, 1H), 3.74 (d, J=14.2 Hz, 1H), 3.68 (d, J=5.0 Hz, 1H), 3.61 (d, J=14.2 Hz, 1H), 3.36-3.25 (m, 1H), 3.08 (s, 3H), 3.02-2.93 (m, 1H), 2.87-2.76 (m, 1H), 2.75-2.66 (m, 1H), 2.61-2.52 (m, 3H), 2.44-2.37 (m, 1H), 2.12 (d, J=13.1 Hz, 1H), 1.98-1.83 (m, 3H), 1.77-1.61 (m, 5H), 1.45-1.36 (m, 1H), 1.32 (d, J=7.1 Hz, 3H), 0.92 (d, J=6.6 Hz, 3H). MS m/z (ESI) 661.5 (M+H)$^+$.

Example 15

Synthesis of Intermediate 1: tert-butyl (S)-6'-chloro-5'-fluoro-3',4,4',5-tetrahydro-2H,2'H-spiro[benzo[b][1,4]oxazepine-3,1'-naphthalene]-7-carboxylate

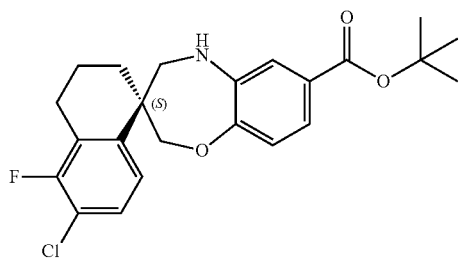

Step A: tert-butyl 4-hydroxy-3-nitrobenzoate

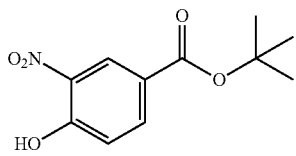

Under Ar, to a solution of 4-fluoro-3-nitrobenzoic acid (50 g, 270 mmol) and tert-butyl 2,2,2-trichloroacetimidate (177 g, 810 mmol) in dry THF (500 mL) was added boron trifluoride etherate (5.56 g, 39.2 mmol) under 20° C. The reaction mixture was stirred at 30° C. for 18 h. NaHCO$_3$ (15 g) was added and the reaction mixture was stirred for another 0.5 h. The mixture was concentrated and triturated with hexane:EtOAc=1:1. The filtrate was concentrated under reduced pressure and the residue was purified by flash chromatography eluted with hexane:EtOAc=20:1 to afford the title compound (48.2 g, 74%) as a yellow solid. $^1$H NMR (400 MHz, CDCl$_3$) δ 8.64 (m, 1H), 8.27 (m, 1H), 7.34 (m, 1H), 1.61 (s, 9H).

Step B: (E)-4-(3-chloro-2-fluorophenyl)but-3-enoic acid

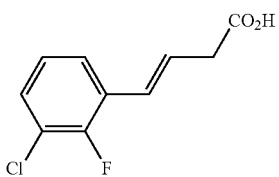

In an argon flushed 1 L three-necked round-bottomed flask, (2-carboxyethyl)triphenylphosphonium bromide (144 g, 347 mmol) was dissolved into a mixed solvent of dry THF (300 mL) and DMSO (300 mL) under argon. After cooling down to −15° C., NaH (29.0 g, 725 mmol, 60% wt in mineral oil) was added slowly. The mixture was allowed to warm up to room temperature and stirred for 30 min. At −10° C., 3-chloro-2-fluorobenzaldehyde (50 g, 315 mmol) was added slowly. The reaction mixture was stirred for 30 min and then allowed to warm up to room temperature overnight. Water was added to quench the reaction and conc. HCl was added to adjust pH to 3-4. The resulting mixture was extracted with ethyl acetate three times. The organic layers were combined, dried over Na$_2$SO$_4$, and concentrated under reduced pressure to give the crude product as a yellow oil, which was loaded onto silica gel column and eluted with MeOH and DCM from 0% to 0.5% to afford the title compound (40 g, 59%) as a white solid. $^1$H NMR (400 MHz, CDCl$_3$) δ 7.38 (dd, J=7.1, 1.6 Hz, 2H), 7.30 (d, J=8.2 Hz, 1H), 7.05 (dd, J=7.9, 1.2 Hz, 1H), 6.68 (d, J=15.8 Hz, 1H), 6.43 (dd, J=15.6, 7.0 Hz, 1H), 3.37 (d, J=7.0 Hz, 2H); MS: 215.1 (M+H$^+$).

Step C: 4-(3-chloro-2-fluorophenyl)butanoic acid

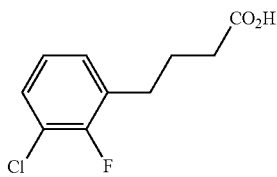

Under Ar, in a 250 mL round-bottomed flask, (E)-4-(3-chloro-4-fluorophenyl)but-3-enoic acid (Step B, 47 g, 219 mmol) was dissolved into ethyl acetate (100 mL) and PtO$_2$ (1.492 g, 6.57 mmol) was added. Then H$_2$ was introduced and the reaction mixture was stirred at room temperature overnight. After filtration, the filtrate was concentrated under reduced pressure to afford the title compound (47 g, 99%) as a light yellow solid. $^1$H NMR (400 MHz, CDCl$_3$) δ 7.26 (t, J=7.4 Hz, 1H), 7.09 (t, J=7.2 Hz, 1H), 7.01 (t, J=7.7 Hz, 1H), 2.75-2.72 (m, 2H), 2.41-2.35 (m, 2H), 1.98-1.94 1.96 (m, 2H). MS: 215.1 (M−H$^−$).

Step D: 6-Chloro-5-fluoro-3,4-dihydronaphthalen-1(2H)-one

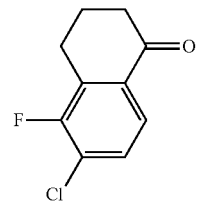 [SMILES: O=C1CCCc2c1ccc(Cl)c2F]

In a 100 mL round-bottomed flask, 4-(3-chloro-4-fluorophenyl)butanoic acid (Step C, 47 g, 217 mmol) was dissolved in TfOH (80 mL) under argon to give a black solution. The reaction mixture was stirred at 80° C. for 3 h. After cooling down to room temperature, the reaction mixture was poured into ice water and the resulting mixture was extracted with ethyl acetate twice. The organic layers were combined, dried over Na$_2$SO$_4$, and concentrated under reduced pressure to give the crude product as a dark oil, which was loaded onto silica gel column and eluted with ethyl acetate and hexane from 0% to 10% to afford the title compound (31 g, 72%) as a brown solid. $^1$H NMR (500 MHz, DMSO-d$_6$) δ 7.72 (d, J=8.4 Hz, 1H), 7.58 (t, J=7.7 Hz, 1H), 2.95 (t, J=5.9 Hz, 2H), 2.62 (t, J=6.1 Hz, 2H), 2.13-2.04 (m, 2H); MS: 199.1 (M+H$^+$).

Step E: (6-chloro-5-fluoro-1,2,3,4-tetrahydronaphthalene-1,1-diyl)dimethanol

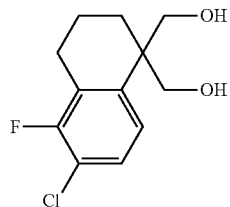 [SMILES: OCC1(CO)CCCc2c1ccc(Cl)c2F]

In a nitrogen flushed 100 mL two-necked round-bottomed flask, NaH (1.0 g, 24.95 mmol, 60% wt in mineral oil) was dissolved into dry DMSO (30 mL) under nitrogen to give a colorless suspension. Trimethylsulfoxonium iodide (5.92 g, 26.86 mmol) was added in one portion and the resulting mixture was stirred for 30 min at room temperature. A solution of 6-chloro-5-fluoro-3,4-dihydronaphthalen-1(2H)-one (Step D, 3.81 g, 19.23 mmol) in dry DMSO was added and the reaction mixture was stirred for 2 h at room temperature. H$_2$O (10 mL) was added to quench the reaction. The resulting mixture was extracted with DCM three times. The organic layers were combined, washed with water twice, dried over Na$_2$SO$_4$, and concentrated under reduced pressure to give the crude product (1.0 g) as a yellow oil, which was directly used without purification.

In a nitrogen flushed 100 mL two-necked round-bottomed flask, the above crude yellow oil (1.0 g) was dissolved into dry THF (60 mL) under nitrogen to give a solution. Boron trifluoride etherate (44.09 mg, 0.312 mmol) was added at −15 dropwise over 10 min, and the reaction mixture was stirred for 2 h at −5° C. After removal of volatiles under reduced pressure, the residue (1.0 g) was directly used without purification.

In a nitrogen flushed 100 mL round-bottomed flask, the above residue (1.0 g) was dissolved into dioxane to give a colorless solution. At 5° C., a formaldehyde (37% solution in H$_2$O, 3.32 g, 40.9 mmol) was added, then a KOH solution in water (2.04 g, 16.36 mmol) was added dropwise over 10 min. The reaction mixture was stirred for 2 h at 45° C. After cooling down to room temperature, H$_2$O (10 mL) was added and the resulting mixture was extracted with DCM twice. The organic layers were combined, dried over Na$_2$SO$_4$, and concentrated under reduced pressure to give the crude product as a yellow oil, which was loaded onto silica gel column and eluted with ethyl acetate and hexane from 0% to 35% to afford the title compound (0.86 g, 18% over 3 steps) as a light yellow oil. MS: 244.8 (M+H$^+$).

Step F: tert-butyl 4-((6-chloro-5-fluoro-1-(hydroxymethyl)-1,2,3,4-tetrahydronaphth al en-1-yl)methoxy)-3-nitrobenzoate

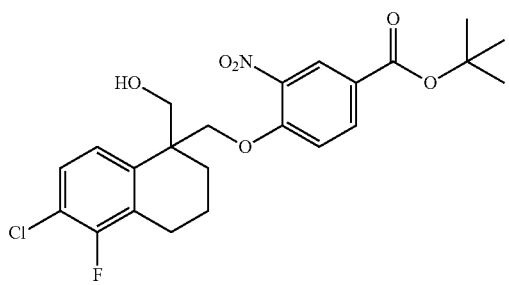 [SMILES: CC(C)(C)OC(=O)c1ccc(OCC2(CO)CCCc3c2ccc(Cl)c3F)c([N+](=O)[O-])c1]

Under Ar, a mixture of (6-chloro-5-fluoro-1,2,3,4-tetrahydronaphthalene-1,1-diyl)dimethanol (Step E, 29.0 g, 119 mmol), tert-butyl 4-fluoro-3-nitrobenzoate (Step A, 29.0 g, 120 mmol) and K$_2$CO$_3$ (34.4 g, 249 mmol) in dry DMF (290 mL) was stirred at 40° C. for 16 h. After cooling down to room temperature, the mixture was diluted with ethyl acetate ("EA"), and the resulting solution was washed with water and brine. The separated EA layer was dried over anhydrous Na$_2$SO$_4$ and concentrated under reduced pressure. The residue was purified by flash chromatography eluted with hexane/EA=4:1 to afford the title compound (24.8 g, 40%) as a yellow solid. MS: 488.2 (M+Na$^+$).

Step G: tert-butyl 4-((6-chloro-5-fluoro-1-formyl-1,2,3,4-tetrahydronaphthalen-1-yl)methoxy)-3-nitrobenzoate

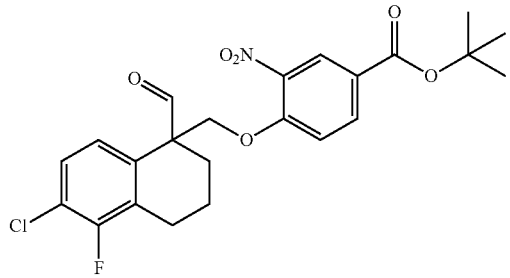

Under Ar, to a solution of tert-butyl 4-((6-chloro-5-fluoro-1-(hydroxymethyl)-1,2,3,4-tetrahydronaphthalen-1-yl)methoxy)-3-nitrobenzoate (Step F, 19.5 g, 41.9 mmol) in dry DCM (200 mL) was added DMP (26.6 g, 62.8 mmol) at 0-5° C. The reaction solution was stirred at room temperature for 2 h. Sat. Na$_2$S$_2$O$_3$ and aq. NaHCO$_3$ were added and the resulting mixture was stirred at room temperature for 1 h. The separated DCM layer was washed with brine, dried over anhydrous Na$_2$SO$_4$, and concentrated under reduced pressure. The residue was purified by flash chromatography eluted with hexane/EA=10:1 to afford the title compound (15.5 g, 80%) as a white solid. MS: 486.1 (M+Na$^+$).

Step H: tert-butyl 6'-chloro-5'-fluoro-3',4,4',5-tetrahydro-2H,2'H-spiro[benzo[b][1,4]oxazepine-3,1'-naphthalene]-7-carboxylate

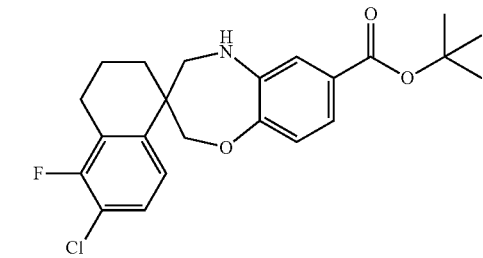 [SMILES: CC(C)(C)OC(=O)c1ccc2c(c1)NCC1(CCCc3c1ccc(Cl)c3F)CO2]

Under Ar, a mixture of tert-butyl 4-((6-chloro-5-fluoro-1-formyl-1,2,3,4-tetrahydronaphthalen-1-yl)methoxy)-3-nitrobenzoate (Step G, 15.5 g, 33.4 mmol) and Fe (18.7 g, 334 mmol) in AcOH (310 mL) was stirred at 80° C. for 2 h. After cooling down to room temperature, the mixture was filtered and the filtrate was concentrated under reduced pressure. The residue was re-taken into THF (310 mL), and phenylsilane (36.2 g, 334 mmol), trifluoromethanesulfonic acid (0.5 g, 3.34 mmol) and TFA (11.4 g, 100 mmol) were added subsequently. The reaction mixture was stirred at 50° C. under Ar for 2 h. After cooling down to room temperature, the reaction mixture was treated with aq. NaHCO$_3$ and extracted 3 times with EA. The EA layers were combined, washed with brine, dried over anhydrous Na$_2$SO$_4$ and concentrated under reduced pressure. The residue was then triturated with EA to afford the title compound (12.0 g, 86%)

as a white solid. $^1$H NMR (400 MHz, DMSO-d$_6$) δ 7.70 (d, J=8.8 Hz, 1H), 7.45-7.41 (m, 1H), 7.33 (d, J=2.0 Hz, 1H), 7.17-7.14 (m, 1H), 6.85 (d, J=8.4 Hz, 1H), 6.07 (m, 1H), 4.16-4.04 (m, 2H), 3.33-3.21 (m, 2H), 2.73-2.65 (m, 2H), 1.84-1.80 (m, 2H), 1.60-1.53 (m, 2H), 1.51 (s, 9H); MS: 419.3 (M+H$^+$).

Step I: tert-butyl (S)-6'-chloro-5'-fluoro-3',4,4',5-tetrahydro-2H,2'H-spiro[benzo[b][1,4]oxazepine-3,1'-naphthalene]-7-carboxylate (Intermediate 1)

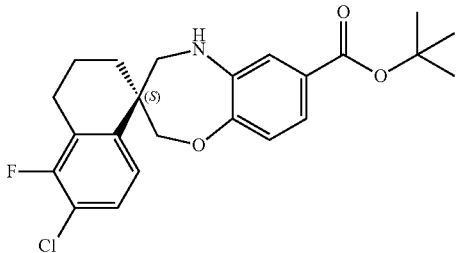

tert-butyl 6'-chloro-5'-fluoro-3',4,4',5-tetrahydro-2H,2'H-spiro[benzo[b][1,4]oxazepine-3,1'-naphthalene]-7-carboxylate (Step H, 160.9 g) was subjected to chiral SFC resolution with a CHIRALPAK IG column to provide the title compound (74.5 g, 98% ee) as a white solid. MS: 418.1 (M+H$^+$).

Example 16

Synthesis of Intermediate 2: tert-butyl (S)-6'-chloro-3',4,4',5-tetrahydro-2H,2'H-spiro[benzo[b][1,4]oxazepine-3,1'-naphthalene]-7-carboxylate

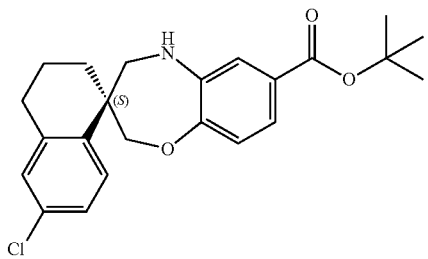

Essentially the same protocol described for the preparation of Intermediate 1 was used to prepare Intermediate 2 (20 g, 98% ee) as a white solid.

Example 17

Synthesis of Intermediate 3: (1R,2R)-2-(((tert-butyldiphenylsilyl)oxy)methyl) cyclobutane-1-carbaldehyde

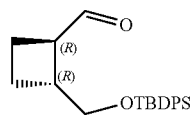

Step A: trans-Cyclobutane-1,2-dicarboxylic acid

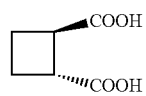

In a dried 1 L round-bottomed flask, equipped with an efficient condenser topped with an oil bubbler, cis/trans cyclobutane-1,2-dicarboxylic acid (180 g, 1.25 mol) was dissolved into 12 N HCl (360 mL) to give a brown solution. The solution was stirred at 120° C. for 160 h. After cooling down to room temperature, the formed precipitate was collected by filtration, washed with ice-cold 12 N HCl (50 mL), and dried in vacuo overnight to afford the title compound (103 g, 57%) as a white solid. $^1$H NMR (400 MHz, D$_2$O) δ 3.20-3.40 (m, 2H), 1.95-2.00 (m, 4H). $^{13}$C NMR (400 MHz, D$_2$O) δ 177.96, 40.54, 21.35.

Step B: trans-(Cyclobutane-1,2-diyl)dimethanol

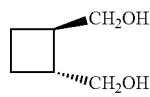

Under N$_2$, in a dried 1 L two necked round-bottomed flask, LiAlH$_4$ (23.72 g, 625 mmol) was dissolved into dry THF (500 mL) to give a gray suspension. A solution of trans-1,2-cyclobutanedicarboxylic acid (Step A, 30 g, 208 mmol) in THF (250 mL) was added dropwise over 50 min below 25° C. The reaction mixture was stirred for overnight at room temperature. H$_2$O (24 mL) was cautiously added to quench the reaction, followed by a 15% NaOH solution (24 mL) and H$_2$O (84 mL). The resulting mixture was stirred for 1 h. After filtration and removal of volatiles under reduced pressure, the residue was purified by silica gel column (hexane:EA, 1:9) to afford the title compound (21.8 g, 90%) as a yellow oil. $^1$H NMR (400 MHz, CDCl$_3$) δ 3.71-3.62 (m, 2H), 3.45-3.34 (m, 2H), 2.96 (s, 2H), 2.22 (m, 2H), 1.96-1.82 (m, 2H), 1.70-1.52 (m, 2H).

Step C: Trans-2-(hydroxymethyl)cyclobutylmethyl benzoate

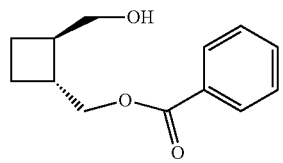 [SMILES: O=C(OC[C@@H]1CC[C@H]1CO)c1ccccc1]

Under N$_2$, in a 250 mL three-necked round-bottomed flask, trans-(cyclobutane-1,2-diyl)dimethanol (Step B, 27 g, 232 mmol) and dichlorodimethylstannane (5.11 g, 23.24 mmol) were dissolved into dry THF (100 mL) under nitrogen to give a yellow solution. K$_2$CO$_3$ (64.2 g, 465 mmol) and BzCl (39.2 g, 279 mmol) were added, and the reaction mixture was stirred at room temperature for 12 h. After filtration and removal of volatiles under reduced pressure, the residue was purified by silica gel column (hexane:EA, 1:1) to afford the title compound (19.54 g, 65%) as a colorless oil. $^1$H NMR (400 MHz, CDCl$_3$) δ 8.08-8.00 (m, 2H), 7.61-7.51 (m, 1H), 7.49-7.39 (m, 2H), 4.39 (dd, J=11.1, 5.6 Hz, 1H), 4.27 (dd, J=11.1, 7.1 Hz, 1H), 3.64 (dd, J=6.9, 3.2 Hz, 2H), 2.60-2.46 (m, 1H), 2.48-2.33 (m, 1H), 2.10-1.94 (m, 2H), 1.76 (m, 2H).

Step D: ((1R,2R)-2-(Hydroxymethyl)cyclobutyl)methyl benzoate

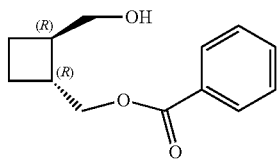

trans-2-(Hydroxymethyl)cyclobutylmethyl benzoate (Step C, 143.4 g) was subjected to chiral SFC resolution with Lux® 5 μm Amylose-1 column to provide the title compound (56.2 g, 98% ee) as a light yellow oil. $^1$H NMR (400 MHz, CDCl$_3$) δ 8.08-8.00 (m, 2H), 7.61-7.51 (m, 1H), 7.49-7.39 (m, 2H), 4.39 (dd, J=11.1, 5.6 Hz, 1H), 4.27 (dd, J=11.1, 7.1 Hz, 1H), 3.64 (dd, J=6.9, 3.2 Hz, 2H), 2.60-2.46 (m, 1H), 2.48-2.33 (m, 1H), 2.10-1.94 (m, 2H), 1.76 (m, 2H); MS: 221.2 (M+H$^+$).

Step E: ((1R,2R)-2-(((tert-butyldiphenylsilyl)oxy)methyl)cyclobutyl)methanol

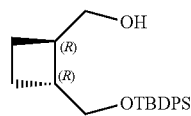

In a round-bottomed flask ((1R,2R)-2-(hydroxymethyl)cyclobutyl)methyl benzoate (Step D, 2 g, 9.1 mmol), imidazole (0.93 g, 13.6 mmol), and TBDPS-Cl (3.0 g, 10.9 mmol) were dissolved into dry DMF (10 mL) under Ar, and then the reaction mixture was stirred for overnight. Sat. NaCl was added to quench the reaction and the mixture was extracted with ethyl acetate twice. The organic layers were combined, dried over Na$_2$SO$_4$, and concentrated under reduced pressure to give a yellow oil, which was directly used for the next step without purification.

The above yellow oil was dissolved into MeOH (20 mL), K$_2$CO$_3$ (6.27 g, 45.4 mmol) was added. The reaction mixture was heated to 35° C. for 3 h. After cooling down to room temperature, sat. NaCl was added and the resulting mixture was extracted with ethyl acetate twice. The organic layers were combined, dried over Na$_2$SO$_4$, and concentrated under reduced pressure to give a yellow oil, which was loaded onto a silica gel column and eluted with ethyl acetate/hexane from 0% to 50% to afford the title compound (3.4 g, quantitatively over 2 steps) as a light yellow oil. MS: 355.4 (M+H$^+$).

Step F: (1R,2R)-2-(((tert-butyldiphenylsilyl)oxy)methyl)cyclobutane-1-carbaldehyde (Intermediate 3)

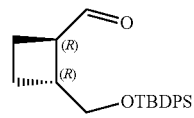

In a round-bottomed flask at −78° C., oxalyl chloride (2.0 M in DCM, 24 mL, 46.5 mmol) was mixed with dry DCM (10 mL). A solution of DMSO (7.27 g, 93 mmol) in dry DCM (10 mL) was added slowly and the mixture was stirred for 30 min. Another solution of ((1R,2R)-2-(((tert-butyldiphenylsilyl)oxy)methyl)cyclobutyl)methanol (Step E, 11 g, 31 mmol) in dry DCM (20 mL) was added slowly and the mixture was stirred for another 1 h. Dry Et$_3$N (12.6 g, 124 mmol) was added slowly. The reaction mixture allowed to warm up to room temperature and stirred for 30 min. Brine was added to quench the reaction and the resulting mixture was extracted with DCM twice. The organic layers were combined, dried over Na$_2$SO$_4$, and concentrated under reduced pressure. The residue was loaded onto a silica gel column and eluted with ethyl acetate/hexane from 0% to 10% to afford the title compound (9.4 g, 86%) as a light yellow oil. MS: 353.4 (M+H$^+$).

Example 18

Synthesis of Intermediate 4: methyl (S)-6-chloro-5-fluoro-5'-(((1R,2R)-2-(hydroxymethyl)cyclobutyl)methyl)-3,4,4',5'-tetrahydro-2H,2'H-spiro[naphthalene-1,3'-pyrido[3,2-b][1,4]oxazepine]-7'-carboxylate

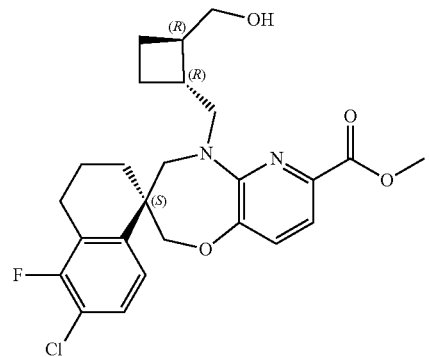

Step A: (6-chloro-5-fluoro-1-(hydroxymethyl)-1,2,3,4-tetrahydronaphthalen-1-yl)methyl benzoate

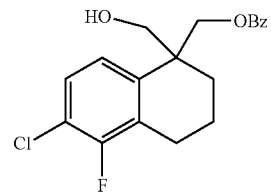

In a nitrogen flushed 100 mL two-necked round-bottomed flask, (6-chloro-5-fluoro-1,2,3,4-tetrahydronaphthalene-1,1-diyl)dimethanol (Step E of Intermediate 1, 5.96 g, 24.4 mmol), dichlorodimethylstannane (6.42 g, 29.2 mmol), and K$_2$CO$_3$ (6.73 g, 48.7 mmol) were dissolved into dry THF (30 mL) under nitrogen to give a white suspension. Benzoyl chloride (1.712 g, 12.2 mmol) was added to the reaction mixture at 0° C. and the reaction mixture was stirred overnight at room temperature. After filtration through a Buchner funnel, the filtrate was concentrated under reduced pressure. The residue was loaded onto a Biotage column and eluted with ethyl acetate/hexane from 0%-45% to afford the title compound (5.43 g, 64%) as a yellow oil. $^1$H NMR (400 MHz, CDCl$_3$) δ 8.07-7.99 (m, 2H), 7.66-7.57 (m, 1H), 7.49 (t, J=7.8 Hz, 2H), 7.35-7.19 (m, 2H), 4.52 (d, J=3.8 Hz, 2H), 3.80 (d, J=3.9 Hz, 2H), 2.86-2.74 (m, 2H), 2.00-1.87 (m, 4H); MS: 349.0 (M+H$^+$).

Step B: (6-chloro-5-fluoro-1-formyl-1,2,3,4-tetrahydronaphthalen-1-yl)methyl benzoate

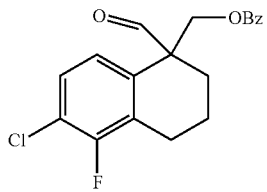

In a nitrogen flushed 25 mL two-necked round-bottomed flask, (6-chloro-5-fluoro-1-(hydroxymethyl)-1,2,3,4-tetrahydronaphthalen-1-yl)methyl benzoate (Step A, 4.23 g, 12.1 mmol) was dissolved into dry DCM (40 mL) under nitrogen to give a colorless solution, DMP (6.17 g, 14.6 mmol) was added into the reaction mixture at 0° C., and the reaction mixture was stirred for 1 h at room temperature. Sat. NaHCO$_3$ (10 mL) and sat. Na$_2$S$_2$O$_3$ (10 mL) were added to quench the reaction. The mixture was extracted with dichloromethane (3×20 mL). The organic layers were combined, dried over Na$_2$SO$_4$, and concentrated under reduced pressure. The residue was loaded onto a Biotage column and eluted with ethyl acetate/hexane from 0%-20% to afford the title compound (2.22 g, 53%) as a white solid. $^1$H NMR (400 MHz, CDCl$_3$) δ 9.64 (s, 1H), 8.01-7.94 (m, 2H), 7.64-7.55 (m, 1H), 7.46 (t, J=7.8 Hz, 2H), 7.29 (m, 1H), 7.02 (dd, J=8.5, 1.4 Hz, 1H), 4.77 (d, J=11.4 Hz, 1H), 4.59 (d, J=11.4 Hz, 1H), 2.85 (m, 2H), 2.23 (t, J=14.1 Hz, 1H), 2.11-2.00 (m, 1H), 1.96 (m, 2H); MS: 346.9 (M+H$^+$).

Step C: (E)-(6-chloro-5-fluoro-1-((hydroxyimino)methyl)-1,2,3,4-tetrahydronaphth al en-1-yl)methyl benzoate

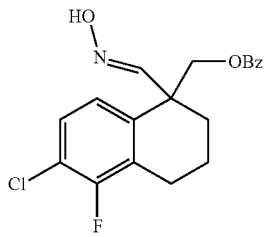

In a nitrogen flushed 25 mL round-bottomed flask, (6-chloro-5-fluoro-1-formyl-1,2,3,4-tetrahydronaphthalen-1-yl)methyl benzoate (Step B, 2.20 g, 6.3 mmol) was dissolved into dry MeOH (5 mL) under nitrogen to give a colorless solution, and sodium acetate (2.60 g, 31.7 mmol) and hydroxylamine hydrochloride (2.20 g, 31.7 mmol) were added. The reaction mixture was stirred at 50° C. for 2 h. After cooling down to room temperature, H$_2$O was added and the resulting mixture was extracted with dichloromethane (3×30 mL). The organic layers were combined, dried over Na$_2$SO$_4$, and concentrated under reduced pressure to afford the crude title compound (2.34 g) as a white solid, which was directly used for next step without purification. $^1$H NMR (400 MHz, CDCl$_3$) δ 8.01-7.94 (m, 2H), 7.62-7.56 (m, 1H), 7.54 (s, 1H), 7.46 (t, J=7.6 Hz, 2H), 7.24 (t, J=8.0 Hz, 1H), 7.09 (dd, J=8.5, 1.3 Hz, 1H), 4.66 (d, J=11.3 Hz, 1H), 4.58 (d, J=11.3 Hz, 1H), 2.82 (m, 2H), 2.17-2.03 (m, 2H), 2.03-1.84 (m, 2H); MS: 362.0 (M+H$^+$).

Step D: (1-(aminomethyl)-6-chloro-5-fluoro-1,2,3,4-tetrahydronaphthalen-1-yl)methanol

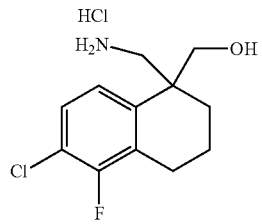 [SMILES: Cl ; NCC1(CO)CCCc2c1ccc(Cl)c2F]

In a nitrogen flushed 25 mL two-necked round-bottomed flask, (E)-(6-chloro-5-fluoro-1-((hydroxyimino)methyl)-1,2,3,4-tetrahydronaphthalen-1-yl)methyl benzoate (4.39 g, 12.13 mmol) was dissolved into dry THF (35 mL) under nitrogen to give a colorless solution, and the reaction mixture was cooled down to 0° C. with an ice/water bath. LiAlH$_4$ in THF (1M, 48.5 mL, 48.5 mmol) was added into the reaction mixture dropwise over 15 min, and the reaction mixture was stirred for 2 h at room temperature. At 0° C., H$_2$O (1.85 mL) was added slowly, followed by 15% aq. NaOH solution (1.85 mL) and H$_2$O (5.55 mL). The mixture was stirred for 10 min at room temperature and then filtered off through a Buchner funnel. The filter cake was rinsed with ethyl acetate (3×30 mL). The combined filtrate was concentrated under reduced pressure and the residue was re-taken into DCM (30 mL). At 0° C., a solution of HCl (4 M in iPrOH, 3.5 mL) was added dropwise and the resulting mixture was stirred for another 20 min. The formed precipitate was collected by filtration, washed with ice-cold DCM (10 mL) and dried in vacuo to afford the title compound (2.34 g, 79%) as a white solid. $^1$H NMR (400 MHz, CD$_3$OD) δ 7.38-7.29 (m, 1H), 7.25 (dd, J=8.6, 1.3 Hz, 1H), 3.81 (dd, J=11.0, 1.1 Hz, 1H), 3.70 (d, J=11.0, 1.1 Hz, 1H), 3.48 (d, J=13.2 Hz, 1H), 3.25 (d, J=13.2 Hz, 1H), 2.94-2.83 (m, 1H), 2.79-2.66 (m, 1H), 2.12 (m, 1H), 1.99-1.82 (m, 1H), 1.89 (m, 1H), 1.77 (m, 1H); MS: 243.9 (M+H$^+$).

Step E: 5-((1-(aminomethyl)-6-chloro-5-fluoro-1,2,3,4-tetrahydronaphthalen-1-yl)methoxy)-6-bromopicolinic acid

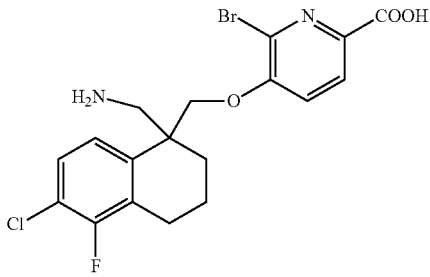 [SMILES: NCC1(COc2ccc(C(=O)O)nc2Br)CCCc2c1ccc(Cl)c2F]

In a nitrogen flushed 25 mL two-necked round-bottomed flask, (1-(aminomethyl)-6-chloro-5-fluoro-1,2,3,4-tetrahydronaphthalen-1-yl)methanol hydrochloride (Step D, 3.11 g, 12.76 mmol) was dissolved into DMSO (40 mL) to give a colorless solution. 6-bromo-5-fluoropicolinic acid (3.37 g, 15.31 mmol) was added followed by KOtBu (5.01 g, 44.7 mmol). The reaction mixture was stirred for 3 h at room temperature, and then adjusted to pH=6~7 with AcOH. Water (20 mL) was poured into the mixture, and the resulting mixture was filtered off through a Buchner funnel. The collected filter cake was rinsed with H$_2$O (50 mL), dried in vacuo to afford the crude title compound (4.72 g) as a brown solid, which was directly used for the next step without purification. MS: 442.9 (M+H$^+$).

Step F: Methyl 5-((1-(aminomethyl)-6-chloro-5-fluoro-1,2,3,4-tetrahydronaphthalen-1-yl)methoxy)-6-bromopicolinate

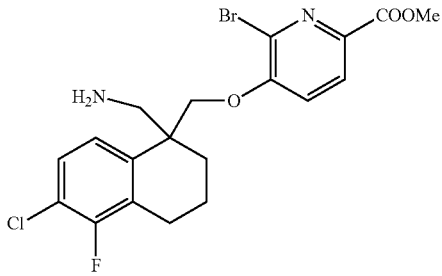 [SMILES: COC(=O)c1ccc(OCC2(CN)CCCc3c2ccc(Cl)c3F)c(Br)n1]

In a nitrogen flushed 25 mL round-bottomed flask, 5-((1-(aminomethyl)-6-chloro-5-fluoro-1,2,3,4-tetrahydronaphthalen-1-yl)methoxy)-6-bromopicolinic acid (Step E, 4.72 g, 10.64 mmol) was dissolved in MeOH (30 mL) and conc. H$_2$SO$_4$ (1 mL) was added under nitrogen to give a brown solution. The reaction mixture was stirred at 80° C. for 3 h. After cooling down to room temperature, aq. K$_2$CO$_3$ was slowly added and the resulting mixture was extracted with ethyl acetate (3×20 mL). The organic layers were combined, dried over Na$_2$SO$_4$, and concentrated under reduced pressure. The residue was loaded onto a Biotage column and eluted with methanol/dichloromethane from 0% to 10% to afford the title compound (4.96 g, quantitatively over 2 steps) as a yellow solid. $^1$H NMR (400 MHz, CDCl$_3$) δ 8.07 (dd, J=8.6, 3.8 Hz, 1H), 7.36 (m, 1H), 7.28-7.21 (m, 1H), 7.17 (dd, J=8.3, 4.0 Hz, 1H), 4.14 (dd, J=8.3, 5.7 Hz, 2H), 3.98 (s, 3H), 3.21 (d, J=4.1 Hz, 2H), 2.92-2.70 (m, 2H), 2.04-1.88 (m, 2H), 1.37-1.20 (m, 2H); MS: 457.0 (M+H$^+$).

Step G: ((1R,2R)-2-formylcyclobutyl)methyl benzoate

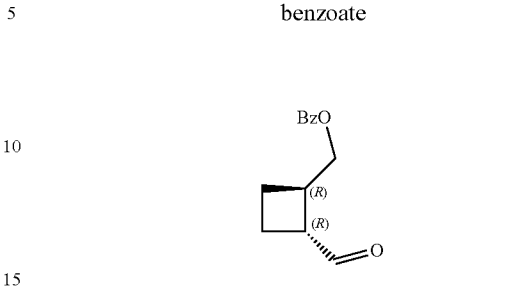

Under Ar, to a solution of ((1R,2R)-2-(hydroxymethyl)cyclobutyl)methyl benzoate (Step D of Intermediate 3, 9 g, 40.9 mmol) in dry CH$_2$Cl$_2$ (200 mL) at 0-10° C. was added PCC (17.61 g, 82 mmol) in small portions. The reaction was stirred at 0° C. for 2 h. The solid was removed and the filtrate was concentrated to afford the title compound (8.2 g, 92%) as a colorless oil that was directly used without purification MS: 218.8 (M+H$^+$); 241.2 (M+Na$^+$).

Step H: Methyl 5-((1-(((((1R,2R)-2-((benzoyloxy)methyl)cyclobutyl)methyl)amino)methyl)-6-chloro-5-fluoro-1,2,3,4-tetrahydronaphth al en-1-yl)methoxy)-6-bromopicolinate

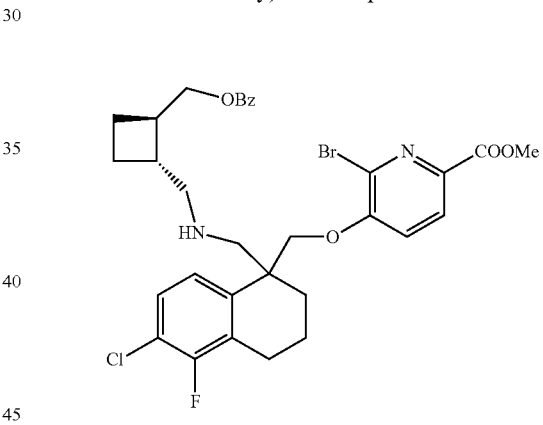

In a nitrogen flushed 25 mL round-bottomed flask, methyl 5-((1-(aminomethyl)-6-chloro-5-fluoro-1,2,3,4-tetrahydronaphthalen-1-yl)methoxy)-6-bromopicolinate (Step F, 2.4 g, 5.24 mmol) and ((1R,2R)-2-formylcyclobutyl)methyl benzoate (Step G, 2.29 g, 10.5 mmol) were dissolved into dry DCM (30 mL) under nitrogen to give a colorless solution. NaBH$_3$CN (0.66 g, 10.5 mmol) was added into the reaction mixture in one portion, and the reaction mixture was stirred at room temperature for 2 h. Sat. NaHCO$_3$ (20 mL) was added to the reaction mixture and the resulting mixture was extracted with ethyl acetate (3×30 mL). The organic layers were combined, dried over Na$_2$SO$_4$, and concentrated under reduced pressure. The residue was loaded onto a Biotage column and eluted with methanol/dichloromethane from 0% to 5% to afford give the title compound (3.16 g, 91%) as a yellow oil. $^1$H NMR (400 MHz, CDCl$_3$) δ 8.11-7.96 (m, 3H), 7.62-7.53 (m, 1H), 7.50-7.27 (m, 3H), 7.25-7.13 (m, 2H), 4.40-4.20 (m, 2H), 4.22-4.05 (m, 2H), 3.97 (s, 3H), 3.23-2.98 (m, 2H), 2.79 (m, 3H), 2.37 (q, J=7.1 Hz, 2H), 2.13-1.67 (m, 6H), 1.67-1.47 (m, 1H), 1.28 (t, J=7.1 Hz, 2H); MS: 659.1 (M+H$^+$).

Step I: Methyl 5'-(((1R,2R)-2-((benzoyloxy)methyl)cyclobutyl)methyl)-6-chloro-5-fluoro-3,4,4',5'-tetrahydro-2H,2'H-spiro[naphthalene-1,3'-pyrido[3,2-b][1,4]oxazepine]-7'-carboxylate

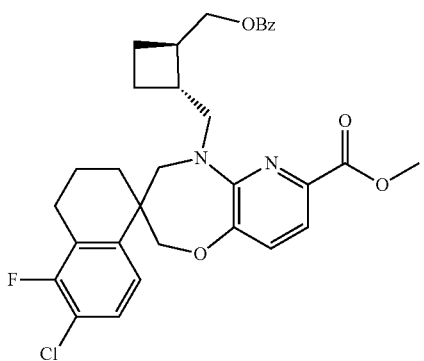

In a nitrogen flushed 25 mL round-bottomed flask, methyl 5-((1-(((((1R,2R)-2-((benzoyloxy)methyl)cyclobutyl)methyl)amino)methyl)-6-chloro-5-fluoro-1,2,3,4-tetrahydronaphthalen-1-yl)methoxy)-6-bromopicolinate (Step H, 310 mg, 0.47 mmol) was dissolved into NMP (5 mL) under nitrogen to give a colorless solution. N-ethyl-N-isopropylpropan-2-amine (911 mg, 7.05 mmol) was added into the reaction mixture. The reaction mixture was stirred at 130° C. for 50 h. After cooling down to room temperature, H₂O (15 mL) was added and the resulting mixture was extracted with ethyl acetate (3×20 mL). The organic layers were combined, dried over Na₂SO₄, and concentrated under reduced pressure. The residue was loaded onto a Biotage column and eluted with ethyl acetate/hexane from 0%-25% to afford the title compound (110 mg, 40%) as a light yellow oil. MS: 579.2 (M+H⁺).

Step J: Methyl 6-chloro-5-fluoro-5'-(((1R,2R)-2-(hydroxymethyl)cyclobutyl)methyl)-3,4,4',5'-tetrahydro-2H,2'H-spiro[naphthalene-1,3'-pyrido[3,2-b][1,4]oxazepine]-7'-carboxylate

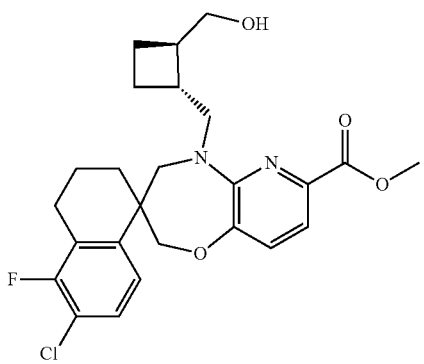

In a nitrogen flushed 25 mL round-bottomed flask, methyl 5'-(((1R,2R)-2-((benzoyloxy)methyl)cyclobutyl)methyl)-6-chloro-5-fluoro-3,4,4',5'-tetrahydro-2H,2'H-spiro[naphthalene-1,3'-pyrido[3,2-b][1,4]oxazepine]-7'-carboxylate (Step I, 860 mg, 1.49 mmol) was dissolved into MeOH (5 mL) under nitrogen to give a colorless solution. K₂CO₃ (821 mg, 5.94 mmol) was added, and the reaction mixture was stirred at room temperature for 3 h. H₂O (10 mL) was added and the resulting mixture was extracted with dichloromethane (3×20 mL). The organic layers were combined, dried over Na₂SO₄, and concentrated under reduced pressure. The residue was loaded onto a Biotage column and eluted with ethyl acetate/hexane from 0% to 40% to afford the title compound (490 mg, 70%) as a colorless oil. MS: 475.1 (M+H⁺).

Step K: Methyl (S)-6-chloro-5-fluoro-5'-(((1R,2R)-2-(hydroxymethyl)cyclobutyl)methyl)-3,4,4',5'-tetrahydro-2H,2'H-spiro[naphthalene-1,3'-pyrido[3,2-b][1,4]oxazepine]-7'-carboxylate (Intermediate 4)

Methyl 6-chloro-5-fluoro-5'-(((1R,2R)-2-(hydroxymethyl)cyclobutyl)methyl)-3,4,4',5'-tetrahydro-2H,2'H-spiro[naphthalene-1,3'-pyrido[3,2-b][1,4]oxazepine]-7'-carboxylate (Step J, 5.21 g) was subjected to chiral SFC resolution with a CHIRALPAK AD column to provide the title compound (2.25 g, 99% ee) as a white solid. ¹H NMR (400 MHz-DMSO-d6) δ 7.52 (d, J=8.7 Hz, 1H), 7.48-7.40 (m, 1H), 7.34 (d, J=7.9 Hz, 1H), 7.22 (d, J=7.9 Hz, 1H), 4.21 (t, J=5.3 Hz, 1H), 4.14 (d, J=12.3 Hz, 1H), 4.02 (d, J=12.3 Hz, 1H), 3.85-3.76 (m, 4H), 3.67 (d, J=14.5 Hz, 1H), 3.48-3.38 (m, 2H), 3.37-3.33 (m, 1H), 3.26-3.18 (m, 1H), 2.89-2.76 (m, 1H), 2.69-2.55 (m, 1H), 2.46-2.34 (m, 1H), 2.25-2.13 (m, 1H), 1.94-1.76 (m, 5H), 1.70-1.58 (m, 1H), 1.57-1.42 (m, 2H); MS: 475.1 (M+H⁺).

Example 19

Synthesis of Intermediate 5: (2R,3S)-3-((R)-3-((1R,2R)-2-(((tert-butyldiphenylsilyl)oxy)methyl)cyclobutane-1-carbonyl)cyclobut-2-en-1-yl)-N,N-bis(4-methoxybenzyl)butane-2-sulfonamide

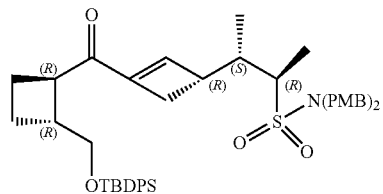

Step A: (2S,3S)-3-methylpent-4-en-2-yl methanesulfonate

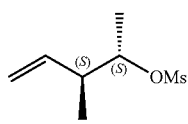

In a round-bottomed flask, (2S,3S)-3-methylpent-4-en-2-ol (25.2 g, 252 mmol) and Et₃N (38.2 g, 377 mmol) were dissolved in dry DCM (300 mL) under Ar at 0° C. MsCl (34.6 g, 302 mmol) was added slowly and the reaction mixture was stirred for 30 min. Brine was added to quench the reaction and the mixture was extracted with ethyl acetate twice. The organic layers were combined, dried over Na₂SO₄, and concentrated under reduced pressure to afford the crude title compound (45 g) as a yellow oil, which was directly used for the next step without purification.

Step B: 2-(((2R,3S)-3-methylpent-4-en-2-yl)thio)pyrimidine

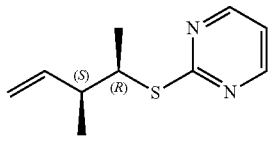

In a round-bottomed flask, (2 S,3S)-3-methylpent-4-en-2-yl methanesulfonate (Step A, 50 g, 281 mmol), $K_2CO_3$ (78 g, 561 mmol) and pyrimidine-2-thiol (47.2 g, 421 mmol) were dissolved into dry DMF (600 mL) under argon to give a suspension. The reaction mixture was stirred for overnight at 40° C. After cooling down to room temperature, brine was added to quench the reaction and the resulting mixture was extracted with ethyl acetate twice. The organic layers were combined, dried over $Na_2SO_4$, and concentrated under reduced pressure, the residue was loaded onto a silica gel column and eluted with ethyl acetate/hexane from 0% to 10% to afford the title compound (24 g, 44%) as a colorless oil. MS: 195.2 (M+H⁺).

Step C: 2-(((2R,3S)-3-methylpent-4-en-2-yl)sulfonyl)pyrimidine

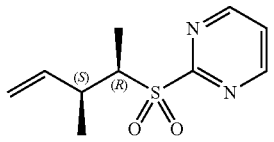

Bis(tetrabutylammonium) sulphate (4.72 g, 4.07 mmol), sodium tungstate dihydrate (1.34 g, 4.07 mmol), and phenylphosphonic acid (0.64 g, 4.07 mmol) were dissolved into hydrogen peroxide (13.83 g, 122 mmol, 3eq). At 0° C., a solution of 2-(((2R,3S)-3-methylpent-4-en-2-yl)thio)pyrimidine (Step B, 7.9 g, 40.7 mmol) in toluene (40 mL) was added slowly, and reaction mixture was stirred for 2 h at 50° C. After cooling down to room temperature, sat. $Na_2S_2O_3$ was added to quench the reaction and the mixture was extracted with ethyl acetate twice. The organic layers were combined, dried over $Na_2SO_4$, and concentrated under reduced pressure to afford the crude title compound (8 g) as a light yellow oil. MS: 227.1 (M+H⁺).

Step D: (2R,3S)-3-methylpent-4-ene-2-sulfonamide

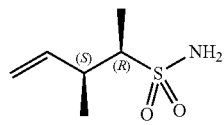

In a round-bottomed flask, 2-(((2R,3S)-3-methylpent-4-en-2-yl)sulfonyl)pyrimidine (Step C, 8 g, 35.4 mmol) was dissolved into MeOH (50 mL) under argon to give a solution. At 0° C., NaOMe (5 M in MeOH, 7.8 mL, 38.9 mmol) was added slowly and the reaction mixture was stirred for 1 h. After removal of volatiles under reduced pressure, the residue was dissolved into water (50 mL) and extracted with ethyl acetate three times. To the collected aqueous layers were added sodium acetate (3.48 g, 42.5 mmol) and (aminooxy)sulfonic acid (4.80 g, 42.5 mmol) at 0° C., and the reaction mixture was stirred for overnight at room temperature. Sat. NaCl was added and the reaction mixture was extracted with ethyl acetate twice. The organic layers were combined, dried over $Na_2SO_4$, and concentrated under reduced pressure to afford the title compound (4 g, 69% over 2 steps) as a light yellow solid. MS: 164.0 (M+H⁺).

Step E: (2R,3S)—N,N-bis(4-methoxybenzyl)-3-methyl pent-4-ene-2-sulfonamide

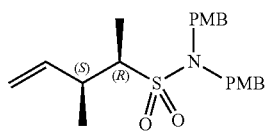

In a round-bottomed flask, (2R,3S)-3-methylpent-4-ene-2-sulfonamide (Step D, 4 g, 24.5 mmol) and $Cs_2CO_3$ (20 g, 61 mmol) were charged into dry DMF (40 mL) under argon. 4-methoxybenzyl chloride (9.59 g, 61.3 mmol, 2.5eq) was added and the reaction mixture was stirred for 2 h at 50° C. After cooling down to room temperature, sat. NaCl was added to quench the reaction, and the resulting mixture was extracted with ethyl acetate twice. The organic layers were combined, dried over $Na_2SO_4$, and concentrated under reduced pressure. The residue was loaded onto a silica gel column and eluted with ethyl acetate/hexane from 0% to 20% to afford the title compound (4.5 g, 46%) as a light yellow solid. MS: 426.4 (M+Na⁺).

Step F: (2R,3S)—N,N-bis(4-methoxybenzyl)-3-(3-oxocyclobutyl)butane-2-sulfonamide

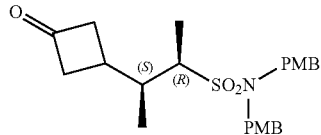

In a round-bottomed flask, (2R,3S)—N,N-bis(4-methoxybenzyl)-3-methyl pent-4-ene-2-sulfonamide (Step E, 27 g, 66.9 mmol) and zinc (17.50 g, 268 mmol) were charged into dry ether (40 mL) under argon. A solution of 2,2,2-trichloroacetyl chloride (24.33 g, 134 mmol) and dimethoxyethane (12.06 g, 134 mmol) in dry ether (15 mL) was added dropwise. Under Ar, the reaction mixture was refluxed for 12 h. After cooling down to room temperature, hexane (50 mL) was added and the resulting mixture was stirred for 30 min. After filtration through celite, the filtrate was washed with sat. $NaHCO_3$ and brine, dried over $Na_2SO_4$, and concentrated under reduced pressure. The residue was loaded onto a silica gel column and eluted with ethyl acetate/hexane from 0% to 30% to afford the title compound (18 g, 60%) as a white solid. ¹H NMR (500 MHz, DMSO-d₆) δ 7.20 (d, J=8.5 Hz, 4H), 6.88 (d, J=8.5 Hz, 4H), 4.36 (d, J=15.2 Hz, 2H), 4.17 (d, J=15.2 Hz, 2H), 3.73 (s, 6H), 3.03-2.95 (m, 1H), 2.92-2.85 (m, 1H), 2.84-2.73 (m, 2H), 2.47-2.41 (m, 1H), 2.17-2.06 (m, 2H), 1.10 (d, J=7.0 Hz, 3H), 0.96 (d, J=5.8 Hz, 3H); MS: 468.5 (M+Na$^+$).

Step G: 3-((2 S,3R)-3-(N,N-bis(4-methoxybenzyl) sulfamoyl)butan-2-yl)cyclobut-1-en-1-yl trifluoromethanesulfonate

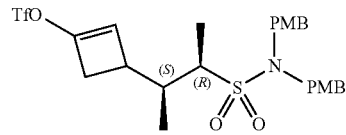

In a argon flushed round-bottomed flask, (2R,3S)—N,N-bis(4-methoxybenzyl)-3-(3-oxocyclobutyl)butane-2-sulfonamide (Step F, 1.7 g, 3.82 mmol) and 1,1,1-trifluoro-N-phenyl-N-((trifluoromethyl)sulfonyl)methanesulfonamide (2.04 g, 5.72 mmol) were dissolved into dry THF (20 mL) under Ar. At −78° C., KHMDS (1.0 M in THF, 4.6 mL, 4.58 mmol) was added dropwise and the reaction mixture was stirred for 2 h. Sat. NH$_4$Cl was added to quench the reaction and the mixture was extracted with ethyl acetate twice. The organic layers were combined, dried over Na$_2$SO$_4$, and concentrated under reduced pressure. The residue was loaded onto a silica gel column and eluted with ethyl acetate/hexane from 0% to 20% to afford the title compound (1.8 g, 82%) as a light yellow oil, which was directly used without purification. MS: 600.5 (M+Na$^+$).

Step H: (R)-3-((2 S,3R)-3-(N,N-bis(4-methoxybenzyl)sulfamoyl)butan-2-yl)cyclobut-1-en-1-yl trifluoromethanesulfonate (Isomer 1) and (S)-3-((2S,3R)-3-(N,N-bis(4-methoxybenzyl)sulfamoyl)butan-2-yl) cyclobut-1-en-1-yl trifluoromethanesulfonate (Isomer 2)

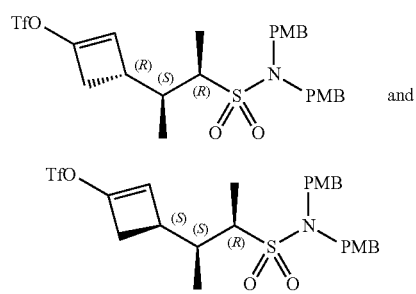

3-((2S,3R)-3-(N,N-bis(4-methoxybenzyl)sulfamoyl)butan-2-yl)cyclobut-1-en-1-yl trifluoromethanesulfonate (Step G, 79.9 g) was subjected to chiral SFC resolution with a CHIRALPAK IH column (CO$_2$:IPA=70:30) to provide the title compounds (the first-eluting diastereomer was designated as Isomer 2, 26.7 g, 100% ee; the second-eluting diastereomer was designated as Isomer 1, 28.3 g, 99.5% ee) as light yellow oil. MS: 600.0 (M+Na$^+$).

Step I: (2R,3S)-3-(3-((R)-((1R,2R)-2-(((tert-butyldiphenyl silyl)oxy)methyl) cyclobutyl)(hydroxy) methyl)cyclobut-2-en-1-yl)-N,N-bis(4-methoxybenzyl)butane-2-sulfonamide (Isomer 1) and (2R,3S)-3-(3-((S)-((1R,2R)-2-(((tert-butyldiphenylsilyl)oxy) methyl)cyclobutyl)(hydroxy)methyl)cyclobut-2-en-1-yl)-N,N-bis(4-methoxybenzyl)butane-2-sulfonamide (Isomer 2)

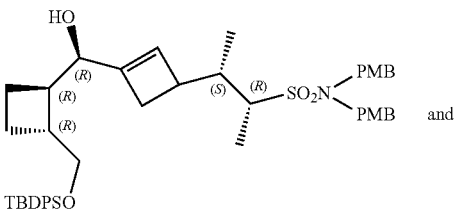

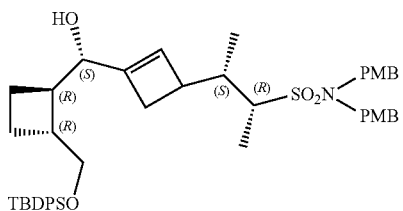

In a argon flushed three-necked round-bottomed flask, chromium(II) chloride (146 g, 1191 mmol) and nickel(II) chloride (3.86 g, 29.8 mmol) were charged into dry DMF (1000 mL) under Ar. At 60° C., a solution of (1R,2R)-2-(((tert-butyldiphenylsilyl)oxy)methyl)cyclobutane-1-carbaldehyde (Intermediate 3, 105 g, 298 mmol) and 3-((2 S,3R)-3-(N,N-bis(4-methoxybenzyl)sulfamoyl)butan-2-yl) cyclobut-1-en-1-yl trifluoromethanesulfonate (Step G, 185 g, 320 mmol) in dry DMF (500 mL) was added slowly, and the reaction mixture was stirred for 6 h. After cooling down to room temperature, sat. NaCl was added to quench the reaction, and the resulting mixture was extracted with ethyl acetate twice. The organic layers were combined, dried over Na$_2$SO$_4$, and concentrated under reduced pressure. The residue was loaded onto a silica gel column and eluted with ethyl acetate/hexane from 0% to 25% to afford the title compounds (the first-eluting diastereomer was designated as Isomer 1, 75 g, 32%; the second-eluting diastereomer was designated as Isomer 2, 80 g, 34%) as light yellow oil. MS: 805.2 (M+Na$^+$).

Step J: (2R,3S)-3-((R)-3-((S)-((1R,2R)-2-(((tert-butyldiphenyl silyl)oxy)methyl) cyclobutyl)(hydroxy)methyl)cyclobut-2-en-1-yl)-N,N-bis(4-methoxybenzyl)butane-2-sulfonamide (Isomer 1) and (2R,3S)-3-((S)-3-((S)-((1R,2R)-2-(((tert-butyldiphenylsilyl)oxy)methyl)cyclobutyl)(hydroxy) methyl)cyclobut-2-en-1-yl)-N,N-bis(4-methoxybenzyl)butane-2-sulfonamide (Isomer 2)

Isomer 1

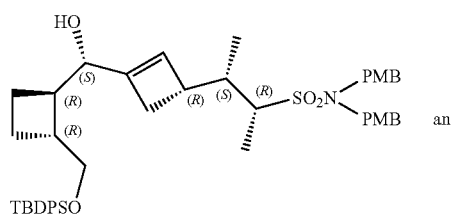

and

Isomer 2

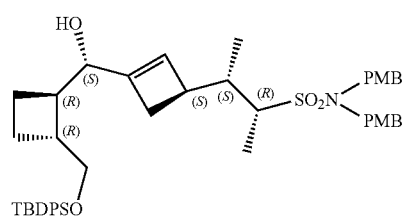

(2R,3S)-3-(3-((S)-((1R,2R)-2-(((tert-butyldiphenyl silyl)oxy)methyl)cyclobutyl) (hydroxy)methyl)cyclobut-2-en-1-yl)-N,N-bis(4-methoxybenzyl)butane-2-sulfonamide (Isomer 2 of Step I, 48.4 g) was subjected to chiral SFC resolution with a Lux® 5 μm Amylose-1 column (Hex(2 mM NH₃-MeOH):IPA=65:35) to provide the title compounds (the first-eluting diastereomer was designated as Isomer 1, 18.8 g, 99.5% ee; the second-eluting diastereomer was designated as Isomer 2, 13.8 g, 98.7% ee) as light yellow oil. MS: 804.3 (M+Na⁺).

Step K: (2R,3S)-3-((R)-3-((S)-((1R,2R)-2-(((tert-butyldiphenylsilyl)oxy)methyl) cyclobutane-1-carbonyl)cyclobut-2-en-1-yl)-N,N-bis(4-methoxybenzyl)butane-2-sulfonamide (Intermediate 5)

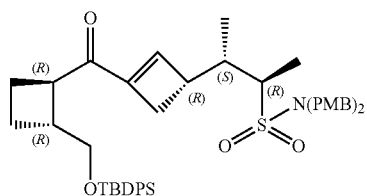

Under Ar, to a solution of (2R,3S)-3-((R)-3-((S)-((1R, 2R)-2-(((tert-butyldiphenylsilyl)oxy)methyl)cyclobutyl) (hydroxy)methyl)cyclobut-2-en-1-yl)-N,N-bis(4-methoxybenzyl)butane-2-sulfonamide (Isomer 1 of Step J, 9.2 g, 11.8 mmol) in dry DCM (100 mL) was added DMP (7.48 g, 17.6 mmol) at 0° C., and the reaction mixture was stirred for 1 h. Aq. NaHCO₃ was added to quench the reaction, followed by aq. sodium thiosulfate. The resulting mixture was stirred for 10 min and then extracted with DCM twice. The organic layers were combined, washed with brine, dried over Na₂SO₄, and concentrated under reduced pressure to give a yellow oil, which was purified by silica gel column chromatography (hexane:EA, 100:0→100:30) to afford the title compound (8.4 g, 92%) as a light yellow oil. MS: 802.8 (M+Na⁺).

Example 20

Synthesis of (1S,12'S,13'R,16'R,16a'R,18a'R)-6-chloro-16'-methoxy-11',12'-dimethyl-3,4,12',13',16', 16a',17',18',18a',19'-decahydro-1'H,2H,3'H, 11'H-spiro[naphthalene-1,2'-[5,7]etheno[13,15] methanocyclobuta[i][1,4]oxazepino[3,4-f][1]thia[2, 7,16]triazacyclohexadecin]-8'(9'H)-one 10',10'-dioxide (Cpd. No. 26 Isomer 1) and (1S,12'S,13'S, 16'R,16a'R,18a'R)-6-chloro-16'-methoxy-11',12'-dimethyl-3,4,12',13',16',16a',17',18',18a',19'-decahydro-1'H,2H,3'H, 11'H-spiro[naphthalene-1,2'-[5,7]etheno[13,15]methanocyclobuta[i][1,4] oxazepino[3,4-f][1]thia[2,7,16] triazacyclohexadecin]-8'(9'H)-one 10',10'-dioxide (Cpd. No. 26 Isomer 2)

Cpd. No. 26 (isomer 1)

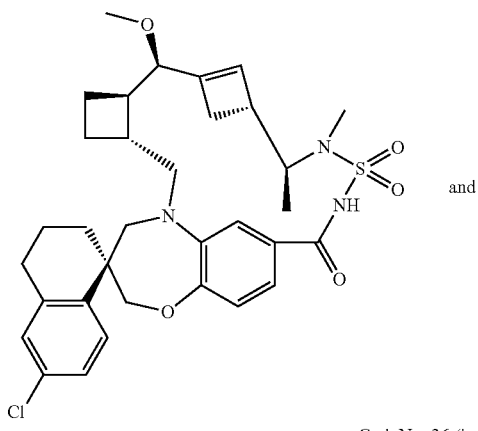

and

Cpd. No. 26 (isomer 2)

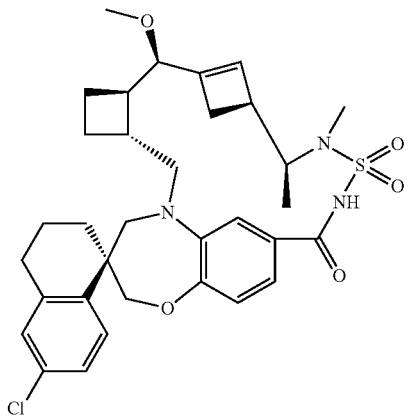

Step A: tert-butyl (S)-(1-hydroxypropan-2-yl)carbamate

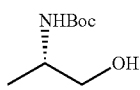

In a round-bottomed flask, (S)-2-aminopropan-1-ol (15 g, 200 mmol) was dissolved into DCM (400 mL). The reaction mixture was cooled to 0° C. with an ice/water bath, and (Boc)$_2$O (47.9 g, 220 mmol) and TEA (40.4 g, 399 mmol) were added. The reaction mixture was warmed to room temperature and stirred overnight. Water was added and the resulting mixture was extracted with DCM twice. The organic layers were combined, washed with brine, dried over Na$_2$SO$_4$ and concentrated under reduced pressure. The residue was loaded onto a silica gel column and eluted with ethyl acetate/hexane from 0% to 40% to afford the title compound (35.7 g, quantitatively) as a colorless oil.

Step B: tert-butyl (S)-(1-oxopropan-2-yl)carbamate

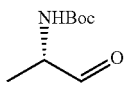

In a three-necked round-bottomed flask, oxalyl chloride (51.8 g, 408 mmol) was dissolved into dry DCM (600 mL) under nitrogen to give a colorless solution. At −78° C., DMSO (57.4 g, 734 mmol) was added to the solution dropwise over 20 min and then the mixture was stirred for 0.5 h. A solution of tert-butyl (1-hydroxypropan-2-yl)carbamate (Step A, 35.74 g, 204 mmol) in dry DCM (180 mL) was added dropwise over 20 min and then the reaction mixture was stirred for 0.5 h. Et$_3$N (175 g, 1734 mmol) was added dropwise over 15 min. The reaction mixture was allowed to warm up to room temperature and stirred for 1 h. Sat. NaHCO$_3$ was added and the resulting mixture was extracted with DCM twice. The organic layers were combined, washed with brine, dried over Na$_2$SO$_4$, and concentrated under reduced pressure. The residue was loaded onto a silica gel column and eluted with ethyl acetate/hexane from 0% to 40% to afford the title compound (29.6 g, 84%) as a light yellow oil. $^1$H NMR (400 MHz, CDCl3) δ 9.58 (s, 1H), 5.12 (s, 1H), 1.47 (s, 9H), 1.36 (d, J=7.4 Hz, 3H).

Step C: tert-butyl (S)-but-3-en-2-ylcarbamate

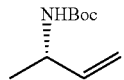

In a three-necked round-bottomed flask, methyltriphenylphosphonium bromide (183 g, 512 mmol) was dissolved into dry THF (500 mL) under nitrogen. At 0° C., KO$_t$Bu (57.5 g, 512 mmol) was added, and the reaction mixture was stirred at 0° C. for 0.5 h. A solution of tert-butyl (1-oxopropan-2-yl)carbamate (Step B, 29.6 g, 171 mmol) in dry THF (180 mL) was added dropwise over 20 min, and the reaction mixture was stirred at 0° C. for 2 h. H$_2$O was added to quench the reaction and the resulting mixture was extracted with ethyl acetate twice. The organic layers were combined, washed with brine, dried over Na$_2$SO$_4$, and concentrated under reduced pressure. The residue was loaded onto a silica gel column and eluted with ethyl acetate/hexane from 0% to 20% to afford the title compound (16.9 g, 58%) as a light yellow oil. $^1$H NMR (400 MHz, CDCl$_3$) δ 5.84 (dd, J=17.2, 10.4 Hz, 1H), 5.16-5.08 (m, 2H), 4.46 (s, 1H), 4.23 (s, 1H), 1.47 (s, 9H), 1.23 (d, J=6.8 Hz, 3H).

Step D: tert-butyl (S)-but-3-en-2-yl(methyl)carbamate

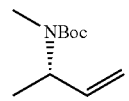

In a two-necked round-bottomed flask, tert-butyl but-3-en-2-ylcarbamate (Step C, 1.0 g, 5.84 mmol) was dissolved into dry DMF (10 ml) under nitrogen. NaH (0.168 g, 7.01 mmol) was added and the reaction mixture was stirred for 30 min. Iodomethane (1.24 g, 8.76 mmol) was added at 0° C. and the reaction mixture was stirred at room temperature for 2 h. H$_2$O was added to quench the reaction mixture and the resulting mixture was extracted with ethyl acetate twice. The organic layers were combined, dried over Na$_2$SO$_4$, and concentrated under reduced pressure. The residue was loaded onto a silica gel column and eluted with ethyl acetate/hexane from 0% to 15% to afford the title compound (590 mg, 55%) as a light yellow oil.

Step E: (S)—N-methylbut-3-en-2-amine

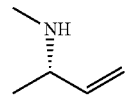

In a round-bottomed flask, tert-butyl but-3-en-2-ylcarbamate (Step D, 16.95 g, 99 mmol) was dissolved into DCM (40 mL). TFA (56.4 g, 495 mmol) was added and the reaction mixture was stirred at room temperature overnight. After removal of volatiles under reduced pressure, the resulting crude product was directly used for the next step without purification.

Step F: N-(4-methoxybenzyl)-2-oxooxazolidine-3-sulfonamide

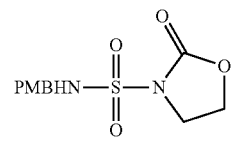

Under N$_2$, to a solution of sulfurisocyanatidic chloride (10 g, 70.7 mmol) in DCM (100 mL) was added dropwise over 30 min a solution of 2-bromoethan-1-ol (8.83 g, 70.7 mmol) in DCM (30 mL) at 0° C. The reaction mixture was stirred for 30 min. A solution of (4-methoxyphenyl)methanamine (10.66 g, 78 mmol) and triethylamine (15.73 g, 155 mmol) in DCM (60 mL) was slowly added, and the reaction mixture was allowed to warm up to room temperature and stirred for 1 h. The reaction mixture was diluted with 0.1N HCl (50 mL) to adjust pH=2. The organic layer was separated, washed with 0.05 N HCl and H$_2$O, dried over Na$_2$SO$_4$, and concentrated under reduced pressure to afford the title compound (18 g, 89%) as a white solid. $^1$H NMR (400 MHz, CDCl$_3$) δ 7.24 (d, J=9.0 Hz, 2H), 6.88 (d, J=8.6 Hz, 2H), 5.98 (t, J=6.2 Hz, 1H), 4.33-4.12 (m, 4H), 3.85-3.71 (dd, J=7.1, 8.7 Hz, 2H), 3.80 (s, 3H); MS: 309.1 (M+Na$^+$).

Step G: N-(4-methoxybenzyl)-(S)—N"-(but-3-en-2-yl)-N"-methyl sulfuric diamide

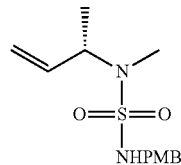

To a solution of N-(4-methoxybenzyl)-2-oxooxazolidine-3-sulfonamide (Step F, 3 g, 10.48 mmol) and N,N-dimethylpyridin-4-amine (0.26 g, 2.1 mmol) in acetonitrile (50 mL) under nitrogen was added triethylamine (3.18 g, 31.4 mmol) in one portion. The reaction mixture was heated to 80° C. for 30 min. A solution of (S)—N-methylbut-3-en-2-amine (Step E, 0.98 g, 11.53 mmol) in acetonitrile (5 mL) was added and the reaction mixture was heated to reflux for overnight. After cooling down to room temperature and removal of volatiles under reduced pressure, the residue was loaded onto a Biotage column and eluted with ethyl acetate/hexane from 0%-45% to afford the title compound (1.6 g, 51%) as a yellow oil. MS: 285.4 (M+H$^+$).

Step H: N,N-di(4-methoxybenzyl)-(S)—N"-(but-3-en-2-yl)-N"-methyl sulfuric diamide

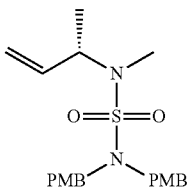

Under N$_2$, to a solution of N-(4-methoxybenzyl)-(S)—N"-(but-3-en-2-yl)-N"-methyl sulfuric diamide (Step G, 1.9 g, 6.68 mmol) in dry DMF (20 mL) was added sodium hydride (0.294 g, 7.35 mmol) in one portion at room temperature and the reaction mixture was stirred for 30 min. 1-(Chloromethyl)-4-methoxybenzene (1.26 g, 8.02 mmol) was added slowly at 0° C. The reaction mixture was allowed to warm up to room temperature and stirred for 2 h. H$_2$O (30 mL) was added to quench the reaction and the resulting mixture was extracted with ethyl acetate three times. The organic layers were combined, washed with brine, dried over Na$_2$SO$_4$, and concentrated under reduced pressure. The residue was loaded onto a Biotage column and eluted with ethyl acetate/hexane from 0% to 50% to afford the title compound (2.7 g, quantitatively) as a colorless oil. $^1$H NMR (400 MHz, CDCl$_3$) δ 7.24-7.15 (m, 4H), 6.94-6.83 (m, 4H), 5.95-5.82 (m, 1H), 5.28-5.17 (m, 2H), 4.59 (dd, J=6.8, 4.0 Hz, 1H), 4.28-4.13 (m, 4H), 3.83 (s, 6H), 2.63 (s, 3H), 1.32 (d, J=6.9 Hz, 3H). MS: 405.5 (M+H$^+$).

Step I: N,N-di(4-methoxybenzyl)-(S)—N'-(1-(3-oxocyclobutyl)ethyl)-N'-methyl sulfuric diamide

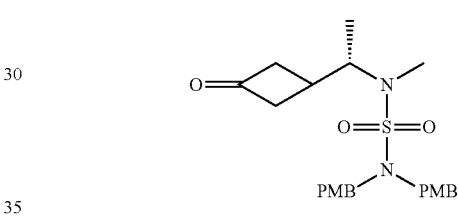

In a nitrogen flushed 25 mL two-necked round-bottomed flask, N,N-di(4-methoxybenzyl)-(S)—N"-(but-3-en-2-yl)-N"-methyl sulfuric diamide (Step H, 2.8 g, 6.92 mmol) and Zn powder (1.81 g, 27.7 mmol) were dissolved into dry dioxane (10 mL) under nitrogen, and 2,2,2-trichloroacetyl chloride (5.03 g, 27.7 mmol) was added dropwise over 10 min at room temperature. The reaction mixture was stirred at 50° C. for overnight. After cooling down to room temperature, hexane was added (5 mL) and the resulting suspension was stirred for 5 min to precipitate the formed zinc salts. The solution was then decanted and treated sequentially with water (20 mL). The mixture was then extracted with ethyl acetate three times. The organic layers were combined, washed with sat. NaHCO$_3$, and brine, dried over Na$_2$SO$_4$, and concentrated under reduced pressure. The residue was dissolved into AcOH (10 mL) and Zn powder (1.81 g, 27.7 mmol) was added. The reaction mixture was stirred at 70° C. for 4 h. After cooling down to room temperature and removal of volatiles under reduced pressure, the residue was loaded onto a Biotage column and eluted with ethyl acetate/hexane from 0% to 55% to afford the title compound (1.08 g, 35%) as a light yellow oil. MS: 447.6 (M+H$^+$).

Step J: 3-((S)-1-((N,N-bis(4-methoxybenzyl)sulfamoyl)(methyl)amino) ethyl)cyclobut-1-en-1-yl trifluoromethanesulfonate

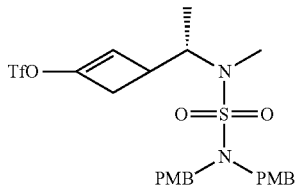

In a nitrogen flushed 25 mL two-necked round-bottomed flask, N,N-di(4-methoxybenzyl)-(S)—N‴-(1-(3-oxocyclobutyl)ethyl)-N‴-methyl sulfuric diamide (Step I, 1.08 g, 2.42 mmol) and 1,1,1-trifluoro-N-phenyl-N-((trifluoromethyl)sulfonyl) methanesulfonamide (1.037 g, 2.90 mmol) were dissolved into dry THF (10 mL) under nitrogen at −78° C. KHMDS (1.0 M in THF, 3.63 mL, 3.63 mmol) was added dropwise to the reaction mixture. The reaction mixture was stirred for 2 h at −78° C. Sat. NH₄Cl (10 mL) was added to quench the reaction and the resulting mixture was extracted with ethyl acetate three times. The organic layers were combined, washed with brine, dried over Na₂SO₄, and concentrated under reduced pressure. The residue was loaded onto a Biotage column and eluted with ethyl acetate/hexane from 0% to 50% to afford the title compound (1.1 g, 79%) as a yellow oil. ¹H NMR (400 MHz, CDCl₃) δ 7.24-7.13 (m, 4H), 6.93-6.84 (m, 4H), 5.42 (s, 1H), 4.27-4.09 (m, 4H), 3.84 (s, 6H), 3.95-3.74 (m, 2H), 3.03-2.98 (m, 1H), 2.84-2.74 (m, 1H), 2.70 (d, J=10.8 Hz, 3H), 1.22 (dd, J=13.0, 6.8 Hz, 3H); MS: 579.6 (M+H⁺).

Step K: tert-butyl (S)-5-(((1R,2R)-2-((benzoyloxy)methyl)cyclobutyl)methyl)-6'-chloro-3',4,4',5-tetrahydro-2H,2'H-spiro[benzo[b][1,4]oxazepine-3,1'-naphthalene]-7-carboxylate

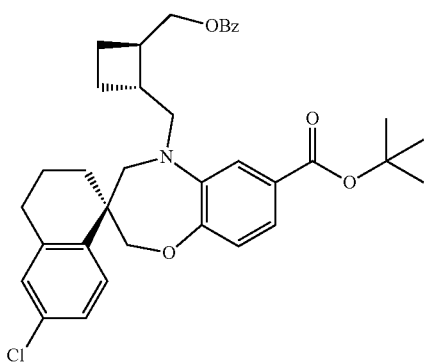

In a round-bottomed flask, TFA (4 ml) was added into THF (4 mL) and the reaction mixture was stirred for 5 min. tert-Butyl (S)-6'-chloro-3',4,4',5-tetrahydro-2H,2'H-spiro[benzo[b][1,4]oxazepine-3,1'-naphthalene]-7-carboxylate (Intermediate 2, 3 g, 7.5 mmol), ((1R,2R)-2-formylcyclobutyl)methyl benzoate (Intermediate 3, 1.97 g, 9.00 mmol) and phenylsilane (1.22 g, 11.25 mmol) was added to the mixture subsequently. The reaction mixture was stirred for 20 min at room temperature. H₂O was added to quench the reaction and the resulting mixture was extracted with ethyl acetate twice. The organic layers were combined, washed with aq NaHCO₃, dried over Na₂SO₄, and concentrated under reduced pressure to afford the crude title compound (4 g) as a yellow oil. MS: 602.5 (M+H⁺).

Step L: tert-butyl (S)-6'-chloro-5-(((1R,2R)-2-(hydroxymethyl)cyclobutyl) methyl)-3',4,4',5-tetrahydro-2H,2'H-spiro[benzo[b][1,4]oxazepine-3,1'-naphthalene]-7-carboxylate

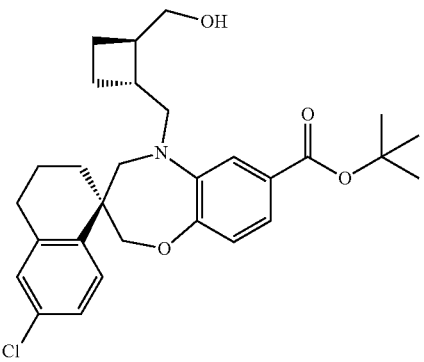 [SMILES: CC(C)(C)OC(=O)c1ccc2c(c1)N(C[C@@H]1CC[C@H]1CO)C[C@@]1(CCCc3cc(Cl)ccc31)CO2]

To a stirred solution of the crude tert-butyl (S)-5-(((1R,2R)-2-((benzoyloxy)methyl)cyclobutyl)methyl)-6'-chloro-3',4,4',5-tetrahydro-2H,2'H-spiro[benzo[b][1,4]oxazepine-3,1'-naphthalene]-7-carboxylate (Step K, 4 g) in MeOH (20 mL) was added K₂CO₃ (1.83 g, 13.3 mmol). The reaction mixture was stirred for 1 h at room temperature. H₂O was added to quench the reaction and the mixture was extracted with ethyl acetate twice. The organic layers were combined, dried over Na₂SO₄, and concentrated under reduced pressure to afford the title compound (2.8 g, 76% over 2 steps) as a white solid. MS: 498.3 (M+H⁺)

Step M: tert-butyl (S)-6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate

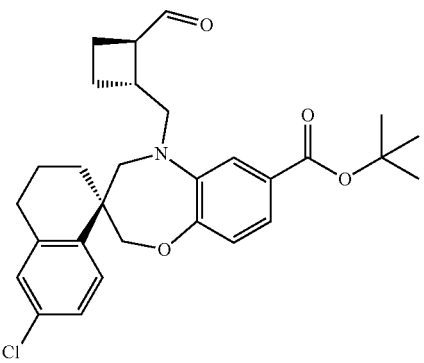 [SMILES: CC(C)(C)OC(=O)c1ccc2c(c1)N(C[C@@H]1CC[C@H]1C=O)C[C@@]1(CCCc3cc(Cl)ccc31)CO2]

Under Ar, to a solution of tert-butyl (S)-6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylate (Step L, 2.8 g, 5.62 mmol) in dry DCM (20 mL) was added DMP (2.86 g, 6.75 mmol). The reaction was stirred for 1 h at room temperature. Aq. NaHCO₃ was added to quench the reaction and the resulting mixture was extracted with DCM twice. The organic layers were combined, dried over Na$_2$SO$_4$, and concentrated under reduced pressure. The residue was purified by silica gel column chromatography (EtOAc:Hexane, 1:20 to afford the title compound (2.2 g, 79%) as a white solid. MS: 496.3 (M+H$^+$).

Step N: tert-butyl (3S)-5-(((1R,2R)-2-((1R)-(3-((S)-1-((N,N-bis(4-methoxybenzyl)sulfamoyl)(methyl)amino)ethyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate (P1) and tert-butyl (3S)-5-(((1R,2R)-2-((1S)-(3-((S)-1-((N,N-bis(4-methoxybenzyl)sulfamoyl)(methyl)amino)ethyl) cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate (P2)

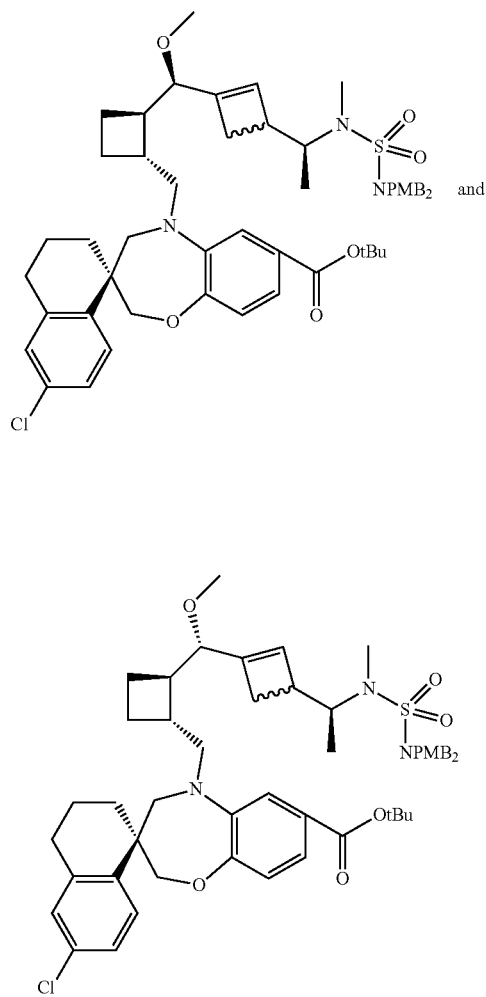

In a nitrogen flushed 50 mL three-necked round-bottomed flask, nickel(II) chloride (25.9 mg, 0.2 mmol) and chromium (II) chloride (492 mg, 4 mmol) were dissolved into dry DMF (5 mL) under nitrogen to give a green solution. At 70° C., a solution of tert-butyl (S)-6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Step M, 248 mg, 0.5 mmol) and 3-((S)-1-((N,N-bis(4-methoxybenzyl)sulfamoyl)(methyl) amino)ethyl)cyclobut-1-en-1-yl trifluoromethanesulfonate (Step J, 347 mg, 0.6 mmol) in dry DMF (5 mL) was added to the reaction mixture in one portion. Then the reaction was stirred for overnight at 70° C. After cooling down to room temperature, H$_2$O (20 mL) was added to quench the reaction mixture and the resulting mixture was extracted with ethyl acetate three times. The organic layers were combined, dried over Na$_2$SO$_4$, and concentrated under reduced pressure. The residue was loaded onto a Biotage column and eluted with ethyl acetate/hexane from 0% to 30% to afford the title compounds (the first-eluting diastereomer was designated as P1, 105 mg, 23%; the second-eluting diastereomer was designated as P2, 98 mg, 22%) as a light yellow oil. MS: 927.6 (M+H$^+$).

Step O: tert-butyl (3S)-5-(((1R,2R)-2-((1R)-(3-((S)-1-((N,N-bis(4-methoxybenzyl)sulfamoyl)(methyl)amino)ethyl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate

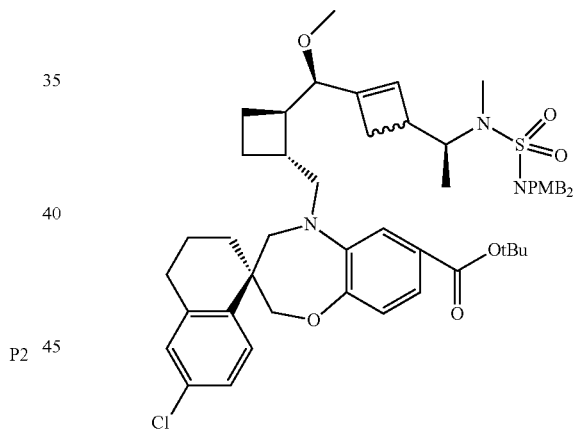

In a nitrogen flushed 50 mL round-bottomed flask, tert-butyl (3S)-5-(((1R,2R)-2-((1R)-(3-((S)-1-((N,N-bis(4-methoxybenzyl)sulfamoyl)(methyl)amino)ethyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate (P1 of Step N, 103 mg, 0.11 mmol) was dissolved into dry THF (10 mL) under nitrogen. NaH (13.3 mg, 0.56 mmol) was added at room temperature and the mixture was stirred for 20 min. Iodomethane (158 mg, 1.112 mmol) was added at 0° C., and then the reaction mixture was stirred for 4 h at room temperature. H$_2$O (10 mL) was added to quench the reaction and the resulting mixture was extracted with ethyl acetate (3×15 mL). The organic layers were combined, dried over Na$_2$SO$_4$, and concentrated under reduced pressure to afford the crude title compound (130 mg) as a yellow oil, which was used for the next step without further purification. MS: 941.6 (M+H$^+$).

Step P: (3S)-6'-chloro-5-(((1R,2R)-2-((1R)-methoxy(3-((S)-1-(methyl(sulfamoyl) amino)ethyl)cyclobut-1-en-1-yl)methyl)cyclobutyl)methyl)-3',4',5-tetrahydro-2H,2'H-spiro[benzo[b][1,4]oxazepine-3,1'-naphthalene]-7-carboxylic acid

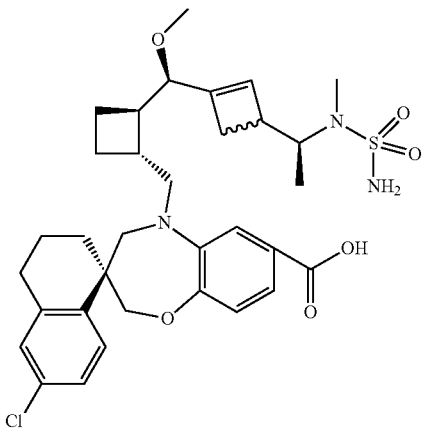 [SMILES: CO[C@@H](C1=CC([C@H](C)N(C)S(N)(=O)=O)C1)[C@@H]1CC[C@H]1CN1C[C@@]2(CCCc3cc(Cl)ccc32)COc2ccc(C(=O)O)cc21]

In a nitrogen flushed 50 mL round-bottomed flask, tert-butyl (3S)-5-(((1R,2R)-2-((1R)-(3-((S)-1-((N,N-bis(4-methoxybenzyl)sulfamoyl)(methyl)amino)ethyl)cyclobut-1-en-1-yl)(methoxy)methyl)cyclobutyl)methyl)-6'-chloro-3',4',5-tetrahydro-2H,2'H-spiro[benzo[b][1,4]oxazepine-3,1'-naphthalene]-7-carboxylate (Step O, 130 mg, 0.14 mmol) was dissolved into DCM (10 mL) under nitrogen to give a yellow solution. TFA (67.7 mg, 0.69 mmol) was added to the reaction mixture in one portion. The reaction mixture was stirred overnight. After removal of volatiles under reduced pressure, the residue was loaded onto a Biotage column and eluted with ethyl acetate/hexane from 0% to 80% to afford the title compound (74 mg, 83% over 2 steps) as a colorless oil. MS: 645.2 (M+H$^+$).

Step Q: (1S,12'S,13'R,16'R,16a'R,18a'R)-6-chloro-16'-methoxy-11',12'-dimethyl-3,4,12,'13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7,16]triazacyclohexadecin]-8'(9'H)-one 10',10'-dioxide (Cpd. No. 26 Isomer 1) and (1S,12'S,13'S,16'R,16a'R,18a'R)-6-chloro-16'-methoxy-11',12'-dimethyl-3,4,12,'13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7,16]triazacyclohexadecin]-8'(9'H)-one 10',10'-dioxide (Cpd. No. 26 Isomer 2)

In a nitrogen flushed 25 mL two-necked round-bottomed flask, (3S)-6'-chloro-5-(((1R,2R)-2-((1R)-methoxy(3-((S)-1-(methyl(sulfamoyl)amino)ethyl)cyclobut-1-en-1-yl)methyl)cyclobutyl)methyl)-3',4',5-tetrahydro-2H,2'H-spiro[benzo[b][1,4]oxazepine-3,1'-naphthalene]-7-carboxylic acid (Step P, 74 mg, 0.12 mmol), triethylamine (116 mg, 1.15 mmol), and N,N-dimethylpyridin-4-amine (28.1 mg, 0.23 mmol) were dissolved into dry DCM (5 mL) under nitrogen to give a colorless solution. 2,4,6-tripropyl-1,3,5,2,4,6-trioxatriphosphinane 2,4,6-trioxide (110 mg, 0.345 mmol) was added at 0° C. and then the reaction mixture was stirred for 3 h at room temperature. After removal of volatiles under reduced pressure, the residue was purified by C18 preparative-HPLC to afford the title compounds (the first-eluting diastereomer was designated as Cpd. No. 26 isomer 1: 3.5 mg (5%) the second-eluting diastereomer was designated as Cpd. No. 26 isomer 2: 10 mg (13%) as white solid.

Cpd. No. 26 Isomer 1: $^1$H NMR (400 MHz, DMSO-d$_6$) δ 11.70 (s, 1H), 7.67 (d, J=8.5 Hz, 1H), 7.28 (dd, J=8.5, 2.4 Hz, 1H), 7.23-7.16 (m, 1H), 7.04 (d, J=2.1 Hz, 1H), 7.02-6.96 (m, 1H), 6.92 (d, J=8.1 Hz, 1H), 6.11 (s, 1H), 4.14 (d, J=12.2 Hz, 1H), 3.95 (d, J=12.2 Hz, 1H), 3.71-3.47 (m, 4H), 3.39 (dd, J=24.2, 14.7 Hz, 2H), 3.16 (s, 3H), 2.93-2.91 (m, 4H), 2.84-2.65 (m, 3H), 2.46-2.42 (m, 2H), 2.25 (d, J=13.4 Hz, 1H), 1.94-1.70 (m, 6H), 1.66-1.50 (m, 2H), 1.25 (d, J=6.6 Hz, 3H); MS: 627.2 (M+H$^+$).

Cpd. No. 26 Isomer 2: $^1$H NMR (400 MHz, DMSO-d$_6$) δ 11.64 (s, 1H), 7.68 (d, J=8.5 Hz, 1H), 7.31-7.15 (m, 2H), 7.04 (s, 1H), 6.95-6.89 (m, 2H), 6.00 (s, 1H), 4.10 (d, J=12.2 Hz, 1H), 3.96-3.89 (m, 2H), 3.77-3.63 (m, 2H), 3.36-3.31 (m, 1H), 3.23-3.19 (m, 4H), 2.91-2.87 (m, 4H), 2.81-2.67 (m, 1H), 2.46 (d, J=4.4 Hz, 1H), 2.23 (d, J=13.2 Hz, 2H), 2.05-1.95 (m, 4H), 1.88-1.82 (m, 3H), 1.65-1.60 (m, 3H), 1.43-1.38 (m, 1H), 1.19 (d, J=6.6 Hz, 3H); MS: 627.4 (M+H$^+$).

Example 21

Synthesis of (1S,12'S,13'R,16'S,16a'R,18a'R)-6-chloro-16'-methoxy-11',12'-dimethyl-3,4,12,'13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7,16]triazacyclohexadecin]-8'(9'H)-one 10',10'-dioxide (Cpd. No. 27 Isomer 1) and (1S,12'S,13'S,16'S,16a'R,18a'R)-6-chloro-16'-methoxy-11',12'-dimethyl-3,4,12,'13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7,16]triazacyclohexadecin]-8'(9'H)-one 10',10'-dioxide (Cpd. No. 27 Isomer 2)

Cpd No. 27 (isomer 1)

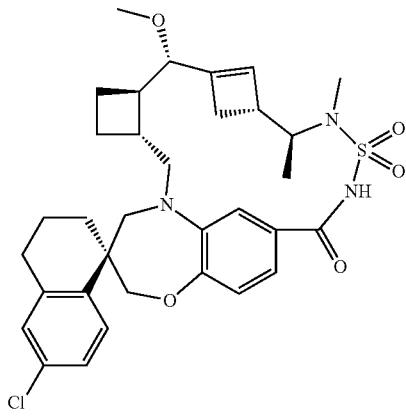

Example 22

Synthesis of (1S,12'S,16'S,16a'R,18a'R)-6-chloro-16'-methoxy-11',12'-dimethyl-3,4,12',13',14',15',16',16a',17',18',18a',19'-dodecahydro-1'H,2H,3'H,11'H-spiro[naphthalene-1,2'-[5,7]etheno[13,15]methanocyclobuta[i][1,4]oxazepino[3,4-f][1]thia[2,7,16]triazacyclohexadecin]-8'(9'H)-one 10',10'-dioxide (Cpd. No. 28)

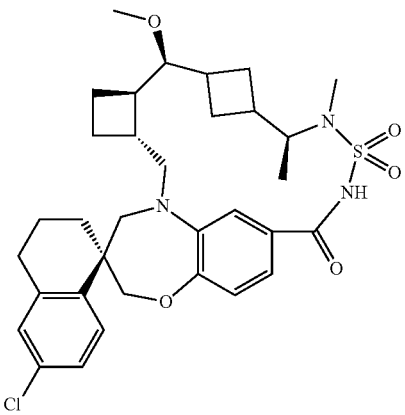 [SMILES: CO[C@H]1C2CC(C2)[C@H](C)N(C)S(=O)(=O)NC(=O)c2ccc3c(c2)N(C[C@@H]2CC[C@H]21)C[C@@]1(CCCc2cc(Cl)ccc21)CO3]

Under Ar, to a solution of Cpd. No. 26 isomer 2 (6 mg, 9.58 μmol) in ethyl acetate (5 mL) was added platinum(IV) oxide (2.18 mg, 9.58 μmol), H$_2$ was introduced and then the reaction mixture was stirred at 25° C. for 2 h. After filtration, the filtrate was concentrated under reduced pressure to give a light yellow oil, which was purified by C18 pre-HPLC column to afford the title compound (2 mg, 33%) as a white solid. MS: 628.5 (M+H$^+$).

Example 23

Synthesis of (1S,12'S,16'R,16a'R,18a'R)-6-chloro-16'-methoxy-11',12'-dimethyl-3,4,12',13',14',15',16',16a',17',18',18a',19'-dodecahydro-1'H,2H,3'H,11'H-spiro[naphthalene-1,2'-[5,7]etheno[13,15]methanocyclobuta[i][1,4]oxazepino[3,4-f][1]thia[2,7,16]triazacyclohexadecin]-8'(9'H)-one 10',10'-dioxide (Cpd. No. 29)

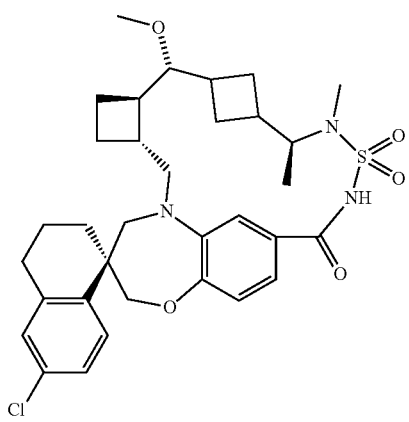 [SMILES: CO[C@@H]1C2CC(C2)[C@H](C)N(C)S(=O)(=O)NC(=O)c2ccc3c(c2)N(C[C@@H]2CC[C@H]21)C[C@@]1(CCCc2cc(Cl)ccc21)CO3]

Cpd. No. 27 (isomer 2)

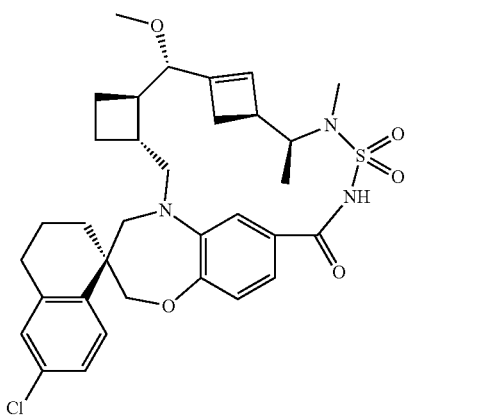

Essentially the same protocol used to prepare Cpd. No. 26 isomers 1 and 2 (using P2 of Step N of EXAMPLE 20 as starting material) was used to afford the two isomers of Cpd. No. 27 (the first-eluting diastereomer was designated as Cpd. No. 27 isomer 1: 14 mg; the second-eluting diastereomer was designated as Cpd. No. 27 isomer 1: 5.1 mg) as white solids.

Cpd. No. 27 isomer 1: $^1$H NMR (400 MHz, DMSO-d$_6$) δ 11.86 (s, 1H), 7.67 (d, J=8.6 Hz, 1H), 7.27 (dd, J=8.5, 2.4 Hz, 1H), 7.24-7.15 (m, 3H), 6.93 (d, J=8.2 Hz, 1H), 5.43 (s, 1H), 4.16 (d, J=12.1 Hz, 1H), 4.11 (d, J=12.0 Hz, 1H), 3.81 (dd, J=13.6, 6.5 Hz, 1H), 3.63-3.44 (m, 5H), 3.08-2.95 (m, 1H), 2.94 (s, 6H), 2.91 (d, J=5.0 Hz, 1H), 2.81-2.70 (m, 3H), 2.23 (d, J=12.5 Hz, 1H), 2.05 (s, 2H), 1.92-1.65 (m, 6H), 1.62-1.58 (m, 1H), 1.20 (d, J=6.4 Hz, 3H); MS: 627.1 (M+H$^+$).

Cpd. No. 27 isomer 2: $^1$H NMR (400 MHz, DMSO-d$_6$) δ 11.61 (s, 1H), 7.68 (d, J=8.5 Hz, 1H), 7.28 (dd, J=8.5, 2.4 Hz, 1H), 7.23-7.10 (m, 2H), 7.00-6.91 (m, 1H), 6.86 (d, J=8.2 Hz, 1H), 5.50 (s, 1H), 4.05 (d, J=12.0 Hz, 1H), 3.99 (d, J=12.2 Hz, 1H), 3.88 (dd, J=15.3, 7.2 Hz, 1H), 3.60-3.47 (m, 5H), 3.36-3.31 (m, 1H), 3.05 (dd, J=15.4, 5.1 Hz, 1H), 2.98-2.92 (m, 4H), 2.92 (s, 3H), 2.85-2.63 (m, 4H), 2.62-2.55 (m, 2H), 2.00-1.78 (m, 4H), 1.68-1.52 (m, 1H), 1.45-1.38 (m, 1H), 1.16 (d, J=6.5 Hz, 3H); MS: 627.2 (M+H$^+$).

Essentially the same protocol used in EXAMPLE 22 (by using Cpd. No. 27 isomer 1 as the starting material) was used to afford the title compound (2.5 mg, 42%) as a white solid. MS: 628.5 (M+H$^+$).

Example 24

Synthesis of (1S,12'S,13'S,16'R,16a'R,18a'R)-6-chloro-16'-methoxy-12'-methyl-11'-(((S)-tetrahydrofuran-2-yl)methyl)-3,4,12',13',16',16a',17',18',18a', 19'-decahydro-1'H,2H,3'H, 11'H-spiro[naphthalene-1,2'-[5,7]etheno[13,15]methanocyclobuta[i][1,4] oxazepino[3,4-f][1]thia[2,7,16] triazacyclohexadecin]-8'(9'H)-one 10',10'-dioxide (Cpd. No. 30 Isomer 1) and (1S,12'S,13'S,16'R, 16a'R,18a'R)-6-chloro-16'-methoxy-12'-methyl-11'-(((R)-tetrahydrofuran-2-yl)methyl)-3,4,12',13',16', 16a',17',18',18a',19'-decahydro-1'H,2H,3'H, 11'H-spiro[naphthalene-1,2'-[5,7]etheno[13,15] methanocyclobuta[i][1,4]oxazepino[3,4-f][1]thia[2, 7,16]triazacyclohexadecin]-8'(9'H)-one 10',10'-dioxide (Cpd. No. 30 Isomer 2) and (1S,12'S,13'R, 16'R,16a'R,18a'R)-6-chloro-16'-methoxy-12'-methyl-11'-(((S)-tetrahydrofuran-2-yl)methyl)-3,4,12',13', 16',16a',17',18',18a',19'-decahydro-1'H,2H,3'H, 11'H-spiro[naphthalene-1,2'-[5,7]etheno[13,15] methanocyclobuta[i][1,4]oxazepino[3,4-f][1]thia[2, 7,16]triazacyclohexadecin]-8'(9'H)-one 10',10'-dioxide (Cpd. No. 30 Isomer 3) and (1S,12'S,13'R,16'R, 16a'R,18a'R)-6-chloro-16'-methoxy-12'-methyl-11'-(((R)-tetrahydrofuran-2-yl)methyl)-3,4,12',13',16', 16a',17',18',18a',19'-decahydro-1'H,2H,3'H,11'H-spiro[naphthalene-1,2'-[5,7]etheno[13,15] methanocyclobuta[i][1,4]oxazepino[3,4-f][1]thia[2, 7,16]triazacyclohexadecin]-8'(9'H)-one 10',10'-dioxide (Cpd. No. 30 Isomer 4)

Cpd. No. 30 isomer 1

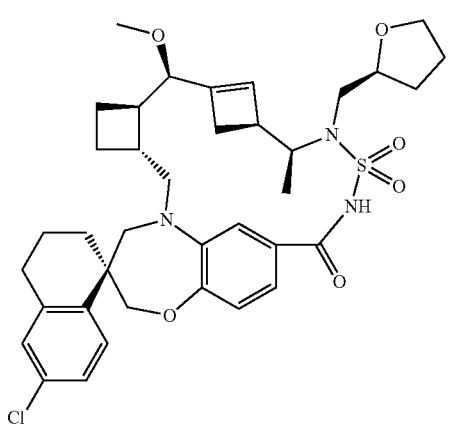

Cpd. No. 30 isomer 2

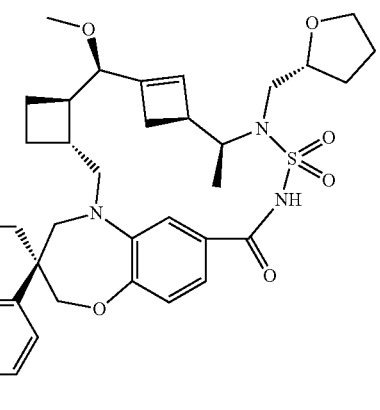

Cpd. No. 30 isomer 3

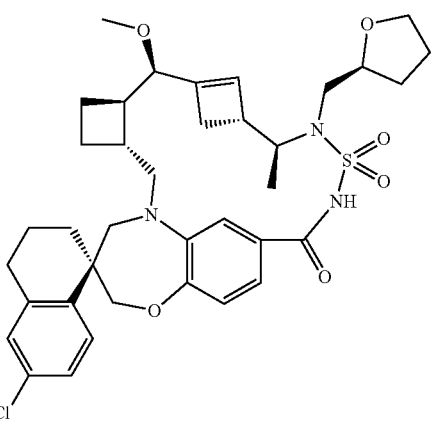

Cpd. No. 30 isomer 4

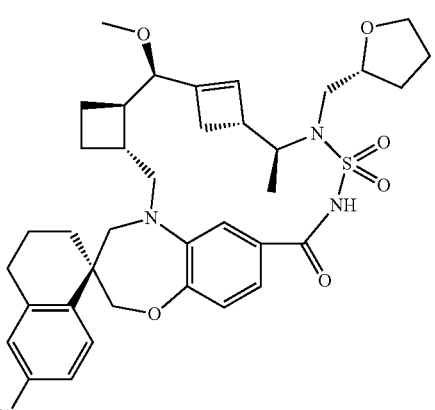

Step A: (S)-but-3-en-2-amine

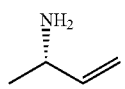

In a round-bottomed flask, tert-butyl (S)-but-3-en-2-yl-carbamate (Step C of EXAMPLE 20, 16.95 g, 99 mmol) was dissolved into DCM (40 mL) to give a light yellow solution. TFA (56.4 g, 495 mmol) was added dropwise over 20 min using and then the reaction mixture was stirred 2 h at room temperature. After removal of volatiles under reduced pressure, the crude title compound (25.3 g) as a yellow oil was used for the next step without purification.

Step B: (2S)—N-((tetrahydrofuran-2-yl)methyl)but-3-en-2-amine

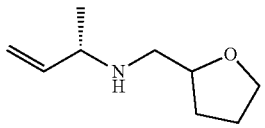

In a nitrogen flushed 25 mL two-necked round-bottomed flask, methyl tetrahydrofuran-2-carboxylate (1 g, 7.68 mmol) was dissolved into dry DCM (10 mL) under nitrogen to give a colorless solution. Diisobutylaluminum hydride (1.0 M in DCM, 15.4 mL, 15.4 mmol) was added dropwise over 10 min at −78° C., and the reaction mixture was stirred for 1 h at −78° C. HOAc (0.5 mL), NaBH(OAc)$_3$ (4.89 g, 23.1 mmol) and (S)-but-3-en-2-amine (545 mg, 7.68 mmol) were added. The reaction mixture was allowed to warm up to room temperature and stirred overnight. After filtration through a Buchner funnel, the filter cake was rinsed with dichloromethane (3×10 mL) and the combined filtrate was concentrated under reduced pressure to afford the crude title compound (2.16 g) as a yellow oil, which was directly used for the next step without purification.

Step C: N-(4-methoxybenzyl)-N'—((S)-but-3-en-2-yl)-N'-((tetrahydrofuran-2-yl)methyl)sulfuric diamide

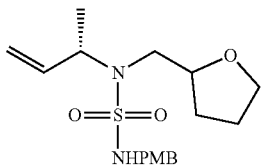

Under N$_2$, to a solution of N-(4-methoxybenzyl)-2-oxooxazolidine-3-sulfonamide (858 mg, 3.00 mmol, 1.000) and DMAP (73.2 mg, 0.599 mmol) in acetonitrile (10 mL) was added Et$_3$N (910 mg, 8.99 mmol) at room temperature. The reaction mixture was heated to 80° C. for 30 min. A solution of (2S)—N-((tetrahydrofuran-2-yl)methyl)but-3-en-2-amine (512 mg, 3.30 mmol) in acetonitrile (5 mL) was added slowly, and the reaction mixture was refluxed for overnight. After cooling down to room temperature and removal of volatiles under reduced pressure, the residue was loaded onto a Biotage column and eluted with ethyl acetate/hexane from 0% to 45% to afford the title compound (160 mg, 15% over 3 steps) as a yellow oil. MS: 355.2 (M+H$^+$).

Step D: N,N-di(4-methoxybenzyl)-N'—((S)-but-3-en-2-yl)-N'-((tetrahydrofuran-2-yl)methyl)sulfuric diamide

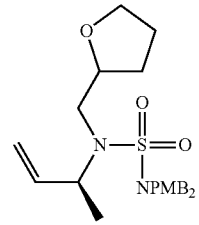

Under N$_2$, to a solution of N-(4-methoxybenzyl)-N'—((S)-but-3-en-2-yl)-N'-((tetrahydrofuran-2-yl)methyl)sulfuric diamide (Step C, 1.2 g, 3.39 mmol) in dry DMF (15 mL) was added sodium hydride (0.15 g, 3.72 mmol) in one portion at room temperature. The reaction mixture was stirred for 30 min and 1-(chloromethyl)-4-methoxybenzene (0.64 g, 4.06 mmol) was added at 0° C. The reaction mixture was allowed to warm up to room temperature and stirred for 2 h. H$_2$O (30 mL) was added to quench the reaction and the resulting mixture was extracted with ethyl acetate (3×50 mL). The organic layers were combined, washed brine, dried over Na$_2$SO$_4$, and concentrated under reduced pressure. The residue was loaded onto a Biotage column and eluted with ethyl acetate/hexane from 0% to 35% to afford the title compound as a colorless oil. MS: 475.2 (M+H$^+$).

Step E: N,N-di(4-methoxybenzyl)-N'—((S)-1-(3-oxocyclobutyl)ethyl)-N'-((tetrahydrofuran-2-yl)methyl)sulfuric diamide

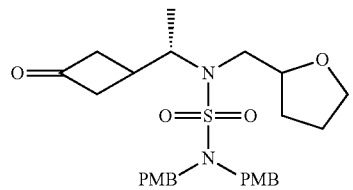

In a nitrogen flushed 25 mL two-necked round-bottomed flask, N,N-di(4-methoxybenzyl)-N'—((S)-but-3-en-2-yl)-N'-((tetrahydrofuran-2-yl)methyl)sulfuric diamide (Step D, 950 mg, 2 mmol) and zinc (523 mg, 8 mmol) were dissolved into dioxane (10 mL) under nitrogen to give a suspension. 2,2,2-trichloroacetyl chloride (1456 mg, 8 mmol) was added to the reaction mixture dropwise over 3 min, and the reaction mixture was stirred at 50° C. for overnight. After cooling down to room temperature, hexane (5 mL) was added and the resulting suspension was stirred for 5 min to precipitate the formed zinc salts. The solution was then decanted and treated with water (20 mL). The resulting mixture was extracted with ethyl acetate (3×20 mL). The organic layers were combined, washed with sat. NaHCO$_3$ and brine, dried over Na$_2$SO$_4$, and concentrated under reduced pressure. The residue was then re-taken into AcOH (10 mL), zinc (523 mg, 8.01 mmol) was added, and the reaction mixture was heated at 70° C. for 4 h. After cooling down to room temperature and removal of volatiles under reduced pressure, the residue was loaded onto a Biotage column and eluted with ethyl acetate/hexane from 0% to 45% to give the title compound (756 mg, 73%) as a colorless oil. MS: 517.2 (M+H$^+$).

Step F: 3-((1S)-1-((N,N-bis(4-methoxybenzyl)sulfamoyl)((tetrahydrofuran-2-yl)methyl)amino)ethyl)cyclobut-1-en-1-yl trifluoromethanesulfonate

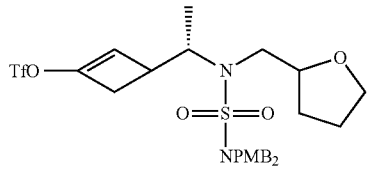

In a nitrogen flushed 25 mL two-necked round-bottomed flask, N,N-di(4-methoxybenzyl)-N'—((S)-1-(3-oxocyclobutyl)ethyl)-N'-((tetrahydrofuran-2-yl)methyl)sulfuric diamide (Step E, 756 mg, 1.463 mmol) and 1,1,1-trifluoro-N-phenyl-N-((trifluoromethyl)sulfonyl)methanesulfonamide (627 mg, 1.756 mmol) were dissolved into dry THF (10 mL) under nitrogen to give a colorless solution. At −78° C., potassium bis(trimethylsilyl)amide (1.0 M in THF, 2.20 mL, 2.2 mmol) was added dropwise over 5 min and the reaction mixture was stirred for 2 h at −78° C. Sat. NH$_4$Cl (10 mL) was added to quench the reaction and the resulting mixture was extracted with ethyl acetate (3×20 mL). The organic layers were combined, washed with brine, dried over Na$_2$SO$_4$, and concentrated under reduced pressure. The residue was loaded onto a Biotage column and eluted with ethyl acetate/hexane from 0% to 50% to afford the title compound (600 mg, 63%) as a yellow oil. MS: 649.2 (M+H$^+$).

Step G: tert-butyl (3S)-5-(((1R,2R)-2-((1R)-(3-((1S)-1-((N,N-bis(4-methoxybenzyl)sulfamoyl)((tetrahydrofuran-2-yl)methyl)amino)ethyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate

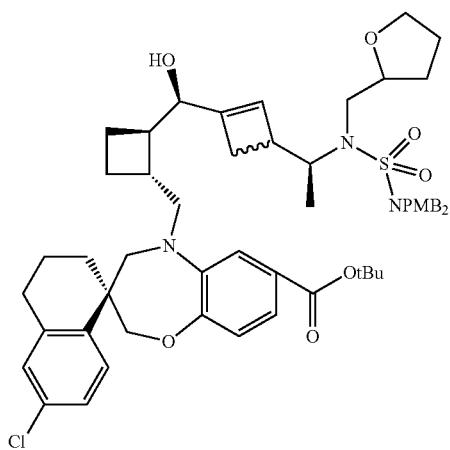

In a nitrogen flushed 50 mL three-necked round-bottomed flask, nickel(II) chloride (29.3 mg, 0.23 mmol) and chromium(II) chloride (555 mg, 4.52 mmol) were dissolved into dry DMF (5 mL) under nitrogen to give a green solution. At 70° C., a solution of tert-butyl (S)-6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Step M of EXAMPLE 20, 280 mg, 0.56 mmol) and 3-((1S)-1-((N,N-bis(4-methoxybenzyl)sulfamoyl)((tetrahydrofuran-2-yl)methyl)amino)ethyl)cyclobut-1-en-1-yl trifluoromethanesulfonate (Step F, 439 mg, 0.677 mmol, 1.2) in dry DMF (5 mL) was added to the reaction mixture in one portion. The reaction mixture was stirred for at 70° C. After cooling down to room temperature, H$_2$O (20 mL) was added to quench the reaction and the mixture was extracted with ethyl acetate (3×20 mL). The organic layers were combined, dried over Na$_2$SO$_4$, and concentrated under reduced pressure. The residue was loaded onto a Biotage column and eluted with ethyl acetate/hexane from 0% to 30% to afford the first-eluting diastereomer, which was designated for the title compound (160 mg, 28%) as a white solid. MS: 996.5 (M+H$^+$).

Step H: tert-butyl (3S)-5-(((1R,2R)-2-((1R)-(3-((1S)-1-((N,N-bis(4-methoxybenzyl)sulfamoyl)((tetrahydrofuran-2-yl)methyl)amino)ethyl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate

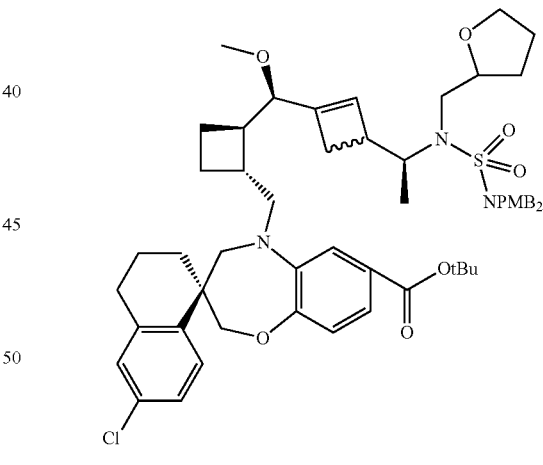

In a nitrogen flushed 50 mL round-bottomed flask, tert-butyl (3S)-5-(((1R,2R)-2-((1R)-(3-((1S)-1-((N,N-bis(4-methoxybenzyl)sulfamoyl)((tetrahydrofuran-2-yl)methyl)amino)ethyl)cyclobut-1-en-1-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate (Step G, 160 mg, 0.16 mmol) was dissolved into dry THF (10 mL) under nitrogen to give a colorless solution. Sodium hydride (19.26 mg, 0.8 mmol) was added at room temperature and the reaction mixture was stirred for 20 min. Iodomethane (228 mg, 1.61 mmol) was added at 0° C. and then the reaction mixture was stirred for 4 h at room temperature. H₂O (10 mL) was added to quench the reaction and the mixture was extracted with ethyl acetate (3×15 mL). The organic layers were combined, dried over Na₂SO₄, and concentrated under reduced pressure to afford the crude product (216 mg) as a yellow oil, which was directly used for the next step without purification. MS: 1010.5 (M+H⁺).

Step (3S)-6'-chloro-5-(((1R,2R)-2-((1R)-methoxy(3-((1S)-1-(sulfamoyl((tetrahydrofuran-2-yl)methyl)amino)ethyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid

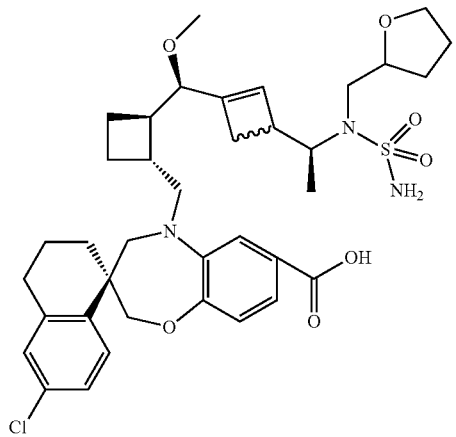 [SMILES: CO[C@@H](C1=CC([C@H](C)N(CC2CCCO2)S(N)(=O)=O)C1)[C@@H]1CC[C@H]1CN1C[C@@]2(CCCc3cc(Cl)ccc32)COc2ccc(C(=O)O)cc21]

In a nitrogen flushed 50 mL round-bottomed flask, tert-butyl (3S)-5-(((1R,2R)-2-((1R)-(3-((1S)-1-((N,N-bis(4-methoxybenzyl)sulfamoyl)((tetrahydrofuran-2-yl)methyl)amino)ethyl)cyclobut-1-en-1-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate (Step H, 216 mg, 0.21 mmol) was dissolved into DCM (10 mL) under nitrogen to give a yellow solution. TFA (105 mg, 1.1 mmol) was added in one portion, and the reaction mixture was stirred overnight. After removal of volatiles under reduced pressure, the residue was loaded onto a Biotage column and eluted with ethyl acetate/hexane from 0% to 80% to afford the title compound (110 mg, 72% over 2 steps) as a colorless oil. MS: 714.3 (M+H⁺).

Step J: (1S,12'S,13'S,16'R,16a'R,18a'R)-6-chloro-16'-methoxy-12'-methyl-11'-(((S)-tetrahydrofuran-2-yl)methyl)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7,16]triazacyclohexadecin]-8'(9'H)-one 10',10'-dioxide (Cpd. No. 30 Isomer 1) and (1S,12'S,13'S,16'R,16a'R,18a'R)-6-chloro-16'-methoxy-12'-methyl-11'-(((R)-tetrahydrofuran-2-yl)methyl)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7,16]triazacyclohexadecin]-8'(9'H)-one 10',10'-dioxide (Cpd. No. 30 Isomer 1) and (1S,12'S,13'R,16'R,16a'R,18a'R)-6-chloro-16'-methoxy-12'-methyl-11'-(((S)-tetrahydrofuran-2-yl)methyl)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7,16]triazacyclohexadecin]-8'(9'H)-one 10',10'-dioxide (Cpd. No. 30 Isomer 1) and (1S,12'S,13'R,16'R,16a'R,18a'R)-6-chloro-16'-methoxy-12'-methyl-11'-(((R)-tetrahydrofuran-2-yl)methyl)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7,16]triazacyclohexadecin]-8'(9'H)-one 10',10'-dioxide (Cpd. No. 30 Isomer 1)

In a nitrogen flushed 25 mL two-necked round-bottomed flask, (3S)-6'-chloro-5-(((1R,2R)-2-((1R)-methoxy(3-((1S)-1-(sulfamoyl((tetrahydrofuran-2-yl)methyl)amino)ethyl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid (Step I, 110 mg, 0.15 mmol), triethylamine (156 mg, 1.54 mmol), and DMAP (37.6 mg, 0.31 mmol) were dissolved into dry DCM (8 mL) under nitrogen to give a colorless solution. 2,4,6-tripropyl-1,3,5,2,4,6-trioxatriphosphinane 2,4,6-trioxide (147 mg, 0.46 mmol) was added at 0° C., and the reaction mixture was stirred for 3 h at room temperature. After removal of volatiles under reduced pressure, the residue was purified by C18 preparative-HPLC to afford four isomers (the first-eluting diastereomer was designated as Cpd. No. 30 isomer 1: 15 mg; the second-eluting diastereomer was designated as Cpd. No. 30 isomer 2: 11 mg; the third-eluting diastereomer was designated as Cpd. No. 30 isomer 3: 14 mg; the fourth-eluting diastereomer was designated as Cpd. No. 30 isomer 4: 2 mg) as white solid.

Cpd. No. 30 isomer 1: ¹H NMR (400 MHz, DMSO-d₆) δ 11.66 (s, 1H), 7.65 (d, J=8.5 Hz, 1H), 7.27 (d, J=8.5 Hz, 1H), 7.18 (s, 1H), 6.98-6.92 (m, 2H), 6.47 (s, 1H), 4.10 (dd, J=12.2, 5.6 Hz, 1H), 4.04-3.82 (m, 3H), 3.82-3.69 (m, 2H), 3.69-3.60 (m, 3H), 3.60-3.48 (m, 2H), 3.24-3.19 (m, 1H), 3.17 (d, J=5.1 Hz, 4H), 3.12-3.07 (m, 1H), 2.88-2.62 (m, 3H), 2.59-2.52 (m, 2H), 2.21-2.10 (m, 1H), 2.05-1.79 (m, 7H), 1.77-1.59 (m, 4H), 1.58-1.51 (m, 1H), 1.48-1.42 (m, 1H), 1.33 (d, J=6.6 Hz, 3H); MS: 696.3 (M+H⁺).

Cpd. No. 30 isomer 2: ¹H NMR (400 MHz, DMSO-d₆) δ 11.51 (s, 1H), 7.67 (d, J=8.5 Hz, 1H), 7.26 (d, J=8.5 Hz, 1H), 7.17 (s, 1H), 6.94-6.89 (m, 2H), 6.11 (s, 1H), 4.09 (d, J=12.4 Hz, 1H), 4.03-3.95 (m, 1H), 3.95-3.86 (m, 1H), 3.97-3.71 (m, 2H), 3.71-3.59 (m, 4H), 3.54-3.44 (m, 1H), 3.32-3.26 (m, 2H), 3.23 (d, J=2.4 Hz, 3H), 3.21-3.13 (m, 2H), 3.07-2.97 (m, 1H), 2.85-2.63 (m, 2H), 2.60-2.51 (m, 2H), 2.28-2.16 (m, 2H), 2.12-2.04 (m, 1H), 2.03-1.93 (m, 3H), 1.90-

1.76 (m, 5H), 1.71-1.60 (m, 1H), 1.60-1.50 (m, 1H), 1.49-1.36 (m, 1H), 1.27 (d, J=6.7 Hz, 3H); MS: 696.4 (M+H+).

Cpd. No. 30 isomer 3: $^1$H NMR (400 MHz, DMSO-d$_6$) δ 11.60 (s, 1H), 7.67 (d, J=8.5 Hz, 1H), 7.27 (d, J=9.2 Hz, 1H), 7.18 (s, 1H), 6.93 (d, J=7.7 Hz, 1H), 6.85 (d, J=8.2 Hz, 1H), 5.58 (s, 1H), 4.10-3.91 (m, 3H), 3.90-3.72 (m, 3H), 3.72-3.47 (m, 4H), 3.46-3.36 (m, 2H), 3.21-3.03 (m, 2H), 3.00 (s, 2H), 2.84-2.64 (m, 4H), 2.63-2.54 (m, 3H), 1.97-1.76 (m, 8H), 1.72-1.50 (m, 3H), 1.50-1.36 (m, 2H), 1.33 (s, 3H); MS: 696.6 (M+H+).

Cpd. No. 30 isomer 4: MS: 696.4 (M+H+).

Example 25

Synthesis of (1S,16'R,16a'R,18a'R)-6-chloro-16'-methoxy-3,4,16',16a',17',18',18a',19'-octahydro-1'H, 2H,3'H,12'H-spiro[naphthalene-1,2'-[5,7]etheno[11,13:13,15]dimethanocyclobuta[i][1,4]oxazepino[3,4-f][1]thia[2,7,16]triazacyclohexadecin]-8'(9'H)-one 10',10'-dioxide (Cpd. No. 31)

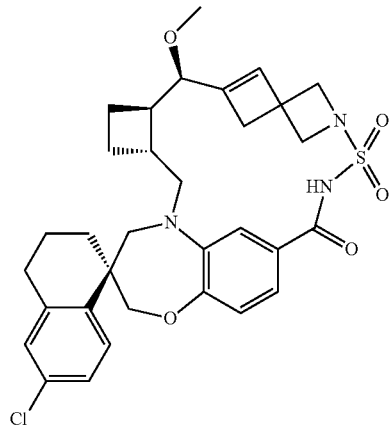 [SMILES: CO[C@H]1C2=CC3(C2)CN(C3)S(=O)(=O)NC(=O)c2ccc3c(c2)N(C[C@@H]2CC[C@H]21)C[C@@]1(CCCc2cc(Cl)ccc21)CO3]

Step A: tert-butyl 6-(((trifluoromethyl)sulfonyl)oxy)-2-azaspiro[3.3]hept-5-ene-2 carboxylate

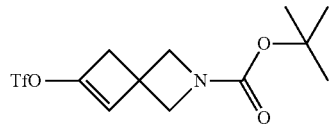 [SMILES: CC(C)(C)OC(=O)N1CC2(C=C(OS(=O)(=O)C(F)(F)F)C2)C1]

Under Ar, to a solution of tert-butyl 6-oxo-2-azaspiro[3.3]heptane-2-carboxylate (2 g, 9.47 mmol) and 1,1,1-trifluoro-N-phenyl-N-((trifluoromethyl)sulfonyl) methanesulfonamide (5.07 g, 14.2 mmol) in dry THF (10 mL) was added slowly KHMDS (1.0 M in THF, 11.4 mL, 11.4 mmol) at −78° C. The reaction mixture was stirred for 3 h at −78° C. Sat. NH$_4$Cl was added to quench the reaction, and the resulting mixture was extracted with ethyl acetate twice. The ethyl acetate layers were combined, washed with brine, dried over Na$_2$SO$_4$, and concentrated under reduced pressure to give a yellow oil, which was purified by silica gel column chromatography (hexane:EA, 1:0→10:1) to afford the title compound (1.8 g, 55%) as a colorless oil.

Step B: tert-butyl (S)-5-(((1R,2R)-2-((R)-(2-(tert-butoxycarbonyl)-2-azaspiro[3.3]hept-5-en-6-yl)(hydroxy)methyl)cyclobutyl)methyl)-6'-chloro-3',4,4',5-tetrahydro-2H,2'H-spiro[benzo-[b][1,4]oxazepine-3,1'-naphthalene]-7-carboxylate

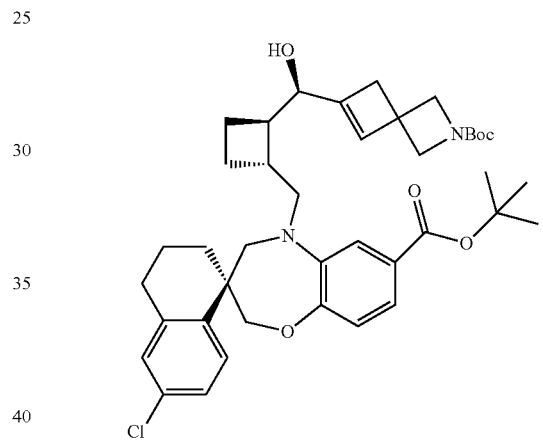

Under Ar, chromium(II) chloride (1487 mg, 12.1 mmol) and nickel(II) chloride (157 mg, 1.21 mmol) were dissolved into dry DMF (25 ml) to give a color suspension. A solution of tert-butyl (S)-6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Step M of EXAMPLE 20, 600 mg, 1.21 mmol) and tert-butyl 6-(((trifluoromethyl)sulfonyl)oxy)-2-azaspiro[3.3]hept-5-ene-2-carboxylate (Step A, 831 mg, 2.419 mmol) in dry DMF (8 mL) was added at room temperature, then the reaction mixture was stirred at 70° C. for 6 h. After cooling down to room temperature, sat. NaCl was added to quench the reaction and the mixture was extracted with ethyl acetate three times. The organic layers were combined, dried over Na$_2$SO$_4$, and concentrated under reduced pressure to give a brown oil, which was purified by silica gel column chromatography (hexane:ethyl acetate, 3:1) to afford the first-eluting diastereomer designated for the title compound (440 mg, 53%) as a colorless oil. MS: 690.9 (M+H+).

309

Step C: tert-butyl (S)-5-(((1R,2R)-2-((R)-(2-(tert-butoxycarbonyl)-2-azaspiro[3.3]hept-5-en-6-yl)(methoxy)methyl)cyclobutyl)methyl)-6'-chloro-3',4,4',5-tetrahydro-2H,2'H-spiro[benzo-[b][1,4]oxazepine-3,1'-naphthalene]-7-carboxylate

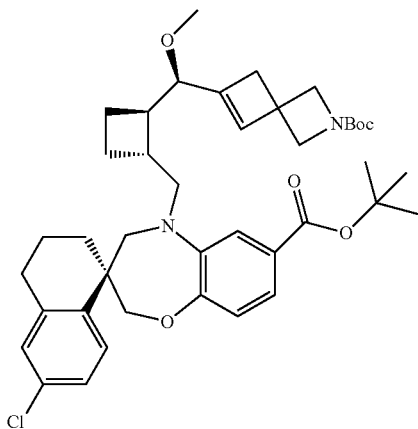 [SMILES: CO[C@@H](C1=CC2(C1)CN(C(=O)OC(C)(C)C)C2)[C@@H]1CC[C@H]1CN1C[C@@]2(CCCc3cc(Cl)ccc32)COc2ccc(C(=O)OC(C)(C)C)cc21]

Under Ar, tert-butyl (S)-5-(((1R,2R)-2-((R)-(2-(tert-butoxycarbonyl)-2-azaspiro[3.3]hept-5-en-6-yl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylate (Step B, 440 mg, 0.64 mmol) was dissolved into dry THF (6 mL) to give a colorless solution. NaH (127 mg, 3.18 mmol) was added and the reaction mixture was stirred at 30° C. for 30 min. MeI (361 mg, 2.55 mmol) was added and the reaction mixture was stirred for 16 h at 30° C. Sat. NaCl was added to quench the reaction and the resulting mixture was extracted with ethyl acetate twice. The organic layers were combined, dried over Na$_2$SO$_4$, and concentrated under reduced pressure to give a brown oil, which was purified by silica gel column chromatography (hexane:ethyl acetate, 6:1) to afford the title compound (380 mg, 85%) as a white solid. MS: 705.1 (M+H$^+$).

Step D: tert-butyl (S)-6'-chloro-5-(((1R,2R)-2-((R)-methoxy(2-azaspiro[3.3]hept-5-en-6-yl)methyl)cyclobutyl)methyl)-3',4,4',5-tetrahydro-2H,2'H-spiro[benzo[b][1,4]oxazepine-3,1'-naphthalene]-7-carboxylate

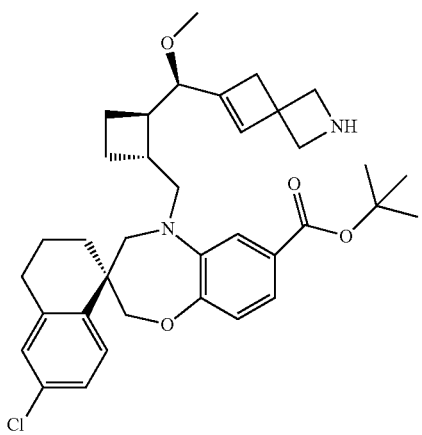 [SMILES: CO[C@@H](C1=CC2(CNC2)C1)[C@@H]1CC[C@H]1CN1C[C@@]2(CCCc3cc(Cl)ccc32)COc2ccc(C(=O)OC(C)(C)C)cc21]

310

Tert-butyl (S)-5-(((1R,2R)-2-((R)-(2-(tert-butoxycarbonyl)-2-azaspiro[3.3]hept-5-en-6-yl)(methoxy)methyl)cyclobutyl)methyl)-6'-chloro-3',4,4',5-tetrahydro-2H,2'H-spiro[benzo[b][1,4]oxazepine-3,1'-naphthalene]-7-carboxylate (Step C, 380 mg, 0.54 mmol) was dissolved into HCl solution in MeOH (2.8 M, 8 mL). The reaction mixture was stirred at 25° C. for 3 h. After removal of volatiles under reduced pressure, the resulting brown oil was purified by silica gel column chromatography (hexane:ethyl acetate, 2:1) to afford the title compound (240 mg, 74%) as a white solid. MS: 605.9 (M+H$^+$).

Step E: tert-butyl (S)-6'-chloro-5-(((1R,2R)-2-((R)-methoxy(2-(N-(4-methoxybenzyl)sulfamoyl)-2-azaspiro[3.3]hept-5-en-6-yl)methyl)cyclobutyl)methyl)-3',4,4',5-tetrahydro-2H,2'H-spiro[benzo[b][1,4]oxazepine-3,1'-naphthalene]-7-carboxylate

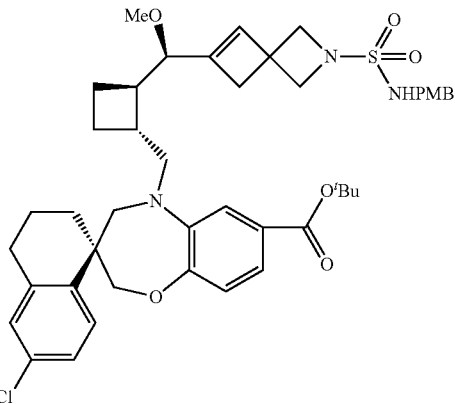

Under Ar, to a solution of N-(4-methoxybenzyl)-2-oxooxazolidine-3-sulfonamide (908 mg, 3.17 mmol) in dry acetonitrile (10 mL) was added tert-butyl (S)-6'-chloro-5-(((1R,2R)-2-((R)-methoxy(2-azaspiro[3.3]hept-5-en-6-yl)methyl)cyclobutyl)methyl)-3',4,4',5-tetrahydro-2H,2'H-spiro[benzo[b][1,4]oxazepine-3,1'-naphthalene]-7-carboxylate (Step D, 240 mg, 0.40 mmol) and DMAP (48.4 mg, 0.40 mmol). Triethylamine (803 mg, 7.93 mmol) was added and the reaction mixture was heated to 85° C. with microwave assistance for 3 h. After cooling down to room temperature and removal of volatiles under reduced pressure, the resulting brown oil was purified by a silica gel column chromatography (hexane:ethyl acetate, 2:1) to afford the title compound (125 mg, 39%) as a white solid. MS: 805.0 (M+H$^+$).

Step F: (S)-6'-chloro-5-(((1R,2R)-2-((R)-methoxy(2-sulfamoyl-2-azaspiro[3.3]hept-5-en-6-yl)methyl)cyclobutyl)methyl)-3',4,4',5-tetrahydro-2H,2'H-spiro[benzo[b][1,4]oxazepine-3,1'-naphthalene]-7-carboxylic acid

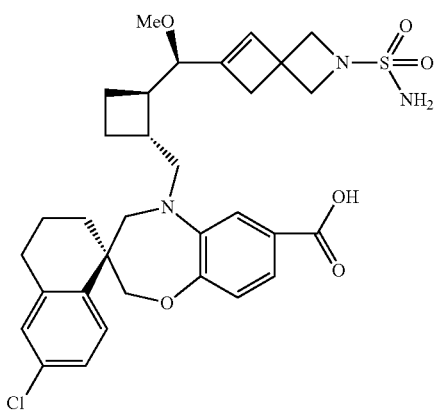 [SMILES: CO[C@@H](C1=CC2(C1)CN(S(N)(=O)=O)C2)[C@@H]1CC[C@H]1CN1C[C@@]2(CCCc3cc(Cl)ccc32)COc2ccc(C(=O)O)cc21]

Under Ar, to a solution of tert-butyl (S)-6'-chloro-5-(((1R,2R)-2-((R)-methoxy(2-(N-(4-methoxybenzyl)sulfamoyl)-2-azaspiro[3.3]hept-5-en-6-yl)methyl)cyclobutyl)methyl)-3',4,4',5-tetrahydro-2H,2'H-spiro[benzo[b][1,4]oxazepine-3,1'-naphthalene]-7-carboxylate (Step E, 125 mg, 0.16 mmol) in DCM (6 ML) was added TFA (6 mL). The reaction mixture was stirred at 25° C. for 3 h. After removal of volatiles under reduced pressure, the resulting brown oil was purified by silica gel column chromatography (dichloromethane:methanol, 10:1) to afford the title compound (62 mg, 64%) as a white solid. MS: 628.5 (M+H$^+$).

Step G: (1S,16'R,16a'R,18a'R)-6-chloro-16'-methoxy-3,4,16',16a',17',18',18a',19'-octahydro-1'H,2H,3'H,12'H-spiro[naphthalene-1,2'-[5,7]etheno[11,13:13,15]dimethanocyclobuta[i][1,4]oxazepino[3,4-f][1]thia[2,7,16]triazacyclohexadecin]-8'(9'H)-one 10',10'-dioxide (Cpd. No. 31)

Under Ar, to a solution of (S)-6'-chloro-5-(((1R,2R)-2-((R)-methoxy(2-sulfamoyl-2-azaspiro[3.3]hept-5-en-6-yl)methyl)cyclobutyl)methyl)-3',4,4',5-tetrahydro-2H,2'H-spiro[benzo[b][1,4]oxazepine-3,1'-naphthalene]-7-carboxylic acid (Step F, 55 mg, 0.09 mmol) in dry DCM (8 mL) was added DMAP (1.07 mg, 8.76 μmol) and Et$_3$N (26.6 mg, 0.26 mmol). At 0° C., 2,4,6-tripropyl-1,3,5,2,4,6-trioxatriphosphinane 2,4,6-trioxide (557 mg, 0.88 mmol) was added and the reaction mixture was stirred at 0° C. for 2 h. The reaction mixture was partitioned with dichloromethane and H$_2$O. The organic layer was separated, washed with brine, dried over Na$_2$SO$_4$, and concentrated under reduced pressure to give a brown oil, which was purified by C18 preparative-HPLC to afford the title compound (9.5 mg, 18%) as a white solid. $^1$H NMR (400 MHz, DMSO-d$_6$) δ 11.64 (brs, 1H), 7.69-7.67 (d, J=8.4 Hz, 1H), 7.27-7.25 (d, J=7.6 Hz, 1H), 7.18 (s, 1H), 7.08 (s, 1H), 6.98-6.96 (d, J=7.6 Hz, 1H), 6.93-6.91 (d, J=7.6 Hz, 1H), 6.02 (s, 1H), 4.50 (s, 1H), 4.37 (s, 1H), 4.15-4.12 (d, J=12.0 Hz, 2H), 3.88-3.86 (d, J=10.4 Hz, 1H), 3.72-3.69 (d, J=10.4 Hz, 1H), 3.66-3.22 (d, J=15.2 Hz, 1H), 3.25-3.2 (m, 1H), 3.18 (s, 3H), 2.83-2.62 (m, 5H), 2.33 (s, 1H), 2.20 (m, 1H), 2.01-1.98 (d, J=10.0 Hz, 3H), 1.83 (s, 2H), 1.58 (m, 3H), 1.45-1.43 (d, J=6.4 Hz, 1H), 1.24 (s, 1H); MS: 610.7 (M+H$^+$).

Example 26

Synthesis of (1S,11'R,12'S,13'R,16'R,16a'R,18a'R,E)-6-chloro-5-fluoro-16'-methoxy-11',12'-dimethyl-16'-(((S)-octahydro-2H-pyrido[1,2-a]pyrazin-2-yl)methyl)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 32)

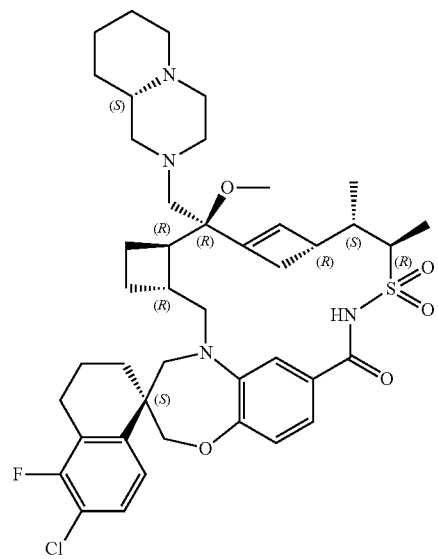

Step A: (2R,3S)-3-((R)-3-((R)-((1R,2R)-2-(((tert-butyldiphenylsilyl)oxy)methyl) cyclobutyl)(1,3-dithian-2-yl)(hydroxy)methyl)cyclobut-2-en-1-yl)-N,N-bis(4-methoxybenzyl)butane-2-sulfonamide (Isomer 1) and (2R,3S)-3-((R)-3-((S)-((1R,2R)-2-(((tert-butyldiphenylsilyl)oxy)methyl)cyclobutyl)(1,3-dithian-2-yl)(hydroxy)methyl)cyclobut-2-en-1-yl)-N,N-bis(4-methoxybenzyl)butane-2-sulfonamide (Isomer 2)

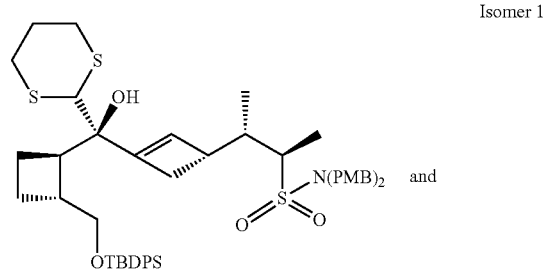

Isomer 1

-continued

Isomer 2

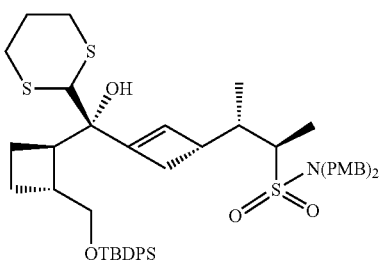

Under Ar, to a solution of 1,3-dithiane (6.47 g, 53.8 mmol) in dry THF (50 mL) was added n-butyllithium (2.5 M in THF, 17.3 mL, 43.1 mmol) slowly at −78° C., then the reaction was warmed up to 0° C. and stirred for 30 min to give Solution I. Under Ar, to another solution of (2R,3S)-3-((R)-3-((1R,2R)-2-(((tert-butyldiphenylsilyl)oxy)methyl) cyclobutane-1-carbonyl)cyclobut-2-en-1-yl)-N,N-bis(4-methoxybenzyl)butane-2-sulfonamide (Intermediate 5, 8.4 g, 10.8 mmol) in dry THF (50 mL) was added lanthanum (III) chloride bis(lithium chloride) complex (0.6 M in THF, 9 mL, 53.8 mmol) at 0° C. and the mixture was stirred for 30 min to give Solution II.

Solution II was added slowly into Solution I at −78° C., and the reaction mixture was stirred for 1 h. Aq. NH₄Cl was added to quench the reaction, and the resulting mixture was extracted with EA twice. The EA layers were combined, washed with brine, dried over Na₂SO₄, and concentrated under reduced pressure to give a yellow oil, which was purified by silica gel column chromatography (hexane:EA, 100:0→20:1) to afford the title compounds (Isomer 1: 5.4 g, 56%; Isomer 2: 3.85 g, 40%) as white solid. MS: 922.4 (M+Na⁺).

Step B: (2R,3S)-3-((R)-3-((R)-((1R,2R)-2-(((tert-butyldiphenylsilyl)oxy)methyl) cyclobutyl)(1,3-dithian-2-yl)(methoxy)methyl)cyclobut-2-en-1-yl)-N,N-bis(4-methoxybenzyl)butane-2-sulfonamide

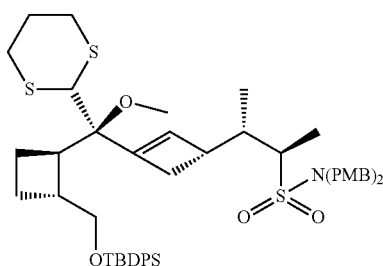

Under Ar, to a solution of (2R,3S)-3-((R)-3-((R)-((1R,2R)-2-(((tert-butyldiphenylsilyl)oxy)methyl)cyclobutyl)(1,3-dithian-2-yl)(hydroxy)methyl)cyclobut-2-en-1-yl)-N,N-bis(4-methoxybenzyl)butane-2-sulfonamide (Isomer 1 of Step A, 1.0 g, 11.8 mmol) in dry THF (15 mL) was added KHMDS (1.0 M in THF, 5.6 mL, 5.55 mmol) slowly at 0° C., and the reaction mixture was stirred for 1 h. MeI (0.79 g, 5.55 mmol) was added slowly at 0°, and the reaction mixture was stirred for another 1 h at room temperature. Aq. NH₄Cl was added to quench the reaction, and the resulting mixture was extracted with EA twice. The EA layers were combined, washed with brine, dried over Na₂SO₄, and concentrated under reduced pressure to give a yellow oil, which was purified by silica gel column chromatography (hexane:EA, 100:0→100:30) to afford the title compound (1.0 g, 98%) as a yellow solid. MS: 936.9 (M+Na⁺).

Step C: (2R,3S)-3-((R)-3-((R)-(1,3-dithian-2-yl)((1R,2R)-2-(hydroxymethyl) cyclobutyl)(methoxy) methyl)cyclobut-2-en-1-yl)-N,N-bis(4-methoxybenzyl)butane-2-sulfonamide

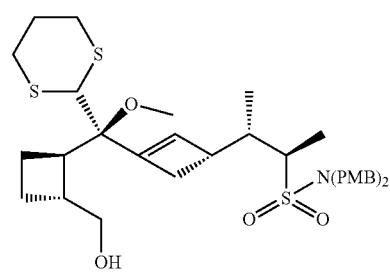

Under Ar, to a solution of (2R,3S)-3-((R)-3-((R)-((1R,2R)-2-(((tert-butyldiphenylsilyl)oxy)methyl)cyclobutyl)(1,3-dithian-2-yl)(methoxy)methyl)cyclobut-2-en-1-yl)-N,N-bis(4-methoxybenzyl)butane-2-sulfonamide (Step B, 0.82 g, 0.90 mmol) in dry THF (15 mL) was added TBAF.3H₂O (552 mg, 1.79 mmol) at room temperature. The reaction mixture was stirred for 6 h. Water was added to quench the reaction, and the resulting mixture was extracted with EA twice. The EA layers were combined, washed with brine, dried over Na₂SO₄, and concentrated under reduced pressure to give a yellow oil, which was purified by silica gel column chromatography (hexane:EA, 100:0→100:60) to afford the title compound (500 mg, 82%) as a light yellow oil. MS: 698.9 (M+Na⁺).

Step D: (2R,3S)-3-((R)-3-((R)-(1,3-dithian-2-yl)((1R,2R)-2-formylcyclobutyl) (methoxy)methyl) cyclobut-2-en-1-yl)-N,N-bis(4-methoxybenzyl)butane-2-sulfonamide

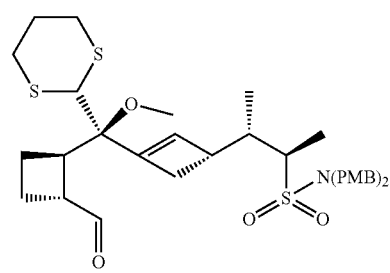

Under Ar, to a solution of (2R,3S)-3-((R)-3-((R)-(1,3-dithian-2-yl)((1R,2R)-2-(hydroxymethyl)cyclobutyl)(methoxy)methyl)cyclobut-2-en-1-yl)-N,N-bis(4-methoxybenzyl)butane-2-sulfonamide (Step C, 500 mg, 0.74 mmol) in dry DCM (15 mL) was added DMP (471 mg, 1.11 mmol) at 0° C. The reaction mixture was stirred for 30 min. Aq. NaHCO₃ was added to quench the reaction, followed by sodium thiosulfate aq, and the resulting mixture was stirred for 10 min. Then the resulting mixture was extracted with DCM twice. The organic layers were combined, washed with brine, dried over Na₂SO₄, and concentrated under reduced pressure to give the crude title compound (500 mg) as a yellow oil, which was directly used for the next step without purification. MS: 697.0 (M+Na⁺).

Step E: tert-butyl (S)-5-(((1R,2R)-2-((R)—((R)-3-((2S,3R)-3-(N,N-bis(4-methoxybenzyl)sulfamoyl)butan-2-yl)cyclobut-1-en-1-yl)(1,3-dithian-2-yl)(methoxy)methyl)cyclobutyl)methyl)-6'-chloro-5'-fluoro-3',4,4',5-tetrahydro-2H,2'H-spiro[benzo[b][1,4]oxazepine-3,1'-naphthalene]-7-carboxylate

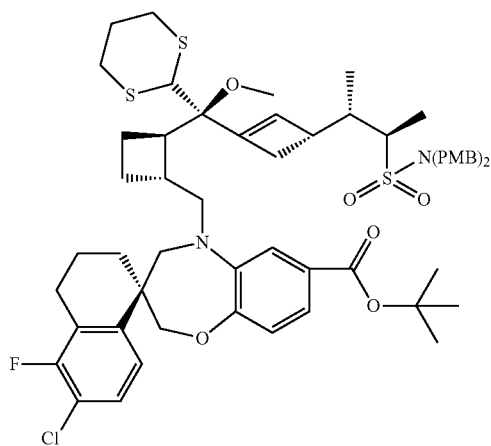

Under Ar, to a solution of the crude (2R,3S)-3-((R)-3-((R)-(1,3-dithian-2-yl)((1R,2R)-2-formylcyclobutyl)(methoxy)methyl)cyclobut-2-en-1-yl)-N,N-bis(4-methoxybenzyl)butane-2-sulfonamide (Step D, 500 mg) in dry THF (3 mL) was added tert-butyl (S)-6'-chloro-5'-fluoro-3',4,4',5-tetrahydro-2H,2'H-spiro[benzo[b][1,4]oxazepine-3,1'-naphthalene]-7-carboxylate (Intermediate 1, 310 mg, 0.74 mmol) at 0° C. The reaction mixture was stirred for 40 min. Phenylsilane (401 mg, 3.71 mmol), THF (3 mL) and TFA (6 mL) were added and the reaction mixture was stirred for overnight at room temperature. Water was added to quench the reaction, and the resulting mixture was extracted with EA twice. The EA layers were combined, washed with brine, dried over Na₂SO₄, and concentrated under reduced pressure to give a yellow oil, which was purified by silica gel column chromatography (hexane:EA, 100:0→100:25) to afford the title compound (730 g, 91% over 2 steps) as a light yellow oil. MS: 1075.7 (M+H⁺).

Step F: tert-butyl (S)-5-(((1R,2R)-2-((R)-1-((R)-3-((2S,3R)-3-(N,N-bis(4-methoxybenzyl)sulfamoyl)butan-2-yl)cyclobut-1-en-1-yl)-1-methoxy-2-oxoethyl)cyclobutyl)methyl)-6'-chloro-5'-fluoro-3',4,4',5-tetrahydro-2H,2'H-spiro[benzo[b][1,4]oxazepine-3,1'-naphthalene]-7-carboxylate

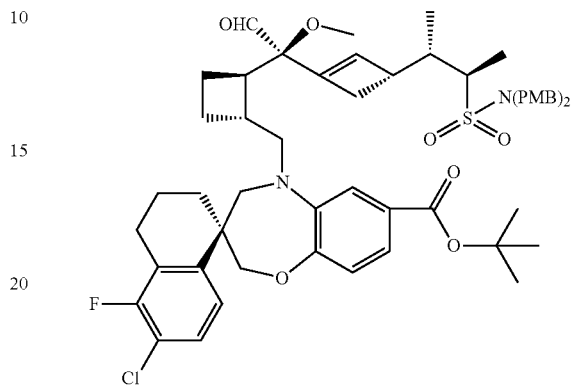

Under Ar, to a solution of tert-butyl (S)-5-(((1R,2R)-2-((R)—((R)-3-((2S,3R)-3-(N,N-bis(4-methoxybenzyl)sulfamoyl)butan-2-yl)cyclobut-1-en-1-yl)(1,3-dithian-2-yl)(methoxy)methyl)cyclobutyl)methyl)-6'-chloro-5'-fluoro-3',4,4',5-tetrahydro-2H,2'H-spiro[benzo[b][1,4]oxazepine-3,1'-naphthalene]-7-carboxylate (Step E, 730 mg, 0.68 mmol) in ACN/H₂O (16 mL/4 mL) was added CaCO₃ (0.68 g, 6.79 mmol), and MeI (0.96 g, 6.79 mmol) at room temperature. The reaction mixture was stirred for 24 h at 55° C. Brine was added to quench the reaction, and the resulting mixture was extracted with EA twice. The EA layers were combined, washed with brine, dried over Na₂SO₄, and concentrated under reduced pressure to give a yellow oil, which was purified by silica gel column chromatography (hexane:EA, 100:0→100:30) to afford the title compound (630 mg, 94%) as a yellow oil. MS: 985.7 (M+H⁺).

Step G: (S)-6'-chloro-5'-fluoro-5-(((1R,2R)-2-((R)-1-methoxy-2-oxo-1-((R)-3-((2S,3R)-3-sulfamoylbutan-2-yl)cyclobut-1-en-1-yl)ethyl)cyclobutyl)methyl)-3',4,4',5-tetrahydro-2H,2'H-spiro[benzo[b][1,4]oxazepine-3,1'-naphthalene]-7-carboxylic acid

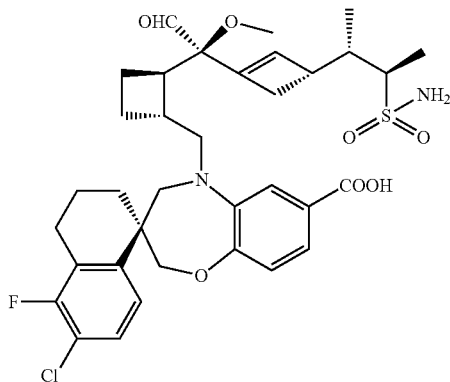 [SMILES: CO[C@@](C=O)(C1=C[C@H]([C@H](C)[C@@H](C)S(N)(=O)=O)C1)[C@@H]1CC[C@H]1CN1C[C@@]2(CCCc3c2ccc(Cl)c3F)COc2ccc(C(=O)O)cc21]

Under Ar, to a solution of tert-butyl (S)-5-(((1R,2R)-2-((R)-1-((R)-3-((2S,3R)-3-(N,N-bis(4-methoxybenzyl)sulfamoyl)butan-2-yl)cyclobut-1-en-1-yl)-1-methoxy-2-oxoethyl)cyclobutyl)methyl)-6'-chloro-5'-fluoro-3',4,4',5-tetrahydro-2H,2'H-spiro[benzo[b][1,4]oxazepine-3,1'-naphthalene]-7-carboxylate (Step F, 630 mg, 0.64 mmol) in dry DCM (3 mL) was added TFA (3 mL) at 0° C. The reaction mixture was allowed to warm up to room temperature and stirred overnight. After removal of volatiles under reduced pressure, the residue was purified by silica gel column chromatography (DCM:MeOH, 100:0→100:6) to afford the title compound (440 mg, quantitatively) as a brown solid. MS: 689.7 (M+H$^+$).

Step H: (1S,11'R,12'S,13'R,16'R,16a'R,18a'R,E)-6-chloro-5-fluoro-16'-methoxy-11',12'-dimethyl-8'-oxo-3,4,8',9',12',13',16',16a',17',18',18a',19'-dodecahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecine]-16'-carbaldehyde 10',10'-dioxide

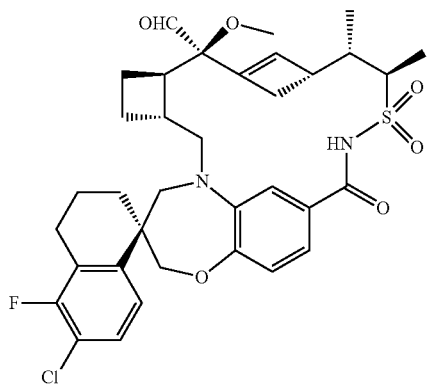 [SMILES: CO[C@@]1(C=O)C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3]

Under Ar, to a solution of (S)-6'-chloro-5'-fluoro-5-(((1R,2R)-2-((R)-1-methoxy-2-oxo-1-((R)-3-((2 S,3R)-3-sulfamoylbutan-2-yl)cyclobut-1-en-1-yl)ethyl)cyclobutyl)methyl)-3',4,4',5-tetrahydro-2H,2'H-spiro[benzo[b][1,4]oxazepine-3,1'-naphthalene]-7-carboxylic acid (Step G, 440 mg, 0.64 mmol) in dry DCM (100 mL) was added DIEPA (825 mg, 6.38 mmol), DMAP (78 mg, 0.64 mmol), an T3P (2.03 g, 3.19 mmol) at 0° C. The resulting mixture was stirred for 2 h at 0° C. Water was added to quench the reaction, and the resulting mixture was extracted with DCM twice. The DCM layers were combined, washed with brine, dried over Na$_2$SO$_4$, and concentrated under reduced pressure to give an off-white solid, which was purified by silica gel column chromatography (DCM:MeOH, 100:0→100:5) to afford the title compound (380 mg, 89%) as a yellow solid. MS: 671.5 (M+H$^+$).

Step I: (1 S, 11'R,12'S,13'R,16'R,16a'R,18a'R,E)-6-chloro-5-fluoro-16'-methoxy-11',12'-dimethyl-16'-(((S)-octahydro-2H-pyrido[1,2-a]pyrazin-2-yl)methyl)-3,4,12,'13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 32)

Under Ar, to a solution of (1S,11'R,12'S,13'R,16'R,16a'R,18a'R,E)-6-chloro-5-fluoro-16'-methoxy-11',12'-dimethyl-8'-oxo-3,4,8',9',12',13',16',16a',17',18',18a',19'-dodecahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecine]-16'-carbaldehyde 10',10'-dioxide (Step H, 50.0 mg, 0.074 mmol) in dry DCM (10 mL) was added titanium(IV) isopropoxide (212 mg, 0.745 mmol), (S)-octahydro-2H-pyrido[1,2-a]pyrazine dihydrochloride (104 mg, 0.745 mmol) and DIEA (96 mg, 0.745 mmol) at 30° C. The reaction mixture was stirred for 2 h. Sodium triacetoxyhydroborate (158 mg, 0.745 mmol) was added, and the reaction mixture was stirred for further 24 h at 30° C. Aq. NH$_4$Cl was added to quench the reaction and the resulting mixture was extracted with DCM twice. The DCM layers were combined, washed with brine, dried over Na$_2$SO$_4$, and concentrated under reduced pressure to give a yellow oil, which was purified by C18 preparative-HPLC to afford the title compound (21 mg, 28%) as a white solid. $^1$H NMR (400 MHz, DMSO-d$_6$) δ 11.78 (s, 1H), 7.52 (d, J=8.7 Hz, 1H), 7.49-7.43 (m, 1H), 6.92-6.88 (m, 2H), 6.70 (s, 1H), 6.28 (s, 1H), 4.11 (d, J=12.3 Hz, 1H), 4.05 (t, J=7.6 Hz, 1H), 3.95 (d, J=12.4 Hz, 1H), 3.75-3.65 (m, 2H), 3.34-3.26 (m, 4H), 3.22-3.05 (m, 2H), 2.98 (s, 3H), 2.97-2.92 (m, 3H), 2.92-2.82 (m, 2H), 2.69 (dd, J=13.4, 3.9 Hz, 1H), 2.65-2.52 (m, 3H), 2.45-2.18 (m, 5H), 2.02-1.94 (m, 2H), 1.93-1.76 (m, 5H), 1.73-1.57 (m, 5H), 1.48-1.36 (m, 3H), 1.32 (d, J=7.2 Hz, 3H), 0.91 (d, J=6.6 Hz, 3H); MS: 795.9 (M+H$^+$).

Example 27

The protocol described in EXAMPLE 26 was used to give the following compounds:

(1S,11'R,12'S,13'R,16'R,16a'R,18a'R,E)-6-chloro-5-fluoro-16'-methoxy-11',12'-dimethyl-16'-(morpholinomethyl)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 33)

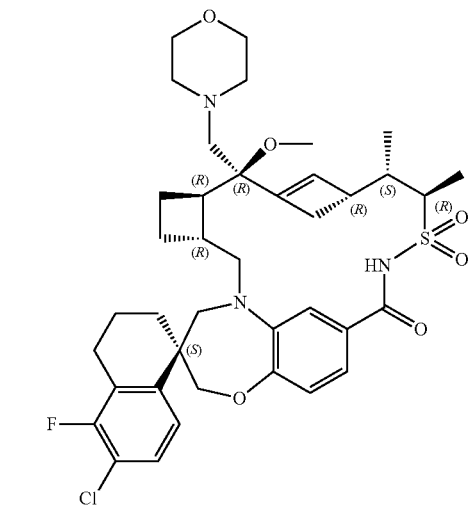

Yield: 5.6 mg as a white solid. $^1$H NMR (400 MHz, DMSO-d$_6$) δ 11.78 (s, 1H), 7.53 (d, J=8.6 Hz, 1H), 7.48-7.43 (m, 1H), 6.94-6.89 (m, 2H), 6.75 (s, 1H), 6.35 (s, 1H), 4.14-4.05 (m, 2H), 3.94 (d, J=12.3 Hz, 1H), 3.89-3.78 (m,

319

2H), 3.78-3.72 (m, 1H), 3.65 (d, J=14.2 Hz, 2H), 3.22-3.00 (m, 8H), 2.91-2.53 (m, 8H), 2.25 (d, J=12.4 Hz, 1H), 2.04-1.85 (m, 4H), 1.82-1.59 (m, 5H), 1.46-1.24 (m, 2H), 1.33 (d, J=7.1 Hz, 3H), 0.92 (d, J=6.6 Hz, 3H); MS: 742.5 (M+H$^+$).

(1S,11'R,12'S,13'R,16'R,16a'R,18a'R,E)-6-chloro-5-fluoro-16'-(((R)-hexahydropyrazino[2,1-c][1,4]oxazin-8(1H)-yl)methyl)-16'-methoxy-11',12'-dimethyl-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 34)

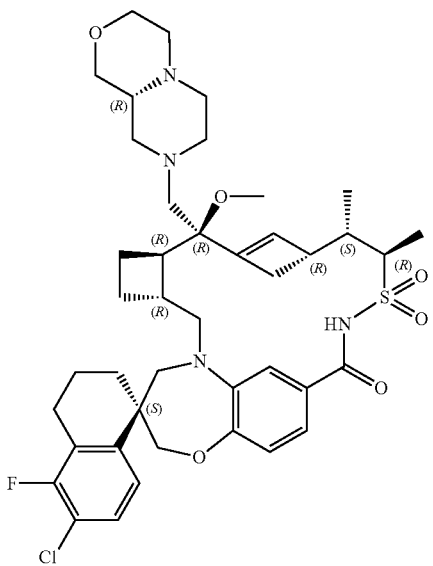

Yield: 29 mg as a white solid. $^1$H NMR (400 MHz, DMSO-d$_6$) δ 11.77 (s, 1H), 7.52 (d, J=8.6 Hz, 1H), 7.49-7.43 (m, 1H), 6.93-6.88 (m, 2H), 6.70 (s, 1H), 6.29 (s, 1H), 4.17-3.88 (m, 4H), 3.75-3.62 (m, 2H), 3.55-3.46 (m, 2H), 3.36-3.13 (m, 10H), 3.06-3.92 (m, 5H), 2.92-2.83 (m, 2H), 2.74-2.51 (m, 3H), 2.34-2.16 (m, 2H), 2.05-1.84 (m, 4H), 1.83-1.56 (m, 5H), 1.49-1.20 (m, 2H), 1.32 (d, J=7.1 Hz, 3H), 0.91 (d, J=6.6 Hz, 3H); MS: 797.7 (M+H$^+$).

320

(1S,11'R,12'S,13'R,16'R,16a'R,18a'R,E)-6-chloro-5-fluoro-16'-methoxy-11',12'-dimethyl-16'-((4-methylpiperazin-1-yl)methyl)-3,4,12',13',16',16a',17',18',18a',19'-decahydro-1'H,2H,3'H, 11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 35)

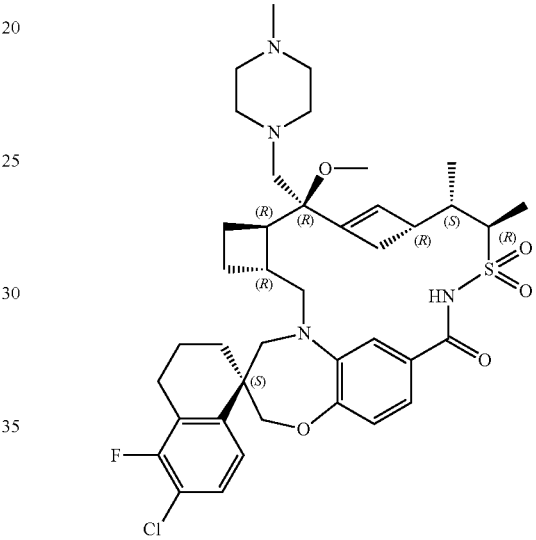

Yield: 7.8 mg as a white solid. $^1$H NMR (400 MHz, DMSO-d$_6$) δ 11.77 (s, 1H), 7.53 (d, J=8.8 Hz, 1H), 7.48-7.43 (m, 1H), 6.93-6.89 (m, 2H), 6.70 (s, 1H), 6.30 (s, 1H), 4.10 (d, J=12.3 Hz, 1H), 4.06 (d, J=7.5 Hz, 1H), 3.96 (d, J=12.3 Hz, 1H), 3.65 (d, J=14.3 Hz, 2H), 3.34-3.22 (m, 6H), 3.16-3.05 (m, 2H), 2.98 (s, 3H), 2.96-2.83 (m, 4H), 2.80 (s, 3H), 2.70 (dd, J=13.2, 4.1 Hz, 1H), 2.64-2.55 (m, 2H), 2.55-2.52 (m, 1H), 2.37-2.18 (m, 2H), 2.03-1.96 (m, 1H), 1.95-1.87 (m, 2H), 1.79-1.57 (m, 5H), 1.48-1.37 (m, 2H), 1.32 (d, J=7.2 Hz, 3H), 0.91 (d, J=6.7 Hz, 3H); MS: 755.7 (M+H$^+$).

1    S,11'R,12'S,13'R,16'R,16a'R,18a'R,E)-6-chloro-5-fluoro-16'-methoxy-11',12'-dimethyl-16'-((4-(tetrahydro-2H-pyran-4-yl)piperazin-1-yl)methyl)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 36)

| 321 | 322 |
|---|---|
| | (1S,11'R,12'S,13'R,16'R,16a'R,18a'R,E)-6-chloro-5-fluoro-16'-methoxy-11',12'-dimethyl-16'-((4-morpholinopiperidin-1-yl)methyl)-3,4,12',13',16',16a',17',18',18a',19'-decahydro-1'H,2H,3'H, 11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 37) |

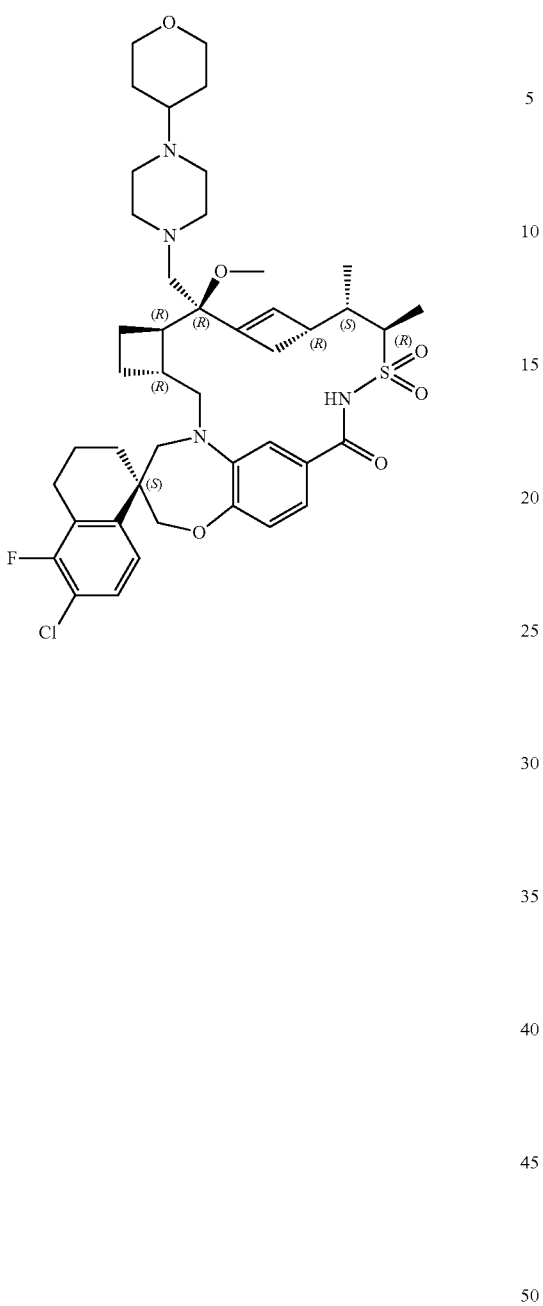

Yield: 6.7 mg as a white solid. $^1$H NMR (400 MHz, DMSO-d$_6$) δ 11.77 (s, 1H), 7.53 (d, J=8.7 Hz, 1H), 7.49-7.43 (m, 1H), 6.94-6.89 (m, 2H), 6.71 (s, 1H), 6.31 (s, 1H), 4.10 (d, J=12.3 Hz, 1H), 4.06 (d, J=7.7 Hz, 1H), 4.04-3.93 (m, 3H), 3.64 (d, J=13.8 Hz, 2H), 3.57-3.49 (m, 10H), 3.15-2.83 (m, 6H), 2.99 (s, 3H), 2.70 (dd, J=13.2, 4.1 Hz, 1H), 2.65-2.52 (m, 3H), 2.42-2.34 (m, 1H), 2.31 (d, J=14.3 Hz, 1H), 2.21 (d, J=13.2 Hz, 1H), 2.05-1.87 (m, 5H), 1.80-1.55 (m, 6H), 1.49-1.35 (m, 1H), 1.32 (d, J=7.2 Hz, 3H), 0.91 (d, J=6.7 Hz, 3H); MS: 825.7 (M+H$^+$).

Yield: 8.1 mg as a white solid. $^1$H NMR (400 MHz, DMSO-d$_6$) δ 11.81 (s, 1H), 7.53 (d, J=8.8 Hz, 1H), 7.49-7.43 (m, 1H), 6.96-6.89 (m, 2H), 6.73 (s, 1H), 6.34 (s, 1H), 4.11-3.91 (m, 5H), 3.88-3.69 (m, 3H), 3.65 (d, J=14.0 Hz, 2H), 3.55-3.30 (m, 12H), 3.10-2.93 (m, 6H), 2.87 (d, J=15.7 Hz, 2H), 2.81-2.09 (m, 2H), 2.69-2.52 (m, 3H), 2.30-1.85 (m, 3H), 1.82-1.60 (m, 6H), 1.48-1.30 (m, 1H), 1.32 (d, J=7.2 Hz, 3H), 0.91 (d, J=6.6 Hz, 3H); MS: 825.7 (M+H$^+$).

323

(1S,11'R,12'S,13'R,16'R,16a'R,18a'R,E)-6-chloro-5-fluoro-16'-methoxy-1',12'-dimethyl-16'-((4-(methylsulfonyl)piperazin-1-yl)methyl)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 38)

324

(1S,11'R,12'S,13'R,16'R,16a'R,18a'R,E)-6-chloro-5-fluoro-16'-methoxy-11',12'-dimethyl-16'-((4-methyl-3-oxopiperazin-1-yl)methyl)-3,4,12',13',16',16a',17',18',18a',19'-decahydro-1'H,2H,3'H, 11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 39)

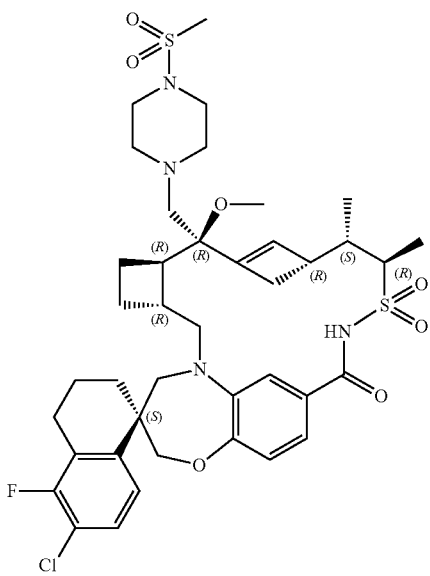

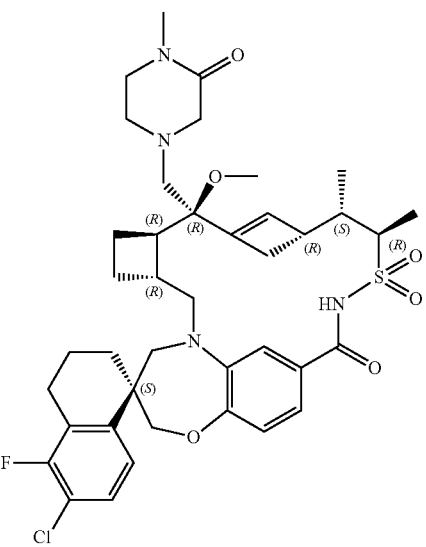

Yield: 7.5 mg as a white solid. $^1$H NMR (400 MHz, DMSO-$d_6$) δ 11.78 (s, 1H), 7.52 (d, J=8.6 Hz, 1H), 7.49-7.43 (m, 1H), 6.95-6.89 (m, 2H), 6.73 (s, 1H), 6.33 (s, 1H), 4.14-4.03 (m, 2H), 3.95 (d, J=12.7 Hz, 1H), 3.65 (d, J=14.6 Hz, 1H), 3.50-3.28 (m, 12H), 3.03 (s, 3H), 2.96 (s, 3H), 2.90-2.83 (m, 1H), 2.63-2.51 (m, 3H), 2.27-2.20 (m, 1H), 2.04-1.60 (m, 11H), 1.46-1.35 (m, 1H), 1.32 (d, J=7.2 Hz, 3H), 0.91 (d, J=6.6 Hz, 3H); MS: 819.8 (M+H$^+$).

Yield: 7.5 mg as a white solid. $^1$H NMR (400 MHz, DMSO-$d_6$) δ 11.76 (s, 1H), 7.51 (d, J=8.7 Hz, 1H), 7.48-7.42 (m, 1H), 6.92-6.88 (m, 2H), 6.72 (s, 1H), 6.30 (s, 1H), 4.11-4.04 (m, 2H), 3.96 (d, J=12.4 Hz, 1H), 3.64 (d, J=14.2 Hz, 1H), 3.47-3.30 (m, 6H), 3.01 (s, 3H), 3.00-2.97 (m, 1H), 2.90-2.82 (m, 3H), 2.85 (s, 3H), 2.74-2.68 (d, J=9.5 Hz, 1H), 2.65-2.52 (m, 3H), 2.22 (d, J=12.8 Hz, 1H), 2.05-1.84 (m, 4H), 1.81-1.58 (m, 5H), 1.43-1.35 (m, 3H), 1.32 (d, J=7.2 Hz, 3H), 0.91 (d, J=6.7 Hz, 3H); MS: 769.7 (M+H$^+$).

325

(1S,11'R,12'S,13'R,16'R,16a'R,18a'R,E)-6-chloro-5-fluoro-16'-methoxy-11',12'-dimethyl-16'-(((3S,5R)-3,4,5-trimethylpiperazin-1-yl)methyl)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 40)

326

(1S,11'R,12'S,13'R,16'R,16a'R,18a'R,E)-6-chloro-5-fluoro-16'-methoxy-11',12'-dimethyl-16'-(piperazin-1-ylmethyl)-3,4,12',13',16',16a',17',18',18a',19'-decahydro-1'H,2H,3'H, 11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 41)

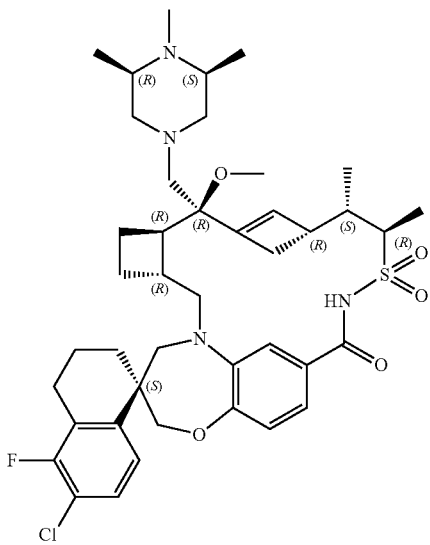

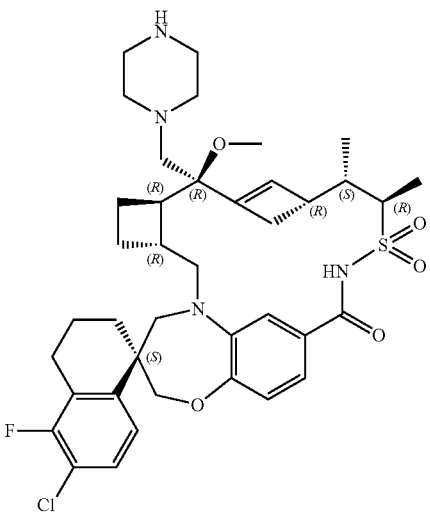

Yield: 8.9 mg as a white solid. $^1$H NMR (400 MHz, DMSO-$d_6$) δ 11.78 (s, 1H), 7.52 (d, J=8.8 Hz, 1H), 7.49-7.43 (m, 1H), 6.91-6.88 (m, 2H), 6.71 (s, 1H), 6.27 (s, 1H), 4.11 (d, J=12.4 Hz, 1H), 4.05 (d, J=7.7 Hz, 1H), 3.95 (d, J=12.4 Hz, 1H), 3.74-3.63 (m, 2H), 3.45-3.23 (m, 7H), 3.07-2.85 (m, 3H), 2.97 (s, 3H), 2.84 (d, J=4.5 Hz, 3H), 2.72-2.55 (m, 3H), 2.37-2.14 (m, 4H), 2.03-1.85 (m, 4H), 1.80-1.57 (m, 5H), 1.32 (d, J=4.3 Hz, 3H), 1.31 (d, J=3.4 Hz, 3H), 1.26 (d, J=6.4 Hz, 3H), 0.91 (d, J=6.7 Hz, 3H); MS: 783.7 (M+H$^+$).

Yield: 1 mg as a white solid. $^1$H NMR (400 MHz, DMSO-$d_6$) δ 11.77 (s, 1H), 8.51 (s, 1H), 7.52 (d, J=8.8 Hz, 1H), 7.48-7.42 (m, 1H), 6.93-6.68 (m, 2H), 6.70 (s, 1H), 6.29 (s, 1H), 4.13-4.05 (m, 2H), 3.95 (d, J=12.3 Hz, 1H), 3.69-3.60 (m, 2H), 3.30-2.83 (m, 12H), 2.98 (s, 3H), 2.74-2.65 (m, 1H), 2.64-2.52 (m, 2H), 2.35-2.17 (m, 2H), 2.03-1.85 (m, 7H), 1.75-1.65 (m, 2H), 1.50-1.42 (m, 2H), 1.32 (d, J=7.3 Hz, 3H), 0.91 (d, J=6.7 Hz, 3H); MS: 741.6 (M+H$^+$).

327

(1S,11'R,12'S,13'R,16'R,16a'R,18a'R,E)-6-chloro-5-fluoro-16'-methoxy-11',12'-dimethyl-16'-((3-oxopiperazin-1-yl)methyl)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 42)

328

(1S,11'R,12'S,13'R,16'R,16a'R,18a'R,E)-6-chloro-16'-(((3S,5R)-3,5-dimethylpiperazin-1-yl)methyl)-5-fluoro-16'-methoxy-11',12'-dimethyl-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 43)

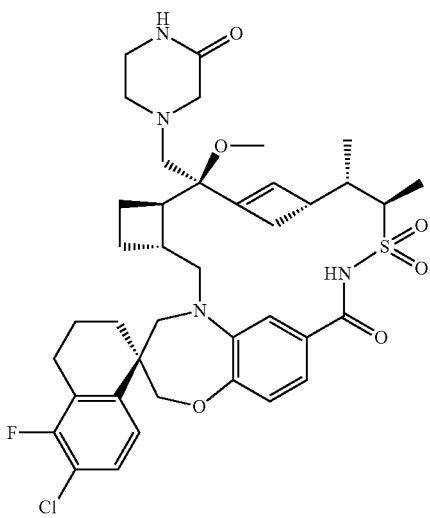 [SMILES: CO[C@@]1(CN2CCNC(=O)C2)C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3]

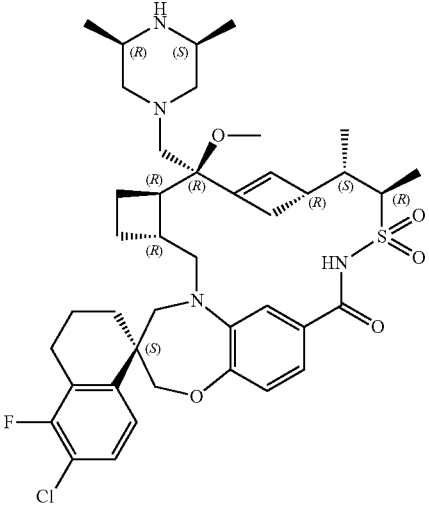

Yield: 2.7 mg as a white solid. $^1$H NMR (400 MHz, DMSO-$d_6$) δ 11.75 (s, 1H), 7.50 (d, J=8.6 Hz, 1H), 7.48-7.42 (m, 1H), 6.93-6.88 (m, 2H), 6.72 (s, 1H), 6.30 (s, 1H), 4.08 (d, J=5.3 Hz, 1H), 4.06 (s, 1H), 3.97 (d, J=12.1 Hz, 1H), 3.65 (d, J=14.0 Hz, 1H), 3.41-3.25 (m, 6H), 3.05-2.98 (m, 1H), 3.01 (s, 3H), 2.90-2.82 (m, 3H), 2.74-2.65 (m, 1H), 2.60-2.52 (m, 3H), 2.21 (d, J=14.0 Hz, 1H), 2.06-1.83 (m, 4H), 1.79-1.71 (m, 1H), 1.68-1.60 (m, 1H), 1.42-1.20 (m, 6H) 1.32 (d, J=7.2 Hz, 3H), 0.91 (d, J=6.6 Hz, 3H); MS: 755.7 (M+H$^+$).

Yield: 5.8 mg as a white solid. $^1$H NMR (400 MHz, DMSO-$d_6$) δ 11.78 (s, 1H), 8.87 (d, J=9.5 Hz, 1H), 7.51 (d, J=8.8 Hz, 1H), 7.49-7.43 (m, 1H), 6.92-6.87 (m, 2H), 6.71 (s, 1H), 6.27 (s, 1H), 4.10 (d, J=12.2 Hz, 1H), 4.07-4.02 (m, 1H), 3.96 (d, J=12.6 Hz, 1H), 3.73-3.63 (m, 2H), 3.33-3.15 (m, 4H), 2.98 (s, 3H), 2.96-2.81 (m, 4H), 2.71-2.55 (m, 4H), 2.32-2.15 (m, 3H), 2.05-1.95 (m, 3H), 1.93-1.83 (m, 2H), 1.80-1.57 (m, 5H), 1.48-1.36 (m, 1H), 1.32 (d, J=7.2 Hz, 3H), 1.22 (d, J=6.8 Hz, 3H), 1.17 (d, J=6.5 Hz, 3H), 0.91 (d, J=6.7 Hz, 3H); MS: 769.6 (M+H$^+$).

329

(1S,11'R,12'S,13'R,16'R,16a'R,18a'R,E)-6-chloro-16'-ethoxy-5-fluoro-16'-(((S)-hexahydropyrazino[2,1-c][1,4]oxazin-8(1H)-yl)methyl)-11',12'-dimethyl-3,4,12,'13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 44)

330

(1S,11'R,12'S,13'R,16'R,16a'R,18a'R,E)-6-chloro-16'-ethoxy-5-fluoro-16'-(((R)-hexahydropyrazino[2,1-c][1,4]oxazin-8(1H)-yl)methyl)-11',12'-dimethyl-3,4,12,'13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 45)

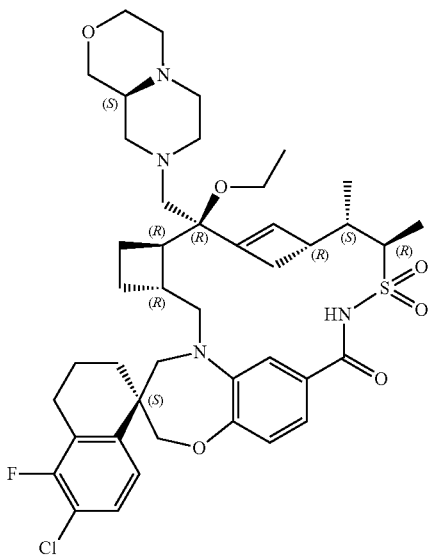

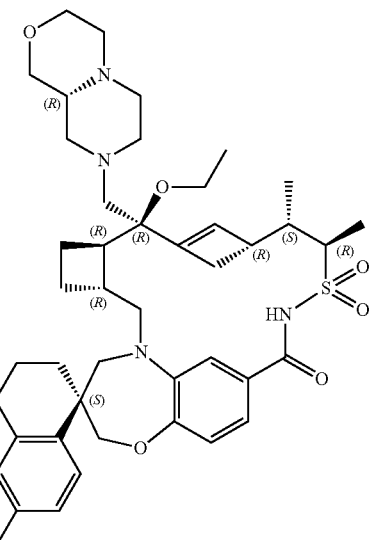

Yield: 24 mg as a white solid. $^1$H NMR (400 MHz, DMSO-$d_6$) δ 11.78 (s, 1H), 7.54 (d, J=8.7 Hz, 1H), 7.50-7.43 (m, 1H), 6.95-6.89 (m, 2H), 6.72 (s, 1H), 6.27 (s, 1H), 4.18-3.86 (m, 5H), 3.74-3.61 (m, 3H), 3.50-3.20 (m, 10H), 3.11-3.04 (m, 1H), 3.02-2.81 (m, 4H), 2.73-2.53 (m, 4H), 2.34-2.04 (m, 2H), 2.03-1.83 (m, 4H), 1.82-1.56 (m, 5H), 1.47-1.36 (m, 2H), 1.31 (d, J=7.2 Hz, 3H), 0.99 (t, J=6.9 Hz, 3H), 0.90 (d, J=6.6 Hz, 3H); MS: 811.7 (M+H$^+$).

Yield: 21.3 mg as a white solid. $^1$H NMR (400 MHz, DMSO-$d_6$) δ 11.78 (s, 1H), 7.52 (d, J=8.7 Hz, 1H), 7.49-7.42 (m, 1H), 6.94-6.88 (m, 2H), 6.69 (s, 1H), 6.25 (s, 1H), 4.16-3.88 (m, 5H), 3.77-3.63 (m, 3H), 3.56-3.48 (m, 2H), 3.38-3.28 (m, 8H), 3.11-3.05 (m, 1H), 3.01-2.83 (m, 4H), 2.73-2.53 (m, 3H), 2.46-2.25 (m, 3H), 2.21 (d, J=13.1 Hz, 1H), 2.03-1.87 (m, 4H), 1.83-1.53 (m, 5H), 1.48-1.37 (m, 2H), 1.31 (d, J=7.2 Hz, 3H), 1.01 (t, J=6.9 Hz, 3H), 0.90 (d, J=6.7 Hz, 3H); MS: 811.7 (M+H$^+$).

331

(1S,11'R,12'S,13'R,16'R,16a'R,18a'R,E)-6-chloro-16'-ethoxy-5-fluoro-11',12'-dimethyl-16'-((S)-octahydropyrazino[2,1-c][1,4]oxazine-8-carbonyl)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 46)

332

(1S,11'R,12'S,13'R,16'R,16a'R,18a'R,E)-6-chloro-5-fluoro-16'-(((S)-hexahydropyrazino[2,1-c][1,4]oxazin-8(1H)-yl)methyl)-16'-hydroxy-11',12'-dimethyl-3,4,12,'13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 47)

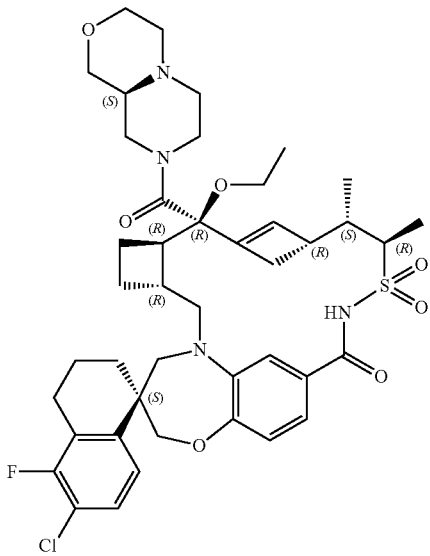

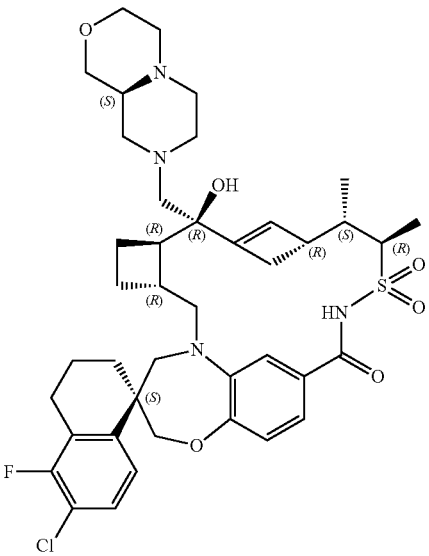

Yield: 6.8 mg (from side product of Cpd. No. 44 at Step I) as a white solid. $^1$H NMR (400 MHz, DMSO-d$_6$) δ 11.78 (s, 1H), 7.52-7.44 (m, 2H), 6.89 (d, J=8.1 Hz, 1H), 6.82 (d, J=8.1 Hz, 1H), 6.65 (s, 1H), 6.23 (s, 1H), 4.68-4.49 (m, 1H), 4.25-3.98 (m, 4H), 3.92 (d, J=12.8 Hz, 1H), 3.69 (d, J=13.8 Hz, 1H), 3.40-3.23 (m, 9H), 3.05-2.78 (m, 5H), 2.76-2.68 (m, 1H), 2.63-2.51 (m, 3H), 2.28-2.17 (m, 1H), 2.04-1.87 (m, 4H), 1.81-1.53 (m, 5H), 1.50-1.23 (m, 3H), 1.32 (d, J=7.2 Hz, 3H), 1.08 (t, J=6.7 Hz, 3H), 0.91 (t, J=7.6 Hz, 3H); MS: 825.6 (M+H$^+$).

Yield: 9.9 mg) as a white solid. $^1$H NMR (400 MHz, DMSO-d$_6$) δ 11.78 (s, 1H), 7.53 (d, J=8.8 Hz, 1H), 7.49-7.43 (m, 1H), 6.96-6.86 (m, 2H), 6.75 (s, 1H), 6.12 (s, 1H), 4.10 (d, J=12.5 Hz, 1H), 4.05 (d, J=7.1 Hz, 1H), 3.92 (d, J=12.5 Hz, 1H), 3.65 (d, J=13.9 Hz, 1H), 3.36-3.16 (m, 12H), 3.04-2.91 (m, 1H), 2.87 (dd, J=13.2, 3.7 Hz, 2H), 2.65-2.52 (m, 3H), 2.49-2.47 (m, 2H), 2.39 (d, J=9.8 Hz, 1H), 2.13 (d, J=13.1 Hz, 1H), 2.06-1.81 (m, 4H), 1.78-1.55 (m, 5H), 1.46-1.37 (m, 3H), 1.32 (d, J=7.2 Hz, 3H), 0.92 (d, J=6.6 Hz, 3H); MS: 783.6 (M+H$^+$).

333

(1S,11'R,12'S,13'R,16'R,16a'R,18a'R,E)-6-chloro-5-fluoro-16'-(((R)-hexahydropyrazino[2,1-c][1,4]oxazin-8(1H)-yl)methyl)-16'-hydroxy-11',12'-dimethyl-3,4,12,'13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 48)

334

(1S,11'R,12'S,13'R,16'R,16a'R,18a'R,E)-16'-(4-acetylpiperazin-1-yl)methyl)-6-chloro-5-fluoro-16'-methoxy-11',12'-dimethyl-3,4,12,'13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 49)

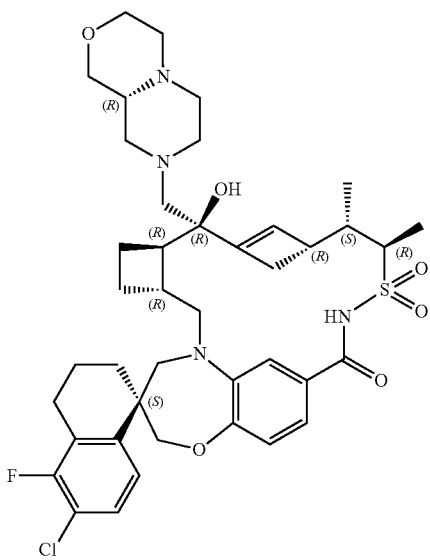

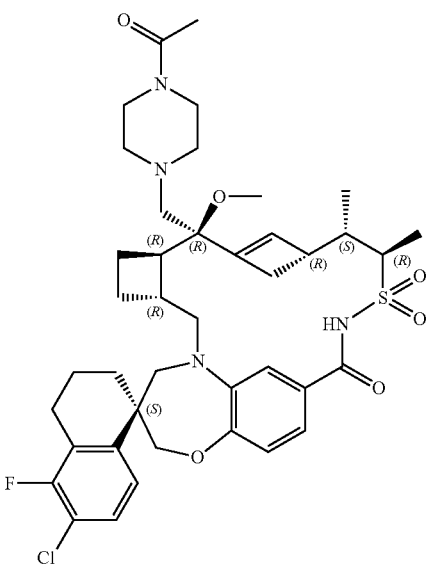

Yield: 4.3 mg as a white solid. $^1$H NMR (400 MHz, DMSO-d$_6$) δ 11.78 (s, 1H), 7.52 (d, J=8.6 Hz, 1H), 7.49-7.42 (m, 1H), 6.94-6.86 (m, 2H), 6.74 (s, 1H), 6.13 (s, 1H), 4.11 (d, J=12.4 Hz, 1H), 4.05 (d, J=7.2 Hz, 1H), 3.92 (d, J=12.4 Hz, 2H), 3.65 (d, J=14.0 Hz, 2H), 3.55-3.48 (m, 4H), 3.31-3.05 (m, 7H), 3.03-2.91 (m, 2 H), 2.87 (d, J=13.6 Hz, 2H), 2.64-2.54 (m, 3H), 2.39 (d, J=9.1 Hz, 1H), 2.14 (d, J=13.0 Hz, 1H), 2.04-1.84 (m, 4H), 1.81-1.56 (m, 5H), 1.48-1.38 (m, 3H), 1.32 (d, J=7.2 Hz, 3H), 0.92 (d, J=6.6 Hz, 3H); MS: 783.6 (M+H$^+$).

Yield: 6.3 mg as a white solid. $^1$H NMR (400 MHz, DMSO-d$_6$) δ 11.77 (s, 1H), 7.53 (d, J=8.6 Hz, 1H), 7.48-7.42 (m, 1H), 6.93-6.89 (m, 2H), 6.75 (s, 1H), 6.34 (s, 1H), 4.13-4.01 (m, 2H), 3.95 (d, J=12.2 Hz, 1H), 3.65 (d, J=14.1 Hz, 1H), 3.48-3.41 (m, 4H), 3.34-3.19 (m, 4H), 3.11-2.99 (m, 4H), 2.92-2.70 (m, 3H), 2.69-2.51 (m, 4H), 2.25 (d, J=13.0 Hz, 1H), 2.03 (s, 3H), 2.00-1.85 (m, 4H), 1.83-1.59 (m, 5H), 1.47-1.22 (m, 3H), 1.33 (d, J=7.2 Hz, 3H), 0.92 (d, J=6.7 Hz, 3H); MS: 783.6 (M+H$^+$).

335

(1S,11'R,12'S,13'R,16'R,16a'R,18a'R,E)-6-chloro-5-fluoro-16'-methoxy-11',12'-dimethyl-16'44-(oxetan-3-yl)piperazin-1-yl)methyl)-3,4,12',13',16',16a',17',18',18a',19'-decahydro-1'H,2H,3'H, 11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 50)

336

(1S,11'R,12'S,13'R,16'R,16a'R,18a'R,E)-6-chloro-5-fluoro-16'-(((S)-hexahydropyrazino[2,1-c][1,4]oxazin-8(1H)-yl)methyl)-16'-methoxy-11',12'-dimethyl-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 51)

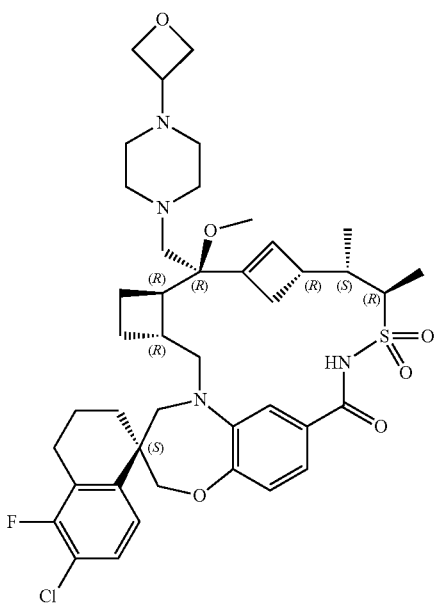

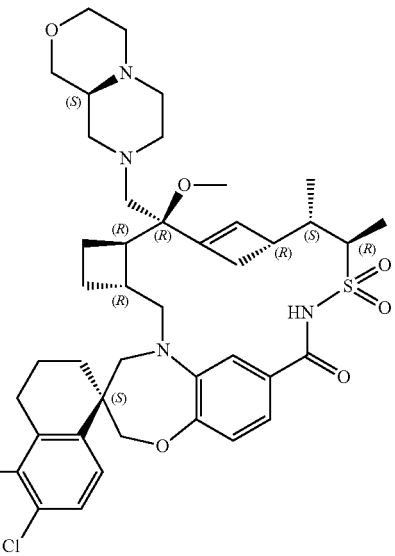

Yield: 42.9 mg as a white solid. $^1$H NMR (400 MHz, DMSO-$d_6$) δ 11.78 (s, 1H), 7.53 (d, J=8.7 Hz, 1H), 7.49-7.42 (m, 1H), 6.95-6.87 (m, 2H), 6.72 (s, 1H), 6.32 (s, 1H), 4.80-4.61 (m, 4H), 4.14-4.02 (m, 2H), 3.94 (d, J=12.2 Hz, 1H), 3.76-3.63 (m, 8H), 3.35 (d, J=14.0 Hz, 2H), 3.02-2.92 (m, 1H), 2.99 (s, 3H), 2.90-2.81 (m, 3H), 2.74-2.68 (m, 1H), 2.66-2.52 (m, 3H), 2.48-2.32 (m, 1H), 2.21 (d, J=13.3 Hz, 1H), 2.04-1.83 (m, 4H), 1.83-1.55 (m, 5H), 1.45-1.29 (m, 2H), 1.32 (d, J=7.1 Hz, 3H), 0.91 (d, J=6.4 Hz, 3H); MS: 797.5 (M+H$^+$).

Yield: 9.3 mg as a white solid. $^1$H NMR (400 MHz, DMSO-$d_6$) δ 7.50 (d, J=8.6 Hz, 1H), 7.48-7.41 (m, 1H), 6.92-6.83 (m, 2H), 6.70 (s, 1H), 6.27 (s, 1H), 4.15-3.90 (m, 3H), 3.74 (d, J=10.5 Hz, 1H), 3.69-3.55 (m, 3H), 3.53-3.43 (m, 1H), 3.42-3.30 (m, 3H), 3.14-3.03 (m, 1H), 3.03-2.70 (m, 5H), 2.95 (s, 3H), 2.70-2.55 (m, 5H), 2.44-2.35 (m, 1H), 2.30-2.15 (m, 4H), 2.05-1.85 (m, 4H), 1.79-1.60 (m, 6H), 1.47-1.34 (m, 1H), 1.29 (d, J=6.7 Hz, 3H), 0.90 (d, J=6.3 Hz, 3H); MS: 797.6 (M+H$^+$).

(1S,11'R,12'S,13'R,16'R,16a'R,18a'R,E)-6-chloro-5-fluoro-16'-methoxy-11',12'-dimethyl-16'-((methylamino)methyl)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 52)

Example 28

Synthesis of N-(((1S,11'R,12'S,13'R,16'R,16a'R,18a'R,E)-6-chloro-5-fluoro-16'-methoxy-11',12'-dimethyl-10',10'-dioxido-8'-oxo-3,4,8',9',12',13',16',16a',17',18',18a',19'-dodecahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-16'-yl)methyl)-N-methylacetamide (Cpd. No. 53)

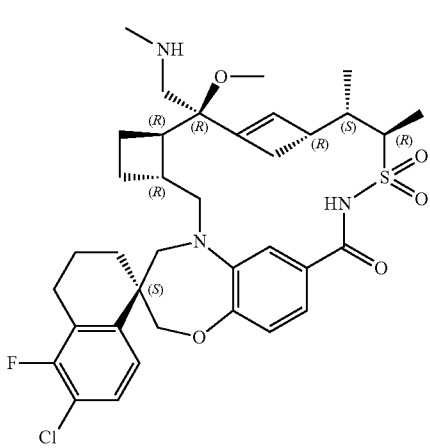

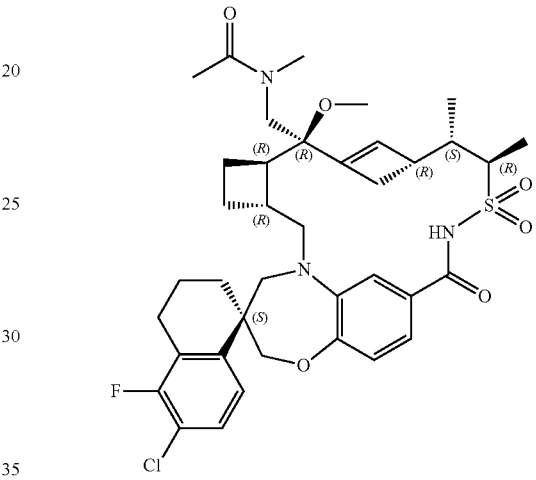

In a 50 mL round-bottomed flask, to a solution of (1S,11'R,12'S,13'R,16'R,16a'R,18a'R,E)-6-chloro-5-fluoro-16'-methoxy-11',12'-dimethyl-16'-((methylamino)methyl)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 52, 25 mg, 0.036 mmol) in dry DCM (5 mL) was added Et$_3$N (11 mg, 0.109 mmol) and DMAP (0.9 mg, 7.29 μmol) under Ar. AcCl (5.72 mg, 0.073 mmol, 2) was added in one portion at 0° C., and the reaction mixture was stirred at room temperature for 1 h. H$_2$O (20 mL) was added to the reaction mixture followed by extraction with DCM twice. The organic layers were combined, dried over Na$_2$SO$_4$ and concentrated under reduced pressure to give a yellow oil, which was purified by C18 preparative-HPLC to afford the title compound (2 mg, 8%) as a white solid. $^1$H NMR (400 MHz, DMSO-d$_6$) δ 11.69 (s, 1H), 7.50 (d, J=8.7 Hz, 1H), 7.47-7.41 (m, 1H), 6.91-6.86 (m, 2H), 6.71 (s, 1H), 6.32 (s, 1H), 4.20 (d, J=15.1 Hz, 1H), 4.12-4.03 (m, 2H), 4.01-3.92 (m, 1H), 3.65 (d, J=14.0 Hz, 1H), 3.27-3.18 (m, 2H), 3.05 (s, 3H), 3.02 (s, 3H), 2.90-2.81 (m, 1H), 2.74-2.63 (m, 2H), 2.61-2.51 (m, 3H), 2.34-2.18 (m, 2H), 2.08 (s, 3H), 1.94-1.84 (m, 3H), 1.77-1.59 (m, 5H), 1.43-1.34 (m, 1H), 1.32 (d, J=7.2 Hz, 3H), 0.91 (d, J=6.6 Hz, 3H); MS: 728.5 (M+H$^+$).

Yield: 13 mg as a white solid. $^1$H NMR (400 MHz, DMSO-d$_6$) δ 11.76 (s, 1H), 7.53 (d, J=8.7 Hz, 1H), 7.49-7.42 (m, 2H)), 6.96-6.88 (m, 2H), 6.73 (s, 1H), 6.39 (s, 1H), 4.13-4.02 (m, 2H), 3.98-3.89 (m, 2H), 3.65 (d, J=14.1 Hz, 1H), 3.60-3.50 (m, 2H), 3.15-3.04 (m, 2H), 3.02 (s, 3H), 2.94-2.85 (m, 1H), 2.80-2.52 (m, 8H), 2.48-2.41 (m, 1H), 2.27 (d, J=13.4 Hz, 1H), 2.01-1.86 (m, 3H), 1.80-1.68 (m, 4H), 1.68-1.59 (m, 1H), 1.45-1.36 (m, 2H), 1.33 (d, J=7.2 Hz, 3H), 0.92 (d, J=6.7 Hz, 3H); MS: 686.5 (M+H$^+$).

Example 29

Synthesis of (1S,11'R,12'S,13'R,16'R,16a'R,18a'R, E)-6-chloro-5-fluoro-16'-(((S)-hexahydropyrazino[2, 1-c][1,4]oxazin-8(1H)-yl)methyl)-16'-methoxy-11', 12'-dimethyl-3,4,12',13',16',16a',17',18',18a',19'-decahydro-1'H,2H,3'H, 11'H-spiro[naphthalene-1,2'-[5,7]etheno[13,15]methanocyclobuta[i][1,4]oxazepino[3,4-f][1]thia[2,5,7]triazacyclohexadecin]-8'(9'H)-one 10',10'-dioxide (Cpd. No. 54)

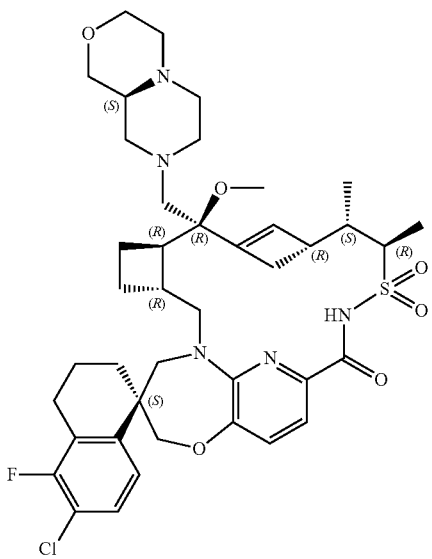

Step A: Methyl (S)-6-chloro-5-fluoro-5'-(((1R,2R)-2-formylcyclobutyl)methyl)-3,4,4',5'-tetrahydro-2H, 2'H-spiro[naphthalene-1,3'-pyrido[3,2-b][1,4]oxazepine]-7'-carboxylate

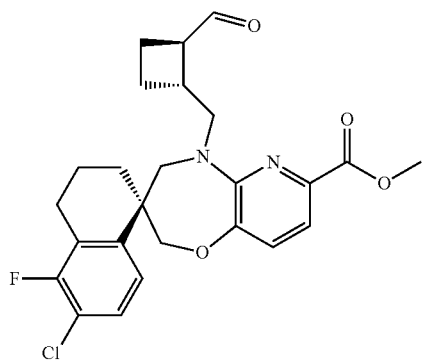 [SMILES: COC(=O)c1ccc2c(n1)N(C[C@@H]1CC[C@H]1C=O)C[C@@]1(CCCc3c1ccc(Cl)c3F)CO2]

Under Ar, to a solution of Intermediate 4 (1.9 g, 4.0 mmol) in dry DCM (20 mL) was added DMP (3.39 g, 8.00 mmol) at 0° C., and the reaction mixture was stirred for 1 h. Aq. NaHCO₃ was added to quench the reaction, followed by aq. sodium thiosulfate, and the resulting mixture was stirred for 10 min. The resulting mixture was extracted with DCM twice. The DCM layers were combined, washed with brine, dried over Na₂SO₄, and concentrated under reduced pressure to give a white solid, which was purified by silica gel column chromatography (hexane:EA, 100:0→100:30) to afford the title compound (1.79 g, 95%) as a white solid. MS: 473.4 (M+H⁺).

Step B: Methyl (1S)-5'-(((1R,2R)-2-(((R)-3-((2S, 3R)-3-(N,N-bis(4-methoxybenzyl)sulfamoyl)butan-2-yl)cyclobut-1-en-1-yl)(hydroxy)methyl)cyclobutyl)methyl)-6-chloro-5-fluoro-3,4,4',5'-tetrahydro-2H,2'H-spiro[naphthalene-1,3'-pyrido[3, 2-b][1,4]oxazepine]-7'-carboxylate

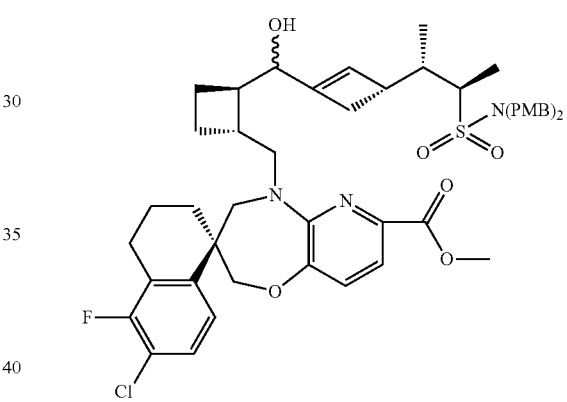

Under Ar, to a solution of chromium(II) chloride (2.326 g, 18.9 mmol) and nickel(II) chloride (0.245 g, 1.89 mmol) in dry DMF (10 mL) was added a solution of methyl (S)-6-chloro-5-fluoro-5'-(((1R,2R)-2-formylcyclobutyl)methyl)-3,4,4',5'-tetrahydro-2H,2'H-spiro[naphthalene-1,3'-pyrido[3,2-b][1,4]oxazepine]-7'-carboxylate (Step A, 1.79 g, 3.78 mmol) and (R)-3-((2S,3R)-3-(N,N-bis(4-methoxybenzyl)sulfamoyl)butan-2-yl)cyclobut-1-en-1-yl trifluoromethanesulfonate (Isomer 1, Step H of Intermediate 5, 2.84 g, 4.92 mmol) in dry DMF (5 mL) at 60° C., and the reaction mixture was stirred for 6 h. After cooling down to room temperature, H₂O was added to quench the reaction, and the resulting mixture was extracted with EA twice. The EA layers were combined, washed with brine, dried over Na₂SO4, and concentrated under reduced pressure to give a green oil, which was purified by silica gel column chromatography (hexane:EA, 100:0→100:40) to afford the title compound (2.9 g, 85%) as a white solid. MS: 902.7 (M+H⁺).

Step C: (1S)-5'-(((1R,2R)-2-(((R)-3-((2S,3R)-3-(N,N-bis(4-methoxybenzyl)sulfamoyl)butan-2-yl)cyclobut-1-en-1-yl)(hydroxy)methyl)cyclobutyl)methyl)-6-chloro-5-fluoro-3,4,4',5'-tetrahydro-2H,2'H-spiro[naphthalene-1,3'-pyrido[3,2-b][1,4]oxazepine]-7'-carboxylic acid

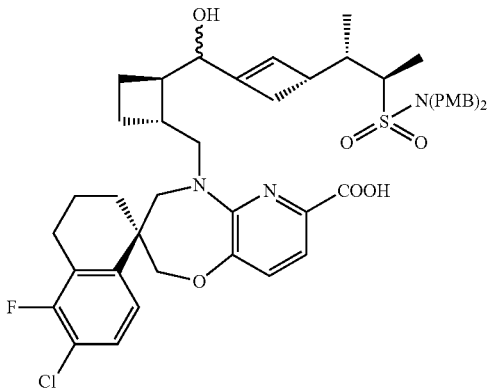

Under Ar, the solution of methyl (1S)-5'-(((1R,2R)-2-(((R)-3-((2S,3R)-3-(N,N-bis(4-methoxybenzyl)sulfamoyl)butan-2-yl)cyclobut-1-en-1-yl)(hydroxy)methyl)cyclobutyl)methyl)-6-chloro-5-fluoro-3,4,4',5'-tetrahydro-2H,2'H-spiro[naphthalene-1,3'-pyrido[3,2-b][1,4]oxazepine]-7'-carboxylate (Step B, 1.3 g, 1.44 mmol) in a mixed solution of THF/MeOH/15% NaOH (5 mL/5 mL/5 mL) was stirred at 80° C. for 1 h. After cooling down to room temperature, the resulting mixture was extracted with EA twice. The EA layers were combined, washed with brine, dried over Na$_2$SO$_4$, and concentrated under reduced pressure to give an off white solid, which was purified by silica gel column chromatography (DCM:MeOH, 100:0→100:5) to afford the title compound (1.25 g, 98%) as a white solid. MS: 888.7 (M+H$^+$).

Step D: (1S)-5'-(((1R,2R)-2-(acetoxy((R)-3-((2S,3R)-3-(N,N-bis(4-methoxybenzyl)sulfamoyl)butan-2-yl)cyclobut-1-en-1-yl)methyl)cyclobutyl)methyl)-6-chloro-5-fluoro-3,4,4',5'-tetrahydro-2H,2'H-spiro[naphthalene-1,3'-pyrido[3,2-b][1,4]oxazepine]-7'-carboxylic acid

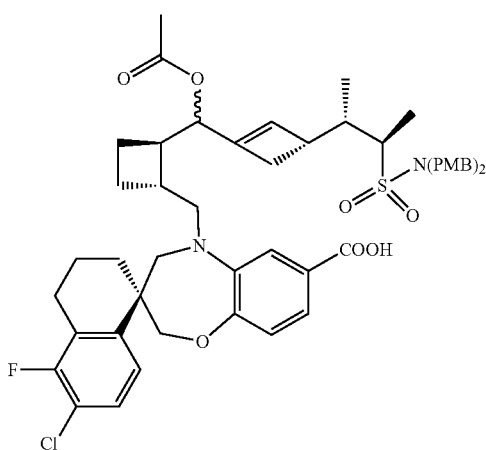

Under Ar, to a solution of (1S)-5'-(((1R,2R)-2-(((R)-3-((2S,3R)-3-(N,N-bis(4-methoxybenzyl)sulfamoyl)butan-2-yl)cyclobut-1-en-1-yl)(hydroxy)methyl)cyclobutyl)methyl)-6-chloro-5-fluoro-3,4,4',5'-tetrahydro-2H,2'H-spiro[naphthalene-1,3'-pyrido[3,2-b][1,4]oxazepine]-7'-carboxylic acid (Step C, 1.25 g, 1.41 mmol) in dry DCM (20 mL) was added DMAP (0.034 g, 0.281 mmol), and DIPEA (0.273 g, 2.11 mmol) at 0° C., followed by acetic anhydride (0.158 g, 1.55 mmol). The reaction mixture was allowed to warm up to room temperature and stirred for 24 h. Water was added to quench the reaction, and the resulting mixture was extracted with EA twice. The EA layers were combined, washed with brine, dried over Na$_2$SO$_4$, and concentrated under reduced pressure to give a white solid, which was purified by silica gel column chromatography (DCM:MeOH, 100:0→100:5) to afford the title compound (1.08 g, 82%) as a white solid. MS: 930.9 (M+H$^+$).

Step E: (1S)-5'-(((1R,2R)-2-(acetoxy((R)-3-((2S,3R)-3-sulfamoylbutan-2-yl)cyclobut-1-en-1-yl)methyl)cyclobutyl)methyl)-6-chloro-5-fluoro-3,4,4',5'-tetrahydro-2H,2'H-spiro[naphthalene-1,3'-pyrido[3,2-b][1,4]oxazepine]-7'-carboxylic acid

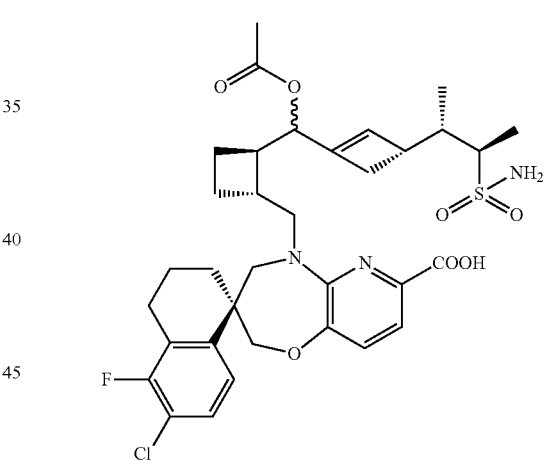

Under Ar, to a solution of (1S)-5'-(((1R,2R)-2-(acetoxy((R)-3-((2S,3R)-3-(N,N-bis(4-methoxybenzyl)sulfamoyl)butan-2-yl)cyclobut-1-en-1-yl)methyl)cyclobutyl)methyl)-6-chloro-5-fluoro-3,4,4',5'-tetrahydro-2H,2'H-spiro[naphthalene-1,3'-pyrido[3,2-b][1,4]oxazepine]-7'-carboxylic acid (Step D, 1.08 g, 1.62 mmol) in dry DCM (10 mL) was added TFA (10 mL) at 0° C., and the reaction mixture was allowed to warm up to room temperature and stirred for 5 h. After removal of volatiles under reduced pressure, the residue was purified by silica gel column chromatography (DCM:MeOH, 100:0→100:5) to afford the title compound (850 mg, quantitatively) as a white solid. MS: 690.8 (M+H$^+$).

Step F: (1S,11'R,12'S,13'R,16a'R,18a'R,E)-6-chloro-5-fluoro-11',12'-dimethyl-10',10'-dioxido-8'-oxo-3,4,8',9',12',13',16',16a',17',18',18a',19'-dodecahydro-1'H,2H,3'H, 11'H-spiro[naphthalene-1,2'-[5,7]etheno[13,15]methanocyclobuta[i][1,4]oxazepino[3,4-f][1]thia[2,5,7]triazacyclohexadecin]-16'-yl acetate Step G: (1 S, 11'R,12'S,13'R,16a'R,18a'R,E)-6-chloro-5-fluoro-16'-hydroxy-11',12'-dimethyl-3,4,12',13',16',16a',17',18',18a',19'-decahydro-1'H,2H,3'H,1 PH-spiro[naphthalene-1,2'-[5,7]etheno[13,15]methanocyclobuta[i][1,4]oxazepino[3,4-f][1]thia[2,5,7]triazacyclohexadecin]-8'(9'H)-one 10',10'-dioxide

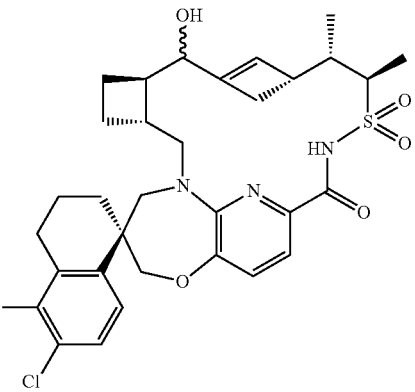

Under Ar, the reaction mixture of (1S,11'R,12'S,13'R,16a'R,18a'R,E)-6-chloro-5-fluoro-11',12'-dimethyl-10',10'-dioxido-8'-oxo-3,4,8',9',12',13',16',16a',17',18',18a',19'-dodecahydro-1'H,2H,3'H,11'H-spiro[naphthalene-1,2'-[5,7]etheno[13,15]methanocyclobuta[i][1,4]oxazepino[3,4-f][1]thia[2,5,7]triazacyclohexadecin]-16'-yl acetate (Step F, 850 mg, 1.26 mmol) in a mixed solvent of THF/MeOH/15% NaOH (3 mL/3 mL/3 mL) was stirred at 25° C. for 1 h. The resulting mixture was extracted with EA twice. The EA layers were combined, washed with brine, dried over Na$_2$SO$_4$, and concentrated under reduced pressure to give an off-white solid, which was purified by silica gel column chromatography (DCM:MeOH, 100:0→100:5) to afford the title compound (800 mg, quantitatively) as a white solid. MS: 630.5 (M+H$^+$).

Step H: (1S,11'R,12'S,13'R,16a'R,18a'R,E)-6-chloro-5-fluoro-11',12'-dimethyl-3,4,12,'13',17',18',18a',19'-octahydro-1'H,2H,3'H, 1 PH-spiro[naphthalene-1,2'-[5,7]etheno[13,15]methanocyclobuta[i][1,4]oxazepino[3,4-f][1]thia[2,5,7]triazacyclohexadecine]-8',16'(9'H,16a'H)-dione 10',10'-dioxide

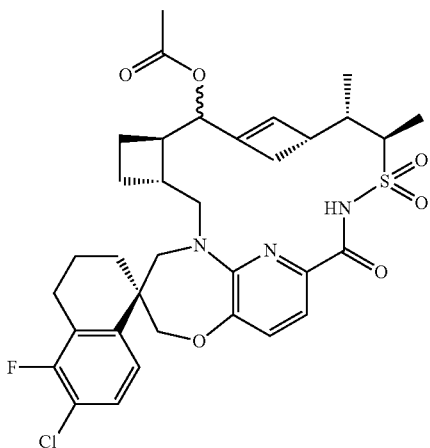 [SMILES: CC(=O)OC1C2=C[C@@H](C2)[C@H](C)[C@@H](C)S(=O)(=O)NC(=O)c2ccc3c(n2)N(C[C@@H]2CC[C@@H]12)C[C@@]1(CCCc2c1ccc(Cl)c2F)CO3]

Under Ar, to a solution of (1S)-5'-(((1R,2R)-2-(acetoxy((R)-3-((2S,3R)-3-sulfamoylbutan-2-yl)cyclobut-1-en-1-yl)methyl)cyclobutyl)methyl)-6-chloro-5-fluoro-3,4,4',5'-tetrahydro-2H,2'H-spiro[naphthalene-1,3'-pyrido[3,2-b][1,4]oxazepine]-7'-carboxylic acid (Step E, 850 mg 1.23 mmol) in dry DCM (50 mL) was added DMAP (75 mg, 0.616 mmol), and DIPEA (796 mg, 6.16 mmol), followed by 50% solution of T3P (3135 mg, 4.93 mmol) in ethyl acetate, the resulting mixture was stirred for 2 h. Water was added to quench the reaction, and the resulting mixture was extracted with DCM twice. The DCM layers were combined and washed with brine, dried over Na$_2$SO$_4$, and concentrated under reduced pressure to give an off-white solid, which was purified by silica gel column chromatography (DCM:MeOH, 100:0→100:5) to afford the title compound (850 mg, quantitatively) as a white solid. MS: 672.5 (M+H$^+$).

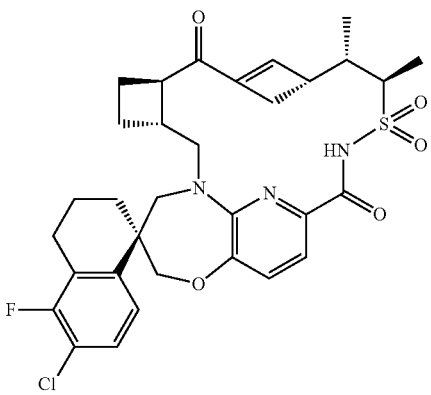 [SMILES: C[C@@H]1[C@@H](C)S(=O)(=O)NC(=O)c2ccc3c(n2)N(C[C@@H]2CC[C@H]2C(=O)C2=C[C@H]1C2)C[C@@]1(CCCc2c1ccc(Cl)c2F)CO3]

Under Ar, to a solution of (1S,11'R,12'S,13'R,16a'R,18a'R,E)-6-chloro-5-fluoro-16'-hydroxy-11',12'-dimethyl-3,4,12',13',16',16a',17',18',18a',19'-decahydro-11'H-spiro[naphthalene-1,2'-[5,7]etheno[13,15]methanocyclobuta[i][1,4]oxazepino[3,4-f][1]thia[2,5,7]triazacyclohexadecin]-8'(9'H)-one 10',10'-dioxide (Step G, 400 mg, 0.635 mmol) in dry DCM (10 mL) was added DMP (538 mg, 1.27 mmol) at 0° C., and the reaction mixture was stirred for 1 h. Aq. NaHCO₃ was added to quench the reaction, followed by aq. sodium thiosulfate, the resulting mixture was stirred for 10 min. The resulting mixture was extracted with DCM twice; the DCM layers were combined, washed with brine, dried over Na₂SO₄, and concentrated under reduced pressure to give a white solid, which was purified by silica gel column chromatography (DCM:MeOH, 100:0→100:5) to afford the title compound (360 mg, 90%) as a white solid. MS: 628.5 (M+H⁺).

Step I: (1S,11'R,12'S,13'R,16'R,16a'R,18a'R,E)-6-chloro-16'-(1,3-dithian-2-yl)-5-fluoro-16'-hydroxy-11',12'-dimethyl-3,4,12',13',16',16a',17',18',18a',19'-decahydro-1'H,2'H,3'H, 11'H-spiro[naphthalene-1,2'-[5,7]etheno[13,15]methanocyclobuta[i][1,4]oxazepino[3,4-f][1]thia[2,5,7]triazacyclohexadecin]-8'(9'H)-one 10',10'-dioxide

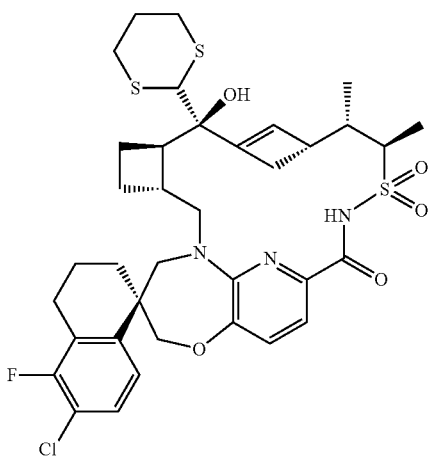 [SMILES: C[C@@H]1[C@@H](C)S(=O)(=O)NC(=O)c2ccc3c(n2)N(C[C@@H]2CC[C@H]2[C@](O)(C2SCCCS2)C2=C[C@H]1C2)C[C@@]1(CCCc2c1ccc(Cl)c2F)CO3]

Under Ar, to a solution of 1,3-dithiane (689 mg, 5.73 mmol) in dry THF (10 mL) was added n-BuLi (1.8 mL, 4.58 mmol, 2.5 M in THF) slowly at −78° C., then the reaction mixture was warmed up to 0° C. and stirred for 30 min to give Solution I; To another solution of (1S,11'R,12'S,13'R,16a'R,18a'R,E)-6-chloro-5-fluoro-11',12'-dimethyl-3,4,12',13',17',18',18a',19'-octahydro-1'H,2'H,3'H, 11'H-spiro[naphthalene-1,2'-[5,7]etheno[13,15]methanocyclobuta[i][1,4]oxazepino[3,4-f][1]thia[2,5,7]triazacyclohexadecine]-8',16'(9'H,16a'H)-dione 10',10'-dioxide (Step H, 360 mg, 0.573 mmol) in dry THF (5 mL) was added lanthanum(III) chloride bis(lithium chloride) complex (0.6 M in THF, 1 mL, 0.573 mmol) and the reaction mixture was stirred at 0° C. for 30 min to give Solution 11. Then Solution 11 was added slowly to Solution I at −78° C. and the reaction mixture was stirred for 1 h. Aq. NH₄Cl was added to quench the reaction, and the resulting mixture was extracted with EA twice. The EA layers were combined, washed with brine, dried over Na₂SO₄, and concentrated under reduced pressure to give a yellow oil, which was purified by silica gel column chromatography (DCM:MeOH, 100:0→100:5) to afford the title compound (350 mg, 82%) as a white solid. MS: 748.5 (M+H⁺).

Step J: (1S,11'R,12'S,13'R,16'R,16a'R,18a'R,E)-6-chloro-16'-(1,3-dithian-2-yl)-5-fluoro-16'-methoxy-11',12'-dimethyl-3,4,12',13',16',16a',17',18',18a',19'-decahydro-1'H,2'H,3'H, 11'H-spiro[naphthalene-1,2'-[5,7]etheno[13,15]methanocyclobuta[i][1,4]oxazepino[3,4-f][1]thia[2,5,7]triazacyclohexadecin]-8'(9'H)-one 10',10'-dioxide

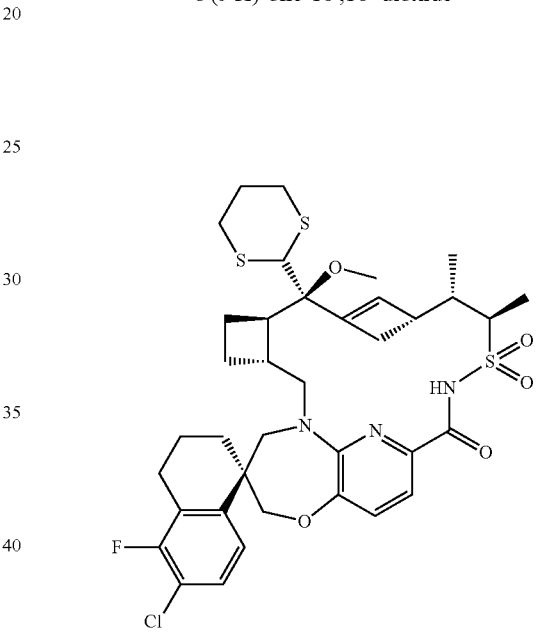

Under Ar, to a solution of (1S,11'R,12'S,13'R,16'R,16a'R,18a'R,E)-6-chloro-16'-(1,3-dithian-2-yl)-5-fluoro-16'-hydroxy-11',12'-dimethyl-3,4,12,'13',16',16a',17',18',18a',19'-decahydro-1'H,2'H,3'H,11'H-spiro[naphthalene-1,2'-[5,7]etheno[13,15]methanocyclobuta[i][1,4]oxazepino[3,4-f][1]thia[2,5,7]triazacyclohexadecin]-8'(9'H)-one 10',10'-dioxide (Step I, 350 mg, 0.47 mmol) in dry THF (5.0 mL) was added KHMDS (2.34 mL, 2.34 mmol, 1.0 M in THF) slowly at 0° C., and the reaction mixture was stirred for 1 h. MeI (332 mg, 2.34 mmol) was added slowly at 0° C., and the reaction mixture was stirred for another 1 h at room temperature. Aq. NH₄Cl was added to quench the reaction, and the resulting mixture was extracted with EA twice. The EA layers were combined, washed with brine, dried over Na₂SO₄, and concentrated under reduced pressure to give a yellow oil, which was purified by silica gel column chromatography (DCM:MeOH, 100:0→100:5) to afford the title compound (320 mg, 90%) as a white solid. MS: 762.5 (M+H⁺).

Step K: (1S,11'R,12'S,13'R,16'R,16a'R,18a'R,E)-6-chloro-5-fluoro-16'-methoxy-11',12'-dimethyl-8'-oxo-3,4,8',9',12',13',16',16a',17',18',18a',19'-dodecahydro-1'H,2H,3'H, 11'H-spiro[naphthalene-1,2'-[5,7]etheno[13,15]methanocyclobuta[i][1,4]oxazepino[3,4-f][1]thia[2,5,7]triazacyclohexadecine]-16'-carbaldehyde 10',10'-dioxide

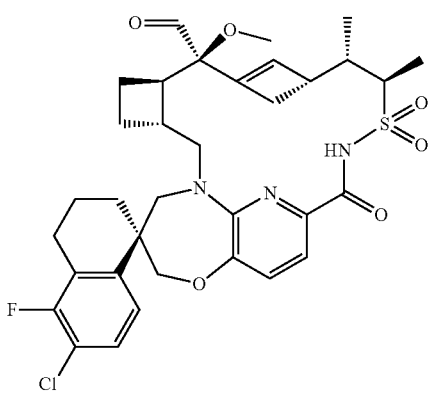 [SMILES: CO[C@@]1(C=O)C2=C[C@@H](C2)[C@H](C)[C@@H](C)S(=O)(=O)NC(=O)c2ccc3c(n2)N(C[C@@H]2CC[C@H]21)C[C@@]1(CCCc2c1ccc(Cl)c2F)CO3]

Under Ar, to a solution of (1S,11'R,12'S,13'R,16'R,16a'R,18a'R,E)-6-chloro-16'-(1,3-dithian-2-yl)-5-fluoro-16'-methoxy-11',12'-dimethyl-3,4,12,'13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,5,7]triazacyclohexadecin]-8'(9'H)-one 10',10'-dioxide (Step J, 330 mg, 0.43 mmol) in a mixed solvent of DCM/ACN/H₂O (6 mL/6 mL/2 mL) was added [bis(trifluoroacetoxy)iodo]benzene (372 mg, 0.866 mmol), and the reaction mixture was stirred for 30 min. Aq. NaHCO₃ was added to quench the reaction, and the resulting mixture was extracted with EA twice. The EA layers were combined, washed with brine, dried over Na₂SO₄, and concentrated under reduced pressure to give a white solid, which was purified by silica gel column chromatography (DCM: MeOH, 100:0→100:5) to afford the title compound (150 mg, 52%) as a white solid. MS: 672.5 (M+H⁺).

Step L: (1S,11'R,12'S,13'R,16'R,16a'R,18a'R,E)-6-chloro-5-fluoro-16'-(((S)-hexahydropyrazino[2,1-c][1,4]oxazin-8(1H)-yl)methyl)-16'-methoxy-11',12'-dimethyl-3,4,12,'13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,5,7]triazacyclohexadecin]-8'(9'H)-one 10',10'-dioxide (Cpd. No. 54)

Under Ar, to a solution of (1S,11'R,12'S,13'R,16'R,16a'R,18a'R,E)-6-chloro-5-fluoro-16'-methoxy-11',12'-dimethyl-8'-oxo-3,4,8',9',12',13',16',16a',17',18',18a',19'-dodecahydro-1'H,2H,3'H,11'H-spiro[naphthalene-1,2'-[5,7]etheno[13,15]methanocyclobuta[i][1,4]oxazepino[3,4-f][1]thia[2,5,7]triazacyclohexadecine]-16'-carbaldehyde 10',10'-dioxide (Step K, 150 mg, 0.223 mmol) in dry DCM (10 mL) was added titanium(IV) isopropoxide (317 mg, 1.116 mmol), (9a5)-octahydropiperazino[2,1-c]morpholine dihydrochloride (240 mg, 1.116 mmol) and DIEA (557 mg, 4.46 mmol) subsequently at 30° C., and the reaction mixture was stirred for 2 h. Sodium triacetoxyhydroborate (473 mg, 2.23 mmol) was added to the mixture and the reaction mixture was stirred for further 24 h at 30° C. Aq. NH₄Cl was added to quench the reaction, and the resulting mixture was extracted with DCM twice. The DCM layers were combined, washed with brine, dried over Na₂SO₄, and concentrated under reduced pressure to give a yellow solid, which was purified by C18 preparative-HPLC to afford the title compound (11.8 mg, 7%) as a white solid. ¹H NMR (400 MHz, DMSO-d₆) δ 11.78 (brs, 1H), 7.51-7.43 (m, 2H), 7.15 (d, J=7.7 Hz, 1H), 6.85 (d, J=7.7 Hz, 1H), 6.12 (s, 1H), 4.12 (d, J=12.6 Hz, 1H), 4.07-3.91 (m, 3H), 3.88-3.69 (m, 2H), 3.62-3.44 (m, 3H), 3.36-3.29 (m, 2H), 3.14-3.04 (m, 1H), 2.97 (s, 3H), 2.93-2.86 (m, 3H), 2.85-2.76 (m, 1H), 2.76-2.53 (m, 6H), 2.47-2.40 (m, 1H), 2.40-2.10 (m, 6H), 2.07-1.87 (m, 3H), 1.87-1.59 (m, 5H), 1.57-1.36 (m, 1H), 1.29 (d, J=7.1 Hz, 3H), 0.95 (d, J=6.7 Hz, 3H). MS: 798.7 (M+H⁺).

Example 30

Synthesis of (1S,11'R,12'S,13'R,16'S,16a'S,18a'R)-6-chloro-5-fluoro-16'-isopropyl-11',12'-dimethyl-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 55)

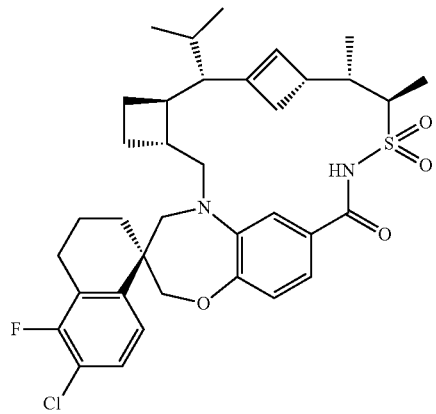 [SMILES: CC(C)[C@@H]1C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3]

Step A: (2R,3S)-3-((R)-3-((R)-((1R,2R)-2-(((tert-butyldiphenylsilyl)oxy) methyl)cyclobutyl)(hydroxy)methyl)cyclobut-2-en-1-yl)-N,N-bis(4-methoxybenzyl)butane-2-sulfonamide (Isomer 1) and (2R,3S)-3-((R)-3-((S)-((1R,2R)-2-(((tert-butyldiphenylsilyl)oxy)methyl)cyclobutyl)(hydroxy)methyl)cyclobut-2-en-1-yl)-N,N-bis(4-methoxybenzyl)butane-2-sulfonamide (Isomer 2)

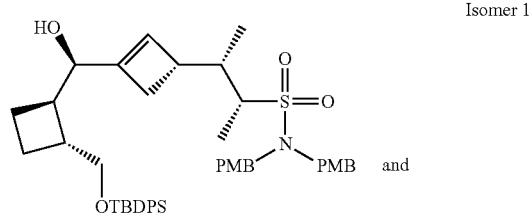

Isomer 1

-continued

Isomer 2

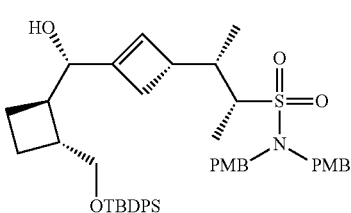

In a flame-dried 250 mL round-bottomed flask, (2R,3S)-3-((R)-3-((1R,2R)-2-(((tert-butyldiphenylsilyl)oxy)methyl)cyclobutane-1-carbonyl)cyclobut-2-en-1-yl)-N,N-bis(4-methoxybenzyl)butane-2-sulfonamide (Intermediate 5, 2.3 g, 2.95 mmol) and cerium(III) chloride heptahydrate (1.43 g, 3.83 mmol) were charged into a mixed solvent of dry THF (64 mL) and MeOH (8.0 mL) under Ar at −10° C. The reaction mixture was stirred at room temperature until cerium(III) chloride heptahydrate was completely dissolved. At −10° C., NaBH$_4$ (0.134 g, 3.54 mmol) was added and the reaction mixture was stirred for 1 h. Sat. NH$_4$Cl (100 mL) was added to quench the reaction and the resulting mixture was extracted with ethyl acetate (3×50 mL). The organic layers were combined, dried over Na$_2$SO$_4$, and concentrated under reduced pressure. The residue was loaded onto a silica gel column chromatography and eluted with methanol/dichloromethane (V/V, 1:100) to afford the title compounds (Isomer 1, 1.5 g, 65%; Isomer 2: 0.6 g, 26%) as light yellow oil. MS: 805.2 (M+Na$^+$).

Step B: (R)—((R)-3-((2S,3R)-3-(N,N-bis(4-methoxybenzyl)sulfamoyl)butan-2-yl)cyclobut-1-en-1-yl)((1R,2R)-2-(((tert-butyldiphenylsilyl)oxy)methyl)cyclobutyl)methyl acetate

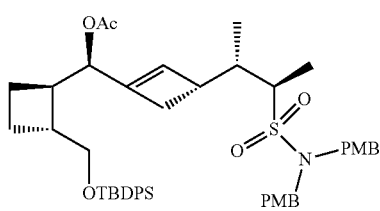

Under Ar, to a solution of (2R,3S)-3-((R)-3-((R)-((1R,2R)-2-(((tert-butyldiphenylsilyl)oxy)methyl)cyclobutyl)(hydroxy)methyl)cyclobut-2-en-1-yl)-N,N-bis(4-methoxybenzyl)butane-2-sulfonamide (Isomer 1 of Step A, 2.9 g, 3.74 mmol) in dry DCM (100 mL) was added DMAP (0.46 g, 3.74 mmol) at 0° C., followed by acetic anhydride (0.76 g, 7.48 mmol). The reaction mixture was allowed to warm up to room temperature and stirred overnight. Water was added to quench the reaction, and the resulting mixture was extracted with DCM twice. The DCM layers were combined, washed with brine, dried over Na$_2$SO$_4$, and concentrated under reduced pressure to give a yellow oil, which was purified by silica gel column chromatography (hexane:EA, 100:0→100:10) to afford the title compound A (3.0 g, 97%) as a colorless oil. MS: 846.6 (M+Na$^+$).

Step C: (R)—((R)-3-((2S,3R)-3-(N,N-bis(4-methoxybenzyl)sulfamoyl)butan-2-yl)cyclobut-1-en-1-yl)((1R,2R)-2-(hydroxymethyl)cyclobutyl)methyl acetate

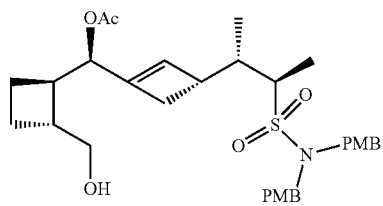

Under Ar, to a solution of (R)—((R)-3-((2S,3R)-3-(N,N-bis(4-methoxybenzyl)sulfamoyl)butan-2-yl)cyclobut-1-en-1-yl)((1R,2R)-2-(((tert-butyldiphenylsilyl)oxy)methyl)cyclobutyl)methyl acetate (Step B, 3.0 g, 3.64 mmol) in dry THF (30 mL) was added acetic acid (0.22 g, 3.64 mmol) at room temperature, followed by TBAF.3H$_2$O (2.36 g, 9.10 mmol). The reaction mixture was stirred overnight. Water was added to quench the reaction, and the resulting mixture was extracted with EA twice. The EA layers were combined, washed with brine, dried over Na$_2$SO$_4$, and concentrated under reduced pressure to give a yellow oil, which was purified by silica gel column chromatography (hexane:EA, 100:0→100:10) to afford the title compound (2.0 g, 94%) as a light yellow oil. MS: 608.9 (M+Na$^+$).

Step D: (R)—((R)-3-((2 S,3R)-3-(N,N-bis(4-methoxybenzyl)sulfamoyl)butan-2-yl)cyclobut-1-en-1-yl)((1R,2R)-2-formylcyclobutyl)methyl acetate

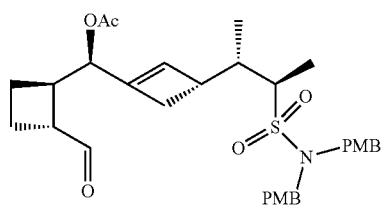

Under Ar, to a solution of (R)—((R)-3-((2S,3R)-3-(N,N-bis(4-methoxybenzyl)sulfamoyl)butan-2-yl)cyclobut-1-en-1-yl)((1R,2R)-2-(hydroxymethyl)cyclobutyl)methyl acetate (Step C, 1.0 g, 3.64 mmol) in dry DCM (20 mL) was added DMP (1.1 g, 2.56 mmol) at 0° C., and the reaction mixture was stirred for 40 min. Aq. NaHCO$_3$ was added to quench the reaction, followed by aq. Sodium thiosulfate, and the resulting mixture was stirred for 10 min. The resulting mixture was extracted with DCM twice. The DCM layers were combined, washed with brine, dried over Na$_2$SO$_4$, and concentrated under reduced pressure to afford the crude title compound (1.0 g) as a yellow oil, which was directly used for the next step without purification. MS: 584.5 (M+H$^+$).

Step E: tert-butyl (S)-5-(((1R,2R)-2-((R)-acetoxy ((R)-3-((2S,3R)-3-(N,N-bis(4-methoxybenzyl)sulfamoyl)butan-2-yl)cyclobut-1-en-1-yl)methyl)cyclobutyl)methyl)-6'-chloro-5'-fluoro-3',4,4',5-tetrahydro-2H,2'H-spiro[benzo[b][1,4]oxazepine-3,1'-naphthalene]-7-carboxylate

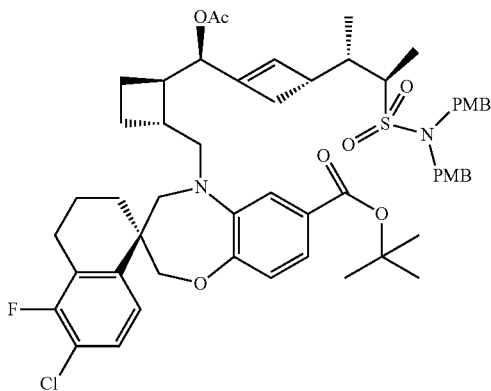

Under Ar, to a solution of the crude (R)—((R)-3-((2S,3R)-3-(N,N-bis(4-methoxybenzyl)sulfamoyl)butan-2-yl)cyclobut-1-en-1-yl)((1R,2R)-2-formylcyclobutyl)methyl acetate (Step D, 1.0 g, 1.71 mmol) in dry THF (5 mL) was added tert-butyl (S)-6'-chloro-5'-fluoro-3',4,4',5-tetrahydro-2H,2'H-spiro[benzo[b][1,4]oxazepine-3,1'-naphthalene]-7-carboxylate (Intermediate 1, 1.07 g, 2.57 mmol) at 0° C. Phenylsilane (5.6 g, 5.14 mmol) in a mixed solvent of THF (10 mL) and TFA (15 mL) was added slowly, and the reaction mixture was stirred overnight at room temperature. Water was added to quench the reaction, and the resulting mixture was extracted with EA twice. The EA layers were combined, washed with brine, dried over Na$_2$SO$_4$, and concentrated under reduced pressure to give a yellow oil, which was purified by silica gel column chromatography (hexane:EA, 100:0→100:25) to afford the title compound (1.43 g, 85% over 2 steps) as a white solid. MS: 985.7 (M+H$^+$).

Step F: (S)-5-(((1R,2R)-2-((R)-acetoxy((R)-3-((2S,3R)-3-sulfamoylbutan-2-yl)cyclobut-1-en-1-yl)methyl)cyclobutyl)methyl)-6'-chloro-5'-fluoro-3',4,4',5-tetrahydro-2H,2'H-spiro[benzo[b][1,4]oxazepine-3,1'-naphthalene]-7-carboxylic acid

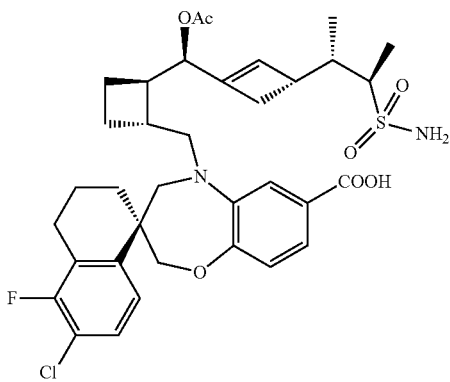 [SMILES: CC(=O)O[C@@H](C1=C[C@H]([C@H](C)[C@@H](C)S(N)(=O)=O)C1)[C@@H]1CC[C@H]1CN1C[C@@]2(CCCc3c2ccc(Cl)c3F)COc2ccc(C(=O)O)cc21]

Under Ar, to a solution of tert-butyl (S)-5-(((1R,2R)-2-((R)-acetoxy((R)-3-((2S,3R)-3-(N,N-bis(4-methoxybenzyl)sulfamoyl)butan-2-yl)cyclobut-1-en-1-yl)methyl)cyclobutyl)methyl)-6'-chloro-5'-fluoro-3',4,4',5-tetrahydro-2H,2'H-spiro[benzo[b][1,4]oxazepine-3,1'-naphthalene]-7-carboxylate (Step E, 1.43 g, 2.07 mmol) in dry DCM (10 mL) was added TFA (10 mL) at 0° C. The reaction mixture was allowed to warm up to room temperature and stirred overnight. After removal of volatiles under reduced pressure, the residue was purified by silica gel column chromatography (DCM:MeOH, 100:0→100:10) to afford the title compound (1.0 g, quantitatively) as a white solid. MS: 711.4 (M+Na$^+$).

Step G: (1S,11'R,12'S,13'R,16'R,16a'R,18a'R,E)-6-chloro-5-fluoro-11',12'-dimethyl-10',10'-dioxido-8'-oxo-3,4,8',9',12',13',16',16a',17',18',18a',19'-dodecahydro-1'1-1,2H,3'H, 11'H-spiro[naphthalene-1,2'-[5,7]etheno[13,15]methanocyclobuta[i][1,4]oxazepino[3,4-f][1]thia[2,7]diazacyclohexadecin]-16'-yl acetate

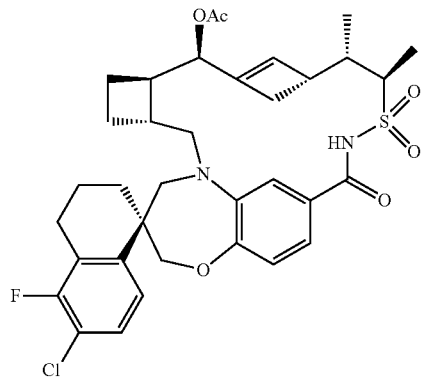 [SMILES: CC(=O)O[C@H]1C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3]

Under Ar, to a solution of (S)-5-(((1R,2R)-2-((R)-acetoxy ((R)-3-((2S,3R)-3-sulfamoylbutan-2-yl)cyclobut-1-en-1-yl) methyl)cyclobutyl)methyl)-6'-chloro-5'-fluoro-3',4,4',5-tetrahydro-2H,2'H-spiro[benzo[b][1,4]oxazepine-3,1'-naphthalene]-7-carboxylic acid (Step F, 1.0 g 1.45 mmol) in dry DCM (100 mL) was added TEA (0.4 mL 2.9 mmol) and T3P (922.7 mg, 2.9 mmol). The reaction mixture was stirred for 2 h. Water was added to quench the reaction, and the resulting mixture was extracted with DCM twice. The DCM layers were combined, washed with brine, dried over Na$_2$SO$_4$, and concentrated under reduced pressure to give an off-white solid, which was purified by silica gel column chromatography (DCM:MeOH, 100:0→100:10) to afford the title compound (0.98 g, quantitatively) as a white solid. MS: 671.4 (M+H$^+$).

Step H: (1S,11'R,12'S,13'R,16'S,16a'S,18a'R)-6-chloro-5-fluoro-16'-isopropyl-11',12'-dimethyl-3,4,12',13',16',16a',17',18',18a',19'-decahydro-1'H,2H,3'H,1 PH-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 55)

Under Ar, to a solution of (1S,11'R,12'S,13'R,16'R,16a'R,18a'R,E)-6-chloro-5-fluoro-11',12'-dimethyl-10',10'-dioxido-8'-oxo-3,4,8',9',12',13',16',16a',17',18',18a',19'-dodecahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-16'-yl acetate (Step G, 30 mg, 0.05 mmol) in dry THF (20 mL) was added copper(I) iodide (8.51 mg, 0.05 mmol) at −40° C.

Isopropylmagnesium bromide (0.13 mL, 0.13 mmol, 1.0 M in THF) was added dropwise, and the reaction mixture was stirred for 1 h at −40° C. and for 0.5 h at −10° C. Aq. NH₄Cl was added to quench the reaction, and the resulting mixture was extracted with EA twice. The EA layers were combined, washed with brine, dried over Na₂SO₄, and concentrated under reduced pressure to give a yellow oil, which was purified by silica gel column chromatography (DCM:MeOH, 100:0→30:1) to afford the title compound (5.0 mg, 17%) as a white powder. ¹H NMR (400 MHz, DMSO-d₆) δ 11.85 (s, 1H), 7.52 (d, J=8.7 Hz, 1H), 7.48-7.40 (m, 1H), 7.01 (d, J=8.1 Hz, 1H), 6.91 (d, J=8.1 Hz, 1H), 6.87-6.83 (m, 1H), 5.47-5.41 (m, 1H), 4.13-4.04 (m, 2H), 3.90-3.76 (m, 1H), 3.67 (d, J=15.0 Hz, 1H), 3.57 (d, J=14.3 Hz, 1H), 3.19 (d, J=14.2 Hz, 1H), 3.08-2.91 (m, 2H), 2.90-2.80 (m, 1H), 2.69-2.51 (m, 2H), 2.43-2.33 (m, 2H), 2.33-2.27 (m, 1H), 2.03-1.79 (m, 5H), 1.79-1.67 (m, 3H), 1.67-1.50 (m, 2H), 1.47-1.34 (m, 1H), 1.26 (d, J=7.1 Hz, 3H), 0.92-0.81 (m, 9H). MS: 655.4 (M+H⁺).

Example 31

(1S,11'R,12'S,13'R,16'R,16a'R,18a'R)-6-chloro-5-fluoro-11',12'-dimethyl-16'-morpholino-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide
(Cpd. No. 56)

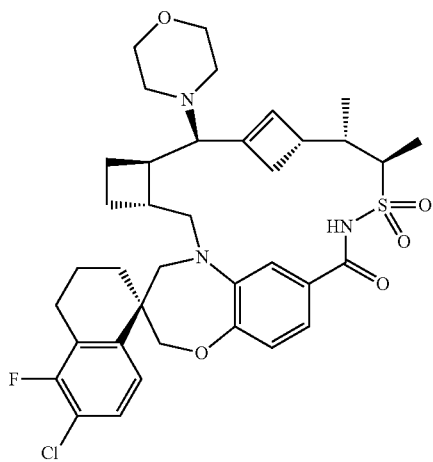 [SMILES: C[C@@H]1[C@@H](C)S(=O)(=O)NC(=O)c2ccc3c(c2)N(C[C@@H]2CC[C@H]2[C@@H](N2CCOCC2)C2=C[C@H]1C2)C[C@@]1(CCCc2c1ccc(Cl)c2F)CO3]

Step A: (1S,11'R,12'S,13'R,16'R,16a'R,18a'R,E)-6-chloro-5-fluoro-16'-hydroxy-11',12'-dimethyl-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide

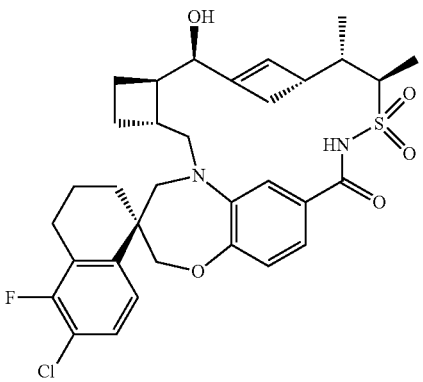 [SMILES: C[C@@H]1[C@@H](C)S(=O)(=O)NC(=O)c2ccc3c(c2)N(C[C@@H]2CC[C@H]2[C@@H](O)C2=C[C@H]1C2)C[C@@]1(CCCc2c1ccc(Cl)c2F)CO3]

Under Ar, a solution of (1S,11'R,12'S,13'R,16'R,16a'R,18a'R,E)-6-chloro-5-fluoro-11',12'-dimethyl-10',10'-dioxido-8'-oxo-3,4,8',9',12',13',16',16a',17',18',18a',19'-dodecahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-16'-yl acetate (Step G of EXAMPLE 30, 0.98 g, 1.45 mmol) in a mixed solvent of THF/MeOH/25% NaOH (10 mL/10 mL/10 mL) was stirred at 40° C. for 1 h. After cooling down to room temperature, the resulting mixture was extracted with DCM twice. The DCM layers were combined, washed with brine, dried over Na₂SO₄, and concentrated under reduced pressure to give an off white solid, which was purified by silica gel column chromatography (DCM:MeOH, 100:0→100:10) to afford the title compound (0.90 g, 98%) as a white solid. MS: 629.5 (M+H⁺).

Step B: (1S,11'R,12'S,13'R,16a'R,18a'R,E)-16'-bromo-6-chloro-5-fluoro-11',12'-dimethyl-3,4,12',13',16',16a',17',18',18a',19'-decahydro-1'H,2H,3'H,1PH-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide

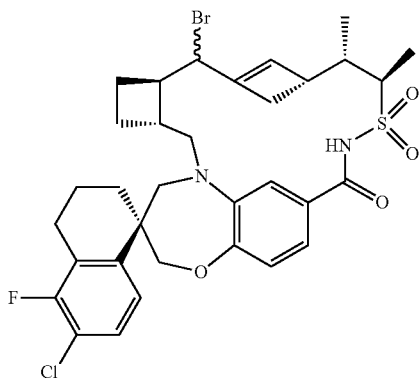 [SMILES: C[C@@H]1[C@@H](C)S(=O)(=O)NC(=O)c2ccc3c(c2)N(C[C@@H]2CC[C@H]2C(Br)C2=C[C@H]1C2)C[C@@]1(CCCc2c1ccc(Cl)c2F)CO3]

Under Ar, to a solution of (1S,11'R,12'S,13'R,16'R,16a'R,18a'R,E)-6-chloro-5-fluoro-16'-hydroxy-11',12'-dimethyl-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Step A, 150 mg, 0.24 mmol) in dry DCM (10 mL) was added Ph₃P (156 mg, 0.6 mmol) at 25° C., followed by CBr₄ (198 mg, 0.6 mmol). The reaction mixture was stirred for 2 h. After removal of volatiles under reduced pressure, the residue was purified by silica gel column chromatography (DCM:MeOH, 100:0→100:5) to afford the title compound (90 mg, 55%) as a yellow oil. MS: 691.3 (M+H⁺).

Step C: (1S,11'R,12'S,13'R,16'R,16a'R,18a'R)-6-chloro-5-fluoro-11',12'-dimethyl-16'-morpholino-3,4,12',13',16',16a',17',18',18a',19'-decahydro-1'H,2H,3'H,1PH-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 56)

Under Ar, to a solution of (1S,11'R,12'S,13'R,16a'R,18a'R,E)-16'-bromo-6-chloro-5-fluoro-11',12'-dimethyl-3,4,12',13',16',16a',17',18',18a',19'-decahydro-1'H,2H,3'H,1PH-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Step B, 30 mg, 0.04 mmol) in dry DMF (5 mL) was added morpholine (37.8 mg, 0.43 mmol) and K₂CO₃ (59.9 mg, 0.43 mmol). The reaction mixture was allowed to warm up to 55° C. for 8 h. After cooling down to room temperature, water was added to quench the reaction, and the resulting mixture was extracted with EA twice. The EA layers were combined, washed with brine, dried over Na₂SO₄, and concentrated under reduced pressure to give a yellow oil, which was purified by C18 preparative-HPLC to afford the first-eluting diastereomer designated as the title compound (8.3 mg, 27%) as a white solid. ¹H NMR (400 MHz, DMSO-d₆) δ 12.02 (s, 1H), 7.52 (d, J=8.6 Hz, 1H), 7.48-7.40 (m, 1H), 7.07 (d, J=9.0 Hz, 1H), 6.93 (d, J=8.1 Hz, 1H), 6.81 (s, 1H), 6.04 (s, 1H), 4.08 (s, 2H), 4.04-3.87 (m, 3H), 3.74-3.61 (m, 4H), 3.57 (d, J=14.2 Hz, 2H), 3.25-3.14 (m, 3H), 3.07 (dd, J=14.9, 9.7 Hz, 2H), 2.85 (d, J=16.6 Hz, 1H), 2.64-2.53 (m, 2H), 2.50-2.39 (m, 2H), 2.07 (s, 2H), 2.06-1.60 (m, 8H), 1.50-1.37 (m, 1H), 1.33 (d, J=6.9 Hz, 3H), 0.92 (d, J=6.6 Hz, 3H); MS: 698.5 (M+H⁺).

Example 32

Synthesis of (1S,11'R,12'S,13'R,16'R,16a'R,18a'R)-6-chloro-16'-(dimethylamino)-5-fluoro-11',12'-dimethyl-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 57)

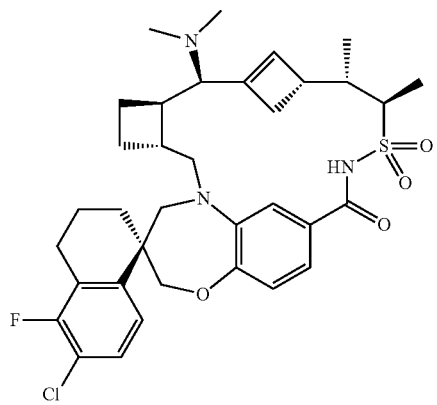 [SMILES: C[C@@H]1[C@@H](C)S(=O)(=O)NC(=O)c2ccc3c(c2)N(C[C@@H]2CC[C@H]2[C@@H](N(C)C)C2=C[C@H]1C2)C[C@@]1(CCCc2c1ccc(Cl)c2F)CO3]

Essentially the same protocol described in EXAMPLE 31 was used to afford the title compound (5 mg) as a white solid. ¹H NMR (400 MHz, DMSO-d₆) δ 12.05 (s, 1H), 7.51 (d, J=8.7 Hz, 1H), 7.47-7.41 (m, 1H) 7.09-7.04 (m, 1H), 6.93 (d, J=8.1 Hz, 1H), 6.79 (s, 1H), 6.05 (s, 1H), 4.08 (s, 2H), 3.96 (d, J=5.6 Hz, 1H), 3.89 (s, 1H), 3.69 (d, J=15.2 Hz, 1H), 3.61-3.49 (m, 2H), 3.20 (d, J=14.2 Hz, 2H), 3.06 (dd, J=15.7, 9.9 Hz, 1H), 2.79 (d, J=4.5 Hz, 6H), 2.64-2.52 (m, 3H), 2.49-2.42 (m, 2H), 2.42-2.30 (m, 1H), 2.08-1.85 (m, 4H), 1.83-1.62 (m, 3H), 1.42 (t, J=11.6 Hz, 1H), 1.33 (d, J=7.0 Hz, 3H), 0.92 (d, J=6.7 Hz, 3H); MS: 656.5 (M+H⁺).

Example 33

Synthesis of (1S,11'R,12'S,13'R,16'R,16a'R,18a'R)-6-chloro-5-fluoro-16'-((2-methoxyethyl)amino)-11',12'-dimethyl-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 58)

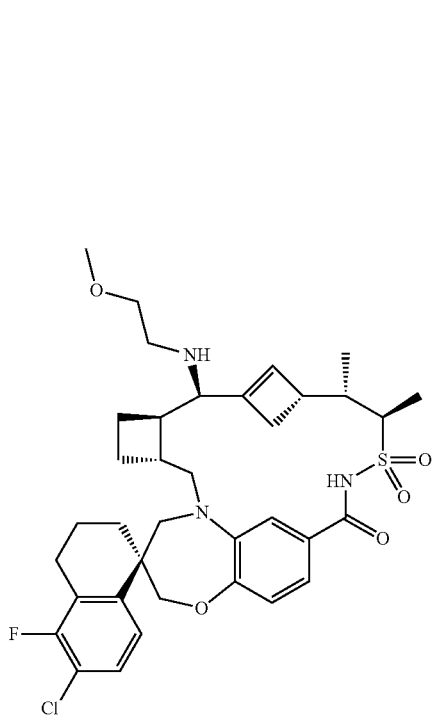 [SMILES: COCCN[C@H]1C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3]

Essentially the same protocol described in EXAMPLE 32 was used to afford the title compound (8 mg) as a white solid. $^1$H NMR (400 MHz, DMSO-d$_6$) δ 11.99 (s, 1H), 7.51 (d, J=8.7 Hz, 1H), 7.47-7.41 (m, 1H), 7.05 (dd, J=8.2, 1.6 Hz, 1H), 6.93 (d, J=8.2 Hz, 1H), 6.80 (s, 1H), 6.03 (d, J=6.0 Hz, 1H), 4.08 (s, 2H), 3.97 (d, J=6.2 Hz, 1H), 3.93-3.86 (m, 2H), 3.68 (d, J=14.8 Hz, 1H), 3.62-3.53 (m, 3H), 3.34 (s, 3H), 3.33-3.24 (m, 2H), 3.19 (d, J=14.2 Hz, 1H), 3.14 (s, 2H), 3.06 (dd, J=15.3, 9.4 Hz, 1H), 2.85 (d, J=16.6 Hz, 1H), 2.64-2.51 (m, 3H), 2.47-2.37 (m, 1H), 2.13 (t, J=9.8 Hz, 1H), 2.06-1.85 (m, 4H), 1.84-1.61 (m, 3H), 1.42 (t, J=11.6 Hz, 1H), 1.32 (d, J=7.0 Hz, 3H), 0.88 (d, J=6.7 Hz, 3H); MS: 686.5 (M+H$^+$).

Example 34

Synthesis of (1S,11'R,12'S,13'R,16'R,16a'R,18a'R,E)-6-chloro-5-fluoro-11',12'-dimethyl-16'-(2-morpholinoethoxy)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 59)

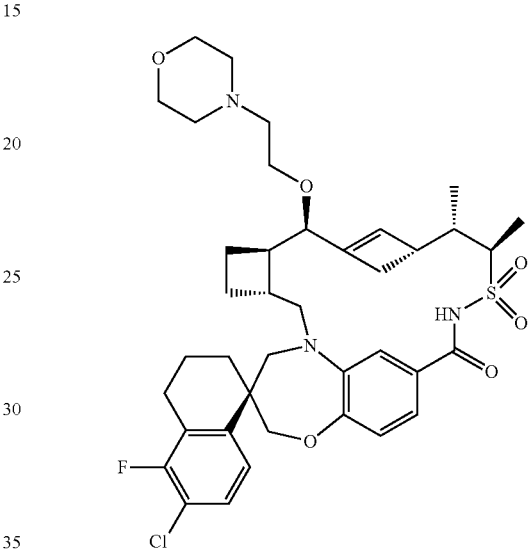

Under Ar, to a solution of (1S,11'R,12'S,13'R,16'R,16a'R,18a'R,E)-6-chloro-5-fluoro-16'-hydroxy-11',12'-dimethyl-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Step A of EXAMPLE 31, 50 mg, 0.08 mmol) in dry DMF (10 mL) was added sodium hydride (15.9 mg, 0.30 mmol) at 0° C., followed by sodium iodide (6.0 mg, 0.04 mmol), and 4-(2-bromoethyl)morpholine (30.8 mg, 0.16 mmol). The reaction mixture was allowed to warm up to room temperature and stirred overnight at 40° C. After cooling down to room temperature, water was added to quench the reaction and the resulting mixture was extracted with EA twice. The organic layers were combined, washed with brine, dried over Na$_2$SO$_4$, and concentrated under reduced pressure to give a yellow oil, which was purified by C18 preparative-HPLC to afford the title compound (5.5 mg, 9%) as a white solid. $^1$H NMR (400 MHz, DMSO-d$_6$) δ 11.78 (s, 1H), 7.51 (d, J=8.7 Hz, 1H), 7.48-7.42 (m, 1H), 6.93-6.89 (m, 2H), 6.71 (s, 1H), 6.34 (s, 1H), 4.13-4.03 (m, 2H), 4.02-3.90 (m, 4H), 3.77 (d, J=14.4 Hz, 1H), 3.72-3.58 (m, 4H), 3.58-3.49 (m, 1H), 3.31-3.23 (m, 3H), 3.20-3.04 (m, 2H), 3.04-2.92 (m, 1H), 2.92-2.82 (m, 1H), 2.79-2.70 (m, 1H), 2.65-2.51 (m, 4H), 2.48-2.40 (m, 1H), 2.17 (d, J=13.5 Hz, 1H), 2.01-1.82 (m, 4H), 1.82-1.63 (m, 5H), 1.50-1.37 (m, 1H), 1.33 (d, J=7.1 Hz, 3H), 0.93 (d, J=6.6 Hz, 3H); MS: 743.9 (M+H$^+$).

Example 35

The protocol described in EXAMPLE 34 was used to give the following compounds.

(1S,11'R,12'S,13'R,16'R,16a'R,18a'R,E)-6-chloro-5-fluoro-16'-(2-methoxyethoxy)-11',12'-dimethyl-3,4, 12',13',16',16a',17',18',18a',19'-decahydro-1'H,2H, 3'H,11'H-spiro[naphthalene-1,2'-[5,7]etheno[13,15] methanocyclobuta[i][1,4]oxazepino[3,4-f][1]thia[2, 7]diazacyclohexadecin]-8'(9'H)-one 10',10'-dioxide (Cpd. No. 60)

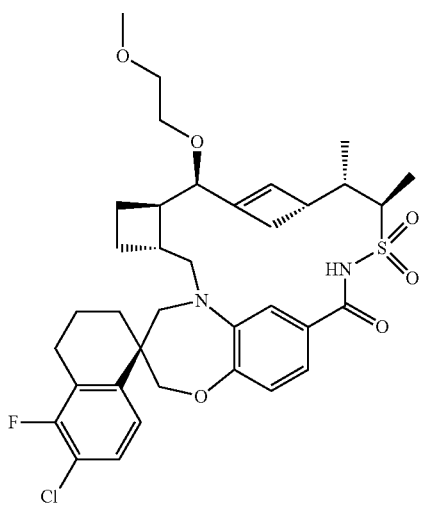 [SMILES: COCCO[C@H]1C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3]

Yield: 6 mg (16%) as a white solid. $^1$H NMR (400 MHz, DMSO-$d_6$) δ 11.74 (s, 1H), 7.51 (d, J=8.6 Hz, 1H), 7.48-7.42 (m, 1H), 6.92-6.87 (m, 2H), 6.73 (s, 1H), 6.24 (s, 1H), 4.10-4.02 (m, 2H), 3.96 (d, J=12.3 Hz, 1H), 3.83 (d, J=4.9 Hz, 1H), 3.75 (d, J=13.4 Hz, 1H), 3.63 (d, J=14.5 Hz, 1H), 3.46-3.39 (m, 3H), 3.22 (s, 3H), 2.99 (t, J=12.5 Hz, 1H), 2.87 (d, J=15.9 Hz, 1H), 2.70 (d, J=10.1 Hz, 1H), 2.62-2.52 (m, 4H), 2.47-2.37 (m, 1H), 2.13 (d, J=13.6 Hz, 1H), 2.04-1.85 (m, 4H), 1.73-1.63 (m, 5H), 1.43-1.34 (m, 1H), 1.32 (d, J=6.6 Hz, 3H), 0.92 (d, J=6.5 Hz, 3H); MS: 687.6 (M+H$^+$).

(1S,11'R,12'S,13'R,16'R,16a'R,18a'R,E)-6-chloro-5-fluoro-11',12'-dimethyl-16'-(2-(methylsulfonyl) ethoxy)-3,4,12',13',16',16a',17',18',18a',19'-decahydro-1'H,2H,3'H,11'H-spiro[naphthalene-1,2'-[5,7] etheno[13,15]methanocyclobuta[i][1,4]oxazepino[3, 4-f][1]thia[2,7]diazacyclohexadecin]-8'(9'H)-one 10',10'-dioxide (Cpd. No. 61)

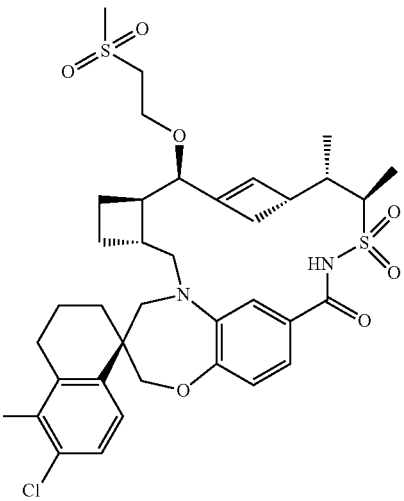

Yield: 12 mg (41%) as a white solid. $^1$H NMR (400 MHz, DMSO-$d_6$) δ 11.75 (s, 1H), 7.51 (d, J=8.7 Hz, 1H), 7.49-7.42 (m, 1H), 6.91-6.88 (m, 2H), 6.72 (s, 1H), 6.32 (s, 1H), 4.12-4.02 (m, 2H), 4.01-3.90 (m, 2H), 3.82-3.73 (m, 1H), 3.71-3.59 (m, 2H), 3.58-3.49 (m, 1H), 3.32-3.28 (m, 2H), 3.28-3.20 (m, 1H), 3.06-2.96 (m, 1H), 2.94 (s, 3H), 2.91-2.82 (m, 1H), 2.75 (dd, J=12.9, 3.9 Hz, 1H), 2.64-2.51 (m, 4H), 2.47-2.39 (m, 1H), 2.15 (d, J=13.0 Hz, 1H), 2.03-1.84 (m, 3H), 1.81-1.60 (m, 5H), 1.44-1.35 (m, 1H), 1.33 (d, J=7.2 Hz, 3H), 0.92 (d, J=6.7 Hz, 3H); MS: 735.5 (M+H$^+$).

361

(1S,11'R,12'S,13'R,16'R,16a'R,18a'R,E)-6-chloro-5-fluoro-11',12'-dimethyl-16'-(pyrimidin-2-yl-methoxy)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 62)

362

(1S,11'R,12'S,13'R,16'R,16a'R,18a'R,E)-6-chloro-5-fluoro-11',12'-dimethyl-16'-((1-methyl-1H-imidazol-2-yl)methoxy)-3,4,12',13',16',16a',17',18',18a',19'-decahydro-1'H,2H,3'H, 11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 63)

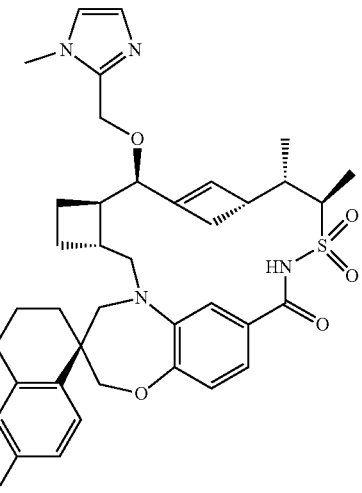

Yield: 5 mg (17%) as a white solid. $^1$H NMR (400 MHz, DMSO-d$_6$) δ 11.79 (s, 1H), 7.69 (s, 1H), 7.64 (s, 1H), 7.55-7.41 (m, 2H), 6.94-6.87 (m, 2H), 6.70 (s, 1H), 6.34 (s, 1H), 4.64 (q, J=13.9 Hz, 2H), 4.12-3.91 (m, 4H), 3.83-3.70 (m, 4H), 3.62 (d, J=13.8 Hz, 1H), 3.31-3.29 (m, 1H), 3.05-2.93 (m, 1H), 2.94-2.81 (m, 1H), 2.68 (d, J=9.7 Hz, 1H), 2.63-2.52 (m, 3H), 2.17 (d, J=12.9 Hz, 1H), 2.05-1.82 (m, 4H), 1.80-1.62 (m, 5H), 1.49-1.37 (m, 1H), 1.33 (d, J=6.9 Hz, 3H), 0.92 (d, J=6.4 Hz, 3H); MS: 723.5 (M+H$^+$).

2-(((1 S, 11'R,12'S,13'R,16'R,16a'R,18a'R,E)-6-chloro-5-fluoro-11',12'-dimethyl-10',10'-dioxido-8'-oxo-3,4,8',9',12',13',16',16a',17',18',18a',19'-dodecahydro-1'H,2H,3'H, 11'H-spiro[naphthalene-1,2'-[5,7]etheno[13,15]methanocyclobuta[i][1,4]oxazepino[3,4-f][1]thia[2,7]diazacyclohexadecin]-16'-yl)oxy)-N,N-dimethylacetamide (Cpd. No. 64)

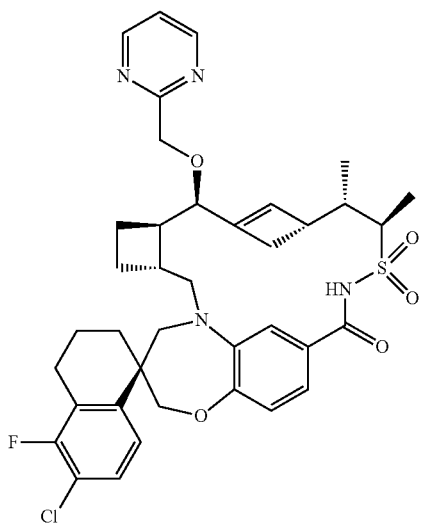 [SMILES: C[C@@H]1[C@@H](C)S(=O)(=O)NC(=O)c2ccc3c(c2)N(C[C@@H]2CC[C@H]2[C@@H](OCc2ncccn2)C2=C[C@H]1C2)C[C@@]1(CCCc2c1ccc(Cl)c2F)CO3]

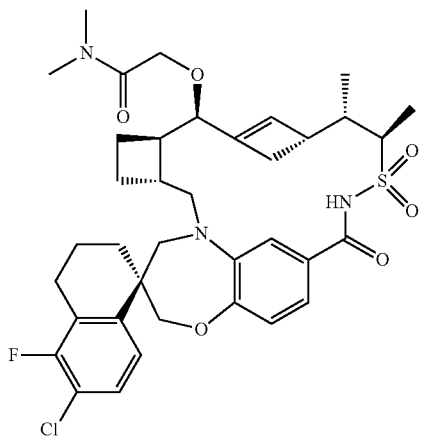 [SMILES: C[C@@H]1[C@@H](C)S(=O)(=O)NC(=O)c2ccc3c(c2)N(C[C@@H]2CC[C@H]2[C@@H](OCC(=O)N(C)C)C2=C[C@H]1C2)C[C@@]1(CCCc2c1ccc(Cl)c2F)CO3]

Yield: 7 mg (24%) as a white solid. $^1$H NMR (400 MHz, DMSO-d$_6$) δ 11.75 (s, 1H), 8.79 (d, J=4.9 Hz, 2H), 7.51 (d, J=8.7 Hz, 1H), 7.46 (d, J=7.8 Hz, 1H), 7.44-7.40 (m, 1H), 6.90-6.88 (m, 2H), 6.72 (s, 1H), 6.20 (s, 1H), 4.52 (d, J=13.2 Hz, 1H), 4.44 (d, J=13.2 Hz, 1H), 4.10-3.93 (m, 4H), 3.70 (d, J=14.3 Hz, 1H), 3.63 (d, J=14.1 Hz, 1H), 3.52-3.28 (m, 1H), 3.09-2.97 (m, 1H), 2.94-2.81 (m, 1H), 2.77 (dd, J=13.2, 4.2 Hz, 1H), 2.63-2.52 (m, 3H), 2.16 (d, J=12.9 Hz, 1H), 2.04-1.94 (m, 2H), 1.94-1.85 (m, 2H) 1.78-1.66 (m, 5H), 1.48-1.35 (m, 1H), 1.32 (d, J=7.2 Hz, 3H), 0.93 (d, J=6.6 Hz, 3H); MS: 721.4 (M+H$^+$).

363

Yield: 5.4 mg (26%) as a white solid. $^1$H NMR (400 MHz, DMSO-$d_6$) δ 11.75 (s, 1H), 7.51 (d, J=8.7 Hz, 1H), 7.48-7.43 (m, 1H), 6.94-6.87 (m, 2H), 6.70 (s, 1H), 6.26 (s, 1H), 4.10-3.94 (m, 4H), 3.92-3.83 (m, 2H), 3.72 (d, J=14.1 Hz, 1H), 3.63 (d, J=14.4 Hz, 1H), 3.34 (d, J=14.3 Hz, 2H), 3.07-2.96 (m, 1H), 2.90 (s, 3H), 2.80 (s, 3H), 2.73 (dd, J=13.3, 4.1 Hz, 1H), 2.63-2.50 (m, 4H), 2.15 (d, J=12.8 Hz, 1H), 2.04-1.86 (m, 3H), 1.79-1.62 (m, 5H), 1.43-1.35 (m, 1H), 1.32 (d, J=7.2 Hz, 3H), 0.92 (d, J=6.7 Hz, 3H); MS: 714.5 (M+H$^+$).

(1S,11'R,12'S,13'R,16'R,16a'R,18a'R,E)-6-chloro-5-fluoro-11',12'-dimethyl-16'-(2-(piperazin-1-yl)ethoxy)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 65)

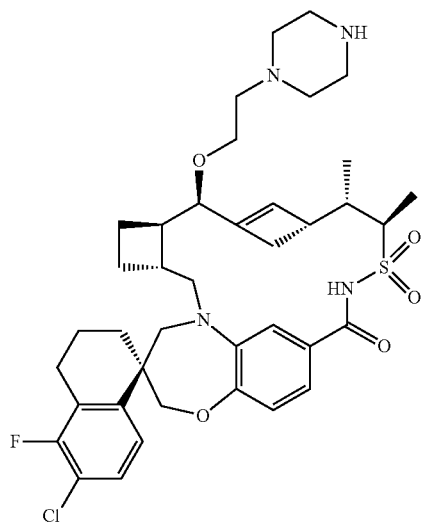 [SMILES: C[C@@H]1[C@@H](C)S(=O)(=O)NC(=O)c2ccc3c(c2)N(C[C@@H]2CC[C@H]2[C@@H](OCCN2CCNCC2)C2=C[C@H]1C2)C[C@@]1(CCCc2c1ccc(Cl)c2F)CO3]

Yield: 9.7 mg (15%) as a white solid. $^1$H NMR (400 MHz, DMSO-$d_6$) δ 11.78 (s, 1H), 8.83 (s, 1H), 7.51 (d, J=8.8 Hz, 1H), 7.49-7.43 (m, 1H), 6.93-6.88 (m, 2H), 6.71 (s, 1H), 6.30 (s, 1H), 4.13-4.01 (m, 2H), 3.97 (d, J=12.4 Hz, 1H), 3.88 (d, J=4.8 Hz, 1H), 3.76 (d, J=13.8 Hz, 1H), 3.64 (d, J=14.1 Hz, 1H), 3.34-3.27 (m, 4H), 3.36-3.14 (m, 4H), 3.04-2.82 (m, 6H), 2.73 (dd, J=13.0, 3.9 Hz, 1H), 2.63-2.57 (m, 1H), 2.57-2.52 (m, 3H), 2.46-2.38 (m, 1H), 2.15 (d, J=13.3 Hz, 1H), 2.03-1.87 (m, 3H), 1.79-1.63 (m, 5H), 1.47-1.37 (m, 1H), 1.33 (d, J=7.2 Hz, 3H), 0.92 (d, J=6.7 Hz, 3H); MS: 741.5 (M+H$^+$).

364

(1S,11'R,12'S,13'R,16'R,16a'R,18a'R,E)-6-chloro-5-fluoro-11',12'-dimethyl-16'-(2-(pyrrolidin-1-yl)ethoxy)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 66)

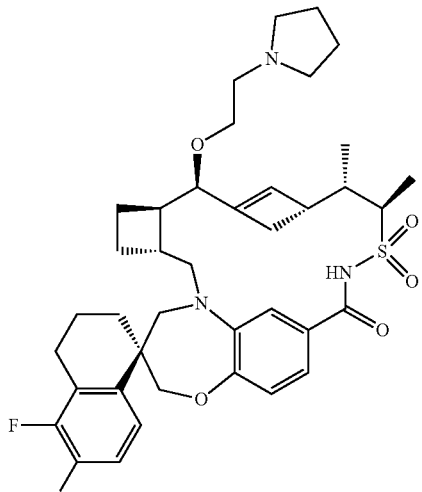

Yield: 6 mg (36%) as a white solid. $^1$H NMR (400 MHz, DMSO-$d_6$) δ 11.79 (s, 1H), 9.46 (s, 1H), 7.51 (d, J=8.8 Hz, 1H), 7.49-7.43 (m, 1H), 6.92-6.89 (m, 2H), 6.71 (s, 1H), 6.33 (s, 1H), 4.07 (dd, J=13.2, 9.7 Hz, 2H), 3.97 (d, J=12.4 Hz, 1H), 3.93 (d, J=4.9 Hz, 1H), 3.77 (d, J=13.3 Hz, 1H), 3.64 (d, J=14.0 Hz, 1H), 3.61-3.45 (m, 4H), 3.35-3.24 (m, 3H), 3.08-2.94 (m, 3H), 2.87 (d, J=16.8 Hz, 1H), 2.75 (dd, J=13.2, 4.2 Hz, 1H), 2.64-2.52 (m, 3H), 2.48-2.42 (m, 1H), 2.17 (d, J=13.4 Hz, 1H), 2.06-1.94 (m, 3H), 1.94-1.80 (m, 4H), 1.78-1.63 (m, 5H), 1.46-1.35 (m, 1H), 1.33 (d, J=7.2 Hz, 3H), 0.93 (d, J=6.7 Hz, 3H); MS: 726.5 (M+H$^+$).

365

(1S,11'R,12'S,13'R,16'R,16a'R,18a'R,E)-6-chloro-5-fluoro-11',12'-dimethyl-16'-(2-morpholino-2-oxoethoxy)-3,4,12',13',16',16a',17',18',18a',19'-decahydro-1'H,2H,3'H, 11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 67)

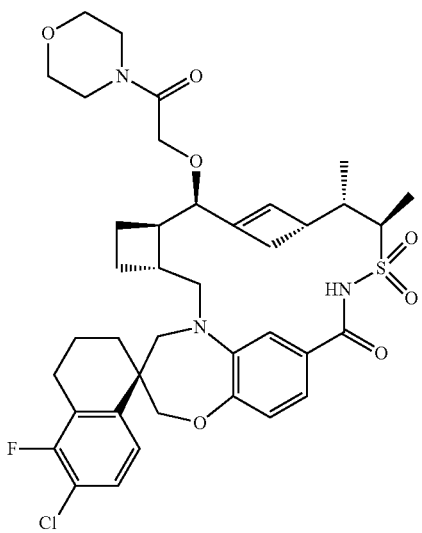 [SMILES: C[C@@H]1[C@@H](C)S(=O)(=O)NC(=O)c2ccc3c(c2)N(C[C@@H]2CC[C@H]2[C@@H](OCC(=O)N2CCOCC2)C2=C[C@H]1C2)C[C@@]1(CCCc2c1ccc(Cl)c2F)CO3]

Yield: 3 mg as a white solid. $^1$H NMR (400 MHz, DMSO-$d_6$) δ 11.80 (s, 1H), 7.55 (d, J=8.6 Hz, 1H), 7.47 (d, J=8.0 Hz, 1H), 7.04 (d, J=9.6 Hz, 1H), 6.94 (d, J=8.0 Hz, 1H), 6.90 (s, 1H), 5.64-5.59 (m, 1H), 4.36-4.28 (m, 1H), 4.10 (s, 2H), 4.03-3.94 (m, 1H), 3.77-3.55 (m, 6H), 3.52-3.26 (m, 2H), 3.23-3.18 (m, 1H), 3.18-2.80 (m, 6H), 2.67-2.50 (m, 3H), 2.46-2.33 (m, 1H), 2.08-1.71 (m, 8H), 1.66-1.54 (m, 1H), 1.54-1.39 (m, 2H), 1.16 (d, J=6.8 Hz, 3H), 0.86 (d, J=5.2 Hz, 3H); MS: 756.7 (M+H$^+$).

366

(1S,11'R,12'S,13'R,16'R,16a'R,18a'R,E)-6-chloro-5-fluoro-11',12'-dimethyl-16'-(2-oxo-2-(pyrrolidin-1-yl)ethoxy)-3,4,12',13',16',16a',17',18',18a',19'-decahydro-1'H,2H,3'H, 11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 68)

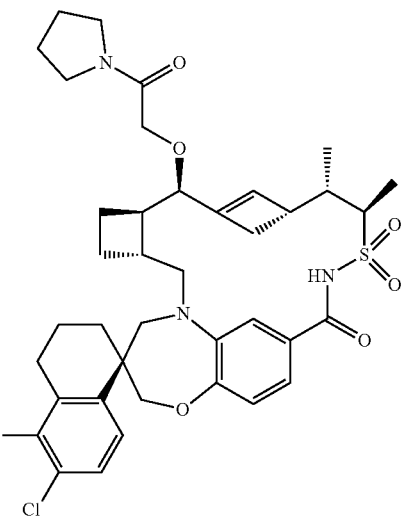

Yield: 6 mg as a white solid. $^1$H NMR (400 MHz, DMSO-$d_6$) δ 11.74 (s, 1H), 7.62-7.41 (m, 2H), 6.98-6.86 (s, 2H), 6.73 (s, 1H), 6.28 (s, 1H), 4.21-3.81 (m, 6H), 3.80-3.60 (m, 2H), 3.60-3.15 (m, 5H), 3.12-2.97 (m, 1H), 2.89 (d, J=16.8 Hz, 1H), 2.76 (d, J=10.0 Hz, 1H), 2.67-2.55 (m, 4H), 2.17 (d, J=12.8 Hz, 1H), 2.10-1.60 (m, 13H), 1.35 (d, J=6.0 Hz, 3H), 0.95 (d, J=5.6 Hz, 3H); MS: 740.7 (M+H$^+$).

367

(1S,11'R,12'S,13'R,16'R,16a'R,18a'R,E)-6-chloro-5-fluoro-11',12'-dimethyl-16'-(2-oxo-2-(piperidin-1-yl)ethoxy)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 69)

368

(1S,11'R,12'S,13'R,16'R,16a'R,18a'R,E)-6-chloro-5-fluoro-11',12'-dimethyl-16'-(2-(4-methylpiperazin-1-yl)-2-oxoethoxy)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 70)

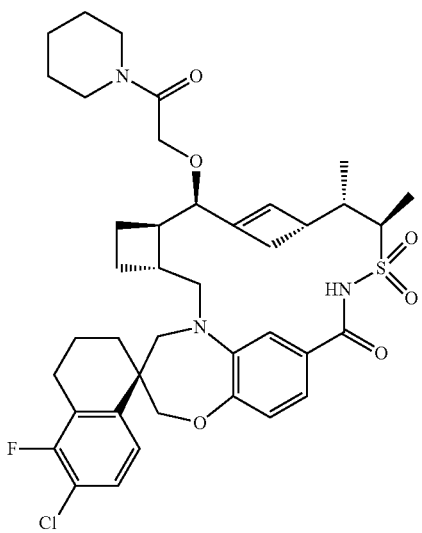 [SMILES: C[C@@H]1[C@@H](C)S(=O)(=O)NC(=O)c2ccc3c(c2)N(C[C@@H]2CC[C@H]2[C@@H](OCC(=O)N2CCCCC2)C2=C[C@H]1C2)C[C@@]1(CCCc2c1ccc(Cl)c2F)CO3]

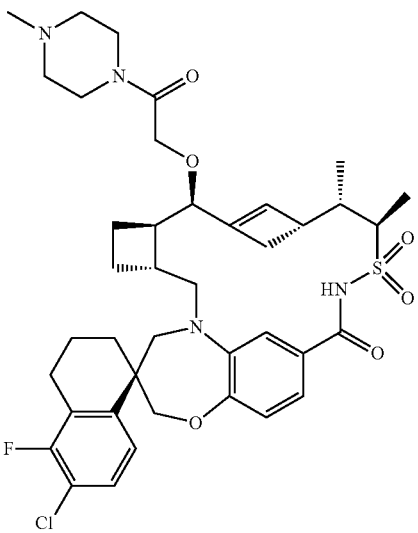

Yield: 7 mg as a white solid. $^1$H NMR (400 MHz, DMSO-d$_6$) δ 11.75 (s, 1H), 7.54 (d, J=8.8 Hz, 1H), 7.48 (t, J=8.0 Hz, 1H), 6.95-6.91 (s, 2H), 6.74 (s, 1H), 6.29 (s, 1H), 4.14-4.05 (m, 2H), 4.05-3.98 (m, 2H), 3.94-3.86 (m, 2H), 3.75 (d, J=14.0 Hz, 1H), 3.67 (d, J=14.3 Hz, 1H), 3.54-3.22 (m, 4H), 3.05 (dd, J=14.8, 11.0 Hz, 1H), 2.95-2.85 (m, 1H), 2.76 (dd, J=13.2, 4.0 Hz, 1H), 2.67-2.55 (m, 4H), 2.19 (d, J=13.4 Hz, 1H), 2.08-1.98 (m, 1H), 1.97-1.89 (m, 2H), 1.84-1.66 (m, 5H), 1.65-1.55 (m, 2H), 1.54-1.40 (m, 6H), 1.35 (d, J=7.2 Hz, 3H), 0.95 (d, J=6.6 Hz, 3H); MS: 754.9 (M+H$^+$).

Yield: 3.3 mg as a white solid. $^1$H NMR (400 MHz, DMSO-d$_6$) δ 7.55 (d, J=8.8 Hz, 1H), 7.49 (t, J=8.0 Hz, 1H), 6.98-6.92 (m, 2H), 6.74 (s, 1H), 6.33 (s, 1H), 4.17-4.01 (m, 4H), 4.00 (d, J=4.0 Hz, 1H), 3.94 (d, J=4.4 Hz, 1H), 3.76 (d, J=13.6 Hz, 1H), 3.68 (d, J=14.0 Hz, 1H), 3.55-3.20 (m, 8H), 3.05 (dd, J=14.4, 11.2 Hz, 1H), 2.91 (d, J=16.4 Hz, 1H), 2.84 (s, 3H), 2.77 (dd, J=13.0, 4.0 Hz, 1H), 2.68-2.56 (m, 5H), 2.21 (d, J=13.2 Hz, 1H), 2.09-1.88 (m, 3H), 1.85-1.66 (m, 5H), 1.55-1.40 (m, 1H), 1.37 (d, J=7.2 Hz, 3H), 0.97 (d, J=6.8 Hz, 3H); MS: 770.9 (M+H$^+$).

369

(1S,11'R,12'S,13'R,16'R,16a'R,18a'R)-6-chloro-5-fluoro-11',12'-dimethyl-16'-(1-methylpiperidin-4-yl)methoxy)-3,4,12',13',16',16a',17',18',18a',19'-decahydro-1'H,2H,3'H, 11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 71)

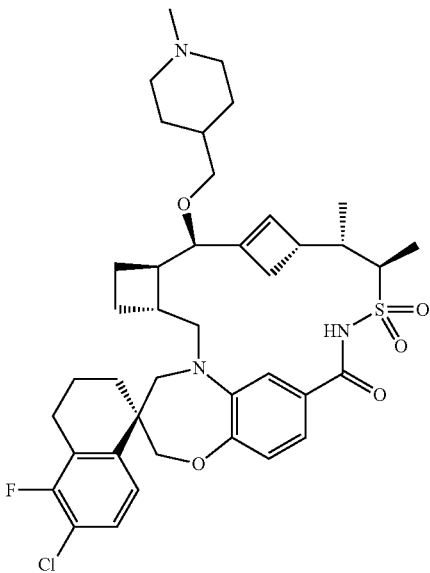 [SMILES: C[C@@H]1[C@@H](C)S(=O)(=O)NC(=O)c2ccc3c(c2)N(C[C@@H]2CC[C@H]2[C@@H](OCC2CCN(C)CC2)C2=C[C@H]1C2)C[C@@]1(CCCc2c1ccc(Cl)c2F)CO3]

Yield: 3 mg as a white solid. $^1$H NMR (400 MHz, DMSO-$d_6$) δ 11.79 (s, 1H), 7.54 (d, J=8.8 Hz, 1H), 7.52-7.44 (m, 1H), 6.95-6.91 (m, 2H), 6.75 (s, 1H), 6.28 (s, 1H), 4.15-4.05 (m, 2H), 4.00 (d, J=12.4 Hz, 1H), 3.87-3.74 (m, 2H), 3.67 (d, J=14.0 Hz, 1H), 3.60-3.20 (m, 4H), 3.20-3.10 (m, 1H), 3.08-2.86 (m, 3H), 2.84 (s, 3 H), 2.80-2.68 (m, 2H), 2.67-2.55 (m, 5H), 2.48-2.37 (m, 1H), 2.25-2.13 (m, 1H), 2.10-1.87 (m, 4H), 1.82-1.66 (m, 5H), 1.66-1.39 (m, 3H), 1.35 (d, J=7.2 Hz, 3H), 0.95 (d, J=6.6 Hz, 3H); MS: 740.8 (M+H$^+$).

370

Example 36

Synthesis of ethyl 2-(((1S,11'R,12'S,13'R,16'R,16a'R,18a'R,E)-6-chloro-5-fluoro-11',12'-dimethyl-10',10'-dioxido-8'-oxo-3,4,8',9',12',13',16',16a',17',18',18a',19'-dodecahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-16'-yl)oxy)acetate (Cpd. No. 72)

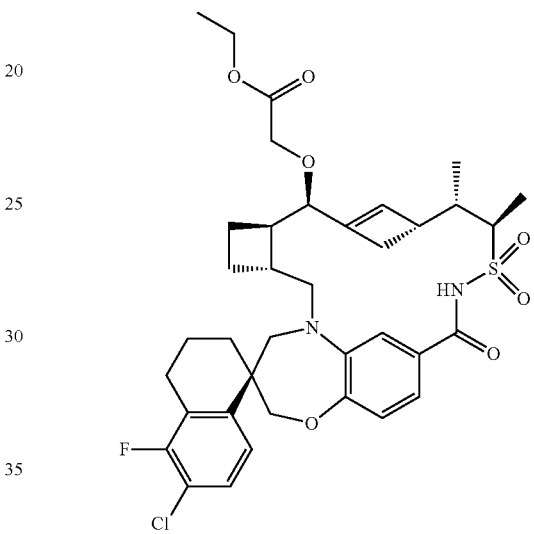

Under Ar, to a solution of (1S,11'R,12'S,13'R,16'R,16a'R,18a'R,E)-6-chloro-5-fluoro-16'-hydroxy-11',12'-dimethyl-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Step A of EXAMPLE 31, 50 mg, 0.08 mmol) in dry DCM (10 mL) was added rhodium(II) acetate dimer (35.1 mg, 0.08 mmol) at room temperature, followed by ethyl 2-diazoacetate (9.1 mg, 0.08 mmol). The reaction mixture was stirred for 2 h at room temperature. Water was added to quench the reaction, and the resulting mixture was extracted with EA twice. The EA layers were combined, washed with brine, dried over Na$_2$SO$_4$, and concentrated under reduced pressure to give a yellow oil, which was purified by C18 preparative-HPLC to afford the title compound (4.0 mg, 7%) as a white solid. $^1$H NMR (400 MHz, DMSO-$d_6$) δ 11.74 (s, 1H), 7.51 (d, J=8.7 Hz, 1H), 7.48-7.42 (m, 1H), 6.93-6.87 (m, 2H), 6.70 (s, 1H), 6.27 (s, 1H), 4.15-3.90 (m, 7H), 3.72 (d, J=14.7 Hz, 1H), 3.63 (d, J=14.1 Hz, 1H), 3.09-2.97 (m, 1H), 2.90-2.80 (m, 2H), 2.78-2.70 (m, 2H), 2.64-2.50 (m, 3H), 2.14 (d, J=13.2 Hz, 1H), 2.05-1.94 (m, 2H), 1.94-1.85 (m, 2H), 1.83-1.63 (m, 5H) 1.49-1.36 (m, 1H), 1.32 (d, J=7.1 Hz, 3H), 1.19 (d, J=7.1 Hz, 3H), 0.92 (d, J=6.5 Hz, 3H); MS: 715.4 (M+H$^+$).

Example 37

Synthesis of isopropyl 2-(((1S,11'R,12'S,13'R,16'R, 16a'R,18a'R,E)-6-chloro-5-fluoro-11',12'-dimethyl-10',10'-dioxido-8'-oxo-3,4,8',9',12',13',16',16a',17', 18',18a',19'-dodecahydro-1'H,2H,3'H,11'H-spiro [naphthalene-1,2'-[5,7]etheno[13,15] methanocyclobuta[i][1,4]oxazepino[3,4-f][1]thia[2, 7]diazacyclohexadecin]-16'-yl)oxy)acetate (Cpd. No. 73)

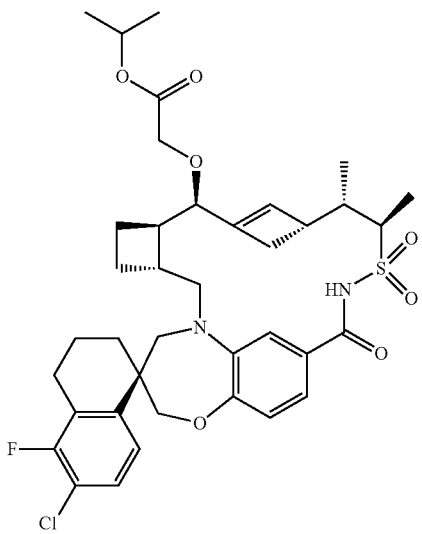 [SMILES: CC(C)OC(=O)CO[C@H]1C2=C[C@@H](C2)[C@H](C)[C@@H](C)S(=O)(=O)NC(=O)c2ccc3c(c2)N(C[C@@H]2CC[C@H]21)C[C@@]1(CCCc2c1ccc(Cl)c2F)CO3]

Example 38

Synthesis of 2-(((1S,11'R,12'S,13'R,16'R,16a'R, 18a'R,E)-6-chloro-5-fluoro-11',12'-dimethyl-10',10'-dioxido-8'-oxo-3,4,8',9',12',13',16,16a',17',18',18a', 19'-dodecahydro-1'H,2H,3'H,11'H-spiro [naphthalene-1,2'-[5,7]etheno[13,15] methanocyclobuta[i][1,4]oxazepino[3,4-f][1]thia[2, 7]diazacyclohexadecin]-16'-yl)oxy)acetic acid (Cpd. No. 74)

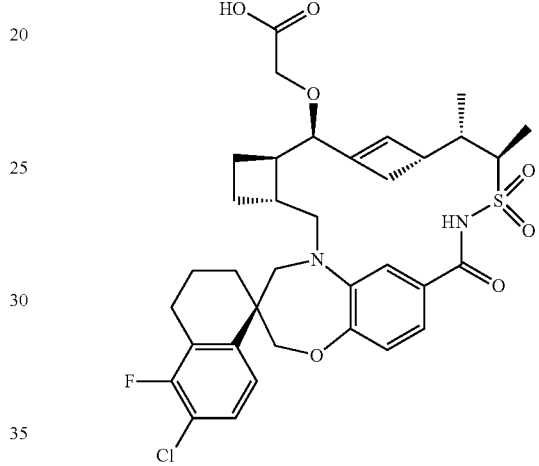

Under Ar, to a solution of ethyl 2-(((1S,11'R,12'S,13'R, 16'R,16a'R,18a'R,E)-6-chloro-5-fluoro-11',12'-dimethyl-10',3,4,8',9',12',13',16',16a',17',18',18a',19'-dodecahydro-1'H,2H,3'H,11'H-spiro[naphthalene-1,2'-[5,7]etheno[13,15] methanocyclobuta[i][1,4]oxazepino[3,4-f][1]thia[2,7] diazacyclohexadecin]-16'-yl)oxy)acetate (Cpd. No. 72, 30 mg, 0.04 mmol) in i-PrOH (8 mL) was added tetraisopropoxytitanium (11.9 mg, 0.04 mmol) at 25° C., and the reaction mixture was stirred for 2 h. Water was added to quench the reaction, and the resulting mixture was extracted with EA twice. The EA layers were combined, washed with brine, dried over $Na_2SO_4$, and concentrated under reduced pressure to give a yellow oil, which was purified by C18 preparative-HPLC to afford the title compound (6.5 mg, 21%) as a white solid. $^1$H NMR (400 MHz, DMSO-$d_6$) δ 11.74 (s, 1H), 7.95 (s, 1H), 7.51 (d, J=8.7 Hz, 1H), 7.48-7.41 (m, 1H), 6.93-6.87 (m, 2H), 6.71 (s, 1H), 6.26 (s, 1H), 4.93 (dd, J=12.5, 6.2 Hz, 1H), 4.12-3.86 (m, 6H), 3.72 (d, J=14.3 Hz, 1H), 3.63 (d, J=14.0 Hz, 1H), 3.08-2.97 (m, 1H), 2.93-2.82 (m, 1H), 2.78-2.69 (m, 1H), 2.64-2.53 (m, 3H), 2.13 (d, J=13.5 Hz, 1H), 2.03-1.87 (m, 4H), 1.81-1.63 (m, 5H), 1.47-1.37 (m, 1H), 1.31 (d, J=6.9 Hz, 3H), 1.20 (s, 3H), 1.17 (s, 3H), 0.92 (d, J=6.4 Hz, 3H); MS: 729.5 (M+H$^+$).

Under Ar, to a solution of ethyl 2-(((1S,11'R,12'S,13'R, 16'R,16a'R,18a'R,E)-6-chloro-5-fluoro-11',12'-dimethyl-10',10'-dioxido-8'-oxo-3,4,8',9',12',13',16,16a',17',18',18a', 19'-dodecahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-16'-yl)oxy)acetate (Cpd. No. 72, 10.0 mg, 0.01 mmol) in a mixed solvent of THF/ MeOH/$H_2O$ (4 mL/4 mL/4 mL) was added lithium hydroxide (0.34 mg, 0.01 mmol) at 25° C. The reaction mixture was stirred for 2 h, Sat. $NH_4Cl$ was added and the resulting mixture was extracted with EA twice. The EA layers were combined, washed with brine, dried over $Na_2SO_4$, and concentrated under reduced pressure to give a yellow oil, which was purified by C18 preparative-HPLC to afford the title compound (2.8 mg, 29%) as a white solid. $^1$H NMR (400 MHz, DMSO-$d_6$) δ 11.75 (s, 1H), 7.51 (d, J=8.7 Hz, 1H), 7.48-7.42 (m, 1H), 6.91-6.88 (m, 2H), 6.70 (s, 1H), 6.26 (s, 1H), 4.11-3.77 (m, 6H), 3.72 (d, J=14.2 Hz, 1H), 3.63 (d, J=14.1 Hz, 1H), 3.10-2.95 (m, 2H), 2.87 (d, J=16.9 Hz, 1H), 2.73 (dd, J=13.1, 4.1 Hz, 1H), 2.63-2.53 (m, 4H), 2.13 (d, J=13.2 Hz, 1H), 2.04-1.95 (m, 2H), 1.94-1.85 (m, 2H), 1.80-1.63 (m, 5H), 1.49-1.35 (m, 1H), 1.32 (d, J=7.2 Hz, 3H), 0.92 (d, J=6.7 Hz, 3H); MS: 687.4 (M+H$^+$).

Example 39

Synthesis of (1S,11'R,12'S,13'R,16'R,16a'R,18a'R,E)-6-chloro-5-fluoro-16'-(2-(4-methoxypiperidin-1-yl)ethoxy)-11',12'-dimethyl-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 75)

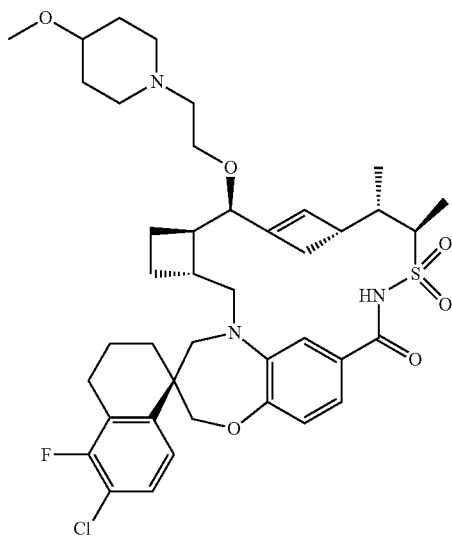

Step A: (1S,11'R,12'S,13'R,16'R,16a'R,18a'R,E)-6-chloro-5-fluoro-11',12'-dimethyl-16'-(2-((tetrahydro-2H-pyran-2-yl)oxy)ethoxy)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide

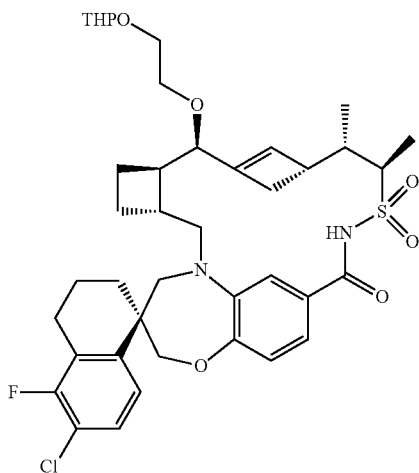

Under Ar, to a solution of (1S,11'R,12'S,13'R,16'R,16a'R,18a'R,E)-6-chloro-5-fluoro-16'-hydroxy-11',12'-dimethyl-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Step A of EXAMPLE 31, 0.70 g, 1.11 mmol) in dry DMF (20 mL) was added sodium hydride (0.27 g, 11.1 mmol) at 0° C. The reaction mixture was stirred for 20 min. Sodium iodide (0.21 g, 1.11 mmol) and 2-(2-bromoethoxy)tetrahydro-2H-pyran (1.2 g, 5.6 mmol) were added. The reaction mixture was allowed to warm up to 40° C. and stirred overnight. After cooling down to room temperature, water was added to quench the reaction and the resulting mixture was extracted with EA twice. The EA layers were combined, washed with brine, dried over $Na_2SO_4$, and concentrated under reduced pressure to give the crude title compound as an off-white solid, which was directly used for the next step without purification. MS: 757.5 (M+H$^+$).

Step B: (1S,11'R,12'S,13'R,16'R,16a'R,18a'R,E)-6-chloro-5-fluoro-16'-(2-hydroxyethoxy)-11',12'-dimethyl-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide

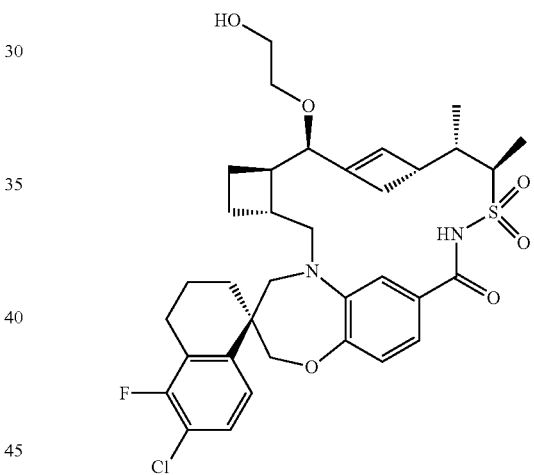

Under Ar, to a solution of the crude (1S,11'R,12'S,13'R,16'R,16a'R,18a'R,E)-6-chloro-5-fluoro-11',12'-dimethyl-16'-(2-((tetrahydro-2H-pyran-2-yl)oxy)eth oxy)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Step A) in a mixed solvent of DCM/MeOH (20 mL/20 mL) was added TsOH.H$_2$O (0.27 g, 11.1 mmol) at 40° C. The reaction mixture was stirred for 2 h. After cooling down to room temperature, water was added to quench the reaction and the resulting mixture was extracted with DCM twice. The DCM layers were combined, washed with brine, dried over $Na_2SO_4$, and concentrated under reduced pressure to give an off-white solid, which was purified by silica gel column chromatography (DCM:MeOH, 100:0→10:1) to afford the title compound (0.50 g, 67% over 2 steps) as a white solid. $^1$H NMR (400 MHz, DMSO-d$_6$) δ 11.71 (br, 1H), 7.51 (d, J=8.7 Hz, 1H), 7.45 (t, J=8.1 Hz, 1H), 6.93-6.87 (m, 2H), 6.74 (s, 1H), 6.23 (s, 1H), 4.12-4.01 (m, 2H), 3.97 (d, J=12.4 Hz, 1H), 3.83 (d, J=5.1 Hz, 1H), 3.76 (d, J=13.3 Hz, 1H), 3.64 (d, J=14.2 Hz, 1H), 3.43 (dd, J=10.4, 5.2 Hz, 2H), 3.37-3.28 (m, 3H), 3.27-3.18 (m, 1H), 3.04-2.94 (m, 1H), 2.91-2.81 (m, 1H), 2.72 (dd, J=13.1, 4.1 Hz, 1H), 2.65-2.50 (m, 3H), 2.49-2.36 (m, 1H), 2.13 (d, J=13.1 Hz, 1H), 2.10-1.92 (m, 3H), 1.79-1.62 (m, 5H), 1.46-1.35 (m, 1H), 1.32 (d, J=7.2 Hz, 3H), 0.93 (d, J=6.7 Hz, 3H); MS: 673.4 (M+H⁺).

Step C: 2-(((1S,11'R,12'S,13'R,16'R,16a'R,18a'R,E)-6-chloro-5-fluoro-11',12'-dimethyl-10',10'-dioxido-8'-oxo-3,4,8',9',12',13',16',16a',17',18',18a',19'-dodecahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-16'-yl)oxy)acetaldehyde

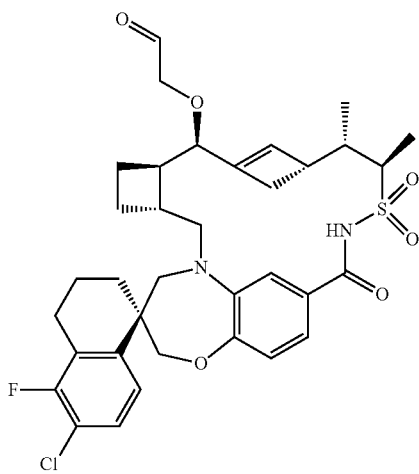 [SMILES: C[C@@H]1[C@@H](C)S(=O)(=O)NC(=O)c2ccc3c(c2)N(C[C@@H]2CC[C@H]2[C@@H](OCC=O)C2=C[C@H]1C2)C[C@@]1(CCCc2c1ccc(Cl)c2F)CO3]

Under Ar, to a solution of (1S,11'R,12'S,13'R,16'R,16a'R,18a'R,E)-6-chloro-5-fluoro-16'-(2-hydroxyethoxy)-11',12'-dimethyl-3,4,12',13',16',16a',17',18',18a',19'-decahydro-1'H,2H,3'H, 11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Step B, 90.0 mg, 0.13 mmol) in dry DMSO (2 mL) was added IBX (56.2 mg, 0.20 mmol) at 22° C. The reaction mixture was stirred for 6 h. Aq. NaHCO₃ was added to quench the reaction, and the resulting mixture was extracted with EA twice. The EA layers were combined, washed with brine, dried over Na₂SO₄, and concentrated under reduced pressure to give the crude title compound (90 mg) as a yellow solid, which was directly used without purification. MS: 671.4 (M+H⁺).

Step D: (1 S, 11'R,12'S,13'R,16'R,16a'R,18a'R,E)-6-chloro-5-fluoro-16'-(2-(4-methoxypiperidin-1-yl)ethoxy)-11',12'-dimethyl-3,4,12',13',16',16a',17',18',18a',19'-decahydro-1'H,2H,3'H, 11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 75)

Under Ar, to a solution of the crude 2-(((1S,11'R,12'S,13'R,16'R,16a'R,18a'R,E)-6-chloro-5-fluoro-11',12'-dimethyl-10',10'-dioxido-8'-oxo-3,4,8',9',12',13',16',16a',17',18',18a',19'-dodecahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-16'-yl)oxy)acetaldehyde (Step C, 30 mg) in dry DCM (10 mL) was added 4-methoxypiperidine hydrochloride (33.9 mg 0.22 mmol) at 0° C., followed by Et₃N (45.2 mg, 0.45 mmol). The reaction mixture was stirred for 20 min. Sodium triacetoxyhydroborate (95 mg, 0.45 mmol) was added, and the reaction mixture was stirred overnight at room temperature. Aq. NH₄Cl was added to quench the reaction, and the resulting mixture was extracted with DCM twice. The DCM layers were combined, washed with brine, dried over Na₂SO₄, and concentrated under reduced pressure to give a yellow oil, which was purified by C18 preparative-HPLC to afford the title compound (3.0 mg, 9%) as a white solid. ¹H NMR (400 MHz, DMSO-d₆) δ 11.80 (s, 1H), 7.54 (d, J=8.6 Hz, 1H), 7.48 (t, J=7.8 Hz, 1H), 6.94 (s, 2H), 6.74 (s, 1H), 6.35 (s, 1H), 4.11 (d, J=11.1 Hz, 2H), 4.01 (s, 1H), 3.97-3.93 (m, 1H), 3.79 (d, J=15.6 Hz, 1H), 3.72-3.64 (m, 6H), 3.22-3.14 (s, 5H), 3.08-2.95 (m, 4H), 2.89 (d, J=16.9 Hz, 2H), 281-2.72 (m, 2H), 2.71-2.57 (m, 5H), 2.20 (d, J=12.8 Hz, 1H), 2.08-1.89 (m, 4H), 1.81-1.70 (m, 5H), 1.52-1.39 (m, 1H), 1.35 (d, J=6.8 Hz, 3H), 0.95 (d, J=6.2 Hz, 3H); MS: 770.5 (M+H⁺).

Example 40

The protocol described in EXAMPLE 39 was used to give the following compounds.

(1S,11'R,12'S,13'R,16'R,16a'R,18a'R,E)-6-chloro-5-fluoro-11',12'-dimethyl-16'-(2-(4-(methylsulfonyl)piperazin-1-yl)ethoxy)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 76)

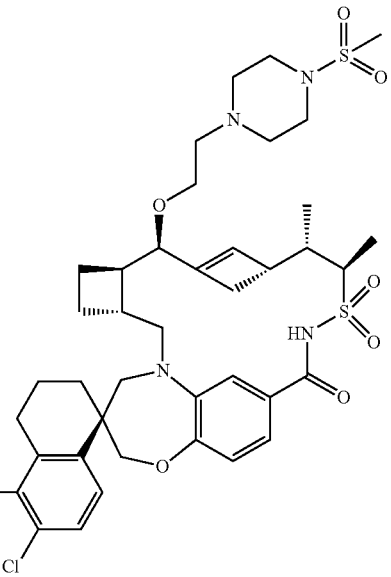

Yield: 8.4 mg (22%) as a white solid. ¹H NMR (400 MHz, DMSO-d₆) δ 7.51 (d, J=8.6 Hz, 1H), 7.48-7.42 (m, 1H), 6.93-6.89 (m, 2H), 6.71 (s, 1H), 6.33 (s, 1H), 4.12-4.03 (m, 2H), 3.97 (d, J=12.1 Hz, 1H), 3.93 (d, J=4.5 Hz, 1H), 3.77 (d, J=13.5 Hz, 1H), 3.64 (d, J=14.5 Hz, 1H), 3.61-3.45 (m, 2H)), 3.34-3.24 (m, 8H), 3.19-3.05 (m, 2H), 2.99 (s, 3H), 2.91-2.70 (m, 1H), 2.63-2.51 (m, 4H), 2.49-2.40 (m, 4H), 2.17 (d, J=12.7 Hz, 1H), 2.02-1.84 (m, 3H), 1.80-1.63 (m, 5H), 1.45-1.36 (m, 1H), 1.33 (d, J=7.2 Hz, 3H), 0.93 (d, J=6.6 Hz, 3H); MS: 819.5 (M+H$^+$).

(1S,11'R,12'S,13'R,16'R,16a'R,18a'R,E)-6-chloro-16'-(2-(dimethylamino)ethoxy)-5-fluoro-11',12'-dimethyl-3,4,12',13',16',16a',17',18',18a',19'-decahydro-1'H,2H,3'H,1 PH-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 77)

(1S,11'R,12'S,13'R,16'R,16a'R,18a'R,E)-6-chloro-5-fluoro-11',12'-dimethyl-16'-(2-(methylamino)ethoxy)-3,4,12',13',16',16a',17',18',18a',19'-decahydro-1'H,2H,3'H, 11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 78)

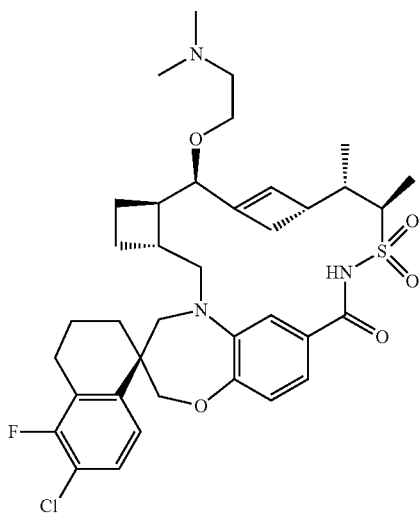 [SMILES: C[C@@H]1[C@@H](C)S(=O)(=O)NC(=O)c2ccc3c(c2)N(C[C@@H]2CC[C@H]2[C@@H](OCCN(C)C)C2=C[C@H]1C2)C[C@@]1(CCCc2c1ccc(Cl)c2F)CO3]

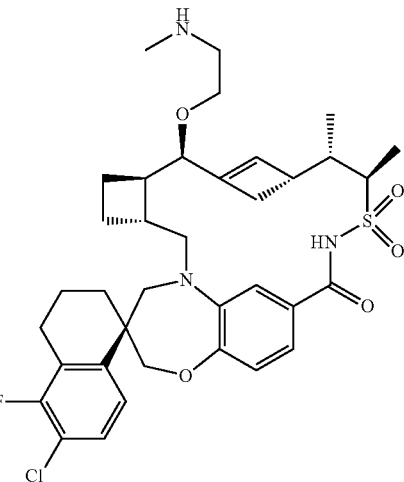

Yield: 10.4 mg (6%) as a white solid. $^1$H NMR (400 MHz, DMSO-d$_6$) δ 11.77 (s, 1H), 7.51 (d, J=8.7 Hz, 1H), 7.49-7.43 (m, 1H), 6.93-6.89 (m, 2H), 6.71 (s, 1H), 6.33 (s, 1H), 4.13-4.03 (m, 2H), 3.97 (d, J=12.4 Hz, 1H), 3.94 (d, J=4.9 Hz, 1H), 3.77-3.55 (m, 3H), 3.53-3.48 (m, 2H), 3.34 (d, J=14.5 Hz, 2H), 3.30-3.17 (m, 2H), 3.03-2.94 (m, 1H), 2.87-2.78 (m, 7H), 2.64-2.52 (m, 3H), 2.18-1.84 (m, 4H), 1.80-1.64 (m, 5H), 1.47-1.36 (m, 1H), 1.33 (d, J=7.1 Hz, 3H), 0.93 (d, J=6.6 Hz, 3H); MS: 700.7 (M+H$^+$).

Yield: 11.5 mg (38%) as a white solid. $^1$H NMR (400 MHz, DMSO-d$_6$) δ 11.77 (s, 1H), 8.30 (s, 1H), 7.51 (d, J=8.7 Hz, 1H), 7.49-7.42 (m, 1H), 6.92-6.89 (m, 2H), 6.72 (s, 1H), 6.31 (s, 1H), 4.1-4.0 (m, 2H), 3.97 (d, J=12.3 Hz, 1H), 3.91 (d, J=5.0 Hz, 1H), 3.78 (d, J=13.8 Hz, 1H), 3.65 (d, J=14.2 Hz, 1H), 3.56-3.48 (m, 1H), 3.45-3.42 (m, 2H), 3.30-3.20 (m, 3H), 2.76-2.52 (m, 8H), 2.48-2.41 (m, 1H), 2.16-1.84 (m, 4H), 1.80-1.64 (m, 5H), 1.46-1.36 (m, 1H), 1.33 (d, J=7.2 Hz, 3H), 0.93 (d, J=6.6 Hz, 3H); MS: 686.5 (M+H$^+$).

379

(1S,11'R,12'S,13'R,16'R,16a'R,18a'R,E)-6-chloro-5-fluoro-11',12'-dimethyl-16'-(2-(6-methyl-2,6-diazaspiro[3.3]heptan-2-yl)ethoxy)-3,4,12',13',16',16a',17',18',18a',19'-decahydro-1'H,2H,3'H, 11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide
(Cpd. No. 81)

380

(1S,11'R,12'S,13'R,16'R,16a'R,18a'R,E)-6-chloro-16'-(2-((2S,6R)-2,6-dimethylmorpholino)ethoxy)-5-fluoro-11',12'-dimethyl-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide
(Cpd. No. 82)

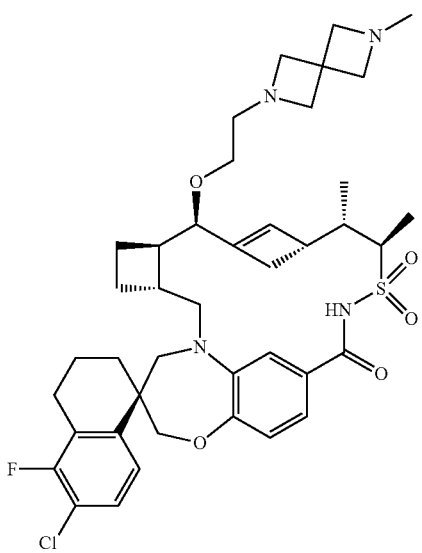 [SMILES: C[C@@H]1[C@@H](C)S(=O)(=O)NC(=O)c2ccc3c(c2)N(C[C@@H]2CC[C@H]2[C@@H](OCCN2CC4(CN(C)C4)C2)C2=C[C@H]1C2)C[C@@]1(CCCc2c1ccc(Cl)c2F)CO3]

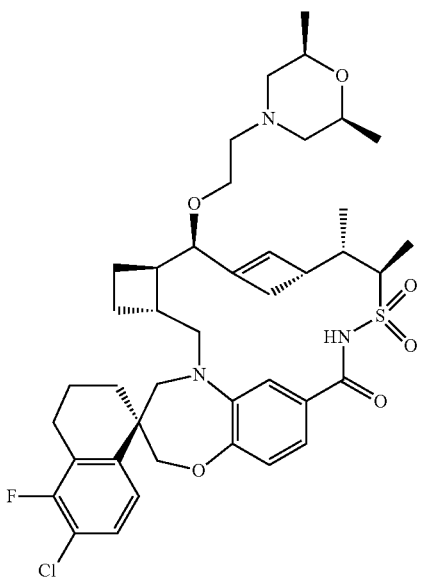 [SMILES: C[C@@H]1[C@@H](C)S(=O)(=O)NC(=O)c2ccc3c(c2)N(C[C@@H]2CC[C@H]2[C@@H](OCCN2C[C@@H](C)O[C@@H](C)C2)C2=C[C@H]1C2)C[C@@]1(CCCc2c1ccc(Cl)c2F)CO3]

Yield: 3.5 mg (10%) as a white solid. $^1$H NMR (400 MHz, DMSO-d$_6$) δ 11.77 (s, 1H), 7.52 (d, J=8.6 Hz, 1H), 7.49-7.42 (m, 1H), 6.93-6.89 (m, 2H), 6.71 (s, 1H), 6.31 (s, 1H), 4.35-4.13 (m, 6H), 4.12-4.02 (m, 3H), 3.98 (d, J=12.3 Hz, 1H), 3.87 (d, J=4.9 Hz, 1H), 3.77 (d, J=14.9 Hz, 1H), 3.65 (d, J=14.2 Hz, 1H), 3.52-3.41 (m, 2H), 3.30-3.19 (m, 4H), 3.05-2.83 (m, 2H), 2.78-2.71 (m, 4H), 2.65-2.53 (m, 3 H), 2.45-2.37 (m, 1H), 2.15 (d, J=13.3 Hz, 1H), 2.00-1.85 (m, 3H), 1.83-1.64 (m, 5H), 1.48-1.36 (m, 1H), 1.32 (d, J=7.2 Hz, 3H), 0.93 (d, J=6.6 Hz, 3H); MS: 769.3 (M+H$^+$).

Yield: 12 mg (11%) as a white solid. $^1$H NMR (400 MHz, DMSO-d$_6$) δ 11.78 (s, 1H), 7.51 (d, J=8.7 Hz, 1H), 7.49-7.42 (m, 1H), 6.93-6.89 (m, 2H), 6.71 (s, 1H), 6.33 (s, 1H), 4.12-4.04 (m, 2H), 3.96-3.65 (m, 6H), 3.68-3.50 (m, 4H), 3.30-3.17 (m, 2H), 3.05-2.80 (m, 2H), 2.78-2.52 (m, 6H), 2.18 (d, J=13.1 Hz, 1H), 2.10-1.85 (m, 4H), 1.84-1.61 (m, 5H), 1.47-1.36 (m, 2H), 1.33 (d, J=7.2 Hz, 3H), 1.12 (d, J=6.1 Hz, 6H), 0.93 (d, J=6.7 Hz, 3H); MS: 770.5 (M+H$^+$).

381

(1S,11'R,12'S,13'R,16'R,16a'R,18a'R,E)-6-chloro-16'-(2-((3S,5R)-3,5-dimethylpiperazin-1-yl)ethoxy)-5-fluoro-11',12'-dimethyl-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 83)

382

(1S,11'R,12'S,13'R,16'R,16a'R,18a'R,E)-6-chloro-5-fluoro-11',12'-dimethyl-16'-(2-((3S,5R)-3,4,5-trimethylpiperazin-1-yl)ethoxy)-3,4,12',13',16',16a',17',18',18a',19'-decahydro-1'H,2H,3'H, 11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 84)

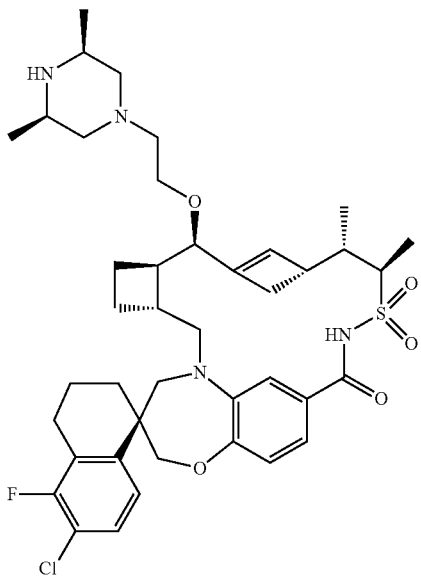 [SMILES: C[C@@H]1[C@@H](C)S(=O)(=O)NC(=O)c2ccc3c(c2)N(C[C@@H]2CC[C@H]2[C@@H](OCCN2C[C@@H](C)N[C@@H](C)C2)C2=C[C@H]1C2)C[C@@]1(CCCc2c1ccc(Cl)c2F)CO3]

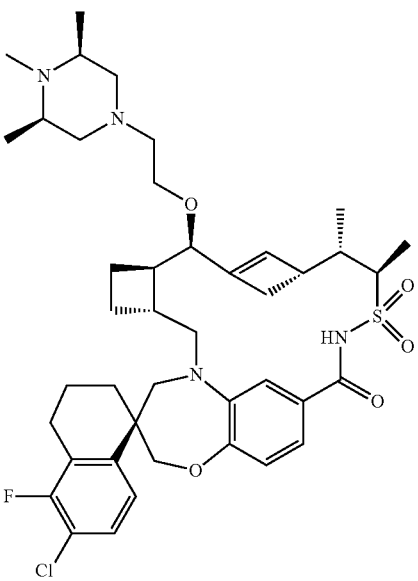 [SMILES: C[C@@H]1[C@@H](C)S(=O)(=O)NC(=O)c2ccc3c(c2)N(C[C@@H]2CC[C@H]2[C@@H](OCCN2C[C@@H](C)N(C)[C@@H](C)C2)C2=C[C@H]1C2)C[C@@]1(CCCc2c1ccc(Cl)c2F)CO3]

Yield: 4 mg (15%) as a white solid. $^1$H NMR (400 MHz, DMSO-d$_6$) δ 11.77 (s, 1H), 7.52 (d, J=8.9 Hz, 1H), 7.49-7.43 (m, 1H), 6.92-6.89 (m, 2H), 6.72 (s, 1H), 6.28 (s, 1H), 4.11-4.03 (m, 2H), 3.97 (d, J=12.3 Hz, 1H), 3.85 (d, J=5.0 Hz, 1H), 3.76 (d, J=13.8 Hz, 1H), 3.64 (d, J=14.5 Hz, 1H), 3.54-3.46 (m, 4H), 3.36-3.25 (m, 9H), 2.75-2.68 (m, 1H), 2.63-2.52 (m, 3H), 2.47-2.36 (m, 1H), 2.16 (d, J=12.7 Hz, 1H), 2.04-1.93 (m, 2H), 1.93-1.84 (m, 2H), 1.78-1.63 (m, 5H), 1.47-1.35 (m, 1H), 1.33 (d, J=7.2 Hz, 3H), 1.18 (d, J=5.6 Hz, 6H), 0.93 (d, J=6.7 Hz, 3H); MS: 769.6 (M+H$^+$).

Yield: 3.7 mg (15%) as a white solid. $^1$H NMR (400 MHz, DMSO-d$_6$) δ 11.76 (s, 1H), 7.51 (d, J=8.7 Hz, 1H), 7.49-7.42 (m, 1H), 6.93-6.89 (m, 2H), 6.72 (s, 1H), 6.27 (s, 1H), 4.07 (t, J=9.9 Hz, 2H), 3.97 (d, J=12.4 Hz, 1H), 3.84 (d, J=4.4 Hz, 1 H), 3.76 (d, J=13.4 Hz, 1H), 3.64 (d, J=14.2 Hz, 2H), 3.34 (d, J=14.4 Hz, 3H), 3.12 (s, 2H), 3.06-2.92 (m, 2H), 2.90-2.74 (m, 2H), 2.74-2.66 (m, 2H), 2.59-2.51 (m, 7H), 2.47-2.37 (m, 1H), 2.16 (d, J=13.1 Hz, 1H), 2.07-1.83 (m, 4H), 1.80-1.60 (m, 5H), 1.46-1.37 (m, 1H), 1.33 (d, J=7.2 Hz, 3H), 1.23 (s, 6H), 0.93 (d, J=6.7 Hz, 3H); MS: 783.5 (M+H$^+$).

383

(1S,11'R,12'S,13'R,16'R,16a'R,18a'R,E)-6-chloro-5-fluoro-11',12'-dimethyl-16'-(2-(3-oxopiperazin-1-yl)ethoxy)-3,4,12',13',16',16a',17',18',18a',19'-decahydro-1'H,2H,3'H, 11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 85)

384

(1S,11'R,12'S,13'R,16'R,16a'R,18a'R,E)-6-chloro-5-fluoro-11',12'-dimethyl-16'-(2-(4-methylpiperazin-1-yl)ethoxy)-3,4,12',13',16',16a',17',18',18a',19'-decahydro-1'H,2H,3'H, 11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 86)

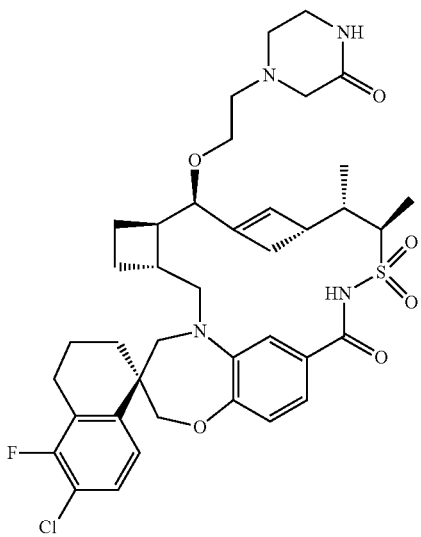 [SMILES: C[C@@H]1[C@@H](C)S(=O)(=O)NC(=O)c2ccc3c(c2)N(C[C@@H]2CC[C@H]2[C@@H](OCCN2CCNC(=O)C2)C2=C[C@H]1C2)C[C@@]1(CCCc2c1ccc(Cl)c2F)CO3]

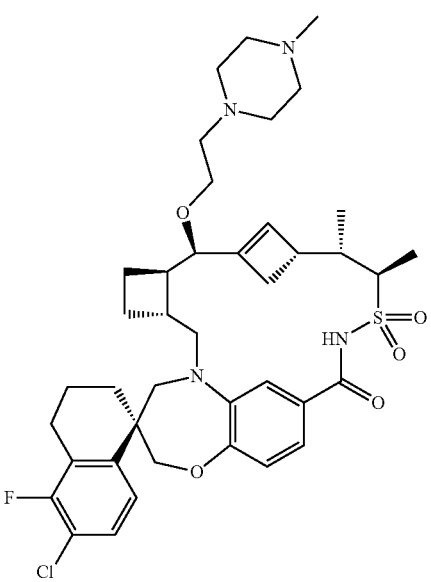 [SMILES: C[C@@H]1[C@@H](C)S(=O)(=O)NC(=O)c2ccc3c(c2)N(C[C@@H]2CC[C@H]2[C@@H](OCCN2CCN(C)CC2)C2=C[C@H]1C2)C[C@@]1(CCCc2c1ccc(Cl)c2F)CO3]

Yield: 3 mg (12%) as a white solid. $^1$H NMR (400 MHz, DMSO-$d_6$) δ 11.78 (s, 1H), 7.51 (d, J=8.8 Hz, 1H), 7.49-7.43 (m, 1H), 6.93-6.89 (m, 2H), 6.72 (s, 1H), 6.33 (s, 1H), 4.11-4.03 (m, 2H), 3.97 (d, J=12.5 Hz, 1H), 3.95-3.89 (m, 1H), 3.77 (d, J=13.2 Hz, 1H), 3.64 (d, J=14.3 Hz, 1H), 3.61-3.45 (m, 2H), 3.34-3.25 (m, 8H), 3.06-2.94 (m, 1H), 2.92-2.71 (m, 2H), 2.63-2.52 (m, 4H), 2.47-2.42 (m, 1H), 2.17 (d, J=13.1 Hz, 1H), 2.03-1.84 (m, 4H), 1.81-1.62 (m, 5H), 1.47-1.36 (m, 1H), 1.33 (d, J=7.2 Hz, 3H), 0.93 (d, J=6.7 Hz, 3H); MS: 755.5 (M+H$^+$).

Yield: 9.5 mg (36%) as a white solid. $^1$H NMR (400 MHz, DMSO-$d_6$) δ 11.77 (s, 1H), 7.51 (d, J=8.7 Hz, 1H), 7.49-7.42 (m, 1H), 6.92-6.89 (s, 2H), 6.72 (s, 1H), 6.29 (s, 1H), 4.11-4.02 (m, 2H), 3.97 (d, J=12.4 Hz, 1H), 3.86 (d, J=4.9 Hz, 1H), 3.76 (d, J=13.5 Hz, 1H), 3.64 (d, J=14.4 Hz, 2H), 3.50-3.27 (m, 5H), 3.04-2.92 (m, 3H), 2.91-2.82 (m, 2H), 2.78-2.65 (m, 5H), 2.64-2.52 (m, 3H), 2.47-2.36 (m, 3H), 2.15 (d, J=13.4 Hz, 1H), 2.04-1.82 (m, 4H), 1.78-1.63 (m, 5H), 1.46-1.36 (m, 1H), 1.33 (d, J=7.2 Hz, 3H), 0.93 (d, J=6.6 Hz, 3H); MS: 755.6 (M+H$^+$).

385

(1S,11'R,12'S,13'R,16'R,16a'R,18a'R,E)-16'-(2-(4-acetylpiperazin-1-yl)ethoxy)-6-chloro-5-fluoro-11',12'-dimethyl-3,4,12',13',16',16a',17',18',18a',19'-decahydro-1'H,2H,3'H, 11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 87)

386

(1S,11'R,12'S,13'R,16'R,16a'R,18a'R,E)-6-chloro-16'-(2-(1,1-dioxidothiomorpholino)ethoxy)-5-fluoro-11',12'-dimethyl-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 88)

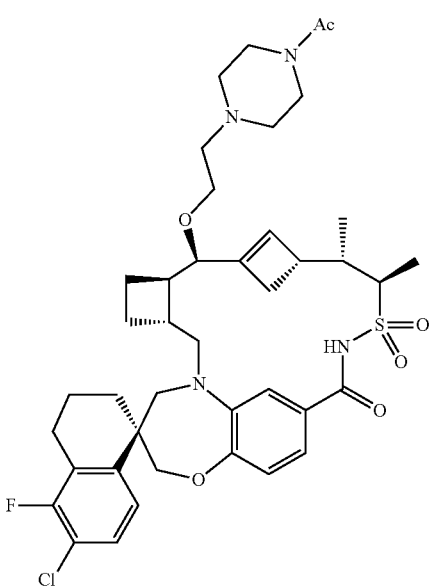 [SMILES: CC(=O)N1CCN(CCO[C@H]2C3=C[C@@H](C3)[C@H](C)[C@@H](C)S(=O)(=O)NC(=O)c3ccc4c(c3)N(C[C@@H]3CC[C@H]32)C[C@@]2(CCCc3c2ccc(Cl)c3F)CO4)CC1]

Yield: 11 mg (32%) as a white solid. $^1$H NMR (400 MHz, DMSO-d$_6$) δ 11.76 (s, 1H), 7.52 (d, J=8.7 Hz, 1H), 7.48-7.41 (m, 1H), 6.93-6.88 (s, 2H), 6.72 (s, 1H), 6.34 (s, 1H), 4.13-4.03 (m, 2H), 4.02-3.90 (m, 3H), 3.77 (d, J=13.9 Hz, 1H), 3.65 (d, J=13.9 Hz, 2H), 3.58-3.48 (m, 2H), 3.48-3.44 (m, 2H), 3.33-3.22 (m, 4H), 3.05-2.92 (m, 3H), 2.91-2.82 (m, 2H), 2.75 (dd, J=13.1, 3.7 Hz, 1H), 2.62-2.52 (m, 3H), 2.47-2.41 (m, 1H), 2.18 (d, J=13.5 Hz, 1H), 2.04 (s, 3H), 2.01-1.93 (m, 1H), 1.90 (s, 2H), 1.81-1.65 (m, 5H), 1.46-1.36 (m, 1H), 1.33 (d, J=7.1 Hz, 3H), 0.93 (d, J=6.6 Hz, 3H); MS: 783.7 (M+H$^+$).

Yield: 7 mg (20%) as a white solid. $^1$H NMR (400 MHz, DMSO-d$_6$) δ 1H NMR (400 MHz, DMSO) δ 11.74 (s, 1H), 7.51 (d, J=8.7 Hz, 1H), 7.48-7.42 (m, 1H), 6.93-6.88 (s, 2H), 6.72 (s, 1H), 6.30 (s, 1H), 4.12-4.04 (m, 2H), 3.97 (d, J=12.3 Hz, 1H), 3.89 (d, J=4.8 Hz, 1H), 3.76 (d, J=13.9 Hz, 2H), 3.64 (d, J=14.1 Hz, 2H), 3.34 (d, J=14.8 Hz, 8H), 3.07-2.94 (m, 3H), 2.87 (d, J=16.9 Hz, 1H), 2.74 (dd, J=12.9, 3.5 Hz, 1H), 2.64-2.52 (m, 4H), 2.47-2.39 (m, 1H), 2.16 (d, J=13.2 Hz, 1H), 1.97 (d, J=14.2 Hz, 1H), 1.94-1.84 (m, 2H), 1.78-1.64 (m, 5H), 1.44-1.36 (m, 1H), 1.33 (d, J=7.2 Hz, 3H), 0.93 (d, J=6.6 Hz, 3H); MS: 790.7 (M+H$^+$).

387

(1S,11'R,12'S,13'R,16'R,16a'R,18a'R)-6-chloro-5-fluoro-11',12'-dimethyl-16'-(2-(4-(tetrahydro-2H-pyran-4-yl)piperazin-1-yl)ethoxy)-3,4,12',13',16',16a',17',18',18a',19'-decahydro-1'H,2H,3'H, 11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 89)

388

(1S,11'R,12'S,13'R,16'R,16a'R,18a'R,E)-6-chloro-5-fluoro-16'-(2-(4-isopropylpiperazin-1-yl)ethoxy)-11',12'-dimethyl-3,4,12',13',16',16a',17',18',18a',19'-decahydro-1'H,2H,3'H, 11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 90)

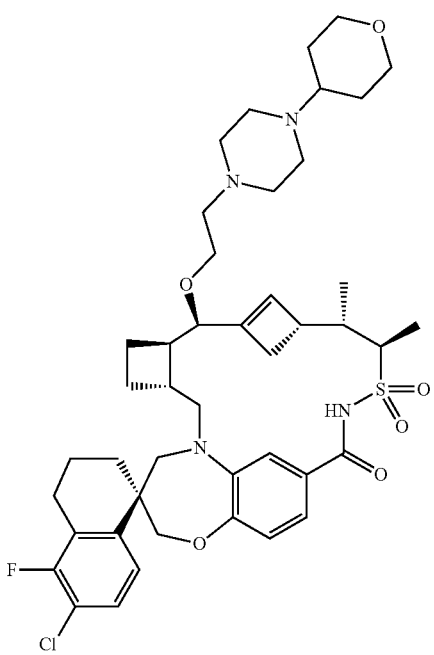 [SMILES: C[C@@H]1[C@@H](C)S(=O)(=O)NC(=O)c2ccc3c(c2)N(C[C@@H]2CC[C@H]2[C@@H](OCCN2CCN(C4CCOCC4)CC2)C2=C[C@H]1C2)C[C@@]1(CCCc2c1ccc(Cl)c2F)CO3]

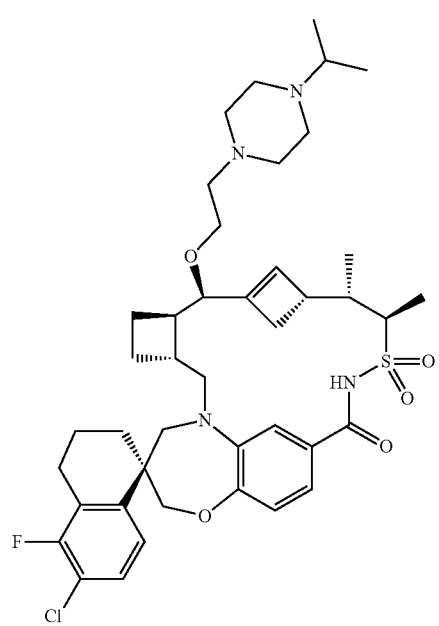 [SMILES: CC(C)N1CCN(CCO[C@H]2C3=C[C@@H](C3)[C@H](C)[C@@H](C)S(=O)(=O)NC(=O)c3ccc4c(c3)N(C[C@@H]3CC[C@H]32)C[C@@]2(CCCc3c2ccc(Cl)c3F)CO4)CC1]

Yield: 30 mg (31%) as a white solid. $^1$H NMR (400 MHz, DMSO-$d_6$) δ 11.76 (s, 1H), 7.52 (d, J=8.8 Hz, 1H), 7.45 (t, J=8.0 Hz, 1H), 6.93-6.89 (m, 2H), 6.72 (s, 1H), 6.30 (s, 1H), 4.13-4.02 (m, 2H), 4.01-3.85 (m, 4H), 3.77 (d, J=13.4 Hz, 1H), 3.64 (d, J=14.0 Hz, 2H), 3.60-3.20 (m, 15H), 3.05-2.81 (m, 2H), 2.73 (dd, J=13.0, 4.0 Hz, 1H), 2.64-2.53 (m, 4H), 2.48-2.38 (m, 1H), 2.16 (d, J=13.0 Hz, 1H), 2.04-1.82 (m, 5H), 1.80-1.63 (m, 5H), 1.60-1.37 (m, 2H), 1.33 (d, J=7.2 Hz, 3H), 0.93 (d, J=6.7 Hz, 3H); MS: 826.9 (M+H$^+$).

Yield: 40 mg (43%) as a white solid. $^1$H NMR (400 MHz, DMSO-$d_6$) δ 11.76 (s, 1H), 7.52 (d, J=8.8 Hz, 1H), 7.45 (t, J=8.0 Hz, 1H), 6.93-6.89 (m, 2H), 6.72 (s, 1H), 6.30 (s, 1H), 4.13-4.02 (m, 2H), 3.97 (d, J=12.4 Hz, 1H), 3.89 (d, J=5.0 Hz, 2H), 3.83-3.26 (m, 14H), 2.97 (dd, J=14.8, 11.4 Hz, 1H), 2.87 (d, J=16.4 Hz, 1H), 2.73 (dd, J=13.0, 3.8 Hz, 1H), 2.65-2.51 (m, 4H), 2.48-2.39 (m, 1H), 2.16 (d, J=13.2 Hz, 1H), 2.04-1.82 (m, 3H), 1.80-1.61 (m, 5H), 1.46-1.35 (m, 1H), 1.33 (d, J=7.2 Hz, 3H), 1.22 (d, J=6.4 Hz, 6H), 0.93 (d, J=6.7 Hz, 3H); MS: 784.8 (M+H$^+$).

Example 41

Synthesis of N-(2-(((1S,11'R,12'S,13'R,16'R,16a'R, 18a'R,E)-6-chloro-5-fluoro-11',12'-dimethyl-10',10'-dioxido-8'-oxo-3,4,8',9',12',13',16',16a',17',18',18a', 19'-dodecahydro-1'H,2H,3'H, 11'H-spiro [naphthalene-1,2'-[5,7]etheno[13,15] methanocyclobuta[i][1,4]oxazepino[3,4-f][1]thia[2, 7]diazacyclohexadecin]-16'-yl)oxy)ethyl)-N-methylmethanesulfonamide (Cpd. No. 79)

Example 42

Synthesis of N-(2-(((1S,11'R,12'S,13'R,16'R,16a'R, 18a'R,E)-6-chloro-5-fluoro-11',12'-dimethyl-10',10'-dioxido-8'-oxo-3,4,8',9',12',13',16',16a',17',18',18a', 19'-dodecahydro-1'H,2H,3'H, 11'H-spiro [naphthalene-1,2'-[5,7]etheno[13,15] methanocyclobuta[i][1,4]oxazepino[3,4-f][1]thia[2, 7]diazacyclohexadecin]-16'-yl)oxy)ethyl)-N-methylacetamide

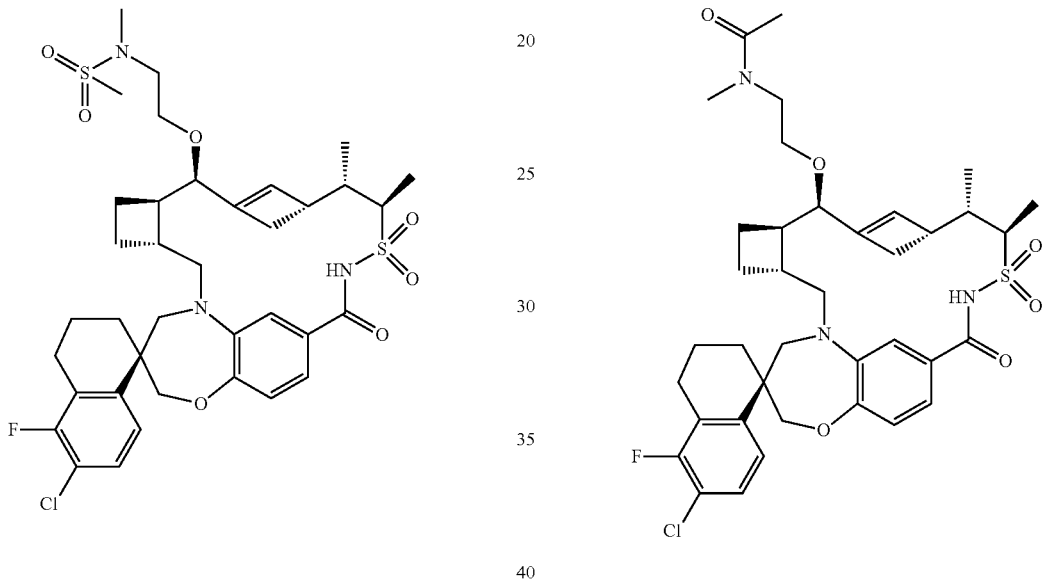

Under Ar, to a solution of (1S,11'R,12'S,13'R,16'R,16a'R, 18a'R,E)-6-chloro-5-fluoro-11',12'-dimethyl-16'-(2-(methylamino)ethoxy)-3,4,12',13',16',16a',17',18',18a',19'-decahydro-1'H,2H,3'H, 11'H-spiro[naphthalene-1,2'-[5,7]etheno [13,15]methanocyclobuta[i][1,4]oxazepino[3,4-f][1]thia[2, 7]diazacyclohexadecin]-8'(9'H)-one 10',10'-dioxide (Cpd. No. 78, 20 mg, 0.03 mmol) in dry DCM (8 mL) was added Et$_3$N (2.95 mg, 0.03 mmol) and MsCl (3.3 mg, 0.03 mmol) at 0° C. The reaction mixture was stirred for 20 min. After removal of the volatiles under reduced pressure, the residue was purified by C18 preparative-HPLC to afford the title compound (4.0 mg, 18%) as a white solid. $^1$H NMR (400 MHz, DMSO-d$_6$) δ 11.74 (s, 1H), 7.51 (d, J=8.7 Hz, 1H), 7.48-7.41 (m, 1H), 6.92-6.88 (m, 2H), 6.72 (s, 1H), 6.28 (s, 1H), 4.11-4.03 (m, 2H), 3.97 (d, J=12.4 Hz, 1H), 3.89 (d, J=5.0 Hz, 1H), 3.76 (d, J=13.5 Hz, 1H), 3.63 (d, J=14.1 Hz, 1H), 3.49-3.40 (m, 1H), 3.23 (d, J=5.9 Hz, 1H), 3.20 (d, J=5.3 Hz, 1H), 3.16 (dd, J=9.4, 4.8 Hz, 1H), 3.00 (dd, J=14.9, 11.4 Hz, 1H), 2.92-2.82 (m, 5H), 2.77 (s, 3H), 2.73 (dd, J=13.2, 4.0 Hz, 1H), 2.62-2.40 (m, 4H), 2.15 (d, J=13.2 Hz, 1H), 2.00-1.86 (m, 3H), 1.77-1.62 (m, 5H), 1.43-1.36 (m, 1H), 1.32 (d, J=7.1 Hz, 3H), 0.92 (d, J=6.6 Hz, 3H); MS: 764.5 (M+H$^+$).

Under Ar, to a solution of (1S,11'R,12'S,13'R,16'R,16a'R, 18a'R,E)-6-chloro-5-fluoro-11',12'-dimethyl-16'-(2-(methylamino)ethoxy)-3,4,12',13',16',16a',17',18',18a',19'-decahydro-1'H,2H,3'H, 11'H-spiro[naphthalene-1,2'-[5,7]etheno [13,15]methanocyclobuta[i][1,4]oxazepino[3,4-f][1]thia[2, 7]diazacyclohexadecin]-8'(9'H)-one 10',10'-dioxide (Cpd. No. 78, 20 mg, 0.03 mmol) in dry DCM (8 mL) was added Et$_3$N (5.9 mg, 0.06 mmol) at 0° C. A solution of AcCl (3.4 mg, 0.04 mmol) in dry DCM (2 mL) was added slowly. The reaction mixture was stirred for 10 min. After removal of volatiles under reduced pressure, the residue was purified by C18 preparative-HPLC to afford the title compound (6.3 mg, 30%) as a white solid. $^1$H NMR (400 MHz, DMSO-d$_6$) δ 11.74 (s, 1H), 7.51 (d, J=8.6 Hz, 1H), 7.48-7.41 (m, 1H), 6.93-6.87 (m, 2H), 6.72 (s, 1H), 6.25 (d, J=9.6 Hz, 1H), 4.11-4.01 (m, 2H), 3.97 (d, J=12.4 Hz, 1H), 3.83 (d, J=4.8 Hz, 1H), 3.75 (d, J=14.7 Hz, 1H), 3.63 (d, J=14.2 Hz, 1H), 3.42 (d, J=9.8 Hz, 2H), 3.01-2.92 (m, 2H), 2.86 (d, J=16.7 Hz, 1H), 2.75 (s, 2H), 2.71-2.53 (m, 4H), 2.49-2.35 (m, 4H), 2.17-2.07 (m, 1H), 2.04-1.84 (m, 6H), 1.77-1.61 (m, 5H), 1.42-1.36 (m, 1H), 1.32 (d, J=7.1 Hz, 3H), 0.92 (d, J=6.5 Hz, 3H); MS: 728.6 (M+H$^+$).

Example 43

Synthesis of (1S,11'R,12'S,13'R,16'R,16a'R,18a'R)-6-chloro-5-fluoro-11',12'-dimethyl-16'-(2-(4-methyl-2-oxopiperazin-1-yl)ethoxy)-3,4,12',13',16',16a',17',18',18a',19'-decahydro-1'H,2'H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 91)

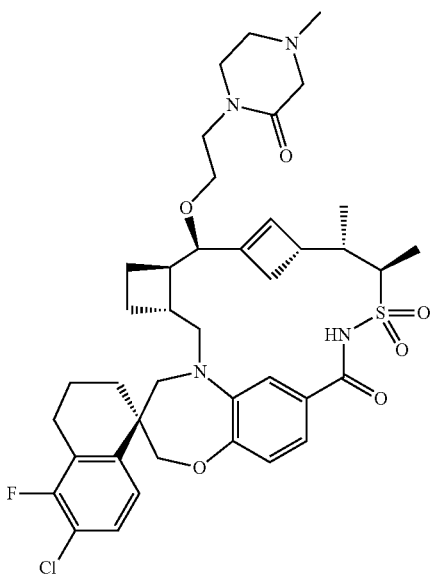 [SMILES: C[C@@H]1[C@@H](C)S(=O)(=O)NC(=O)c2ccc3c(c2)N(C[C@@H]2CC[C@H]2[C@@H](OCCN2CCN(C)CC2=O)C2=C[C@H]1C2)C[C@@]1(CCCc2c1ccc(Cl)c2F)CO3]

Step A: (1S,11'R,12'S,13'R,16'R,16a'R,18a'R)-16'-(2-bromoethoxy)-6-chloro-5-fluoro-11',12'-dimethyl-3,4,12',13',16',16a',17',18',18a',19'-decahydro-1'H,2'H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide

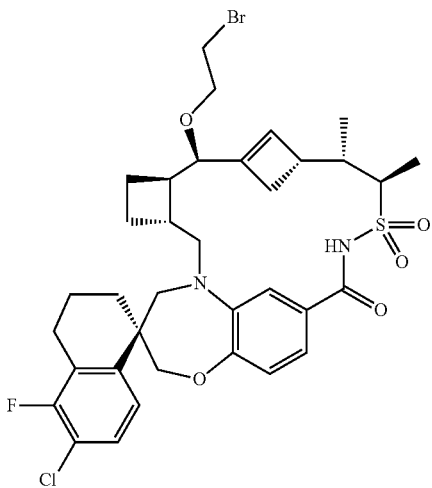 [SMILES: C[C@@H]1[C@@H](C)S(=O)(=O)NC(=O)c2ccc3c(c2)N(C[C@@H]2CC[C@H]2[C@@H](OCCBr)C2=C[C@H]1C2)C[C@@]1(CCCc2c1ccc(Cl)c2F)CO3]

In a flame-dried 50 mL round-bottomed flask, (1S,11'R,12'S,13'R,16'R,16a'R,18a'R,E)-6-chloro-5-fluoro-16'-(2-hydroxyethoxy)-11',12'-dimethyl-3,4,12',13',16',16a',17',18',18a',19'-decahydro-1'H,2'H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Step B of EXAMPLE 39, 80 mg, 0.119 mmol) and triphenylphosphane (78 mg, 0.30 mmol) were dissolved into dry DCM (5 mL) under argon at 0° C. CBr$_4$ (79 mg, 0.24 mmol) was added and the reaction mixture was stirred at room temperature for 1 h. Sat. NaHCO$_3$ (10 mL) was added to quench the reaction and the resulting mixture was extracted with DCM twice. The organic layers were combined, dried over Na$_2$SO$_4$, and concentrated under reduced pressure. The residue was loaded onto a silica gel column and was eluted with ethyl acetate/hexane=1:10 to afford the title compound (87 mg, 99%) as a pale white solid. MS: 736.3 (M+H$^+$).

Step B: (1S,11'R,12'S,13'R,16'R,16a'R,18a'R)-6-chloro-5-fluoro-11',12'-dimethyl-16'42-(4-methyl-2-oxopiperazin-1-yl)ethoxy)-3,4,12',13',16',16a',17',18',18a',19'-decahydro-1'H,2'H,3'H, 11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 91)

In a flame-dried 50 mL round-bottomed flask, to a solution of (1S,11'R,12'S,13'R,16'R,16a'R,18a'R)-16'-(2-bromoethoxy)-6-chloro-5-fluoro-11',12'-dimethyl-3,4,12',13',16',16a',17',18',18a',19'-decahydro-1'H,2'H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Step A, 40 mg, 0.05 mmol) in dry DMF (5 mL) was added 4-methylpiperazin-2-one (62.0 mg, 0.54 mmol) and NaI (24.43 mg, 0.163 mmol) under argon at 0° C. NaH (13.0 mg, 0.54 mmol) was added at 0° C. and the reaction mixture was stirred for 2 h. Sat. NaHCO$_3$ (10 mL) was added to quench the reaction and the mixture was extracted with ethyl acetate twice. The organic layers were combined, dried over Na$_2$SO$_4$, and concentrated under reduced pressure. The residue was purified by C18 preparative-HPLC to afford the title compound (10 mg, 24%) as a white solid. $^1$H NMR (400 MHz, DMSO-d$_6$) δ 11.71 (s, 1H), 7.51 (d, J=8.7 Hz, 1H), 7.45 (t, J=8.1 Hz, 1H), 6.93-6.88 (s, 2H), 6.74 (s, 1H), 6.23 (s, 1H), 4.12-4.01 (m, 2H), 3.97 (d, J=12.4 Hz, 1H), 3.83 (d, J=5.1 Hz, 1H), 3.76 (d, J=13.3 Hz, 1H), 3.61-3.18 (m, 12H), 2.99 (dd, J=14.8, 11.2 Hz, 1H), 2.87 (d, J=16.9 Hz, 1H), 2.81 (s, 3H), 2.72 (dd, J=13.1, 4.1 Hz, 1H), 2.65-2.50 (m, 3H), 2.47-2.36 (m, 1H), 2.13 (d, J=13.1 Hz, 1H), 2.02-1.82 (m, 3H), 1.80-1.62 (m, 5H), 1.46-1.35 (m, 1H), 1.32 (d, J=7.2 Hz, 3H), 0.93 (d, J=6.7 Hz, 3H); MS: 770.8 (M+H$^+$).

Example 44

Synthesis of (1S,11'R,12'S,13'R,16'R,16a'R,18a'R)-6-chloro-16'-(2-(1,1-dioxidoisothiazolidin-2-yl)ethoxy)-5-fluoro-11',12'-dimethyl-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 92)

Example 45

Synthesis of (1S,11'R,12'S,13'R,16'R,16a'R,18a'R)-6-chloro-5-fluoro-16'-methoxy-11',12'-dimethyl-16'-((4-morpholinopiperidin-1-yl)methyl)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,5,7]triazacyclohexadecin]-8'(9'H)-one 10',10'-dioxide (Cpd. No. 93)

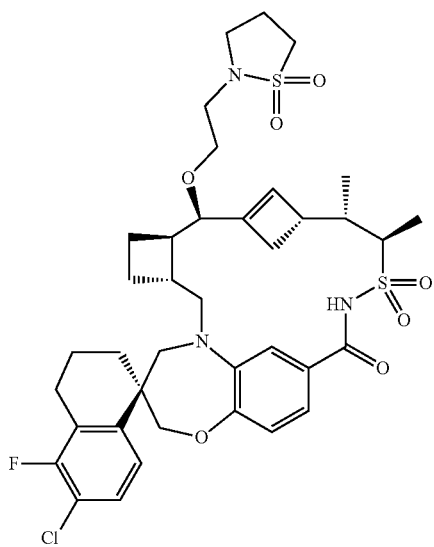 [SMILES: C[C@@H]1[C@@H](C)S(=O)(=O)NC(=O)c2ccc3c(c2)N(C[C@@H]2CC[C@H]2[C@@H](OCCN2CCCS2(=O)=O)C2=C[C@H]1C2)C[C@@]1(CCCc2c1ccc(Cl)c2F)CO3]

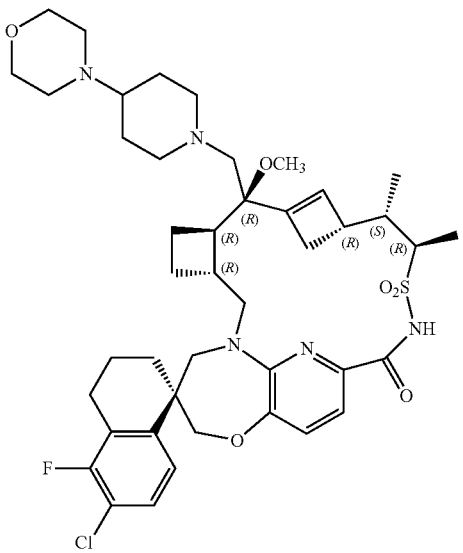

The protocol described in EXAMPLE 43 was used to give the title compound (3 mg) as a white solid. $^1$H NMR (400 MHz, DMSO-d$_6$) δ 11.71 (s, 1H), 7.52 (d, J=8.8 Hz, 1H), 7.45 (t, J=8.1 Hz, 1H), 6.94-6.70 (m, 3H), 6.27 (s, 1H), 4.11-4.02 (m, 2H), 3.97 (d, J=12.6 Hz, 1H), 3.87 (d, J=5.0 Hz, 1H), 3.76 (d, J=13.1 Hz, 1H), 3.64 (d, J=14.0 Hz, 1H), 3.48-3.42 (m, 1H), 3.41-3.30 (m, 2H), 3.23 (t, J=6.8 Hz, 3H), 3.17-3.10 (m, 2H), 3.05-2.94 (m, 3H), 2.93-2.81 (m, 1H), 2.77-2.67 (m, 1H), 2.64-2.38 (m, 2H), 2.26-2.10 (m, 3H), 2.04-1.85 (m, 4H), 1.79-1.64 (m, 5H), 1.44-1.34 (m, 1H), 1.32 (d, J=6.8 Hz, 3H), 0.92 (d, J=6.5 Hz, 3H); MS: 776.8 (M+H$^+$).

The protocol described in EXAMPLE 29 was used to afford the title compound (102 mg) as a white solid. $^1$H NMR (400 MHz, DMSO-d$_6$) δ 7.52-7.41 (m, 2H), 7.14 (d, J=7.7 Hz, 1H), 6.84 (d, J=7.7 Hz, 1H), 6.13 (s, 1H), 4.17-4.02 (m, 2H), 4.02-3.89 (m, 2H), 3.79 (d, J=14.4 Hz, 1H), 3.69-3.58 (m, 4H), 3.58-3.50 (m, 2H), 2.98 (s, 3H), 2.96-2.71 (m, 6H), 2.69-2.56 (m, 6H), 2.45-2.38 (m, 1H), 2.36-2.22 (m, 2H), 2.22-2.09 (m, 2H), 2.04-1.78 (m, 6H), 1.77-1.60 (m, 4H), 1.56-1.36 (m, 4H), 1.27 (d, J=7.2 Hz, 3H), 0.93 (d, J=6.6 Hz, 3H); MS: 826.8 (M+H$^+$).

Example 46

Synthesis of (1S,11'R,12'S,13'R,16'R,16a'R,18a'R, E)-6-chloro-5-fluoro-11',12'-dimethyl-16'-(pyridin-2-ylmethoxy)-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 94)

Example 47

Synthesis of 1S,11'R,12'S,13'R,16'R,16a'R,18a'R)-6-chloro-16'-(2-(4,4-difluoropiperidin-1-yl)ethoxy)-5-fluoro-11',12'-dimethyl-3,4,12',13',16',16a',17',18',18a',19'-decahydro-1'H,2H,3'H,11'H-spiro[naphthalene-1,2'-[5,7]etheno[13,15]methanocyclobuta[i][1,4]oxazepino[3,4-f][1]thia[2,7]diazacyclohexadecin]-8'(9'H)-one 10',10'-dioxide (Cpd. No. 95)

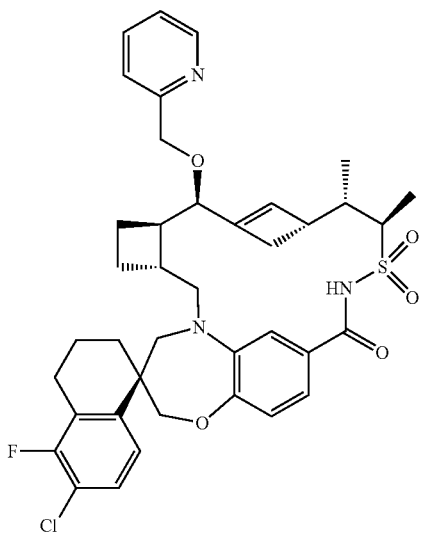 [SMILES: C[C@@H]1[C@@H](C)S(=O)(=O)NC(=O)c2ccc3c(c2)N(C[C@@H]2CC[C@H]2[C@@H](OCc2ccccn2)C2=C[C@H]1C2)C[C@@]1(CCCc2c1ccc(Cl)c2F)CO3]

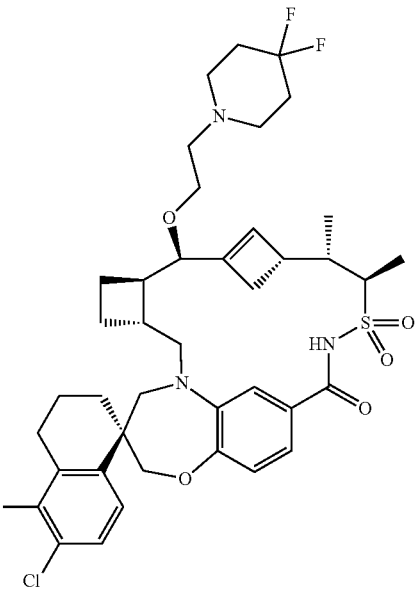

The protocol described in EXAMPLE 34 was used to afford the title compound (15 mg, 33%) as a white solid. $^1$H NMR (400 MHz, DMSO-d$_6$) δ 11.73 (br, 1H), 8.55 (s, 1H), 7.90 (t, J=7.2 Hz, 1H), 7.55-7.33 (m, 4H), 6.94-6.86 (m, 2H), 6.74 (s, 1H), 6.27 (s, 1H), 4.51 (d, J=13.6 Hz, 1H), 4.42 (d, J=13.6 Hz, 1H), 4.12-3.91 (m, 4H), 3.74 (d, J=14.0 Hz, 1H), 3.61 (d, J=14.4 Hz, 1H), 3.08-2.95 (m, 1H), 2.87 (d, J=17.8 Hz, 1H), 2.75 (d, J=10.4 Hz, 1H), 2.68-2.53 (m, 4H), 2.17 (d, J=13.0 Hz, 1H), 2.04-1.83 (m, 4H), 1.83-1.62 (m, 5H), 1.51-1.30 (m, 4H), 0.93 (d, J=6.2 Hz, 3H); MS: 720.6 (M+H$^+$).

The protocol described in EXAMPLE 39 was used to afford the title compound (11 mg, 19%) as a white solid. $^1$H NMR (400 MHz, DMSO-d$_6$) δ 11.75 (br, 1H), 7.52 (d, J=8.8 Hz, 1H), 7.45 (t, J=8.2 Hz, 1H), 6.94-6.89 (m, 2H), 6.72 (s, 1H), 6.34 (s, 1H), 4.13-4.03 (m, 2H), 4.02-3.91 (m, 2H), 3.77 (d, J=13.2 Hz, 1H), 3.68-3.50 (m, 4H), 3.50-3.10 (m, 5H), 3.00 (dd, J=15.2, 11.2 Hz, 1H), 2.87 (d, J=16.8 Hz, 1H), 2.75 (dd, J=13.2, 4.0 Hz, 1H), 2.67-2.42 (m, 6H), 2.41-2.13 (m, 4H), 2.02-1.84 (m, 3H), 1.83-1.63 (m, 5H), 1.45-1.36 (m, 1H), 1.33 (d, J=7.2 Hz, 3H), 0.93 (d, J=6.6 Hz, 3H); MS: 776.9 (M+H$^+$).

Example 48

Synthesis of (1S,12'S,13'R,16'R,16a'R,18a'R)-6-chloro-5-fluoro-16'-methoxy-12'-methyl-3,4,12',13',16',16a',17',18',18a',19'-decahydro-1'H,2H,3'H,11'H-spiro[naphthalene-1,2'-[5,7]etheno[13,15]methanocyclobuta[i][1,4]thiazepino[3,4-f][1]thia[2,7]diazacyclohexadecin]-8'(9'H)-one 10',10'-dioxide (Cpd. No. 24 Isomer 1) and (1S,12'S,13'S,16'R,16a'R,18a'R)-6-chloro-5-fluoro-16'-methoxy-12'-methyl-3,4,12',13',16',16a',17',18',18a',19'-decahydro-1'H,2H,3'H, 11'H-spiro[naphthalene-1,2'-[5,7]etheno[13,15]methanocyclobuta[i][1,4]thiazepino[3,4-f][1]thia[2,7]diazacyclohexadecin]-8'(9'H)-one 10',10'-dioxide (Cpd. No. 24 Isomer 2)

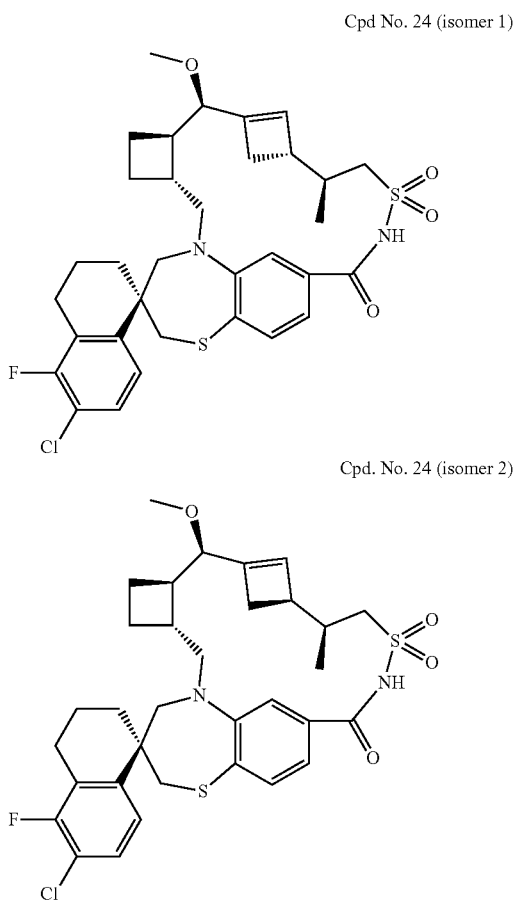

Cpd No. 24 (isomer 1)

Cpd. No. 24 (isomer 2)

Step A: tert-butyl 4-mercapto-3-nitrobenzoate

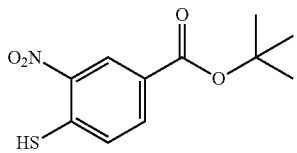 [SMILES: CC(C)(C)OC(=O)c1ccc(S)c([N+](=O)[O-])c1]

A solution of tert-butyl 4-fluoro-3-nitrobenzoate (5.00 g, 25.1 mmol) in acetone (25 mL) was added dropwise into a solution of NaSH (7.50 g, 133.8 mmol) in H$_2$O (25 mL) at 0° C. during the period of 30 min. The reaction mixture was then stirred for another 1 h. After removal of volatiles under reduced pressure, the resulting brown oil was treated with conc. HCl (5.00 mL) to adjust pH to 4-5 at 0° C. The formed precipitate was collected by filtration, washed with water, and dried in vacuo to afford the title compound (6.0 g, 94%) as a light yellow solid. $^1$H NMR (400 MHz, CDCl$_3$) δ 8.81 (d, J=1.8 Hz, 1H), 8.02 (dd, J=8.3, 1.9 Hz, 1H), 7.50 (d, J=8.3 Hz, 1H), 4.21 (s, 1H), 1.63 (s, 9H).

Step B: tert-butyl 4-(((6-chloro-5-fluoro-1-(hydroxymethyl)-1,2,3,4-tetrahydronaphthalen-1-yl)methyl)thio)-3-nitrobenzoate

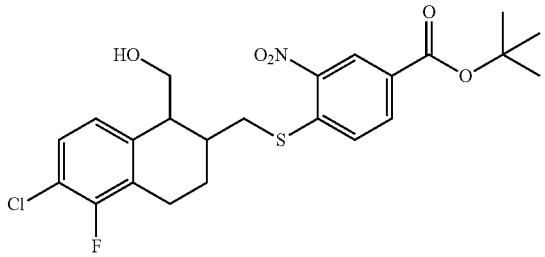 [SMILES: CC(C)(C)OC(=O)c1ccc(SCC2CCc3c(ccc(Cl)c3F)C2CO)c([N+](=O)[O-])c1]

In a nitrogen flushed 100 mL three-necked round-bottomed flask PPh$_3$ (1.38 g, 5.28 mmol) was dissolved into dry THF (50 mL) under nitrogen to give a colorless solution. DEAD (0.92 g, 5.28 mmol) was added in one portion. The mixture was cooled down to 0° C. and stirred for 15 min. (6-Chloro-5-fluoro-1,2,3,4-tetrahydronaphthalene-1,1-diyl) dimethanol (Step E of Intermediate 1, 0.86 g, 3.52 mmol) was added and the mixture was further stirred for 15 min. tert-Butyl 4-mercapto-3-nitrobenzoate (Step A, 0.90 g, 3.52 mmol) was added and the reaction mixture was stirred for 5 h at 30° C. After removal of the volatiles under reduced pressure, the residue was loaded onto a silica gel column and eluted with hexane and ethyl acetate (2:1) to afford the title compound (1.58 g, 93%) as a white solid. $^1$H NMR (400 MHz, CDCl$_3$) δ 8.71 (d, J=1.9 Hz, 1H), 8.10 (dd, J=8.5, 1.9 Hz, 1H), 7.49 (d, J=8.6 Hz, 1H), 7.22 (d, J=4.5 Hz, 1H), 7.17 (t, J=8.1 Hz, 1H), 3.91 (dd, J=11.2, 5.4 Hz, 1H), 3.81 (dd, J=11.2, 6.1 Hz, 1H), 3.46 (d, J=11.5 Hz, 1H), 3.36 (d, J=11.5 Hz, 1H), 2.93 (s, 1H), 2.82 (t, J=6.7 Hz, 1H), 2.75 (t, J=5.7 Hz, 1H), 2.15-2.08 (m, 1H), 2.01-1.93 (m, 1H), 1.91-1.86 (m, 1H), 1.71 (t, J=5.8 Hz, 1H), 1.63 (s, 9H).

Step C: tert-butyl 4-(((6-chloro-5-fluoro-1-formyl-1,2,3,4-tetrahydronaphthalen-1-yl)methyl)thio)-3-nitrobenzoate

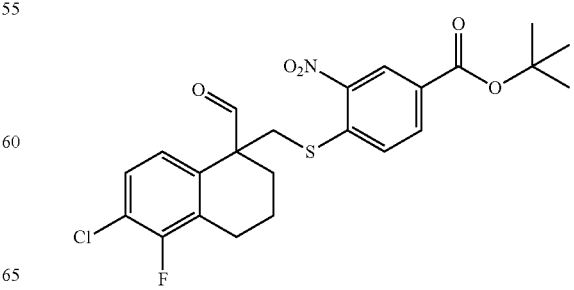

Under N₂, tert-butyl 4-(((6-chloro-5-fluoro-1-(hydroxymethyl)-1,2,3,4-tetrahydronaphthalen-1-yl)methyl)thio)-3-nitrobenzoate (Step B, 1.58 g, 3.28 mmol) was dissolved into dry DCM (50 mL). At 0° C., DMP (1.39, 3.28 mmol) was added in three portions, and the reaction mixture was stirred for 2 h at room temperature. The mixture was diluted with DCM, washed with sat. Na₂S₂O₃, sat. NaHCO₃, and brine. Then organic layer was separated, dried over Na₂SO₄, and concentrated under reduced pressure to give a yellow oil, which was purified by silica gel column chromatography (hexane:EtOAc, 50:1) to afford the title compound (0.50 g, 32%) as a white solid. MS: 479.9 (M+H⁺).

Step D: tert-butyl 6'-chloro-5'-fluoro-3',4,4',5-tetrahydro-2H,2'H-spiro[benzo[b][1,4]thiazepine-3,1'-naphthalene]-7-carboxylate

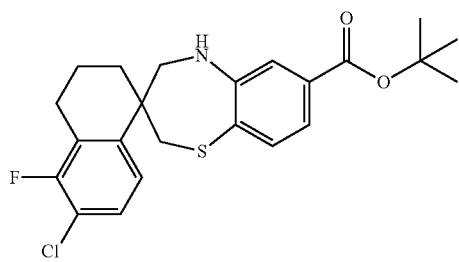 [SMILES: CC(C)(C)OC(=O)c1ccc2c(c1)NCC1(CCCc3c1ccc(Cl)c3F)CS2]

In a nitrogen flushed 100 mL round-bottomed flask, tert-butyl 4-(((6-chloro-5-fluoro-1-formyl-1,2,3,4-tetrahydronaphthalen-1-yl)methyl)thio)-3-nitrobenzoate (Step C, 0.50 g, 1.05 mmol) was dissolved into AcOH to give a colorless solution. Iron powder (588 mg, 10.50 mmol) was added and the reaction mixture was heated at 75° C. for 2.5 h. After cooling down to room temperature, the mixture was filtered through glass fiber paper, and the filtrate was concentrated under reduced pressure to give a yellow oil that was re-dissolved into dry THF (50 mL). Phenylsilane (1.13 g, 10.50 mmol) and TFA (359 mg, 3.15 mmol) were added and the reaction mixture was heated to 65° C. for 14 h. After cooling down to room temperature and removal of volatiles under reduced pressure, the residue was loaded onto silica gel column and eluted with EtOAc and heptane (10:1) to afford the title compound (0.40 g, 88% over 2 steps) as a white solid. ¹H NMR (400 MHz, CDCl₃) δ 7.75 (dd, J=8.6, 1.5 Hz, 1H), 7.30 (dd, J=8.1, 1.8 Hz, 1H), 7.23 (t, J=8.2 Hz, 1H), 7.21-7.18 (m, 2H), 4.01 (t, J=5.1 Hz, 1H), 3.83 (d, J=14.9 Hz, 1H), 3.72 (d, J=14.7 Hz, 1H), 3.42 (dd, J=14.8, 6.1 Hz, 1H), 3.00 (d, J=14.6 Hz, 1H), 2.89-2.80 (m, 2H), 2.72 (dd, J=16.0, 9.4 Hz, 1H), 2.03 (dd, J=12.3, 7.4 Hz, 1H), 1.88-1.72 (m, 2H), 1.65 (s, 9H).

Step E: tert-butyl 5-(((1R,2R)-2-((benzoyloxy)methyl)cyclobutyl)methyl)-6'-chloro-5'-fluoro-3',4,4',5-tetrahydro-2H,2'H-spiro[benzo[b][1,4]thiazepine-3,1'-naphthalene]-7-carboxylate

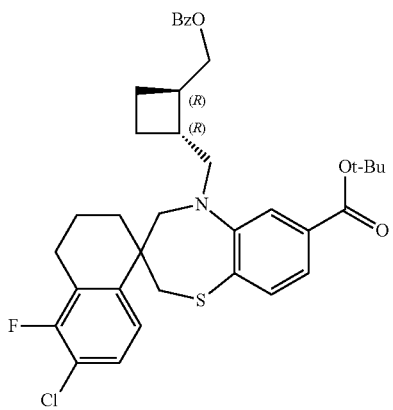

In a nitrogen flushed 100 mL round-bottomed flask, tert-butyl 6'-chloro-5'-fluoro-3',4,4',5-tetrahydro-2H,2'H-spiro[benzo[b][1,4]thiazepine-3,1'-naphthalene]-7-carboxylate (Step D, 1.6 g, 3.69 mmol) was dissolved into a mixed solvent of THF (12 mL) and TFA (4 mL) to give a solution. ((1R,2R)-2-Formylcyclobutyl)methyl benzoate (Step G of Intermediate 4, 2.41 g, 11.1 mmol) and PhSiH₃ (0.4 g, 3.69 mmol) were added and the reaction mixture as stirred overnight. Water was added to quench the reaction, and the resulting mixture was extracted with EtOAc twice. The combined organic layers were dried over Na₂SO₄ and concentrated under reduced pressure to give a yellow oil. The yellow oil was loaded onto a silica gel column and eluted with EA and heptane (1:3) to afford the title compound (2.2 g, 94%) as a white solid. MS: 636.1 (M+H⁺).

Step F: tert-butyl (S)-6'-chloro-5'-fluoro-5-(((1R,2R)-2-(hydroxymethyl)cyclobutyl)methyl)-3',4,4',5-tetrahydro-2H,2'H-spiro[benzo[b][1,4]thiazepine-3,1'-naphthalene]-7-carboxylate

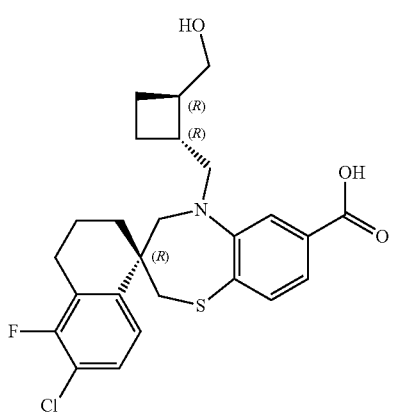

-continued

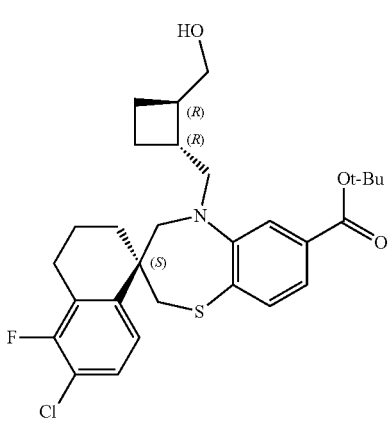

P2

Under N₂, to a stirred solution of tert-butyl 5-(((1R,2R)-2-((benzoyloxy)methyl)cyclobutyl)methyl)-6'-chloro-5'-fluoro-3',4,4',5-tetrahydro-2H,2'H-spiro[benzo[b][1,4]thiazepine-3,1'-naphthalene]-7-carboxylate (Step E, 2.2 g, 3.46 mmol) in a mixed solvent of dry MeOH and CH₂Cl₂ (30 mL, 3:1, v/v) was added K₂CO₃ (1.91 g, 13.83 mmol) at 30° C. The mixture was stirred at 30° C. for 3 h and then quenched with aq. NH₄Cl. The resulting mixture was extracted by DCM twice. The combined organic layers were concentrated under reduced pressure to give a yellow oil, which was purified by silica gel column chromatography (EtOAc:Hexane, 1:4→1:1) to afford the two separable title compounds (P1: 840 mg, 46%; P2: 800 mg, 44%) as colorless oil. MS: 532.1 (M+H⁺).

Step G: tert-butyl (S)-6'-chloro-5'-fluoro-5-(((1R,2R)-2-formylcyclobutyl)methyl)-3',4,4',5-tetrahydro-2H,2'H-spiro[benzo[b][1,4]thiazepine-3,1'-naphthalene]-7-carboxylate

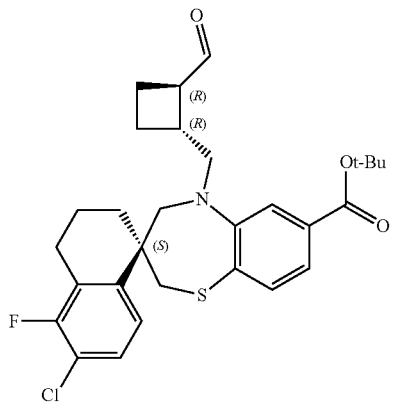

Under N₂, to a stirred solution of tert-butyl (S)-6'-chloro-5'-fluoro-5-(((1R,2R)-2-(hydroxymethyl)cyclobutyl)methyl)-3',4,4',5-tetrahydro-2H,2'H-spiro[benzo[b][1,4]thiazepine-3,1'-naphthalene]-7-carboxylate (Step F, 0.5 g, 500 mg, 0.94 mmol) in dry CH₂Cl₂ (10 mL) was added DMP (400 mg, 0.94 mmol). The reaction was stirred for 1 h, and then quenched with aq. NaHCO₃. The resulting mixture was extracted with CH₂Cl₂ twice. The combined organic layers were dried over Na₂SO₄, and concentrated under reduced pressure to give a yellow oil, which was purified by silica gel column chromatography (EtOAc:Hexane, 1:20) to afford the title compound (400 mg, 80%) as a white solid. MS: 530.1 (M+H⁺).

Step H: tert-butyl (3S)-5-(((1R,2R)-2-((3-((S)-1-(N,N-bis(4-methoxybenzyl) sulfamoyl)propan-2-yl)cyclobut-1-en-1-yl)(hydroxy)methyl)cyclobutyl)methyl)-6'-chloro-5'-fluoro-3',4,4',5-tetrahydro-2H,2'H-spiro[benzo[b][1,4]oxazepine-3,1'-naphthalene]-7-carboxylate

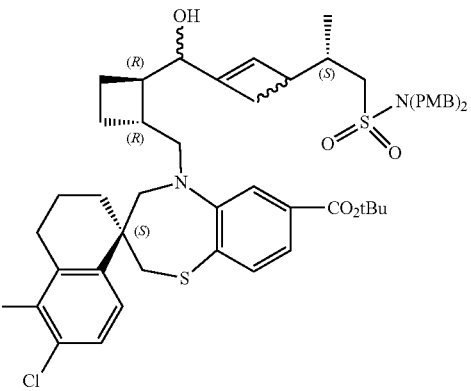

Under N₂, to a solution of chromium(II) chloride (556 mg, 4.53 mmol) and nickel(II) chloride (29.3 mg, 0.226 mmol) in dry DMF (10 mL) was added a solution of tert-butyl (S)-6'-chloro-5'-fluoro-5-(((1R,2R)-2-formylcyclobutyl)methyl)-3',4,4',5-tetrahydro-2H,2'H-spiro[benzo[b][1,4]thiazepine-3,1'-naphthalene]-7-carboxylate (Step 300 mg, 0.566 mmol) and 3-((S)-1-(N,N-bis(4-methoxybenzyl)sulfamoyl)propan-2-yl)cyclobut-1-en-1-yl trifluoromethanesulfonate (Step 10 of EXAMPLE 5, 415 mg, 0.736 mmol) in dry DMF (5 mL) at 60° C., and the reaction mixture was stirred for 6 h. After cooling down to room temperature, H₂O was added to quench the reaction, and the resulting mixture was extracted with EA twice. The combined EA layers were washed with brine, dried over Na₂SO₄, and concentrated under reduced pressure to give a green oil, which was purified by silica gel column chromatography (hexane:EA, 100:0→100:40) to afford the title compound (80 mg, 15%) as a colorless oil. MS: 946.0 (M+H⁺).

Step I: tert-butyl (3S)-5-(((1R,2R)-2-((1R)-(3-((S)-1-(N,N-bis(4-methoxybenzyl)sulfamoyl)propan-2-yl)cyclobut-1-en-1-yl)(methoxy)methyl)cyclobutyl)methyl)-6'-chloro-5'-fluoro-3',4,4',5-tetrahydro-2H,2'H-spiro[benzo[b][1,4]oxazepine-3,1'-naphthalene]-7-carboxylate

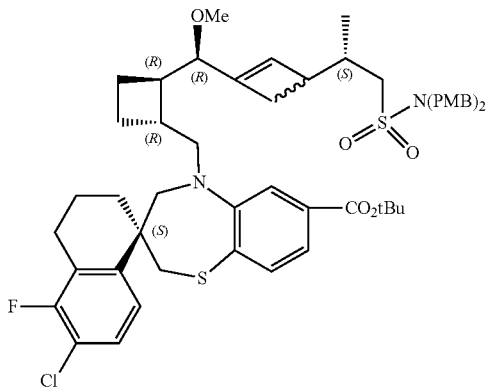

In a nitrogen flushed 50 mL round-bottomed flask, tert-butyl (3S)-5-(((1R,2R)-2-((3-((S)-1-(N,N-bis(4-methoxybenzyl)sulfamoyl)propan-2-yl)cyclobut-1-en-1-yl)(hydroxy)methyl)cyclobutyl)methyl)-6'-chloro-5'-fluoro-3',4,4',5-tetrahydro-2H,2'H-spiro[benzo[b][1,4]oxazepine-3,1'-naphthalene]-7-carboxylate (80 mg, 0.085 mmol) and NaH (10.15 mg, 0.423 mmol) were dissolved into dry THF (5 mL) under nitrogen to give a colorless solution at 0° C. MeI (240 mg, 1.69 mmol) was added and the reaction mixture was stirred for 2 h at room temperature. Water was added to quench the reaction and the resulting mixture was concentrated under reduced pressure to give a yellow oil, which was added to a silica gel column and eluted with heptane/EA from 0 to 20% to afford the title compound (60 mg, 74%) as a white solid. MS: 961.0 (M+H$^+$).

Step J: (3S)-6'-chloro-5'-fluoro-5-(((1R,2R)-2-((1R)-methoxy(3-((S)-1-sulfamoylpropan-2-yl)cyclobut-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid

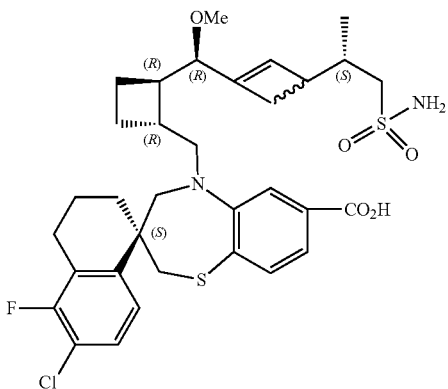

In a nitrogen flushed 50 mL round-bottomed flask, tert-butyl (3S)-5-(((1R,2R)-2-((1R)-(3-((S)-1-(N,N-bis(4-methoxybenzyl)sulfamoyl)propan-2-yl)cyclobut-1-en-1-yl)(methoxy)methyl)cyclobutyl)methyl)-6'-chloro-5'-fluoro-3',4,4',5-tetrahydro-2H,2'H-spiro[benzo[b][1,4]oxazepine-3,1'-naphthalene]-7-carboxylate (85 mg, 0.089 mmol) was dissolved into DCM (5 mL) to give a light yellow solution. TFA (1 mL) was added and the reaction mixture was stirred for 16 h. After removal of volatiles under reduced pressure, the residue was directly used for the next step without purification. MS: 664.0 (M+H$^+$).

Step K: (1S,12'S,13'R,16'R,16a'R,18a'R)-6-chloro-5-fluoro-16'-methoxy-12'-methyl-3,4,12',13',16',16a', 17',18',18a',19'-decahydro-1'H,2H,3'H,11'H-spiro[naphthalene-1,2'-[5,7]etheno[13,15]methanocyclobuta[i][1,4]thiazepino[3,4-f][1]thia[2,7]diazacyclohexadecin]-8'(9'H)-one 10',10'-dioxide (Cpd. No. 24 Isomer 1) and (1S,12'S,13'S,16'R,16a'R,18a'R)-6-chloro-5-fluoro-16'-methoxy-12'-methyl-3,4,12,'13',16',16a',17',18', 18a',19'-decahydro-1'H,2H,3'H,11'H-spiro[naphthalene-1,2'-[5,7]etheno[13,15]methanocyclobuta[i][1,4]thiazepino[3,4-f][1]thia[2,7]diazacyclohexadecin]-8'(9'H)-one 10',10'-dioxide (Cpd. No. 24 Isomer 2)

In a nitrogen flushed 50 mL three-necked round-bottomed flask (3S)-6'-chloro-5'-fluoro-5-(((1R,2R)-2-((1R)-methoxy(3-((S)-1-sulfamoylpropan-2-yl)cycl yl)methyl)cyclobutyl)methyl)-3',4,4',5-tetrahydro-2H,2'H-spiro[benzo[b][1,4]oxazepine-3,1'-naphthalene]-7-carboxylic acid (70 mg, 0.11 mmol) was dissolved into dry DCM (10 mL) to give a light yellow solution; DMAP (25.8 mg, 0.211 mmol), Et$_3$N (107 mg, 1.055 mmol) and T$_3$P (101 mg, 0.317 mmol) was added to the reaction subsequently and the reaction mixture was stirred for 2 h at room temperature. After removal of volatiles under reduced pressure, the residue was purified by C18 preparative HPLC to afford the title compounds (the first-eluting diastereomer was designated as Cpd. No. 24 isomer 1: 4 mg; the second-eluting diastereomer was designated as Cpd. No. 24 isomer 2: 14 mg) as white solids.

Cpd. No. 24 isomer 1: $^1$H NMR (400 MHz, DMSO-d$_6$) δ 11.90 (br, 1H), 7.64 (d, J=8.8 Hz, 1H), 7.41 (t, J=8.4 Hz, 1H), 7.24 (t, J=6.6 Hz, 1H), 6.98 (d, J=8.4 Hz, 1H), 6.88 (s, 1H), 6.11 (s, 1H), 4.28 (d, J=13.6 Hz, 1H), 3.84 (d, J=14.8 Hz, 1H), 3.59-3.50 (m, 1H), 3.45 (d, J=4.8 Hz, 1H), 3.40-3.27 (m, 2H), 3.26-3.13 (m, 3H), 3.12-3.02 (m, 4H), 2.81-2.74 (m, 2H), 2.70 (dd, J=13.4, 4.0 Hz, 1H), 2.65-2.56 (m, 1H), 2.55-2.40 (m, 2H), 2.12 (d, J=13.6 Hz, 1H), 2.09-1.79 (m, 4H), 1.76-1.66 (m, 3H), 1.58-1.39 (m, 1H), 1.11 (d, J=6.6 Hz, 3H); MS: 646.0 (M+H$^+$).

Cpd. No. 24 isomer 2: $^1$H NMR (400 MHz, DMSO-d$_6$) δ 12.00 (br, 1H), 7.68 (d, J=8.4 Hz, 1H), 7.41 (t, J=8.4 Hz, 1H), 7.27 (d, J=8.0 Hz, 1H), 6.97 (d, J=5.4 Hz, 1H), 6.90 (s, 1H), 6.00 (s, 1H), 4.14 (d, J=15.2 Hz, 1H), 3.76-3.56 (m, 4H), 3.27-3.04 (m, 9H), 2.81-2.72 (m, 2H), 2.63-2.56 (m, 1H), 2.55-2.32 (m, 2H), 2.10-1.97 (m, 2H), 1.93-1.79 (m, 3H), 1.79-1.67 (m, 3H), 1.67-1.57 (m, 1H), 1.13 (d, J=6.8 Hz, 3H); MS: 646.3 (M+H$^+$).

Example 49

Mcl-1 Activity

The inhibition of Mcl-1, and cell viability in NCI-H929 and OPM-2 cells of representative Compounds of the Disclosure are provided in Table 2. AMG-176 is a known Mcl-1 inhibitor. Caenepeel et al., *Cancer Discov.* 2018 Sep. 25. pii: CD-18-0387. doi: 10.1158/2159-8290.CD-18-0387. [Epub ahead of print].

Inhibition of Mcl-1 by Fluorescence Polarization (FP) Assay.

The relative binding potency of representative Compounds of the Disclosure was determined by a fluorescence polarization (FP) assay (Long et al, *BMC Biotechnology* 13:45 (2013)). The method used a fluorescein labelled peptide (FAM-Bid) which binds to the Mcl-1 protein leading to an increased anisotropy measured in milli-polarization (mP) values using a plate reader. A 21-residue Bid BH3 peptide (residues 79-99) [Swiss-Prot: P55957] was labeled at the N-terminus with 6-carboxyfluorescein succinimidyl ester (FAM) to give FAM-Bid as a tracer in the FP competitive binding assay. Tag-free Mcl-1 protein (residues 171-323) was used in the FP assay (Mady et al, *Scientific Reports* 8: 10210-10210 (2018); Yang et al, *ACS Med. Chem. Lett.* 3:308-312 (2012)). The addition of compounds which binds competitively to the same site as the labelled peptide will result in a greater proportion of unbound peptide in the system indicated by a decreased mP value.

A 10-points serial dilution of each compound was prepared in DMSO and 5 μL solution was transferred into flat bottomed, 96-well back plate (final DMSO concentration 5%). 120 μL of Buffer (PBS, 0.01% BGG (Sigma Cat. #SRE0011), 0.01% Triton X-100), containing the Fluorescein labelled peptide (Final concentration 2 nM) and Mcl-1 protein (final concentration 20 nM) was then added. Assay plates were incubated 30 mins at room temperature with gentle shaking before FP was measured on a Biotek Synergy 1MF reader (Ex. 485 nm, Em. 528 nm, Cut off 510 nm) and mP calculated. The binding of increasing doses of test compounds was expressed as a percentage reduction in mP compared to a window established between 5% DMSO only and 100% inhibition controls (no Mcl-1 protein). 10-points dose response curves were plotted with GraphPad software using Sigmoidal Dose-Response Model and the $IC_{50}$ values were determined by nonlinear regression fitting of the competition curves. Cell Viability Assay (NCI-H929 cells)

NCI-H929 cells were obtained from American Type Culture Collection (ATCC). Cells were maintained in the recommended culture medium (RPMI 1640) with 10% FBS and 0.05 mM BME at 37° C. and an atmosphere of 5% $CO_2$.

The effect of Compounds on cell viability was determined using Cell Counting Kit-8 (CCK-8) assay according to the manufacturer's instructions. 95 μL of NCI-H929 cell suspension (20000 cells/well) in culture medium were seeded into 96-well plates and cultured 4 hrs. Each tested compound was serially diluted in in DMSO, then 5 μL of the compound or DMSO was diluted in 95 μL medium once more. At last, 5 μL of the compound dilution was added to the corresponding well of the cell plate. After the addition of the tested compound, the cells were incubated at 37° C. in an atmosphere of 5% $CO_2$ for 24 hrs. At the end, 10 μL of CCK-8 solution was added to each well of the plate and incubated for 1-4 hours. The plates were read at 450 nm on the microplate reader (BioTek Synergy 1MF). The readings were normalized to the vehicle cells, and the $IC_{50}$ was calculated by nonlinear regression analysis using GraphPad Prism 6 software. Cell Viability Assay (OPM-2 cells)

OPM-2 cells were obtained from Deutsche Sammlung von Mikroorganismen and Zellkulturen GmbH (DSMZ). Cells were maintained in the recommended culture medium with 10% FBS at 37° C. and an atmosphere of 5% $CO_2$.

The effect of representative Compounds of the Disclosure on cell viability was determined using Cell Counting Kit-8 (CCK-8) assay (Shanghai Life iLab Bio Technology) according to the manufacturer's instructions. Each tested compound was serially diluted in culture medium, 100 μL of the compound dilution was added into 96-well plates. 100 μL of an OPM-2 cell suspension (20000 cells/well) in culture medium were seeded into the corresponding well of the plate and the cells were incubated at 37° C. in an atmosphere of 5% $CO_2$ for 24 hours. In the next day, 20 μL of CCK-8 solution was added to each well of the plate and incubated for 4 hours.

The plates were read at 450 nm on the microplate spectrophotometer (SpectraMax plus 384, Molecular devices). The readings were normalized to the vehicle cells, and the $IC_{50}$ was calculated by nonlinear regression analysis using GraphPad Prism 6 software.

Example 50

In Vivo Xenograft Studies

Figure 2:
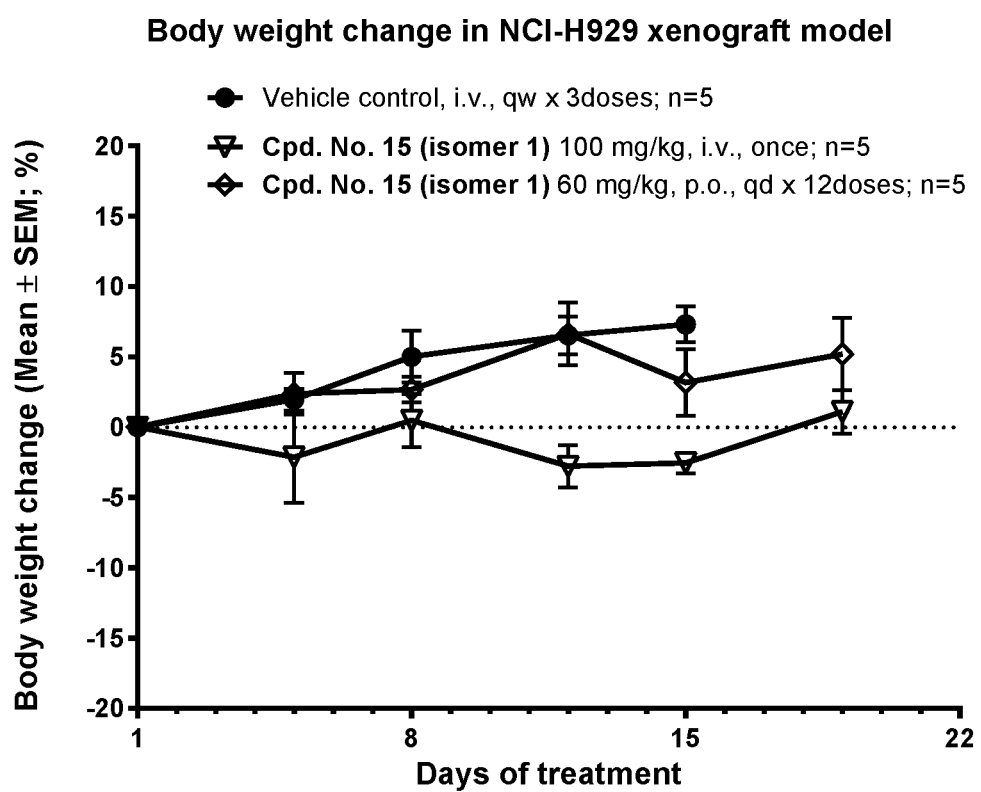
FIG. 2 is a line graph showing the body weight change of tumor-bearing mice treated with Cpd. No. 15 (isomer 1) in the subcutaneous tumor model of NCI-H929 at the indicated doses and routes of administration.
Figure 3:
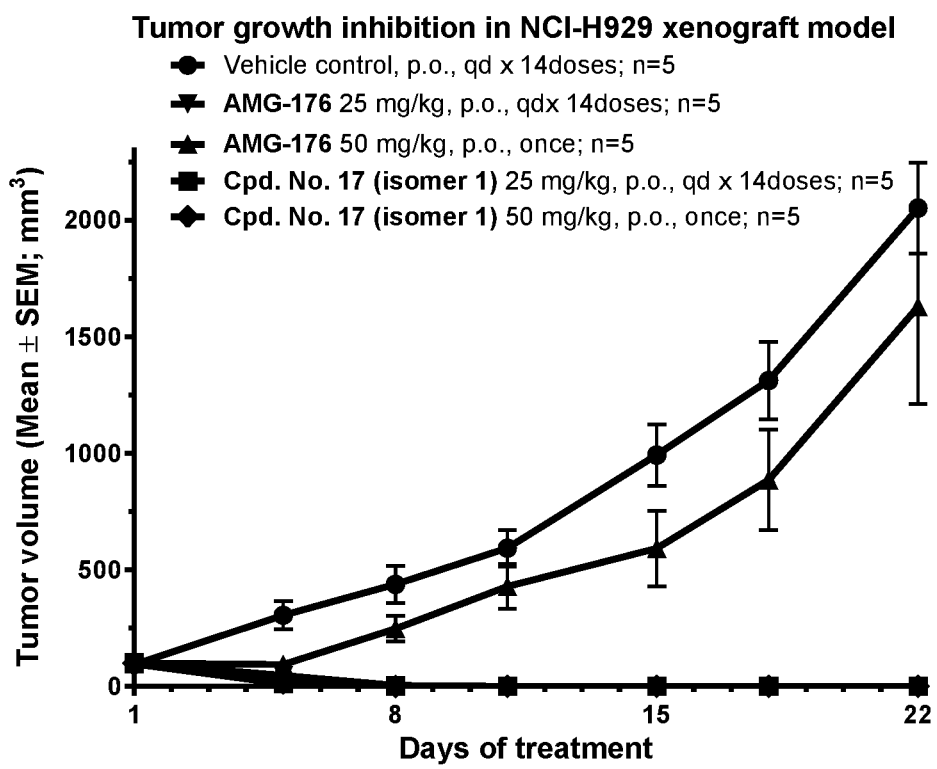
FIG. 3 is a line graph showing the anti-tumor efficacy of AMG-176 and Cpd. No. 17 (isomer 1) in the subcutaneous tumor model of NCI-H929 at the indicated doses and routes of administration.
Figure 4:
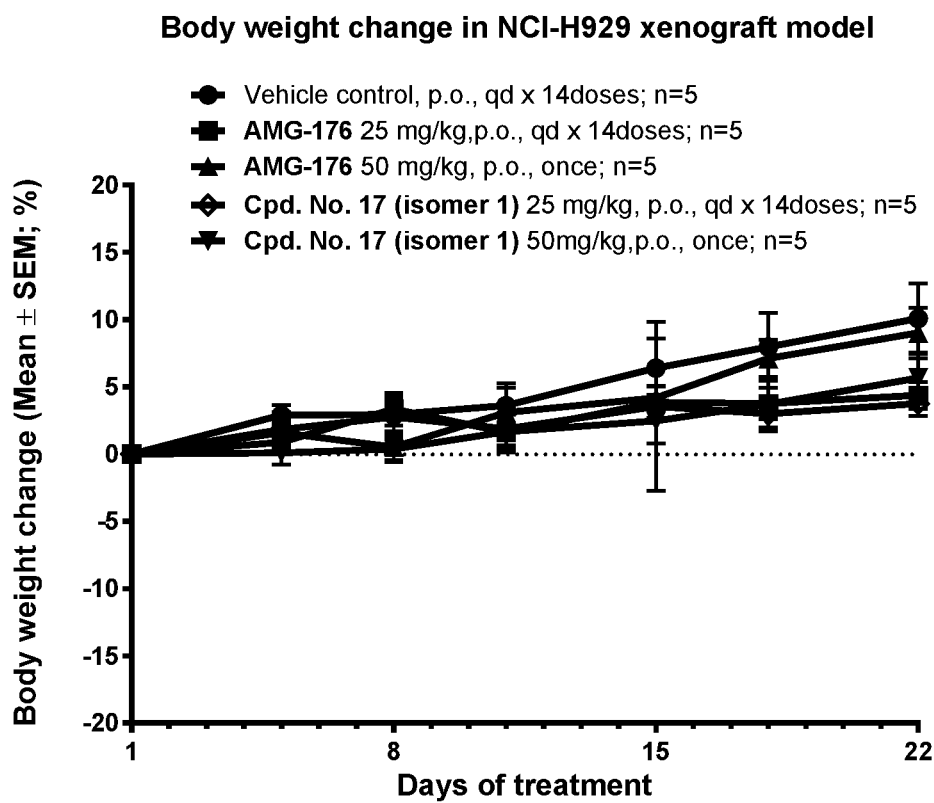
FIG. 4 is a line graph showing the body weight change of tumor-bearing mice treated with AMG-176 and Cpd. No. 17 (isomer 1) in the subcutaneous tumor model of NCI-H929 at the indicated doses and routes of administration.
Figure 5:
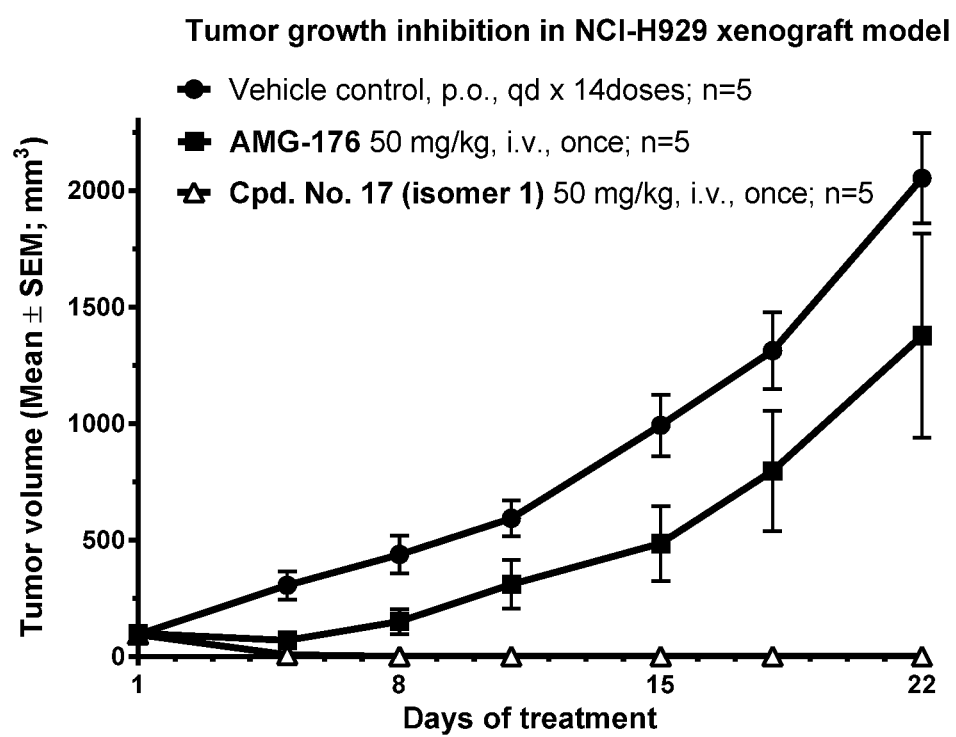
FIG. 5 is a line graph showing the anti-tumor efficacy of AMG-176 and Cpd. No. 17 (isomer 1) in the subcutaneous tumor model of NCI-H929 at the indicated doses and routes of administration.
Figure 6:
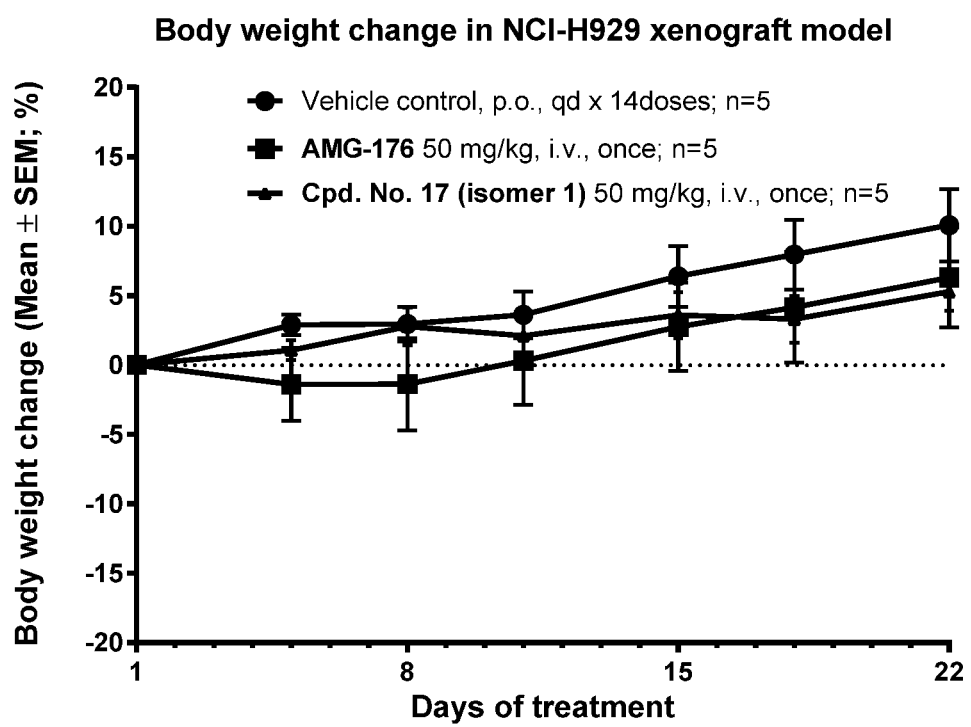
FIG. 6 is a line graph showing the body weight change of tumor-bearing mice treated with AMG-176 and Cpd. No. 17 (isomer 1) in the subcutaneous tumor model of NCI-H929 at the indicated doses and routes of administration.
Figure 7:
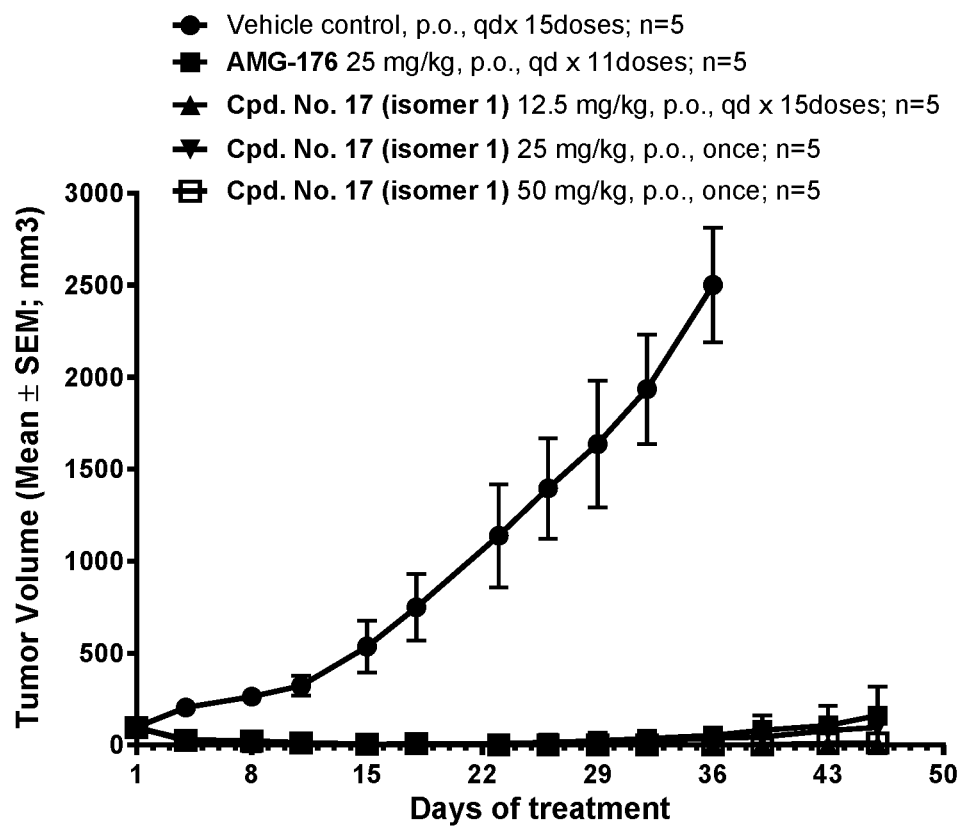
FIG. 7 is a line graph showing the anti-tumor efficacy of AMG-176 and Cpd. No. 17 (isomer 1) in the subcutaneous tumor model of NCI-H929 at the indicated doses and routes of administration.
Figure 8:
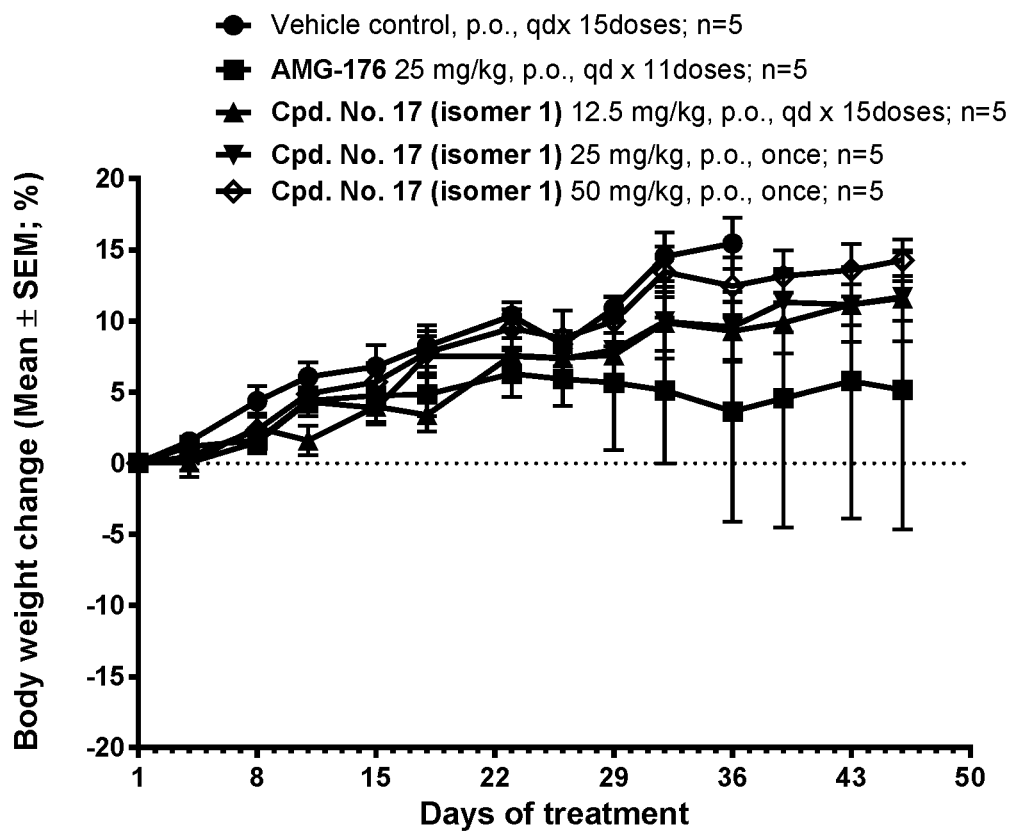
FIG. 8 is a line graph showing the anti-tumor efficacy of AMG-176 and Cpd. No. 17 (isomer 1) in the subcutaneous tumor model of MV-4-11 at the indicated doses and routes of administration.
Figure 9:
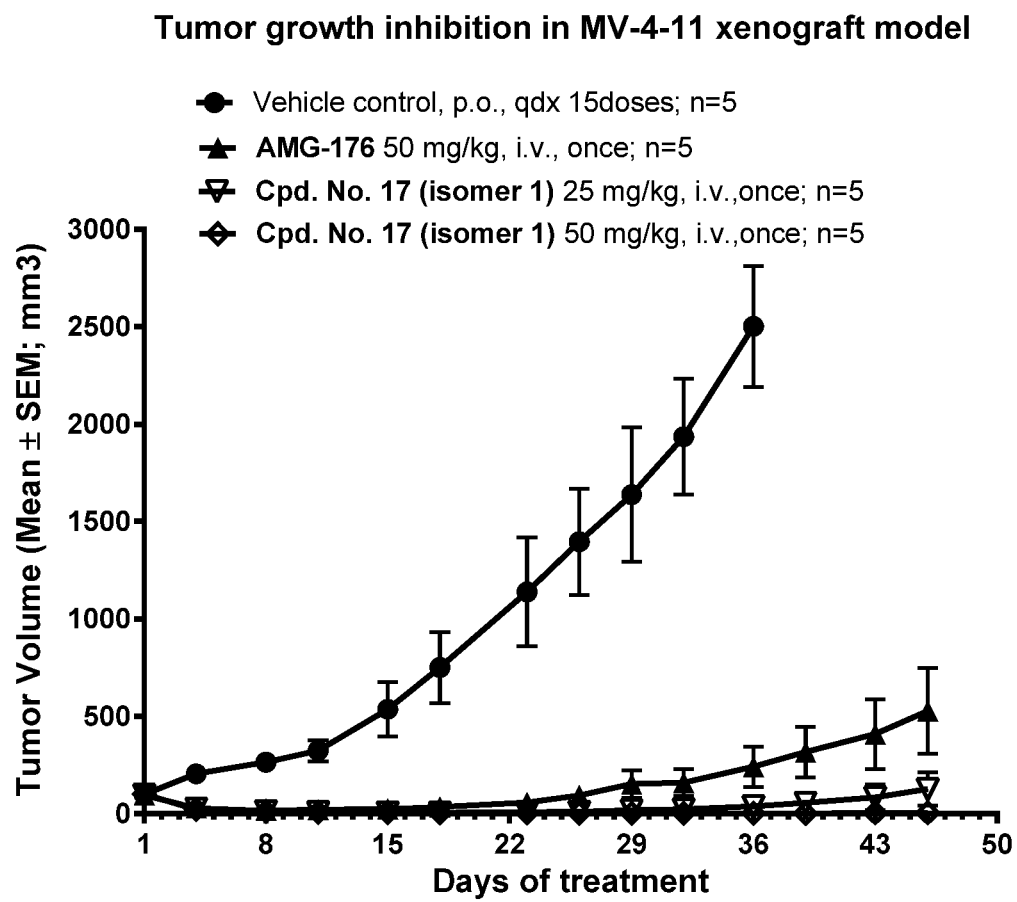
FIG. 9 is a line graph showing the anti-tumor efficacy of AMG-176 and Cpd. No. 17 (isomer 1) in the subcutaneous tumor model of MV-4-11 at the indicated doses and routes of administration.
Figure 10:
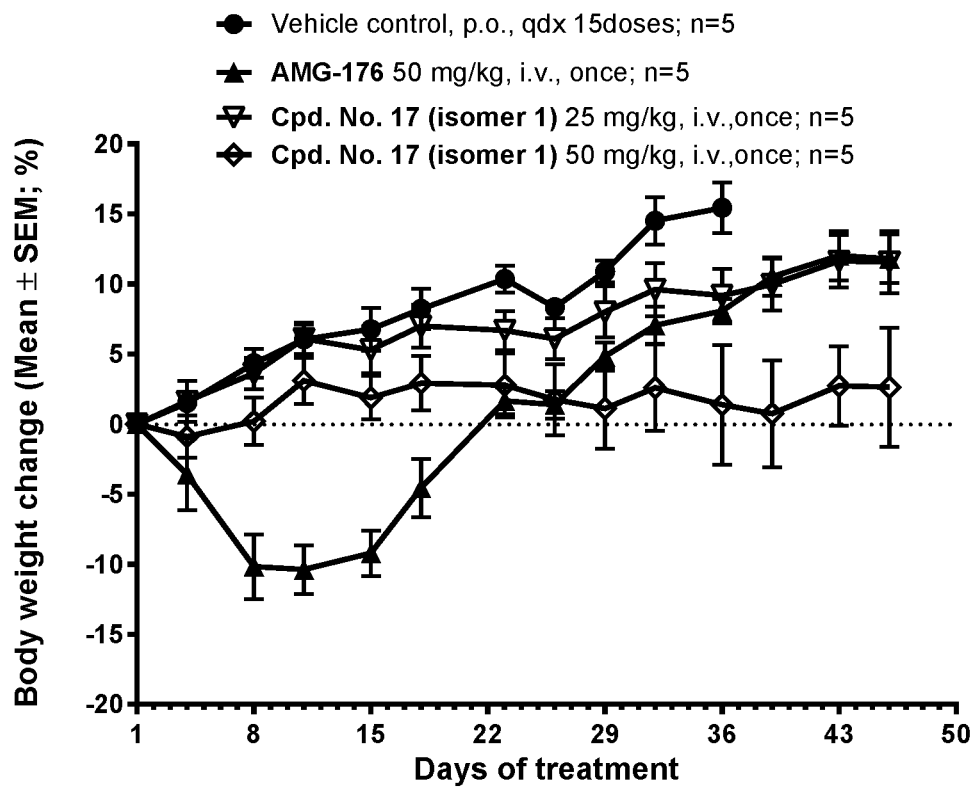
FIG. 10 is a line graph showing the body weight change of tumor-bearing mice treated with AMG-176 and Cpd. No. 17 (isomer 1) in the subcutaneous tumor model of MV-4-11 at the indicated doses and routes of administration.
Figure 11:
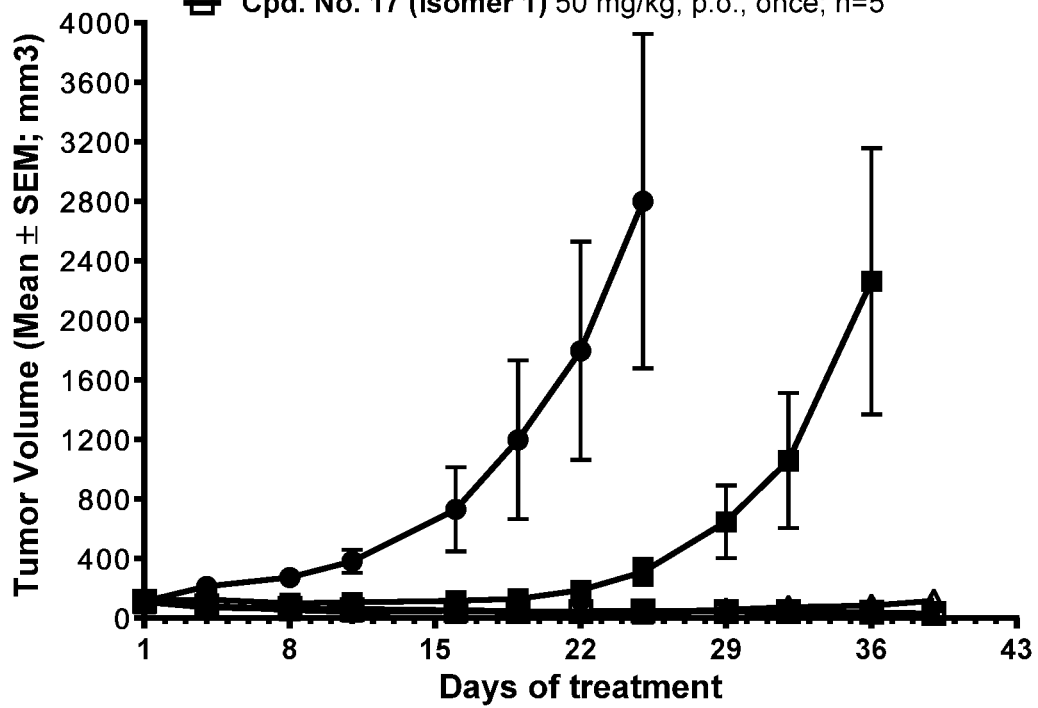
FIG. 11 is a line graph showing the anti-tumor efficacy of AMG-176 and Cpd. No. 17 (isomer 1) in the subcutaneous tumor model of OPM-2 at the indicated doses and routes of administration.
Figure 12:
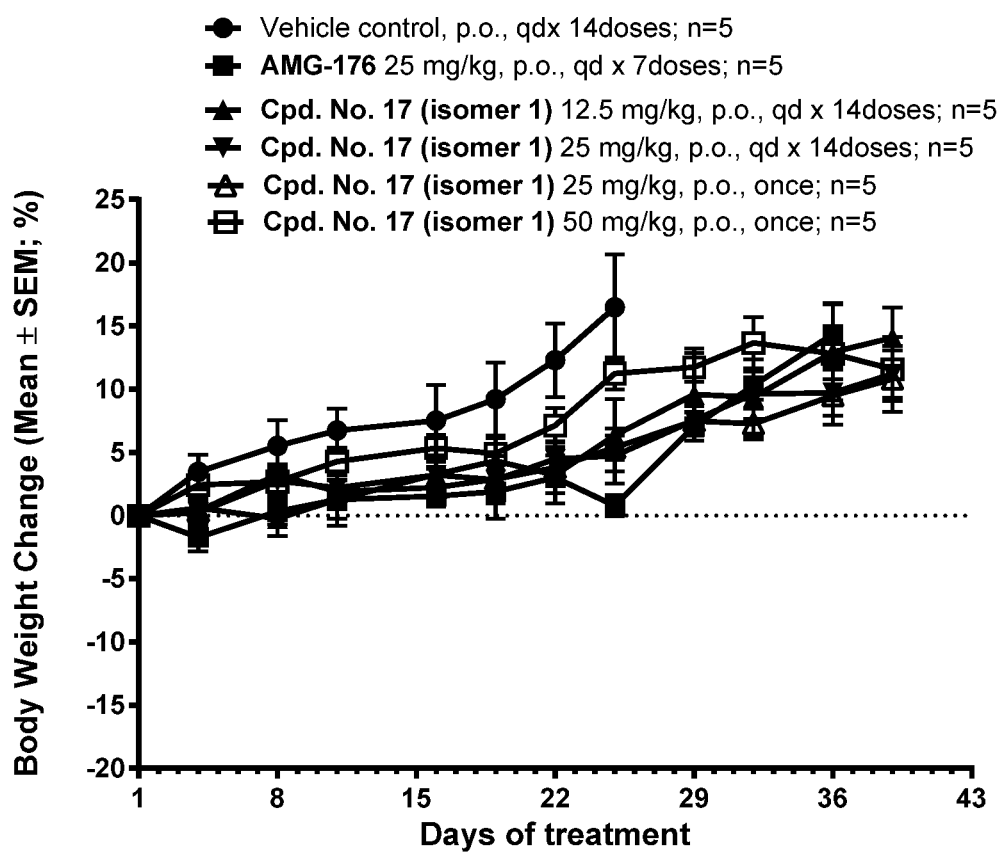
FIG. 12 is a line graph showing the body weight change of tumor-bearing mice treated with AMG-176 and Cpd. No. 17 (isomer 1) in the subcutaneous tumor model of OPM-2 at the indicated doses and routes of administration.
Figure 13:
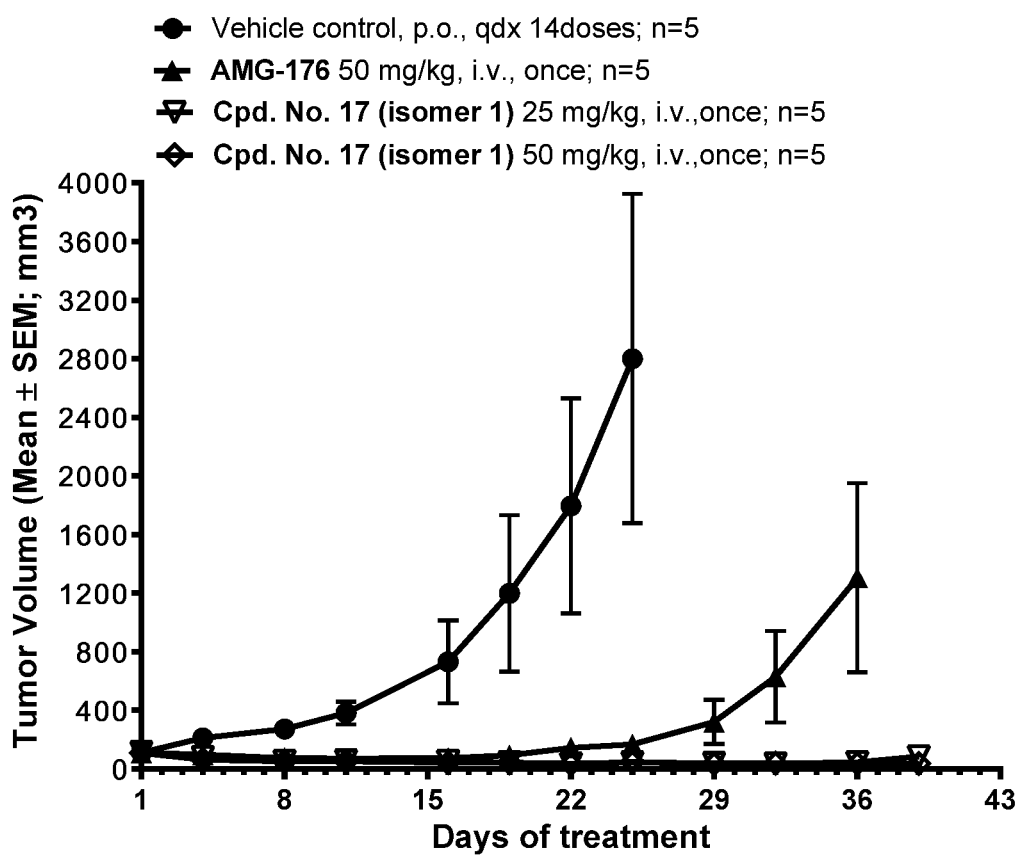
FIG. 13 is a line graph showing the anti-tumor efficacy of AMG-176 and Cpd. No. 17 (isomer 1) in the subcutaneous tumor model of OPM-2 at the indicated doses and routes of administration.
Figure 14:
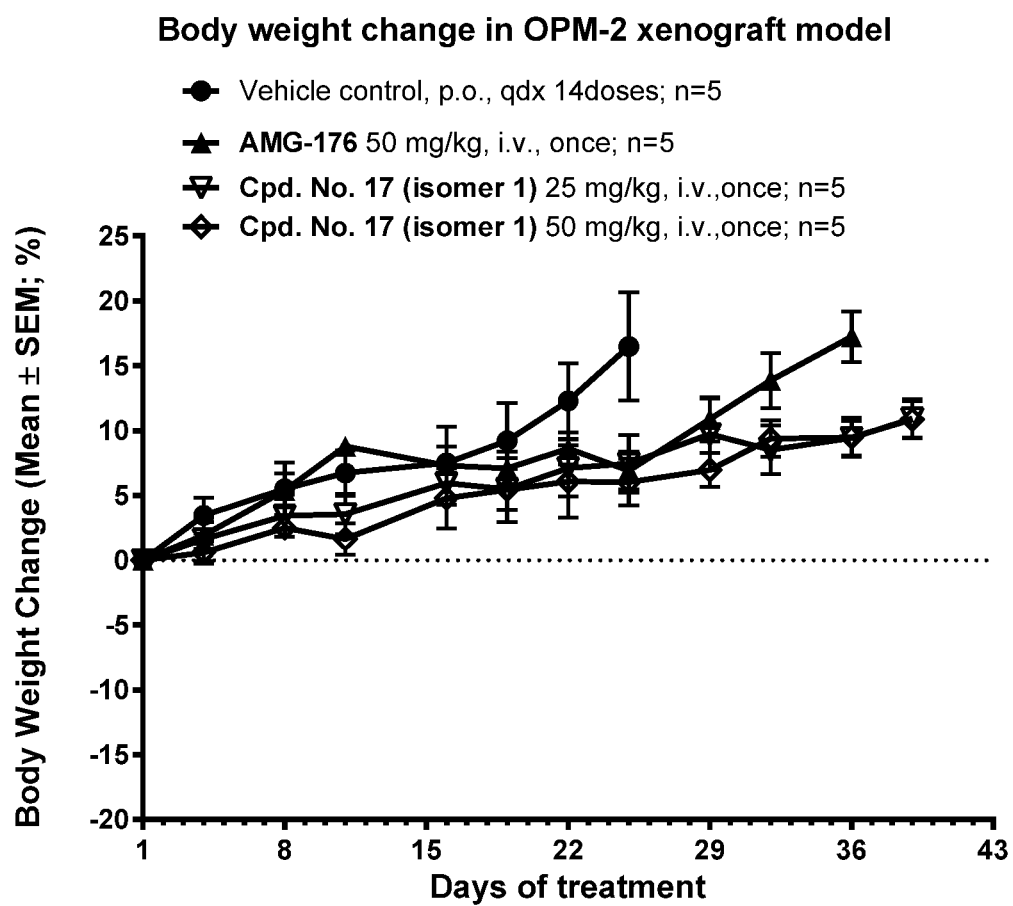
FIG. 14 is a line graph showing the body weight change of tumor-bearing mice treated with AMG-176 and Cpd. No. 17 (isomer 1) in the subcutaneous tumor model of OPM-2 at the indicated doses and routes of administration.
Figure 15:
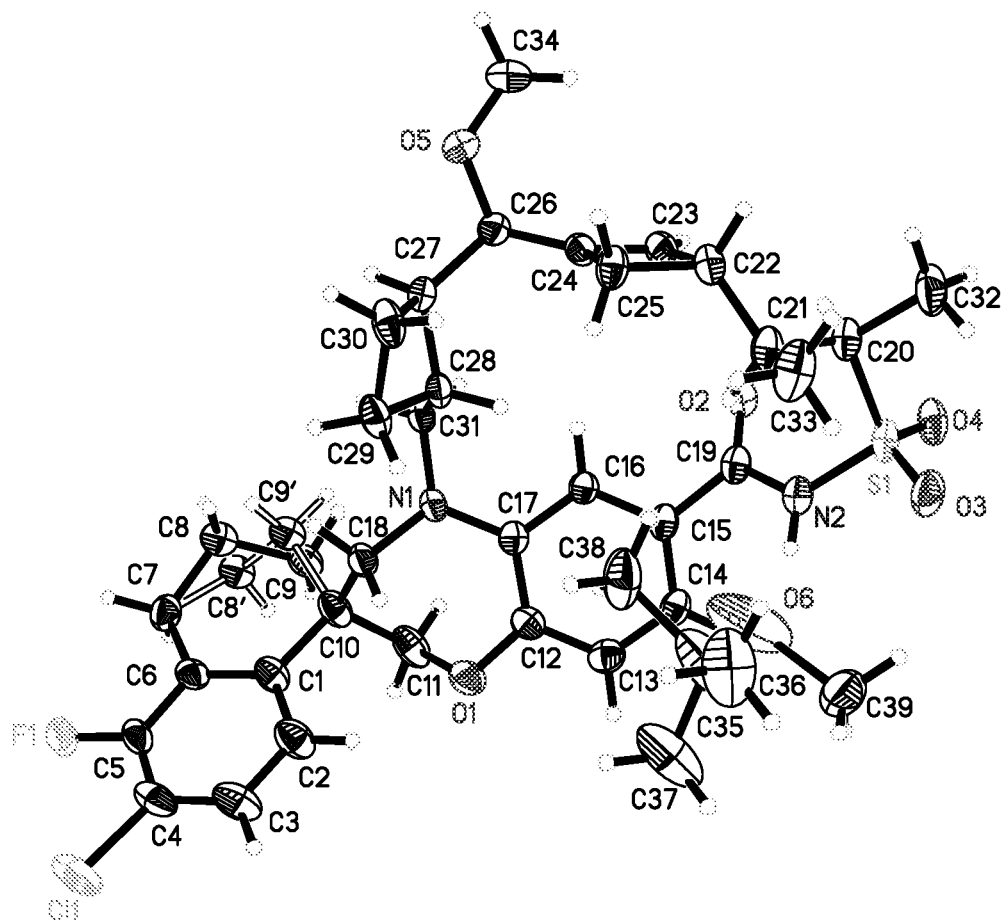
FIG. 15 is an Oak Ridge Thermal Ellipsoid Plot (ORTEP) drawing of a single crystal of Cpd. No. 17 (Isomer 1).

Female SCID mice at 4-6 weeks old were purchased from Shanghai Laboratory Animal Center (SLAC) and 1×10⁷ MV-4-11 cells per mouse in 0.2 ml of PBS with 30% Matrigel were inoculated subcutaneously to the right flank of mice. Volumes of the tumor were estimated as $V=LW^2/2$, where L and W stand for tumor length and width. Mice with tumor at 50-150 mm³ were randomized into treatment groups (5 mice per group) and started treatment. Compounds were administered at selected doses by p.o. or i.v. administration. The individual relative tumor volume (RTV) is calculated as following: $RTV=V_t/V_0$, where $V_t$ is the volume on each day of measurement and $V_0$ is the volume on the initial day of treatment. Therapeutic effect of compound is expressed with relative tumor proliferation rate (T/C). The calculation formula is: T/C=mean RTV of the treated group/mean RTV of the control group. Treatments producing >20% lethality and/or 20% net body weight loss were considered toxic. Similar procedures were used in the for the NCI-H929 and OPM-2 xenograft experiments. See FIGS. 1, 3, 5, 7, 9, 11, and 13. Body weight changes in tumor-bearing mice were also measured. See FIGS. 2, 4, 6, 8, 10, 12, and 14. These studies show that Cpd. No. 17 (isomer 1) produces surprisingly better tumor growth inhibition and less body weight change (indicating less toxicity to the animals) as compared to AMG-176.

Example 51

Pharmacokinetic Studies

Administration: Mice in the IV group was dosed at 2 mg/kg (20% PEG 400+10% Cremophor EL+70% PBS 7.4) via tail vein injection (N=9). Mice in the PO group was dosed at 10 mg/kg (20% PEG 400+10% Cremophor EL+70% PBS 7.4) via oral gavage (N=9). All the mice were fasted overnight before dosing and had free access to food 4 hr post dosing.

Sampling: The animal was restrained manually at the designated time points (0.083, 0.25, 0.5, 1, 2, 4, 6, 8 and 24 hr), approximately 110 μL of blood sample was collected via retro-orbital puncture or cardiac puncture for terminal bleeding under the anesthesia with Isoflurane inhalation into K2EDTA tubes. The blood samples were maintained in wet ice first and centrifuged to obtain plasma (2000 g, 4° C., 5 min) within 15 minutes post sampling. All the plasma samples were stored at approximately −70° C. until analysis.

| Parameters | Units | AMG-176 IV 2 mg/kg | AMG-176 PO 10 mg/kg | Cpd. No. 13 (mixture) IV 2 mg/kg | Cpd. No. 13 (mixture) PO 10 mg/kg | Cpd. No. 14 (isomer 1) IV 2 mg/kg | Cpd. No. 14 (isomer 1) PO 10 mg/kg |
|---|---|---|---|---|---|---|---|
| $C_0/C_{max}$ | ng/mL | 1548 | 2497 | 861 | 1270 | 1508 | 3923 |
| $T_{max}$ | hr | — | 1.0 | — | 4.0 | — | 2.0 |
| $T_{1/2}$ | hr | 7.2 | 7.4 | 6.5 | 4.5 | 3.6 | 3.6 |
| CL | L/hr/kg | 0.270 | — | 0.384 | — | 0.424 | — |
| Vss | L/kg | 2.3 | — | 3.2 | — | 1.7 | — |
| $MRT_{0-last}$ | hr | 6.3 | 7.4 | 6.2 | 6.6 | 3.9 | 5.6 |
| $AUC_{0-last}$ | hr*ng/mL | 6800 | 32691 | 4778 | 14429 | 4689 | 31450 |
| $AUC_{0-inf}$ | hr*ng/mL | 7448 | 36459 | 5205 | 14899 | 4720 | 31765 |
| $V_z/F$ | L/kg | — | 2.9 | — | 4.4 | — | 1.6 |
| F | % | — | 97.9 | — | 57.2 | — | 134.6 |

| Parameters | Units | Cpd. No. 15 (isomer 1) IV 2 mg/kg | Cpd. No. 15 (isomer 1) PO 10 mg/kg | Cpd. No. 16 (mixture) IV 2 mg/kg | Cpd. No. 16 (mixture) PO 10 mg/kg | Cpd. No. 17 (isomer 1) IV 2 mg/kg | Cpd. No. 17 (isomer 1) PO 10 mg/kg |
|---|---|---|---|---|---|---|---|
| $C_0/C_{max}$ | ng/mL | 2744 | 2717 | 1258 | 1693 | 997 | 4353 |
| $T_{max}$ | hr | — | 2.0 | — | 2.0 | — | 4.0 |
| $T_{1/2}$ | hr | 4.9 | 3.4 | 1.6 | 4.9 | 7.0 | 10.6 |
| CL | L/hr/kg | 0.254 | — | 0.818 | — | 0.131 | — |
| Vss | L/kg | 1.5 | — | 1.7 | — | 1.2 | — |
| $MRT_{0-last}$ | hr | 4.8 | 6.1 | 1.9 | 4.5 | 6.7 | 8.3 |
| $AUC_{0-last}$ | hr*ng/mL | 7584 | 33046 | 2380 | 8360 | 13892 | 55960 |
| $AUC_{0-inf}$ | hr*ng/mL | 7874 | 33347 | 2445 | 8623 | 15219 | 70708 |
| $V_z/F$ | L/kg | — | 1.5 | — | 8.3 | — | 2.2 |
| F | % | — | 84.7 | — | 70.5 | — | 92.9 |

| Parameters | Units | Cpd. No. 20 (isomer 1) IV 2 mg/kg | Cpd. No. 20 (isomer 1) PO 10 mg/kg | Cpd. No. 21 (isomer 1) IV 2 mg/kg | Cpd. No. 21 (isomer 1) PO 10 mg/kg |
|---|---|---|---|---|---|
| $C_0/C_{max}$ | ng/mL | 6088 | 4860 | 5164 | 5257 |
| $T_{max}$ | hr | — | 1 | — | 2 |
| $T_{1/2}$ | hr | 6.7 | 4.9 | 3.7 | 2.8 |
| CL | L/hr/kg | 0.267 | — | 0.228 | — |
| Vss | L/kg | 0.8 | — | 0.6 | — |
| $MRT_{0-last}$ | hr | 2.4 | 3.6 | 2.7 | 4.9 |
| $AUC_{0-last}$ | hr*ng/mL | 7354 | 22267 | 8743 | 41227 |
| $AUC_{0-inf}$ | hr*ng/mL | 7501 | 22581 | 8783 | 41342 |
| $V_z/F$ | L/kg | — | 3.1 | — | 9.9 |
| F | % | — | 60.2 | — | 94.1 |

Having now fully described the methods, compounds, and compositions herein, it will be understood by those of skill in the art that the same can be performed within a wide and equivalent range of conditions, formulations, and other parameters without affecting the scope of the methods, compounds, and compositions provided herein or any embodiment thereof.

All patents, patent applications, and publications cited herein are fully incorporated by reference herein in their entirety.

What is claimed is:

1. A compound of Formula I-A:

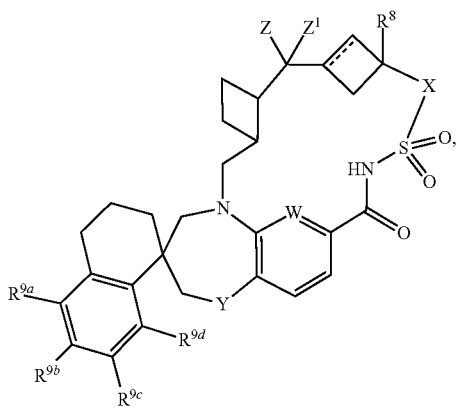

wherein:

X is selected from the group consisting of:

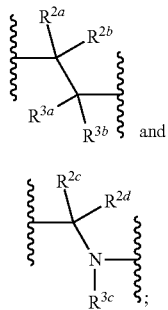

wherein the bond projecting to the right is attached to the —S(=O)$_2$— group;

$R^8$ is selected from the group consisting of hydrogen and $C_1$-$C_3$ alkyl; or X and $R^8$ taken together form a spirocycle of Formula X-3:

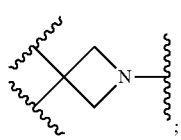

wherein the bond projecting to the right is attached to the —S(=O)$_2$— group;

Y is selected from the group consisting of —O— and —S—;

Z is selected from the group consisting of —R, —N($R^{1a}$)($R^{1b}$), and —O$R^1$;

$Z^1$ is selected from the group consisting of hydrogen, (hydroxy)$C_1$-$C_4$ alkyl, ($C_1$-$C_3$ alkoxy)$C_1$-$C_3$ alkyl, (heterocyclo)$C_1$-$C_4$ alkyl, (alkylsulfonyl)$C_1$-$C_4$ alkyl, (phenyl)$C_1$-$C_4$ alkyl, (heteroaryl)$C_1$-$C_4$ alkyl, (amino)$C_1$-$C_4$ alkyl, (amido)$C_1$-$C_4$ alkyl, (carboxy)$C_1$-$C_4$ alkyl, (alkoxycarbonyl)$C_1$-$C_4$ alkyl, (aminocarbonyl)$C_1$-$C_4$ alkyl, (aminosulfonyl)$C_1$-$C_4$ alkyl, and —C(=O)$R^{15}$;

R is selected from the group consisting of $C_1$-$C_6$ alkyl, $C_3$-$C_6$ cycloalkyl, and 4- to 10-membered heterocyclo;

$R^1$ is selected from the group consisting of hydrogen, $C_1$-$C_6$ alkyl, (hydroxy)$C_1$-$C_4$ alkyl, ($C_1$-$C_3$ alkoxy)$C_1$-$C_3$ alkyl, (heterocyclo)$C_1$-$C_4$ alkyl, (alkylsulfonyl)$C_1$-$C_4$ alkyl, (phenyl)$C_1$-$C_4$ alkyl, (heteroaryl) $C_1$-$C_4$ alkyl, (amino)$C_1$-$C_4$ alkyl, (amido)$C_1$-$C_4$ alkyl, (carboxy)$C_1$-$C_4$ alkyl, (alkoxycarbonyl)$C_1$-$C_4$ alkyl, (aminocarbonyl)$C_1$-$C_4$ alkyl, and (aminosulfonyl)$C_1$-$C_4$ alkyl;

$R^{1a}$ is selected from the group consisting of hydrogen, $C_1$-$C_6$ alkyl, (hydroxy)$C_1$-$C_4$ alkyl, ($C_1$-$C_3$ alkoxy)$C_1$-$C_3$ alkyl, (heterocyclo)$C_1$-$C_4$ alkyl, (alkylsulfonyl)$C_1$-$C_4$ alkyl, (phenyl)$C_1$-$C_4$ alkyl, (heteroaryl)$C_1$-$C_4$ alkyl, (amino)$C_1$-$C_4$ alkyl, (amido)$C_1$-$C_4$ alkyl, (carboxy)$C_1$-$C_4$ alkyl, (alkoxycarbonyl)$C_1$-$C_4$ alkyl, (aminocarbonyl)$C_1$-$C_4$ alkyl, and (aminosulfonyl)$C_1$-$C_4$ alkyl;

$R^{1b}$ is selected from the group consisting of hydrogen and $C_1$-$C_3$ alkyl;

$R^{2a}$ is selected from the group consisting of hydrogen and $C_1$-$C_3$ alkyl;

$R^{3a}$ is selected from the group consisting of hydrogen and $C_1$-$C_3$ alkyl; or $R^{2a}$ and $R^{3a}$ taken together with the carbon atoms to which they are attached form a $C_3$-$C_6$ cycloalkyl or 4- to 10-membered heterocyclo;

$R^{2b}$ is selected from the group consisting of hydrogen and $C_1$-$C_3$ alkyl;

$R^{2c}$ is selected from the group consisting of hydrogen and $C_1$-$C_3$ alkyl;

$R^{2d}$ is selected from the group consisting of hydrogen and $C_1$-$C_3$ alkyl;

$R^{3b}$ is selected from the group consisting of hydrogen and $C_1$-$C_3$ alkyl;

$R^{3c}$ is selected from the group consisting of hydrogen, $C_1$-$C_6$ alkyl, (hydroxy)$C_1$-$C_4$ alkyl, ($C_1$-$C_3$ alkoxy)$C_1$-$C_3$ alkyl, (heterocyclo)$C_1$-$C_4$ alkyl, (alkylsulfonyl)$C_1$-$C_4$ alkyl, (phenyl)$C_1$-$C_4$ alkyl, (heteroaryl)$C_1$-$C_4$ alkyl, (amino)$C_1$-$C_4$ alkyl, (amido)$C_1$-$C_4$ alkyl, (carboxy)$C_1$-$C_4$ alkyl, (alkoxycarbonyl)$C_1$-$C_4$ alkyl, (aminocarbonyl)$C_1$-$C_4$ alkyl, and (aminosulfonyl)$C_1$-$C_4$ alkyl;

$R^{9a}$, $R^{9c}$, and $R^{9d}$ are independently selected from the group consisting of hydrogen and halo;

$R^{9b}$ is halo;

$R^{15}$ is 4- to 10-membered heterocyclo;

W is selected from the group consisting of —CH= and —N=;

=== represents a single or double bond;

each $C_3$-$C_7$ cycloalkyl is unsubstituted or substituted with one, two, or three substituents independently selected from the group consisting of halo, hydroxy, amino, cyano, $C_1$-$C_6$ alkyl, $C_1$-$C_4$ alkoxy, $C_3$-$C_6$ cycloalkyl, 4- to 7-membered heterocyclo, alkylsulfonyl, alkylcarbonyl, and phenyl;

each 4- to 10-membered heterocyclo is unsubstituted or substituted with one, two, three, or four substituents independently selected from the group consisting of halo, hydroxy, amino, cyano, $C_1$-$C_6$ alkyl, $C_1$-$C_4$ alkoxy, $C_3$-$C_6$ cycloalkyl, 4- to 7-membered heterocyclo, alkylsulfonyl, alkylcarbonyl, and phenyl; and each phenyl is unsubstituted or substituted with one, two, three, or four substituents independently selected from the group consisting of halo, hydroxy, amino, cyano, $C_1$-$C_6$ alkyl, $C_1$-$C_4$ alkoxy, $C_3$-$C_6$ cycloalkyl, 4- to 7-membered heterocyclo, alkylsulfonyl, alkylcarbonyl, and phenyl, or a pharmaceutically acceptable salt thereof.

2. The compound of claim 1 selected from the group consisting of:
II-A
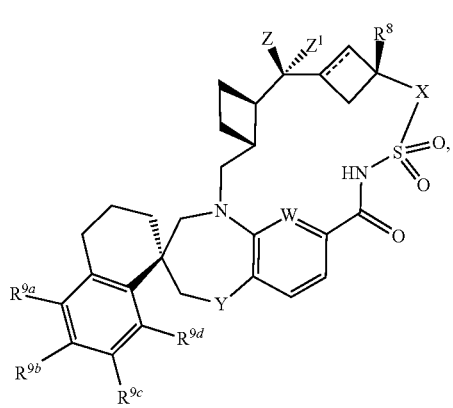
III-A
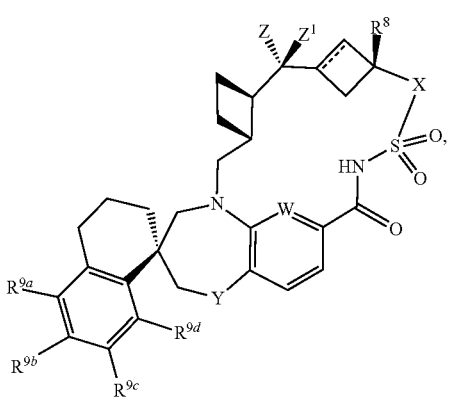
IV-A
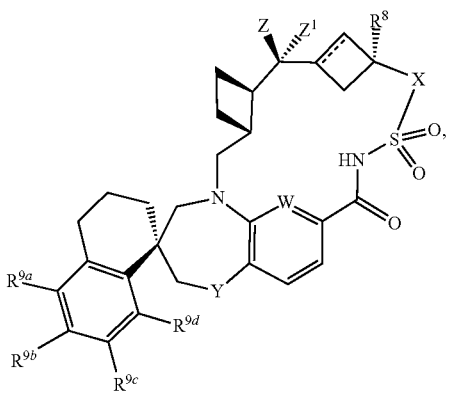
V-A
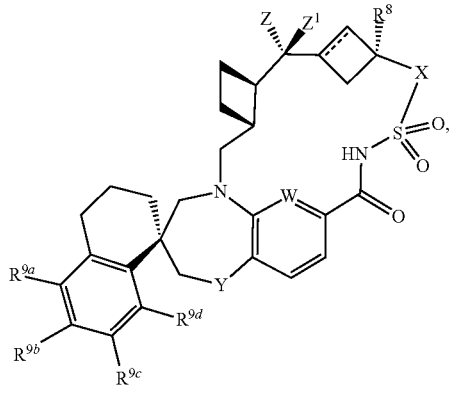
VI-A
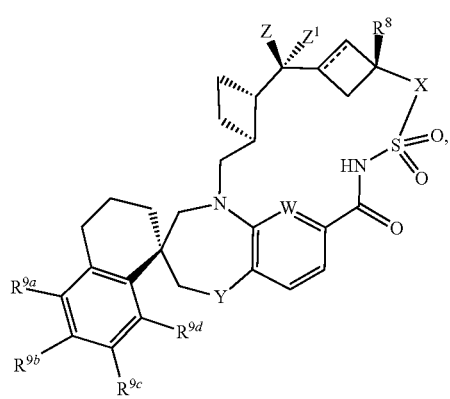
VII-A
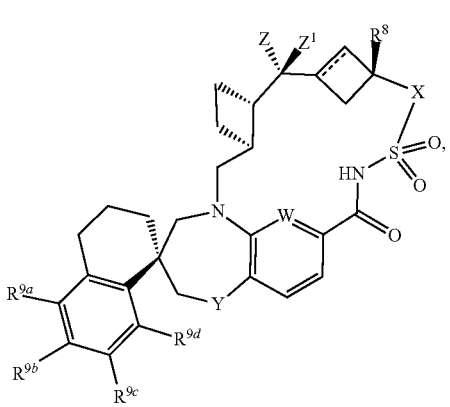
VIII-A
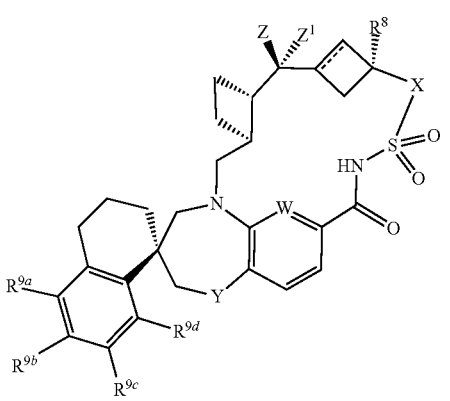
IX-A
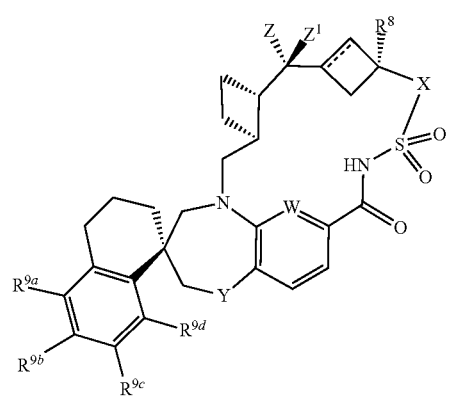

-continued
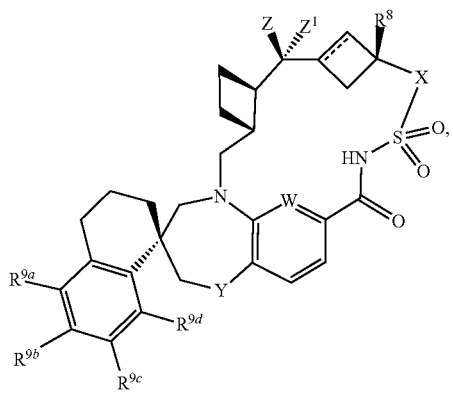
X-A
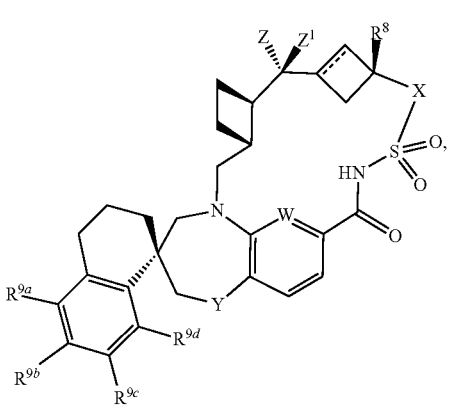
XI-A
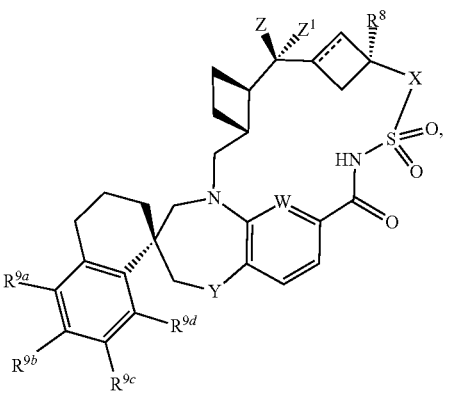
XII-A
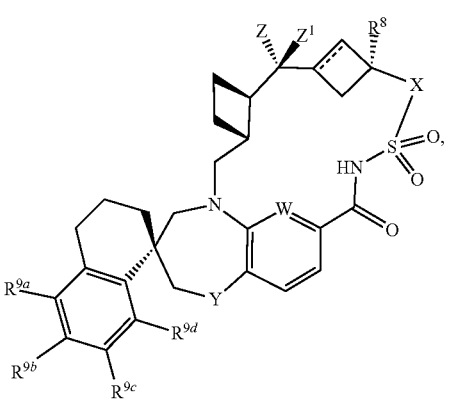
XIII-A
-continued
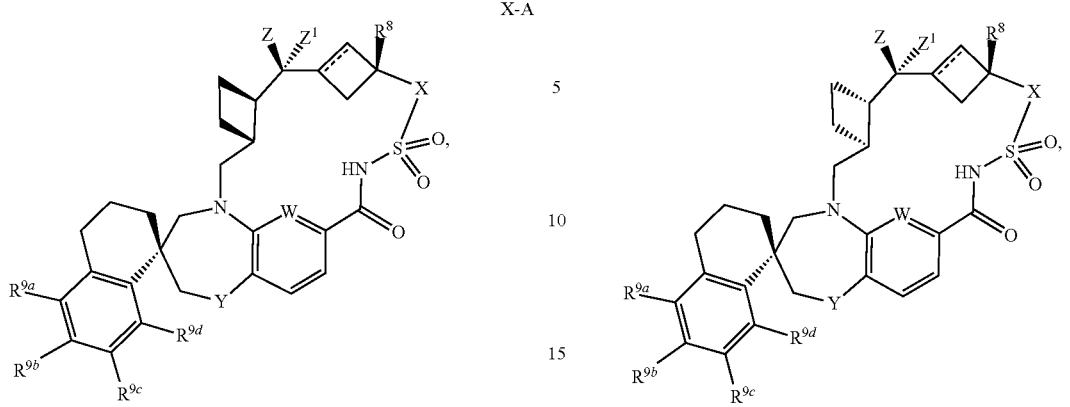
XIV-A
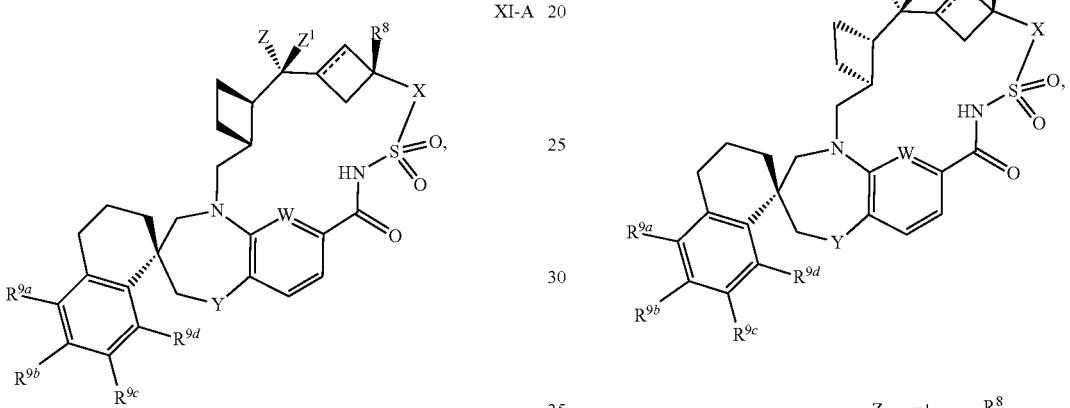
XV-A
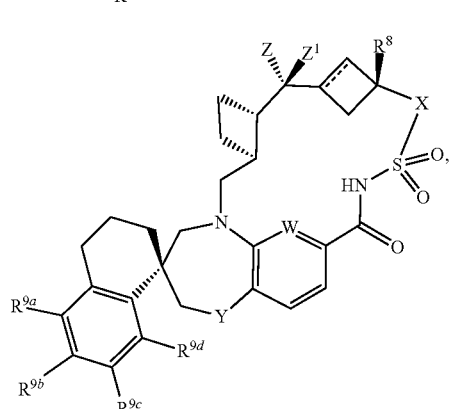
XVI-A
and
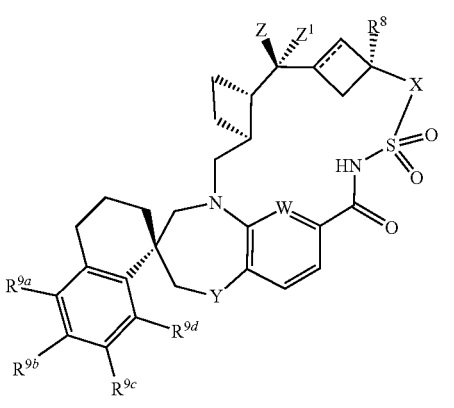
XVII-A
or a pharmaceutically acceptable salt thereof.

3. The compound of claim 1, wherein X is selected from the group consisting of:

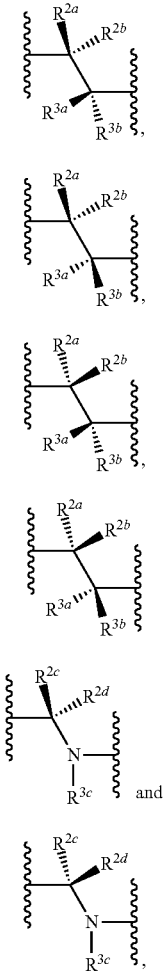

X-1-A

X-1-B

X-1-C

X-1-D

X-2-A

X-2-B or a pharmaceutically acceptable salt thereof.

4. The compound of claim 1, wherein Z is —OR$^1$, —R, or —N(R$^{1a}$)(R$^{1b}$), and Z$^1$ is hydrogen, or a pharmaceutically acceptable salt thereof.

5. The compound of claim 4, wherein R$^1$ is selected from the group consisting of (hydroxy)C$_1$-C$_4$ alkyl, (C$_1$-C$_3$ alkoxy)C$_1$-C$_3$ alkyl, (heterocyclo)C$_1$-C$_4$ alkyl, (alkylsulfonyl)C$_1$-C$_4$ alkyl, (phenyl)C$_1$-C$_4$ alkyl, (heteroaryl) C$_1$-C$_4$ alkyl, (amino)C$_1$-C$_4$ alkyl, (amido)C$_1$-C$_4$ alkyl, (carboxy) C$_1$-C$_4$ alkyl, (alkoxycarbonyl)C$_1$-C$_4$ alkyl, (aminocarbonyl) C$_1$-C$_4$ alkyl, (aminosulfonyl)C$_1$-C$_4$ alkyl, and —C(=O)R$^{15}$, or a pharmaceutically acceptable salt thereof.

6. The compound of claim 1, wherein:
Z is —OR$^1$;
R$^1$ is selected from the group consisting of hydrogen and C$_1$-C$_3$ alkyl; and
Z$^1$ is selected from the group consisting of (hydroxy)C$_1$-C$_4$ alkyl, (C$_1$-C$_3$ alkoxy)C$_1$-C$_3$ alkyl, (heterocyclo)C$_1$-C$_4$ alkyl, (alkylsulfonyl)C$_1$-C$_4$ alkyl, (phenyl)C$_1$-C$_4$ alkyl, (heteroaryl) C$_1$-C$_4$ alkyl, (amino)C$_1$-C$_4$ alkyl, (amido)C$_1$-C$_4$ alkyl, (carboxy)C$_1$-C$_4$ alkyl, (alkoxycarbonyl)C$_1$-C$_4$ alkyl, (aminocarbonyl)C$_1$-C$_4$ alkyl, (aminosulfonyl)C$_1$-C$_4$ alkyl, and —C(=O)R$^{15}$, or a pharmaceutically acceptable salt thereof.

7. The compound of claim 1, wherein R$^{3c}$ is selected from the group consisting of hydrogen, C$_1$-C$_4$ alkyl, and (heterocyclo)C$_1$-C$_4$ alkyl, or a pharmaceutically acceptable salt thereof.

8. The compound of claim 1 of Formula I:

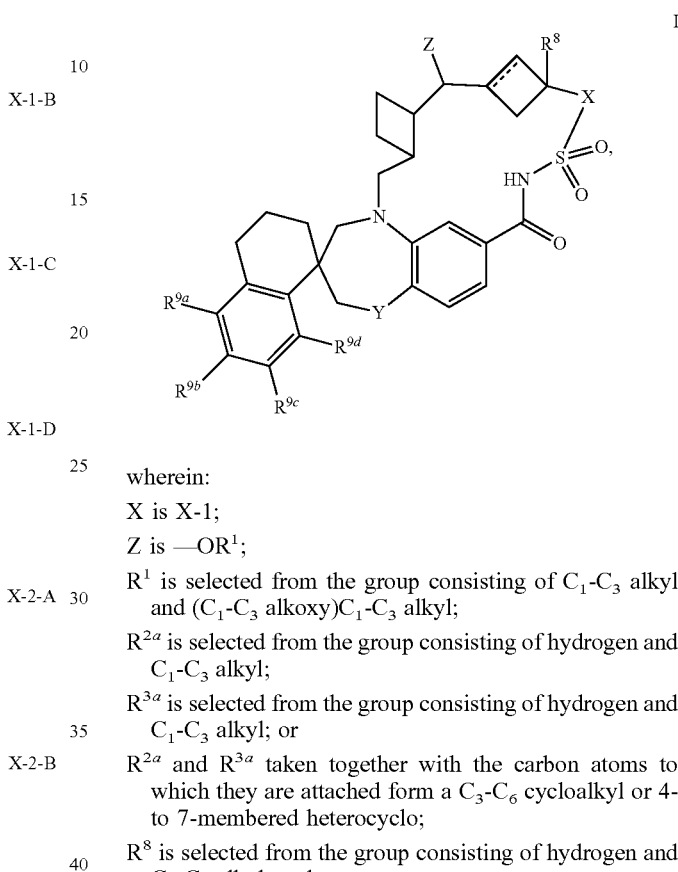

I wherein:
X is X-1;
Z is —OR$^1$;
R$^1$ is selected from the group consisting of C$_1$-C$_3$ alkyl and (C$_1$-C$_3$ alkoxy)C$_1$-C$_3$ alkyl;
R$^{2a}$ is selected from the group consisting of hydrogen and C$_1$-C$_3$ alkyl;
R$^{3a}$ is selected from the group consisting of hydrogen and C$_1$-C$_3$ alkyl; or
R$^{2a}$ and R$^{3a}$ taken together with the carbon atoms to which they are attached form a C$_3$-C$_6$ cycloalkyl or 4- to 7-membered heterocyclo;
R$^8$ is selected from the group consisting of hydrogen and C$_1$-C$_3$ alkyl; and
each C$_3$-C$_6$ cycloalkyl, or 4- to 7-membered heterocyclo is unsubstituted or substituted with one, two, or three substituents independently selected from the group consisting of halo, C$_1$-C$_3$ alkyl, and C$_1$-C$_3$ alkoxy,
or a pharmaceutically acceptable salt thereof.

9. The compound of claim 8 selected from the group consisting of:

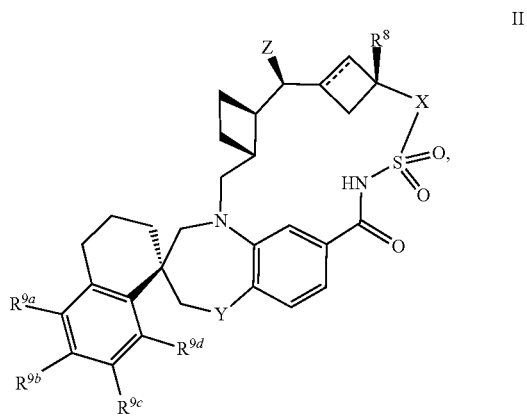

II

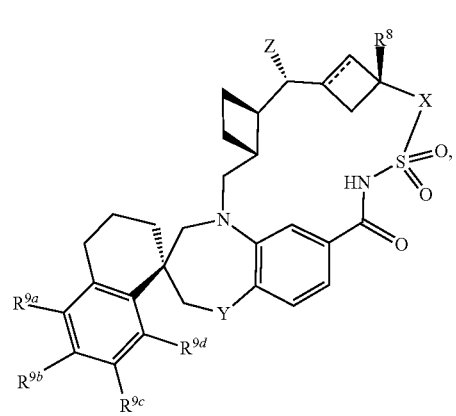
III
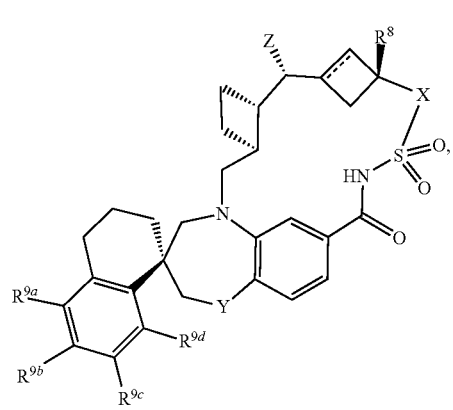
VII
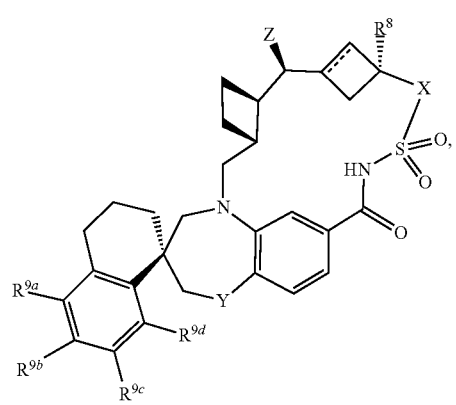
IV
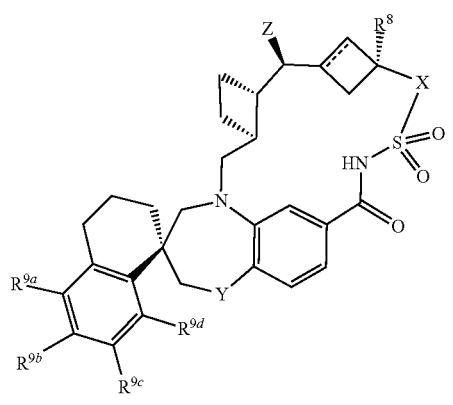
VIII
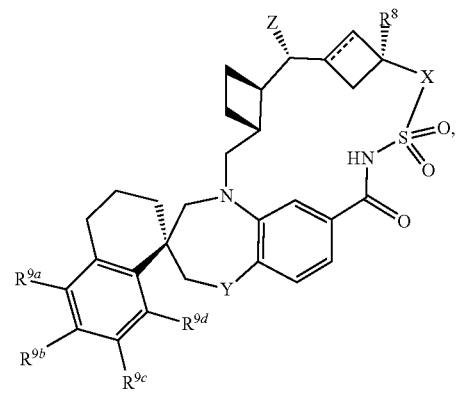
V
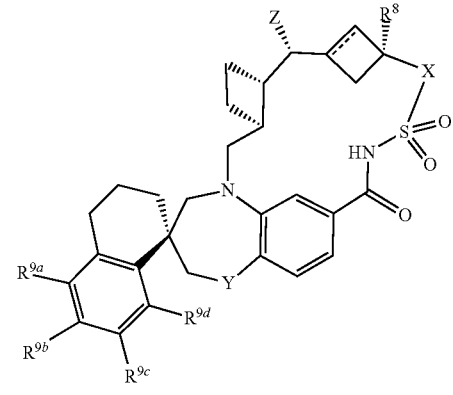
IX
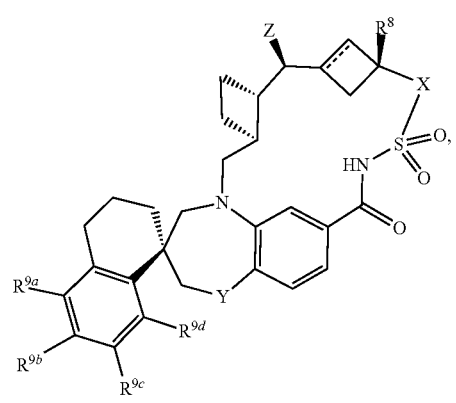
VI
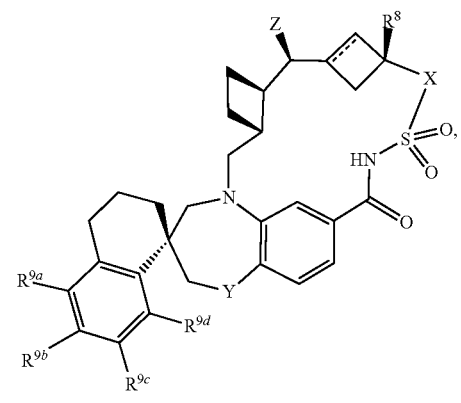
X XI
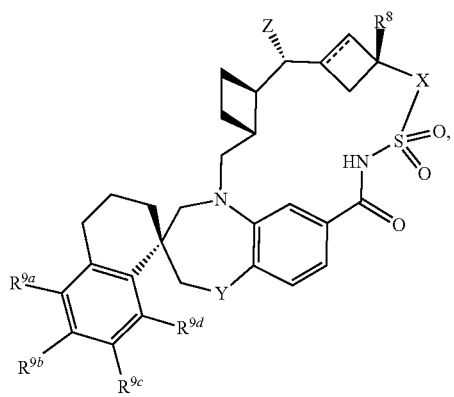

XII
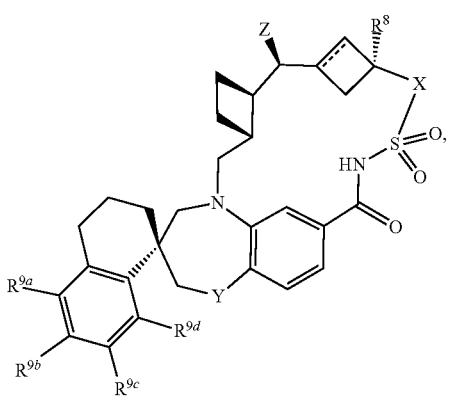

XIII
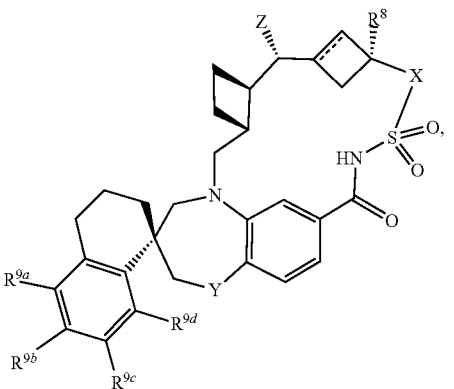

XIV
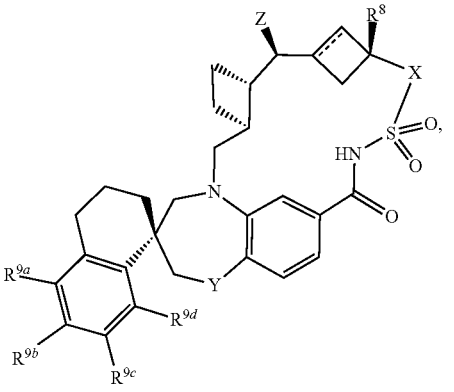

XV
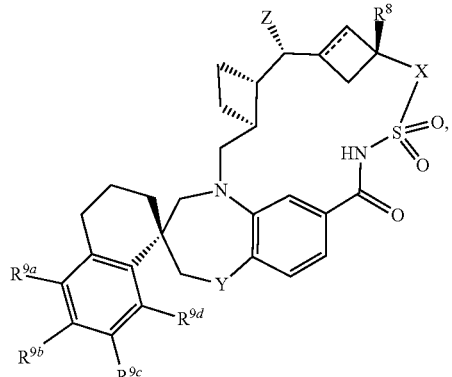

XVI
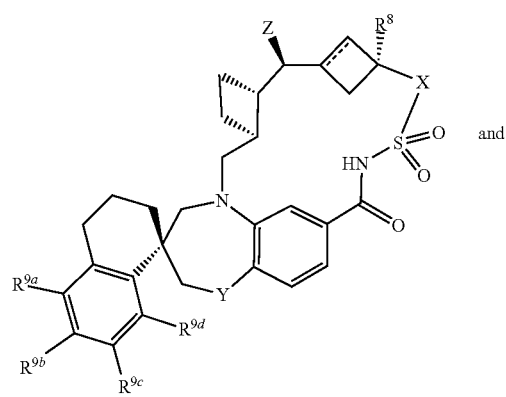

and

XVII
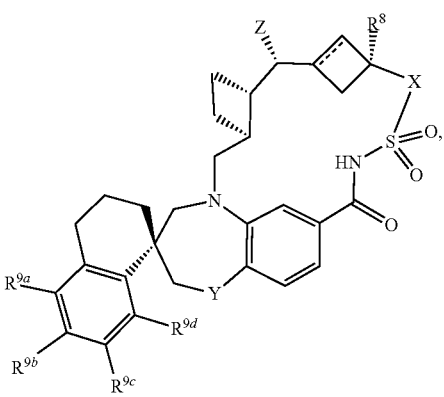

or a pharmaceutically acceptable salt thereof.

10. The compound of claim 3, wherein X-1 is selected from the group consisting of X-1-A, X-1-B, X-1-C and X-1-D, or a pharmaceutically acceptable salt thereof.

11. The compound of claim 1, wherein Z is —OR$^1$ and R$^1$ is methyl or —CH$_2$CH$_2$OCH$_3$, or a pharmaceutically acceptable salt thereof.

12. The compound of claim 1, wherein R$^{2a}$ is hydrogen, methyl, or ethyl, or a pharmaceutically acceptable salt thereof.

13. The compound of claim 1, wherein R$^{2b}$ is hydrogen or methyl, or a pharmaceutically acceptable salt thereof.

14. The compound of claim 1, wherein R$^{3a}$ is hydrogen or methyl, or a pharmaceutically acceptable salt thereof.

15. The compound of claim 1, wherein R$^{3b}$ is hydrogen or methyl, or a pharmaceutically acceptable salt thereof.

16. The compound of claim 8, wherein R$^{2a}$ and R$^{3a}$ taken together with the carbon atoms to which they are attached form a $C_3$-$C_6$ cycloalkyl or 4- to 7-membered heterocyclo, or a pharmaceutically acceptable salt thereof.

17. The compound of claim 1, wherein $R^8$ is hydrogen or methyl, or a pharmaceutically acceptable salt thereof.

18. The compound of claim 1 wherein $R^{9b}$ is chloro, or a pharmaceutically acceptable salt thereof.

19. The compound of claim 1, wherein $R^{9a}$ and $R^{9b}$ are independently selected from the group consisting of hydrogen and fluoro, or a pharmaceutically acceptable salt thereof.

20. The compound of claim 1, wherein $R^{9d}$ is hydrogen, or a pharmaceutically acceptable salt thereof.

21. The compound of claim 1 selected from the group consisting of

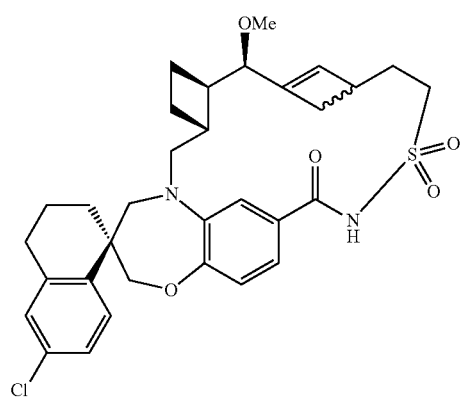

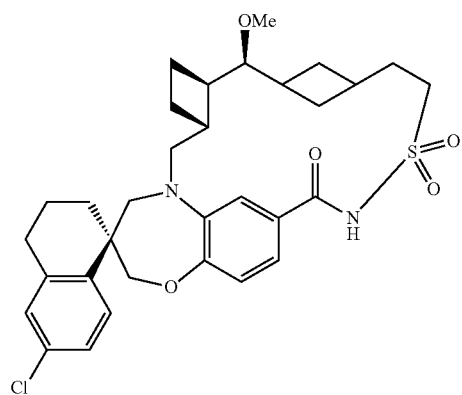

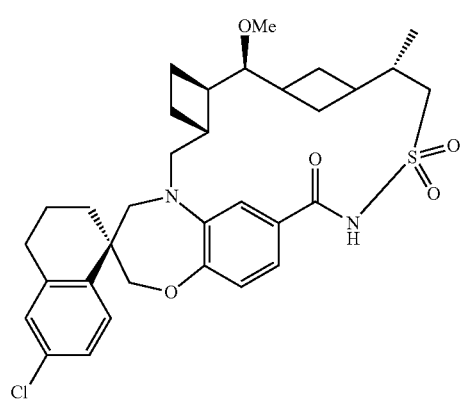

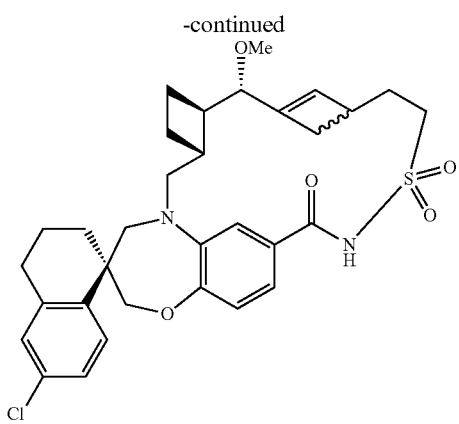

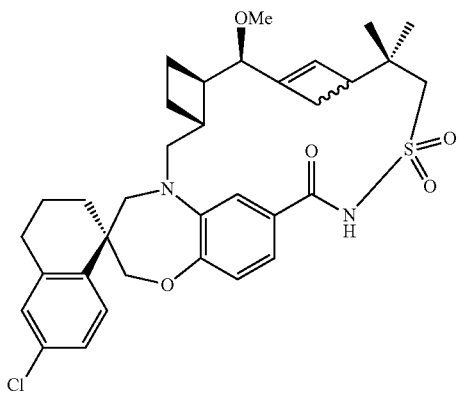

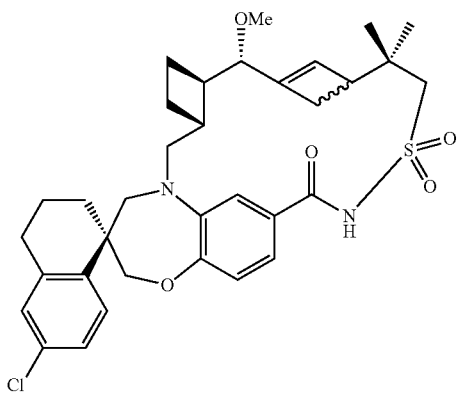

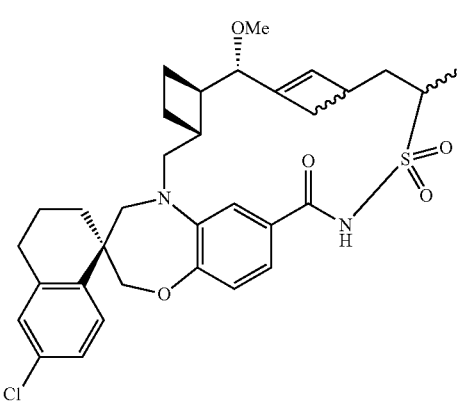

423
-continued
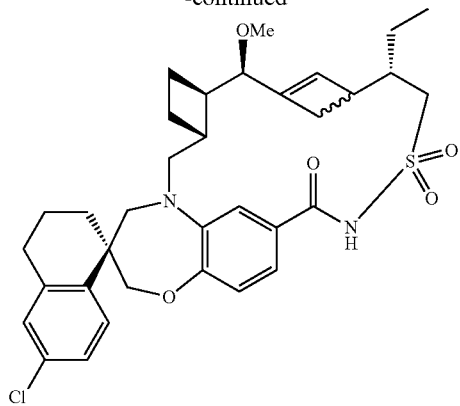
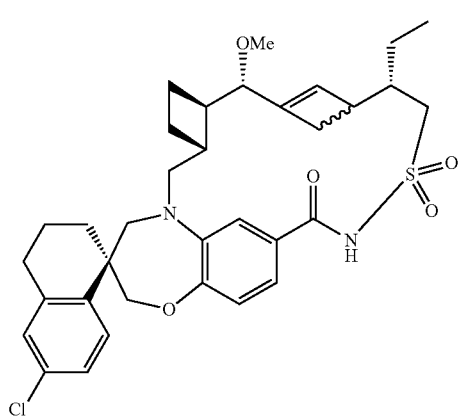
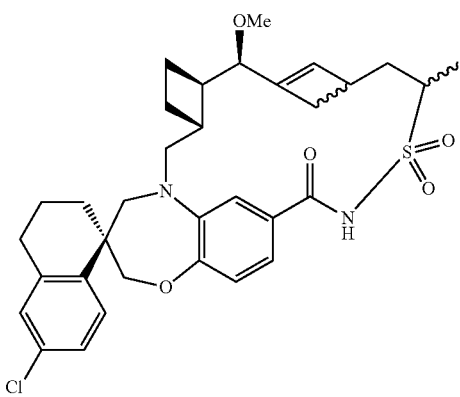
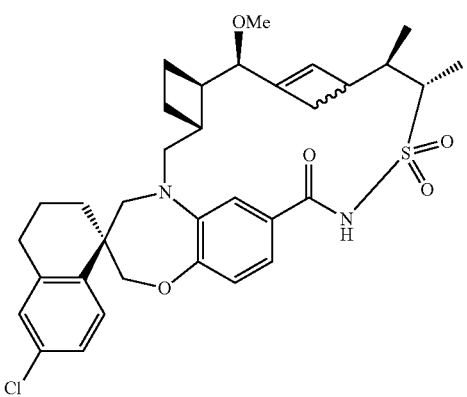
424
-continued
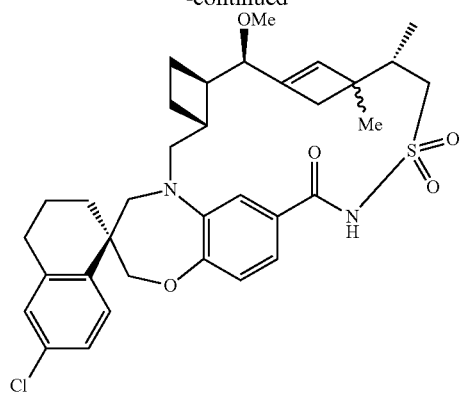
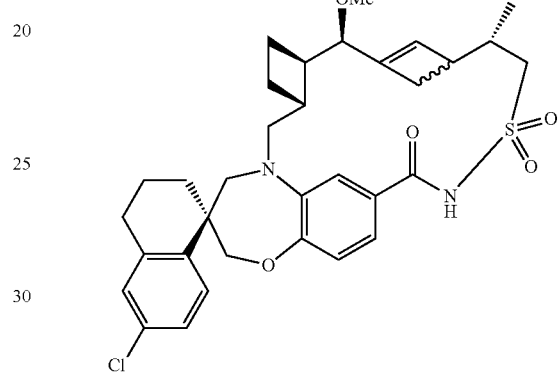
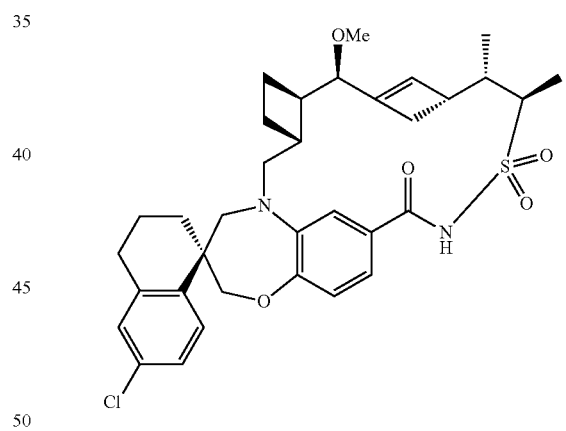
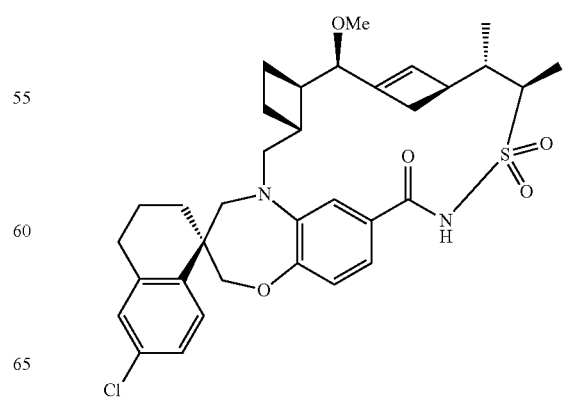

425
-continued
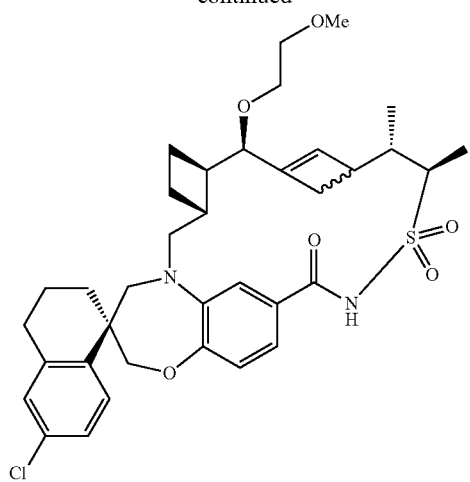
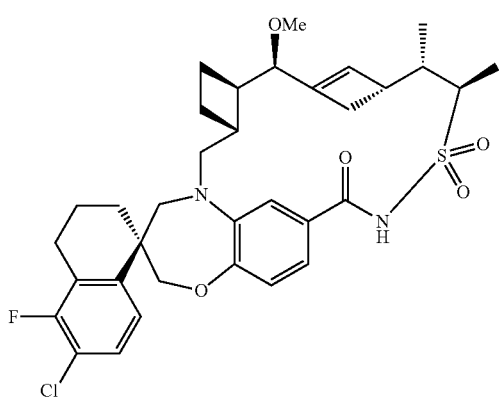
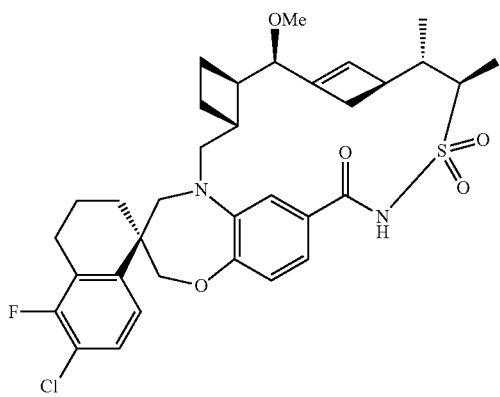
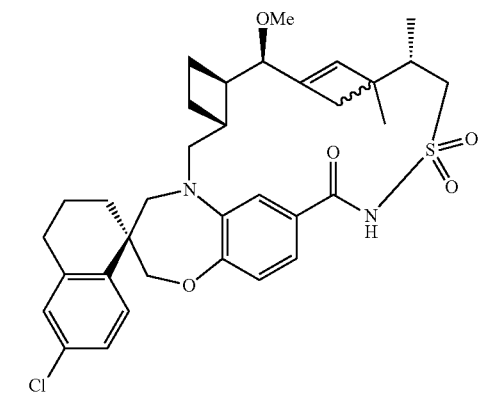
426
-continued
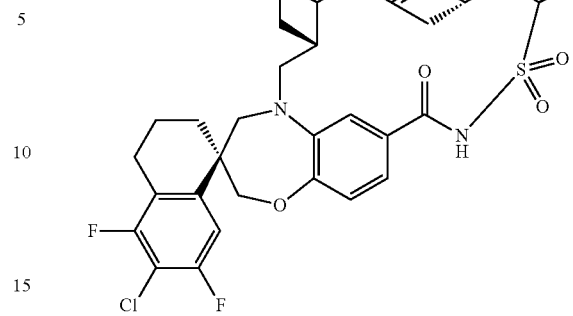
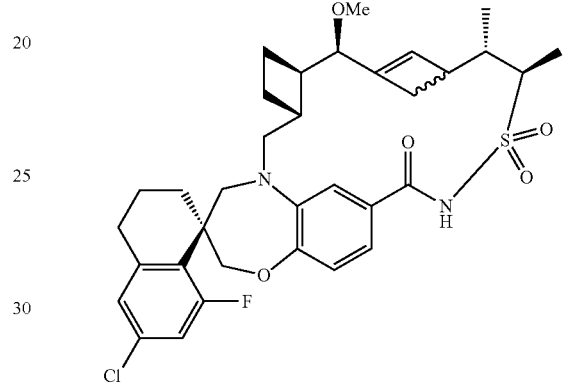
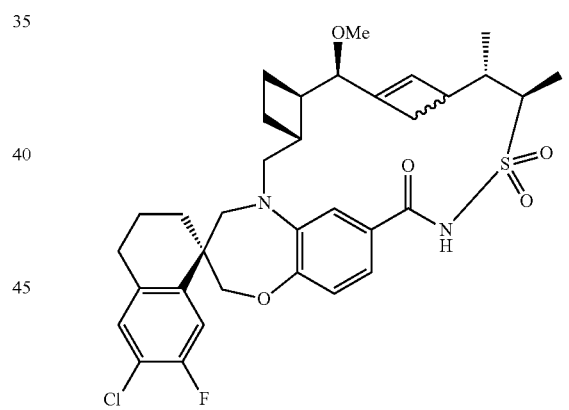
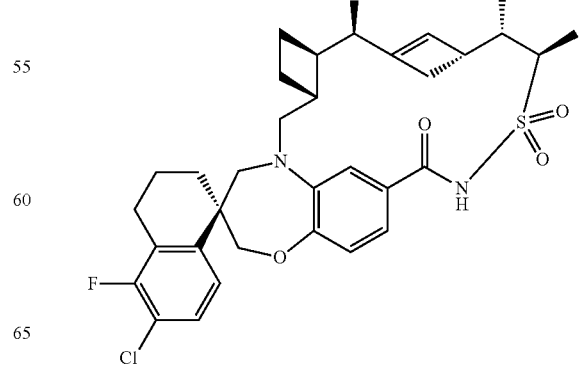

427
-continued
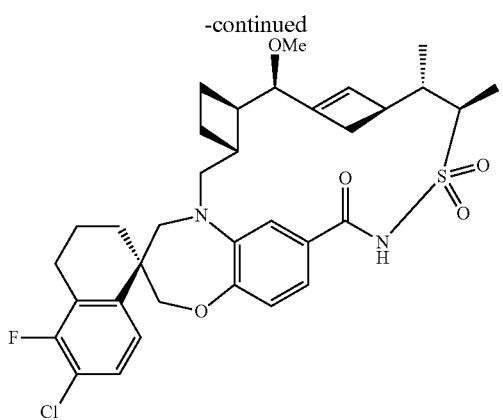
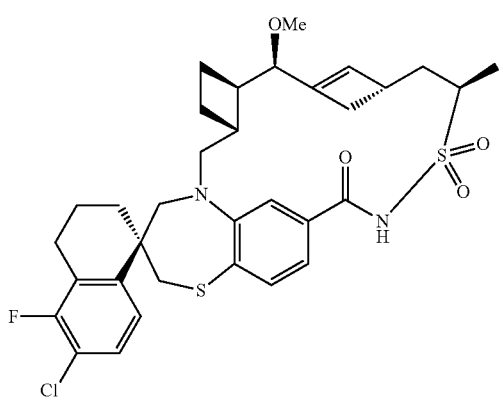
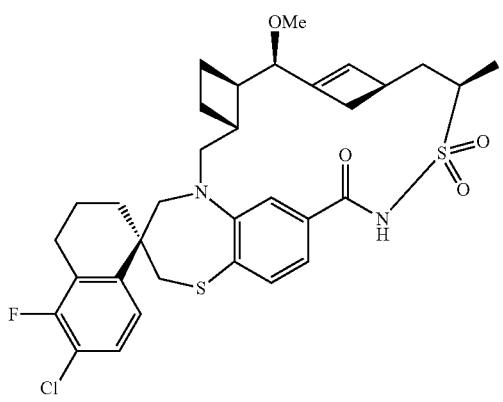
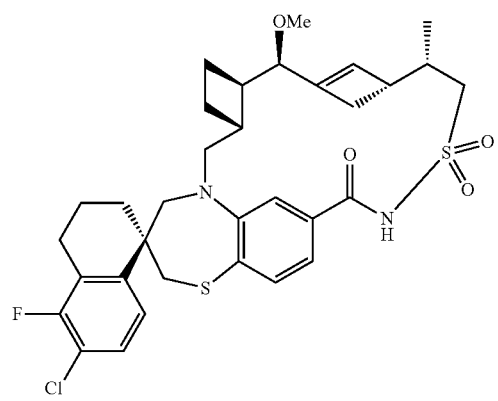
428
-continued
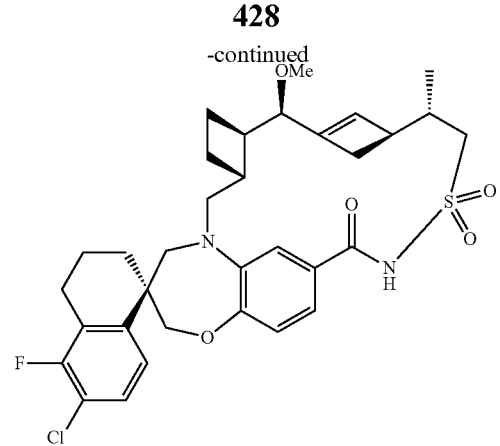
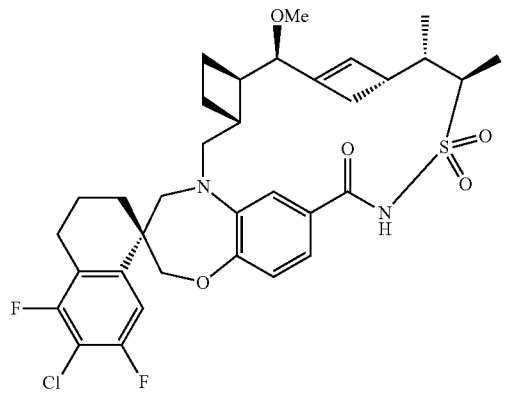
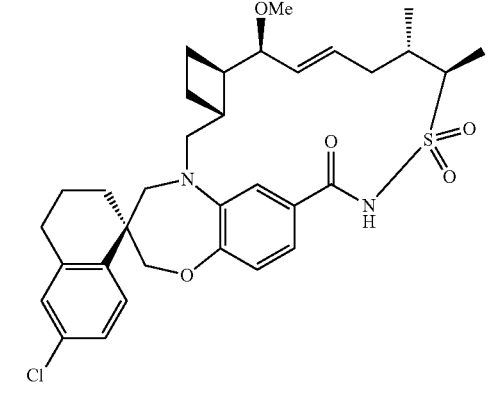
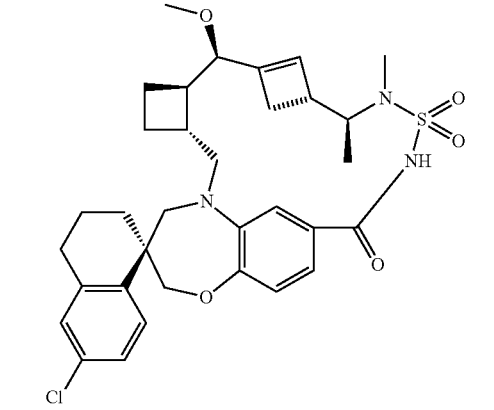

429
-continued
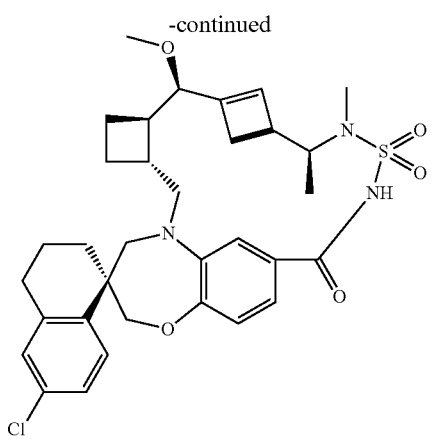
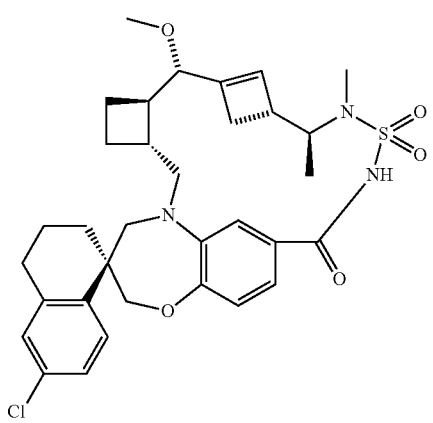
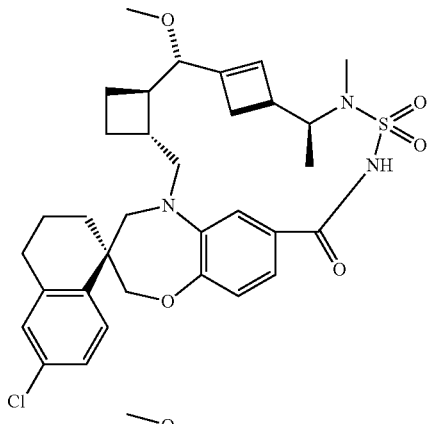
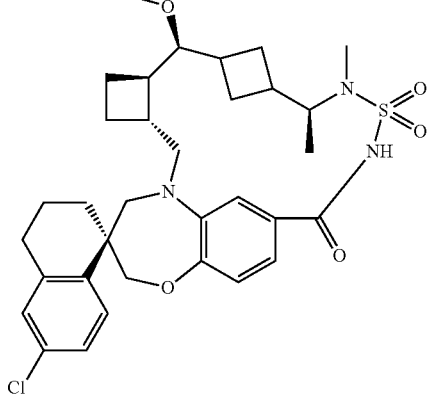
430
-continued
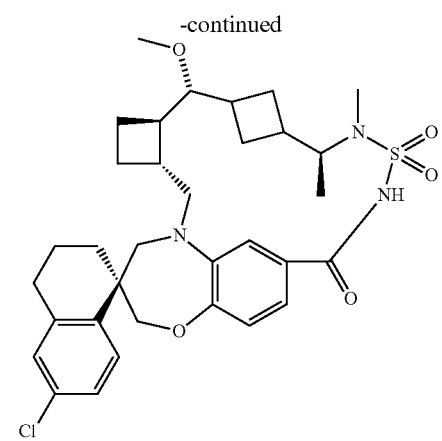
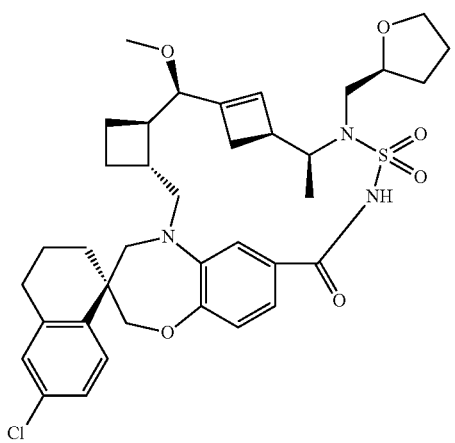
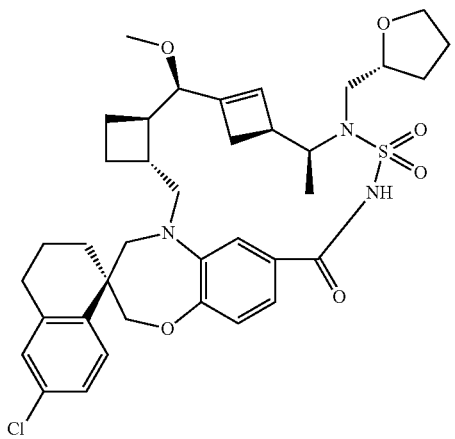
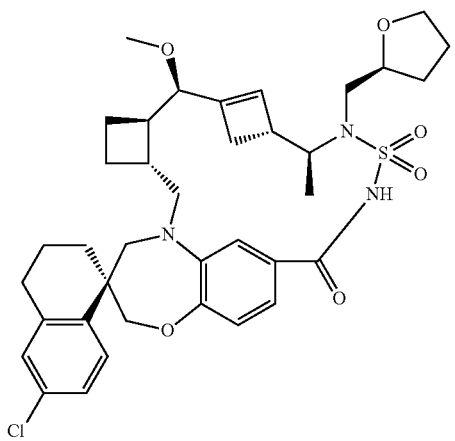

431
-continued
432
-continued
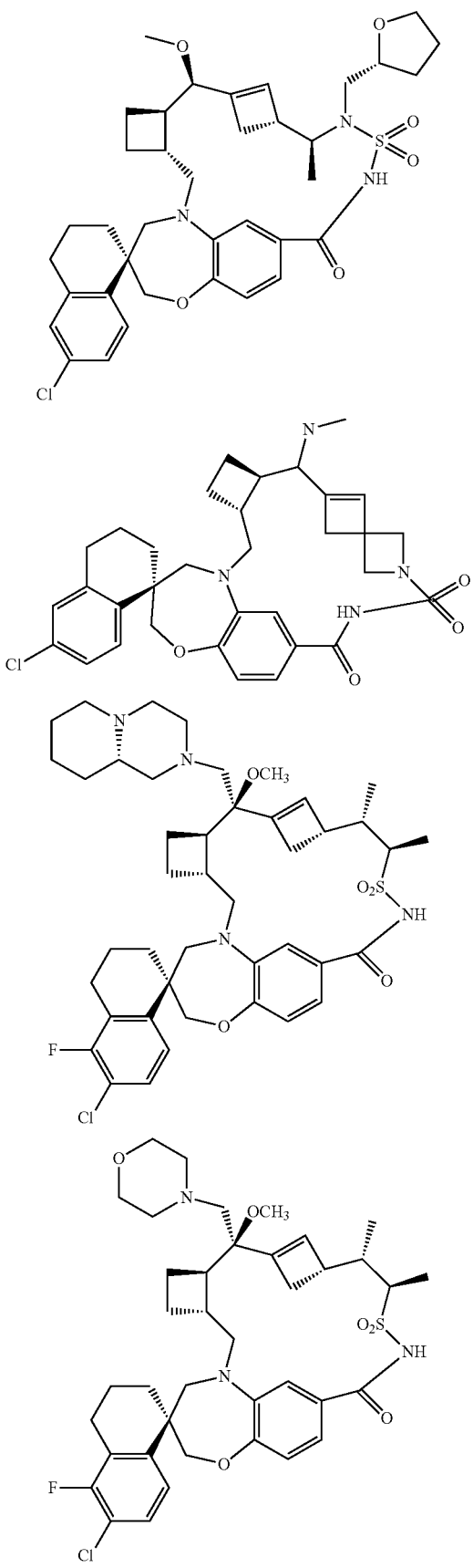
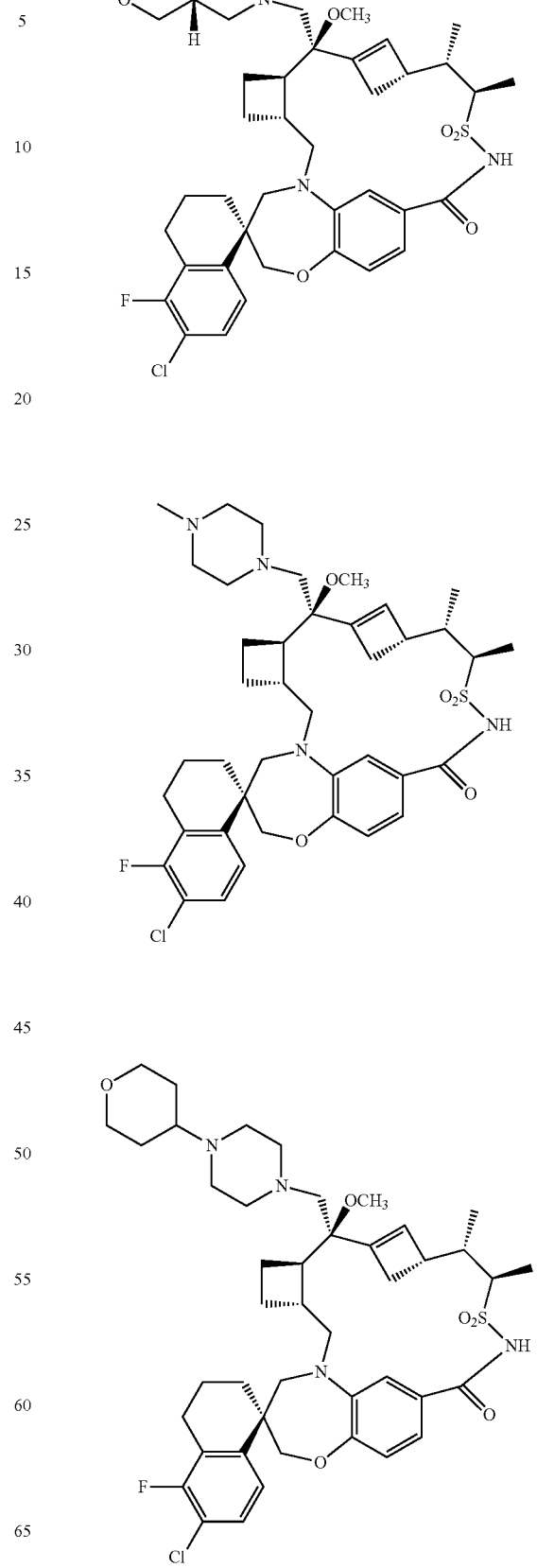

433
-continued
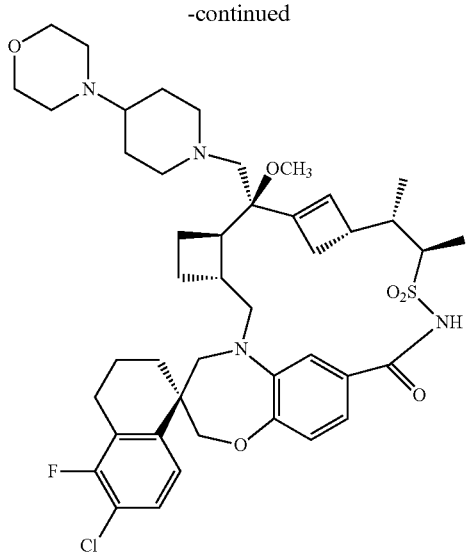
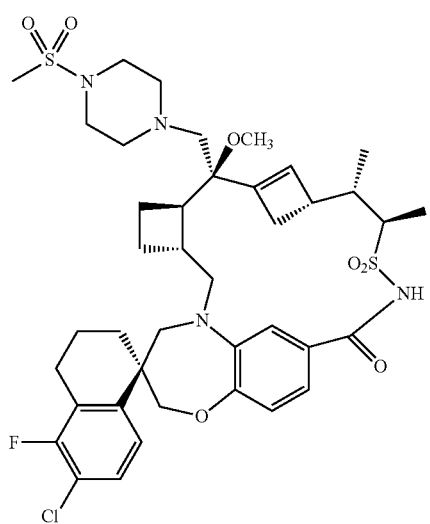
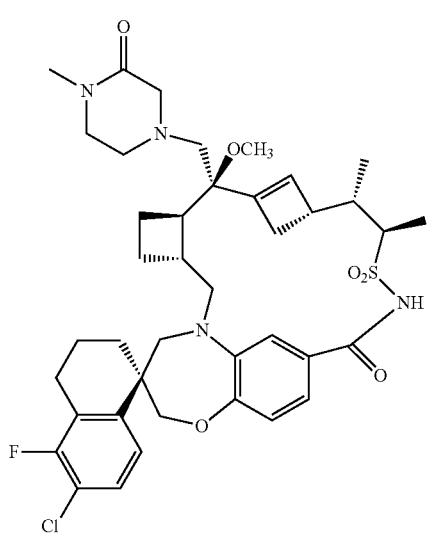
434
-continued
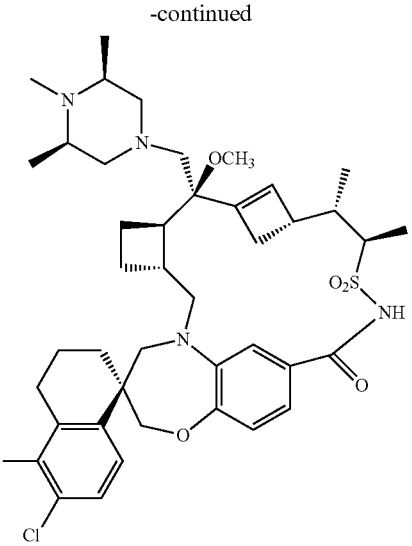
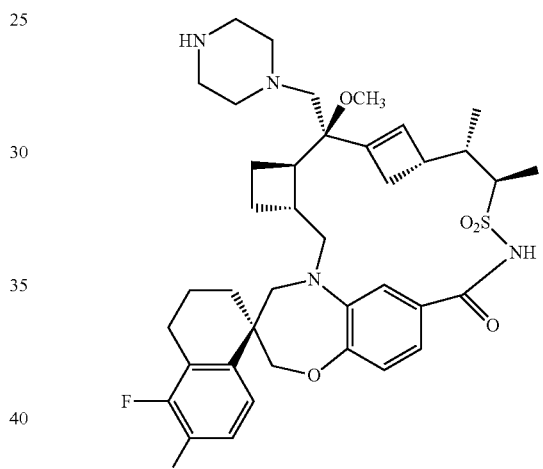
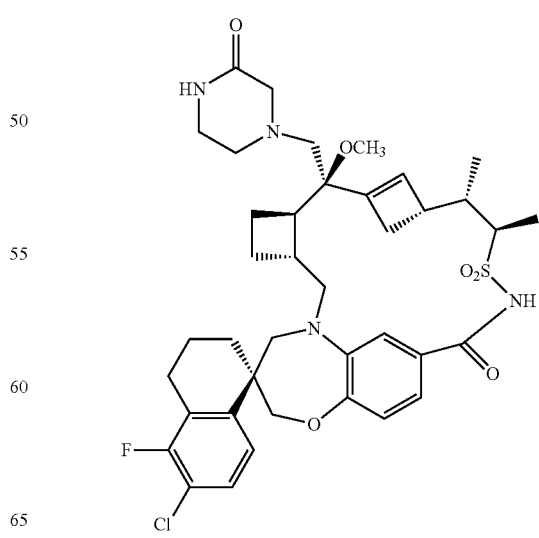

435
-continued
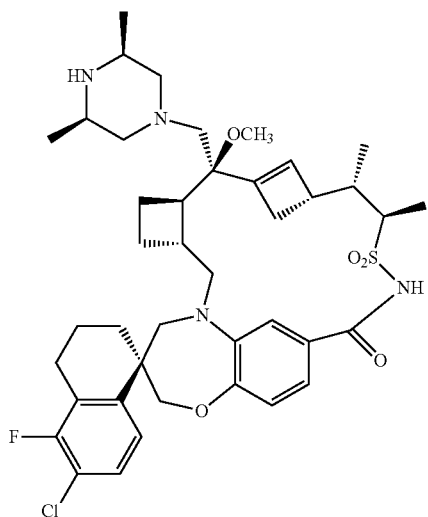
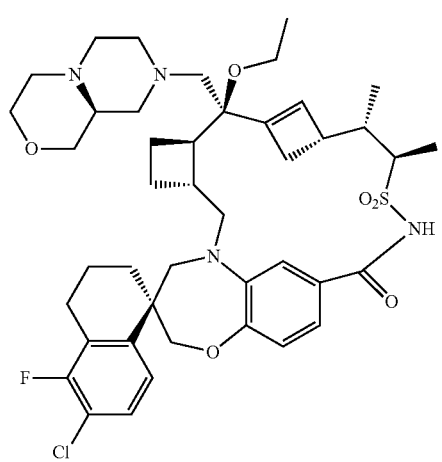
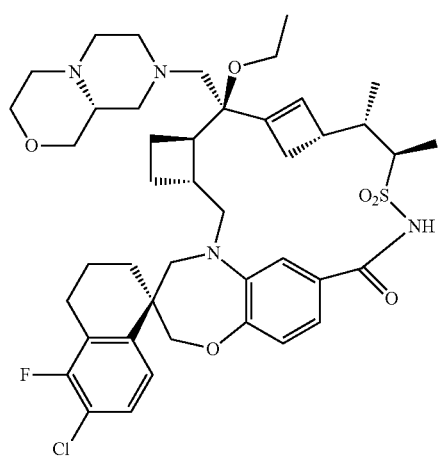
436
-continued
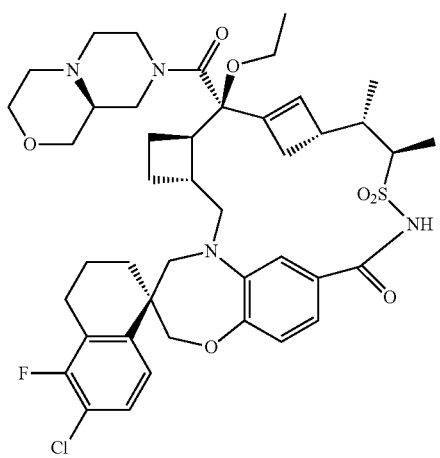
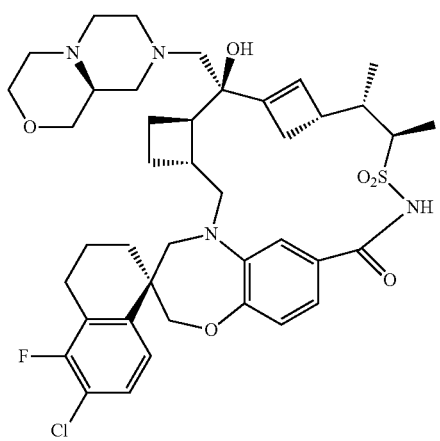
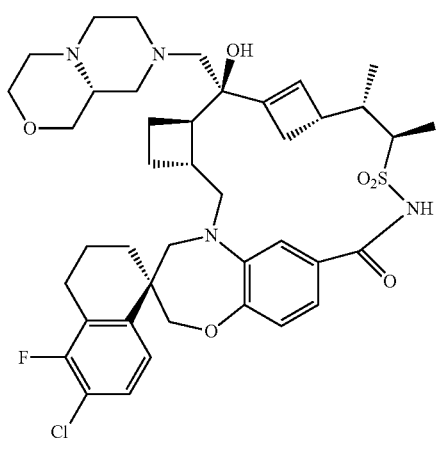

437
-continued
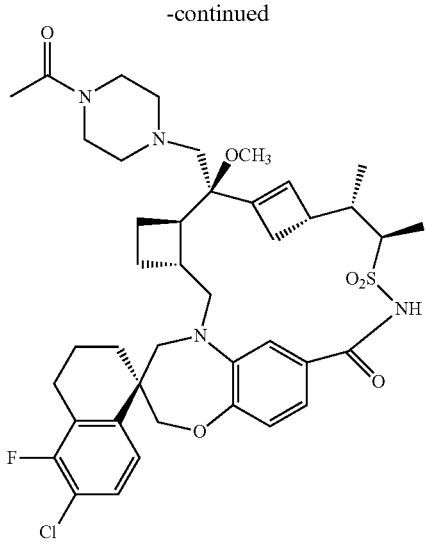
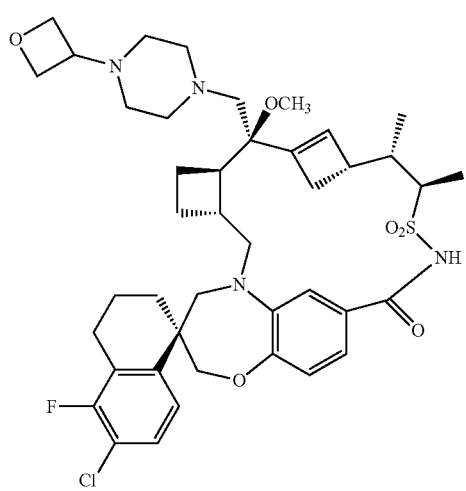
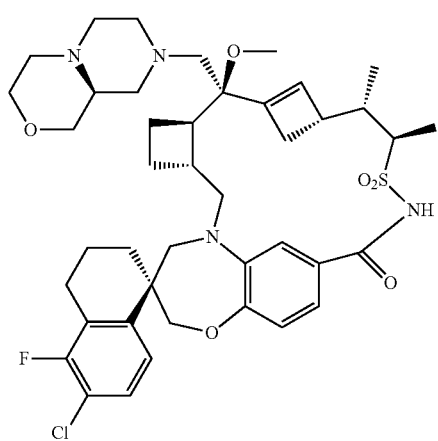
438
-continued
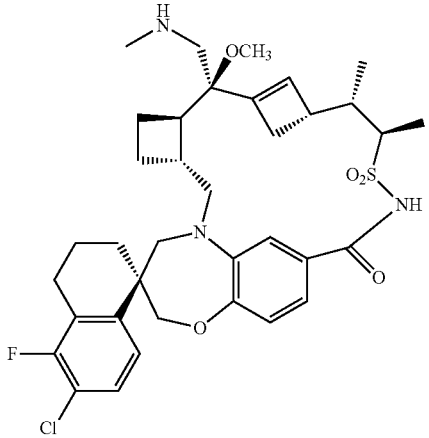
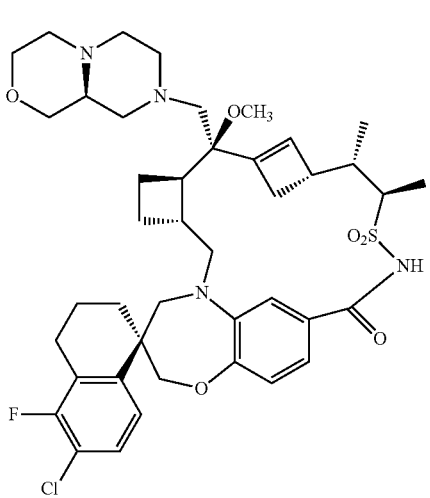

| 439 -continued | 440 -continued |
|---|---|
| 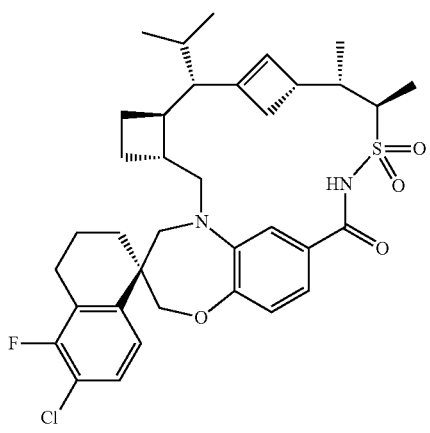 | 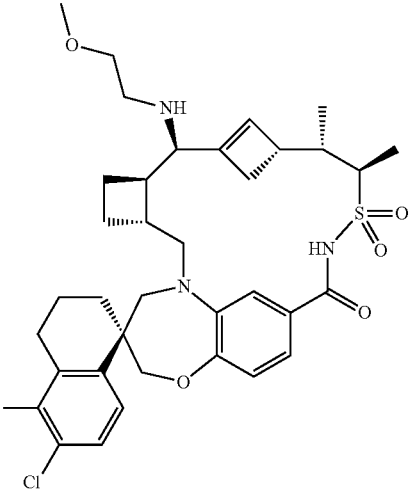 |
| 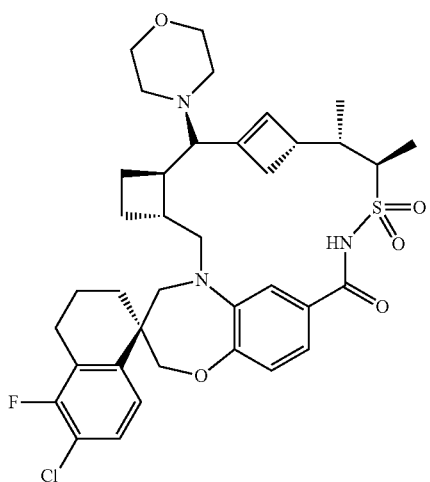 | 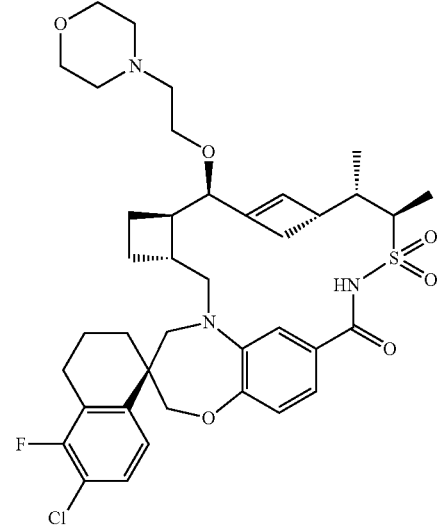 |
| 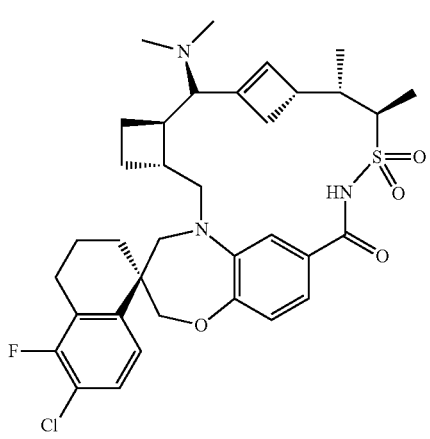 | 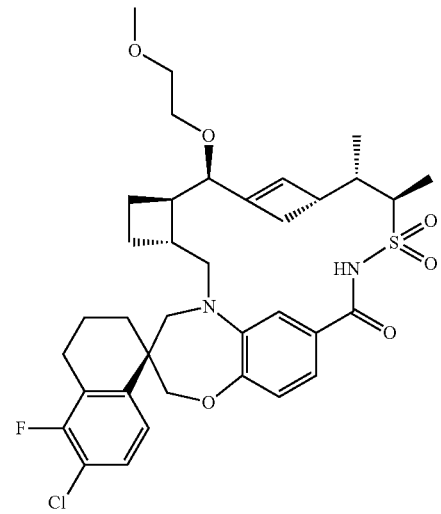 |

441
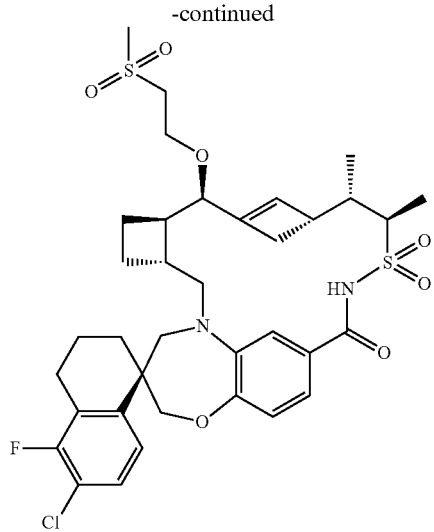
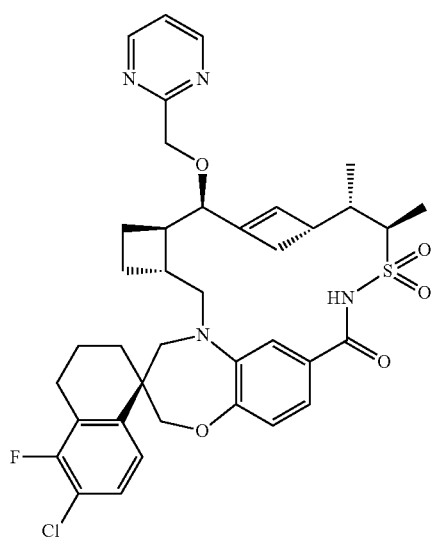
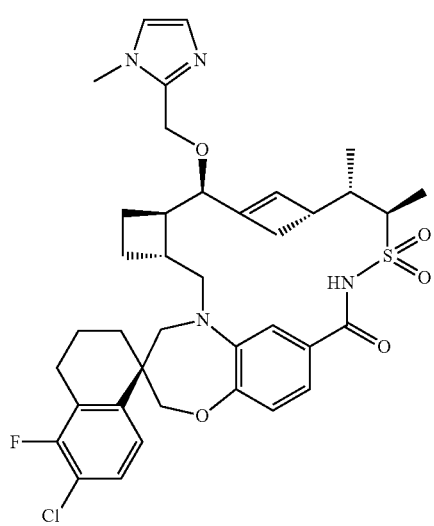
442
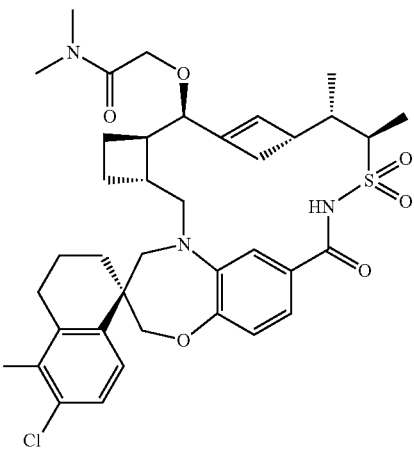
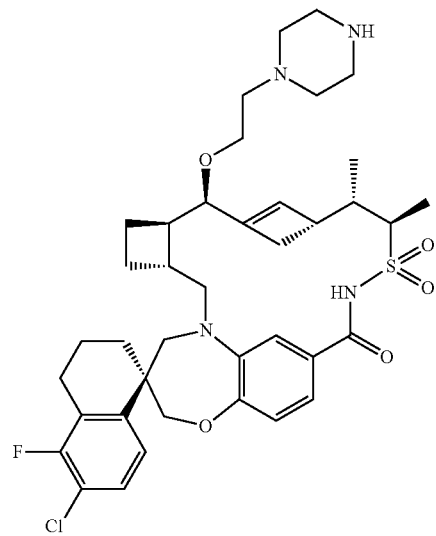
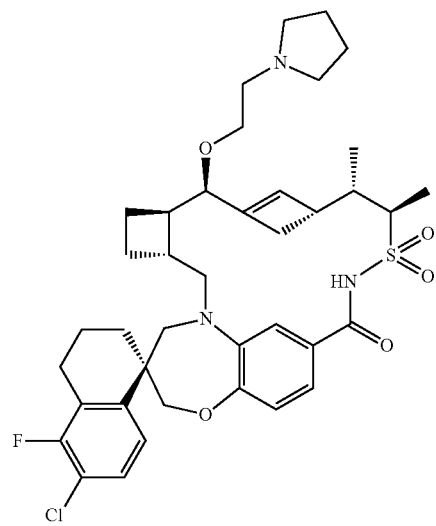

443
-continued
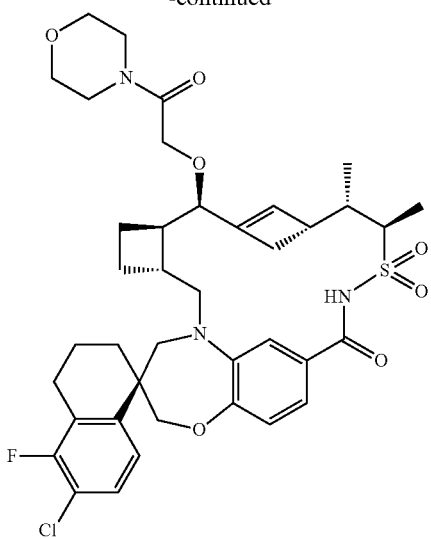
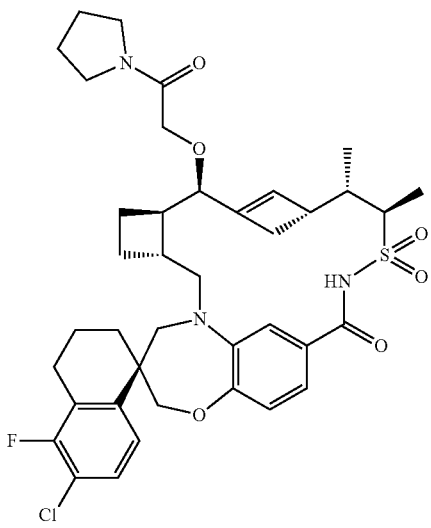
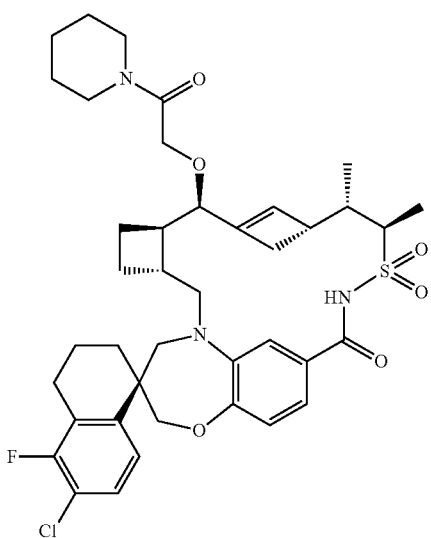
444
-continued
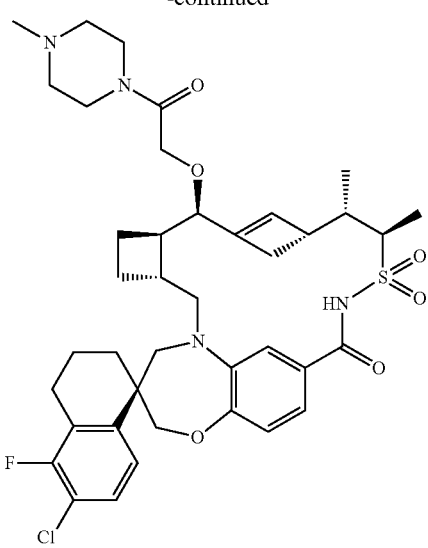
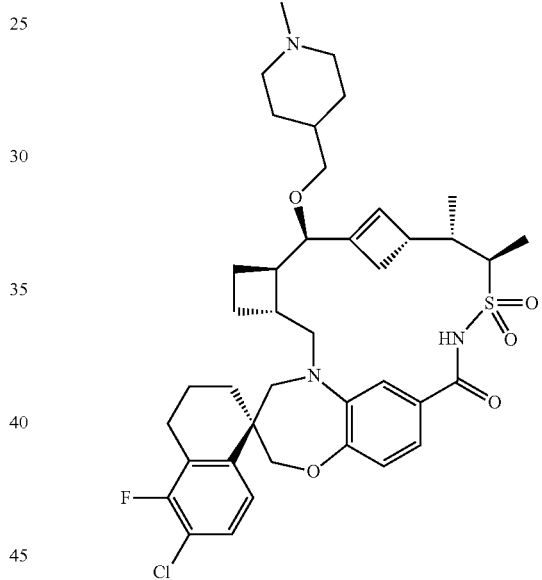
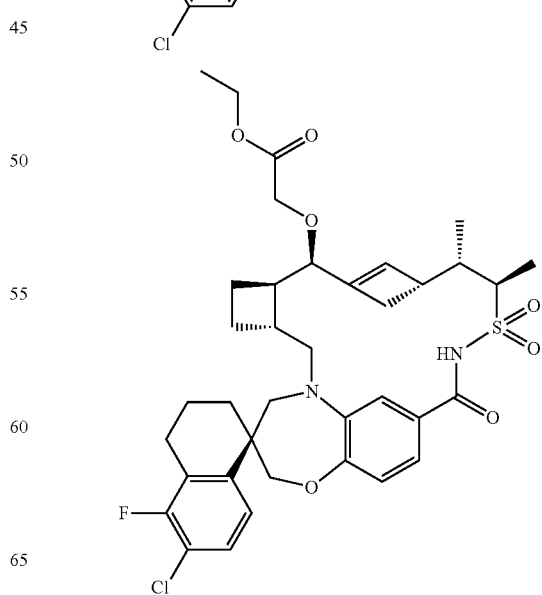

445
-continued
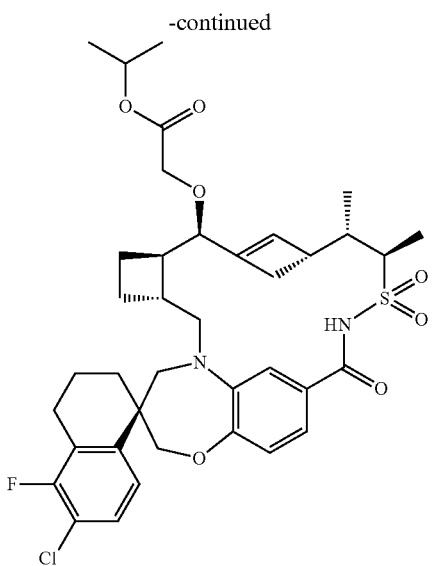
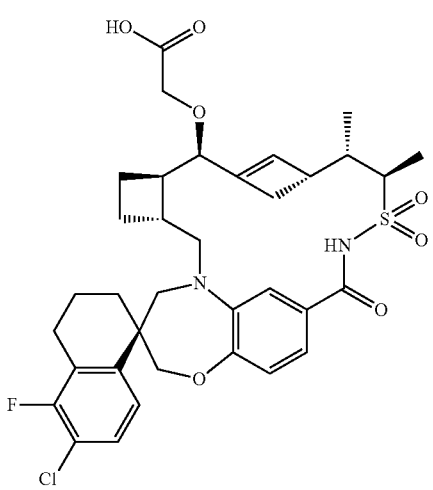
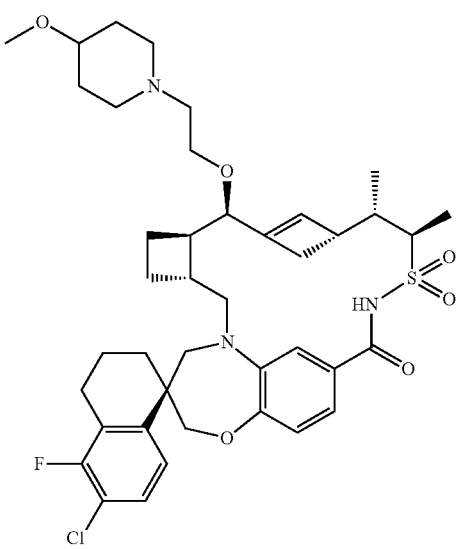
446
-continued
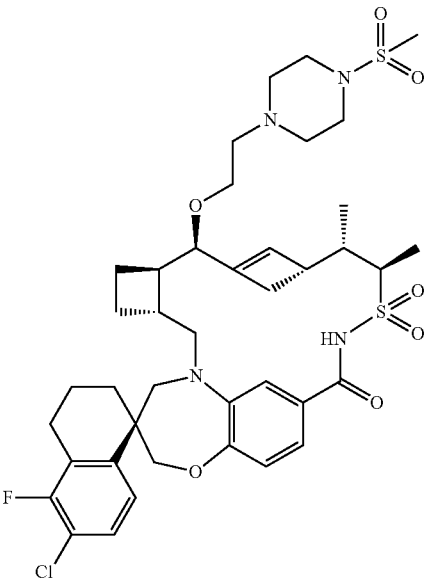
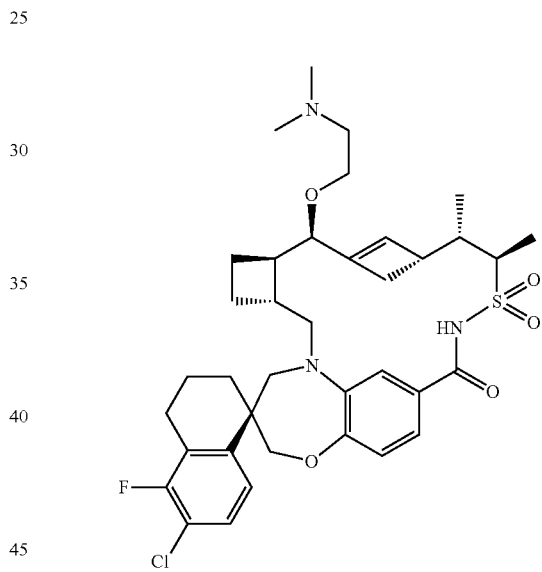
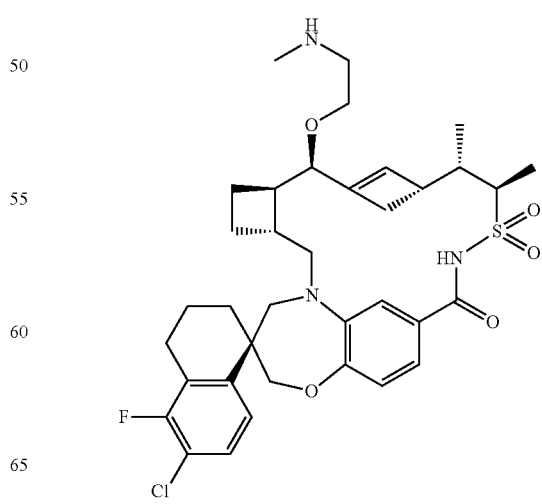

447
-continued
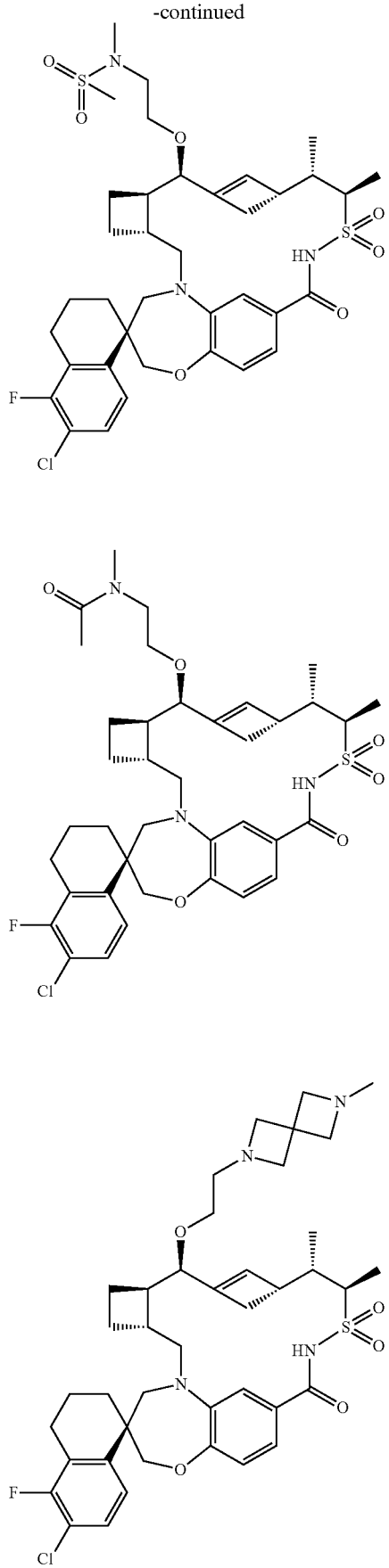
448
-continued
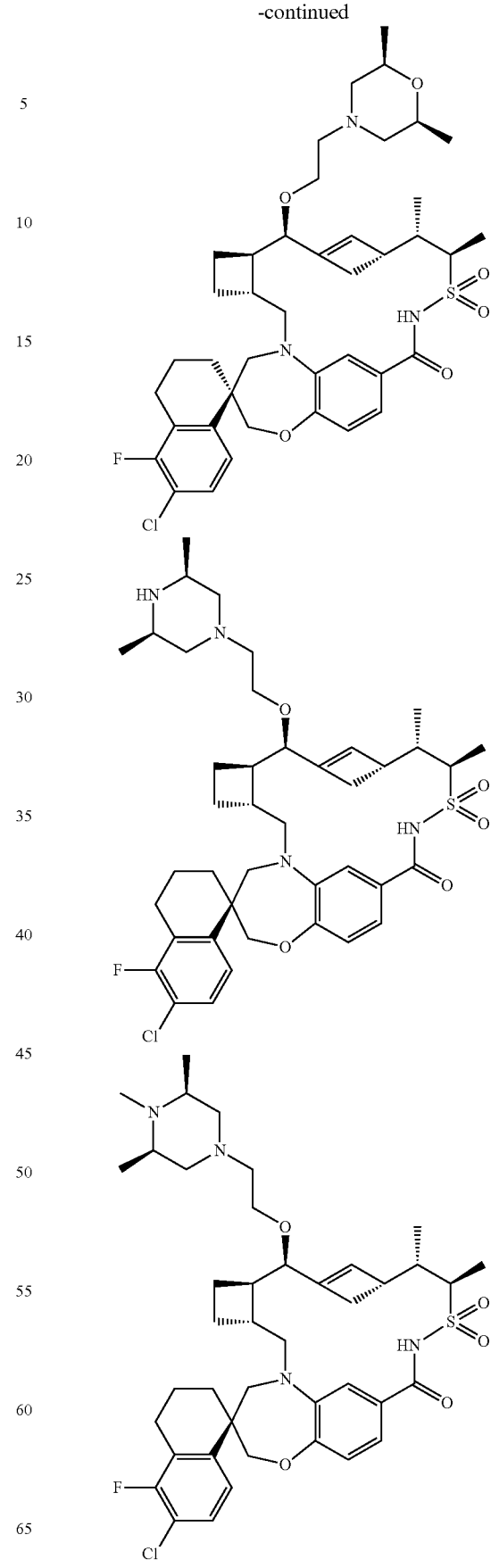

449
-continued
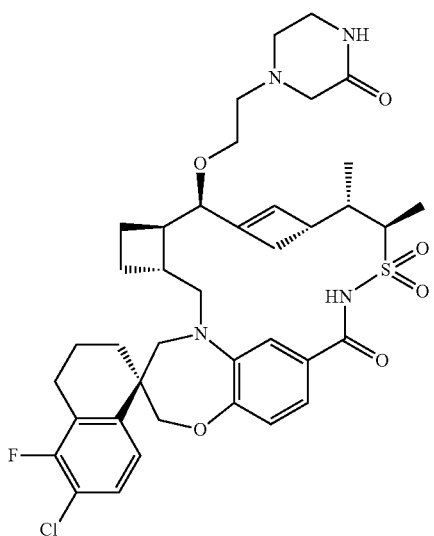
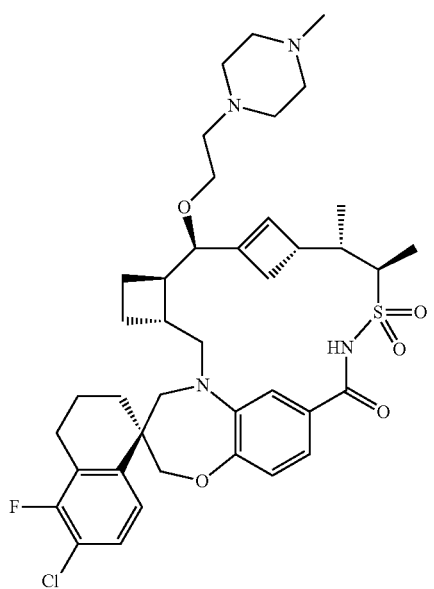
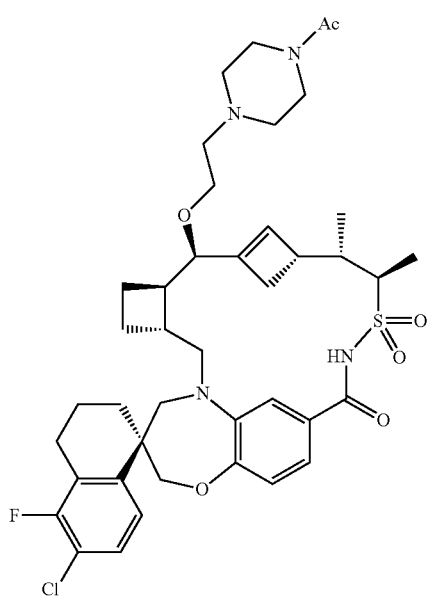
450
-continued
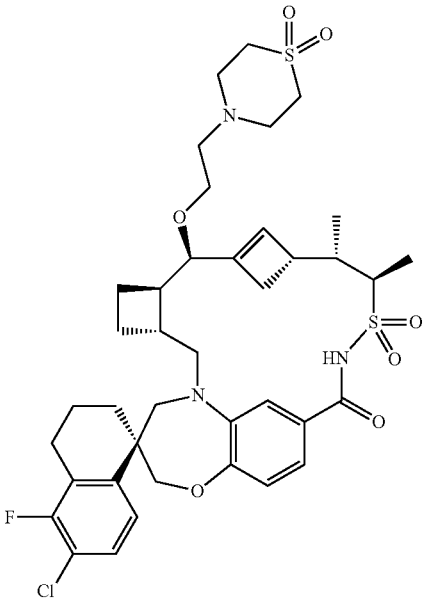
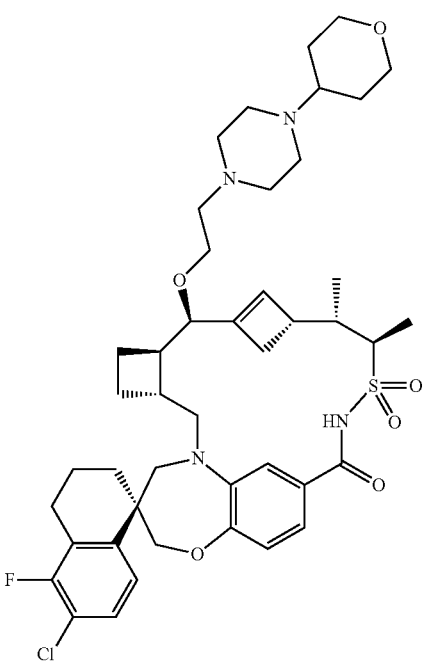

451
-continued
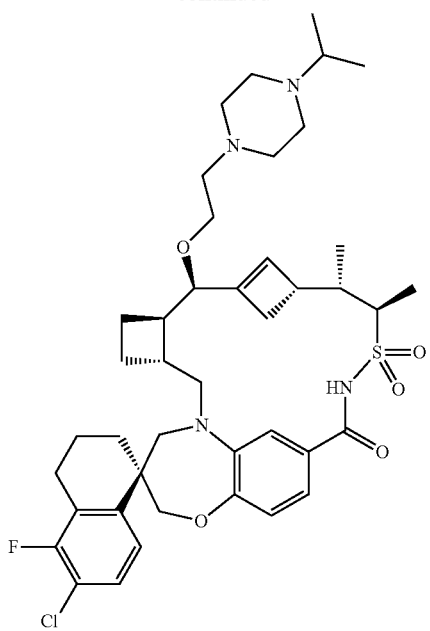
452
-continued
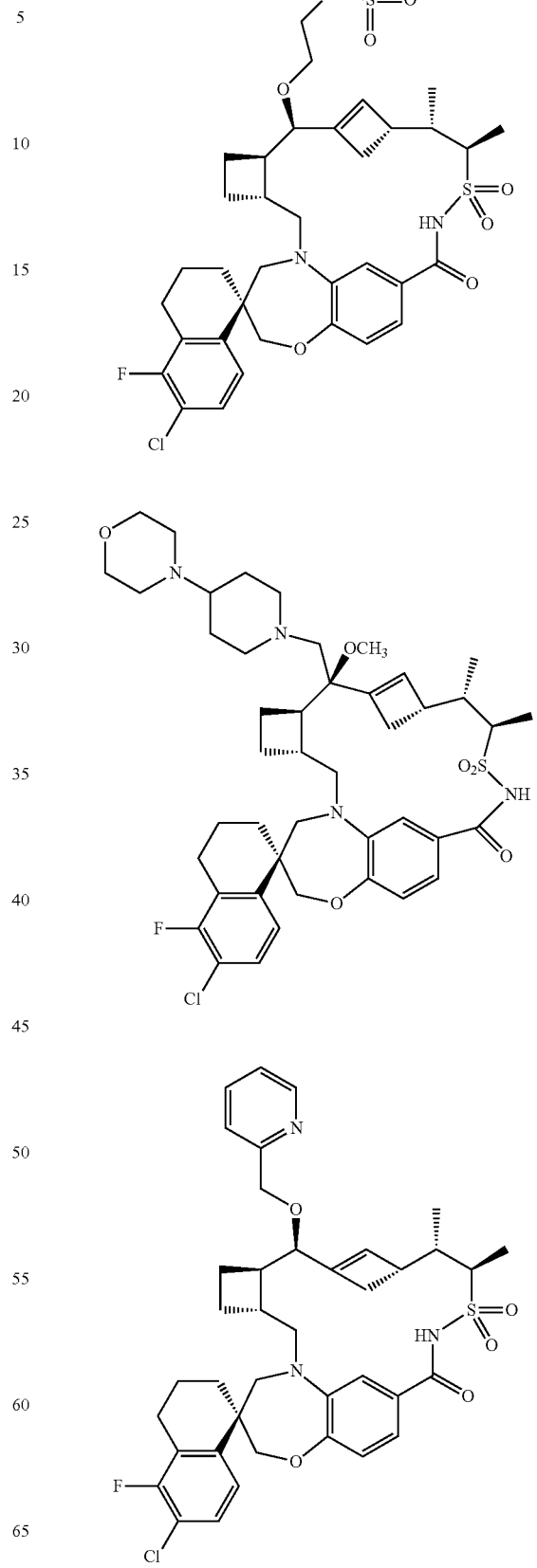
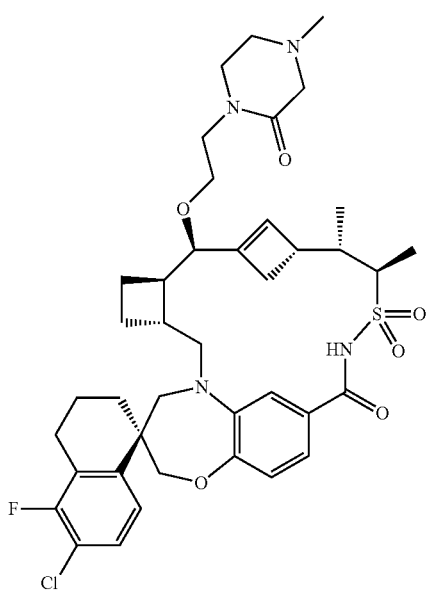

453

-continued

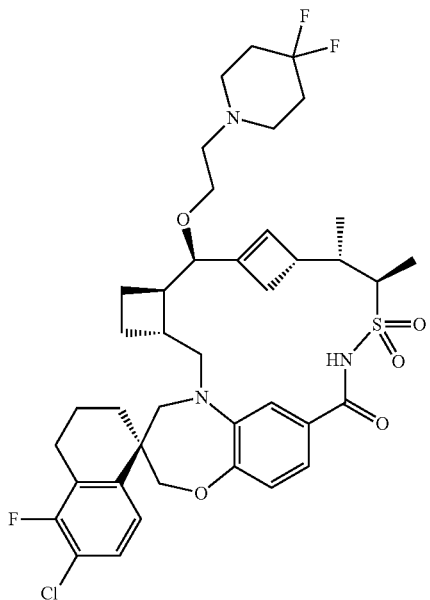 [SMILES: C[C@@H]1[C@@H](C)S(=O)(=O)NC(=O)c2ccc3c(c2)N(C[C@@H]2CC[C@H]2[C@@H](OCCN2CCC(F)(F)CC2)C2=C[C@H]1C2)C[C@@]1(CCCc2c1ccc(Cl)c2F)CO3]

or a pharmaceutically acceptable salt thereof.

22. The compound of claim 21 selected from the group consisting of:

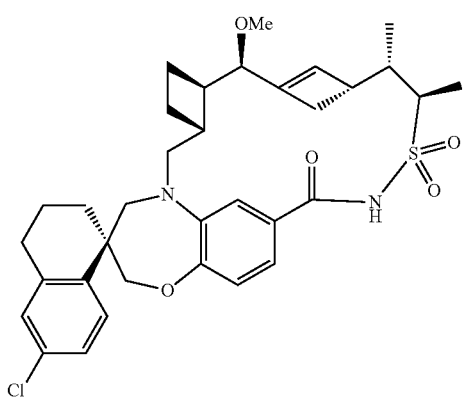

,

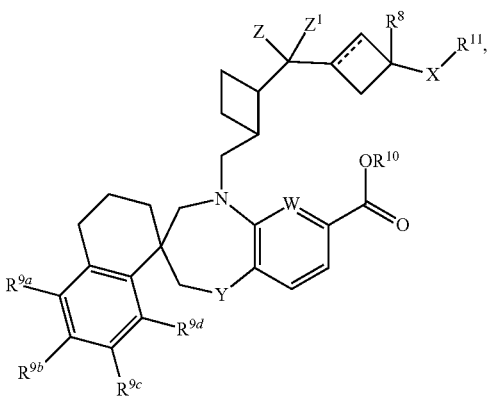

, and

-continued

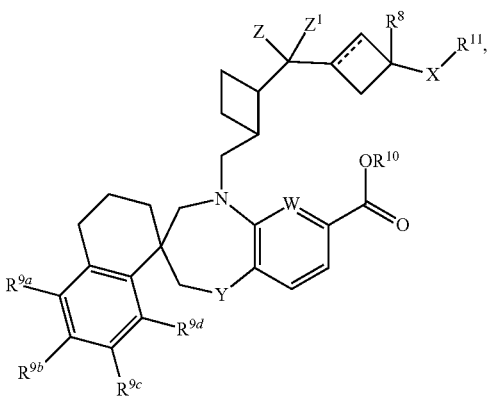

or a pharmaceutically acceptable salt thereof.

23. A pharmaceutical composition comprising the compound of claim 1, or a pharmaceutically acceptable salt thereof, and one or more pharmaceutically acceptable excipients.

24. A kit comprising the compound of claim 1, or a pharmaceutically acceptable salt thereof, and instructions for administering the compound, or a pharmaceutically acceptable salt thereof, to a subject having cancer, a chronic autoimmune disorder, an inflammatory condition, a proliferative disorder, sepsis, or a viral infection.

25. A compound of Formula XVIII-A:

XVIII-A

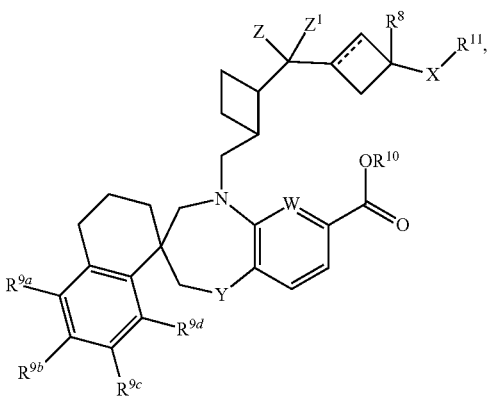

wherein:
X selected from the group consisting of:

X-1

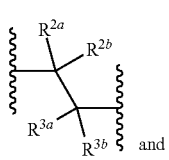 and

X-2

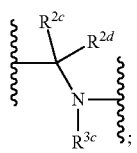;

wherein the carbon atom bearing $R^{3a}$ and $R^{3b}$ of X-1 and the nitrogen atom of X-2 are attached to $R^{11}$;

$R^8$ is selected from the group consisting of hydrogen and $C_1$-$C_3$ alkyl; or X and $R^8$ taken together form a spirocycle of Formula X-3:

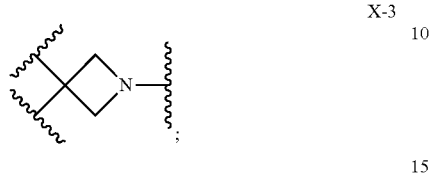

wherein the nitrogen atom of X-3 is attached $R^{11}$;

Y is selected from the group consisting of —O— and —S—;

Z is selected from the group consisting of —R, —N($R^{1a}$)($R^{1b}$), and —O$R^1$;

$Z^1$ is selected from the group consisting of hydrogen, (hydroxy)$C_1$-$C_4$ alkyl, ($C_1$-$C_3$ alkoxy)$C_1$-$C_3$ alkyl, (heterocyclo)$C_1$-$C_4$ alkyl, (alkylsulfonyl)$C_1$-$C_4$ alkyl, (phenyl)$C_1$-$C_4$ alkyl, (heteroaryl) $C_1$-$C_4$ alkyl, (amino)$C_1$-$C_4$ alkyl, (amido)$C_1$-$C_4$ alkyl, (carboxy)$C_1$-$C_4$ alkyl, (alkoxycarbonyl)$C_1$-$C_4$ alkyl, (aminocarbonyl)$C_1$-$C_4$ alkyl, (aminosulfonyl)$C_1$-$C_4$ alkyl, and —C(=O)$R^{15}$;

R is selected from the group consisting of $C_1$-$C_6$ alkyl, $C_3$-$C_6$ cycloalkyl, and 4- to 10-membered heterocyclo;

$R^1$ is selected from the group consisting of hydrogen, $C_1$-$C_6$ alkyl, (hydroxy)$C_1$-$C_4$ alkyl, ($C_1$-$C_3$ alkoxy)$C_1$-$C_3$ alkyl, (heterocyclo)$C_1$-$C_4$ alkyl, (alkylsulfonyl)$C_1$-$C_4$ alkyl, (phenyl)$C_1$-$C_4$ alkyl, (heteroaryl) $C_1$-$C_4$ alkyl, (amino)$C_1$-$C_4$ alkyl, (amido)$C_1$-$C_4$ alkyl, (carboxy)$C_1$-$C_4$ alkyl, (alkoxycarbonyl)$C_1$-$C_4$ alkyl, (aminocarbonyl)$C_1$-$C_4$ alkyl, and (aminosulfonyl)$C_1$-$C_4$ alkyl;

$R^{3a}$ is selected from the group consisting of hydrogen, $C_1$-$C_6$ alkyl, (hydroxy)$C_1$-$C_4$ alkyl, ($C_1$-$C_3$ alkoxy)$C_1$-$C_3$ alkyl, (heterocyclo)$C_1$-$C_4$ alkyl, (alkylsulfonyl)$C_1$-$C_4$ alkyl, (phenyl)$C_1$-$C_4$ alkyl, (heteroaryl)$C_1$-$C_4$ alkyl, (amino)$C_1$-$C_4$ alkyl, (amido)$C_1$-$C_4$ alkyl, (carboxy)$C_1$-$C_4$ alkyl, (alkoxycarbonyl)$C_1$-$C_4$ alkyl, (aminocarbonyl)$C_1$-$C_4$ alkyl, and (aminosulfonyl)$C_1$-$C_4$ alkyl;

$R^{1b}$ is selected from the group consisting of hydrogen and $C_1$-$C_3$ alkyl;

$R^{2a}$ is selected from the group consisting of hydrogen and $C_1$-$C_3$ alkyl;

$R^{3a}$ is selected from the group consisting of hydrogen and $C_1$-$C_3$ alkyl; or $R^{2a}$ and $R^{3a}$ taken together with the carbon atoms to which they are attached form a $C_3$-$C_6$ cycloalkyl or 4- to 10-membered heterocyclo;

$R^{2b}$ is selected from the group consisting of hydrogen and $C_1$-$C_3$ alkyl;

$R^{2c}$ is selected from the group consisting of hydrogen and $C_1$-$C_3$ alkyl;

$R^{2d}$ is selected from the group consisting of hydrogen and $C_1$-$C_3$ alkyl;

$R^{3b}$ is selected from the group consisting of hydrogen and $C_1$-$C_3$ alkyl;

$R^{3c}$ is selected from the group consisting of hydrogen, $C_1$-$C_6$ alkyl, (hydroxy)$C_1$-$C_4$ alkyl, ($C_1$-$C_3$ alkoxy)$C_1$-$C_3$ alkyl, (heterocyclo)$C_1$-$C_4$ alkyl, (alkylsulfonyl)$C_1$-$C_4$ alkyl, (phenyl)$C_1$-$C_4$ alkyl, (heteroaryl)$C_1$-$C_4$ alkyl, (amino)$C_1$-$C_4$ alkyl, (amido)$C_1$-$C_4$ alkyl, (carboxy)$C_1$-$C_4$ alkyl, (alkoxycarbonyl)$C_1$-$C_4$ alkyl, (aminocarbonyl)$C_1$-$C_4$ alkyl, and (aminosulfonyl)$C_1$-$C_4$ alkyl;

$R^{9a}$, $R^{9c}$, and $R^{9d}$ are independently selected from the group consisting of hydrogen and halo;

$R^{9b}$ is halo;

$R^{15}$ is 4- to 10-membered heterocyclo;

W is selected from the group consisting of —CH= and —N=;

═══ represents a single or double bond;

$R^{10}$ is selected from the group consisting of hydrogen and $C_1$-$C_6$ alkyl;

when X is X-1, then $R^{11}$ is selected from the group consisting of —O$R^{12}$, —S$R^{14}$, —S(=O)$_2$$R^{14}$, and —S(=O)—O$^-$M$^+$;

$R^{12}$ is selected from the group consisting of hydrogen and —C(=O)$R^{13}$;

$R^{13}$ is selected from the group consisting of phenyl and naphthyl;

$R^{14}$ is selected from the group consisting of amino and 5- or 6-membered heteroaryl; and M$^+$ selected from the group consisting of Li$^+$, Na$^+$, and K$^+$; and when X is X-2, then $R^{11}$ is —S(=O)$_2$NH$_2$; and each $C_3$-$C_6$ cycloalkyl is unsubstituted or substituted with one, two, or three substituents independently selected from the group consisting of halo, hydroxy, amino, cyano, $C_1$-$C_6$ alkyl, $C_1$-$C_4$ alkoxy, $C_3$-$C_6$ cycloalkyl, 4- to 10-membered heterocyclo, alkylsulfonyl, alkylcarbonyl, and phenyl;

each 4- to 10-membered heterocyclo is unsubstituted or substituted with one, two, three, or four substituents independently selected from the group consisting of halo, hydroxy, amino, cyano, $C_1$-$C_6$ alkyl, $C_1$-$C_4$ alkoxy, $C_3$-$C_6$ cycloalkyl, 4- to 10-membered heterocyclo, alkylsulfonyl, alkylcarbonyl, and phenyl; and each phenyl is unsubstituted or substituted with one, two, three, or four substituents independently selected from the group consisting of halo, hydroxy, amino, cyano, $C_1$-$C_6$ alkyl, $C_1$-$C_4$ alkoxy, $C_3$-$C_6$ cycloalkyl, 4- to 10-membered heterocyclo, alkylsulfonyl, alkylcarbonyl, and phenyl, or a pharmaceutically acceptable salt thereof.

26. The compound of claim 25 selected from the group consisting of:

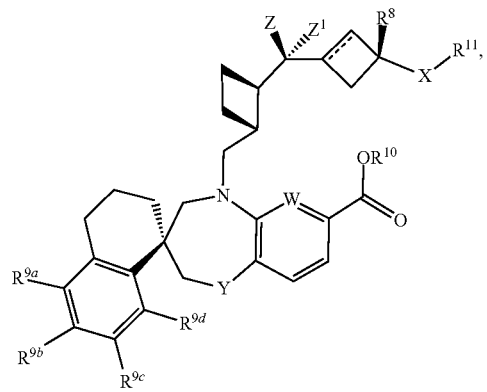

XIX-A

XX-A
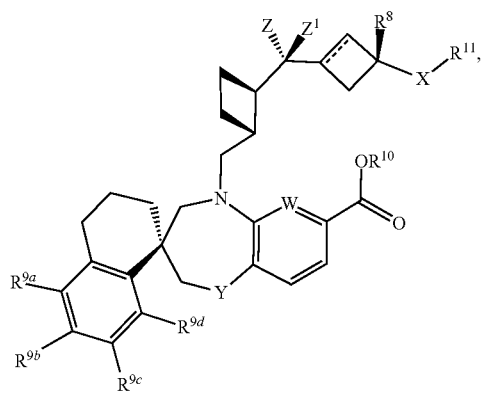
XXI-A
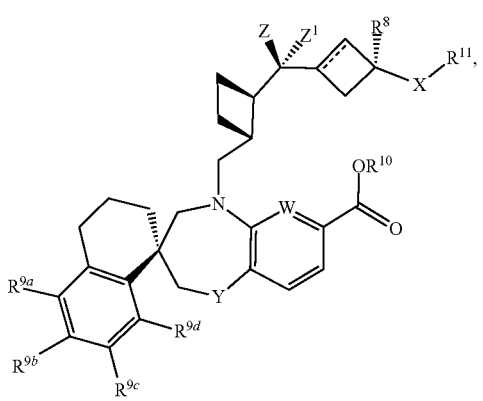
XXII-A
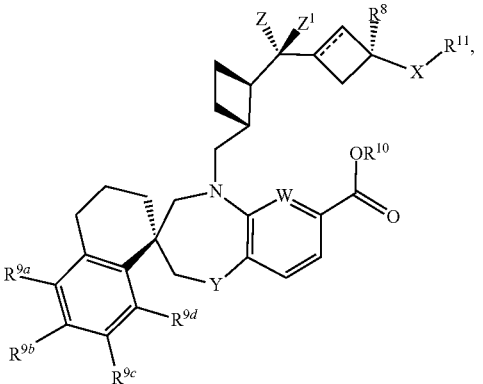
XXIII-A
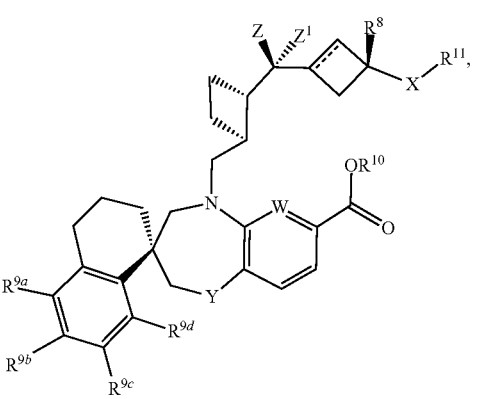
XXIV-A
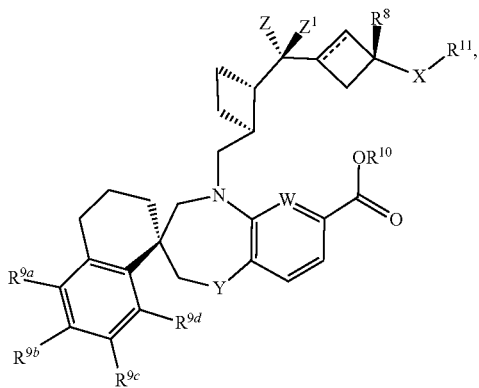
XXV-A
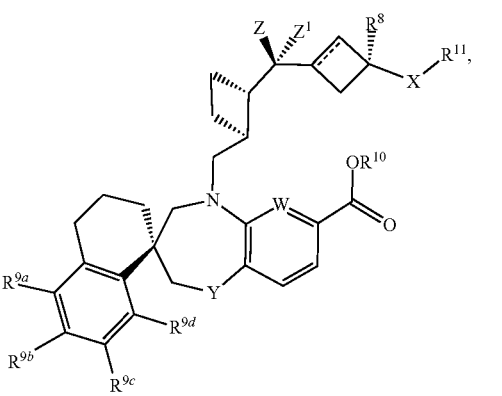
XXVI-A
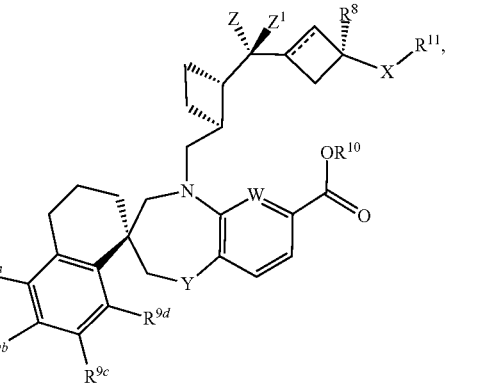
XXVII-A
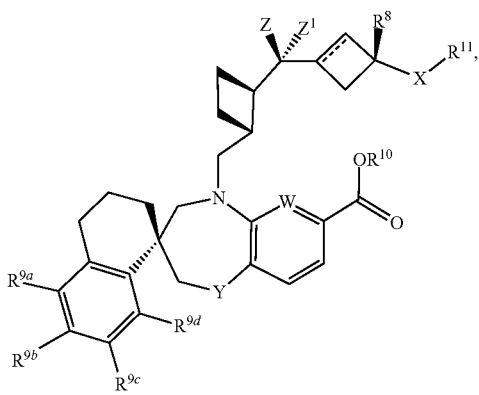

XXVIII-A
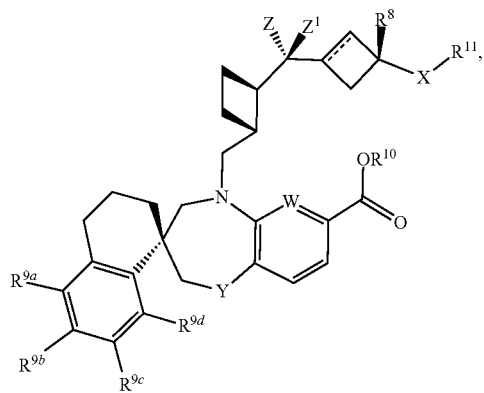
XXIX-A
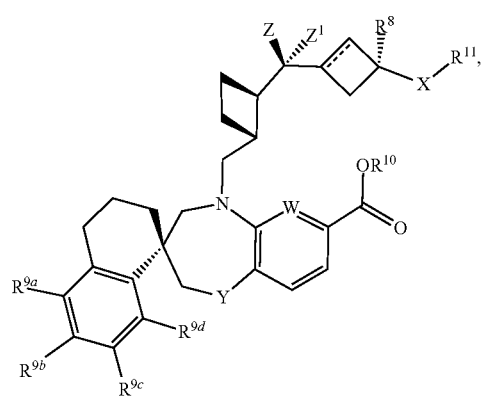
XXX-A
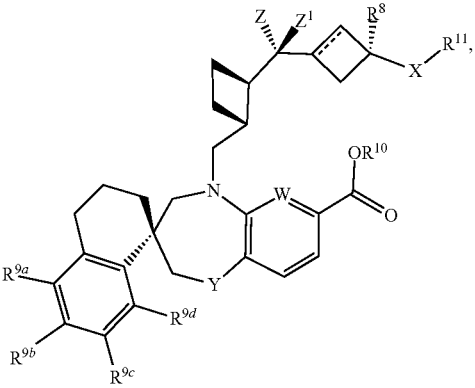
XXXI-A
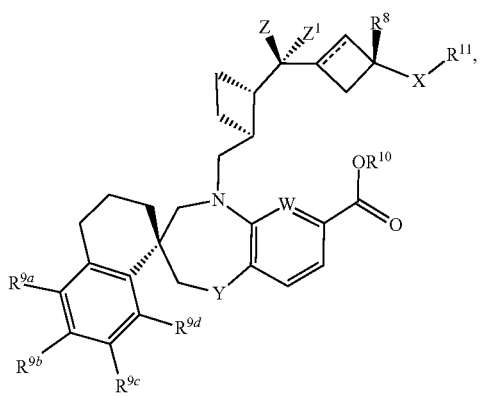
XXXII-A
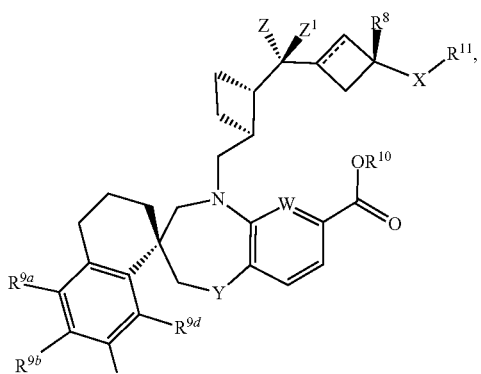
XXXIII-A
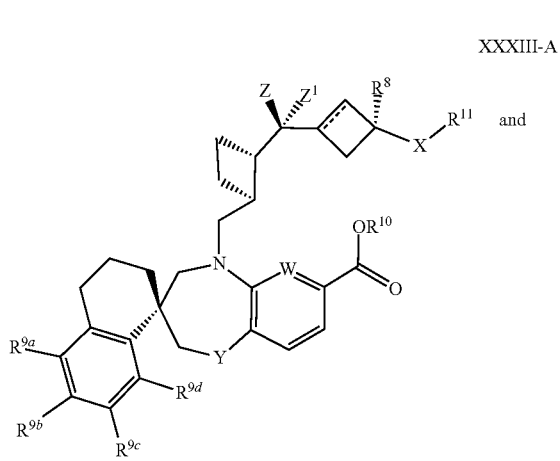
and
XXXIV-A
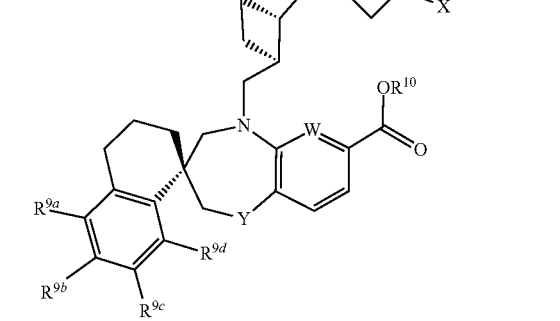
or a pharmaceutically acceptable salt thereof.
27. The compound of claim 25, wherein X is selected from the group consisting of:
X-1-A
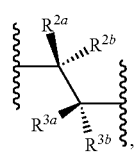

-continued

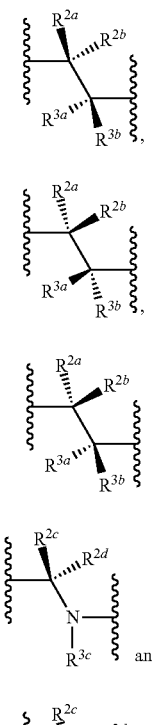

X-1-B

X-1-C

X-1-D

X-2-A

X-2-B or a pharmaceutically acceptable salt thereof.

28. The compound of claim 25, wherein Z is —OR¹, —R, or —N(R$^{1a}$)(R$^{1b}$), and Z¹ is hydrogen, or a pharmaceutically acceptable salt thereof.

29. The compound of claim 28, wherein R¹ is selected from the group consisting of (hydroxy)$C_1$-$C_4$ alkyl, ($C_1$-$C_3$ alkoxy)$C_1$-$C_3$ alkyl, (heterocyclo)$C_1$-$C_4$ alkyl, (alkylsulfonyl)$C_1$-$C_4$ alkyl, (phenyl)$C_1$-$C_4$ alkyl, (heteroaryl) $C_1$-$C_4$ alkyl, (amino)$C_1$-$C_4$ alkyl, (amido)$C_1$-$C_4$ alkyl, (carboxy)$C_1$-$C_4$ alkyl, (alkoxycarbonyl)$C_1$-$C_4$ alkyl, (aminocarbonyl)$C_1$-$C_4$ alkyl, (aminosulfonyl)$C_1$-$C_4$ alkyl, and —C(=O)R¹⁵, or a pharmaceutically acceptable salt thereof.

30. The compound of claim 25, wherein:
Z is —OR¹;
R¹ is selected from the group consisting of hydrogen and $C_1$-$C_3$ alkyl; and
Z¹ is selected from the group consisting of (hydroxy)$C_1$-$C_4$ alkyl, ($C_1$-$C_3$ alkoxy)$C_1$-$C_3$ alkyl, (heterocyclo)$C_1$-$C_4$ alkyl, (alkylsulfonyl)$C_1$-$C_4$ alkyl, (phenyl)$C_1$-$C_4$ alkyl, (heteroaryl) $C_1$-$C_4$ alkyl, (amino)$C_1$-$C_4$ alkyl, (amido)$C_1$-$C_4$ alkyl, (carboxy)$C_1$-$C_4$ alkyl, (alkoxycarbonyl)$C_1$-$C_4$ alkyl, (aminocarbonyl)$C_1$-$C_4$ alkyl, (aminosulfonyl)$C_1$-$C_4$ alkyl, and —C(=O)R¹⁵, or a pharmaceutically acceptable salt thereof.

31. The compound of claim 25, wherein R$^{3c}$ is selected from the group consisting of hydrogen, $C_1$-$C_4$ alkyl, and (heterocyclo)$C_1$-$C_4$ alkyl, or a pharmaceutically acceptable salt thereof.

32. The compound of claim 25 of Formula XVIII:

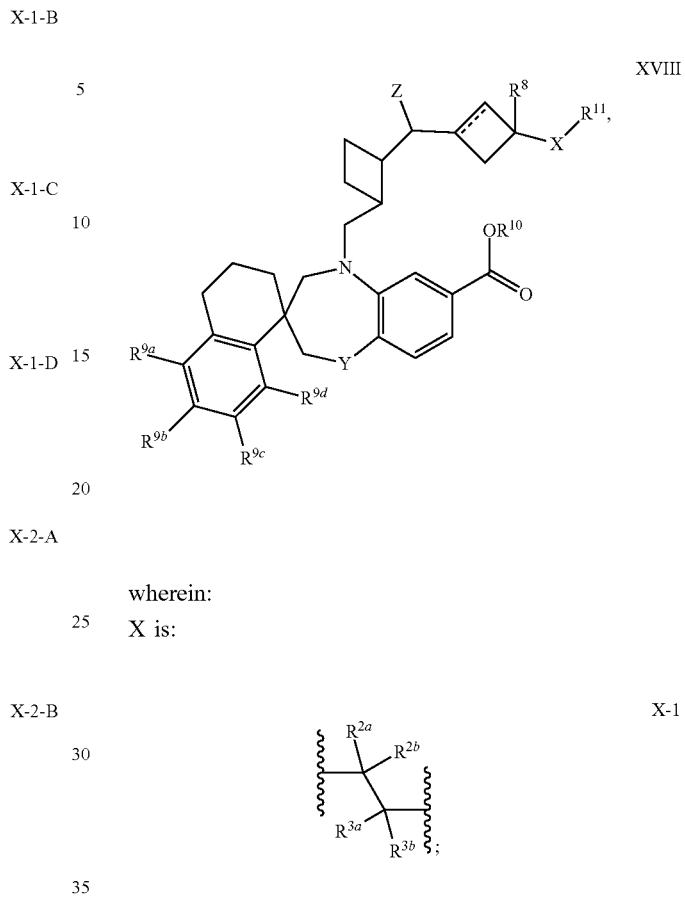

XVIII wherein:
X is:

X-1

Z is —OR¹;
R¹ is selected from the group consisting of hydrogen, $C_1$-$C_3$ alkyl and ($C_1$-$C_3$ alkoxy)$C_1$-$C_3$ alkyl;
R$^{2a}$ is selected from the group consisting of hydrogen and $C_1$-$C_3$ alkyl;
R$^{3a}$ is selected from the group consisting of hydrogen and $C_1$-$C_3$ alkyl; or
R$^{2a}$ and R$^{3a}$ taken together with the carbon atoms to which they are attached form a $C_3$-$C_6$ cycloalkyl or 4- to 7-membered heterocyclo;
R⁸ is selected from the group consisting of hydrogen and $C_1$-$C_3$ alkyl;
R¹¹ is selected from the group consisting of —OR¹², —SR¹⁴, —S(=O)₂R¹⁴, and —S(=O)—O⁻M⁺;
R¹² is selected from the group consisting of hydrogen and —C(=O)R¹³;
R¹³ is selected from the group consisting of phenyl and naphthyl;
R¹⁴ is selected from the group consisting of amino and 5- or 6-membered heteroaryl; and
M⁺ selected from the group consisting of Li⁺, Na⁺, and K⁺,
wherein each $C_3$-$C_6$ cycloalkyl, or 4- to 7-membered heterocyclo is unsubstituted or substituted with one, two, or three substituents independently selected from the group consisting of halo, $C_1$-$C_3$ alkyl, and $C_1$-$C_3$ alkoxy.

33. The compound of claim 32 selected from the group consisting of:
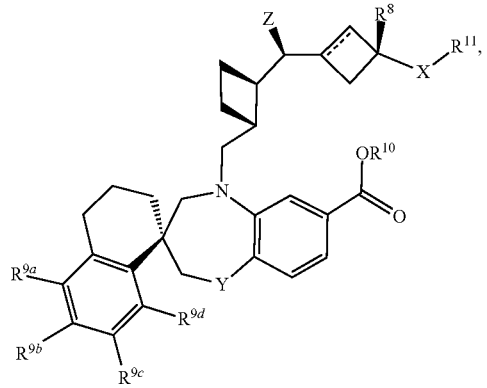
XIX
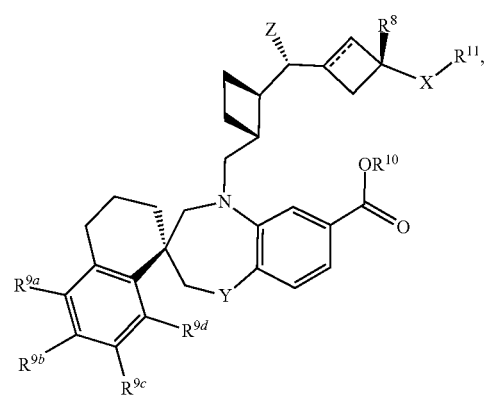
XX
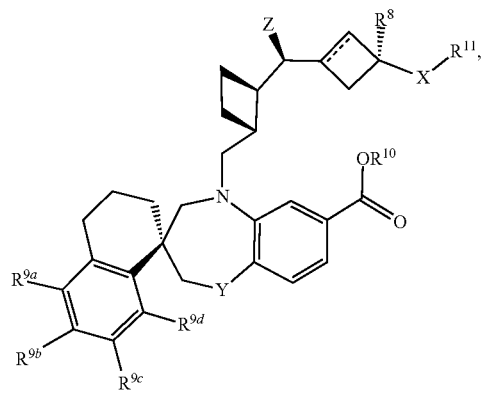
XXI
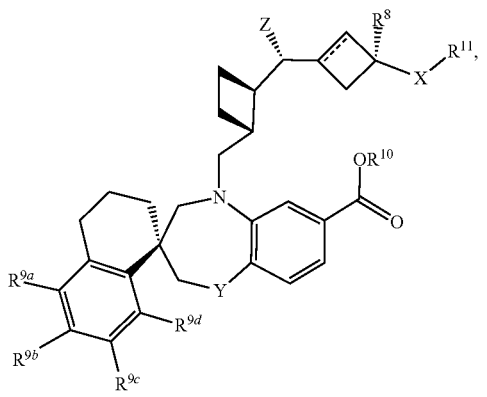
XXII
-continued
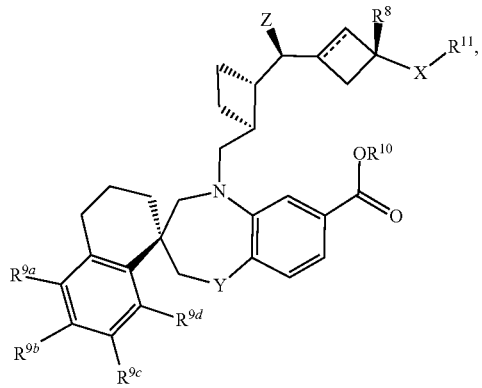
XXIII
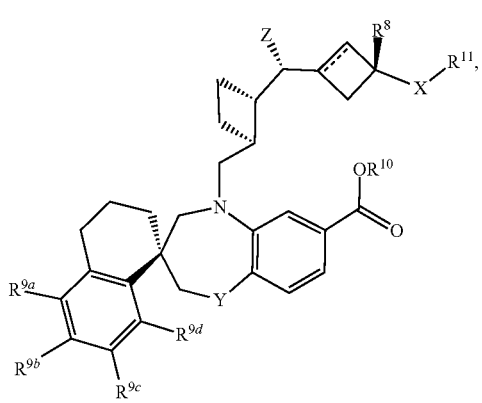
XXIV
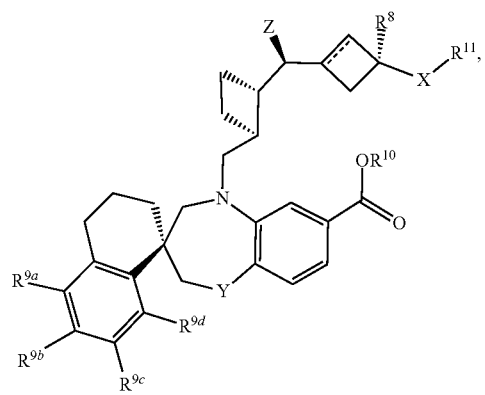
XXV
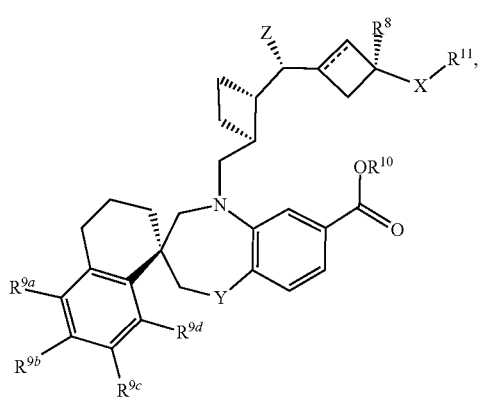
XXVI -continued
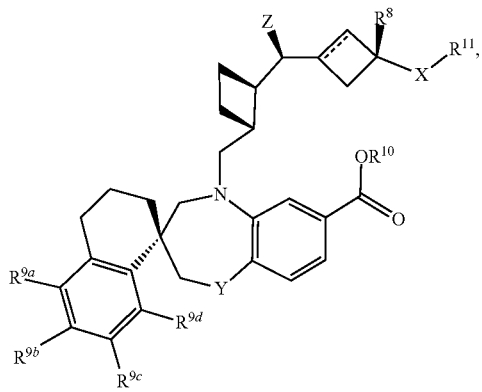
XXVII
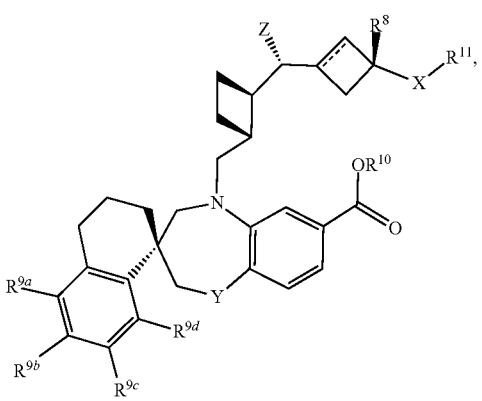
XXVIII
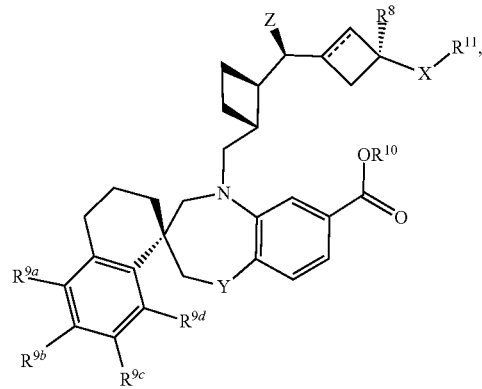
XXIX
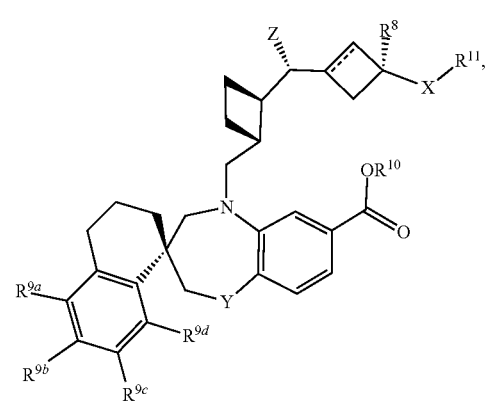
XXX
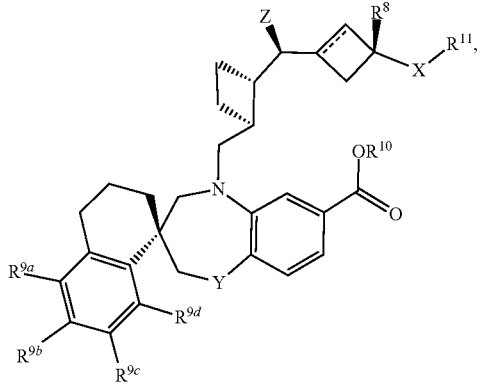
XXXI
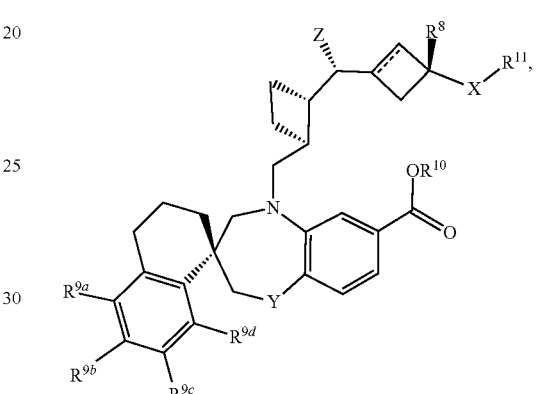
XXXII
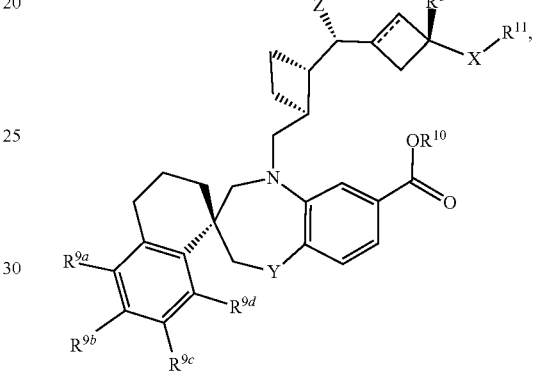
XXXIII and
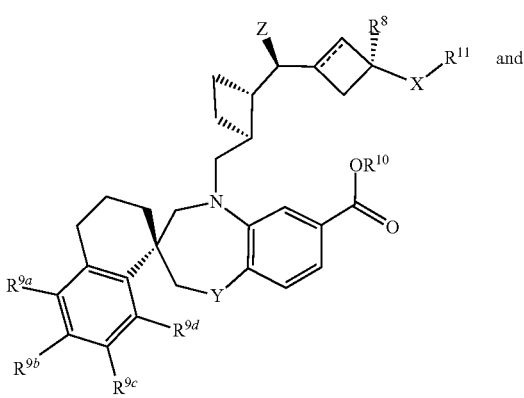
XXXIV

34. The compound of claim 33 selected from
467
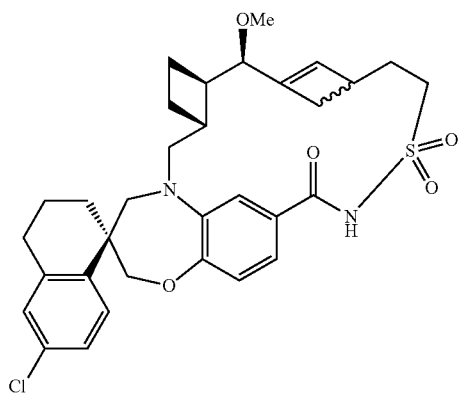
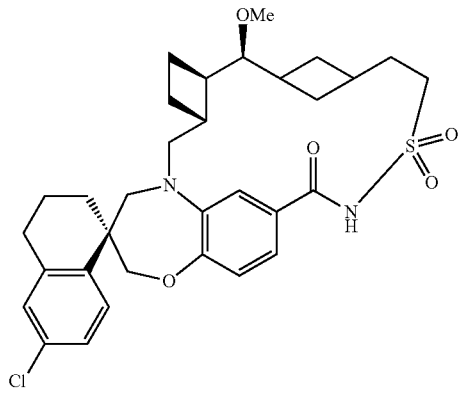
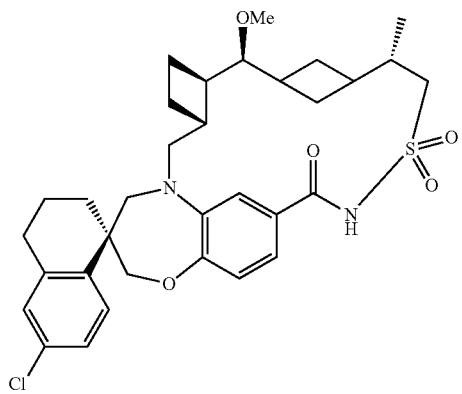
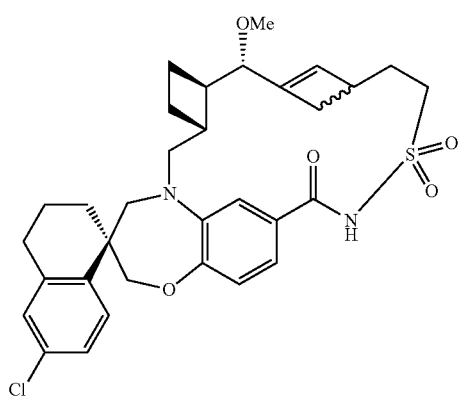
468
-continued
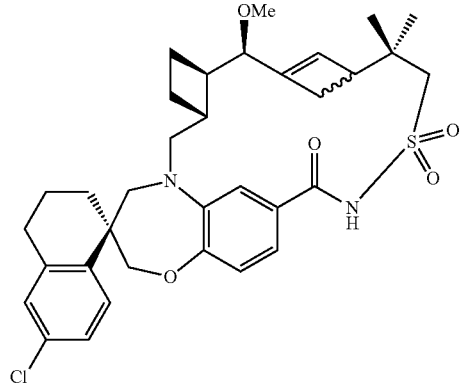
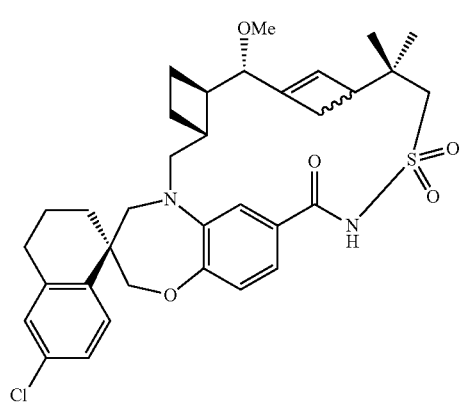
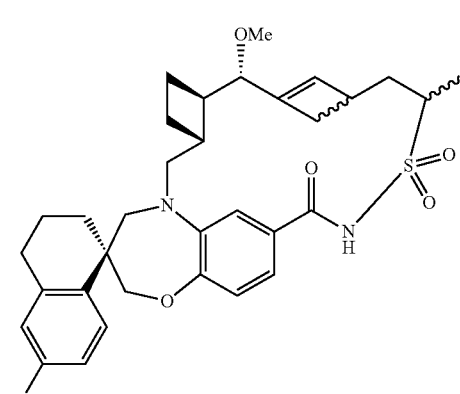
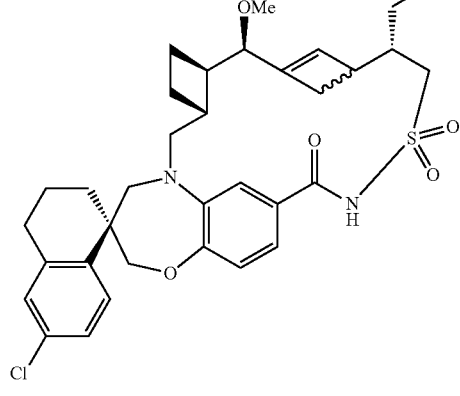

| 469 | 470 |
|---|---|
| -continued | -continued |
| 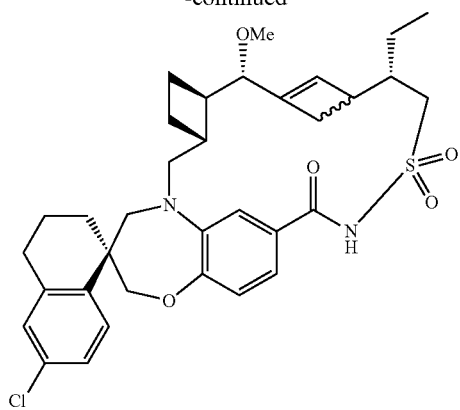 | 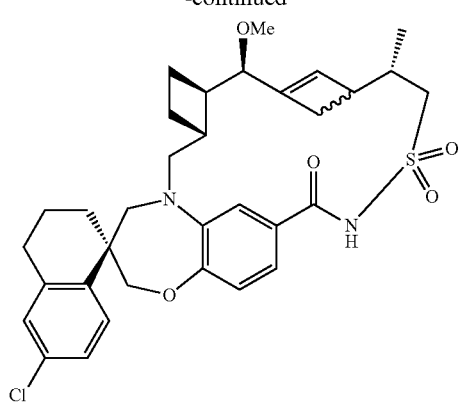 |
| 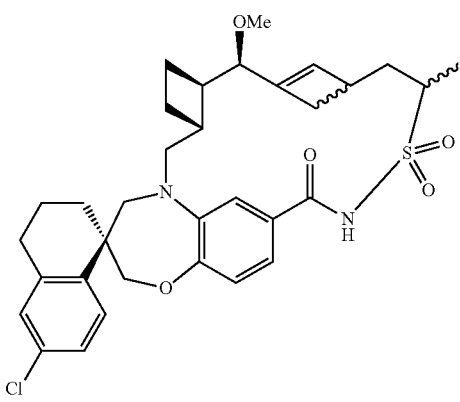 | 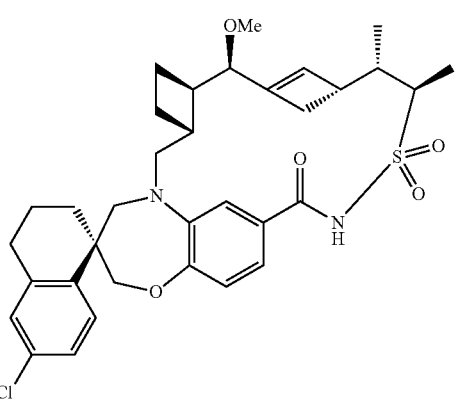 |
| 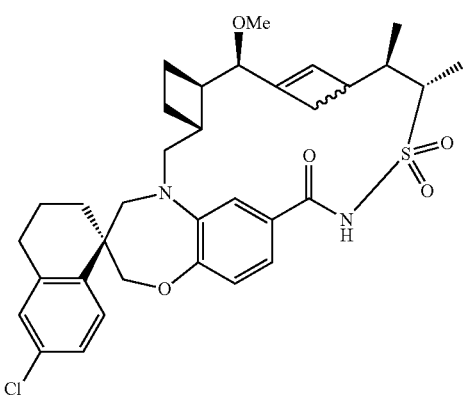 | 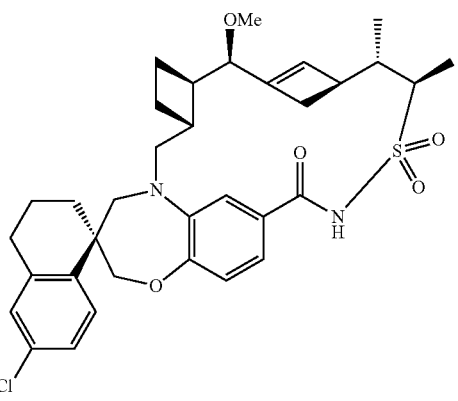 |
| 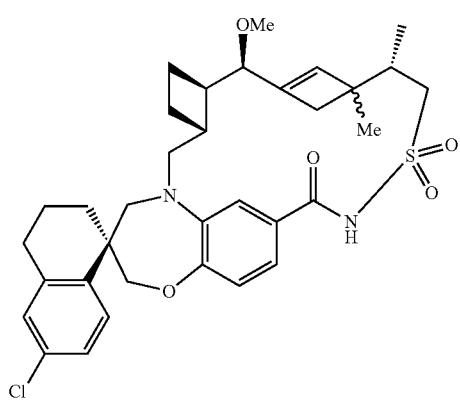 | 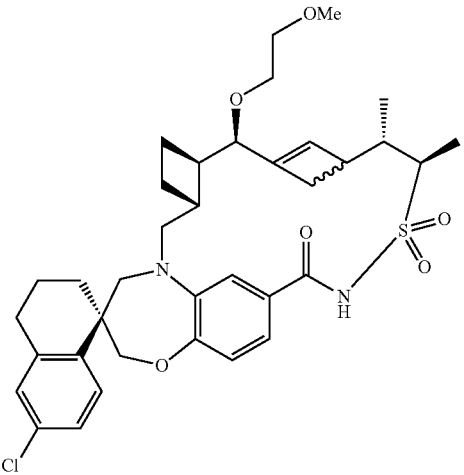 |

471
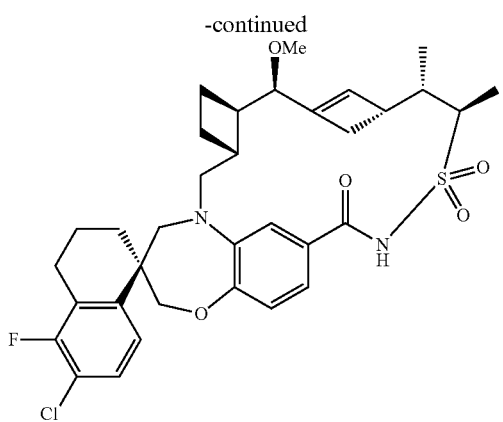
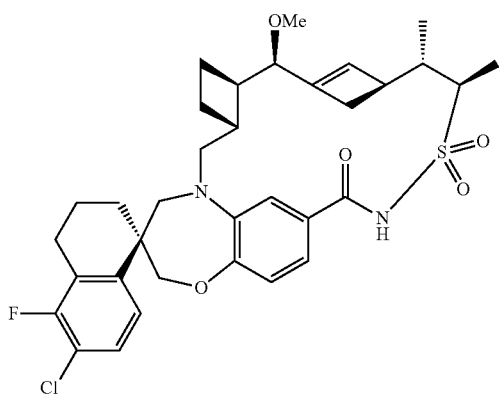
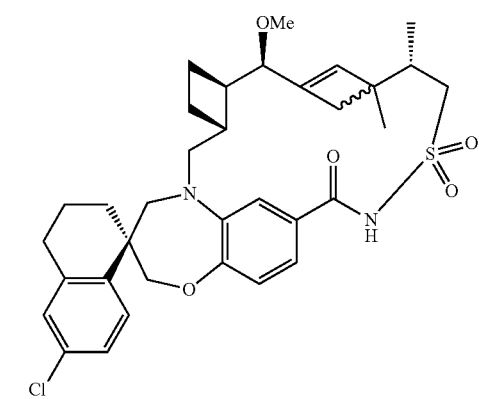
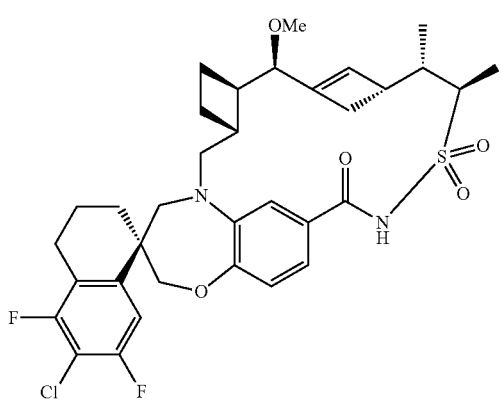
472
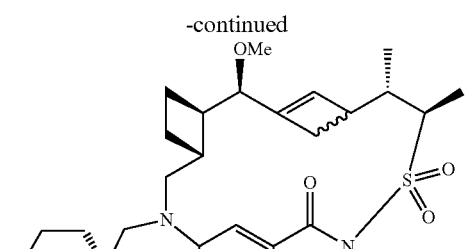
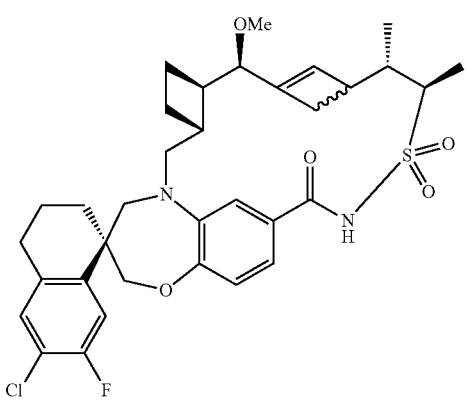
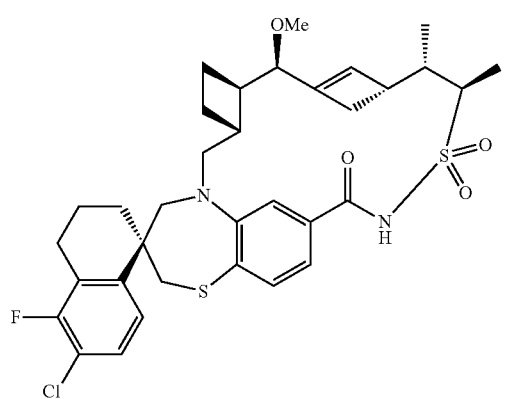
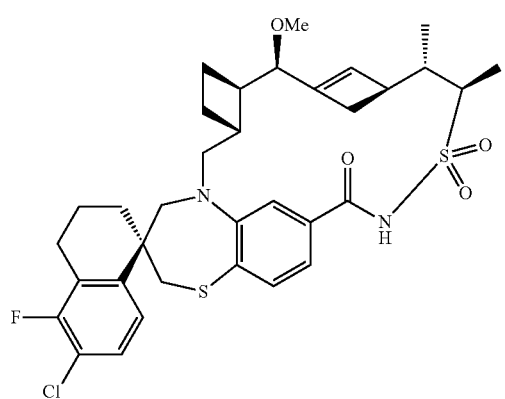

473
-continued

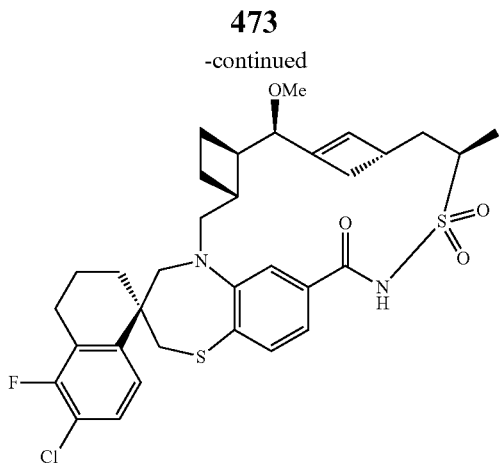

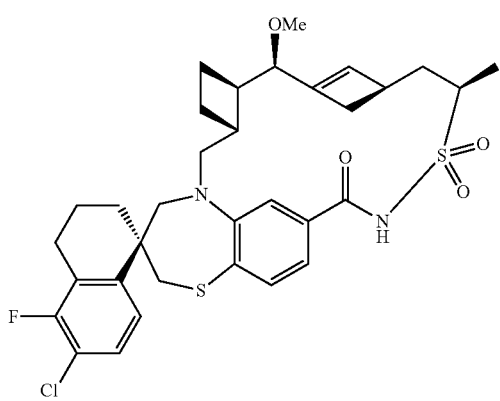

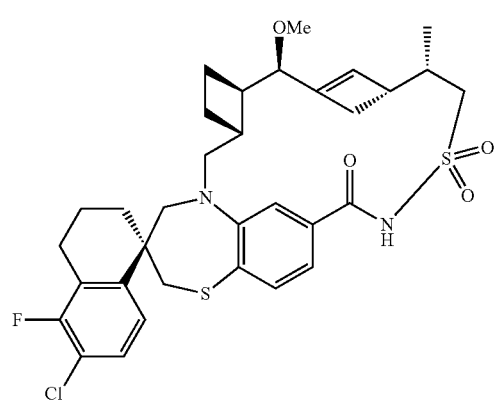

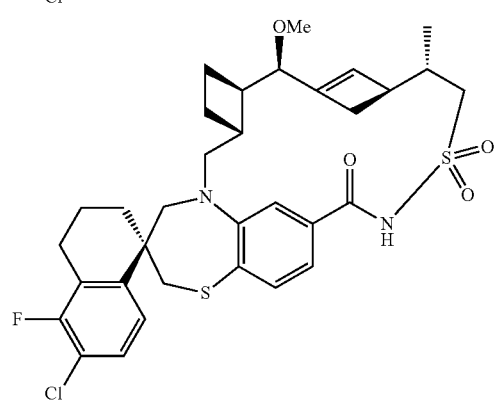

474
-continued

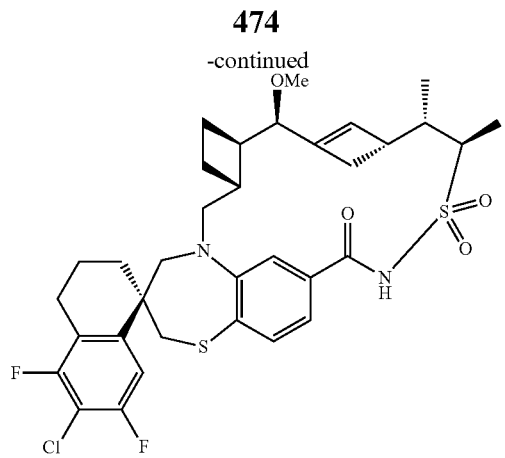

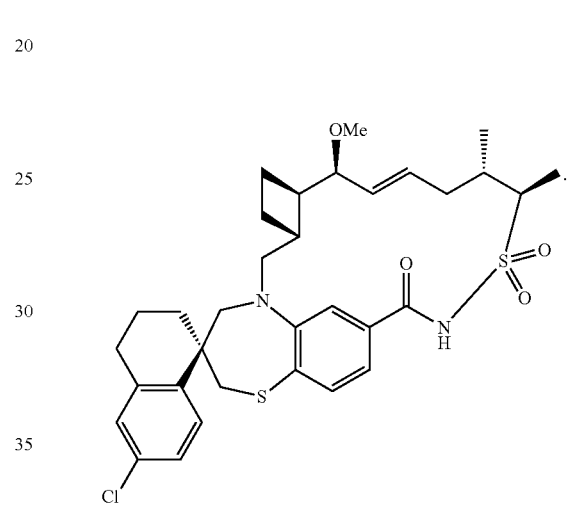

35. The compound of claim 25, wherein Z is —OR$^1$, methyl, or CH$_2$CH$_2$OCH$_3$.

36. The compound of claim 25, wherein R$^{2a}$ is hydrogen, methyl, or ethyl.

37. The compound of claim 25, wherein R$^{2b}$ is hydrogen or methyl.

38. The compound of claim 25, wherein R$^{3a}$ is hydrogen or methyl.

39. The compound of claim 25, wherein R$^{3b}$ is hydrogen or methyl.

40. The compound of claim 25, wherein R$^{2a}$ and R$^{3a}$ taken together with the carbon atoms to which they are attached form a C$_3$-C$_6$ cycloalkyl or 4- to 7-membered heterocyclo.

41. The compound of claim 25, wherein R$^8$ is hydrogen or methyl.

42. The compound of claim 25, wherein R$^{9b}$ is chloro.

43. The compound of claim 25, wherein R$^{9a}$ and R$^{9c}$ are independently selected from the group consisting of hydrogen and fluoro.

44. The compound of claim 25, wherein R$^{9d}$ is hydrogen.

45. The compound of claim 25 selected from
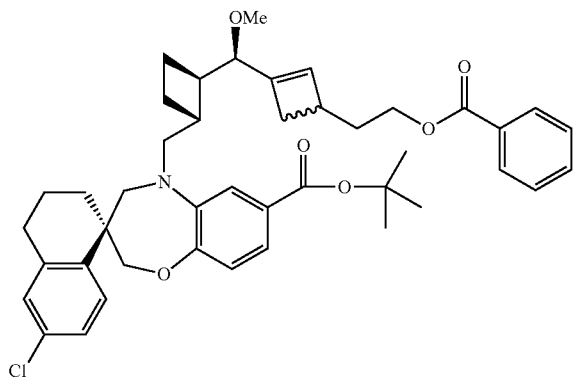
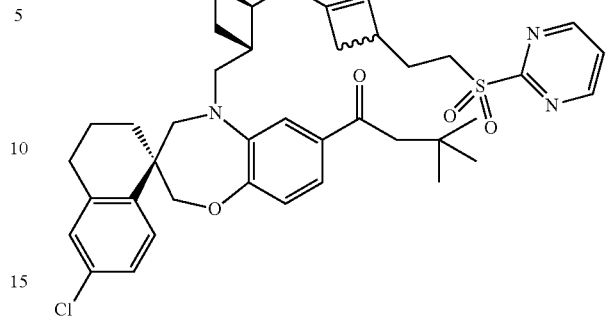
-continued
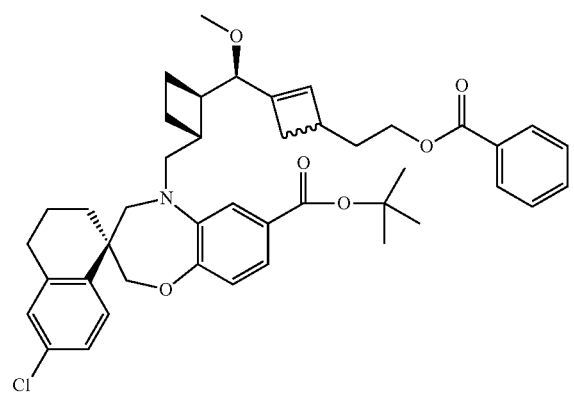
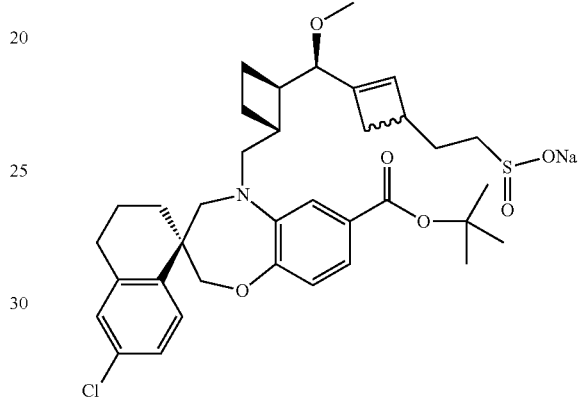
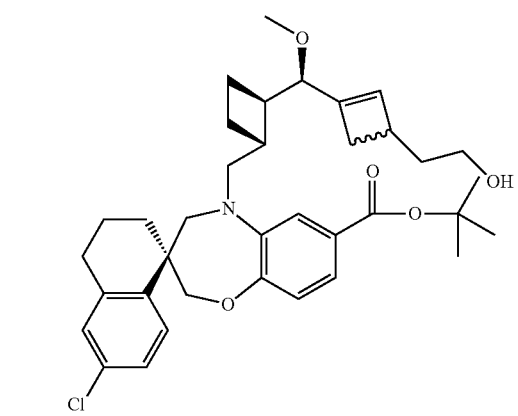
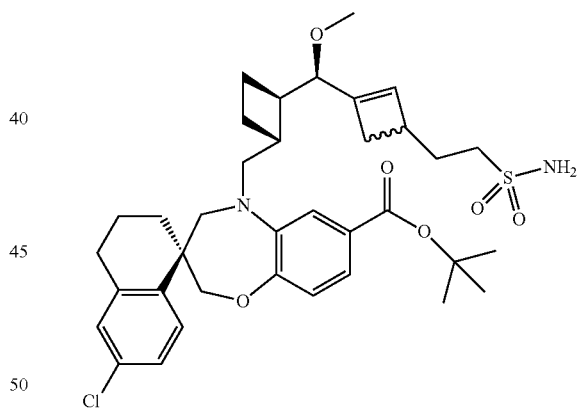
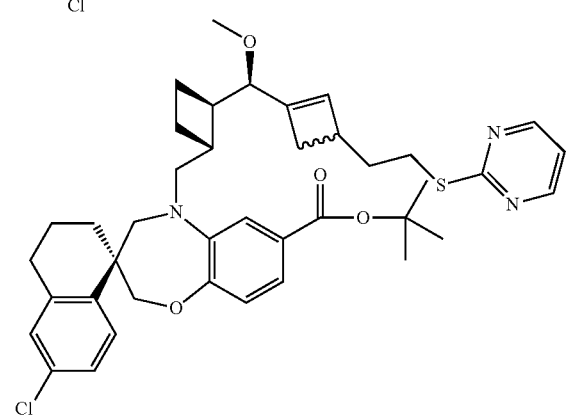
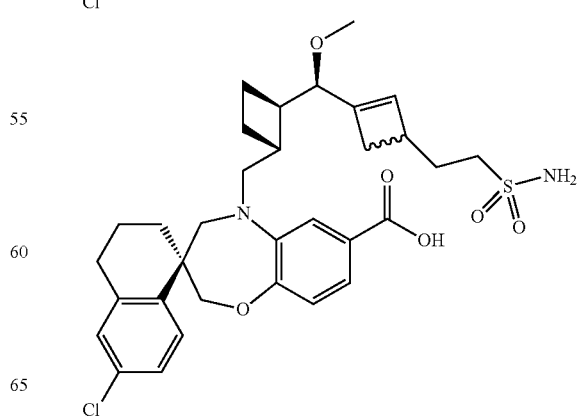

477
-continued
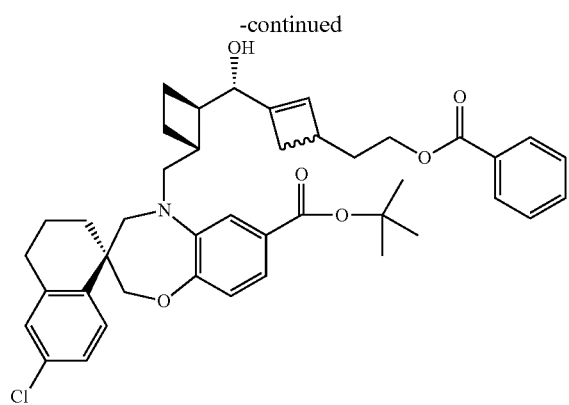
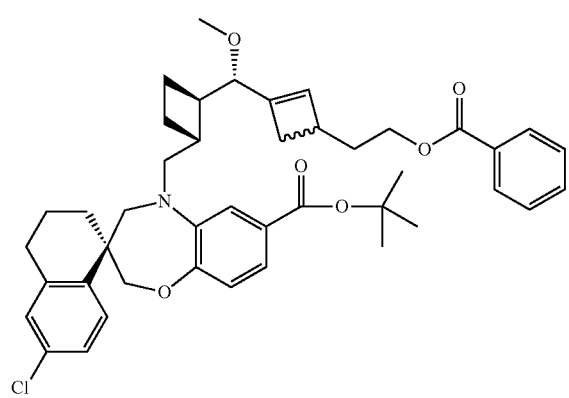
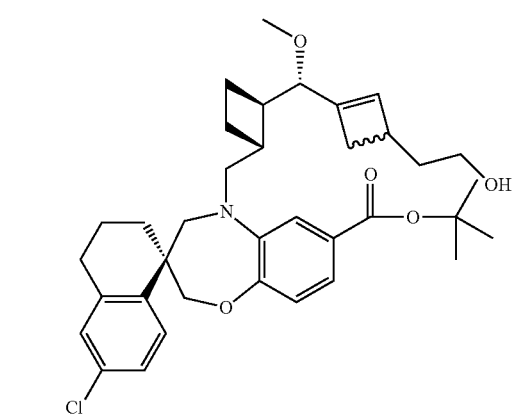
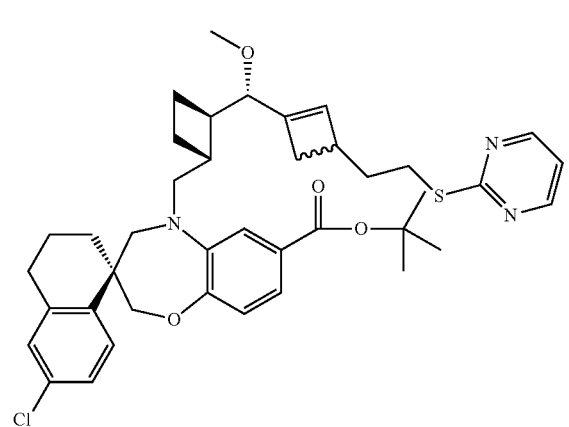
478
-continued
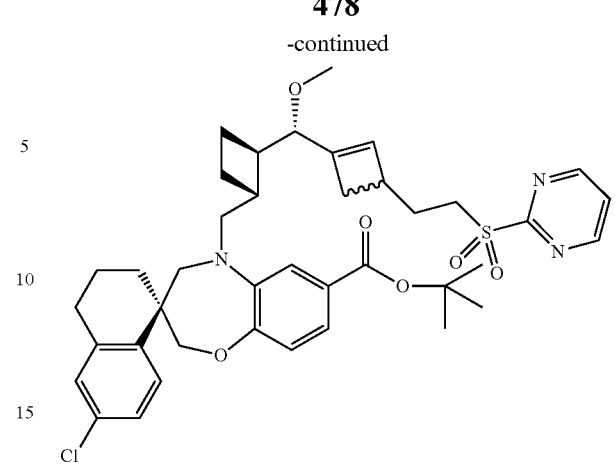
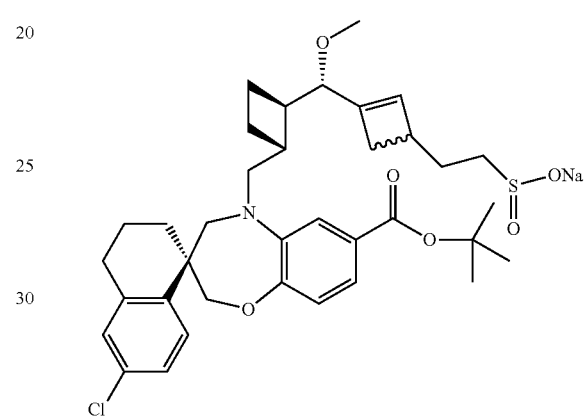
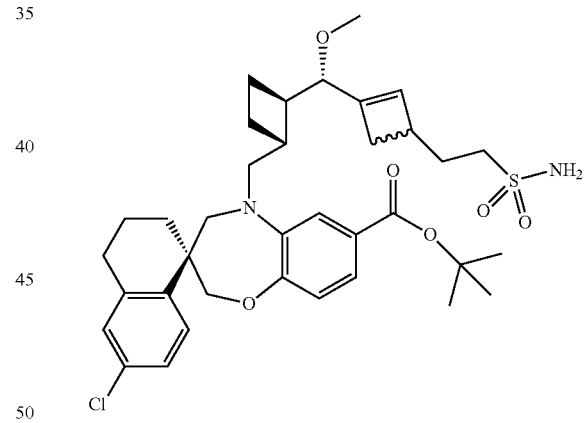
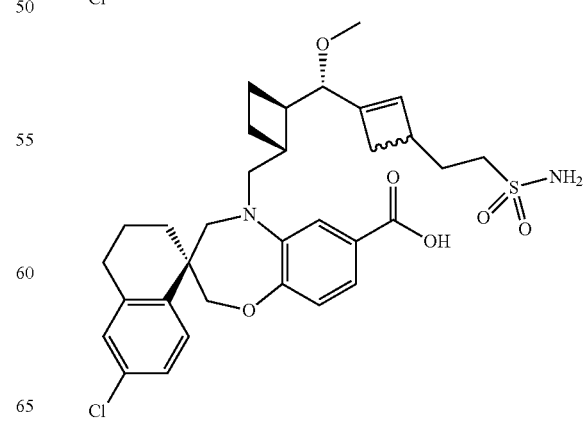

479
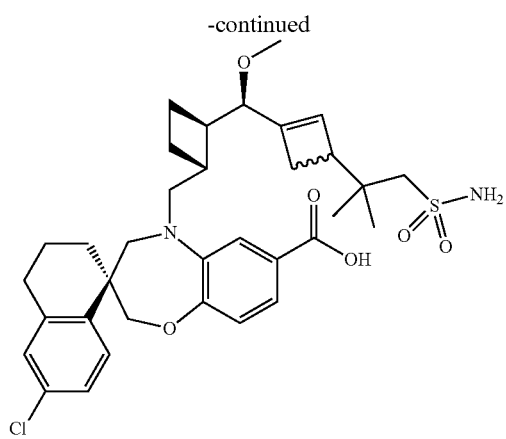
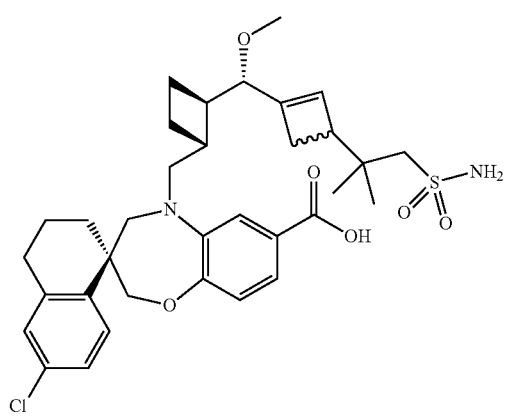
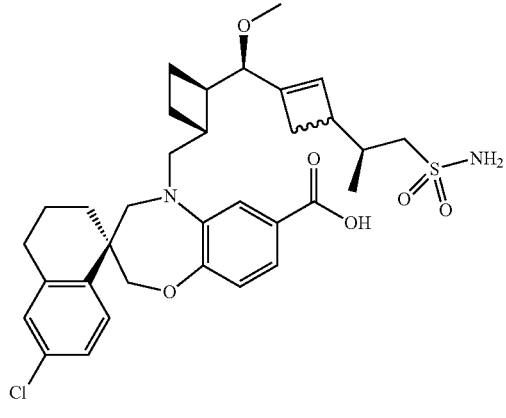
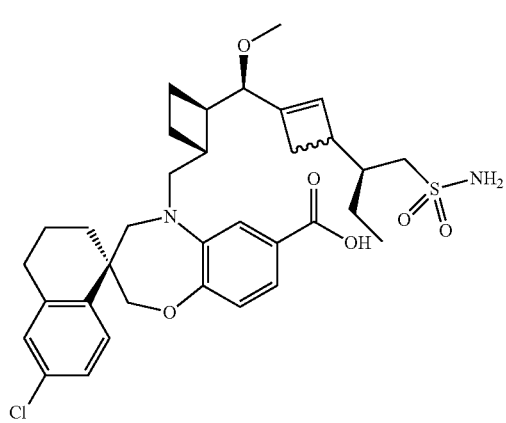
480
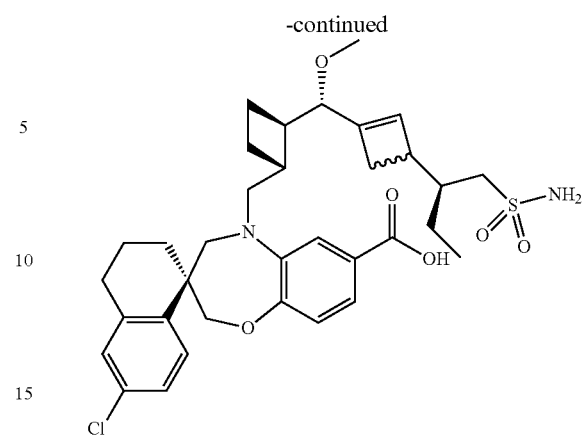
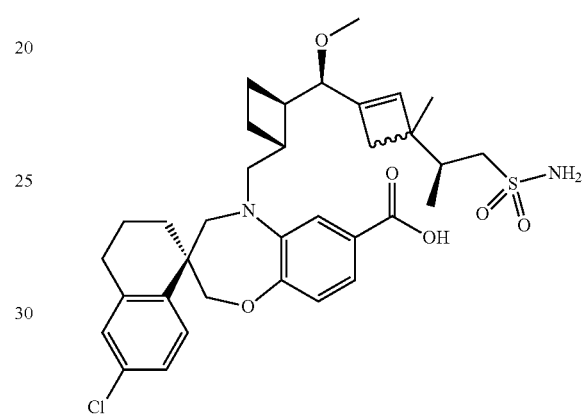
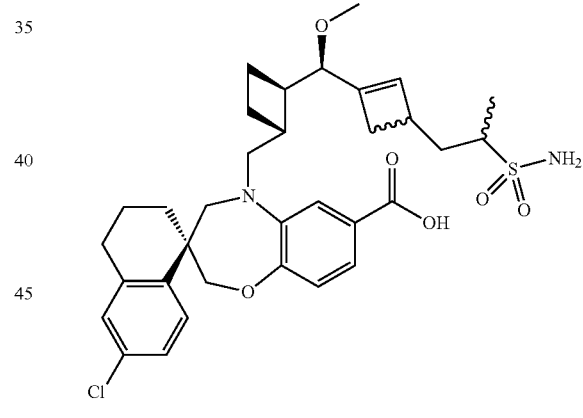
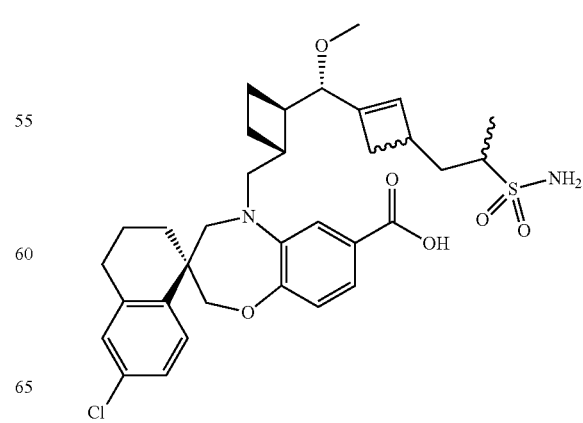

481
-continued
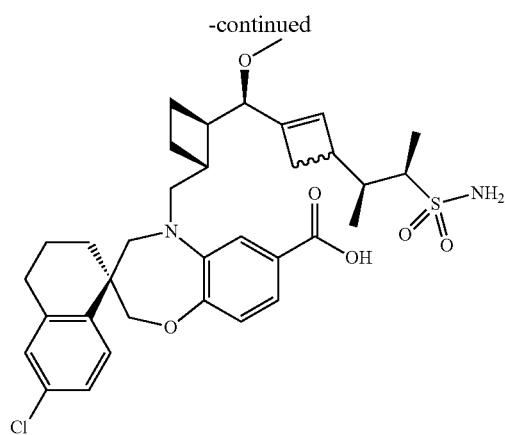
482
-continued
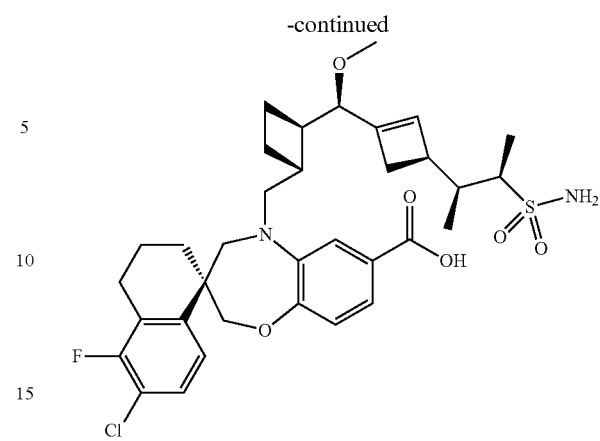
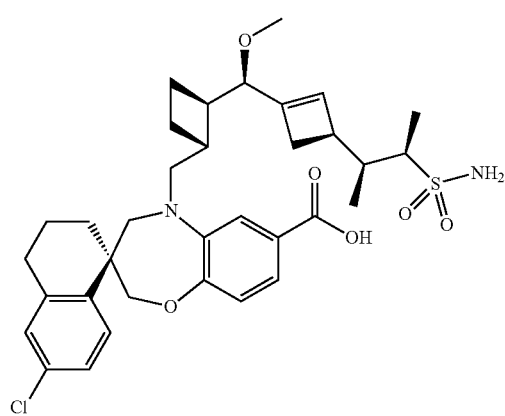
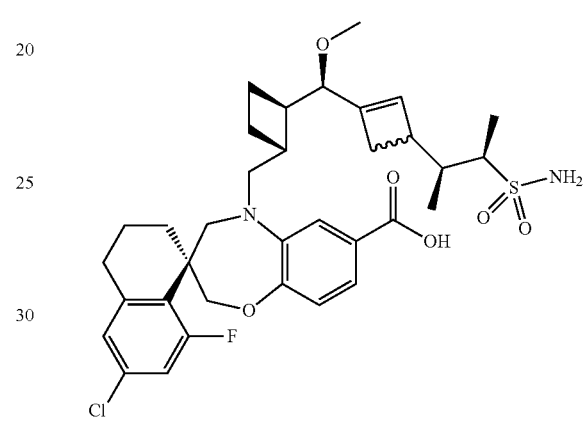
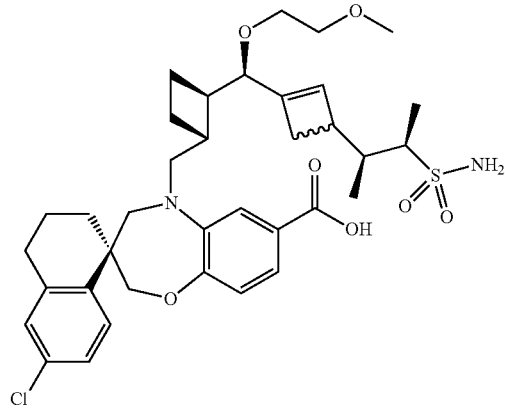
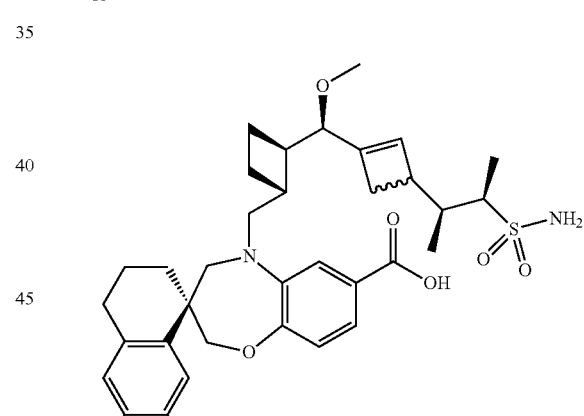
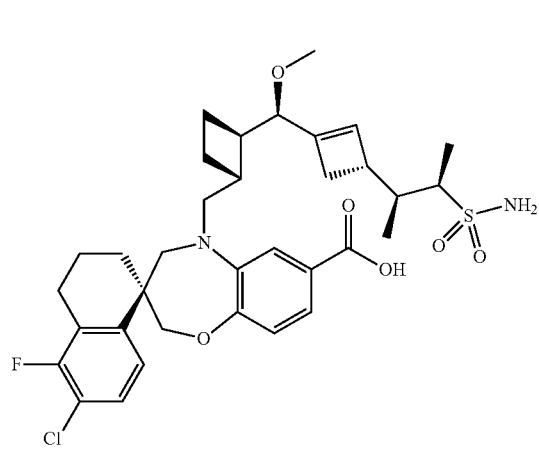
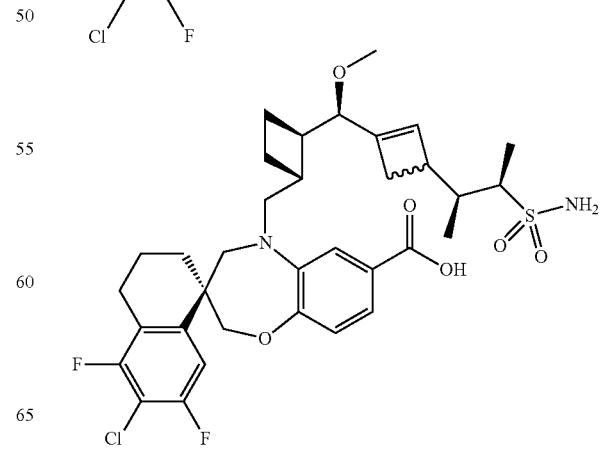

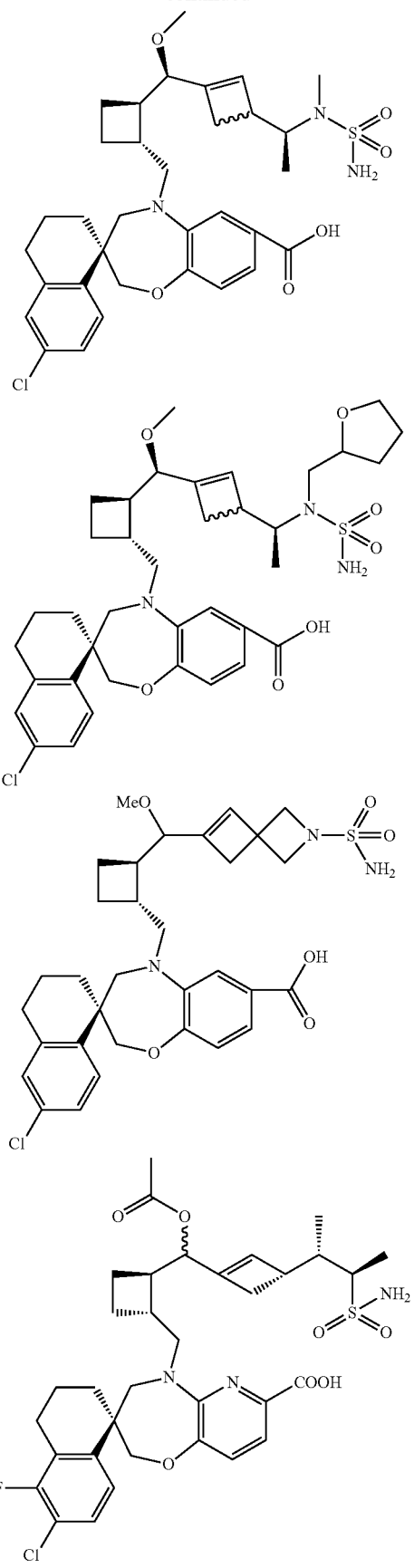
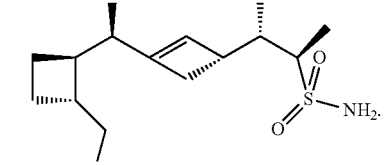
46. A method of preparing a compound the compound of Formula I-A of claim 1 comprising cyclizing a compound of Formula XVIII-A:
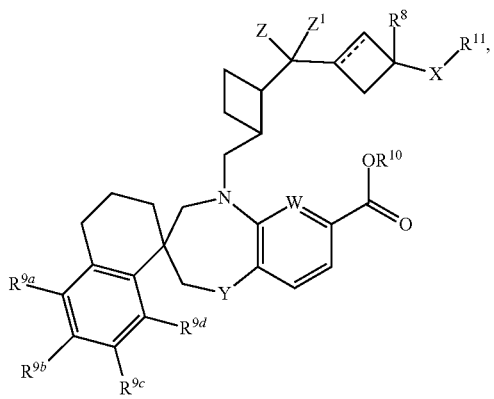
wherein:
X selected from the group consisting of:
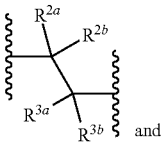
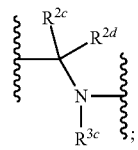
wherein the carbon atom bearing $R^{3a}$ and $R^{3b}$ of X-1 and the nitrogen atom of X-2 are attached to $R^{11}$;
$R^8$ is selected from the group consisting of hydrogen and $C_1$-$C_3$ alkyl; or X and R⁸ taken together form a spirocycle of Formula X-3:

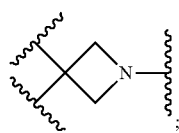

X-3 wherein the nitrogen atom of X-3 is attached R¹¹;
Y is selected from the group consisting of —O— and —S—;
Z is selected from the group consisting of —R, —N(R¹ᵃ)(R¹ᵇ), and —OR¹;
Z¹ is selected from the group consisting of hydrogen, (hydroxy)C₁-C₄ alkyl, (C₁-C₃ alkoxy)C₁-C₃ alkyl, (heterocyclo)C₁-C₄ alkyl, (alkylsulfonyl)C₁-C₄ alkyl, (phenyl)C₁-C₄ alkyl, (heteroaryl) C₁-C₄ alkyl, (amino)C₁-C₄ alkyl, (amido)C₁-C₄ alkyl, (carboxy)C₁-C₄ alkyl, (alkoxycarbonyl)C₁-C₄ alkyl, (aminocarbonyl)C₁-C₄ alkyl, (aminosulfonyl)C₁-C₄ alkyl, and —C(=O)R¹⁵;
R is selected from the group consisting of C₁-C₆ alkyl, C₃-C₆ cycloalkyl, and 4- to 10-membered heterocyclo;
R¹ is selected from the group consisting of hydrogen, C₁-C₆ alkyl, (hydroxy)C₁-C₄ alkyl, (C₁-C₃ alkoxy)C₁-C₃ alkyl, (heterocyclo)C₁-C₄ alkyl, (alkylsulfonyl)C₁-C₄ alkyl, (phenyl)C₁-C₄ alkyl, (heteroaryl) C₁-C₄ alkyl, (amino)C₁-C₄ alkyl, (amido)C₁-C₄ alkyl, (carboxy)C₁-C₄ alkyl, (alkoxycarbonyl)C₁-C₄ alkyl, (aminocarbonyl)C₁-C₄ alkyl, and (aminosulfonyl)C₁-C₄ alkyl;
R¹ᵃ is selected from the group consisting of hydrogen, C₁-C₆ alkyl, (hydroxy)C₁-C₄ alkyl, (C₁-C₃ alkoxy)C₁-C₃ alkyl, (heterocyclo)C₁-C₄ alkyl, (alkylsulfonyl)C₁-C₄ alkyl, (phenyl)C₁-C₄ alkyl, (heteroaryl)C₁-C₄ alkyl, (amino)C₁-C₄ alkyl, (amido)C₁-C₄ alkyl, (carboxy)C₁-C₄ alkyl, (alkoxycarbonyl)C₁-C₄ alkyl, (aminocarbonyl)C₁-C₄ alkyl, and (aminosulfonyl)C₁-C₄ alkyl;
R¹ᵇ is selected from the group consisting of hydrogen and C₁-C₃ alkyl;
R²ᵃ is selected from the group consisting of hydrogen and C₁-C₃ alkyl;
R³ᵃ is selected from the group consisting of hydrogen and C₁-C₃ alkyl; or
R²ᵃ and R³ᵃ taken together with the carbon atoms to which they are attached form a C₃-C₆ cycloalkyl or 4- to 10-membered heterocyclo;
R²ᵇ is selected from the group consisting of hydrogen and C₁-C₃ alkyl;
R²ᶜ is selected from the group consisting of hydrogen and C₁-C₃ alkyl;
R²ᵈ is selected from the group consisting of hydrogen and C₁-C₃ alkyl;
R³ᵇ is selected from the group consisting of hydrogen and C₁-C₃ alkyl;
R³ᶜ is selected from the group consisting of hydrogen, C₁-C₆ alkyl, (hydroxy)C₁-C₄ alkyl, (C₁-C₃ alkoxy)C₁-C₃ alkyl, (heterocyclo)C₁-C₄ alkyl, (alkylsulfonyl)C₁-C₄ alkyl, (phenyl)C₁-C₄ alkyl, (heteroaryl)C₁-C₄ alkyl, (amino)C₁-C₄ alkyl, (amido)C₁-C₄ alkyl, (carboxy)C₁-C₄ alkyl, (alkoxycarbonyl)C₁-C₄ alkyl, (aminocarbonyl)C₁-C₄ alkyl, and (aminosulfonyl)C₁-C₄ alkyl;
R⁹ᵃ, R⁹ᶜ, and R⁹ᵈ are independently selected from the group consisting of hydrogen and halo;
R⁹ᵇ is halo;
R¹⁵ is 4- to 10-membered heterocyclo;
W is selected from the group consisting of —CH= and —N=;
═══ represents a single or double bond;
R¹⁰ is hydrogen;
R¹¹ is —S(=O)₂NH₂; and
each C₃-C₆ cycloalkyl is unsubstituted or substituted with one, two, or three substituents independently selected from the group consisting of halo, hydroxy, amino, cyano, C₁-C₆ alkyl, C₁-C₄ alkoxy, C₃-C₆ cycloalkyl, 4- to 10-membered heterocyclo, alkylsulfonyl, alkylcarbonyl, and phenyl;
each 4- to 10-membered heterocyclo is unsubstituted or substituted with one, two, three, or four substituents independently selected from the group consisting of halo, hydroxy, amino, cyano, C₁-C₆ alkyl, C₁-C₄ alkoxy, C₃-C₆ cycloalkyl, 4- to 10-membered heterocyclo, alkylsulfonyl, alkylcarbonyl, and phenyl; and
each phenyl is unsubstituted or substituted with one, two, three, or four substituents independently selected from the group consisting of halo, hydroxy, amino, cyano, C₁-C₆ alkyl, C₁-C₄ alkoxy, C₃-C₆ cycloalkyl, 4- to 10-membered heterocyclo, alkylsulfonyl, alkylcarbonyl, and phenyl, or a pharmaceutically acceptable salt thereof,
in a solvent to give a compound of Formula I-A.

47. A method of preparing a compound the compound of Formula I of claim 8 comprising cyclizing a compound of Formula XVIII:

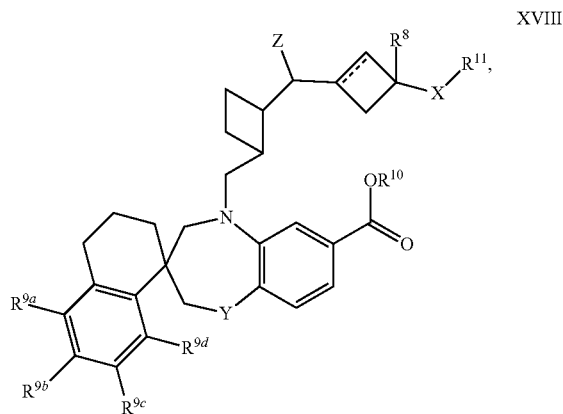

XVIII wherein:
X is:

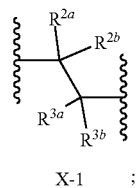

X-1 ;

wherein the bond projecting to the right is attached to the —S(=O)₂— group of R¹¹,
Y is selected from the group consisting of —O— and —S—;
Z is —OR¹;

$R^1$ is selected from the group consisting of $C_1$-$C_3$ alkyl and ($C_1$-$C_3$ alkoxy)$C_1$-$C_3$ alkyl;

$R^{2a}$ is selected from the group consisting of hydrogen and $C_1$-$C_3$ alkyl;

$R^{3a}$ is selected from the group consisting of hydrogen and $C_1$-$C_3$ alkyl; or $R^{2a}$ and $R^{3a}$ taken together with the carbon atoms to which they are attached form a $C_3$-$C_6$ cycloalkyl or 4- to 7-membered heterocyclo;

$R^{2b}$ is selected from the group consisting of hydrogen and $C_1$-$C_3$ alkyl;

$R^{3b}$ is selected from the group consisting of hydrogen and $C_1$-$C_3$ alkyl;

$R^8$ is selected from the group consisting of hydrogen and $C_1$-$C_3$ alkyl;

$R^{9a}$, $R^{9c}$, and $R^{9d}$ are independently selected from the group consisting of hydrogen and halo;

$R^{9b}$ is halo; and

═══ represents a single or double bond, $R^{10}$ is hydrogen; and $R^{11}$ is —$SO_2NH_2$, wherein each $C_3$-$C_6$ cycloalkyl, or 4- to 7-membered heterocyclo is unsubstituted or substituted with one, two, or three substituents independently selected from the group consisting of halo, $C_1$-$C_3$ alkyl, and $C_1$-$C_3$ alkoxy, in a solvent to give a compound of Formula I.

* * * * *